US009216972B2

(12) United States Patent
Dhar et al.

(10) Patent No.: US 9,216,972 B2
(45) Date of Patent: Dec. 22, 2015

(54) TRICYCLIC HETEROCYCLIC COMPOUNDS

(75) Inventors: T. G. Murali Dhar, Newtown, PA (US);
Hai-Yun Xiao, Belle Mead, NJ (US);
Scott Hunter Watterson, Pennington,
NJ (US); Soo S. Ko, Hockessin, DE
(US); Alaric J. Dyckman,
Lawrenceville, NJ (US); Charles M.
Langevine, Brooklyn, NY (US);
Jagabandhu Das, Mercerville, NJ (US);
Robert J. Cherney, Newtown, PA (US)

(73) Assignee: Bristol-Myers Squibb Company,
Princeton, NJ (US)

( * ) Notice: Subject to any disclaimer, the term of this
patent is extended or adjusted under 35
U.S.C. 154(b) by 341 days.

(21) Appl. No.: 13/504,541

(22) PCT Filed: Oct. 29, 2010

(86) PCT No.: PCT/US2010/054594
§ 371 (c)(1),
(2), (4) Date: Apr. 27, 2012

(87) PCT Pub. No.: WO2011/059784
PCT Pub. Date: May 19, 2011

(65) Prior Publication Data
US 2012/0214767 A1 Aug. 23, 2012

Related U.S. Application Data

(60) Provisional application No. 61/255,999, filed on Oct. 29, 2009.

(51) Int. Cl.
C07D 413/04 (2006.01)
C07D 231/54 (2006.01)
C07D 261/20 (2006.01)
C07D 277/84 (2006.01)
C07D 403/06 (2006.01)
C07D 413/06 (2006.01)
C07D 413/14 (2006.01)
C07D 417/04 (2006.01)
C07D 417/14 (2006.01)
C07D 419/04 (2006.01)
C07D 487/10 (2006.01)
C07D 498/04 (2006.01)

(52) U.S. Cl.
CPC ............ C07D 413/04 (2013.01); C07D 231/54
(2013.01); C07D 261/20 (2013.01); C07D
277/84 (2013.01); C07D 403/06 (2013.01);
C07D 413/06 (2013.01); C07D 413/14
(2013.01); C07D 417/04 (2013.01); C07D
417/14 (2013.01); C07D 419/04 (2013.01);
C07D 487/10 (2013.01); C07D 498/04
(2013.01)

(58) Field of Classification Search
CPC .................................................. C07D 413/04
See application file for complete search history.

(56) References Cited

U.S. PATENT DOCUMENTS

| 3,046,116 | A | 7/1962 | Schmidt |
| 3,843,666 | A | 10/1974 | Coombs et al. |
| 5,670,522 | A | 9/1997 | Leeson |
| 5,880,121 | A | 3/1999 | Hrib |
| 6,080,745 | A | 6/2000 | Davey |
| 6,251,922 | B1 | 6/2001 | Jahne et al. |
| 6,583,089 | B1 | 6/2003 | Witschel |
| 7,115,545 | B1 | 10/2006 | Witschel |
| 2004/0259904 | A1 | 12/2004 | Tong et al. |
| 2004/0267017 | A1 | 12/2004 | Bierer |
| 2005/0027125 | A1 | 2/2005 | Linden |
| 2005/0288273 | A1 | 12/2005 | Boyer, Jr. |

(Continued)

FOREIGN PATENT DOCUMENTS

| GB | 1354097 | 4/1971 |
| GB | 1354098 | 4/1971 |
| JP | 47-22226 | 6/1972 |

(Continued)

OTHER PUBLICATIONS

Mayo Clinic. "Multiple Sclerosis." Available from: < http://www.mayoclinic.com/health/multiple-sclerosis/DS00188 >. Updated Dec. 2012.*
Mayo Clinic. "Myasthenia gravis." Available from: < http://www.mayoclinic.com/health/myasthenia-gravis/DS00375 >. Updated Apr. 23, 2013.*
Mayo Clinic. "Rheumatoid arthritis." Available from: < http://www.mayoclinic.com/health/rheumatoid-arthritis/DS00020>. Updated Jul. 27, 2013.*
Mayo Clinic. "Dementia." Available from: < http://www.mayoclinic.com/health/dementia/DS01131/METHOD=print >. Updated Apr. 16, 2013.*
National Cancer Institute. "What is Cancer?" Available from: < Available from: < http://www.cancer.gov/cancertopics/cancerlibrary/what-is-cancer >. Updated: Feb. 8, 2013.*

(Continued)

Primary Examiner — Andrew D Kosar
Assistant Examiner — John S Kenyon
(74) Attorney, Agent, or Firm — Gary D. Greenblatt

(57) ABSTRACT

Disclosed are compounds of Formula (I)

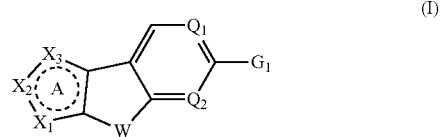

(I)

or stereoisomers or salts thereof, wherein: $X_1$, $X_2$, $X_3$, W, $Q_1$, $Q_2$, and $G_2$ are defined herein. Also disclosed are methods of using such compounds as selective agonists for G protein-coupled receptor $S1P_1$, and pharmaceutical compositions comprising such compounds. These compounds are useful in treating, preventing, or slowing the progression of diseases or disorders in a variety of therapeutic areas, such as autoimmune diseases and vascular disease.

16 Claims, No Drawings

(56) References Cited

U.S. PATENT DOCUMENTS

| | | |
|---|---|---|
| 2007/0281963 A1 | 12/2007 | Fukumoto et al. |
| 2008/0200535 A1 | 8/2008 | Ohmori et al. |
| 2009/0312338 A1 | 12/2009 | Wishart |
| 2010/0215741 A1 | 8/2010 | Lazzari |

FOREIGN PATENT DOCUMENTS

| | | | |
|---|---|---|---|
| JP | 47-16454 | | 9/1972 |
| JP | 48-99161 | | 12/1973 |
| JP | 2004 018489 | | 1/2004 |
| WO | WO 97/25317 | | 7/1997 |
| WO | WO 98/13356 | | 4/1998 |
| WO | WO 99/17769 | | 4/1999 |
| WO | WO9942455 | * | 8/1999 |
| WO | WO 00/08001 | | 2/2000 |
| WO | WO 00/27822 | | 5/2000 |
| WO | WO 01/87846 | | 11/2001 |
| WO | WO 02/066446 | | 8/2002 |
| WO | WO 03/097609 | | 11/2003 |
| WO | WO 03/105840 | | 12/2003 |
| WO | WO 2005/095387 | | 10/2005 |
| WO | WO 2006/052555 | | 5/2006 |
| WO | WO 2008/028168 | | 3/2008 |
| WO | WO 2008/039520 | | 4/2008 |
| WO | WO 2008/051403 | | 5/2008 |
| WO | WO 2008/053300 | | 5/2008 |
| WO | WO 2008/094896 | | 8/2008 |
| WO | WO 2008/118790 | | 10/2008 |
| WO | WO 2009/078983 | | 6/2009 |
| WO | WO 2009/089305 | | 7/2009 |
| WO | WO 2010/011316 | | 1/2010 |

OTHER PUBLICATIONS

Kumar, S., et al. "Efficient Routes to Pyrazolo[3,4-b]indoles and Pyrazolo[1,5-a]benzimidazoles via Palladium- and Copper-Catalyzed Intramolecular C—C and C—N Bond Formation." J. Org. Chem. (2009), vol. 74, pp. 7046-7051. Published online: Aug. 11, 2009.*

Goldberg, S.D., et al. "Discovery of the first known small-molecule inhibitors of heme-regulated eukaryotic initiation factor 2α (HRI) kinase." Bioorganic & Medicinal Chemistry Letters. (2009), vol. 19, pp. 6548-6551. Published online: Oct. 13, 2009.*

Jensen, W.B. Journal of Chemical Education. (2007), vol. 74, No. 9. Sep. 1997, pp. 1063-1064.*

Patani, et al. "Bioisosterism: A Rational Approach in Drug Design." Chem. Rev. (1996), vol. 96, 3147-3176.*

Lima. L.M., et al. "Bioisosterism: A Useful Strategy for Molecular Modification and Drug Design." Curr. Med. Chem. (2005), vol. 12, pp. 23-49.*

Bodner Research Web. "The Chemistry of the Halogens." © 2009. Available from: < http://web.archive.org/web/20090414155348/ http://chemed.chem.purdue.edu/genchem/topicreview/bp/ch10/ group7.php >.*

International Preliminary Report on Patentability for PCT/US2010/ 054594, issued May 1, 2012.

Takikawa, H., et al., "Catalytic Enantioselective Crossed Aldehyde-Ketone Benzoin Cyclization," Angew. Chem. Int. Ed. (2006), 45, pp. 3492-3494.

Hachisu, Y., et al. "Catalytic Intramolecular Crossed Aldehyde-Ketone Benzoin Reactions: A Novel Synthesis of Functionalized Preanthraquinones," J. Am. Chem. Soc. (2003) 125(28), p. 8432-8433.

European Search Report, EP10774099.5, issued Sep. 9, 2013.

European Search report, EP13154679.8, issued Mar. 13, 2013.

European Search Report, EP13154833.1 issued Apr. 17, 2013.

International Preliminary Report on Patentability for PCT/US2010/ 054594 issued Sep. 9, 2013.

Shen, H.C., et al., "Discovery of Novel Tricyclic Full Agonists for the G-Protein-Coupled Niacin Receptor 109A with Minimized Flushing in Rats," Journal of Medicinal Chemistry, vol. 52, No. 8, pp. 2587-2602 (2009).

Dinges, J., et al., "1.4-Dihydroindeno[1,2-c]pyrazoles with Acetylenic Side Chains as Novel and Potent Multitargeted Receptor Tyrosine Kinase Inhibitors with Low Affinity for the hERG Ion Channel," Journal of Medicinal Chemistry, vol. 50, No. 9, pp. 2011-2029 (2007).

Tao, Z., et al., "Discovery of 4'-(1,4-dihydro-indeno[1,2-c]pyrazol-3-yl)benzonitriles and 4'-(1,4-dihydro-indeno[1,2-c]pyrazol-3-yl)-pyridine-2'-carbonitriles as potent checkpoint kinase 1 (Chk1) inhibitors," Bioorganic & Medicinal Chemistry Letters, vol. 17, No. 21, pp. 5944-5951, (2007).

Official Action Summary, Japanese Patent Application No. 2012-537086, dated Sep. 2, 2014.

Ponomarev, O.A. et al., "Nature of the excited states of dialkylamino derivatives or aromatic and heteroaromatic compounds with an annelated oxazole ring", Teoreticheskaya i Eksperimental'naya Khimiya, vol. 26, No. 6 (1990) pp. 644-650.

Ponomarev, O.A. et al., "Spin-orbit interactions of the ππ*—states in molecules with annelated oxazole rings", Teoreticheskaya i Eksperimental'naya Khimiya, vol. 26, No. 4 (1990) pp. 403-406.

* cited by examiner

TRICYCLIC HETEROCYCLIC COMPOUNDS

FIELD OF THE INVENTION

The present invention generally relates to tricyclic heterocyclic compounds useful as $S1P_1$ agonists. Provided herein are tricyclic heterocyclic compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Down-regulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Publication No. 2007/0203100), WO 06/047195, WO 06/100633, WO 06/115188, WO 06/131336, WO 2007/024922, WO 07/109,330, WO 07/116,866, WO 08/023,783 (U.S. Publication No. 2008/0200535), WO 08/029,370, WO 08/114,157, WO 08/074,820, WO 09/043,889, WO 09/057,079, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

BRIEF STATEMENT OF THE INVENTION

The present invention provides tricyclic heterocyclic compounds, which are useful as modulators of $S1P_1$ activity, including stereoisomers, salts, solvates, and prodrugs thereof.

The present invention also provides processes and intermediates for making the compounds of the present invention or stereoisomers, salts, or prodrugs thereof.

The present invention also provides pharmaceutical compositions comprising a compound of Formula (I), or stereoisomers, pharmaceutically acceptable salts, or prodrugs thereof; and a pharmaceutically acceptable carrier.

The present invention also provides a method of treating a disease or disorder associated with the activity of G protein-coupled receptor $S1P_1$, the method comprising administering to a mammalian patient a compound of Formula (I) or stereoisomers, pharmaceutically acceptable salts, or prodrugs thereof.

The present invention also provides the compounds of the present invention or stereoisomers, pharmaceutically acceptable salts, or prodrugs thereof, for use in therapy.

The present invention also provides the use of the compounds of the present invention or stereoisomers, pharmaceutically acceptable salts, or prodrugs thereof, for the manufacture of a medicament for the treatment or prophylaxis of $S1P_1$ receptor-related conditions, such as autoimmune and vascular diseases.

The compounds of Formula (I) and compositions comprising the compounds are $S1P_1$ agonists, which are selective for $S1P_1$ activity over $S1P_3$ activity. The compounds of Formula (I) and compositions comprising said compounds may be used in treating, preventing or curing various $S1P_1$ receptor-related conditions while reducing or minimizing the side effects due to $S1P_3$ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION OF THE INVENTION

In a first aspect, the present invention provides compounds of Formula (I):

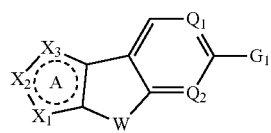

(I)

or a stereoisomer, a salt, or prodrug thereof, wherein:
(i) $X_1$ is C-$G_2$, one of $X_2$ and $X_3$ is N, and the other of $X_2$ and $X_3$ is O or S;
(ii) $X_2$ is C-$G_2$, one of $X_1$ and $X_3$ is N, and the other of $X_1$ and $X_3$ is O or S;
(iii) $X_1$ is C-$G_2$, one of $X_2$ and $X_3$ is N, and the other of $X_2$ and $X_3$ is NH or NCH$_3$; or
(iv) one of $X_1$ and $X_2$ is N-$G_2$, the other of $X_1$ and $X_2$ is N or $CR_1$, and $X_3$ is N or $CR_1$, provided that zero or one of $X_1$, $X_2$ and $X_3$ is $CR_1$;
wherein the broken circle represents two non-adjacent double bonds within Ring A;
$R_1$ is H, F, Cl, —CN, —OH, $C_{1-4}$alkyl, $C_{1-4}$alkoxy, $C_{1-3}$fluoroalkyl, $C_{1-3}$fluoroalkoxy, or $C_{3-6}$cycloalkyl;
W is —(CR$_2$R$_2$)$_n$—, —O—, —NR$_3$—, —NR$_3$C(O)—, —C(O)NR$_3$—, —(CR$_2$R$_2$)$_m$O—, —(CR$_2$R$_2$)$_m$NR$_3$—, —O(CR$_2$R$_2$)$_m$—, —NR$_3$(CR$_2$R$_2$)$_m$—, —CR$_2$R$_2$NR$_3$C(O)—, —CR$_2$R$_2$C(O)NR$_3$—, —NR$_3$C(O)CR$_2$R$_2$—, —C(O)NR$_3$CR$_2$R$_2$—, —CR$_2$R$_2$OCR$_2$R$_2$—, —CR$_2$R$_2$NR$_3$CR$_2$R$_2$—, —CR$_4$=CR$_4$—, —CR$_2$R$_2$CR$_4$=CR$_4$—, or —CR$_4$=CR$_4$CR$_2$R$_2$—;
each $R_2$ is independently H, F, Cl, —CN, —OH, $C_{1-3}$alkyl, $C_{1-4}$alkoxy, $C_{1-3}$fluoroalkyl, $C_{1-3}$fluoroalkoxy, and/or $C_{3-4}$cycloalkyl; or two geminal $R_2$ groups together with the carbon atom to which they are attached form a $C_{3-6}$spirocycloalkyl ring;
each $R_3$ is independently H, $C_{1-6}$alkyl, $C_{2-3}$fluoroalkyl, and/or $C_{3-6}$cycloalkyl;
each $R_4$ is H, F, —CN, $C_{1-3}$alkyl, $C_{1-4}$alkoxy, $C_{1-3}$fluoroalkyl, $C_{1-3}$fluoroalkoxy, and/or $C_{3-4}$cycloalkyl;
each m is independently 1 and/or 2;
n is 1, 2, or 3;
$Q_1$ and $Q_2$ are independently N and/or $CR_5$;
each $R_5$ is independently H, F, Cl, Br, $C_{1-4}$alkyl, $C_{1-4}$alkoxy, $C_{1-3}$fluoroalkyl, $C_{1-3}$fluoroalkoxy, and/or cyclopropyl;
$G_1$ is:
(i) —(CR$_c$R$_c$)$_a$OH, —(CR$_c$R$_c$)$_a$CN, —(CR$_c$R$_c$)$_a$C(O)OH, —(CR$_c$R$_c$)$_a$NR$_6$R$_6$, —(CR$_c$R$_c$)$_a$C(O)NR$_6$R$_6$, —(CR$_c$R$_c$)$_a$C(O)NR$_6$S(O)$_2$(C$_{1-4}$alkyl), —(CR$_c$R$_c$)$_a$NR$_6$C(O)(C$_{1-4}$alkyl), —(CR$_c$R$_c$)$_a$NR$_6$(CR$_c$R$_c$)$_a$COOH, or —(CR$_c$R$_c$)$_a$B$_1$;
(ii) $C_{1-12}$alkyl;
(iii) —(C$_{0-4}$alkylene)B$_2$;
(iv) —(C$_{0-4}$alkylene)O(C$_{1-4}$alkyl);
(v) —(C$_{0-4}$alkylene)C(O)(C$_{1-4}$alkyl);
(vi) —(C$_{0-4}$alkylene)NR$_6$B$_3$;
(vii) —(C$_{0-4}$alkylene)C(O)NR$_6$(C$_{1-4}$alkyl);
(viii) —(C$_{0-4}$alkylene)S(O)$_2$NR$_6$(C$_{1-4}$alkyl);
(ix) —(C$_{0-4}$alkylene)OC(O)NR$_6$R$_6$; or
(x) —(C$_{0-4}$alkylene)OC(O)B$_3$;
wherein each of groups (ii) to (x) is substituted with $R_a$ and zero to 7 $R_b$ as valence allows;
$B_1$ is a 4- to 6-membered heterocyclyl substituted with 1 to 6 $R_b$;
$B_2$ is $C_{3-6}$cycloalkyl, 1- and 2-ring heterocyclyl, or 1- and 2-ring heteroaryl, with the proviso that $B_2$ is not oxazolidinone;
$B_3$ is $C_{1-4}$alkyl, $C_{3-6}$cycloalkyl, or 1-ring heterocyclyl;
each $R_a$ is independently —(CR$_c$R$_c$)$_a$OH, —(CR$_c$R$_c$)$_a$CN, —(CR$_c$R$_c$)$_a$C(O)OH, —(C$_{0-4}$alkylene)NR$_6$R$_6$, —S(O)$_2$(C$_{1-4}$alkyl), —(CR$_c$R$_c$)$_a$C(O)NR$_6$R$_6$, —(CR$_c$R$_c$)$_a$C(O)NR$_6$S(O)$_2$(C$_{1-4}$alkyl), —(CR$_c$R$_c$)$_a$NR$_6$C(O)(C$_{1-4}$alkyl), —(CR$_c$R$_c$)$_a$NR$_6$(CR$_c$R$_c$)$_a$COOH, and/or —(CR$_c$R$_c$)$_a$OP(O)(OH)$_2$;
each $R_b$ is independently $R_a$, F, Cl, —CN, —OH, —NH$_2$, $C_{1-4}$alkyl, $C_{1-3}$fluoroalkyl, $C_{1-4}$alkoxy, $C_{1-3}$fluoroalkoxy, and/or $C_{3-5}$cycloalkyl, or two geminal $R_b$ along with the carbon atom to which they are attached form a $C_{3-6}$spirocyclic ring having zero, 1, or 2 heteroatoms independently selected from N and/or O, wherein said spirocyclic ring is substituted with zero to 3 substituents independently selected from $C_{1-4}$alkyl, $C_{1-3}$fluoroalkyl, $C_{3-6}$cycloalkyl, and/or =O as valence allows;
each $R_c$ is independently H, F, —OH, —C(O)OH, —C(O)NR$_6$R$_6$, $C_{1-2}$alkyl, $C_{3-6}$cycloalkyl, $C_{4-6}$heterocycloalkyl, $C_{1-3}$hydroxyalkyl, —(C$_{1-3}$alkylene)OP(O)(OH)$_2$, and/or $C_{1-2}$fluoroalkyl, or two geminal $R_c$ along with the carbon atom to which they are attached form a $C_{3-6}$spirocyclic ring;
each $R_6$ is independently H, $C_{1-6}$alkyl, $C_{1-3}$fluoroalkyl, $C_{1-4}$hydroxyalkyl, $C_{3-6}$cycloalkyl, and/or $C_{3-6}$cyanocycloalkyl, or two geminal $R_6$ groups together with the nitrogen atom to which they are attached form a 4- to 6-membered heterocyclyl ring having zero or one additional heteroatom selected from N and O, wherein said heterocyclyl ring is substituted with zero to 6 $R_d$;
each $R_d$ is independently $C_{1-4}$alkyl, $C_{1-3}$fluoroalkyl, and/or $C_{3-6}$cycloalkyl, or two geminal $R_d$ are =O;
each a is independently zero, 1, 2, 3, 4, and/or 5;

$G_2$ is:
(i) $C_{1-6}$alkyl or —$NR_3R_3$;
(ii) phenyl or naphthyl, each substituted with zero, 1, 2, 3, or 4 $R_e$;
(iii) 5- to 10-membered heteroaryl substituted with zero, 1, 2, or 3 $R_e$;
(iv) $C_{3-6}$cycloalkyl substituted with zero, 1, or 2 $R_e$;
(v) —$(CR_5R_5)_aNR_7C(O)R_7$;
(vi) —$(CR_5R_5)_aC(O)NR_7R_7$; or
(vii) —$(CR_5R_5)_aCR_eR_e(C_{1-3}$alkyl), —$(CR_5R_5)_aCR_eR_eB_4$, —$NR_3(CR_5R_5)_aB_4$, —$(CR_5R_5)_a$—$CR_8$=$CR_8$—$(CR_5R_5)_aCR_eR_eB_4$, or —$(CR_5R_5)_aO(CR_5R_5)_aCR_eR_eB_4$;

$B_4$ is phenyl substituted with zero, 1, or 2 $R_f$;
each $R_2$ is independently
(i) H;
(ii) $C_{1-6}$alkyl and/or $C_{3-6}$cycloalkyl, each substituted with zero, 1, 2, or 3 $R_e$; and/or
(iii) phenyl, naphthalenyl, and/or 1- to 2-ring heterocyclyl or heteroaryl having 1 to 3 heteroatoms independently selected from N, O, and/or S, wherein each of said phenyl, naphthalenyl, heterocyclyl, and heteroaryl is substituted with zero, 1, or 2 $R_f$; and/or
(iv) two geminal $R_7$ along with the nitrogen atom to which they are attached form a 4- to 7-membered heterocyclyl ring having zero or 1 additional heteroatom selected from N and O, wherein said 4- to 7-membered heterocyclyl ring is substituted with zero, 1, or 2 $R_e$;

each $R_8$ is independently H, F, and/or —$CH_3$;
each $R_e$ is independently:
(i) H, $C_{1-6}$alkyl, $C_{2-6}$alkenyl, $C_{2-6}$alkynyl, F, Cl, $C_{1-6}$alkoxy, $C_{1-4}$fluoroalkyl, $C_{1-4}$chloroalkyl, —CN, —OH, —$C(O)ONR_3R_3$, —$NR_3R_3$, —$S(O)_mR_3$, —$(CR_2R_2)_aC(O)NR_3R_3$, and/or $C_{3-6}$cycloalkyl;
(ii) aryl, heteroaryl, heterocyclyl, —$(CH_2)_{1-2}$-(aryl), —O(aryl), —O(heteroaryl), and/or —O(heterocyclyl), wherein each of said aryl, heteroaryl, and heterocyclyl has 1- or 2-rings, each of said heteroaryl and heterocyclyl have 1 to 3 heteroatoms independently selected from N, O, and/or S, and each of said aryl, heteroaryl, and heterocyclyl is substituted with zero, 1, or 2 $R_f$; and/or
(iii) two geminal $R_e$ along with the carbon atom to which they are attached form a $C_{3-6}$spirocycloalkyl ring; and each $R_f$ is independently F, Cl, —CN, $C_{1-3}$alkyl, $C_{1-3}$alkoxy, phenoxy, $C_{1-3}$fluoroalkyl, $C_{1-3}$fluoroalkoxy, $C_{3-6}$cycloalkyl, alkoxyalkyl, and/or fluoroalkoxyalkyl.

One embodiment provides compounds of Formula (I) or stereoisomers, salts, or prodrugs thereof, wherein $X_1$ is C-$G_2$, one of $X_2$ and $X_3$ is N, and the other of $X_2$ and $X_3$ is O or S. Compounds of this embodiment have the structure represented by Formula (II):

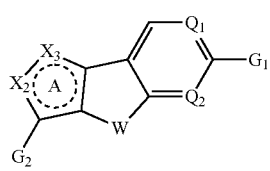

(II)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_1$ is C-$G_2$, $X_2$ is N, and $X_3$ is O or S. Compounds of this embodiment have the structure represented by Formula (IIa):

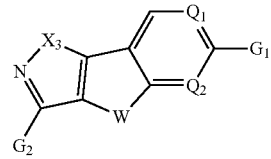

(IIa)

wherein W, $Q_1$, $Q_2$, $G_1$, and $G_2$ are defined in the first aspect of the invention. This embodiment includes compounds in which $X_3$ is O, having the structure represented by Formula (IIb):

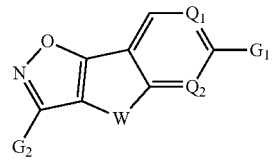

(IIb)

wherein W, $Q_1$, $Q_2$, $G_1$, and $G_2$ are defined in the first aspect of the invention. This embodiment also includes compounds in which $X_3$ is S, having the structure represented by Formula (IIc):

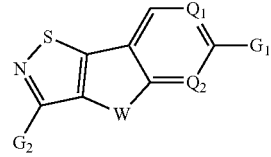

(IIc)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_1$ is C-$G_2$, $X_2$ is O or S, and $X_3$ is N. Compounds of this embodiment have the structure represented by Formula (IId):

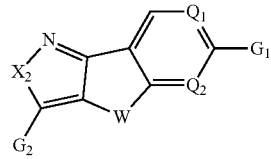

(IId)

wherein W, $Q_1$, $Q_2$, $G_1$, and $G_2$ are defined in the first aspect of the invention. This embodiment includes compounds in which $X_2$ is O, having the structure represented by Formula (IIe):

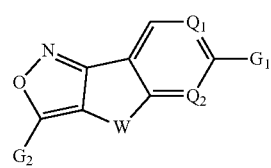

(IIe)

wherein W, $Q_1$, $Q_2$, $G_1$, and $G_2$ are defined in the first aspect of the invention. This embodiment also includes compounds in which $X_2$ is S, having the structure represented by Formula (IIf):

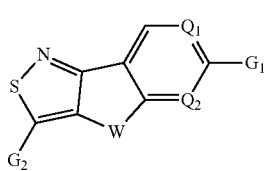

(IIf)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_2$ is C-$G_2$, one of $X_1$ and $X_3$ is N, and the other of $X_1$ and $X_3$ is O or S. Compounds of this embodiment have the structure represented by Formula (III):

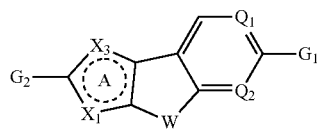

(III)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_1$ is N, $X_2$ is C-$G_2$, and $X_3$ is O or S. Compounds of this embodiment have the structure represented by Formula (IIIa):

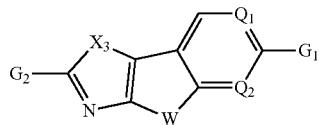

(IIIa)

wherein W, $Q_1$, $Q_2$, $G_1$, and $G_2$ are defined in the first aspect of the invention. This embodiment includes compounds in which $X_3$ is O, having the structure represented by Formula (IIIb):

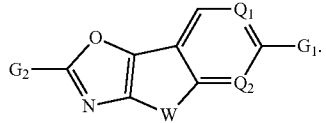

(IIIb)

This embodiment also includes compounds in which $X_3$ is S, having the structure represented by Formula (IIIc):

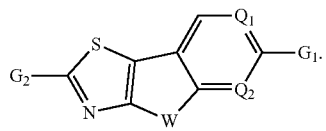

(IIIc)

One embodiment provides compounds of Formula (I) or stereoisomers, salts, or prodrugs thereof, wherein $X_1$ is O or S, $X_2$ is C-$G_2$, and $X_3$ is N. Compounds of this embodiment have the structure represented by Formula (IIId):

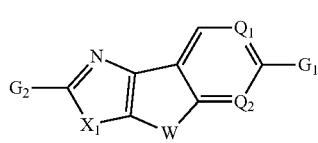

(IIId)

wherein W, $Q_1$, $Q_2$, $G_1$, and $G_2$ are defined in the first aspect of the invention. This embodiment includes compounds in which $X_1$ is O, having the structure represented by Formula (IIIe):

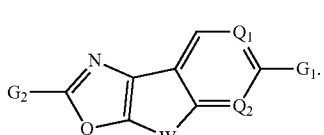

(IIIe)

This embodiment also includes compounds in which $X_1$ is S, having the structure represented by Formula (IIIf):

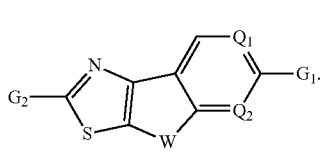

(IIIf)

One embodiment provides compounds of Formula (I) or stereoisomers, salts, or prodrugs thereof, wherein $X_1$ is C-$G_2$, one of $X_2$ and $X_3$ is N, and the other of $X_2$ and $X_3$ is NH or NCH$_3$.

One embodiment provides compounds of Formula (I) or stereoisomers, salts, or prodrugs thereof, wherein $X_1$ is C-$G_2$, $X_2$ is NH or NCH$_3$, and $X_3$ is N. Compounds of this embodiment have the structure represented by Formula (IVa):

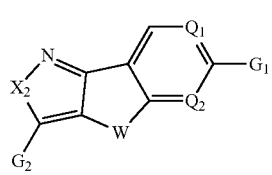

(IVa)

wherein W, $Q_1$, $Q_2$, $G_1$, and $G_2$ are defined in the first aspect of the invention. This embodiment includes compounds in which $X_2$ is NH, having the structure represented by Formula (IVb):

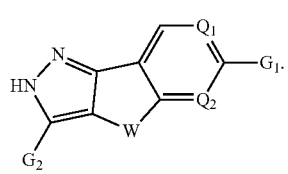

(IVb)

This embodiment also includes compounds in which $X_2$ is $NCH_3$, having the structure represented by Formula (IVc):

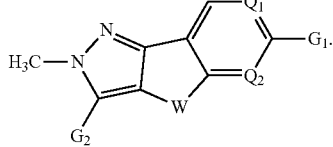
(IVc)

One embodiment provides compounds of Formula (I) or stereoisomers, salts, or prodrugs thereof, wherein $X_1$ is $C-G_2$, $X_2$ is N, and $X_3$ is NH or $NCH_3$. Compounds of this embodiment have the structure represented by Formula (IVd):

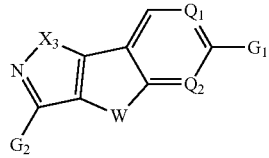
(IVd)

wherein W, $Q_1$, $Q_2$, $G_1$, and $G_2$ are defined in the first aspect of the invention. This embodiment includes compounds in which $X_3$ is NH, having the structure represented by Formula (IVe):

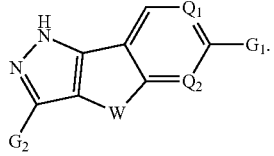
(IVe)

This embodiment also includes compounds in which $X_3$ is $NCH_3$, having the structure represented by Formula (IVf):

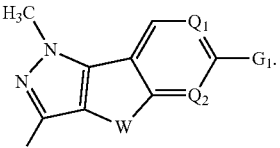
(IVf)

One embodiment provides compounds of Formula (I) or stereoisomers, salts, or prodrugs thereof, wherein one of $X_1$ and $X_2$ is $N-G_2$; the other of $X_1$ and $X_2$ is N or $CR_1$; and $X_3$ is N or $CR_1$, provided that zero or one of $X_1$, $X_2$ and $X_3$ is $CR_1$.

One embodiment provides compounds of Formula (I) or stereoisomers, salts, or prodrugs thereof, wherein $X_1$ is $N-G_2$, $X_2$ is N or $CR_1$, and $X_3$ is N or $CR_1$, provided that zero or one of $X_2$ and $X_3$ is $CR_1$. Compounds of this embodiment have the structure represented by Formula (V):

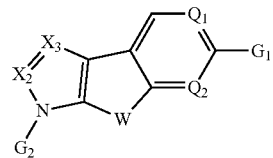
(V)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_1$ is $N-G_2$, $X_2$ is N, and $X_3$ is N or $CR_1$. Compounds of this embodiment have the structure represented by Formula (Va):

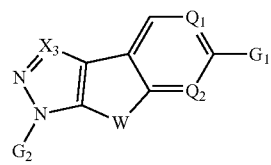
(Va)

wherein W, $Q_1$, $Q_2$, $G_1$, and $G_2$ are defined in the first aspect of the invention. This embodiment includes compounds in which $X_3$ is N, having the structure represented by Formula (Vb):

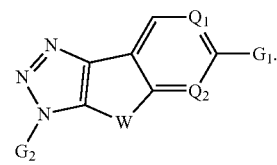
(Vb)

This embodiment also includes compounds in which $X_3$ is $CR_1$, having the structure represented by Formula (Vc):

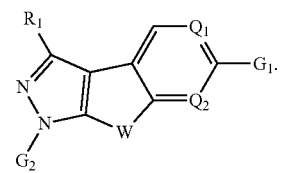
(Vc)

One embodiment provides compounds of Formula (I) or stereoisomers, salts, or prodrugs thereof, wherein $X_1$ is $N-G_2$, $X_2$ is $CR_1$, and $X_3$ is N. Compounds of this embodiment have the structure represented by Formula (Vd):

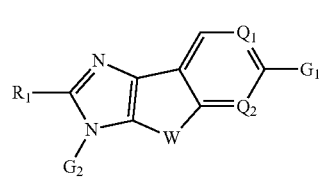
(Vd)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_1$ is N or $CR_1$, $X_2$ is N-$G_2$, and $X_3$ is N or $CR_1$, provided that zero or one of $X_1$ and $X_3$ is $CR_1$. Compounds of this embodiment have the structure represented by Formula (VI):

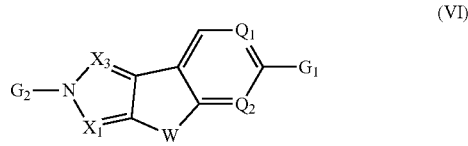

(VI)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein $X_1$ is N; $X_2$ is N-$G_2$; and $X_3$ is N or $CR_1$. Compounds of this embodiment have the structure represented by Formula (VIa):

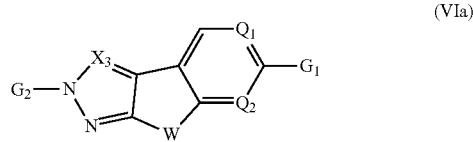

(VIa)

wherein W, $Q_1$, $Q_2$, $G_1$, and $G_2$ are defined in the first aspect of the invention. This embodiment includes compounds in which $X_3$ is N, having the structure represented by Formula (VIb):

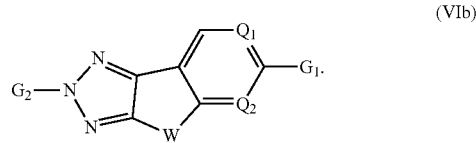

(VIb)

This embodiment also includes compounds in which $X_3$ is $CR_1$, having the structure represented by Formula (VIc):

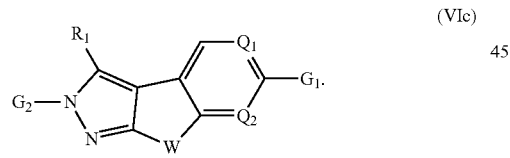

(VIc)

One embodiment provides compounds of Formula (I) or stereoisomers, salts, or prodrugs thereof, wherein $X_1$ is $CR_1$; $X_2$ is N-$G_2$; and $X_3$ is N. Compounds of this embodiment have the structure represented by Formula (VId):

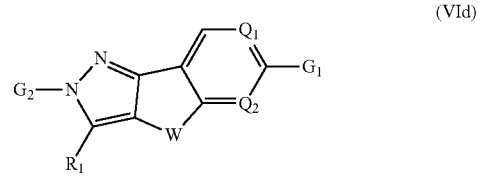

(VId)

wherein W, $Q_1$, $Q_2$, $G_1$, and $G_2$ are defined in the first aspect of the invention.

One embodiment provides compounds of Formula (I) or stereoisomers, salts, or prodrugs thereof, wherein one of $X_1$ and $X_2$ is C-$G_2$, the other of $X_1$ and $X_2$ is N, O, or S, and $X_3$ is N, O, or S, provided that only one of $X_1$, $X_2$, and $X_3$ is N, wherein W, $Q_1$, $Q_2$, $G_1$, and $G_2$ are defined in the first aspect of the invention. Compounds of this embodiment include the compounds of Formula (II) and Formula (III), such as, the compounds of Formula (IIb), Formula (IIc), Formula (IIe), Formula (IIf), Formula (IIIb), Formula (IIIc), Formula (IIIe), and Formula (IIIf).

One embodiment provides compounds of Formula (I) or stereoisomers, salts, or prodrugs thereof, wherein one of $X_1$ and $X_2$ is N-$G_2$, the other of $X_1$ and $X_2$ is N or C—$R_1$, and $X_3$ is N or C—$R_1$, provided that zero or one of $X_1$, $X_2$, and $X_3$ is N or C—$R_1$, wherein W, $Q_1$, $Q_2$, $G_1$, and $G_2$ are defined in the first aspect of the invention. Compounds of this embodiment include the compounds of Formula (V) and Formula (VI), such as, the compounds of Formula (Vb), Formula (Vc), Formula (Vd), Formula (VIb), Formula (VIc), and Formula (VId).

One embodiment provides compounds of Formula (I) or stereoisomers, salts, or prodrugs thereof, wherein $Q_1$ is $CR_5$ and $Q_2$ is $CR_5$. Compounds of this embodiment have the structure represented by Formula (Ia):

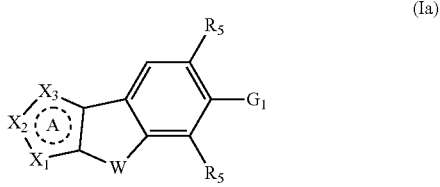

(Ia)

wherein $X_1$, $X_2$, $X_3$, $R_5$, W, and $G_1$ are defined in the first aspect of the invention.

One embodiment provides compounds of Formula (I) or stereoisomers, salts, or prodrugs thereof, wherein $Q_1$ is $CR_5$ and $Q_2$ is N and/or $CR_5$. Compounds of this embodiment have the structure represented by Formula (Ib):

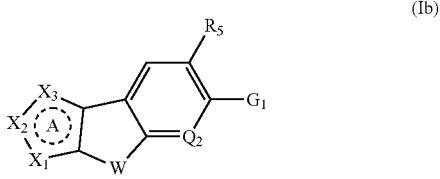

(Ib)

wherein $X_1$, $X_2$, $X_3$, $R_5$, W, and $G_1$ are defined in the first aspect of the invention. This embodiment includes compounds in which $Q_2$ is N, having the structure represented by Formula (Ic):

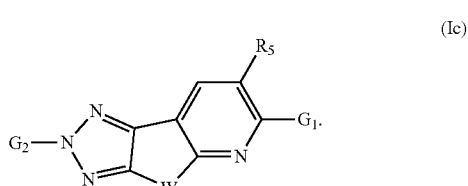

(Ic)

This embodiment also includes compounds in which $Q_1$ is $CR_5$, having the structure represented by Formula (Ia).

One embodiment provides compounds of Formula (I) or stereoisomers, salts, or prodrugs thereof, wherein $Q_2$ is $CR_5$ and $Q_1$ is N and/or $CR_5$. Compounds of this embodiment have the structure represented by Formula (Id):

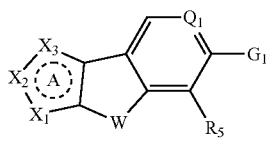

(Id)

wherein $X_1$, $X_2$, $X_3$, $R_5$, W, and $G_1$ are defined in the first aspect of the invention. This embodiment includes compounds in which $Q_1$ is N, having the structure represented by Formula (Ie):

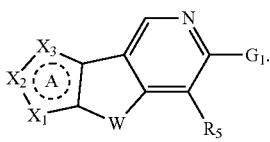

(Ie)

This embodiment also includes compounds in which $Q_2$ is $CR_5$, having the structure represented by Formula (Ia).

One embodiment provides compounds of Formula (I) or stereoisomers, salts, or prodrugs thereof, wherein W is —$(CR_2R_2)_n$— and n is 1, 2, or 3. Compounds of this embodiment have structures represented by Formula (VIIa) to (VIIc):

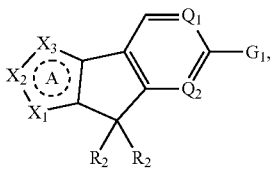

(VIIa)

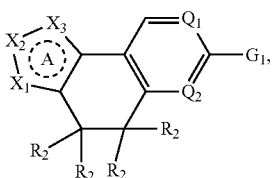

(VIIb)

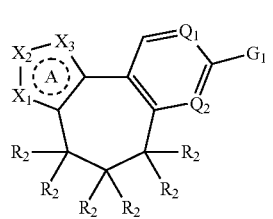

(VIIc)

wherein $X_1$, $X_2$, $X_3$, $Q_1$, $Q_2$, $R_2$, and $G_1$ are defined in the first aspect of the invention. Examples include compounds in which W is —$CH_2$—, —$CH_2CH_2$—, —$CH_2C(CH_3)_2$—, or —$CH_2CF_2$—. Other examples include compounds in which each $R_2$ is independently H and/or —$CH_3$.

One embodiment provides compounds of Formula (I) or stereoisomers, salts, or prodrugs thereof, wherein W is —O—, —$(CR_2R_2)_mO$—, —$O(CR_2R_2)_m$—, or —$CR_2R_2OCR_2R_2$—, and m is 1 or 2. Compounds of this embodiment have structures represented Formula (VIIIa) to (VIIIf):

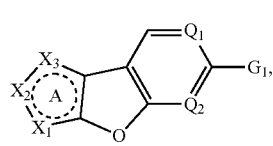

(VIIIa)

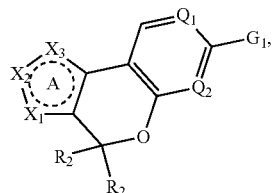

(VIIIb)

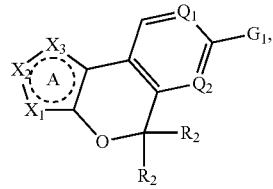

(VIIIc)

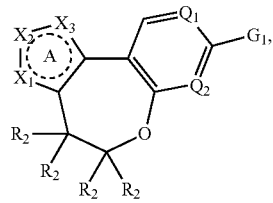

(VIIId)

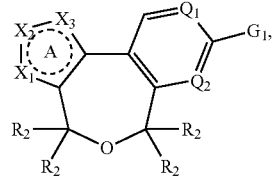

(VIIIe)

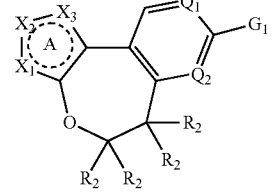

(VIIIf)

wherein $X_1$, $X_2$, $X_3$, $Q_1$, $Q_2$, $R_2$, and $G_1$ are defined in the first aspect of the invention. Examples include compounds in which W is —O—, —$CH_2O$—, —$OCH_2$—, or —$CH_2CH_2O$—. Other examples include compounds in which each $R_2$ is independently H and/or —$CH_3$.

One embodiment provides compounds of Formula (I) or stereoisomers, salts, or prodrugs thereof, wherein W is —$NR_3$—, —$(CR_2R_2)_mNR_3$—, —$NR_3(CR_2R_2)_m$—, or —$CR_2R_2NR_3CR_2R_2$—, and m is 1 or 2. Compounds of this embodiment have structures represented Formula (IXa) to (IXf):

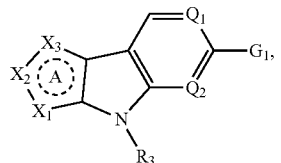
(IXa)

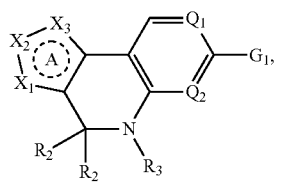
(IXb)

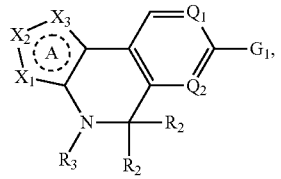
(IXc)

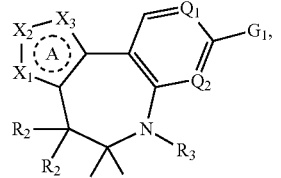
(IXd)

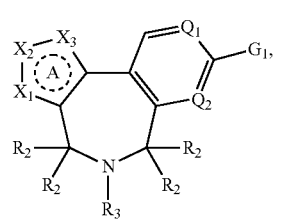
(IXe)

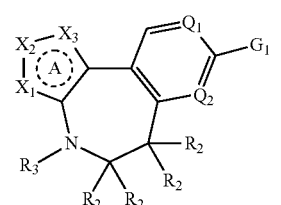
(IXf)

wherein $X_1$, $X_2$, $X_3$, $Q_1$, $Q_2$, $R_2$, $R_3$, and $G_1$ are defined in the first aspect of the invention. Examples include compounds in which W is —CH$_2$N(CH$_3$)—.

One embodiment provides compounds of Formula (I) or stereoisomers, salts, or prodrugs thereof, wherein —NR$_3$C(O)—, —C(O)NR$_3$—, —CR$_2$R$_2$NR$_3$C(O)—, —CR$_2$R$_2$C(O)NR$_3$—, —NR$_3$C(O)CR$_2$R$_2$—, or —C(O)NR$_3$CR$_2$R$_2$—. Compounds of this embodiment have structures represented Formula (Xa) to (Xf):

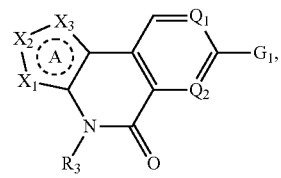
(Xa)

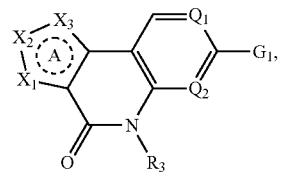
(Xb)

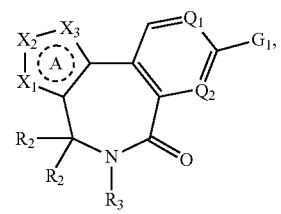
(Xc)

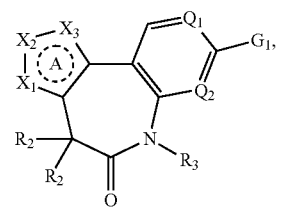
(Xd)

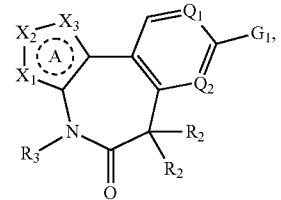
(Xe)

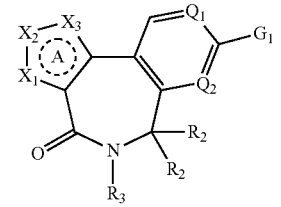
(Xf)

wherein $X_1$, $X_2$, $X_3$, $Q_1$, $Q_2$, $R_2$, $R_3$, and $G_1$ are defined in the first aspect of the invention.

One embodiment provides compounds of Formula (I) or stereoisomers, salts, or prodrugs thereof, wherein W is —CR$_4$=CR$_4$—, —CR$_2$R$_2$CR$_4$=CR$_4$—, or —CR$_4$=CR$_4$CR$_2$R$_2$—. Compounds of this embodiment have structures represented by Formula (XIa) to (XIc):

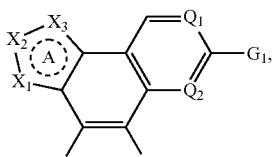

(XIa)

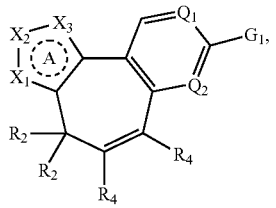

(XIb)

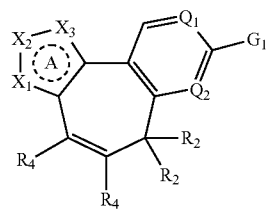

(XIc)

wherein $X_1$, $X_2$, $X_3$, $Q_1$, $Q_2$, $R_2$, and $G_1$ are defined in the first aspect of the invention. Examples include compounds in which W is —CH═CH—, —CH$_2$—CH═CH—, or —CH═CH—CH$_2$. Further examples include compounds in which each $R_4$ is H. Other examples include compounds in which each $R_4$ is H and each $R_2$ is H and/or —CH$_3$.

One embodiment provides compounds of Formula (I) or stereoisomers, salts, or prodrugs thereof, wherein:
$G_1$ is:
(i) —(CR$_c$R$_c$)$_a$OH, —(CR$_c$R$_c$)$_a$CN, —(CR$_c$R$_c$)$_a$C(O)OH, —(CR$_c$R$_c$)$_a$NR$_6$R$_6$, —(CR$_c$R$_c$)$_a$C(O)NR$_6$R$_6$, —(CR$_c$R$_c$)$_a$C(O)NR$_6$S(O)$_2$(C$_{1-4}$alkyl), —(CR$_c$R$_c$)$_a$NR$_6$C(O)(C$_{1-4}$alkyl), —(CR$_c$R$_c$)$_a$NR$_6$(CR$_c$R$_c$)$_a$COOH, or —(CR$_c$R$_c$)$_a$B$_1$;
(ii) C$_{1-12}$alkyl;
(iii) —(C$_{0-4}$alkylene)B$_2$; or
(iv) —(C$_{0-4}$alkylene)O(C$_{1-4}$alkyl);
wherein each of groups (ii) to (iv) is substituted with R$_a$ and zero to 7 R$_b$ as valence allows;
B$_1$ is a 4- to 6-membered heterocyclyl substituted with 1 to 6 R$_b$;
B$_2$ is 1- and 2-ring heterocyclyl, or 1- and 2-ring heteroaryl, with the proviso that B$_2$ is not oxazolidinone;
each R$_a$ is independently —(CR$_c$R$_c$)$_a$OH, —(CR$_c$R$_c$)$_a$CN, —(CR$_c$R$_c$)$_a$C(O)OH, —(C$_{0-4}$alkylene)NR$_6$R$_6$, —S(O)$_2$(C$_{1-4}$alkyl), —(CR$_c$R$_c$)$_a$C(O)NR$_6$R$_6$, —(CR$_c$R$_c$)$_a$C(O)NR$_6$S(O)$_2$(C$_{1-4}$alkyl), —(CR$_c$R$_c$)$_a$NR$_6$C(O)(C$_{1-4}$alkyl), —(CR$_c$R$_c$)$_a$NR$_6$(CR$_c$R$_c$)$_a$COOH, and/or —(CR$_c$R$_c$)$_a$OP(O)(OH)$_2$;
each R$_b$ is independently R$_a$, F, Cl, —CN, —OH, —NH$_2$, C$_{1-4}$alkyl, C$_{1-3}$fluoroalkyl, C$_{1-4}$alkoxy, C$_{1-3}$fluoroalkoxy, and/or C$_{3-5}$cycloalkyl, or two geminal R$_b$ along with the carbon atom to which they are attached form a C$_{3-6}$spirocyclic ring having zero, 1, or 2 heteroatoms independently selected from N and/or O, wherein said spirocyclic ring is substituted with zero to 3 substituents independently selected from C$_{1-4}$alkyl, C$_{1-3}$fluoroalkyl, C$_{3-6}$cycloalkyl, and/or ═O as valence allows;
each R$_c$ is independently H, F, —OH, —C(O)OH, —C(O)NR$_6$R$_6$, C$_{1-2}$alkyl, C$_{3-6}$cycloalkyl, C$_{4-6}$heterocycloalkyl, C$_{1-3}$hydroxyalkyl, —(C$_{1-3}$alkylene)OP(O)(OH)$_2$, and/or C$_{1-2}$fluoroalkyl, or two geminal R$_c$ along with the carbon atom to which they are attached form a C$_{3-6}$spirocyclic ring;
each R$_6$ is independently H, C$_{1-6}$alkyl, C$_{1-3}$fluoroalkyl, and/or C$_{3-6}$cycloalkyl, or two geminal R$_6$ groups together with the nitrogen atom to which they are attached form a 4- to 6-membered heterocyclyl ring having zero or one additional heteroatom selected from N and O, wherein said heterocyclyl ring is substituted with zero to 6 R$_d$;
each R$_d$ is independently C$_{1-4}$alkyl, C$_{1-3}$fluoroalkyl, and/or C$_{3-6}$cycloalkyl, or two geminal R$_d$ are ═O;
each a is independently zero, 1, 2, 3, 4, and/or 5.

One embodiment provides compounds of Formula (I) or stereoisomers, salts, or prodrugs thereof, wherein $G_1$ is:

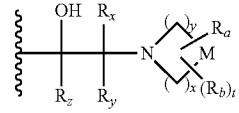

wherein:
x is 1 or 2;
y is 1 or 2;
M is CH$_2$ when (x+y) is 2, 3, or 4; or
M is O or NH when (x+y) is 4;
R$_a$ is —(CR$_c$R$_c$)$_a$OH, —(CR$_c$R$_d$)$_a$C(O)OH, —(CR$_c$R$_e$)$_a$C(O)NR$_6$R$_6$, —(CR$_c$R$_c$)$_a$tetrazolyl; or —(CR$_c$R$_c$)$_a$C(O)NR$_6$S(O)$_2$(C$_{1-4}$ alkyl);
each R$_b$ is independently F, Cl, —CN, C$_{1-4}$ alkyl, C$_{1-2}$fluoralkyl, —OH, C$_{1-3}$alkoxy, and/or —NH$_2$;
R$_x$ and R$_y$ are independently H and/or C$_{1-6}$ alkyl, or R$_x$ and R$_y$ together with the carbon atom to which they are attached, form a 3- to 6-membered ring containing zero or 1 heteroatom selected from O and N;
R$_z$ is H or C$_{1-4}$ alkyl; and
t is zero, 1, 2, 3, or 4. For example, suitable $G_1$ groups include:

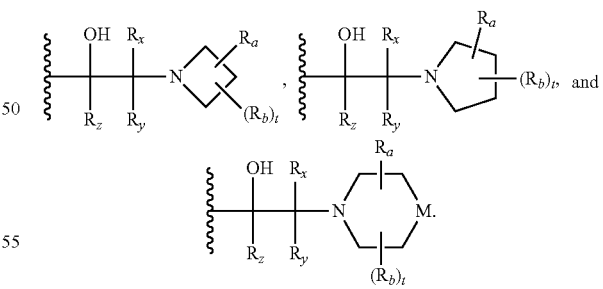

Other suitable $G_1$ groups include:

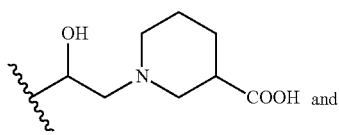

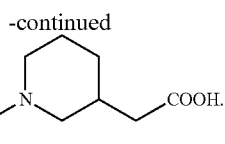

One embodiment provides compounds of Formula (I) or stereoisomers, salts, or prodrugs thereof, in which G₁ is:

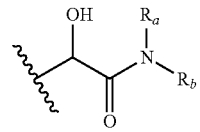

wherein:
R_a is —(CR_cR_c)_aOH, —(CR_cR_d)_aC(O)OH, —(CR_cR_c)_aC(O)NR₆R₆, —(CR_cR_c)_atetrazolyl; or —(CR_cR_c)_aC(O)NR₆S(O)₂(C_{1-4}alkyl); and
each R_b is independently F, Cl, —CN, C_{1-4} alkyl, C_{1-2}fluoralkyl, —OH, C_{1-3}alkoxy, and/or —NH₂.

One embodiment provides compounds of Formula (I) or stereoisomers, salts, or prodrugs thereof, wherein G₁ is —(CR_cR_c)_aB₁ wherein B₁ is a 4- to 6-membered heterocyclyl substituted with 1 to 6 R_b, and R_b, R_c, and a are defined in the first aspect of the invention. For example, compounds of this embodiment include G₁ groups in which B₁ is azetidinyl, pyrrolidinyl, or piperidinyl. Examples of suitable G₁ groups include:

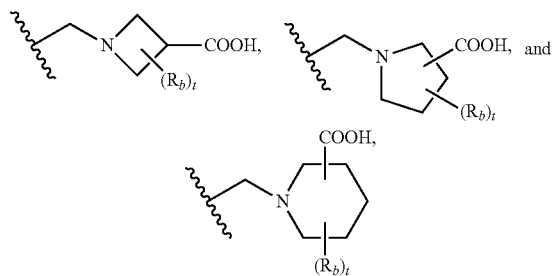

wherein t is zero, 1, 2, 3, or 4.

One embodiment provides compounds of Formula (I) or stereoisomers, salts, or prodrugs thereof, wherein G₁ is —(CR_cR_c)_aB₁ wherein B₁ is a 4- to 6-membered heterocyclyl substituted with 1 to 6 R_b, and R_b, R_c, and a are defined in the first aspect of the invention. For example, compounds of this embodiment include G₁ groups in which B₁ is azetidinyl substituted with 2 to 6 R_b, wherein two geminal R_b along with the carbon atom to which they are attached form a C_{3-6}spirocyclic ring having zero, 1, or 2 heteroatoms independently selected from N and/or O, wherein said spirocyclic ring is substituted with zero to 3 substituents independently selected from C_{1-4}alkyl, C_{1-3}fluoroalkyl, C_{3-6}cycloalkyl, and/or =O, as valence allows. One example of a suitable G₁ group is:

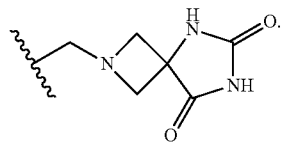 [SMILES: *CN1CC2(C1)NC(=O)NC2=O]

One embodiment provides compounds of Formula (I) or stereoisomers, salts, or prodrugs thereof, wherein G₂ is C_{1-6}alkyl or —NR₃R₃, wherein R₃ is defined in the first aspect of the invention.

One embodiment provides compounds of Formula (I) or stereoisomers, salts, or prodrugs thereof, wherein G₂ is phenyl or naphthyl, each substituted with zero, 1, 2, 3, or 4 R_e, and R_e is defined in the first aspect of the invention. For example, this embodiment includes compounds in which G₂ is phenyl independently substituted with zero to 4 substituents selected from C_{1-6}alkyl, C_{1-6}alkoxy, C_{1-4}-fluoroalkyl, and/or —CN. Other examples of G₂ include:

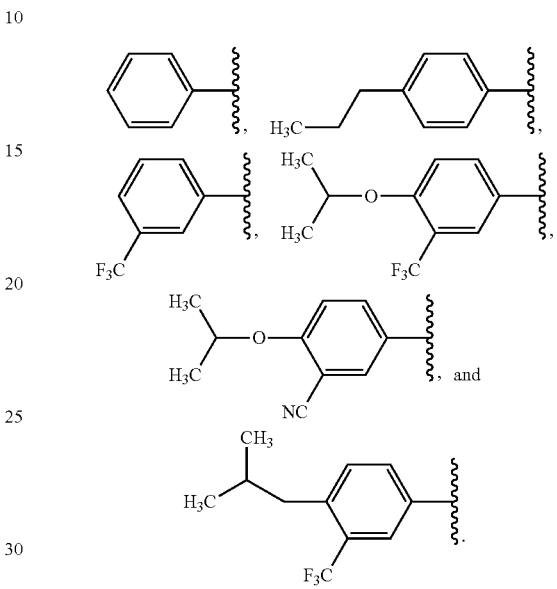

One embodiment provides compounds of Formula (I) or stereoisomers, salts, or prodrugs thereof, wherein G₂ is 5- to 10-membered heteroaryl substituted with zero, 1, 2, or 3 R_e; and R_e is defined in the first aspect of the invention. Examples of suitable heteroaryl groups for G₂ include, but are not limited to, pyrazolyl, imidazolyl, isoxazolyl, oxazolyl, triazolyl, oxadiazolyl, pyridinyl, pyridazinyl, pyrimidinyl, pyrazinyl, indolyl, benzimidazolyl, indazolyl, benzotriazolyl, pyrrolopyridinyl, imidazopyridinyl, pyrazolopyridinyl, isoindolyl, indazolyl, purinyl, imidazopyridinyl, pyrazolopyridinyl, imidazopyrimidinyl, quinolinyl, isoquinolinyl, cinnolinyl, quinazolinyl, quinoxalinyl, and naphthyridinyl. Included in this embodiment are compounds in which G₂ is a 5-membered heteroaryl having one nitrogen atom and zero or one additional heteroatom selected from N, O, or S. Suitable G₂ groups include isoxazolyl, pyrazolyl, and isothiazolyl, each of which is substituted with zero, 1, or 2 substituents independently selected from —CN, butyl, propoxy, methyl cyclopropyl, —CF₃, phenyl, and/or chlorophenyl. For example, suitable G₂ groups include:

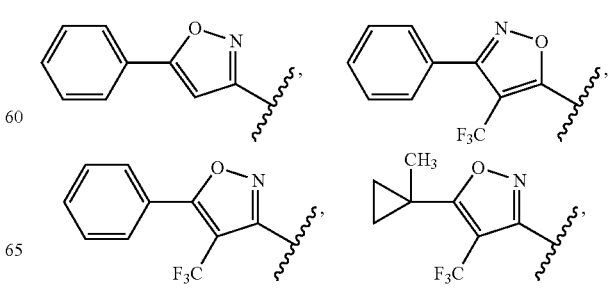

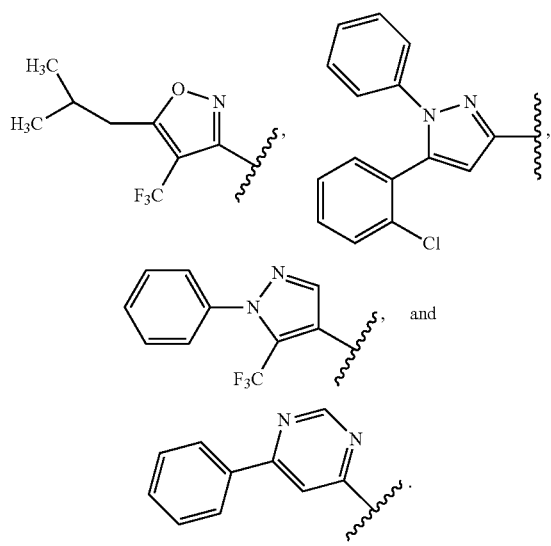

One embodiment provides compounds of Formula (I) or stereoisomers, salts, or prodrugs thereof, wherein $G_2$ is —$(CR_5R_5)_aCR_eR_c(C_{1-3}$alkyl), —$(CR_5R_5)_aCR_eR_eB_4$, —$NR_3(CR_5R_5)_aB_4$, —$(CR_5R_5)_a$—$CR_8$=$CR_8$—$(CR_5R_5)_a$ $CR_eR_eB_4$, or —$(CR_5R_5)_aO(CR_5R_5)_aCR_eR_eB_4$; and $B_4$, $R_3$, $R_5$, $R_8$, $R_e$, and a are defined in the first aspect of the invention. Included in this embodiment are compounds in which $G_2$ is —$(CR_5R_5)_aCR_eR_eB_4$ or —$(CR_5R_5)_aO(CR_5R_5)_aCR_eR_eB_4$, and each a is independently 1, 2, and/or 3. For example, suitable $G_2$ groups include, but are not limited to, —$(CH_2)_a$ $CR_eR_eB_4$ or —$(CH_2)_aO(CH_2)_aCR_eR_eB_4$ wherein each $R_2$ is independently H and/or $C_{1-2}$alkyl; or two geminal $R_e$ along with the carbon atom to which they are attached form a $C_{5-6}$spirocycloalkyl ring. Examples of $G_2$ include:

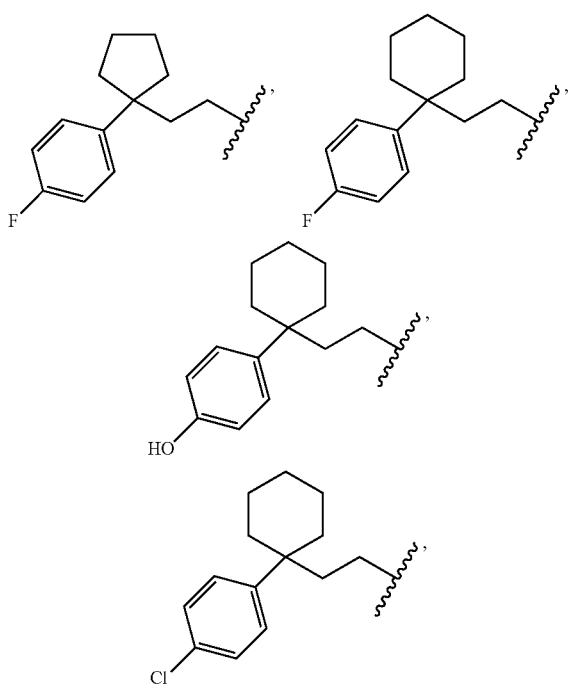

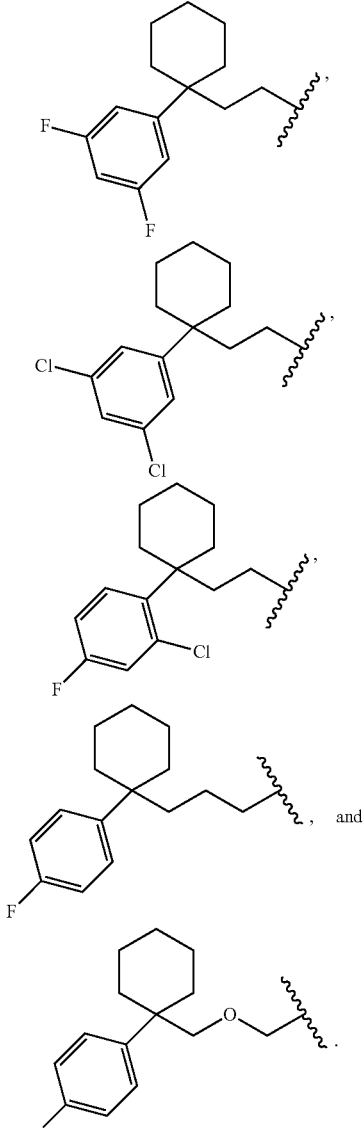

One embodiment provides compounds of Formula (I) or stereoisomers, salts, or prodrugs thereof, wherein $G_2$ is $C_{3-6}$cycloalkyl substituted with zero, 1, or 2 $R_e$, and $R_e$ is defined in the first aspect of the invention. Included in this embodiment are compounds in which $G_2$ is $C_{3-6}$cycloalkyl substituted with phenyl or heteroaryl, wherein the phenyl or heteroaryl group is substituted with zero, 1, or 2 substituents independently selected from F, Cl, —CN, $C_{1-3}$alkyl, $C_{1-3}$alkoxy, $C_{1-3}$fluoroalkyl, $C_{1-3}$fluoroalkoxy, $C_{3-6}$cycloalkyl, alkoxyalkyl, and/or fluoroalkoxyalkyl. Examples of $G_2$ include cyclohexyl substituted with phenyl, wherein the phenyl group is substituted with zero, 1, or 2 substituents independently selected from F, Cl, —CN, methyl, —$OCH_3$, —$CF_3$, and/or —$OCF_3$. One example of $G_2$ is:

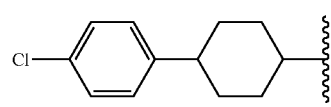

One embodiment provides compounds of Formula (I) or stereoisomers, salts, or prodrugs thereof, wherein $G_2$ is —(CR$_5$R$_5$)$_a$C(O)NR$_7$R$_7$, and R$_5$, R$_7$, and a are defined in the first aspect of the invention. Included in this embodiment are compounds in which G$_2$ is —C(O)NHR$_7$. Also included in this embodiment are compounds in which G$_2$ is —C(O)NHR$_7$ wherein R$_7$ is C$_{1-6}$alkyl and/or C$_{3-6}$cycloalkyl, each substituted with zero, 1, 2, or 3 R$_e$; or phenyl, naphthalenyl, and/or 1- to 2-ring heterocyclyl or heteroaryl having 1 to 3 heteroatoms independently selected from N, O, and/or S, wherein each of said phenyl, naphthalenyl, heterocyclyl, and heteroaryl is substituted with zero, 1, or 2 R$_f$. Examples of G$_2$ include:

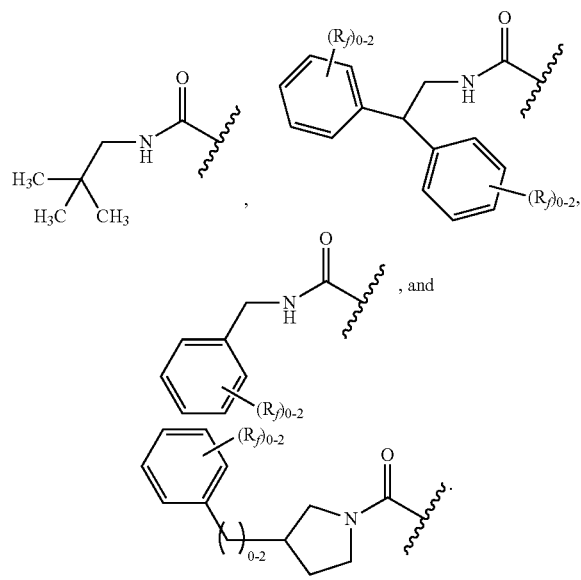

One embodiment provides compounds of Formula (I) or stereoisomers, salts, or prodrugs thereof, wherein R$_1$ is H, F, Cl, —CN, —OH, C$_{1-3}$alkyl, C$_{1-3}$alkoxy, C$_{1-2}$fluoroalkyl, C$_{1-2}$fluoroalkoxy, or C$_{3-6}$cycloalkyl. Included in this embodiment are compounds in which R$_1$ is H, F, —CN, —OH, methyl, —OCH$_3$, and —OCF$_3$. Also included are compounds in which R$_1$ is H.

One embodiment provides compounds of Formula (I) or stereoisomers, salts, or prodrugs thereof, wherein each R$_2$ is independently H, F, Cl, —CN, —OH, C$_{1-3}$alkyl, C$_{1-4}$alkoxy, C$_{1-2}$fluoroalkyl, C$_{1-2}$fluoroalkoxy, and/or C$_{3-4}$cycloalkyl. Included in this embodiment are compounds in which each R$_2$ is independently H, F, —CN, —OH, methyl, —OCH$_3$, —CF$_3$, and/or —OCF$_3$. Also included are compounds in which each R$_2$ is H.

One embodiment provides compounds of Formula (I) or stereoisomers, salts, or prodrugs thereof, wherein two geminal R$_2$ groups together with the carbon atom to which they are attached form a C$_{3-6}$spirocycloalkyl ring.

One embodiment provides compounds of Formula (I) or stereoisomers, salts, or prodrugs thereof, wherein each R$_3$ is independently H, C$_{1-3}$alkyl, C$_{2-3}$fluoroalkyl, and/or C$_{3-6}$cycloalkyl. Included in this embodiment are compounds in which each R$_3$ is independently H and/or methyl. Also included are compounds in which each R$_3$ is H.

One embodiment provides compounds of Formula (I) or stereoisomers, salts, or prodrugs thereof, wherein each R$_4$ is H, F, —CN, C$_{1-2}$alkyl, C$_{1-2}$alkoxy, C$_{1-2}$fluoroalkyl, C$_{1-2}$fluoroalkoxy, and/or C$_{3-4}$cycloalkyl. Included in this embodiment are compounds in which each R$_4$ is independently H, F,
—CN, —CH$_3$, —OCH$_3$, —CF$_3$, —OCF$_3$, and/or C$_{3-4}$cycloalkyl. Also included are compounds in which each R$_4$ is H.

One embodiment provides compounds of Formula (I) or stereoisomers, salts, or prodrugs thereof, wherein each R$_5$ is independently H, F, Cl, Br, C$_{1-3}$alkyl, C$_{1-3}$alkoxy, C$_{1-2}$fluoroalkyl, C$_{1-2}$fluoroalkoxy, and/or cyclopropyl. Included in this embodiment are compounds in which each R$_4$ is independently H, F, Cl, —CH$_3$, —OCH$_3$, —CF$_3$, —OCF$_3$, and/or cyclopropyl. Also included in this embodiment are compounds in which each R$_5$ is H.

One embodiment provides compounds of Formula (I) or stereoisomers, salts, or prodrugs thereof, wherein each R$_6$ is independently H, C$_{1-6}$alkyl, C$_{1-3}$fluoroalkyl, and/or C$_{3-6}$cycloalkyl. Included in this embodiment are compounds in which each R$_6$ is independently H, C$_{1-4}$alkyl, —CF$_3$, and/or C$_{3-6}$cycloalkyl. Also included are compounds in which each R$_6$ is independently H, C$_{1-2}$alkyl, —CF$_3$, and/or C$_{5-6}$cycloalkyl.

One embodiment provides compounds of Formula (I) or stereoisomers, salts, or prodrugs thereof, wherein two geminal R$_6$ groups together with the nitrogen atom to which they are attached form a 4- to 6-membered heterocyclyl ring having zero or one additional heteroatom selected from N and O, wherein said heterocyclyl ring is substituted with zero to 6 R$_d$, and R$_d$ is defined in the first aspect of the invention. Examples of suitable heterocyclyl rings include, but are not limited to, azetidinyl, pyrrolidinyl, piperidinyl, morpholinyl, and piperazinyl.

One embodiment provides compounds of Formula (I) or stereoisomers, salts, or prodrugs thereof, wherein each R$_7$ is independently:
(i) H;
(ii) C$_{1-6}$alkyl and/or C$_{3-6}$cycloalkyl, each substituted with zero, 1, 2, or 3 R$_e$; and/or
(iii) phenyl, naphthalenyl, and/or 1- to 2-ring heterocyclyl or heteroaryl having 1 to 3 heteroatoms independently selected from N, O, and/or S, wherein each of said phenyl, naphthalenyl, heterocyclyl, and heteroaryl is substituted with zero, 1, or 2 R$_f$;
wherein R$_e$ and R$_f$ are defined in the first aspect of the invention. Included in this embodiment are compounds in which each R$_7$ is independently H, C$_{1-4}$alkyl, C$_{3-6}$cycloalkyl, phenyl, naphthalenyl, azetidinyl, pyrrolidinyl, piperidinyl, morpholinyl, and/or piperazinyl.

One embodiment provides compounds of Formula (I) or stereoisomers, salts, or prodrugs thereof, wherein two geminal R$_7$ along with the nitrogen atom to which they are attached form a 4- to 7-membered heterocyclyl ring having zero or 1 additional heteroatom selected from N and O, wherein said 4- to 7-membered heterocyclyl ring is substituted with zero, 1, or 2 R$_e$, wherein R$_e$ is defined in the first aspect of the invention. Examples of suitable heterocyclyl rings include, but are not limited to, azetidinyl, pyrrolidinyl, piperidinyl, morpholinyl, and piperazinyl.

One embodiment provides compounds of Formula (I) or stereoisomers, salts, or prodrugs thereof, wherein each R$_8$ is independently H and/or —CH$_3$.

One embodiment provides compounds of Formula (I) or stereoisomers, salts, or prodrugs thereof, wherein:
(i) X$_1$ is C-G$_2$, one of X$_2$ and X$_3$ is N, and the other of X$_2$ and X$_3$ is O or S;
(ii) X$_2$ is C-G$_2$, one of X$_1$ and X$_3$ is N, and the other of X$_1$ and X$_3$ is O;
(iii) X$_1$ is C-G$_2$, one of X$_2$ and X$_3$ is N, and the other of X$_2$ and X$_3$ is NH or NCH$_3$; or
(iv) X$_1$ is N-G$_2$, X$_2$ is N, and X$_3$ is CH;

$Q_1$ is CH, C(CH$_3$), or CF;
$Q_2$ is CH or N;
W is —CH$_2$—, —CH$_2$CH$_2$—, —CH$_2$C(CH$_3$)$_2$—, —CH$_2$CF$_2$—, —CH=CH—, —CH$_2$N(CH$_3$)—, —CH$_2$O—, or —CH$_2$CH$_2$O—;
$G_1$ is —OH, —CH$_2$OH, —CH(OH)CH$_2$OH, —(CH$_2$)$_{0-2}$COOH, —CH(OH)(CH$_2$)$_{0-2}$COOH, —CH$_2$NH(CH$_2$)$_{1-2}$OH, —CH$_2$NR$_g$(CH$_2$)$_{1-2}$COOH, —CH$_2$NR$_g$(CH$_2$)$_{1-2}$C(O)NH$_2$, —CH$_2$NR$_g$(CH$_2$)$_{1-2}$OP(O)(OH)$_2$, —OCH$_2$CH(OH)CH$_2$OH, —(CH$_2$)$_{0-2}$C(NH$_2$)(CH$_3$)CH$_2$OH, —(CH$_2$)$_{0-2}$CR$_g$(NH$_2$)C(O)OH, —(CH$_2$)$_{0-2}$C(NH$_2$)(CH$_3$)(CH$_2$)$_{1-2}$OP(O)(OH)$_2$, —CH$_2$CH$_2$C(NH$_2$)(CH$_2$OH)$_2$, —CH$_2$NHCH(CH$_2$OH)$_2$, —CH$_2$N(CH$_2$CH$_2$OH)$_2$, —CH$_2$NHCH$_2$CH(OH)CH$_2$OH, —CH(OH)C(O)NHCH$_2$CN, —CH(OH)C(O)NHCH$_2$CH$_2$S(O)$_2$CH$_3$, —CR$_g$(OH)C(O)NHCH$_2$CH$_2$OH, —CH$_2$(hydroxy pyrrolidinyl), —CH$_2$(hydroxymethyl pyrrolidinyl),

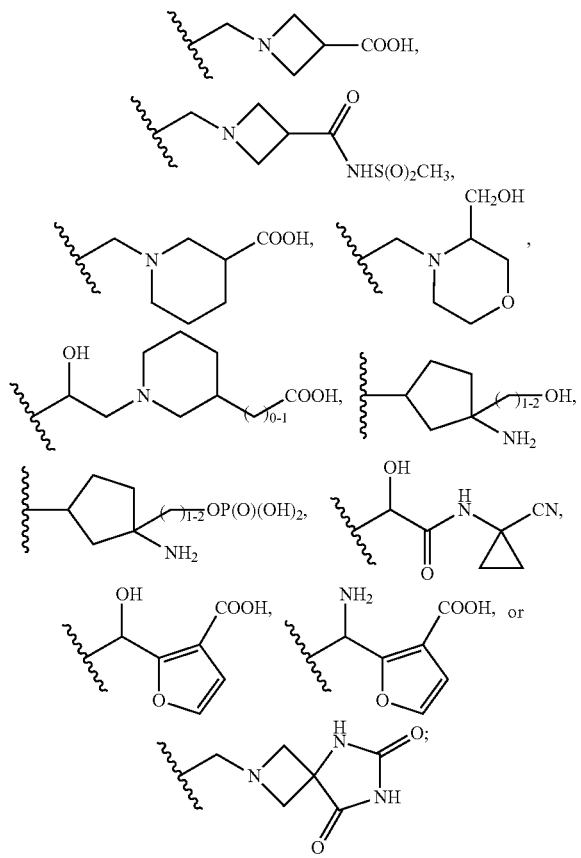

$G_2$ is:
(i) pentyl or —NH$_2$;
(ii) phenyl substituted with one or two substituents independently selected from propyl, butyl, —CN, —CF$_3$, cyclohexyl, —OCH$_2$CH$_3$, and/or —OCH(CH$_3$)$_2$;
(iii) pyrazolyl, isoxazolyl, isothiazolyl, or pyrimidinyl substituted with one or two substituents independently selected from —CF$_3$, —CN, butyl, methyl cyclopropyl, cyclohexyl, phenyl, chlorophenyl, pyridinyl, and/or fluoropyridinyl;
(iv) cyclohexyl substituted with chlorophenyl;
(v) —NHC(O)—(CH$_2$)$_{0-2}$-(phenyl) or —NHC(O)(pentyl);
(vi) —C(O)NHCH$_2$C(CH$_3$)$_3$, —C(O)NR$_g$—(CHR$_g$)$_{0-3}$-A$_1$, —C(O)NR$_g$—CH$_2$C(R$_g$)(A$_1$)(A$_1$), or —C(O)NHCH$_2$(tetrahydronaphthalenyl),
wherein A$_1$ is phenyl substituted with zero to 2 substituents independently selected from Cl, —CH$_3$, —OCH$_3$, —OCH$_2$CH$_3$, —OCH(CH$_3$)$_2$, and/or phenoxy;
(vii)

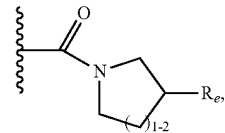

wherein R$_e$ is naphthalenyl or —(CH$_2$)$_{0-2}$(phenyl) and said phenyl is substituted with zero to 1 substituents selected from F, Cl, or OCH$_3$; or
(viii) —(CR$_5$R$_5$)$_a$CR$_e$R$_e$B$_4$ or —CH=CH—CR$_e$R$_e$B$_4$, wherein B$_4$ is phenyl substituted with zero to 2 substituents independently selected from F, Cl, —OH, and/or butyl; and each R$_e$ is independently H and/or —CH$_3$, or two geminal R$_e$ along with the carbon atom to which they are attached form a C$_{4-6}$spirocycloalkyl ring; and each R$_g$ is independently H and/or —CH$_3$.

One embodiment provides a compound of Formula (I) or stereoisomers, salts, or prodrugs thereof, wherein said compound is selected from: 1-((5,5-dimethyl-3-(3-phenyl-4-(trifluoromethyl)isoxazol-5-yl)-4,5-dihydronaphtho[1,2-c]isoxazol-7-yl)methyl)azetidine-3-carboxylic acid (1); 1-((3-(4-propylphenyl)-4H-chromeno[4,3-c]isoxazol-7-yl)methyl)azetidine-3-carboxylic acid, trifluoroacetic acid salt (2); 1-((3-(4-propylphenyl)-4H-chromeno[3,4-d]isoxazol-7-yl)methyl)azetidine-3-carboxylic acid, trifluoroacetic acid salt (3); 1-((3-(5-(1-methylcyclopropyl)-4-(trifluoromethyl)isoxazol-3-yl)-4,5-dihydronaphtho-[1,2-c]isoxazol-7-yl)methyl)azetidine-3-carboxylic acid (4); 1-((3-(5-isobutyl-4-(trifluoromethyl)isoxazol-3-yl)-4,5-dihydronaphtho[1,2-c]isoxazol-7-yl)methyl)azetidine-3-carboxylic acid (5); 1-((3-(5-phenyl-4-(trifluoromethyl)isoxazol-3-yl)-4,5-dihydronaphtho[1,2-c]isoxazol-7-yl)methyl)azetidine-3-carboxylic acid (6); 1-((3-(3-phenyl-4-(trifluoromethyl)isoxazol-5-yl)-4,5-dihydronaphtho[1,2-c]isoxazol-7-yl)methyl)azetidine-3-carboxylic acid (7); 3-(3-phenyl-4-(trifluoromethyl)isoxazol-5-yl)-4,5-dihydronaphtho[1,2-c]isoxazol-7-ol (8); 3-(4-propylphenyl)-4,5-dihydronaphtho[1,2-c]isoxazol-7-ol (9); 3-(4-propylphenyl)-4H-indeno[1,2-c]isoxazol-6-ol (10); 1-(3-(4-propylphenyl)-4,5-dihydronaphtho[1,2-c]isoxazol-7-yl)methyl)azetidine-3-carboxylic acid (11); (R)-3-(3-(4-propylphenyl)-4,5-dihydronaphtho[1,2-c]isoxazol-7-yloxy)propane-1,2-diol (12); (3S)-1-(2-hydroxy-2-(3-(5-phenyl-4-(trifluoromethyl)isoxazol-3-yl)-4,5-dihydronaphtho[1,2-c]isoxazol-7-yl)ethyl)piperidine-3-carboxylic acid (13); 1-((3-(4-isopropoxy-3-(trifluoromethyl)phenyl)-4,5-dihydronaphtho[1,2-c]isoxazol-7-yl)methyl)azetidine-3-carboxylic acid (14); 1-((3-(3-cyano-4-isopropoxyphenyl)-4,5-dihydronaphtho[1,2-c]isoxazol-7-yl)methyl)azetidine-3-carboxylic acid (15); 3-((3-(3-cyano-4-isopropoxyphenyl)-4,5-dihydronaphtho[1,2-c]isoxazol-7-yl)methylamine)propanoic acid (16); 1-((3-(4-isopropoxy-2-(trifluoromethyl)phenyl)-4,5-dihydronaphtho[1,2-c]isoxazol-7-yl)methyl)azetidine-3-carboxylic acid (17); 2-((3-(5-phenyl-4-(trifluoromethyl)isoxazol-3-yl)-4,5-dihydronaphtho[1,2-c]isoxazol-7-yl)methyl)-2,5,7-triazaspiro[3.4]octane-6,8-dione (18); 2-((3R)-1-(2-hydroxy-2-(3-(5-phenyl-4-(trifluoromethyl)isoxazol-3-yl)-4,5- dihydronaphtho[1,2-c]isoxazol-7-yl)ethyl)piperidin-3-yl) acetic acid (19); 1-((3-(4-propylphenyl)-4,5-dihydronaphtho[2,1-d]isoxazol-7-yl)methyl)azetidine-3-carboxylic acid (20); 3-(3-(3-cyano-4-isopropoxyphenyl)-4,5-dihydronaphtho[1,2-c]isoxazol-7-yl)propanoic acid (21); 1-((3-(3-phenyl-4-(trifluoromethyl)isoxazol-5-yl)-4,5-dihydro-2H-benzo[g]indazol-7-yl)methyl)azetidine-3-carboxylic acid (22); 1-((3-(4-isobutyl-3-(trifluoromethyl)phenyl)-4,5-dihydronaphtho[1,2-c]isoxazol-7-yl)methyl)azetidine-3-carboxylic acid (23); (3-(3-(trifluoromethyl)phenyl)-4,5-dihydronaphtho[1,2-c]isoxazol-7-yl)methanol (24); 1-((3-(3-(trifluoromethyl)phenyl)-4,5-dihydronaphtho[1,2-c]isoxazol-7-yl)methyl)azetidine-3-carboxylic acid (25); 1-((3-(2-(1-(4-fluorophenyl)cyclohexyl)ethyl)-4,5-dihydronaphtho[1,2-c]isoxazol-7-yl)methyl)azetidine-3-carboxylic acid (26); 1-((3-(4-(4-chlorophenyl)cyclohexyl)-4,5-dihydronaphtho[1,2-c]isoxazol-7-yl)methyl)azetidine-3-carboxylic acid (27); 1-((3-(2-(1-(3,5-dichlorophenyl)cyclohexyl)ethyl)-4,5-dihydronaphtho[1,2-c]isoxazol-7-yl)methyl)azetidine-3-carboxylic acid (28); 1-((3-(3-(4-chlorophenyl)-3-methylbutyl)-4,5-dihydronaphtho[1,2-c]isoxazol-7-yl)methyl)azetidine-3-carboxylic acid (29); 1-((3-(((1-(4-fluorophenyl)cyclohexyl)methoxy)methyl)-4,5-dihydronaphtho[1,2-c]isoxazol-7-yl)methyl)azetidine-3-carboxylic acid (30); 1-((3-(3-(1-(4-fluorophenyl)cyclohexyl)propyl)-4,5-dihydronaphtho[1,2-c]isoxazol-7-yl)methyl) azetidine-3-carboxylic acid (31); 3-(5-phenylisoxazol-3-yl)-4,5-dihydronaphtho[1,2-c]isoxazol-7-ol (32); 3-(5-(2-chlorophenyl)-1-phenyl-1H-pyrazol-3-yl)-4,5-dihydronaphtho[1,2-c]isoxazol-7-ol (33); 3-(6-phenylpyrimidin-4-yl)-4,5-dihydronaphtho[1,2-c]isoxazol-7-ol (34); 3-(2-(1-(4-hydroxyphenyl)cyclohexyl)ethyl)-4,5-dihydronaphtho[1,2-c]isoxazol-7-ol (35); 3-(2-(1-(2-chloro-4-fluorophenyl)cyclohexyl)ethyl)-4,5-dihydronaphtho[1,2-c]isoxazol-7-ol (36); 3-(2-(1-(3,5-difluorophenyl)cyclohexyl)ethyl)-4,5-dihydronaphtho[1,2-c]isoxazol-7-ol (37); 3-(2-(1-(3,5-dichlorophenyl)cyclohexyl)ethyl)-4,5-dihydronaphtho[1,2-c]isoxazol-7-ol (38); 3-(2-(1-(3fluorophenyl)cyclopentyl)ethyl)-4,5-dihydronaphtho[1,2-c]isoxazol-7-ol (39); (E)-3-(2-(1-(4-chlorophenyl)cyclohexyl)vinyl)-4,5-dihydronaphtho[1,2-c]isoxazol-7-ol (40); 3-(4-isobutylphenyl)-4,5-dihydronaphtho[1,2-c]isoxazol-7-ol (41); 1-((2-(2-(1-(4-fluorophenyl)cyclohexyl)ethyl)naphtho[1,2-d]oxazol-7-yl)methyl)azetidine-3-carboxylic acid (42); (S)-3-(2-(3-phenyl-4-(trifluoromethyl)isoxazol-5-yl)-4,5-dihydronaphtho[2,1-d]oxazol-7-yloxy)propane-1,2-diol (43); 1-((3-(3-phenyl-4-(trifluoromethyl)isoxazol-5-yl)-4,5-dihydronaphtho[2,1-d]isoxazol-7-yl)methyl)azetidine-3-carboxylic acid, TFA salt (44); 1-((3-(2,2-diphenylethylcarbamoyl)-4,5-dihydronaphtho[2,1-d]isoxazol-7-yl)methyl) azetidine-3-carboxylic acid, TFA salt (45); 1-((3-(2-chlorobenzylcarbamoyl)-4,5-dihydronaphtho[2,1-d]isoxazol-7-yl)methyl)azetidine-3-carboxylic acid (46); 1-((3-(neopentylcarbamoyl)-4,5-dihydronaphtho[2,1-d]isoxazol-7-yl)methyl)azetidine-3-carboxylic acid (47); 1-((2-(3-phenyl-4-(trifluoromethyl)isoxazol-5-yl)-4,5-dihydronaphtho[2,1-d]oxazol-7-yl)methyl)azetidine-3-carboxylic acid (48); 1-((2-(5-phenyl-4-(trifluoromethyl)isoxazol-3-yl)-4,5-dihydronaphtho[2,1-d]oxazol-7-yl)methyl) azetidine-3-carboxylic acid (49); 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol (50); (2S)-2-amino-2-methyl-4-(3-(1-phenyl-5-(trifluoromethyl)-1H-pyrazol-4-yl)-4,5-dihydronaphtho[1,2-c]isoxazol-7-yl) butanoic acid (51); 2-amino-2-methyl-4-(3-(1-phenyl-5-(trifluoromethyl)-1H-pyrazol-4-yl)-4,5-dihydronaphtho[1,2-c]isoxazol-7-yl)butyl dihydrogen phosphate (52); 1-((3-(5-phenyl-4-(trifluoromethyl)isoxazol-3-yl)-4H-chromeno[3,4-d]isoxazol-7-yl)methyl)azetidine-3-carboxylic acid (53); 1-((3-(5-phenyl-4-(trifluoromethyl)isoxazol-3-yl)-4,5-dihydroisoxazolo[5,4-f]quinolin-7-yl)methyl)azetidine-3-carboxylic acid (54); 1-((3-(5-phenyl-4-(trifluoromethyl)isoxazole-3-yl)-2,3-dihydrobenzo[b]oxepino-[4,5-d]isoxazol-8-yl)methyl)-azetidine-3-carboxylic acid (55); 1-((2-(3-phenyl-4-(trifluoromethyl)isoxazol-5-yl)-4,5-dihydronaphtho[2,1-d]thiazol-7-yl)methyl)azetidine-3-carboxylic acid (56); 1-((2-(2-(1-(4-fluorophenyl)cyclohexyl)ethyl)-4,5-dihydronaphtho[2,1-d]thiazol-7-yl)methyl)azetidine-3-carboxylic acid, TFA (57); 1-((2-(4-(4-chlorophenyl)cyclohexyl)-4,5-dihydronaphtho[2,1-d]thiazol-7-yl)methyl)azetidine-3-carboxylic acid, TFA (58); 1-((2-(5-phenyl-4-(trifluoromethyl)isoxazol-3-yl)-4,5-dihydronaphtho[2,1-d]thiazol-7-yl)methyl)azetidine-3-carboxylic acid (59); 1-((3-(3-phenyl-4-(trifluoromethyl)isoxazol-5-yl)-4H-chromeno[3,4-d]isoxazol-7-yl)methyl)-azetidine-3-carboxylic acid (60); 1-((3-(3-phenyl-4-(trifluoromethyl)isoxazol-5-yl)-4H-chromeno[4,3-c]isoxazol-7-yl)methyl)-azetidine-3-carboxylic acid (61); 1-((3-(5-Phenyl-4-(trifluoromethyl)isoxazol-3-yl)-4H-chromeno[4,3-c]isoxazol-7-yl)methyl)-azetidine-3-carboxylic acid (62); 1-((3-(3-(Pyridin-2-yl)-4-(trifluoromethyl)isoxazol-5-yl)-4,5-dihydronaphtho[1,2-c]isoxazol-7-yl)methyl)azetidine-3-carboxylic acid (63); 1-((8-Methyl-3-(5-phenyl-4-(trifluoromethyl)isoxazol-3-yl)-4,5-dihydronaphtho[1,2-c]isoxazol-7-yl)methyl)azetidine-3-carboxylic acid (64); (3S)-1-(2-Hydroxy-2-(8-methyl-3-(5-phenyl-4-(trifluoromethyl)isoxazol-3-yl)-4,5-dihydronaphthol[1,2-c]isoxazol-7-yl)ethyl)piperidine-3-carboxylic acid (65); 1-((5,5-Difluoro-3-(5-phenyl-4-(trifluoromethyl)isoxazol-3-yl)-4,5-dihydronaphtho[1,2-c]isoxazol-7-yl)methyl)azetidine-3-carboxylic acid (66); 1-((8-Fluoro-3-(3-phenyl-4-(trifluoromethyl)isoxazol-5-yl)-4,5-dihydronaphtho[1,2-c]isoxazol-7-yl)azetidine-3-carboxylic acid (67); 3-(methyl ((3-(5-phenyl-4-(trifluoromethyl)isoxazol-3-yl)-4,5-dihydronaphtho[1,2-c]isoxazol-7-yl)methyl)amino) propanoic acid (68); 3-((3-(5-Phenyl-4-(trifluoromethyl)isoxazol-3-yl)-4,5-dihydronaphtho[1,2-c]isoxazol-7-yl)methyl)amino)propanoic acid (69); (3S)-1-((3-(5-phenyl-4-(trifluoromethyl)isoxazol-3-yl)-4,5-dihydronaphtho[1,2-c]isoxazol-7-yl)methyl)piperidine-3-carboxylic acid (70); 2-((3-(5-Phenyl-4-(trifluoromethyl)isoxazol-3-yl)-4,5-dihydronaphtho[1,2-c]isoxazol-7-yl)methylamino)acetic acid (71); 3-hydroxy-2-((3-(5-phenyl-4-(trifluoromethyl)isoxazol-3-yl)-4,5-dihydronaphtho[1,2-c]isoxazol-7-yl)methylamino)propanoic acid (72); 3-(Methyl((3-(5-phenyl-4-(trifluoromethyl)isoxazol-3-yl)-4,5-dihydronaphtho[1,2-c]isoxazol-7-yl)methyl)amino)propanamide (73); 4-((3-(5-Phenyl-4-(trifluoromethyl)isoxazol-3-yl)-4,5-dihydronaphtho[1,2-c]isoxazol-7-yl)methyl)morpholino-3-yl)methanol (74); 1-((3-(5-cyclohexyl-4-(trifluoromethyl)isoxazol-3-yl)-4,5-dihydronaphtho[1,2-c]isoxazol-7-yl)methyl)azetidine-3-carboxylic acid (75); 3-(5-Cyclohexyl-4-(trifluoromethyl)isoxazol-3-yl)-4,5-dihydronaphtho[1,2-c]isoxazole-7-carboxylic acid (76); 1-((5-methyl-3-(3-phenyl-4-(trifluoromethyl)isoxazol-5-yl)-4,5-dihydroisoxazolo[4,3-c]quinolin-7-yl)methyl)azetidine-3-carboxylic acid (77); 1-((1-methyl-3-(5-phenyl-4-(trifluoromethyl)isoxazol-3-yl)-4,5-dihydro-1H-benzo[g]indazol-7-yl)methyl)azetidine-3-carboxylic acid, TFA (78); 1-((2-methyl-3-(5-phenyl-4-(trifluoromethyl)isoxazol-3-yl)-4,5-dihydro-2H-benzo[g]indazol-7-yl)methyl)azetidine-3-carboxylic acid, TFA (79); 1-((3-(3,4-diethoxyphenyl)-4,5-dihydronaphtho[1,2-c]isoxazol-7-yl)methyl)azetidine-3-carboxylic acid (80); (3S)-1-(2-(3-(3,4-diethoxyphenyl)-4,5-dihydronaphtho[1,2-c]isoxazol-7-yl)-2-hydroxyethyl)piperidine-3-carboxylic acid, HCl (81); (3S)-1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylic acid, HCl (82); (±)1-(2-(3-phenyl-4-(trifluoromethyl)isoxazol-5-yl)-4,5-dihydronaphtho[2,1-d]thiazol-7-yl)ethane-1,2-diol (83); 2-hydroxy-N-(2-hydroxyethyl)-2-(2-(3-phenyl-4-(trifluoromethyl)isoxazol-5-yl)-4,5-dihydronaphtho[2,1-d]thiazol-7-yl)acetamide (84); N-(1-cyanocyclopropyl)-2-hydroxy-2-(2-(3-phenyl-4-(trifluoromethyl)isoxazol-5-yl)-4,5-dihydronaphtho[2,1-d]thiazol-7-yl)acetamide (85); 1-((2-pentyl-4,5-dihydronaphtho[2,1-d]thiazol-7-yl)methyl)azetidine-3-carboxylic acid, TFA (86); 1-((3-(5-phenyl-4-(trifluoromethyl)isoxazol-3-yl)-4H-indeno[1,2-c]isoxazol-6-yl)methyl)azetidine-3-carboxylic acid (87); 2-(methyl((3-(5-phenyl-4-(trifluoromethyl)isoxazol-3-yl)-4,5-dihydronaphtho[1,2-c]isoxazol-7-yl)methyl)amino)acetic acid (88); (±) 2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid (89); (±) 2-(amino(3-(1-phenyl-5-(trifluoromethyl)-1H-pyrazol-4-yl)-4,5-dihydronaphtho[1,2-c]isoxazol-7-yl)methyl)furan-3-carboxylic acid (90); (±) 2-amino-4-(3-(5-phenyl-4-(trifluoromethyl)isoxazol-3-yl)-4,5-dihydronaphtho[1,2-c]isoxazol-7-yl)butanoic acid (91); 2-amino-2-(2-(3-(5-phenyl-4-(trifluoromethyl)isoxazol-3-yl)-4,5-dihydronaphtho[1,2-c]isoxazol-7-yl)ethyl)propane-1,3-diol (92); 2-amino-2-methyl-4-(3-(5-phenyl-4-(trifluoromethyl)isoxazol-3-yl)-4,5-dihydronaphtho[1,2-c]isoxazol-7-yl)butan-1-ol (93); 2-amino-2-methyl-4-(3-(5-phenyl-4-(trifluoromethyl)isoxazol-3-yl)-4,5-dihydronaphtho[1,2-c]isoxazol-7-yl)butanoic acid (94); 2-amino-2-methyl-4-(3-(5-phenyl-4-(trifluoromethyl)isoxazol-3-yl)-4,5-dihydronaphtho[1,2-c]isoxazol-7-yl)butyl dihydrogen phosphate (95); (±) 2-amino-2-methyl-3-(3-(5-phenyl-4-(trifluoromethyl)isoxazol-3-yl)-4,5-dihydronaphtho[1,2-c]isoxazol-7-yl)propyl dihydrogen phosphate (96); 2-((3-(5-phenyl-4-(trifluoromethyl)isoxazol-3-yl)-4,5-dihydronaphtho[1,2-c]isoxazol-7-yl)methylamino)ethyl dihydrogen phosphate (97); 2-amino-2-(3-(5-phenyl-4-(trifluoromethyl)isoxazol-3-yl)-4,5-dihydronaphtho[1,2-c]isoxazol-7-yl)propyl dihydrogen phosphate (98); (1-amino-3-(3-(5-phenyl-4-(trifluoromethyl)isoxazol-3-yl)-4,5-dihydronaphtho[1,2-c]isoxazol-7-yl)cyclopentyl)methyl dihydrogen phosphate (99); (1-amino-3-(2-(3-phenyl-4-(trifluoromethyl)isoxazol-5-yl)-4,5-dihydronaphtho[2,1-d]thiazol-7-yl)cyclopentyl)methyl dihydrogen phosphate (100); 2-(1-amino-3-(2-(3-phenyl-4-(trifluoromethyl)isoxazol-5-yl)-4,5-dihydronaphtho[2,1-d]thiazol-7-yl)cyclopentyl)ethyl dihydrogen phosphate (101); 1-(3-(5-phenyl-4-(trifluoromethyl)isoxazol-3-yl)-4,5-dihydronaphtho[1,2-c]isoxazol-7-yl)ethane-1,2-diol (102); 1-((3-(3-phenyl-4-(trifluoromethyl)isothiazol-5-yl)-4,5-dihydronaphtho[1,2-c]isoxazol-7-yl)methyl)azetidine-3-carboxylic acid (103); 2-amino-2-methyl-4-(3-(1-phenyl-5-(trifluoromethyl)-1H-pyrazol-4-yl)-4,5-dihydronaphtho[1,2-c]isoxazol-7-yl)butyl dihydrogen phosphate (104); 1-((3-(5-phenyl-4-(trifluoromethyl)isothiazol-3-yl)-4,5-dihydronaphtho[1,2-c]isoxazol-7-yl)methyl)azetidine-3-carboxylic acid (105); 1-((3-(4-cyano-3-phenylisothiazol-5-yl)-4,5-dihydronaphtho[1,2-c]isoxazol-7-yl)methyl)azetidine-3-carboxylic acid (106); 2-amino-2-methyl-3-(3-(5-phenyl-4-(trifluoromethyl)isoxazol-3-yl)-4,5-dihydronaphtho[1,2-c]isoxazol-7-yl)propan-1-ol (107); 2-((3-(5-phenyl-4-(trifluoromethyl)isoxazol-3-yl)-4,5-dihydronaphtho[1,2-c]isoxazol-7-yl)methylamino)ethanol (108); (±)4-hydroxy-4-(3-(5-phenyl-4-(trifluoromethyl)isoxazol-3-yl)-4,5-dihydronaphtho[1,2-c]isoxazol-7-yl)butanoic acid (109); 2,2'-((3-(5-phenyl-4-(trifluoromethyl)isoxazol-3-yl)-4,5-dihydronaphtho[1,2-c]isoxazol-7-yl)methylazanediyl)diethanol (110); (2R)-3-((3-(5-phenyl-4-(trifluoromethyl)isoxazol-3-yl)-4,5-dihydronaphtho[1,2-c]isoxazol-7-yl)methylamino)propane-1,2-diol (111); (2S)-3-((3-(5-phenyl-4-(trifluoromethyl)isoxazol-3-yl)-4,5-dihydronaphtho[1,2-c]isoxazol-7-yl)ethylamino)propane-1,2-diol (112); 2-((3-(5-phenyl-4-(trifluoromethyl)isoxazol-3-yl)-4,5-dihydronaphtho[1,2-c]soxazol-7-yl)ethylamino)propane-1,3-diol (113); (3R)-1-((3-(5-phenyl-4-(trifluoromethyl)isoxazol-3-yl)-4,5-dihydronaphtho[1,2-c]isoxazol-7-yl)methyl)pyrrolidin-3-ol (114); (3S)-1-((3-(5-phenyl-4-(trifluoromethyl)isoxazol-3-yl)-4,5-dihydronaphtho[1,2-c]isoxazol-7-yl)methyl)pyrrolidin-3-ol (115); ((2R)-1-((3-(5-phenyl-4-(trifluoromethyl)isoxazol-3-yl)-4,5-dihydronaphtho[1,2-c]isoxazol-7-yl)methyl)pyrrolidin-2-yl)methanol (116); ((2S)-1-((3-(5-phenyl-4-(trifluoromethyl)isoxazol-3-yl)-4,5-dihydronaphtho[1,2-c]isoxazol-7-yl)methyl)pyrrolidin-2-yl)methanol (117); 1-((3-(4-cyclohexyl-3-(trifluoromethyl)phenyl)-4,5-dihydronaphtho[1,2-c]isoxazol-7-yl)methyl)azetidine-3-carboxylic acid (118); 2-amino-2-methyl-4-(2-(3-phenyl-4-(trifluoromethyl)isoxazol-5-yl)-4,5-dihydronaphtho[2,1-d]thiazol-7-yl)butan-1-ol (119); 2-amino-2-methyl-4-(2-(3-phenyl-4-(trifluoromethyl)isoxazol-5-yl)-4,5-dihydronaphtho[2,1-d]thiazol-7-yl)butyl dihydrogen phosphate (120); (1-amino-3-(3-(5-phenyl-4-(trifluoromethyl)isoxazol-3-yl)-4,5-dihydronaphtho[1,2-c]isoxazol-7-yl)cyclopentyl)methanol (121); 1-((3-(1-(5-fluoropyridin-2-yl)-5-(trifluoromethyl)-1H-pyrazol-4-yl)-4,5-dihydronaphtho[1,2-c]isoxazol-7-yl)methyl)azetidine-3-carboxylic acid (122); (1-amino-3-(2-(3-phenyl-4-(trifluoromethyl)isoxazol-5-yl)-4,5-dihydronaphtho[2,1-d]thiazol-7-yl)cyclopentyl)methanol (123); 2-(1-amino-3-(2-(3-phenyl-4-(trifluoromethyl)isoxazol-5-yl)-4,5-dihydronaphtho[2,1-d]thiazol-7-yl)cyclopentyl)ethanol (124); 2-amino-2-(3-(5-phenyl-4-(trifluoromethyl)isoxazol-3-yl)-4,5-dihydronaphtho[1,2-c]isoxazol-7-yl)propan-1-ol (125); N-(methylsulfonyl)-1-((3-(3-phenyl-4-(trifluoromethyl)isoxazol-5-yl)-4,5-dihydronaphtho[1,2-c]isoxazol-7-yl)methyl)azetidine-3-carboxamide (126); (±)-2-hydroxy-2-(3-(4-propylphenyl)-4,5-dihydronaphtho[1,2-c]isoxazol-7-yl)acetic acid (127); (±)-N-(cyanomethyl)-2-hydroxy-2-(3-(4-propylphenyl)-4,5-dihydronaphtho[1,2-c]isoxazol-7-yl)acetamide (128); (±)-2-Hydroxy-N-(2-hydroxyethyl)-2-(3-(4-propylphenyl)-4,5-dihydronaphtho[1,2-c]isoxazol-7-yl)acetamide (129); (±)-2-hydroxy-N-(2-(methylsulfonyl)ethyl)-2-(3-(4-propylphenyl)-4,5-dihydronaphtho[1,2-c]isoxazol-7-yl)acetamide (130); 2-Hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)acetamide (131); N-(1-cyanocyclopropyl)-2-hydroxy-2-(3-(5-phenyl-4-(trifluoromethyl)isoxazol-3-yl)-4,5-dihydronaphtho[1,2-c]isoxazol-7-yl)acetamide (132); 2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)acetamide (133); 2-Hydroxy-N-(2-hydroxyethyl)-2-(3-(5-phenyl-4-(trifluoromethyl)isoxazol-3-yl)-4,5-dihydronaphtho[1,2-c]isoxazol-7-yl)propanamide (134); 2-Hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)propanamide (135); 1-((3-(4-propylphenyl)-4,5-dihydro-3H-benzo[e]indazol-7-yl)methyl)azetidine-3-carboxylic acid (136); (1-amino-3-(2-pentyl-4,5-dihydronaphtho[2,1-d]thiazol-7-yl)cyclopentyl)methanol (137); (1-amino-3-(2-pentyl-4,5-dihydronaphtho[2,1-d]thiazol-7-yl)cyclopentyl)methyl dihydrogen phosphate (138);

(R)-3-(2-amino-4,5-dihydronaphtho[1,2-d]thiazol-7-yloxy)propane-1,2-diol (139); N-(7-hydroxy-4,5-dihydronaphtho[1,2-d]thiazol-2-yl)benzamide (140); N-(7-hydroxy-4,5-dihydronaphtho[1,2-d]thiazol-2-yl)-2-phenylacetamide (141); N-(7-hydroxy-4,5-dihydronaphtho[1,2-d]thiazol-2-yl)-3-phenylpropanamide (142); N-(7-hydroxy-4,5-dihydronaphtho[1,2-d]thiazol-2-yl)hexanamide (143); 1-((3-(2-methoxybenzylcarbamoyl)-4,5-dihydronaphtho[2,1-d]isoxazol-7-yl)methyl)azetidine-3-carboxylic acid (144); 1-((3-(2-ethoxybenzylcarbamoyl)-4,5-dihydronaphtho[2,1-d]isoxazol-7-yl)methyl)azetidine-3-carboxylic acid (145); 1-((3-(2-methylbenzylcarbamoyl)-4,5-dihydronaphtho[2,1-d]isoxazol-7-yl)methyl)azetidine-3-carboxylic acid (146); 1-((3-(4-chlorobenzylcarbamoyl)-4,5-dihydronaphtho[2,1-d]isoxazol-7-yl)methyl)azetidine-3-carboxylic acid (147); 1-((3-(2,2-diphenylpropylcarbamoyl)-4,5-dihydronaphtho[2,1-d]isoxazol-7-yl)methyl)azetidine-3-carboxylic acid (148); 1-((3-(2-phenylpropylcarbamoyl)-4,5-dihydronaphtho[2,1-d]isoxazol-7-yl)methyl)azetidine-3-carboxylic acid (149); 1-((3-(phenethylcarbamoyl)-4,5-dihydronaphtho[2,1-d]isoxazol-7-yl)methyl)azetidine-3-carboxylic acid (150); 1-((3-(2-chlorophenethylcarbamoyl)-4,5-dihydronaphtho[2,1-d]isoxazol-7-yl)methyl)azetidine-3-carboxylic acid (151); 1-((3-(3-phenylpropylcarbamoyl)-4,5-dihydronaphtho[2,1-d]isoxazol-7-yl)methyl)azetidine-3-carboxylic acid (152); 1-((3-(benzyl(methyl)carbamoyl)-4,5-dihydronaphtho[2,1-d]isoxazol-7-yl)methyl)azetidine-3-carboxylic acid (153); 1-((3-(3-chlorobenzylcarbamoyl)-4,5-dihydronaphtho[2,1-d]isoxazol-7-yl)methyl)azetidine-3-carboxylic acid (154); 1-((3-(3-chlorophenethylcarbamoyl)-4,5-dihydronaphtho[2,1-d]isoxazol-7-yl)methyl)azetidine-3-carboxylic acid (155); 1-((3-(3-phenylpyrrolidine-1-carbonyl)-4,5-dihydronaphtho[2,1-d]isoxazol-7-yl)methyl)azetidine-3-carboxylic acid (156); 1-((3-(3-benzylpyrrolidine-1-carbonyl)-4,5-dihydronaphtho[2,1-d]isoxazol-7-yl)methyl)azetidine-3-carboxylic acid (157); 1-((3-(3-phenethylpyrrolidine-1-carbonyl)-4,5-dihydronaphtho[2,1-d]isoxazol-7-yl)methyl)azetidine-3-carboxylic acid (158); 1-((3-(2-(4-methoxyphenyl)-2-phenylethylcarbamoyl)-4,5-dihydronaphtho[2,1-d]isoxazol-7-yl)methyl)azetidine-3-carboxylic acid (159); 1-((3-(3-(naphthalen-1-yl)piperidine-1-carbonyl)-4,5-dihydronaphtho[2,1-d]isoxazol-7-yl)methyl)azetidine-3-carboxylic acid (161); 1-((3-(3-phenylpiperidine-1-carbonyl)-4,5-dihydronaphtho[2,1-d]isoxazol-7-yl)methyl)azetidine-3-carboxylic acid (162); 1-((3-((1,2,3,4-tetrahydronaphthalen-1-yl)methylcarbamoyl)-4,5-dihydronaphtho[2,1-d]isoxazol-7-yl)methyl)azetidine-3-carboxylic acid (163); 1-((3-(3-(4-fluorophenyl)pyrrolidine-1-carbonyl)-4,5-dihydronaphtho[2,1-d]isoxazol-7-yl)methyl)azetidine-3-carboxylic acid (164); 1-((3-(3-(2-chlorophenyl)pyrrolidine-1-carbonyl)-4,5-dihydronaphtho[2,1-d]isoxazol-7-yl)methyl)azetidine-3-carboxylic acid (165); 1-((3-(3-(3-methoxyphenyl)pyrrolidine-1-carbonyl)-4,5-dihydronaphtho[2,1-d]isoxazol-7-yl)methyl)azetidine-3-carboxylic acid (166); 1-((3-(2-isopropoxybenzylcarbamoyl)-4,5-dihydronaphtho[2,1-d]isoxazol-7-yl)methyl)azetidine-3-carboxylic acid (167); 1-((3-(2-phenoxybenzylcarbamoyl)-4,5-dihydronaphtho[2,1-d]isoxazol-7-yl)methyl)azetidine-3-carboxylic acid (168); 1-((3-(3-methylbenzylcarbamoyl)-4,5-dihydronaphtho[2,1-d]isoxazol-7-yl)methyl)azetidine-3-carboxylic acid (169); 1-((3-(4-methylbenzylcarbamoyl)-4,5-dihydronaphtho[2,1-d]isoxazol-7-yl)methyl)azetidine-3-carboxylic acid (169); 1S,3S)-3-((3-(3-phenyl-4-(trifluoromethyl)isoxazol-5-yl)-4,5-dihydronaphtho[1,2-c]isoxazol-7-yl)methylamino)cyclobutanecarboxylic acid (170A); (1S,3S)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid (170B); (1R,3R)-3-((3-(3-phenyl-4-(trifluoromethyl)isoxazol-5-yl)-4,5-dihydronaphtho[1,2-c]isoxazol-7-yl)methylamino)cyclobutanecarboxylic acid (171A); and (1R,3R)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid (171B).

The compounds of Formula (I) have GTPγS S1P$_1$ EC$_{50}$ values of 15 μM or less as measured by the S1P$_1$ Receptor GTPγS Binding Assay described herein below. Preferably, the compounds of Formula (I) have GTPγS S1P$_1$ EC$_{50}$ values in the range of 0.01 nM to 5 μM, and more preferably, in the range of from 0.01 nM to 1 μM. Other preferred compounds of Formula (I) have GTPγS S1P$_1$ EC$_{50}$ values in the range of from 0.01 nM to 100 nM.

The compounds of Formula (I) are selective for S1P$_1$ activity over S1P$_3$ activity as measured by the selectivity ratio of the GTPγS S1P$_3$ EC$_{50}$ value to the GTPγS S1P$_1$ EC$_{50}$ value. The S1P$_1$ Receptor GTPγS Binding Assay and the S1P$_3$ Binding Assay are described herein below. The compounds of Formula (I) have selectivity ratios (GTPγS S1P$_3$/S1P$_1$) of at least 3.5 or greater, preferably at least 50 or greater, and more preferably at least 100 or greater. For example, suitable compounds of Formula (I) can have selectivity ratios in the range of from 50 to 50,000. Other suitable compounds of Formula (I) can have selectivity ratios in the range of from 100 to 50,000.

In one embodiment, the compounds of Formula (I) are provided having GTPγS S1P$_1$ EC$_{50}$ values in the range of from 0.01 nM to 100 nM and selectivity ratios (GTPγS S1P$_3$/S1P$_1$) of at least 50, and more preferably, at least 100.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. For example, "$C_{1-6}$alkylene" denotes straight and branched chain alkylene groups with one to six carbon atoms. Further, for example, "$C_{0-4}$alkylene" denotes a bond and straight and branched chain alkylene groups with one to four carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$, and 2,2,2-trifluoroethyl (—$CH_2CF_3$). When numbers appear in a subscript after the symbol "C", the subscript defines with more specificity the number of carbon atoms that a particular haloalkyl group may contain. For example, "$C_{1-4}$ haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "chloroalkyl" as used herein is intended to include both branched and straight-chain saturated aliphatic hydrocarbon groups substituted with one or more chlorine atoms. For example, "$C_{1-4}$chloroalkyl" is intended to include $C_1$, $C_2$, $C_3$, and $C_4$ alkyl groups substituted with one or more chlorine atoms. Representative examples of chloroalkyl groups include, but are not limited to, —$CCl_3$ and —$CH_2CCl_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$hydroxyalkyl.

The term "cyano" refers to the group —CN.

The term "cyanoalkyl" includes both branched and straight-chain saturated alkyl groups substituted with one or more cyano groups. For example, "cyanoalkyl" includes —$CH_2CN$, —$CH_2CH_2CN$, and $C_{1-4}$cyanoalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$cycloalkyl" denotes cycloalkyl groups with three to six carbon atoms.

The term "cyanocycloalkyl" refers to a cycloalkyl group in which one or more hydrogen atoms are replaced by cyano group(s).

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$alkynyl" denotes straight and branched chain alkynyl groups with two to six carbon atoms.

The term "alkoxy," as used herein, refers to an alkyl group attached to the parent molecular moiety through an oxygen atom, for example, methoxy group (—$OCH_3$).

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

"Chloroalkoxy" and "—O(chloroalkyl)" represent a chloroalkyl group as defined above attached through an oxygen linkage (—O—). For example, "$C_{1-4}$chloroalkoxy" is intended to include $C_1$, $C_2$, $C_3$, and $C_4$ chloroalkoxy groups.

The term "alkoxyalkyl" as used herein, refers to an alkoxy group attached through an alkylene group.

The term "fluoroalkoxyalkyl" as used herein, refers to a fluoroalkoxy group attached through an alkylene group.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "phenoxy," as used herein, refers to a phenyl group attached through an oxygen group (—O-phenyl).

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The term "heterocyclylalkyl," as used herein, refers to an heterocyclyl group, as defined herein, appended to the parent molecular moiety through an alkylene group, as defined herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418, (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, Bundgaard, H. ed., Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The human immune system has evolved to defend the body from microorganisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderrna and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, and chronic bacterial infection.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

The methods of treating $S1P_1$-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the $S1P_1$ receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo[1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, Il-1 such as anakinra (KINERET®) (an IL-1 receptor antagonist), IL-2, IL-4, IL-5, IL-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Fourth Edition, Wiley and Sons (2006)).

General methods for the synthesis of tricycles, useful for this invention are outlined in the following Schemes.

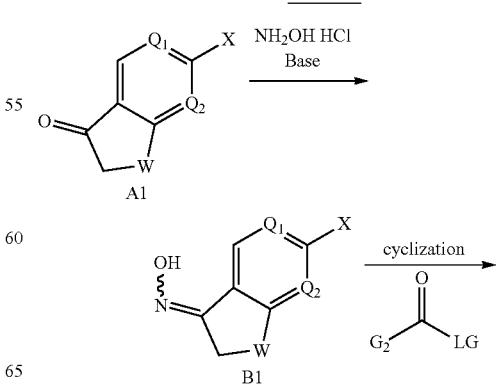

Scheme 1

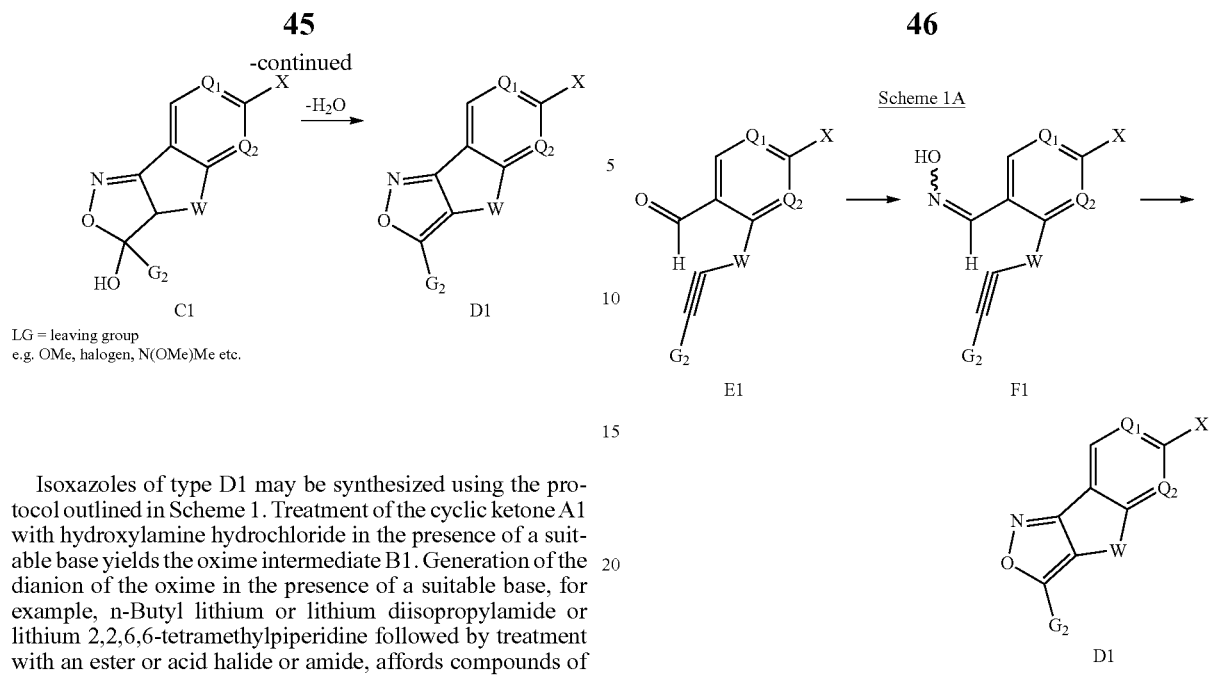

LG = leaving group
e.g. OMe, halogen, N(OMe)Me etc.

Isoxazoles of type D1 may be synthesized using the protocol outlined in Scheme 1. Treatment of the cyclic ketone A1 with hydroxylamine hydrochloride in the presence of a suitable base yields the oxime intermediate B1. Generation of the dianion of the oxime in the presence of a suitable base, for example, n-Butyl lithium or lithium diisopropylamide or lithium 2,2,6,6-tetramethylpiperidine followed by treatment with an ester or acid halide or amide, affords compounds of the type C1 (see, for example, *Synthesis,* 989-992 (1994); *J. Org. Chem.,* 5828-5832 (1994); *Syn. Comm.,* 3391-3404 (2000)). Alternatively, the oxime OH can be protected, for example, using a trimethylsilyl group followed by deprotonation using a base as described above. Dehydration of C1 employing for example, Burgess reagent, sulfuric acid, p-toluenesulfonic acid, or thionyl chloride, leads to tricyclic isoxazoles of the type D1. Cyclic ketones of type A1 are either commercially available or can be prepared by methods well known in the art (see for example, *Bioorg. Med. Chem.,* 7434-7445 (2006); *Bioorg. Med. Chem.,* 4876-4890 (2007)).

Alternatively, compounds of type D1 may be prepared by the sequence of reactions shown in Scheme 1A.

Reaction of the acetylenic aldehyde E1 with hydroxylamine affords the oxime F1. Subjecting the oxime to 1,3-dipolar cycloaddition in the presence of an oxidizing agent such as N-chlorosuccinamide in a solvent such as dichloromethane or DMF affords the desired isoxazoles D1 (see for example, *Org. Lett.,* 323 (2002)).

The group X in D1 may be modified into other groups as shown in Schemes 2 and 3.

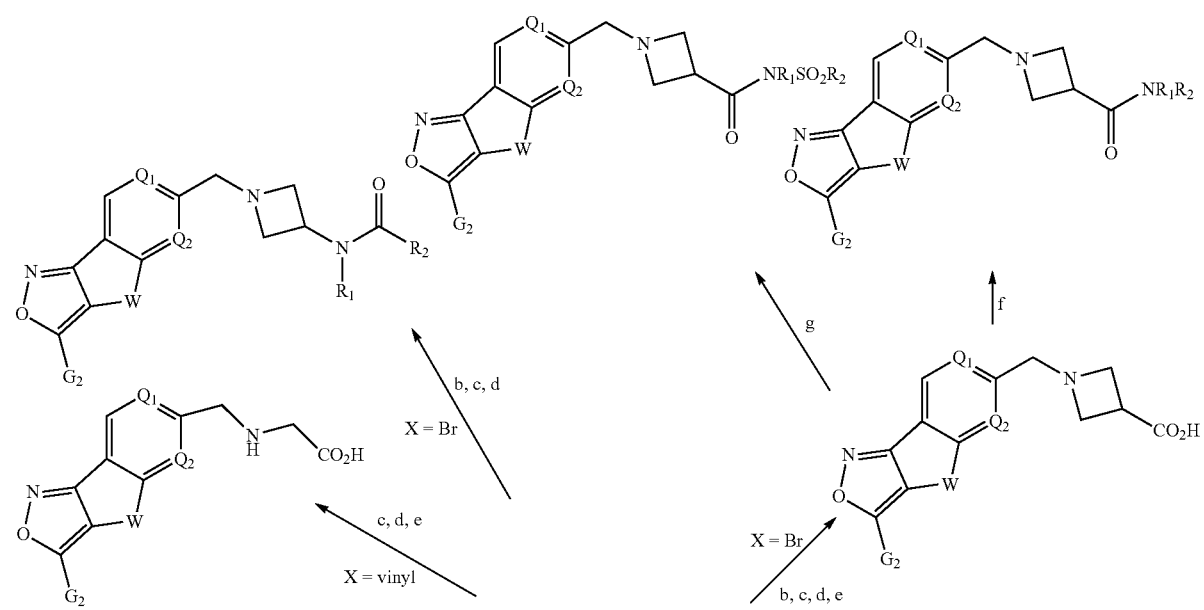

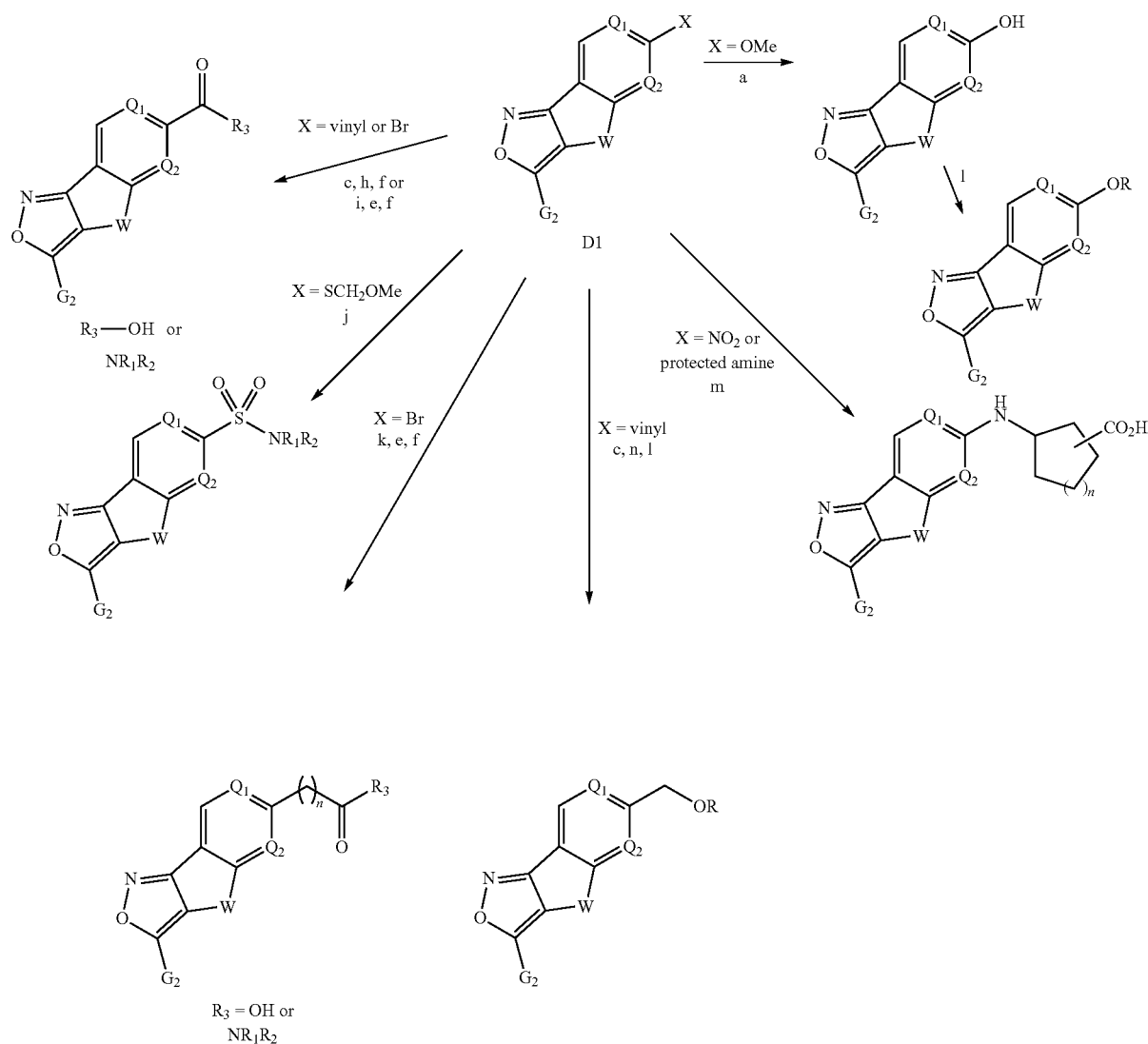

a) BBr$_3$, CH$_2$Cl$_2$; (b) tributylvinyl tin, Pd(PPh$_3$)$_4$, LiCl; (c) O$_3$, CH$_2$Cl$_2$, or OsO$_4$, NaIO$_4$; (d) azetidine carboxylic acid or ester, or appropriately substituted amine, MeOH, Cl(CH$_2$)$_2$Cl, NaCNBH$_4$; (e) TFA, CH$_2$Cl$_2$ or NaOH; (f) NHR$_1$R$_2$, BOP, Et$_3$N, THF; (g) (1) NH$_2$SO$_2$NR$_2$, EDAP, DMAP, CH$_2$Cl$_2$; (2) NaH, DMF, R$_1$—C$_1$ or R$_1$—Br; (h) NaClO$_2$, 2-methyl-2-butene, NaH$_2$PO$_4$, H$_2$O, tert-BuOH; (i) CO, MeOH, Pd(OAc)$_2$, PPh$_3$; (j) (1) Cl$_2$, dioxane; (2) R$_1$R$_2$NH; (k) ZnBr(CH$_2$)$_m$CO$_2$R, dichlorobis(tri-O-tolylphosphine)palladium (II); (l) NaH, DMF, R—Br; (m) Na(OAc)$_3$BH, AcOH, CH$_2$Cl$_2$, appropriately substituted ketone; (n) NaBH$_4$, MeOH.

Scheme 3

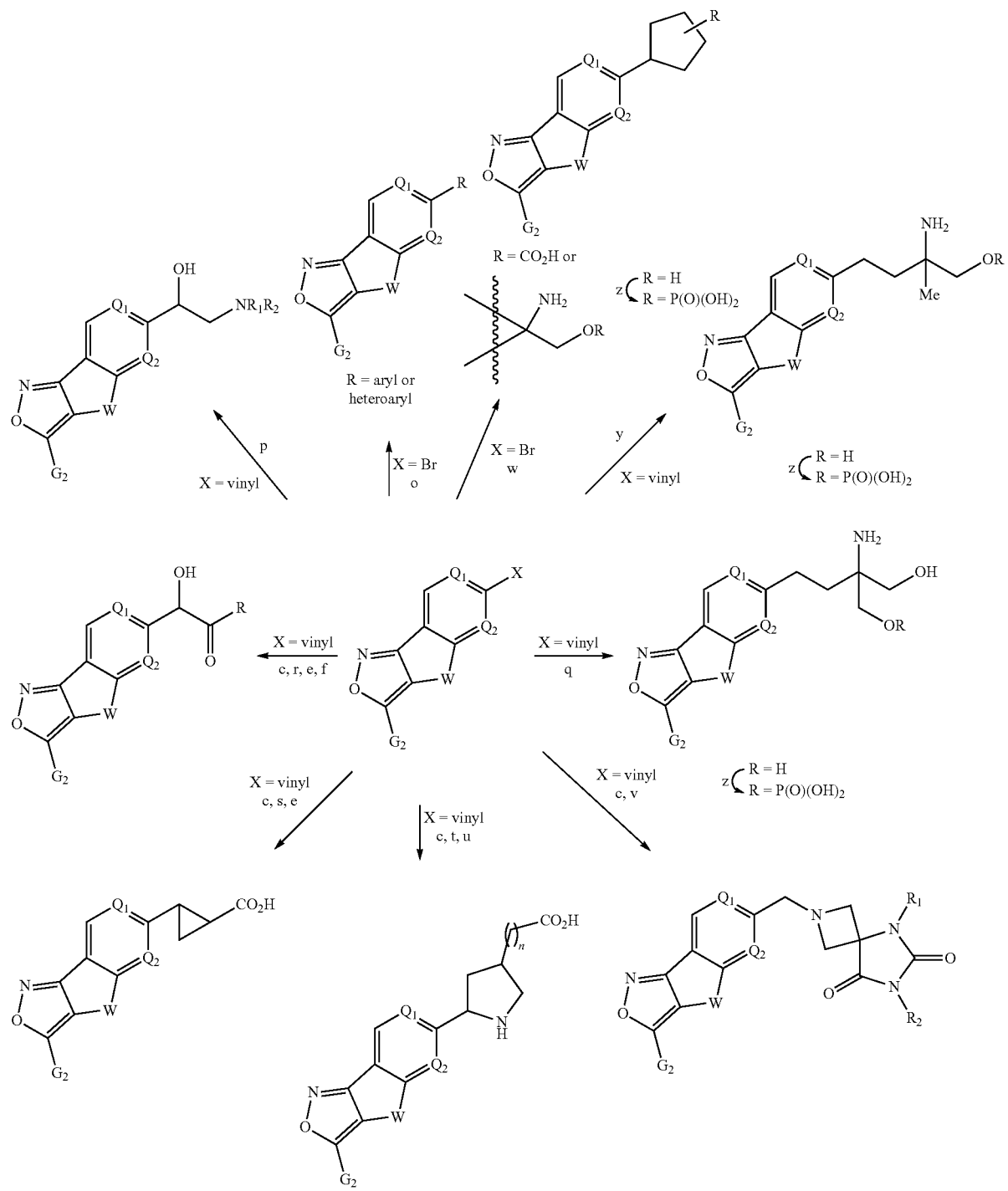

For reagents a-n, see Scheme 2. (o) RB(OH)₂, Pd(PPh)₃, K₂CO₃, EtOH; (p) (i) m-CPBA, CH₂Cl₂; (ii) NR₁R₂, EtOH; (q) (i) 9-BBN, NaOH, H₂O₂; (ii) CBr₄, PPh₃; (iii) dimethylacetamidomalonate, NaOMe, MeOH; (iv) LAH, THF; (r) (i) TMSCN, ZnI₂, CH₂Cl₂; (ii) HCl, H₂O, AcOH; (s) (i) PPhCHCO₂Et, THF; (ii) CH₂N₂, Pd(OAc)₂, THF; (t) (i) p-toluenesulfonamide, Si(OEt)₄; (ii) ((trimethylsilyl)methyl) allyl acetate, Pd(OAc)₂, PPh₃; (u) (i) 9-BBN, NaOH, H₂O₂; (ii) Jones reagent; (v) spirocyclic azetidine-hydantoin, NaCNBH₄, mol. sieves, CH₂Cl₂; (w) substituted cyclopentyl BF₃⁻K⁺, K₃PO₄, Pd(OAc)₂, 2-PCy₂-2'6'-(O-iPr)-2-biphenyl, toluene-H₂O (y) (i) 9-BBN, NaOH, H₂O₂; (ii) CBr₄, PPh₃; (iii) alanine, N-(phenylmethylene)-1-methylethyl ester, NaHMDS; (iv) HCl; (v) LAH, THF (z) (i) NaHMDSi, tetrabenzyldiphosphate; (ii) H₂, Pd(OH)₂, MeOH, Isoxazoles of the type E2 may be synthesized using the protocol outlined in Scheme 4.

Scheme 4

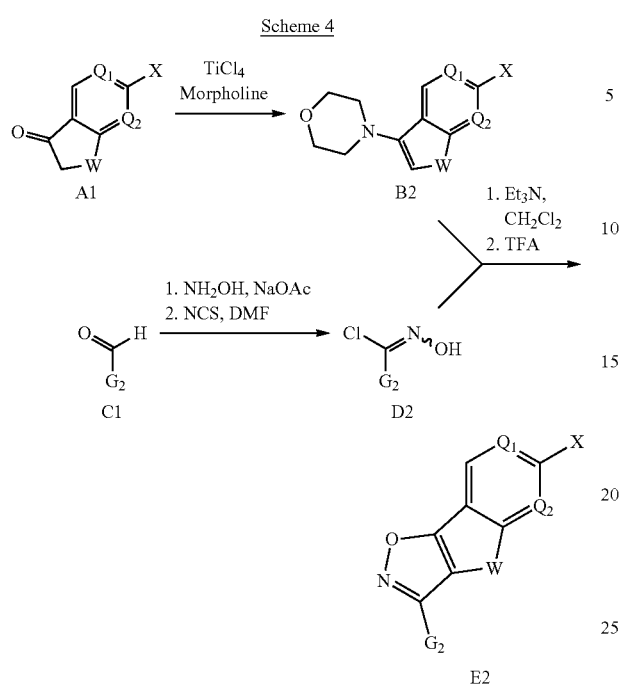

Treatment of the cyclic ketone A1 with a secondary amine, for example morpholine and titanium tetrachloride leads to the formation of the eneamine B2. Conversion of the aldehyde C2 to the chlorooxime D2 can be accomplished by initial treatment with hydroxylamine with sodium acetate or pyridine followed by treatment with N-chlorosuccinamide in the presence of a solvent such as DMF. 1,3-dipolar cycloaddition of the chlorooxime D2 with the eneamine B2 is accomplished in the presence of a suitable base such as triethylamine (see for example, *J. Het. Chem.*, 203-208 (1992)). Reaction of the intermediate dihydrooxazole-morpholine adduct with an acid such as HCl or TFA in a suitable solvent such as EtOH or dichloroethane afforded the desired isoxazoles E2. Cyclic ketones of type A1 are either commercially available or can be prepared by methods well known in the art (see for example, *Bioorg. Med. Chem.*, 7434-7445 (2006); *Bioorg. Med. Chem.*, 4876-4890 (2007)). Aldehydes of the type C2 are either commercially available or can be prepared by methods well known in the art.

The group X in E2 may be modified into other groups as shown in Schemes 2 and 3.

Pyrazoles of the type C3, D3 and E3 may be prepared by the sequence of reactions outlined in Scheme 5.

Scheme 5

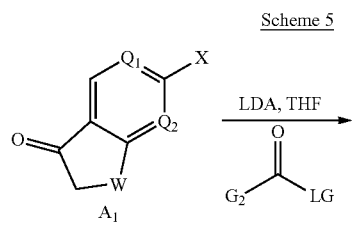

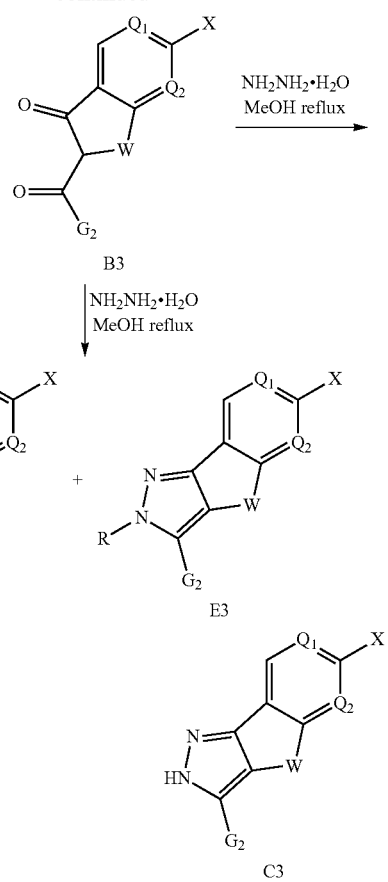

LG = leaving group
e.g. OMe, halogen, N(OMe)Me etc.

The 1,3-diketone B3 may be synthesized by the reaction of the ketone A3 with an acid halide or an ester or a tertiary amide in the presence of a suitable base such as lithium diisopropylamide or lithium hexamethyldisilazane. Treatment of the 1,3-diketone B3, with hydrazine or a substituted hydrazine leads to the formation of the pyrazoles C3, D3 and E3.

Alternatively, pyrazoles of the type D3 may be synthesized in a regiospecific manner using the sequence of reactions outlined in Scheme 6

Scheme 6

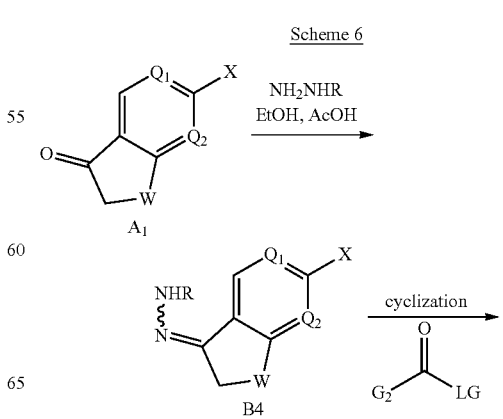

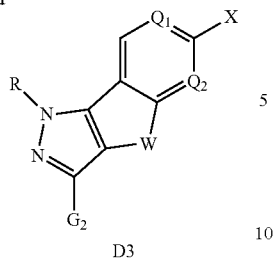

D3

LG = leaving group
e.g. OMe, halogen, N(OMe)Me etc.

Treatment of the cyclic ketone A1 with a substituted hydrazine in a solvent such as ethanol in the presence of an acid such as acetic acid yields hydrazones of the type B4. Cyclization of the hydrazone using conditions outlined in Scheme 1 yields the desired pyrazole D3.

The group X in C3, E3 and D3 may be modified into other groups as shown in Schemes 2 and 3.

Isothiazoles of type C7 and C8 may be synthesized using the reaction sequences outlined in Schemes 7 and 8.

Scheme 7

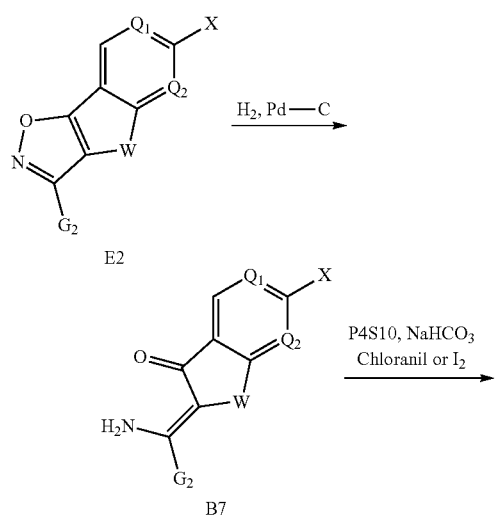

Scheme 8

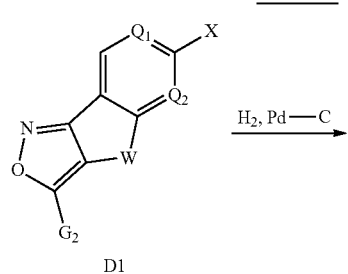

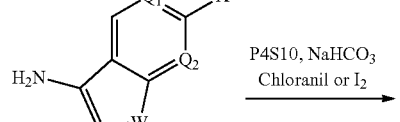

B8

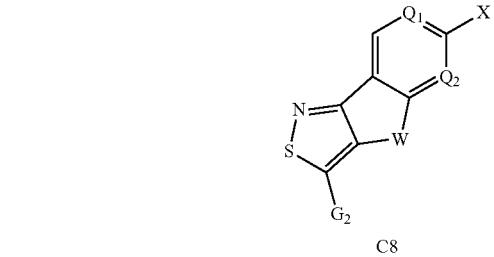

C8

Isoxazoles of type E2 (Scheme 4) or D1 (Scheme 1) on reduction, for example using hydrogen gas or Raney-Ni or Pd/C afford the eneamino ketone B7 and B8. Sulfurization with phosphorous pentasulfide followed by oxidation using chloranil or iodine yields the isoxazoles C7 and C8 (for example, see *J. Am. Chem. Soc.*, 2721 (1985)).

Alternatively, eneamino ketones of the type B7 may be synthesized from B3 (Scheme 5) as outlined in Scheme 9 (See for example, *New J. Chem.*, 28 (2002)).

Scheme 9

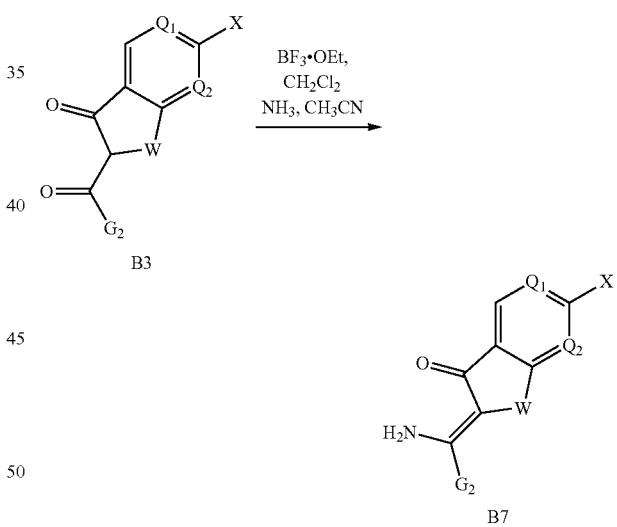

The group X in C7 and C8 may be modified into other groups as shown in Schemes 2 and 3.

Oxazoles of the type E9 may be synthesized by the sequence of reactions outlined in Scheme 10.

Scheme 10

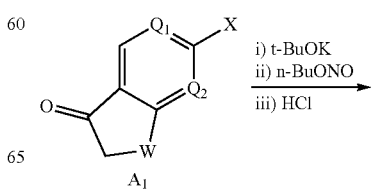

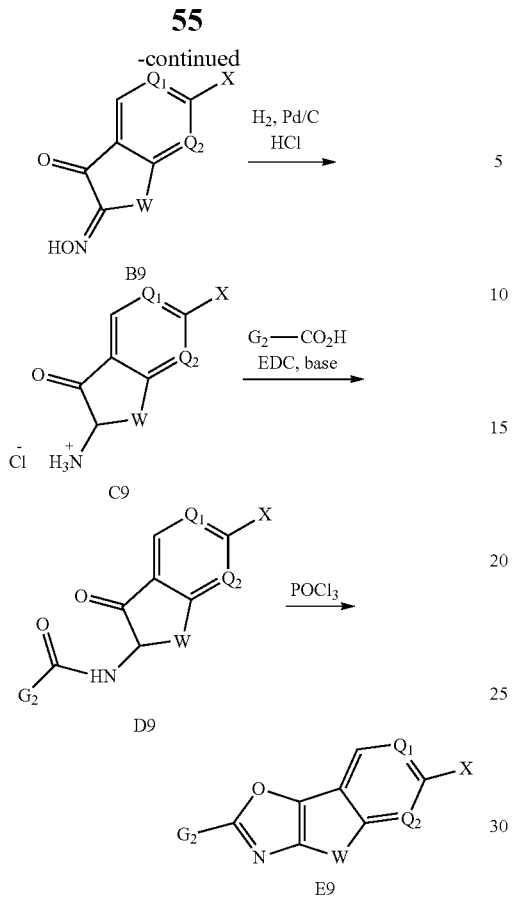

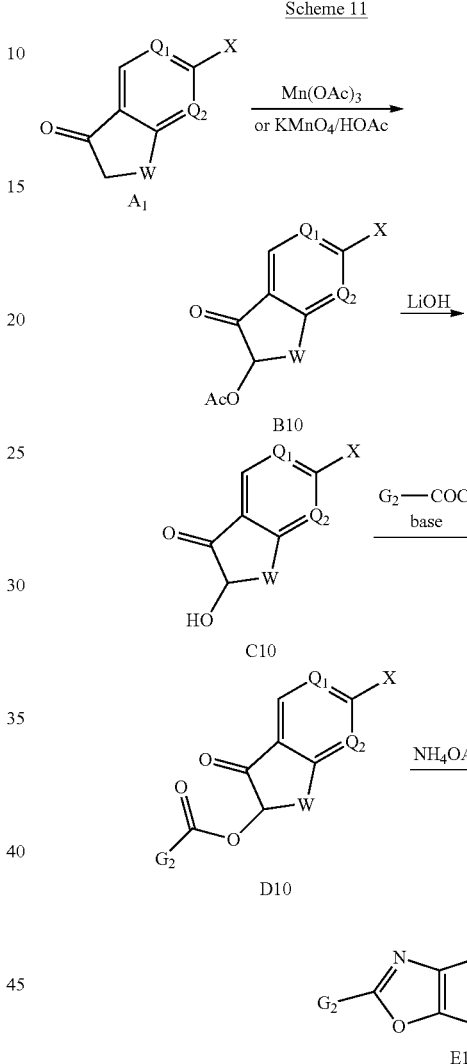

Treatment of the cyclic ketone A1 with potassium t-butoxide and n-butylnitrite followed by conc. HCl affords the corresponding oxime B9. Catalytic hydrogenation of the oxime in the presence of HCl yields the α-amino-ketone hydrochloride salt C9 (see reference *J. Heterocyclic Chem.*, 29:1245 (1992)). Coupling of the amino-ketone C9 with an appropriate acid G2-COOH in the presence of a coupling reagent like 1-(3-dimethylaminopropyl)-3-ethylcarbodiimide hydrochloride (EDC) and 1-hydroxybenzotriazole (HOBT) in the presence of a tertiary amine such as N,N-diisopropylethylamine in a solvent such as DMF or dichloromethane affords the amide D9. Treatment of D9 with phosphorous oxychloride affords the tricyclic oxazoles of type E9. Cyclic ketones of type A1 are either commercially available or can be prepared by methods well known in the art (see for example, *Bioorg. Med. Chem.*, 7434-7445 (2006); *Bioorg. Med. Chem.*, 4876-4890 (2007)).

The group X in E9 may be modified into other groups as shown in Schemes 2 and 3.

Oxazoles of type E10 may be synthesized using the protocol outlined in Scheme 11. Treatment of the cyclic ketone A1 with manganese(III) acetate or potassium permanganate and acetic acid affords α-acetoxy-ketone B10 (see references, *Tetrahedron*, 60:3427-3432 (2004) and *Tetrahedron*, 64:6196-6201 (2008). Hydrolysis of B10 with LiOH or NaOH gives the corresponding α-hydroxy-ketone C10. Conversion of the hydroxyl group to an ester D10 can be accomplished by treating C10 with an appropriate acyl chloride G2-COCl, which is prepared from the corresponding acid G2-COOH and thionyl chloride or oxalyl chloride and catalytic amount of DMF, in the presence of a base such as triethylamine or Hunig's base and with or without a catalytic amount of 4-dimethylamino-pyridine. Treatment of D10 with ammonium acetate in acetic acid affords the tricyclic oxazoles of type E10. Cyclic ketones of type A1. are either commercially available or can be prepared by methods well known in the art (see for example, *Bioorg. Med. Chem.*, 7434-7445 (2006); *Bioorg. Med. Chem.*, 4876-4890 (2007)).

The group X in E10 may be modified into other groups as shown in Schemes 2 and 3.

Thiazoles of type C11 may be synthesized using the protocol outlined in Scheme 12. Treatment of the cyclic ketone A1 with NBS and catalytic amount of p-toluenesulfonic acid affords α-bromo-ketone B11 (Prayst, I. et al., *Tet. Lett.*, 47:4707 (2006)). Conversion of the bromo-ketone B11 into the corresponding thiazole C11 by treating it with a thioamide G2-C(S)NH₂ is well known in the art (for example, see Davies, J. R. et al., *Tetrahedron*, 60:3969 (2004)). Cyclic ketones of type A1 are either commercially available or can be prepared by methods well known in the art (for example, see *Bioorg. Med. Chem.*, 7434-7445 (2006); *Bioorg. Med. Chem.*, 4876-4890 (2007)).

Scheme 12

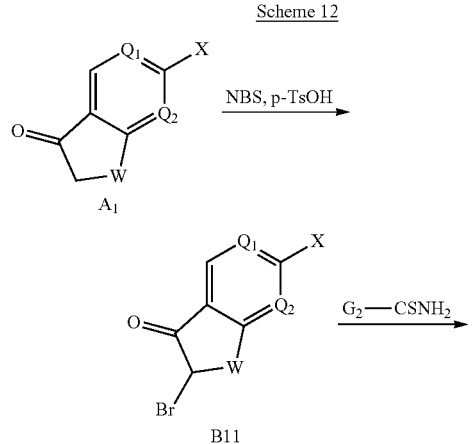

The group X in C11 may be modified into other groups as shown in Schemes 2 and 3.

Triazoles of the type C12 can be prepared using a protocol outlined in Scheme 13.

Scheme 13

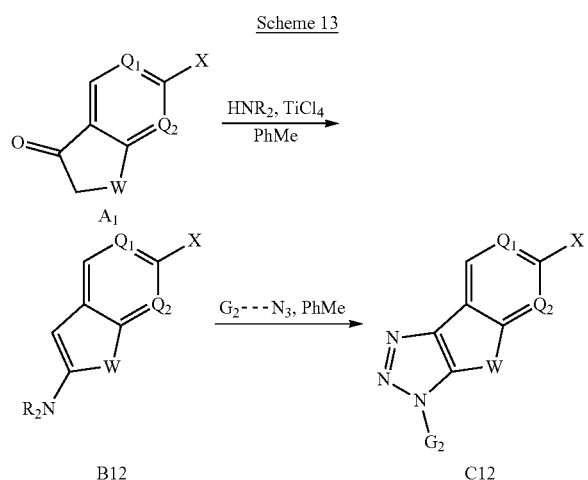

Treatment of the cyclic ketone A1 with a secondary amine, for example morpholine and titanium tetrachloride leads to the formation of the enamine B12. Conversion of the enamine into the corresponding triazole can be accomplished by a cycloaddition reaction with an appropriately substituted azide (see for example, *J. Med. Chem.*, 7(5):584-589 (1964) Cyclic ketones of type A1 are either commercially available or can be prepared by methods well known in the art (for example, see *Bioorg. Med. Chem.*, 7434-7445 (2006); *Bioorg. Med. Chem.*, 4876-4890 (2007)). Azides useful for the cycloaddition shown above can be prepared by methods well known in the art (see for example, *Organic Letters*, 9(9):1809-1811 (2007)). The group X in C12 may be modified into other groups as shown in Schemes 2 and 3.

Triazoles of the type C13 can be prepared using the sequence outlined in Scheme 14.

Scheme 14

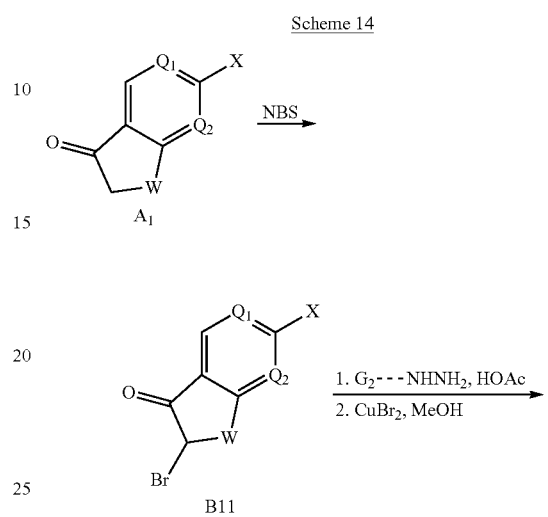

Treatment of B11 (see Scheme 12) with hydrazine in the presence of copper(II)bromide affords triazoles of the type C13 (see for example *J. Het. Chem.*, 22(6):1671-1673 (1985)). The group X in C13 may be modified into other groups as shown in Schemes 2 and 3.

Imidazoles of the type D14 can be prepared using the protocol outlined in Scheme 15.

Scheme 14

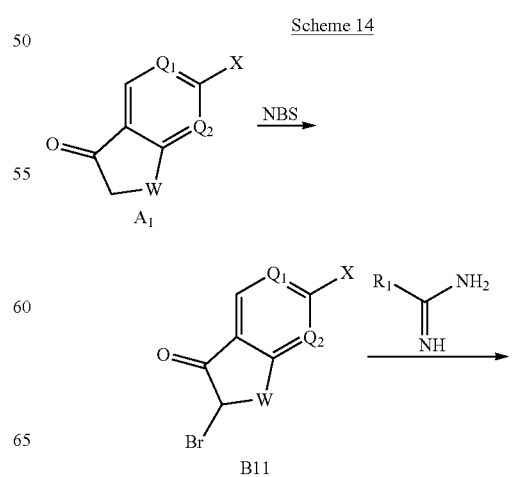

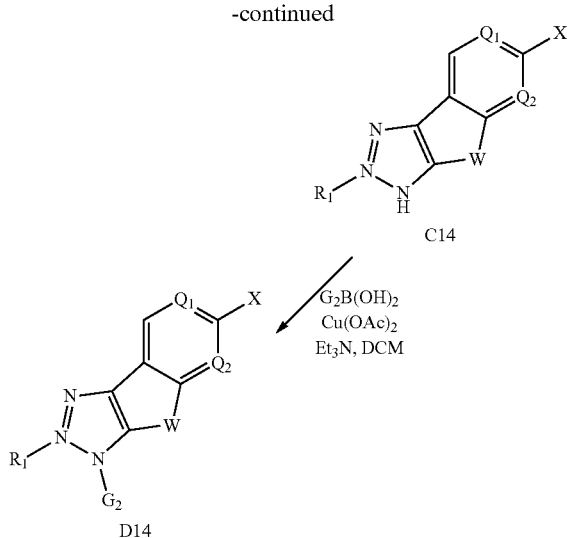

Treatment of B11 (see Scheme 12) with an amidine yield imidazoles of the type C14. Substituted imidazoles of the type D14 can be synthesized from imidazoles of the type C14 using a variety of methods known in the literature (see for example *Synth. Comm.*, 37(6):1001-1009 (2007); *Synlett*, 19:3068-3072 (2008); *J. Org. Chem.*, 73(22):9121-9124 (2008); *J. Org. Chem.*, 71(25):9522-9524 (2006)). If a mixture of products is obtained during this coupling step, these can be easily separated and purified by a variety of separation techniques available. The group X in C14 may be modified into other groups as shown in Schemes 2 and 3.

Pyrazoles of the type C15 and D15 can be prepared using the sequence outlined in Scheme 16. (See for example, *Bioorg. Med. Chem. Letters*, 15(5):1315-1319 (2005); *Bioorg. Med. Chem. Letters*, 13(5):789-794 (2003); *Tetrahedron*, 58(8):1557-1563 (2002)).

Scheme 16

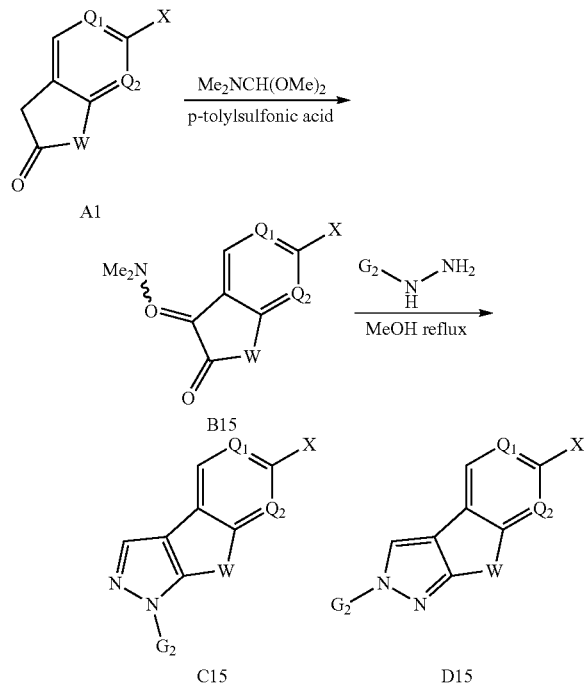

The dimethylamino-methylene derivative B15 may be synthesized by the reaction of the ketone A1 with 1,1-dimethoxy-N,N-dimethylmethanamine in the presence of catalytic amount of acid (such as p-tolylsulfonic acid).

Treatment of the dimethylamino-methylene derivative B15, with a substituted hydrazine leads to the formation of the pyrazoles C15 and D15. The mixture of products is obtained during this coupling step, can be easily separated and purified by a variety of separation techniques available. The group X in C15 and D15 may be modified into other groups as shown in Schemes 2 and 3.

Pyrazoles of the type C16 and D16 can be prepared using the sequence outlined in Scheme 17.

Scheme 17

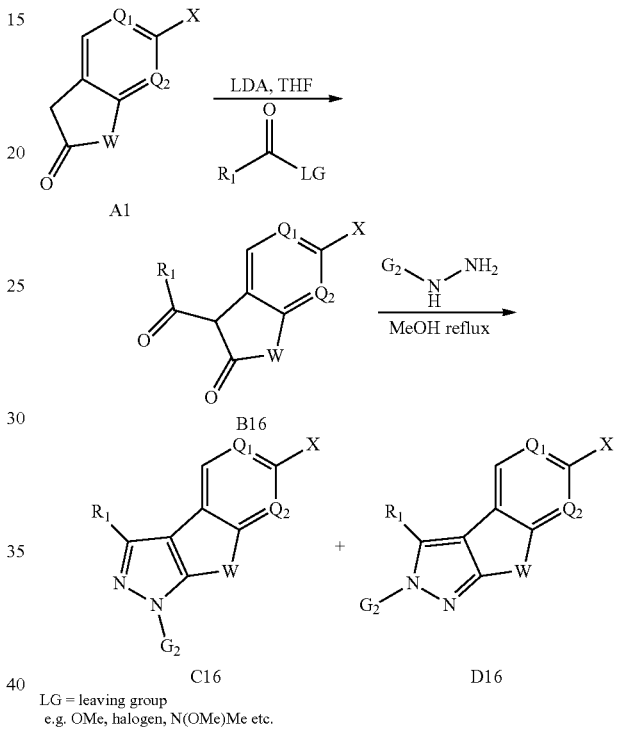

LG = leaving group
e.g. OMe, halogen, N(OMe)Me etc.

The 1,3-diketone B16 may be synthesized by the reaction of the ketone A1 with an acid halide or an ester or a tertiary amide in the presence of a suitable base such as lithium diisopropylamide or lithium hexamethyldisilazane. Treatment of the 1,3-diketone B16, with a substituted hydrazine leads to the formation of the pyrazoles C16 and D16. The mixture of products is obtained during this coupling step, can be easily separated and purified by a variety of separation techniques available. The group X in C16 and D16 may be modified into other groups as shown in Schemes 2 and 3.

Pyrazoles of the type C17 can be prepared using the sequence outlined in Scheme 18 (for example, see *Synthetic Communications*, 38(23):4150-4159 (2008); *Archiv der Pharmazie* (Weinheim, Germany), 341(3):181-190 (2008), *Bioorg. Med. Chem.*, 15(10):3463-3473 (2007)).

Scheme 18

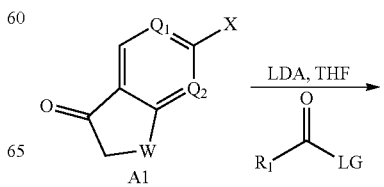

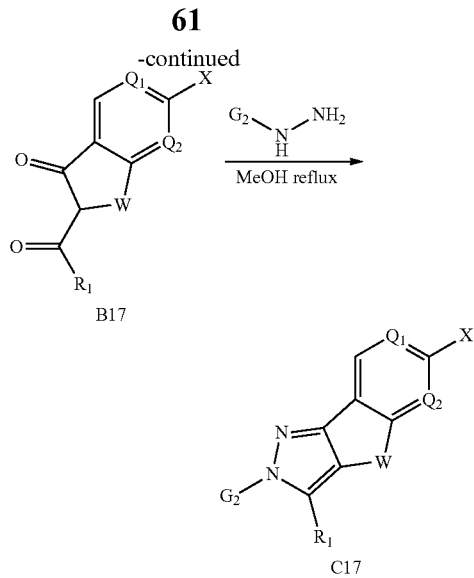

LG = leaving group
e.g. OMe, halogen, N(OMe)Me etc.

The 1,3-diketone B17 may be synthesized by the reaction of the ketone A1 with an acid halide or an ester or a tertiary amide in the presence of a suitable base such as lithium diisopropylamide or lithium hexamethyldisilazane. Treatment of the 1,3-diketone B17, with a substituted hydrazine leads to the formation of the pyrazoles C17. If a mixture of products is obtained during this coupling step, these can be easily separated and purified by a variety of separation techniques available. The group X in C17 may be modified into other groups as shown in Schemes 2 and 3.

ABBREVIATIONS

Ac acetyl
AcOH acetic acid
anhyd. anhydrous
aq. aqueous
9-BBN 9-borabicyclo[3.3.1]nonane
CDI carbonyldiimidazole
Bn benzyl
BOP bis(2-oxo-3-oxazolidinyl)phosphonic
Bu butyl
Boc tert-butoxycarbonyl
Cbz-N N-carbobenzyloxy
$CH_2N_2$ diazomethane
$CH_2Cl_2$ dichloromethane
DCM dichloromethane
DIBAL-H diisobutylaluminum hydride
DMA N,N-dimethylacetamide
DMAP dimethylaminopyridine
DMF dimethylformamide
DMSO dimethylsulfoxide
EDAP ethyldilethylaminopropyl carbodiimide
EDCI 1-(3-dimethylaminopropyl)-3-ethylcarbodiimide hydrochloride
EtOAc ethyl acetate
Et ethyl
EtOH ethanol
H hydrogen
h hour(s)
hrs hour(s)
i iso
HATU (2-(7-Aza-1H-benzotriazole-1-yl)-1,1,3,3-tetramethyluronium hexafluorophosphate)
HMPA hexamethylphosphoramide
HOAc acetic acid
HCl hydrochloric acid
HPLC high pressure liquid chromatography
LAH lithium aluminum hydride
LC liquid chromatography
LDA lithium diisopropylamine
m-CPBA meta-chloroperoxybenzoic acid
Me methyl
MeOH methanol
min. minute(s)
mins minute(s)
$M^{+1}$ $(M+H)^+$
MS mass spectrometry
n normal
NaHMDS sodium bis(trimethylsilyl)amide
NCS N-chlorosuccinamide
NMO N-methylmorpholine-N-oxide
2-$PCy_2$-2'6'-(O-iPr)-2-biphenyl 2-(Dicyclohexylphosphino)-2',6'-isopropoxybiphenyl
PhCONCS benzyolyisothiocyanate
Pd/C palladium on carbon
$Pd(OAc)_2$ palladium acetate
$Pd(PPh_3)_4$ tetrakis(triphenylphosphine)palladium
Ph phenyl
$PPh_3$ triphenylphosphine
Pr propyl
PSI pounds per square inch
Ret Time retention time
rt or RT room temperature
sat. saturated
TEMPO 2,2,6,6-tetramethylpiperidine 1-oxyl
TFA trifluoroacetic acid
THF tetrahydrofuran
TMS trimethylsilane
TMSCN trimethylsilyl cyanide

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps. The intent of describing alternative preparations is to further enable the preparation of the examples of this invention. In some instances some functional groups in the outlined examples and claims may be replaced by well known biosteric replacements known in the art, for example, replacement of a carboxylic acid group with a tetrazole or a phosphate moiety.

Those experiments specifying that they were performed in a microwave oven were conducted in a SmithSynthesizer oven manufactured by Personal Chemistry or a DIS- COVER® microwave oven manufactured by CEM corporation. The microwave ovens generate a temperature which can be selected to be between 60-250° C. The microwave ovens automatically monitor the pressure which is between 0-300 PSI. Reaction hold times and temperature set points are reported.

Abbreviations for Analytical HPLC Conditions:

Condition A: Column: CHROMOLITH® SpeedROD 4.6× 50 mm (4 min.); Solvent A=10% MeOH, 90% $H_2O$, 0.1% TFA; Solvent B=90% MeOH, 10% $H_2O$, 0.1% TFA.

Condition B: YMC COMBISCREEN® ODS-A 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$.

Condition C: Column: YMC COMBISCREEN® S5 50×4.6 mm (4 min; Solvent A=Water 90%/MeOH 10%/ $H_3PO_4$ 0.2%; Solvent B=MeOH 90%/$H_2O$ 10%/$H_3PO_4$ 0.2%.

Condition D: Column: Sunfire C18 3.5 um, 3.0×150 mm; (12 min); Solvent A=0.05% TFA in $H_2O$:MeCN (95:5); Solvent B=0.05% TFA in $H_2O$:MeCN (5:95).

Condition E: Column: BEH C18 2.1×50 mm 1.7 u, Solvent A=100% $H_2O$ w/0.05% TFA; Solvent B=100% ACN w/0.05% TFA.

Condition F: Column: Mac-mod Halo C18, 4.6×50 mm, 2.7-μm particles; solvent A: 5:95 acetonitrile:water with 10 mM ammonium acetate; solvent B: 95:5 acetonitrile:water with 10 mM ammonium acetate.

Condition G: Column: Waters Sunfire C18, 3.5-μm particles (3.0×150 mm); 10-100% B gradient over 12 min, then a 3-minute hold at 100% B. Mobile Phase A=0.05% TFA in $CH_3CN$:Water (10:90), Mobile Phase B=0.1% TFA in $CH_3CN$:Water (90:10); Flow Rate=0.5 ml/min; uv detection 220 nM.

Intermediate 1

6-Vinyl-3,4-dihydronaphthalen-1(2H)-one oxime

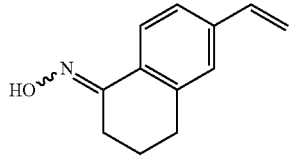

(I-1)

Step A: 5-Oxo-5,6,7,8-tetrahydronaphthalen-2-yl trifluoromethanesulfonate

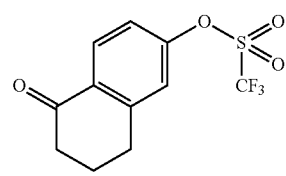

(I-1A)

To a solution of 6-hydroxy-3,4-dihydronaphthalen-1(2H)-one (2 g, 12.33 mmol) in anhydrous pyridine (10 mL) was added trifluoromethanesulfonic anhydride (2.5 mL, 14.80 mmol) at 0° C. over a period of 5 min. The reaction mixture was allowed to come to room temperature and stirred at room temperature for 4 h. The reaction mixture was concentrated under reduced pressure. The resulting brownish red residue was partitioned between ether (60 mL) and water (30 mL). The ether layer was sequentially washed with 1N hydrochloric acid (20 mL), sat. aq. $NaHCO_3$ (20 mL), brine (20 mL), dried over sodium sulfate, concentrated, and purified by silica gel column chromatography using hexane/ethyl acetate to yield 5-oxo-5,6,7,8-tetrahydronaphthalen-2-yl trifluoromethanesulfonate (3.4 g, 11.55 mmol, 94% yield) as a liquid. $^1$H NMR (400 MHz, $CDCl_3$) δ ppm 8.14 (1H, d, J=8.4 Hz), 7.17-7.24 (2H, m), 3.02 (2H, t, J=6.1 Hz), 2.69 (2H, t, J=6.5 Hz), 2.15-2.22 (2H, m).

Step B: 6-Vinyl-3,4-dihydronaphthalen-1(2H)-one

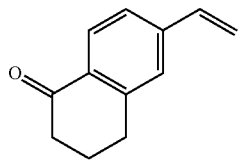

(I-1B)

To a solution of 5-oxo-5,6,7,8-tetrahydronaphthalen-2-yl-trifluoromethanesulfonate (Intermediate I-1A, 3.4 g, 11.55 mmol) in anhydrous dioxane was sequentially added tributyl (vinyl)stannane (3.73 mL, 12.71 mmol), lithium chloride (1.470 g, 34.7 mmol), and tetrakis(triphenylphosphine)palladium(0) (1.335 g, 1.155 mmol). The reaction mixture was purged with nitrogen gas for 5 min. and heated at 100° C. for 14 h. The reaction mixture was cooled to room temperature and filtered. The yellow residue was washed with ethyl acetate (3×20 ml). The filtrate was concentrated under reduced pressure. To the red oil was added ether (50 mL) and the contents were stirred at room temperature for 15 min. The contents were filtered and the resulting brick red residue was washed with ether (3×20 mL). The filtrate was concentrated under reduced pressure and the resulting red oil was purified by silica gel column chromatography using hexane/ethyl acetate to yield 6-vinyl-3,4-dihydronaphthalen-1(2H)-one (1.6 g, 9.29 mmol, 80% yield) as a pale yellow oil. $^1$H NMR (400 MHz, $CDCl_3$) δ ppm 2.10-2.17 (m, 2H) 2.63-2.67 (m, 2H) 2.96 (t, J=6.05 Hz, 2H) 5.37-5.41 (m, 1H) 5.87 (dd, J=17.61, 0.66 Hz, 1H) 6.72 (dd, J=17.61, 11.00 Hz, 1H) 7.26 (s, 1H) 7.36 (dd, J=8.14, 1.10 Hz, 1H) 8.00 (d, J=8.14 Hz, 1H).

Intermediate 1

To 6-vinyl-3,4-dihydronaphthalen-1(2H)-one (Intermediate I-1B, 1.6 g, 9.29 mmol) in methanol (10 mL) was sequentially added hydroxylamine hydrochloride (0.775 g, 11.15 mmol) and sodium acetate (0.915 g, 11.15 mmol). The reaction mixture was heated at 80° C. (oil bath temp.) for 1.5 h. The reaction mixture was concentrated under reduced pressure and to the residue was added water (30 mL). The contents were triturated and filtered. The solid material was washed with water (2×20 mL) and dried overnight to yield 6-vinyl-3,4-dihydronaphthalen-1(2H)-one oxime (1.2 g, 6.41 mmol, 69.0% yield) as a white solid. $^1$H NMR (400 MHz, $CDCl_3$) δ ppm 1.81-1.94 (m, 2H) 2.71-2.87 (m, 4H) 5.23-5.32 (m, 1H)

5.78 (dd, J=17.61, 0.88 Hz, 1H) 6.69 (dd, J=17.61, 10.78 Hz, 1H) 7.18 (s, 1H) 7.28 (s, 1H) 7.85 (d, J=8.14 Hz, 1H) 8.23 (br. s., 1H).

Intermediate 2

6-Methoxy-3,4-dihydronaphthalen-1(2H)-one oxime

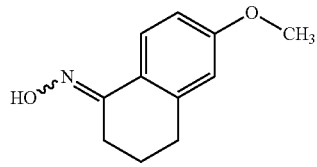
(I-2)

A solution of 6-methoxy-3,4-dihydronaphthalen-1(2H)-one (5 g, 28.4 mmol), hydroxylamine hydrochloride (2.366 g, 34.0 mmol) and sodium acetate (2.79 g, 34.0 mmol) in anhydrous methanol (20 mL) was heated at 80° C. (oil bath temp.) for 2 h. The reaction mixture was cooled to room temperature and concentrated under reduced pressure. Next, 75 mL of water was added to the resulting solid and the contents were triturated and filtered. The solid was washed with addition water (2×50 mL), toluene (50 mL) and then dried for 80 h to yield 4.2 g of the oxime as a white solid. A second crop of additional product (1.1 g of pink solid) was obtained from the mother liquor. $^1$H NMR (400 MHz, CDCl$_3$) δ ppm 1.83-1.91 (m, 2H) 2.70-2.83 (m, 4H) 3.81 (s, 3H) 6.66 (d, J=2.76 Hz, 1H) 6.77 (dd, J=8.78, 2.76 Hz, 1H) 7.83 (d, J=8.78 Hz, 1H) 8.32 (br. s., 1H).

Intermediate 3

Methyl 3-phenyl-4-(trifluoromethyl)isoxazole-5-carboxylate

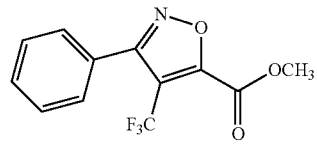
(I-3)

Step A: 4,4-Trifluorobut-2-yn-1-ol

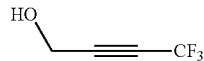
(I-3A)

To a solution of diisopropylamine (24.7 mL, 176 mmol) in ether (100 mL) at −78° C. was added a 10 M solution of butyllithium in ether (17.6 mL, 176 mmol) over 5 min. After 10 min. at −78° C., 2-bromo-3,3,3-trifluoroprop-1-ene (14.0 g, 80 mmol) was added to the pale yellow solution. After an additional 10 min., paraformaldehyde (2.40 g, 80 mmol) was added, the dry-ice bath was removed, and the reaction mixture was stirred at room temperature overnight. The reaction was quenched with a 1N aqueous solution of hydrochloric acid (100 mL), diluted with ether (500 mL), washed with a 1N aqueous solution of hydrochloric acid (2×100 mL), brine (100 mL), and dried over anhydrous sodium sulfate. Concentration under reduced pressure afforded a dark liquid which was distilled under Low-Vacuum (~50 Torr, ~50° C.) to give 4,4,4-trifluorobut-2-yn-1-ol (7.1 g, 57.2 mmol, 72% yield) as a pale yellow liquid. $^1$H NMR (500 MHz, CDCl$_3$) δ ppm 2.31 (br. s., 1H) and 4.38-4.42 (m, 2H).

Step B: (Z)—N-Hydroxybenzimidoyl chloride

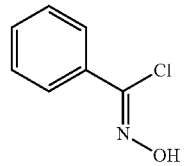
(I-3B)

(Ref.: Liu, K.-C. et al., J. Org. Chem., 45:3916-1918 (1980))

To a colorless, homogeneous solution of (E)-benzaldehyde oxime (24.4 g, 201 mmol) in N,N-dimethylformamide (60 mL) at room temperature was added N-chlorosuccinimide (26.9 g, 201 mmol) portion-wise over 30 min. During each addition, the reaction mixture turned yellow and then gradually returned to near colorlessness. Additionally, an exotherm was noted with each portion added. (It was extremely important to make sure that the reaction was initiated after the addition of the first ~⅕ of the N-chlorosuccinimide.). After the addition was complete, the homogeneous reaction mixture was stirred overnight at room temperature. The reaction mixture was diluted with 250 mL of water and extracted with ether (3×100 mL). The organic layers were combined, washed with water (2×100 mL), 10% aqueous solution of lithium chloride (2×100 mL), and brine (100 mL). The four aqueous layers were back extracted with ether (100 mL), and the combined organic layers (400 mL) were dried over anhydrous sodium sulfate. Concentration under reduced pressure afforded (Z)—N-hydroxybenzimidoyl chloride (30.84 g, 198 mmol, 98% yield) as a fluffy, pale yellow solid. The product had an HPLC ret. time=1.57 min. (condition A); LC/MS $M^{+1}$=155.8; $^1$H NMR (500 MHz, DMSO-d$_6$) δ ppm 7.30-7.64 (m, 3H), 7.73-7.87 (m, 2H), and 12.42 (s, 1H).

Step C: 3-Phenyl-4-(trifluoromethyl)isoxazol-5-yl)methanol

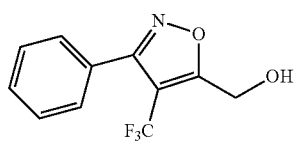
(I-3C)

To a pale yellow, homogeneous mixture of (Z)—N-hydroxybenzimidoyl chloride (Intermediate I-3B, 5.50 g, 35.4 mmol) and 4,4,4-trifluorobut-2-yn-1-ol (Intermediate I-3A, 5.46 g, 39.6 mmol) in dichloroethane (85 mL) in a 250 mL round bottom flask at 70° C. was added triethylamine (9.85 mL, 70.7 mmol) in 22 mL of dichloroethane over 2.5 h via an addition funnel (the first ~50% over 2 h and the remaining 50% over 0.5 h). The reaction mixture was stirred at room temperature overnight, diluted with dichloromethane (100 mL), washed with water (100 mL), and the organic layer was collected. The aqueous layer was extracted with dichloromethane (2×50 mL), and the combined organic layers were dried over anhydrous sodium sulfate. The solvent was removed under reduced pressure. Analysis indicated that the product mixture was composed of a 86:14 mixture of the desired regioisomer, (3-phenyl-4-(trifluoromethyl)isoxazol-5-yl)methanol, and the undesired regioisomer, (3-phenyl-5-(trifluoromethyl)isoxazol-4-yl)methanol. The mixture was purified by silica gel chromatography using a mixture of ethyl acetate and hexane to afford (3-phenyl-4-(trifluoromethyl)isoxazol-5-yl)methanol (5.34 g, 21.96 mmol, 62.1% yield) as a pale yellow oil. The compound had an HPLC ret. time=1.91 min. (condition A); LC/MS M$^{+1}$=244.2; $^1$H NMR (500 MHz, CDCl$_3$) δ ppm 2.21 (br. s., 1H), 4.97 (s, 2H), 7.47-7.56 (m, 3H), and 7.65 (d, J=6.60 Hz, 2H).

Step D:
3-Phenyl-4-(trifluoromethyl)isoxazole-5-carboxylic acid

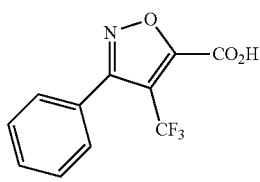

(I-3D)

A mixture of (3-phenyl-4-(trifluoromethyl)isoxazol-5-yl)methanol (Intermediate I-3C, 2.1 g, 8.64 mmol), TEMPO (0.094 g, 0.604 mmol), and a sodium phosphate buffer (0.67 M) (32.2 mL, 21.59 mmol) in acetonitrile (30 mL) was heated to 35° C. A fresh solution of sodium phosphate buffer (40 mL, pH ~6.5) consisting of a 1:1 solution of NaH$_2$PO$_4$ (20 mL, 0.67 M) and Na$_2$HPO$_4$ (20 mL, 0.67 M) was prepared and used. Solutions of sodium chlorite (3.91 g, 34.5 mmol) in water (4.5 mL) and bleach (4.3 mL, 6% wt.) were added simultaneously over 40 min. The reaction was monitored by HPLC, and after 2 h, ~30% of the starting material remained. After 6 h, 10% remained. Additional bleach (100 μL) was added, and the reaction mixture was left at room temperature overnight.

Additional bleach (100 μL) was added. The resulting mixture was allowed to stir at 35° C. for additional 2 h. The reaction was quenched by the slow addition of a solution of sodium sulfite (2.07 mL, 43.2 mmol) in water (90 mL) at 0° C., resulting in the disappearance of the brown reaction color. The solvent was removed under reduced pressure, and the remaining aqueous residue was extracted with ethyl acetate (3×40 mL). The organic layers were combined, washed with water (8 mL), washed with brine (8 mL), and dried over anhydrous sodium sulfate. Concentration under reduced pressure afforded 3-phenyl-4-(trifluoromethyl)isoxazole-5-carboxylic acid (2.2 g, 8.55 mmol, 99% yield) as a pale yellow solid. The product was >99% pure by HPLC with a ret. time=1.60 min. (condition A); LC/MS M$^{+1}$=258.1; $^1$H NMR (500 MHz, DMSO-d$_6$) δ ppm 7.55-7.63 (m, 5H).

Intermediate 3

To a solution of 3-phenyl-4-(trifluoromethyl)isoxazole-5-carboxylic acid (Intermediate I-3D, 0.500 g, 1.94 mmol) in dichloromethane (5 mL) and methanol (1 mL) at room temperature was added trimethyldiazomethane (2.0 M in ether) (1.26 mL, 2.53 mmol) slowly over 5 min. The resulting reaction mixture was stirred for 30 min. The reaction mixture was diluted with dichloromethane (40 mL) and washed with brine (20 mL). The aqueous layer was extracted with dichloromethane (2×20 mL), and the organic layers were combined and dried over anhydrous sodium sulfate. Concentration under reduced pressure afforded methyl 3-phenyl-4-(trifluoromethyl)isoxazole-5-carboxylate (0.513 g, 1.89 mmol, 97% yield) as a yellow oil. The product had an HPLC ret. time=2.55 min. (condition A); LC/MS M$^{+1}$=272.0; $^1$H NMR (400 MHz, CDCl$_3$) δ ppm 4.07 (s, 3H), 7.47-7.56 (m, 3H), and 7.59 (d, J=7.04 Hz, 2H).

Intermediate 4

3-Phenyl-4-(trifluoromethyl)isoxazole-5-carbonyl fluoride

(I-4)

To a mixture of 3-phenyl-4-(trifluoromethyl)isoxazole-5-carboxylic acid (Intermediate I-3D, 3.00 g, 11.7 mmol) and pyridine (1.13 mL, 14.0 mmol) in dichloromethane (100 mL) at room temperature was added 2,4,6-trifluoro-1,3,5-triazine (cyanuric fluoride) (1.18 mL, 14.0 mmol). The reaction mixture was stirred at room temperature overnight, diluted with dichloromethane (300 mL), washed with an ice-cold solution of 0.5N aqueous hydrochloric acid (2×100 mL), and the organic layer was collected. The aqueous layer was back-extracted with dichloromethane (200 mL), and the combined organic layers were dried anhydrous sodium sulfate and concentrated to afford 3-phenyl-4-(trifluoromethyl)isoxazole-5-carbonyl fluoride (2.91 g, 11.2 mmol, 96% yield) as a yellow, viscous oil. The product was found to react readily with methanol and on analysis was characterized as the methyl ester, which had an HPLC ret. time=2.56 min. —(Condition A); LC/MS M$^{+1}$=272.3 (methyl ester).

Intermediate 5

Methyl 5-phenyl-4-(trifluoromethyl)isoxazole-3-carboxylate

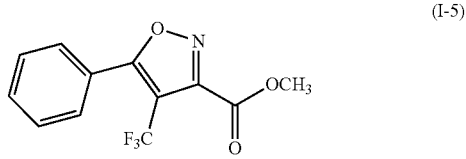 [SMILES: COC(=O)c1noc(-c2ccccc2)c1C(F)(F)F]

(I-5)

Step A: Ethyl 5-phenylisoxazole-3-carboxylate

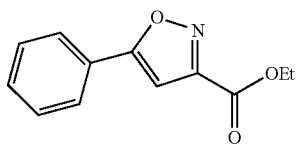
(I-5A)

To a mixture of (Z)-ethyl 2-chloro-2-(hydroxyimino)acetate (3.03 g, 20 mmol) and ethynylbenzene (4.39 mL, 40 mmol) in ether (80 mL) at room temperature was added a solution of triethylamine (5.58 mL, 40.0 mmol) in ether (20 mL) dropwise over 60 minutes. The reaction mixture was stirred for 2 h at room temperature and filtered. The filtrate was concentrated to give an yellow oil which was purified by flash silica gel chromatography using a mixture of ethyl acetate in hexane (0-12%) to afford ethyl 5-phenylisoxazole-3-carboxylate (3.06 g, 14.09 mmol, 70% yield) as a white solid. The compound had an HPLC retention time=2.99 minutes (YMC-Combi 4.6×50 mm S-5 ODS column) eluting with 10-90% aqueous methanol+0.2% phosphoric acid over a 4 minute gradient. MS:(M+H)=218.12. $^1$H NMR (400 MHz, CDCl$_3$) δ ppm 1.45 (t, J=7.3 Hz, 3H), 4.48 (q, J=7.3, 2H), 6.93 (s, 1H), 7.45-7.53 (m, 3H), and 7.77-7.85 (m, 2H).

Step B: Ethyl 4-iodo-5-phenylisoxazole-3-carboxylate

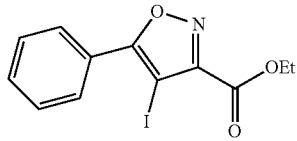
(I-5B)

A mixture of ethyl 5-phenylisoxazole-3-carboxylate (Intermediate I-5A, 3.05 g, 14.0 mmol) and N-iodosuccinimide (3.79 g, 16.9 mmol) in TFA (78 mL) was stirred at room temperature for 3.5 h. The volatiles were removed under reduced pressure, and the residue was partitioned between ethyl acetate (150 mL) and water (150 mL). The organic layer was washed with a 1N aqueous solution of sodium hydroxide (150 mL), washed with a 3% aqueous solution of sodium bisulfite (2×150 mL), washed with brine (150 mL), and dried over anhydrous magnesium sulfate. Concentration under reduced pressure afforded ethyl 4-iodo-5-phenylisoxazole-3-carboxylate (4.69 g, 13.7 mmol, 97% yield) as a light yellow oil. The compound had an HPLC retention time=3.36 minutes (condition A); MS:(M+H)=343.97; $^1$H NMR (400 MHz, CDCl$_3$) δ ppm 1.47 (t, J=7.1 Hz, 3H), 4.50 (q, J=7.0 Hz, 2H), 7.52-7.56 (m, 3H), and 8.05 (m, 2H).

Step C: Ethyl 5-phenyl-4-(trifluoromethyl)isoxazole-3-carboxylate

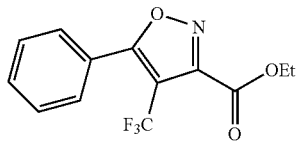
(I-5C)

To a solution of ethyl 4-iodo-5-phenylisoxazole-3-carboxylate (Intermediate I-5B, 4.62 g, 13.5 mmol) and copper (I) iodide (0.513 g, 2.69 mmol) in N,N-dimethylformamide (59.8 mL) and HMPA (7.48 mL) at room temperature was added methyl 2,2-difluoro-2-(fluorosulfonyl)acetate (6.86 mL, 53.9 mmol) at once. The reaction mixture was immediately immersed in an oil bath at 75-80° C. Stirring was continued at this temperature for 3.5 h. After cooling to room temperature, the reaction mixture was cooled in an ice bath. A saturated aqueous solution of ammonium chloride (~50 mL) was added slowly to quench the reaction. The mixture was partitioned between ethyl ether (400 mL) and a saturated aqueous solution of ammonium chloride (400 mL). The organic layer was washed with a saturated aqueous solution of ammonium chloride (200 mL), washed with water (2×200 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (3.6 g, 12.6 mmol, 94% yield) as a colorless oil. The compound had an HPLC retention time=3.44 minutes (condition A); MS:(M+H)=286.01; $^1$H NMR (400 MHz, CDCl$_3$) δ ppm 1.45 (t, J=7.2 Hz, 3H), 4.51 (q, J=7.3 Hz, 2H), 7.52-7.62 (m, 3H), and 7.69 (d, J=7.5 Hz, 2H).

Step D: 5-Phenyl-4-(trifluoromethyl)isoxazole-3-carboxylic acid

(I-5D)

To a solution of ethyl 5-phenyl-4-(trifluoromethyl)isoxazole-3-carboxylate (Intermediate I-5C, 3.6 g, 12.6 mmol) in methanol (100 mL) and water (20 mL) at room temperature was added lithium hydroxide, monohydrate (0.583 g, 13.9 mmol). The reaction mixture was stirred at room temperature for 30 minutes. The methanol was removed under reduced pressure, and the residue was diluted with water (~100 mL). Ethyl ether (200 mL) was added, and the pH of the aqueous layer was adjusted to <1 with a 1N aqueous solution of hydrochloric acid. The mixture was transferred to a separatory funnel, and after agitation, the layers were separated. The organic layer was washed with brine (100 mL), dried over anhydrous magnesium sulfate, and concentrated to afford 5-phenyl-4-(trifluoromethyl)isoxazole-3-carboxylic acid (3.12 g, 12.13 mmol, 96% yield) as a white, crystalline solid. The compound had an HPLC retention time=2.58 minutes (condition B); MS:(M+Na)=279.95; $^1$H NMR (400 MHz, CDCl$_3$) δ ppm 7.53-7.64 (m, 3H), and 7.70 (d, J=7.5 Hz, 2H).

Intermediate 5

To a solution of 5-phenyl-4-(trifluoromethyl)isoxazole-3-carboxylic acid (Intermediate I-5D, 0.500 g, 1.94 mmol) in dichloromethane (5 mL) and methanol (1 mL) at room temperature was added trimethyldiazomethane (2.0 M in ether) (1.17 mL, 2.33 mmol) slowly over 10 min. During the addition, the solution remained colorless and the evolution of gas nitrogen was noted. Toward the end of the addition, the bubbling ceased and the solution became pale yellow. The reaction mixture was stirred overnight. The reaction mixture was diluted with dichloromethane (40 mL) and washed with brine (20 mL). The aqueous layer was extracted with dichloromethane (2×20 mL), and the organic layers were combined and dried over anhydrous sodium sulfate. Concentration under reduced pressure afforded methyl 5-phenyl-4-(trifluoromethyl)isoxazole-3-carboxylate (0.509 g, 1.88 mmol, 97% yield) as a yellow oil. The product had an HPLC with a ret. time=2.52 min. (condition A); $^1$H NMR (400 MHz, CDCl$_3$) δ ppm 4.05 (s, 3H), 7.50-7.64 (m, 3H), and 7.70 (d, J=7.48 Hz, 2H).

Intermediate 6 tert-Butyl azetidine-3-carboxylate acetic acid salt

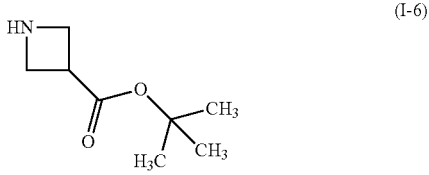
(I-6)

Step A:
1-(Benzyloxycarbonyl)azetidine-3-carboxylic acid

(I-6A)

To a solution of azetidine-3-carboxylic acid (88 g, 0.871 mol) and sodium bicarbonate (161 g, 1.92 mol) in water (1.75 L) at room temperature was added a solution of benzyl 2,5-dioxopyrrolidin-1-ylcarbonate (239 g, 0.959 mol) in THF (3.5 L). The reaction mixture was stirred at room temperature overnight. The solvent was removed under reduced pressure, and the aqueous layer was washed with ethyl acetate (2×500 mL). The aqueous layer was acidified with a 1.0 N aqueous hydrochloric acid solution and was then extracted with ethyl acetate (3×750 mL). The organic layer was washed with water, followed by brine, and dried over anhydrous sodium sulfate. Concentration under reduced pressure afforded 1-(benzyloxycarbonyl)azetidine-3-carboxylic acid as colorless oil (202 g, 99% yield). The compound had an HPLC retention time=2.27 min (condition B); LC/MS M$^{+1}$=236.15. $^1$H NMR (400 MHz, CDCl$_3$) δ ppm 3.39-3.49 (m, 1H), 4.22 (d, J=7.28 Hz, 4H), 5.11 (s, 2H), and 7.29-7.39 (m, 5H).

Step B: 1-Benzyl 3-tert-butyl azetidine-1,3-dicarboxylate

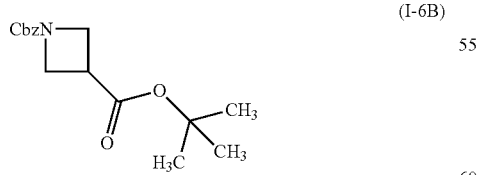
(I-6B)

To a solution of 1-(benzyloxycarbonyl)azetidine-3-carboxylic acid (Intermediate I-6A, 200 g, 0.851 mol) in dichloromethane (6.0 L) at 0° C. was added t-butanol (158 g, 2.13 mol), DMAP (52.0 g, 0.425 mol), and EDCI (163 g, 0.853 mol). The reaction mixture was stirred at room temperature overnight. Next, the reaction mixture was concentrated and the residue was dissolved in ethyl acetate. The organic layer washed with 10% aqueous citric acid, 10% aqueous sodium bicarbonate solution, and brine. Drying over anhydrous sodium sulfate and concentration under reduced pressure afforded 1-benzyl-3-tert butyl-azetidine-1,3-dicarboxylate (200 g, 81% yield) as a colorless oil. The compound had an HPLC retention time=3.27 min. (condition B); LC/MS M$^{+1}$=292.15. $^1$H NMR (400 MHz, CDCl$_3$) δ ppm 1.46 (s, 9H), 3.24-3.33 (m, 1H), 4.14 (d, J=7.53 Hz, 4H), 5.10 (s, 2H), and 7.30-7.39 (m, 5H).

Intermediate 6

A mixture of 1-benzyl-3-tert-butyl-azetidine-1,3-dicarboxylate (Intermediate I-6B, 140 g, 0.480 mol) and 10% palladium on carbon (28.0 g) in ethyl acetate (1.40 L) was placed in an autoclave under 3.0 kg/cm$^2$ of hydrogen pressure overnight. The reaction mixture was filtered through CELITE®, and the CELITE® bed was washed with ethyl acetate. Acetic acid (28.9 g, 0.480 mol) was added to the filtrate and it was concentrated under reduced pressure maintaining the temperature below 50° C. to give tert-butyl azetidine-3-carboxylate acetic acid salt (96 g, 92% yield) as a colorless oil. $^1$H NMR (400 MHz, CDCl$_3$) δ ppm 1.47 (s, 9H), 2.02 (s, 3H), 3.52-3.63 (m, 1H), and 4.00-4.10 (m, 4H).

Intermediate 7

Ethyl 3-(1-(4-fluorophenyl)cyclohexyl)propanoate

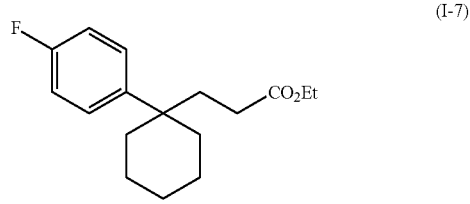 [SMILES: CCOC(=O)CCC1(c2ccc(F)cc2)CCCCC1]
(I-7)

Step A: 1-(4-Fluorophenyl)cyclohexanecarbaldehyde

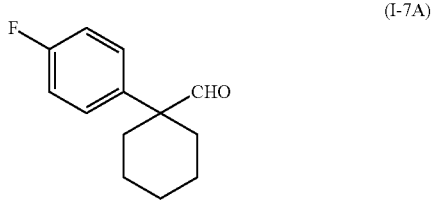 [SMILES: O=CC1(c2ccc(F)cc2)CCCCC1]
(I-7A)

To a solution of 1-(4-fluorophenyl)cyclohexanecarbonitrile (14 g, 68.9 mmol) in toluene (140 mL) at 0° C. was added 1 M diisobutylaluminum hydride (100 mL, 100 mmol) in dichloromethane dropwise, and the mixture was stirred for 3 hrs at room temperature. To the mixture was added 170 mL of 2N HCl slowly with stirring. After stirring for 20 mins, the product was extracted with ethyl acetate, and the extracts were washed with water and brine. It was dried over sodium sulfate and evaporated to give 1-(4-fluorophenyl)cyclohexanecarbaldehyde (14.2 g, 100% yield) as an oil. $^1$H NMR (400 MHz, CDCl$_3$) δ ppm 9.34 (1H, s), 7.28 (2H, dd, J=9.02, 5.28 Hz), 7.04 (2H, t, J=8.80 Hz), 2.28 (2H, dd, J=13.29, 4.72 Hz), 1.76-1.85 (2H, m), 1.24-1.73 (6H, m).

Step B: (E)-Ethyl 3-(1-(4-fluorophenyl)cyclohexyl)acrylate

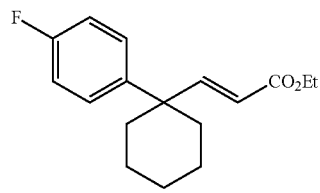

(I-7B)

To a solution of ethyl 2-(diethoxyphosphoryl)acetate (0.714 mL, 3.57 mmol) in 10 mL of THF at 0° C. was added 1 M potassium tert-butoxide in THF (3.57 mL, 3.57 mmol) dropwise, and the mixture was stirred for 15 mins at the same temperature. Then a solution of 1-(4-fluorophenyl)cyclohexanecarbaldehyde (Intermediate I-7A, 368 mg, 1.784 mmol) in 3 mL of THF was added dropwise, and the mixture was stirred at room temperature for 18 hrs. The reaction mixture was partitioned between ethyl acetate and water. The ethyl acetate extract was washed with brine, dried over sodium sulfate and evaporated to give an oily residue which was purified by Combiflash (80 g silica gel) eluting with hexane followed by 5:95 EtOAc-hexane to give the desired (E)-ethyl 3-(1-(4-fluorophenyl)cyclohexyl)acrylate (453 mg, 92% yield). $^1$H NMR (400 MHz, CDCl$_3$) δ ppm 7.28 (2H, dd, J=9.02, 5.28 Hz), 7.01 (2H, t, J=8.80 Hz), 6.95 (1H, d, J=16.07 Hz), 5.60 (1H, d, J=16.07 Hz), 4.16 (2H, q, J=7.26 Hz), 1.99-2.08 (2H, m), 1.85-1.94 (2H, m), 1.39-1.62 (6H, m), 1.27 (3H, t, J=7.15 Hz).

Intermediate 7

To a solution of (E)-ethyl 3-(1-(4-fluorophenyl)cyclohexyl)acrylate (Intermediate I-7B, 1 g, 3.62 mmol) in methanol (25 mL) was added 10% Pd/C (~0.5 g, wet 50%) under argon, and the mixture was stirred under hydrogen atmosphere (50 psi) for 16 hrs. The reaction mixture was filtered through CELITE® and evaporated to give the desired ethyl 3-(1-(4-fluorophenyl)cyclohexyl)propanoate (1 g, 99% yield) as an oil. $^1$H NMR (400 MHz, CDCl$_3$) δ ppm 7.25 (2H, dd, J=9.02, 5.28 Hz), 7.00 (2H, t, J=8.80 Hz), 4.02 (2H, q, J=7.26 Hz), 2.00-2.08 (2H, m), 1.89-1.96 (2H, m), 1.81-1.87 (2H, m), 1.34-1.61 (8H, m), 1.18 (3H, t, J=7.15 Hz).

Intermediate 8

Ethyl 3-(1-(3,5-dichlorophenyl)cyclohexyl)propanoate

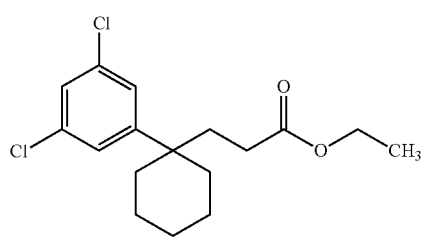

(I-8)

Step A: 1-(3,5-Dichlorophenyl)cyclohexanecarbonitrile

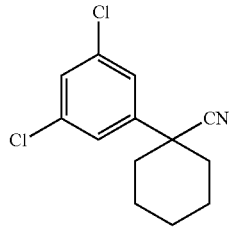

(I-8A)

To a solution of 2-(3,5-dichlorophenyl)acetonitrile (2 g, 10.75 mmol) in N,N-dimethylformamide (40 mL) at 0° C. was added 60% sodium hydride (0.946 g, 23.65 mmol) and the mixture was stirred for 1 min. Then 1,5-dibromopentane (1.464 mL, 10.75 mmol) was added, and the mixture was stirred at 0° C. for 1 hr and at room temperature for 14 hrs. About 100 mL of water was added, and the product was extracted with ethyl acetate. The extract was washed with water and brine. The combined aqueous layers were extracted with ethyl acetate once and washed with brine. The extracts were dried over sodium sulfate and evaporated to give an oily residue. It was purified by Combiflash (120 g silica gel) by eluting with 5:95 EtOAc-hexane to give the desired 1-(3,5-dichlorophenyl)cyclohexanecarbonitrile (2.16 g, 79% yield) as a crystalline solid. $^1$H NMR (400 MHz, CDCl$_3$) δ ppm 7.38 (2H, d, J=1.76 Hz), 7.32 (1H, t, J=1.76 Hz), 2.14 (2H, d, J=11.86 Hz), 1.67-1.94 (8H, m).

This compound was converted to the titled ethyl 3-(1-(3,5-dichlorophenyl)cyclohexyl)propanoate using the protocol outlined for intermediate 7. 1H NMR (400 MHz, CDCl$_3$) δ ppm 7.05-7.12 (3H, m), 3.93 (2H, q, J=7.32 Hz), 1.68-1.94 (6H, m), 1.18-1.53 (8H, m), 1.11 (3H, t, J=7.03 Hz).

Intermediate 9

Ethyl 4-(4-chlorophenyl)-4-methylpentanoate

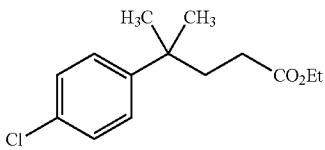

(I-9)

Step A: 2-(4-Chlorophenyl)-2-methylpropanal

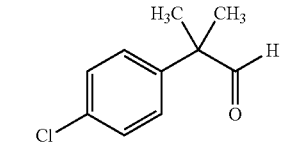

(I-9A)

To a stirring solution of oxalyl chloride (1.422 mL, 16.25 mmol) in 40 mL of dichloromethane at −5° C. was added dimethylsulfoxide (1.153 mL, 16.25 mmol) dropwise. After 15 min of stirring, a solution of 2-(4-chlorophenyl)-2-methylpropan-1-ol (1.0 g, 5.42 mmol) in 15 mL of dichloromethane was added dropwise and the resulting mixture was stirred for 30 min at the same temperature. Then triethylamine (3.02 mL, 21.66 mmol) was added and the resulting mixture was stirred for 1 hr at −20° C. with gradual warm-up to room temperature over 2 hrs. The reaction was quenched with water and extracted with ether. The organic layer was separated and washed with brine. It was then dried over anhyd. magnesium sulfate, concentrated and chromatographed using silica gel flash chromatography to yield 2-(4-chlorophenyl)-2-methylpropanal (0.82 g, 4.49 mmol, 83% yield) as a clear oil. ¹H NMR (400 MHz, CDCl₃) δ ppm 9.48 (1H, s), 7.33-7.39 (2H, m), 7.21 (2H, d, J=8.79 Hz), 1.46 (6H, s).

Step B: Ethyl 4-(4-chlorophenyl)-4-methylpent-2-enoate

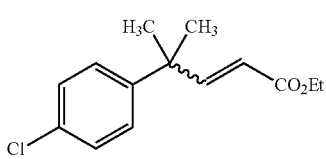

(I-9B)

To a stirring suspension of the triethyl phosphonoacetate (1.695 mL, 8.54 mmol) in 10 mL THF at 0° C. was added 1 M potassium tert-butoxide in THF (8.54 mL, 8.54 mmol). The resulting reddish orange solution was stirred for 30 min and then treated with a solution of the 2-(4-chlorophenyl)-2-methylpropanal (Intermediate I-9A, 0.78 g, 4.27 mmol) in 2.5 mL of THF and slowly warmed to room temperature. The reaction mixture was stirred at room temperature for 3 hrs and quenched with saturated. aq. ammonium chloride. The reaction mixture was partitioned between ethyl acetate and water. The organic layer was then washed with brine, dried over anhyd. magnesium sulfate, concentrated and chromatographed using silica gel flash chromatography to yield ethyl 4-(4-chlorophenyl)-4-methylpent-2-enoate (0.48 g, 1.899 mmol, 44.5% yield) as a clear oil. ¹H NMR (400 MHz, CDCl₃) δ ppm 7.28 (2H, d, J=8.79 Hz), 7.22 (2H, d, J=8.79 Hz), 7.08 (1H, d, J=16.26 Hz), 5.79 (1H, d, J=15.82 Hz), 4.20 (2H, q, J=7.03 Hz), 1.29 (3H, t, J=7.25 Hz).

Intermediate 9

Ethyl 4-(4-chlorophenyl)-4-methylpent-2-enoate (Intermediate I-9B, 0.24 g, 0.950 mmol) was dissolved in methanol (20 mL) and treated with 10% Pd/C (0.06 g, 0.282 mmol) under a hydrogen atmosphere for 1 hr using a balloon. The reaction mixture was filtered through CELITE®. The filtrate was concentrated under reduced pressure to yield ethyl 4-(4-chlorophenyl)-4-methylpentanoate in quantitative yield. LC/MS M⁺¹=255.11.

Intermediate 10

Methyl 2-((1-(4-fluorophenyl)cyclohexyl)methoxy)acetate

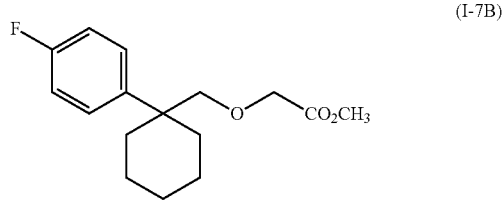 [SMILES: COC(=O)COCC1(c2ccc(F)cc2)CCCCC1]

(I-7B)

Step A: (1-(4-Fluorophenyl)cyclohexyl)methanol

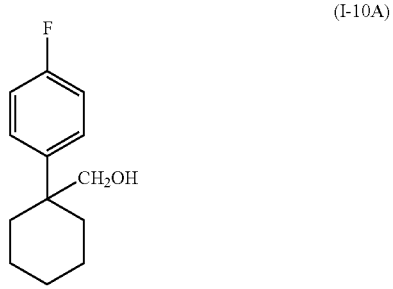 [SMILES: OCC1(c2ccc(F)cc2)CCCCC1]

(I-10A)

A 1 M solution of borane-THF complex (16.7 mL, 16.7 mmol) was slowly added to a solution of (1-(4-fluorophenyl)cyclohexane carboxylic acid (928 mg, 4.18 mmol) in THF (15 mL) at room temperature under a nitrogen atmosphere. After 20 min., the reaction mixture was refluxed for 16 hrs, cooled to room temperature and quenched by the dropwise addition of 1N HCl until further addition caused no more gas evolution. Ethyl acetate and 1N sodium hydroxide were added. The organic layer was washed with 1N sodium hydroxide (2×), brine, dried over sodium sulfate, filtered, and evaporated in vacuo to yield the (1-(4-fluorophenyl)cyclohexyl)methanol (950 mg, 100% yield) as a light tan oil containing some solid.

Step B: tert-Butyl 2-((1-(4-fluorophenyl)cyclohexyl)methoxy)acetate

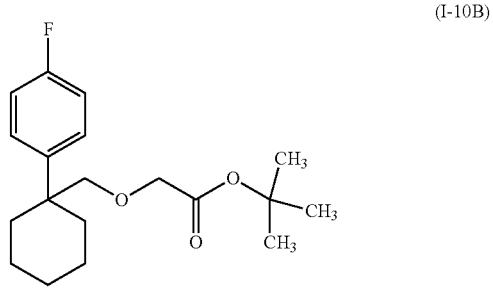 [SMILES: CC(C)(C)OC(=O)COCC1(c2ccc(F)cc2)CCCCC1]

(I-10B)

A solution of (1-(4-fluorophenyl)cyclohexyl)methanol (Intermediate I-10A, 108.5 mg, 0.52 mmol) in toluene 91 mL) was cooled to 0° C. A 5N aq. sodium hydroxide solution (500 μL) was added followed by tetra-n-butyl ammonium hydrogen sulfate (44 mg, 0.13 mmol) and stirring was continued for 30 min at 0° C. Tert-butyl bromoacetate (152 mg, 0.78 mmol) was added, the ice bath was removed, and stirring was continued for 2 hrs. The reaction mixture was diluted with ethyl acetate and water. The organic extract was separated, washed with water and brine, dried over sodium sulfate and concentrated in vacuo to obtain a colorless oil, which was purified by flash chromatography on silica gel (Teledyne-Isco REDISEP® 12 g silica gel column). Elution with hexanes (50 mL), followed by 1% and 3% EtOAc in hexanes (100 mL each) afforded tert-butyl 2-((1-(4-fluorophenyl)cyclohexyl)methoxy)acetate (100 mg, 60% yield) as a viscous oil. ¹H NMR (400 MHz, CDCl₃) δ ppm 7.28-7.46 (2H, m), 6.92-7.09 (2H, m), 3.78 (2H, s), 3.39 (2H, s), 2.09 (2H, d, J=15.31 Hz), 1.67-1.86 (2H, m), 1.47-1.59 (4H, m), 1.44 (9H, s), 1.31-1.38 (2H, m).

Step C: 2-((1-(4-Fluorophenyl)cyclohexyl)methoxy)acetic acid

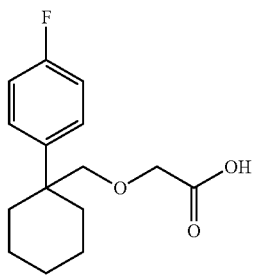
(I-10C)

A solution of tert-butyl 2-((1-(4-fluorophenyl)cyclohexyl)methoxy)acetate (Intermediate I-10B, 100 mg, 0.31 mmol) in TFA (1 mL) was stirred at room temperature for 85 min. TFA was removed in vacuo, and the residue was co-evaporated with ether. The residual oil was dried in vacuo to yield 2-((1-(4-fluorophenyl)cyclohexyl)methoxy)acetic acid (79 mg, 96% yield) as a white solid. $^1$H NMR (400 MHz, CDCl$_3$) δ ppm 7.30-7.43 (2H, m), 6.93-7.17 (2H, m), 3.91 (2H, s), 3.46 (2H, s), 2.13 (2H, d, J=13.55 Hz), 1.60-1.76 (2H, m), 1.55 (3H, dd, J=12.17, 3.64 Hz), 1.26-1.44 (3H, m).

Intermediate 10

This compound was prepared according to the general procedure described in the synthesis of Preparation 27A. $^1$H NMR (400 MHz, CDCl$_3$) δ ppm 7.37 (2H, dd, J=9.02, 5.50 Hz), 7.02 (2H, t, J=8.80 Hz), 3.91 (2H, s), 3.70 (3H, s), 3.43 (2H, s), 2.05-2.14 (2H, m), 1.70-1.80 (2H, m), 1.48-1.61 (4H, m), 1.35-1.40 (2H, m).

Intermediate 11

Methyl 4-(1-(4-fluorophenyl)cyclohexyl)butanoate

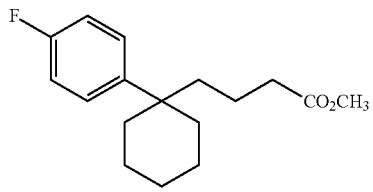
(I-11)

Step A: (E)-3-(1-(4-Fluorophenyl)cyclohexyl)prop-2-en-1-ol

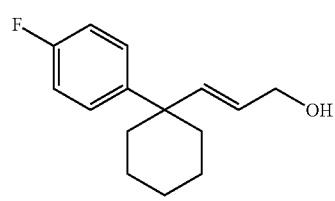
(I-11A)

To a solution of (E)-ethyl 3-(1-(4-fluorophenyl)cyclohexyl)acrylate (Intermediate I-7B, 1.5 g, 5.43 mmol) in toluene (30 mL) was added 2.5 M DIBAL-H in toluene (6.51 mL, 16.28 mmol) dropwise at room temperature, and the mixture was stirred at the same temperature for 5.5 hrs. The reaction was quenched by dropwise addition of methanol (1.34 mL) and stirring was continued for a few minutes. Then water (1.96 mL) was added dropwise and the mixture was stirred overnight at room temperature. The resulting mixture was filtered through CELITE® and evaporated to give an oily residue. It was purified by Combiflash (silica gel, 40 g) eluting with 5:95 followed by 1:9 and 2:8 ethyl acetate-hexane to give the desired (E)-3-(1-(4-fluorophenyl)cyclohexyl)prop-2-en-1-ol (964 mg, 76% yield) along with 232 mg of the unreacted starting material. $^1$H NMR (400 MHz, CDCl$_3$) δ ppm 7.30 (2H, dd, J=8.91, 5.39 Hz), 7.00 (2H, t, J=8.80 Hz), 5.70 (1H, d, J=15.85 Hz), 5.43 (1H, dt, J=15.74, 5.94, 5.83 Hz), 4.11 (2H, dd, J=5.72, 1.32 Hz), 1.97-2.05 (2H, m), 1.78-1.86 (2H, m), 1.53-1.63 (3H, m), 1.40-1.52 (5H, m).

Step B: (E)-4-(1-(4-Fluorophenyl)cyclohexyl)but-3-enenitrile

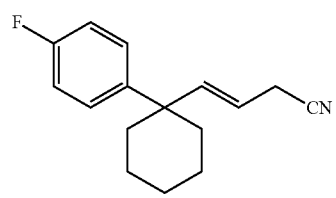
(I-11B)

To a solution of (E)-3-(1-(4-fluorophenyl)cyclohexyl)prop-2-en-1-ol (Intermediate I-11A, 912 mg, 3.89 mmol) and triphenylphosphine (1531 mg, 5.84 mmol) in THF (20 mL) at −20° C. was added diethyl azodicarboxylate (0.924 mL, 5.84 mmol) dropwise and the mixture was stirred at a temperature in the range of from about 20 to about −10° C. for 20 mins. Then 2-hydroxy-2-methylpropanenitrile (0.109 mL, 1.196 mmol) was added slowly at −20° C., and the mixture was stirred for 1 hr at a temperature in the range of from about −20 to about 10° C. and for 20 hrs at room temperature. The reaction was quenched with a few drops of methanol and stirred for 20 mins. After evaporation of the solvent the residue was purified by column chromatography (80 g silica gel) eluting with 1:9 followed by 2:8 ethyl acetate-hexane to give the desired (E)-4-(1-(4-fluorophenyl)cyclohexyl)but-3-enenitrile (760 mg, 80% yield) as an oil. $^1$H NMR (400 MHz, CDCl$_3$) δ ppm 7.25-7.30 (2H, m), 7.01 (2H, t, J=8.80 Hz), 5.85 (1H, d, J=15.63 Hz), 5.10 (1H, ddd, J=15.74, 5.72, 5.61 Hz), 3.06 (2H, dd, J=5.61, 1.65 Hz), 1.98-2.06 (2H, m), 1.77-1.86 (2H, m), 1.41-1.60 (6H, m).

Step C: (E)-Methyl 4-(1-(4-fluorophenyl)cyclohexyl)but-3-enoate

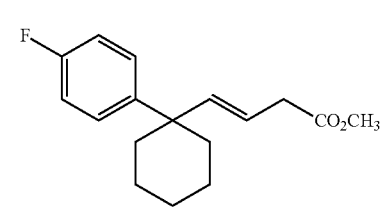
(I-11C)

HCl gas was bubbled through a solution of (E)-4-(1-(4-fluorophenyl)cyclohexyl)but-3-enenitrile (Intermediate I-11B, 769 mg, 3.16 mmol) in anhydrous methanol (20 mL), and the mixture was stirred in a sealed tube at 60° C. for 1 hr. After cooling, about 10 mL of water was added and the mixture was stirred at room temperature overnight. The mixture was then added to ethyl acetate and washed with water, brine dried over sodium sulfate and concentrated under reduced pressure to give the (E)-methyl 4-(1-(4-fluorophenyl)cyclohexyl)but-3-enoate (560 mg, 2.03 mmol, 64.1% yield) as an oil. $^1$H NMR (400 MHz, CDCl$_3$) δ ppm 7.30 (2H, dd, J=9.02, 5.28 Hz), 6.99 (2H, t, J=8.80 Hz), 5.51-5.56 (1H, m), 5.35-5.45 (1H, m), 3.68 (3H, s), 3.05 (2H, dd, J=6.82, 1.10 Hz), 1.90-2.00 (2H, m), 1.79-1.88 (2H, m), 1.45-1.63 (6H, m).

Intermediate 11

To a solution of (E)-methyl 4-(1-(4-fluorophenyl)cyclohexyl)but-3-enoate (Intermediate I-11C, 421 mg, 1.523 mmol) in methanol (20 mL) was added about 100 mg of 10% Pd on carbon (wet, 50%), and the mixture was stirred under hydrogen (50 psi) overnight. The catalyst was filtered off and the solvent was evaporated off to give the desired methyl 4-(1-(4-fluorophenyl)cyclohexyl)butanoate (quantitative yield) as an oil. $^1$H NMR (400 MHz, CDCl$_3$) δ ppm 7.26 (2H, dd, J=8.91, 5.39 Hz), 7.00 (2H, t, J=8.80 Hz), 4.07 (2H, q, J=7.12 Hz), 2.12 (2H, t, J=7.37 Hz), 2.04 (2H, dd, J=13.42, 5.72 Hz), 1.24-1.63 (12H, m), 1.21 (3H, t, J=7.15 Hz).

Intermediate 12

N-Hydroxy-3-phenyl-4-(trifluoromethyl)isoxazole-5-carbimidoyl chloride

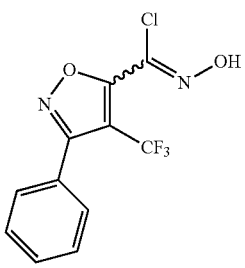

(I-12)

Step A: (3-Phenyl-4-(trifluoromethyl)isoxazol-5-yl)methanol

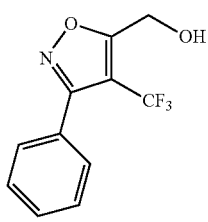

(I-12A)

To 3-phenyl-4-(trifluoromethyl)isoxazole-5-carboxylic acid (Intermediate I-3D, 1 g, 3.89 mmol) in THF (10 mL), cooled to −10° C., was added N-methylmorpholine (0.470 mL, 4.28 mmol) followed by isobutyl chloroformate (0.562 mL, 4.28 mmol) over a period of 3 min. After 15 min. at −10° C., this heterogeneous reaction mixture was added to a suspension of sodium borohydride (0.191 g, 5.06 mmol) in THF (12 mL) and methanol (3.0 mL) at −78° C. over a period of 10 min. using a Pasteur pipette. The reaction mixture was stirred at −78° C. for 10 min. The reaction mixture was allowed to warm to −20° C. over a period of 30 min. and quenched by the slow addition of AcOH in water (1:9 mL). The reaction mixture was allowed to come to room temperature, concentrated under reduced pressure and the residue partitioned between ethyl acetate (60 mL) and water (10 mL). The ethyl acetate layer was separated and washed sequentially with sat. aq. sodium bicarbonate (10 mL), brine (10 mL), dried over sodium sulfate and concentrated. The resulting oil was subjected to silica gel column chromatography using hexane/ethyl acetate to yield (3-phenyl-4-(trifluoromethyl)isoxazol-5-yl)methanol (0.44 g, 1.809 mmol, 46.5% yield) as an oil. $^1$H NMR (500 MHz, CDCl$_3$) δ ppm 2.21 (br. s., 1H), 4.97 (s, 2H), 7.47-7.56 (m, 3H), and 7.65 (d, J=6.60 Hz, 2H); LCMS M$^{+1}$=244.

Step B: 3-Phenyl-4-(trifluoromethyl)isoxazole-5-carbaldehyde

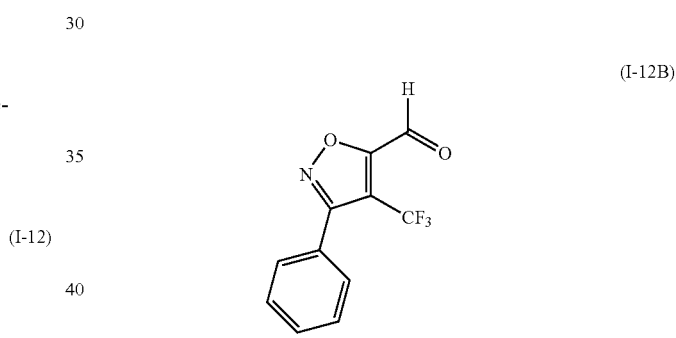

(I-12B)

To (3-phenyl-4-(trifluoromethyl)isoxazol-5-yl)methanol (Intermediate I-12A, 0.4 g, 1.645 mmol) in dichloromethane (5 mL) was added Dess-Martin Periodinane (0.767 g, 1.809 mmol) over a period of 2 min. at 0° C. under a nitrogen atmosphere. The milky suspension was stirred at 0° C. for 10 min. and at room temperature for 30 min. An additional 65 mgs of Dess-Martin reagent was added at room temperature and the contents were stirred at room temperature for 3 h. To the reaction mixture was added 10 mL of a 1:1 mixture of sat. aq. NaHCO$_3$ and aq. sodium thiosulfate, slowly at room temperature. After stirring the reaction mixture for 10 min. at room temperature, the dichloromethane layer was separated and the aqueous layer re-extracted with dichloromethane (10 mL). The combined dichloromethane layers were dried over sodium sulfate and concentrated under reduced pressure to yield 3-phenyl-4-(trifluoromethyl)isoxazole-5-carbaldehyde (0.385 g, 1.596 mmol, 97% yield) as an oil, which was used as such for the subsequent step without further purification. $^1$H NMR (400 MHz, CDCl$_3$) δ ppm 10.14 (s, 1H) 7.63-7.70 (m, 2H) 7.47-7.60 (m, 3H).

Step C: 3-Phenyl-4-(trifluoromethyl)isoxazole-5-carbaldehyde oxime

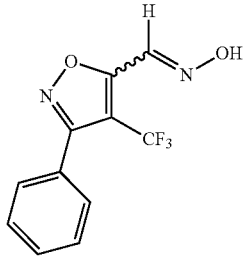

(I-12C)

To 3-phenyl-4-(trifluoromethyl)isoxazole-5-carbaldehyde (Intermediate I-12B, 0.38 g, 1.576 mmol) in ethanol (5 mL) were sequentially added hydroxylamine hydrochloride (0.131 g, 1.891 mmol) and sodium acetate (0.155 g, 1.891 mmol) at room temperature. The reaction mixture was heated at 80° C. for 20 min. The reaction mixture was concentrated and water (10 ml) was added. A pale yellow solid separated out from solution, and was filtered, washed with water (2×5 mL) and dried overnight to yield 3-phenyl-4-(trifluoromethyl)isoxazole-5-carbaldehyde oxime (0.35 g, 1.366 mmol, 87% yield) as a pale yellow solid. $^{1}$H NMR (400 MHz, CDCl$_3$) δ ppm 8.74 (br. s., 1H) 8.32 (s, 1H) 7.62-7.67 (m, 2H) 7.47-7.57 (m, 3H).

Intermediate 12

To 3-phenyl-4-(trifluoromethyl)isoxazole-5-carbaldehyde oxime (Intermediate I-12C, 0.34 g, 1.327 mmol) in N,N-dimethylformamide (1 mL) was added N-chlorosuccinamide (0.177 g, 1.327 mmol) in batches over a period of 2 min. at room temperature. The reaction mixture was stirred at room temperature for 30 min. An additional 0.09 g of N-chlorosuccinamide was added in one lot at room temperature and the contents were stirred for 20 min. The reaction mixture was partitioned between ethyl acetate (20 mL) and brine (2×20 mL). The ethyl acetate layer was dried over sodium sulfate and purified by silica gel column chromatography using hexane/ethyl acetate to yield N-hydroxy-3-phenyl-4-(trifluoromethyl)isoxazole-5-carbimidoyl chloride (0.250 g, 0.860 mmol, 64.8% yield) as a white solid. LC/MS M$^{+1}$=291.2.

Intermediate 13

N-Hydroxy-5-phenyl-4-(trifluoromethyl)isoxazole-3-carbimidoyl chloride

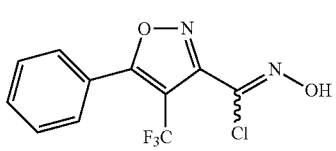

(I-13)

Step A: (5-Phenyl-4-(trifluoromethyl)isoxazol-3-yl)methanol

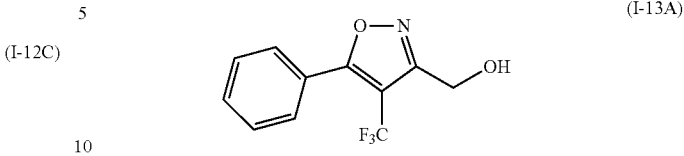

(I-13A)

To a solution of 5-phenyl-4-(trifluoromethyl)isoxazole-3-carboxylic acid (Intermediate 1-5D, 3.0 g, 11.7 mmol) in THF (20 mL) at 0° C. was added N-methylmorpholine (1.92 mL, 17.5 mmol) followed by isobutyl chloroformate (2.30 mL, 17.5 mmol) via syringe over 5 min. The resulting suspension was stirred at 0° C. for 15 min. The suspension was then added to a suspension of sodium borohydride (0.794 g, 21.0 mmol) in THF (40 mL) and methanol (12 mL) at −78° C. via a 10 mL syringe. During the addition, frothing was observed. The reaction mixture was stirred for 60 min. The reaction mixture was slowly warmed to approximately −20° C. and quenched with a 20 mL of a 1:9 mixture of acetic acid in water. The reaction mixture was then stirred at room temperature for 60 min. The solvent was removed under reduced pressure, and the residue was diluted with ethyl acetate (120 mL), washed with water (20 mL), saturated aqueous solution of sodium bicarbonate (2×20 mL) and brine (20 mL). The organic layer was collected, the aqueous layers were back-extracted with ethyl acetate (100 mL), and the combined organic layers were dried over anhydrous sodium sulfate. Concentration under reduced pressure followed by purification by flash silica gel chromatography using a mixture of ethyl acetate in hexane (1% to load; 5%-9%-12%) afforded (5-phenyl-4-(trifluoromethyl)isoxazol-3-yl)methanol (1.79 g, 7.36 mmol, 63% yield) as a clear, colorless oil. The compound had an HPLC ret. time=2.02 min. (condition A); LC/MS M$^{+1}$=243.8.

Step B: 5-Phenyl-4-(trifluoromethyl)isoxazole-3-carbaldehyde

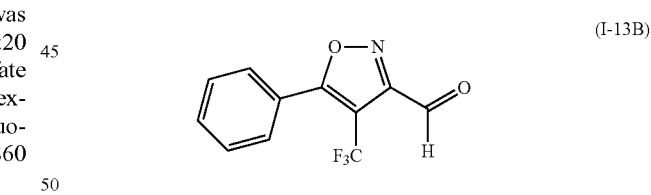

(I-13B)

To a mixture of (5-phenyl-4-(trifluoromethyl)isoxazol-3-yl)methanol (step A, 1.79 g, 7.36 mmol) in dichloromethane (23 mL) at 0° C. was added Dess-Martin Periodinane (3.43 g, 8.10 mmol). The reaction mixture was stirred at 0° C. for 10 min. and then at room temperature for 30 min. An additional 1.0 g of the Dess-Martin Periodinane was added, and the reaction mixture was stirred for an additional 30 min. A 1:1 mixture of saturated aqueous sodium thiosulfate and saturated aqueous bicarbonate (50 mL) was added slowly. The organic layer was collected, and the aqueous layer was extracted with dichloromethane (50 mL). The combined organic layers were dried over anhydrous sodium sulfate and concentrated under reduce pressure to give 5-phenyl-4-(trifluoromethyl)isoxazole-3-carbaldehyde (1.87 g, 7.75 mmol, quantitative yield) as a pale yellow oil. The compound had an HPLC ret. time=2.09 min. (condition A).

Step C: 5-Phenyl-4-(trifluoromethyl)isoxazole-3-carbaldehyde oxime

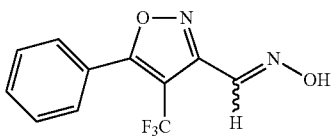

(I-13C)

A mixture of 5-phenyl-4-(trifluoromethyl)isoxazole-3-carbaldehyde (step B, 0.415 g, 1.721 mmol), hydroxylamine hydrochloride (0.179 g, 2.58 mmol), and sodium acetate (0.212 g, 2.58 mmol) in methanol (5 mL) was heated at reflux for 45 min. The reaction mixture was cooled to room temperature and concentrated under reduced pressure. The residue was suspended in water (10 mL), and the solid was collected by vacuum filtration, washed with water (2×5 mL), and dried overnight under reduced pressure to give 5-phenyl-4-(trifluoromethyl)isoxazole-3-carbaldehyde oxime (0.360 g, 1.41 mmol, 82% yield). The compound had an HPLC ret. time=2.43 min. (condition A); LC/MS $M^{+1}$=256.9.

Intermediate 13

To a solution of (E)-5-phenyl-4-(trifluoromethyl)isoxazole-3-carbaldehyde oxime (step C, 0.360 g, 1.41 mmol) in N,N-dimethylformamide (1.0 mL) at room temperature was added N-chlorosuccinimide (0.281 g, 2.11 mmol) in one portion. The resulting green, homogeneous reaction mixture was stirred at room temperature for 30 min. An additional 220 mg of NCS was added, and the reaction mixture was stirred for an additional 30 min. The reaction mixture was diluted with ethyl acetate (35 mL), washed with a 10% aqueous solution of lithium chloride (2×), and brine. The combined aqueous layers were extracted with ethyl acetate (35 mL), and dried over anhydrous sodium sulfate. Concentration under reduced pressure gave a pale green solid which was triturated with ether and filtered. The white solid was rinsed with ether, and the filtrate was concentrated under reduced pressure and dried under reduced pressure overnight to give a quantitative yield of N-hydroxy-5-phenyl-4-(trifluoromethyl)isoxazole-3-carbimidoyl chloride as a green solid. The compound had an HPLC ret. time=2.72 min. (condition A); LC/MS $M^{+1}$=291.0. $^1$H NMR (400 MHz, CDCl$_3$) δ ppm 7.51-7.58 (m, 2H), 7.58-7.64 (m, 1H), 7.70 (d, J=7.48 Hz, 2H), 8.04 (s, 1H), and 9.69 (s, 1H).

Intermediate 14

5-Phenyl-4-(trifluoromethyl)isoxazole-3-carbonyl fluoride

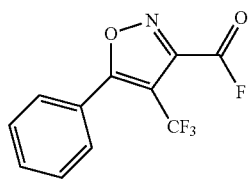

(I-14)

To a mixture of 5-phenyl-4-(trifluoromethyl)isoxazole-3-carboxylic acid (I-5D, 197 mg, 0.766 mmol) and pyridine (0.074 mL, 0.919 mmol) in dichloromethane (5 mL) at room temperature was added cyanuric fluoride (0.078 mL, 0.919 mmol). The reaction mixture was stirred at room temperature for 18 h. The mixture was diluted with dichloromethane (40 mL) and washed with an ice-cold 0.5N aqueous solution of hydrochloric acid (20 mL). The aqueous layer was extracted with dichloromethane (20 mL), and the combined organic layers were washed with ice-cold water (20 mL) and dried over anhydrous magnesium sulfate. Concentration under reduced pressure afforded 5-phenyl-4-(trifluoromethyl)isoxazole-3-carbonyl fluoride (199 mg, 0.768 mmol, 100% yield) as a pale yellow oil. The compound had an HPLC retention time=2.53 min. (methyl ester)-Column: Chromolith Speed-ROD 4.6×50 mm (4 min.); Solvent A=10% MeOH, 90% H$_2$O, 0.1% TFA; Solvent B=90% MeOH, 10% H$_2$O, 0.1% TFA.

Example 1

1-((5,5-Dimethyl-3-(3-phenyl-4-(trifluoromethyl)isoxazol-5-yl)-4,5-dihydronaphtho[1,2-c]isoxazol-7-yl)methyl)azetidine-3-carboxylic acid

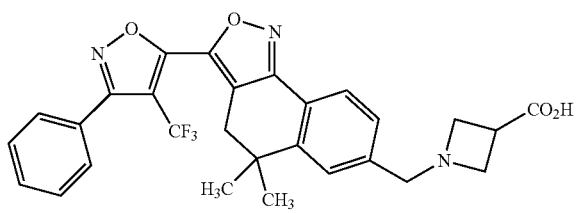

(1)

Preparation 1A: 6-Hydroxy-4,4-dimethyl-3,4-dihydronaphthalen-1(2H)-one

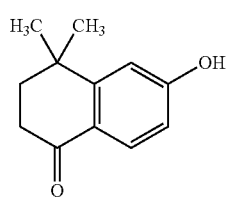

(1A)

To a solution of 6-methoxy-4,4-dimethyl-3,4-dihydronaphthalen-1(2H)-one (1.0 g, 4.90 mmol) in dichloromethane (50 mL) at 0° C. was slowly added tribromoborane (1.0 M in dichloromethane) (24.5 mL, 24.5 mmol), resulting in a dark solution. The ice-bath was removed, and the reaction mixture was stirred overnight. The reaction mixture was diluted with dichloromethane (100 mL) and washed with water (2×25 mL). The aqueous layer was extracted with dichloromethane (2×25 mL), and the combined organic layers were dried over anhydrous sodium sulfate and concentrated to give a red, viscous oil. The residue was purified by flash silica gel chromatography using a mixture of ethyl acetate in hexane (5%-12.5%-20%) to give 6-hydroxy-4,4-dimethyl-3,4-dihydronaphthalen-1(2H)-one (0.299 g, 1.57 mmol, 32% yield) as an orange solid. The product had an HPLC ret. time=1.68 min. (condition A); LC/MS M$^{+1}$=190.9.

Preparation 1B: 8,8-Dimethyl-5-oxo-5,6,7,8-tetrahydronaphthalen-2-yl trifluoromethanesulfonate

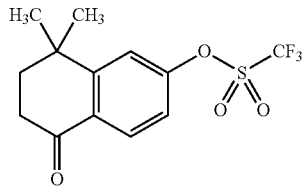

(1B)

To a solution of 6-hydroxy-4,4-dimethyl-3,4-dihydronaphthalen-1(2H)-one (Preparation 1A, 0.291 g, 1.53 mmol) in pyridine (3 mL) immersed in a water bath was added trifluoromethanesulfonic anhydride (0.310 mL, 1.84 mmol) over 5 min. The ice-bath was removed, and the reaction mixture was stirred at room temperature for 3.5 h. The pyridine was removed under reduced pressure, and the residue was diluted with ether (70 mL) and washed with water (2×25 mL). The organic layer was collected, and the aqueous layer was back-extracted with ether (25 mL). The combined organic layers were washed with 1N aqueous hydrochloric acid (20 mL), 1N aqueous sodium hydroxide (20 mL), brine (20 mL), and dried over anhydrous sodium sulfate. The ether was removed under reduced pressure, and the crude product was purified by flash silica gel chromatography using a mixture of ethyl acetate in hexane (5%-12.5%-20%) to afford 8,8-dimethyl-5-oxo-5,6,7,8-tetrahydronaphthalen-2-yl trifluoromethanesulfonate (0.443 g, 1.37 mmol, 90% yield) as a pale yellow oil. The product had an HPLC ret. time=2.82 min. (condition A); LC/MS M$^{+1}$=323.00.

Preparation 1C: 4,4-Dimethyl-6-vinyl-3,4-dihydronaphthalen-1(2H)-one

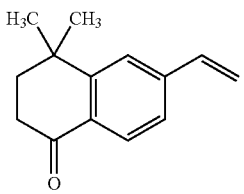

(1C)

To a solution of 8,8-dimethyl-5-oxo-5,6,7,8-tetrahydronaphthalen-2-yl trifluoromethanesulfonate (Preparation 1B, 0.443 g, 1.37 mmol) in dioxane (2.5 mL) in a sealed tube was added sequentially tributyl(vinyl)stannane (0.444 mL, 1.51 mmol) and lithium chloride (0.175 g, 4.12 mmol). The mixture was degassed under reduced pressure and charged with nitrogen (2×). To the mixture was added tetrakis(triphenylphosphine) palladium(0) (0.159 g, 0.137 mmol), and the mixture was stirred under a strong stream of nitrogen for 5 min. The reaction mixture was sealed, immersed in an oil bath at 100° C., and stirred at room temperature overnight. The reaction mixture was filtered under reduced pressure, and the solid was rinsed with ethyl acetate (~50 mL total). The filtrate was concentrated under reduced pressure, and the resulting residue was diluted with ether (~25 mL). The resulting solid was removed by vacuum filtration and rinsed with ether (~25 mL). The filtrate was concentrated under reduced pressure and purified by flash silica gel chromatography using a mixture of ethyl acetate in hexane (5%-10%) to give 4,4-dimethyl-6-vinyl-3,4-dihydronaphthalen-1(2H)-one (0.201 g, 1.00 mmol, 73. % yield) as a colorless oil. The product had an HPLC ret. time=2.55 min. (condition A); LC/MS M$^{+1}$=200.9.

Preparation 1D: (E)-4,4-Dimethyl-6-vinyl-3,4-dihydronaphthalen-1(2H)-one oxime

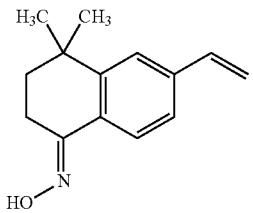

(1D)

To a mixture of 4,4-dimethyl-6-vinyl-3,4-dihydronaphthalen-1(2H)-one (Preparation 1C, 0.201 g, 1.004 mmol) and hydroxylamine hydrochloride (0.084 g, 1.20 mmol) in methanol (3 mL) at room temperature was added sodium acetate (0.099 g, 1.20 mmol). The heterogeneous reaction mixture was heated at reflux for 1.5 h. The heterogeneous mixture was concentrated, and the solid residue was diluted with dichloromethane, washed with water, and dried over anhydrous sodium sulfate. Concentration under reduced pressure afforded (E)-4,4-dimethyl-6-vinyl-3,4-dihydronaphthalen-1(2H)-one oxime (0.210 g, 0.975 mmol, 97% yield) as a pale yellow solid. The product had an HPLC ret. time=2.64 min. (condition A); LC/MS M$^{+1}$=216.0.

Preparation 1E: 5,5-Dimethyl-3-(3-phenyl-4-(trifluoromethyl)isoxazol-5-yl)-7-vinyl-4,5-dihydronaphtho-[1,2-c]isoxazole

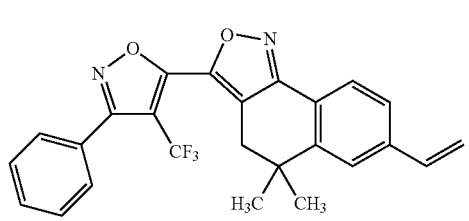

(1E)

To a solution of (E)-4,4-dimethyl-6-vinyl-3,4-dihydronaphthalen-1(2H)-one oxime (Preparation 1D, 0.210 g, 0.973 mmol) and THF (4 mL) at 0° C. was slowly added lithium diisopropylamide (0.973 mL, 1.95 mmol). The mixture was stirred for 20 min. at 0° C. A 1.88 M solution of methyl 3-phenyl-4-(trifluoromethyl)isoxazole-5-carboxylate (Intermediate I-3, 0.345 mL, 0.649 mmol) in THF was then added via syringe, and the reaction mixture was stirred for an additional 20 min. at 0° C. The reaction mixture was quenched with 1N aqueous hydrochloric acid (~1.0 mL) and then partitioned between ethyl acetate and brine. The organic layer was collected and dried over anhydrous sodium sulfate. Concentration under reduced pressure afforded a brown oil.

To the oil was added toluene (6 mL) and p-toluenesulfonic acid monohydrate (0.247 g, 1.30 mmol), and the reaction mixture was stirred at 100° C. for 60 min. By HPLC, the reaction had only partially proceeded. The dark mixture was stirred over the weekend at room temperature. The reaction mixture was stirred at 100° C. for most of the day. By HPLC, there was still significant hydroxy intermediate remaining, so the temperature of the oil bath was raised from 100° C. to 115° C. for 2 h. By HPLC, there was still ~20% of the hydroxy intermediate remaining, so the reaction mixture was stirred at 115° C. for 6 h. By HPLC, there was only a small amount of the intermediate left, and the reaction was stopped. After cooling to room temperature, the toluene was removed under reduced pressure, and the residue was azeotroped with methanol (3×). The brown solid residue was suspended in ~20 mL of methanol, sonicated for 5 min., and filtered under vacuum. The solid was washed with methanol and dried to give the product (137 mg, 48% yield) as a brown solid. The solid was further purified by flash silica gel chromatography using a 5% mixture of ethyl acetate in hexane to give 5,5-dimethyl-3-(3-phenyl-4-(trifluoromethyl)isoxazol-5-yl)-7-vinyl-4,5-dihydronaphtho[1,2-c]isoxazole (0.036 g, 0.082 mmol, 12.7% yield) as a pale yellow solid. The product had an HPLC ret. time=3.81 min. (condition A); LC/MS $M^{+1}$=437.1; $^1$H NMR (400 MHz, CDCl$_3$) δ ppm 1.41 (s, 6H) 3.02 (s, 2H), 5.39 (d, J=11.22 Hz, 1H), 5.88 (d, J=17.61 Hz, 1H), 6.79 (dd, J=17.61, 10.78 Hz, 1H), 7.47 (dd, J=7.92, 1.54 Hz, 1H), 7.51-7.59 (m, 4H), 7.66-7.71 (m, 2H), and 8.03 (d, J=7.92 Hz, 1H).

Preparation 1F: 5,5-Dimethyl-3-(3-phenyl-4-(trifluoromethyl)isoxazol-5-yl)-4,5-dihydronaphtho[1,2-c]isoxazole-7-carbaldehyde

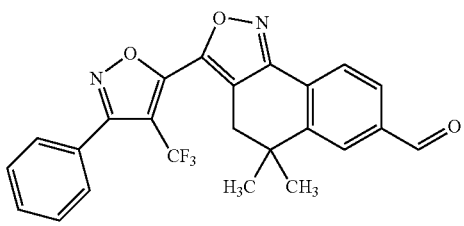

(1F)

To a mixture of 5,5-dimethyl-3-(3-phenyl-4-(trifluoromethyl)isoxazol-5-yl)-7-vinyl-4,5-dihydronaphtho[1,2-c]isoxazole (Preparation 1E, 0.036 g, 0.082 mmol) and NMO in water (0.017 mL, 0.082 mmol) in THF (1.5 mL) at room temperature was added osmium tetroxide in water (0.013 mL, 1.65 µmol). The reaction mixture was stirred at room temperature for 7 hours. A solution of sodium periodate (0.026 g, 0.124 mmol) in water (1 mL) was added via syringe. The resulting cloudy reaction mixture was stirred overnight at room temperature concentrated under reduced pressure, and the residue was diluted with ethyl acetate (30 mL) and washed with water (15 mL). The organic layer was washed with brine and dried over anhydrous sodium sulfate. Concentration under reduced pressure afforded 5,5-dimethyl-3-(3-phenyl-4-(trifluoromethyl)isoxazol-5-yl)-4,5-dihydronaphtho[1,2-c]isoxazole-7-carbaldehyde (0.034 g, 0.078 mmol, 94% yield) as a tan solid. The product had an HPLC ret. time=3.51 min. (condition A); LC/MS $M^{+1}$=439.1.

Example 1

To a mixture of 5,5-dimethyl-3-(3-phenyl-4-(trifluoromethyl)isoxazol-5-yl)-4,5-dihydronaphtho[1,2-c]isoxazole-7-carbaldehyde (Preparation 1E, 0.034 g, 0.078 mmol) and azetidine-3-carboxylic acid (9.41 mg, 0.093 mmol) in methanol (0.5 mL) and dichloroethane (0.5 mL) at room temperature was added 3 drops of acetic acid via a Pasteur pipette. The reaction mixture was heated at 60° C. for 1 h. The reaction mixture was cooled to room temperature, sodium cyanoborohydride (5.94 mg, 0.093 mmol) was added, and the mixture was stirred at room temperature for 30 min. The reaction mixture was diluted with dichloromethane, washed with water, washed with brine, and dried over anhydrous sodium sulfate. Concentration under reduced pressure afforded the product (40 mg) as a dark tan solid. The solid was triturated with methanol with sonication and filtered under reduced pressure to give a dark gray solid (13 mg). By HPLC, the solid appeared to be the product.

The filtrate was concentrated under reduced pressure to give the product (27 mg) as a yellow solid which was purified by flash silica gel chromatography using a mixture of methanol, dichloromethane, and ammonium hydroxide (10:90:0-20:80:1) to give 1-((5,5-dimethyl-3-(3-phenyl-4-(trifluoromethyl)isoxazol-5-yl)-4,5-dihydronaphtho[1,2-c]isoxazol-7-yl)methyl)azetidine-3-carboxylic acid (0.009 g, 0.017 mmol, 22% yield) as a yellow solid. The compound was diluted with methanol with sonication, resulting in a cloudy solution which was passed through a CELITE® plug. The solvent was removed, and the compound was further purified by recrystallization from methanol to give 1-((5,5-dimethyl-3-(3-phenyl-4-(trifluoromethyl)isoxazol-5-yl)-4,5-dihydronaphtho[1,2-c]isoxazol-7-yl)methyl)azetidine-3-carboxylic acid (0.002 g, 3.82 µmol, 4.9% yield) as a white solid. The product had an HPLC time=2.99 min. (condition A); $^1$H NMR (500 MHz, CDCl$_3$) δ ppm 1.37 (s, 6H), 3.01 (s, 2H), 3.50 (s, 2H), 4.03-4.11 (m, 2H), 4.17-4.27 (m, 3H), 7.45 (d, J=6.94 Hz, 1H), 7.51-7.59 (m, 3H), 7.66 (d, J=7.21 Hz, 3H), and 8.05 (d, J=7.77 Hz, 1H).

Examples 2 and 3

1-((3-(4-Propylphenyl)-4H-chromeno[4,3-c]isoxazol-7-yl)methyl)azetidine-3-carboxylic acid, trifluoroacetic acid salt (2), and 1-((3-(4-Propylphenyl)-4H-chromeno[3,4-d]isoxazol-7-yl)methyl)azetidine-3-carboxylic acid, trifluoroacetic acid salt (3)

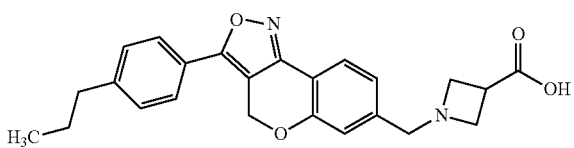

(2)

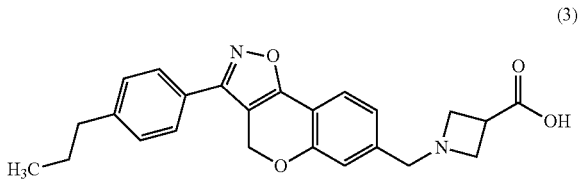

(3)

Preparation 2A: 3-Chloro-1-(2,4-dihydroxyphenyl)propan-1-one

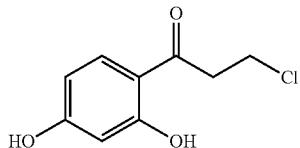

(2A)

To a stirred mixture of resorcinol (10 g, 91 mmol) and 3-chloropropanoic acid (9.95 g, 92 mmol) was added trifluoromethanesulfonic acid (50 g, 333 mmol) in one portion. The solution was warmed to 80° C. for 30 min, cooled to room temperature over 15 min, and poured into dichloromethane (200 mL). The resulting solution was slowly poured into water (200 mL), and the layers were separated. The aqueous layer was extracted with dichloromethane (2×100 mL), dried over anhydrous sodium sulfate, and filtered. Concentration under reduced pressure afforded 3-chloro-1-(2,4-dihydroxyphenyl)propan-1-one (13.62 g, 67.9 mmol, 74.8% yield) as an orange semi-solid. The compound was used without any further purification. LC/MS $M^{+1}$=200; $^1$H NMR (400 MHz, CDCl$_3$) δ ppm 12.39 (1H, s), 7.56 (1H, d, J=8.58 Hz), 7.19 (1H, s), 6.17-6.49 (1H, m), 5.23 (1H, s), 3.78-4.01 (2H, m), and 3.34 (2H, t, J=6.71 Hz).

Preparation 2B: 7-Hydroxychroman-4-one

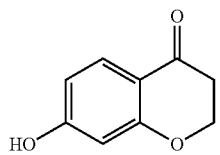

(2B)

To a stirred 2 M solution of sodium hydroxide (500 mL, 1000 mmol) at 5° C. was added 3-chloro-1-(2,4-dihydroxyphenyl)propan-1-one (Preparation 2A, 13.6 g, 67.9 mmol) in one portion. The solution was warmed to room temperature over 2 h, re-cooled to 5° C., and the pH was adjusted to ~2 with 6 M aqueous sulfuric acid (~50 mL). An orange precipitant formed which was collected by vacuum filtration and dried under reduced pressure. The filtrate was extracted with ethyl acetate (3×100 mL), washed with brine, and dried over anhydrous sodium sulfate. Concentration under reduced pressure gave an orange solid. The two recovered solids were combined to give 7-hydroxychroman-4-one (9.0 g, 54.8 mmol, 81% yield). LC/MS $M^{+1}$=165.0; $^1$H NMR (400 MHz, CDCl$_3$) δ ppm 7.77 (1H, d, J=8.58 Hz), 6.45 (1H, dd, J=8.69, 2.31 Hz), 6.33 (1H, d, J=2.42 Hz), 5.62 (1H, br. s.), 4.33-4.66 (2H, m), and 2.58-2.90 (2H, m).

Preparation 2C: 4-Oxochroman-7-yl trifluoromethanesulfonate

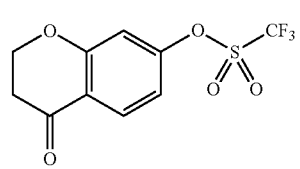

(2C)

To a solution of 7-hydroxychroman-4-one (Preparation 2B, 2.024 g, 12.3 mmol) in pyridine (10 mL) at 0° C. was added trifluoromethanesulfonic anhydride (2.500 mL, 14.8 mmol) over 5 min. The ice-bath was removed, and the reaction mixture was stirred at room temperature for 2.5 h. Pyridine was removed under reduced pressure, and the residue was diluted with ether (70 mL) and washed with water (30 mL). The organic layer was collected, and the aqueous layer was back-extracted with ether (25 mL). The combined organic layers were washed with 1N aqueous hydrochloric acid, 1N aqueous sodium hydroxide, brine, and dried over anhydrous sodium sulfate. Ether was removed under reduced pressure, and the crude product was purified by flash silica gel chromatography using a mixture of ethyl acetate in hexane (5%-15%-20%) to afford 4-oxochroman-7-yl trifluoromethanesulfonate (3.13 g, 10.6 mmol, 86% yield) as a yellow oil. The product had an HPLC ret. time=2.40 min. (condition A); LC/MS $M^{+1}$=297.2.

Preparation 2D: 7-Vinylchroman-4-one

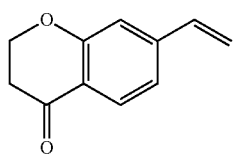

(2D)

To a solution of 4-oxochroman-7-yl trifluoromethanesulfonate (Preparation 2C, 2.00 g, 6.75 mmol) in dioxane (10 mL) in a sealed tube was added sequentially tributyl(vinyl)stannane (2.18 mL, 7.43 mmol) and lithium chloride (0.859 g, 20.3 mmol). The mixture was degassed under reduced pressure and charged with nitrogen (2×). To the mixture was added tetrakis(triphenylphosphine) palladium(0) (0.780 g, 0.675 mmol), and the mixture was stirred under a strong stream of nitrogen for 5 min. The reaction mixture was sealed, immersed in an oil bath at 100° C., and stirred overnight. The reaction mixture was cooled to room temperature and filtered under reduced pressure. The solid was washed with ethyl acetate (4×50 mL), and the filtrate was concentrated. The crude product mixture was diluted with ether (~100 mL), sonicated for several minutes, and filtered (the cake was rinsed with ether). The filtrate was concentrated under reduced pressure, and the residue was purified by flash silica gel chromatography using a mixture of ethyl acetate in hexane (5%-12%-15%) to give 7-vinylchroman-4-one (0.938 g, 5.38 mmol, 80% yield) as a yellow oil. The product had a HPLC ret. time=1.93 min. (condition A); LC/MS $M^{+1}$=174.9; $^1$H NMR (400 MHz, CDCl$_3$) δ ppm 2.78-2.85 (m, 2H), 4.52-4.58 (m, 2H), 5.42 (d, J=10.78 Hz, 1H), 5.88 (d, J=17.61 Hz, 1H), 6.69 (dd, J=17.61, 11.00 Hz, 1H), 6.98 (d, J=1.54 Hz, 1H), 7.09 (dd, J=8.25, 1.43 Hz, 1H), and 7.87 (d, J=8.14 Hz, 1H).

Preparation 2E: 3-(4-Propylbenzoyl)-7-vinylchroman-4-one

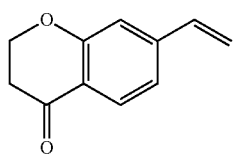

(2E)

To a flame-dried 10 mL round-bottom flask under nitrogen charged with butyllithium (2.5 M in hexanes) (0.875 mL, 2.19 mmol) in THF (1 mL) at 0° C. was added diisopropylamine (0.312 mL, 2.19 mmol) dropwise. The solution was stirred at 0° C. for 20 min. The solution was then cooled to −78° C., and 7-vinylchroman-4-one (Preparation 2D, 1.79 M in THF) (1.02 mL, 1.82 mmol) was added dropwise via syringe. The mixture was stirred for 20 min. at −78° C. 4-propylbenzoyl fluoride (0.303 g, 1.823 mmol) in 1 mL of THF was then added dropwise via syringe, and the reaction mixture was stirred at −78° C. for 60 min. and then warmed to room temperature. The reaction was quenched with 1N aqueous hydrochloric acid (5 mL) and extracted with ethyl acetate (3×20 mL). The organic layer was washed with brine, dried over anhydrous sodium sulfate, and concentrated under reduced pressure. The yellow residue was purified by flash silica gel chromatography using a mixture of ethyl acetate in hexane (5%-12%) to give 3-(4-propylbenzoyl)-7-vinylchroman-4-one (0.179 g, 0.559 mmol, 31% yield). The compound was triturated with methanol with sonication, filtered, washed with methanol, and dried to give 3-(4-propylbenzoyl)-7-vinylchroman-4-one (0.125 g, 0.390 mmol, 21% yield) as a yellow solid. LC/MS $M^{+1}$=321.2. $^1$H NMR (500 MHz, DMSO-$d_6$) δ ppm 0.91 (t, 3H), 1.58-1.68 (m, J=7.42, 7.42, 7.42, 7.42, 7.21 Hz, 2H), 2.65 (t, J=7.63 Hz, 2H) 4.71-4.77 (m, 1H), 4.78-4.83 (m, 1H), 5.20 (dd, J=9.16, 4.99 Hz, 1H), 5.47 (d, J=11.10 Hz, 1H), 6.05 (d, J=17.76 Hz, 1H), 6.73-6.82 (m, 1H), 7.17 (s, 1H) 7.24 (dd, J=8.18, 1.25 Hz, 1H), 7.38 (d, J=8.32 Hz, 2H), 7.73 (d, J=8.05 Hz, 1H), and 7.96 (d, J=8.32 Hz, 2H).

Preparation 2F: Mixture of 3-(4-Propylphenyl)-7-vinyl-4H-chromeno[4,3-c]isoxazole and 3-(4-Propylphenyl)-7-vinyl-4H-chromeno[3,4-d]isoxazole

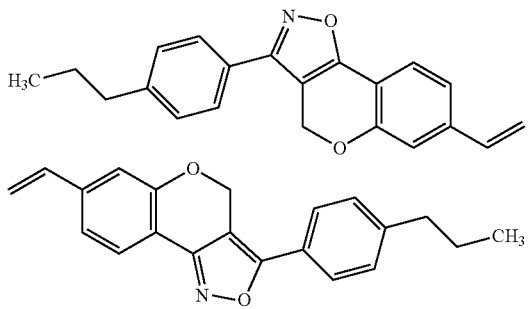

Three reactions were run as follows:

1.) A mixture of 3-(4-propylbenzoyl)-7-vinylchroman-4-one (Preparation 2E, 0.020 g, 0.062 mmol), hydroxylamine hydrochloride (8.68 mg, 0.125 mmol), and pyridine (1.0 mL) was heated at 160° C. for 30 min. in a microwave.

2.) A mixture of 3-(4-propylbenzoyl)-7-vinylchroman-4-one (0.032 g, 0.100 mmol), hydroxylamine hydrochloride (0.021 g, 0.300 mmol), and pyridine (1.0 mL) was heated at 160° C. for 30 min. in a microwave.

3.) A mixture of 3-(4-propylbenzoyl)-7-vinylchroman-4-one (0.048 g, 0.150 mmol), hydroxylamine hydrochloride (0.031 g, 0.449 mmol), and pyridine (1.0 mL) was heated at 160° C. for 30 min. in a microwave.

The crude reactions mixtures were diluted individually with water (1:2 mL, 2:2 mL, and 3:3 mL). The resulting solids were collected together in a 15 mL fritted funnel under vacuum, washed well with water, and dried to give 71 mg of the mixture of isoxazole regioisomers as an off-white solid. The solid was triturated with methanol with sonication to give 40 mg of the mixture of 3-(4-propylphenyl)-7-vinyl-4H-chromeno[4,3-c]isoxazole and 3-(4-propylphenyl)-7-vinyl-4H-chromeno[3,4-d]isoxazole as a white solid. The product mixture (mixture of the two regioisomeric isoxazoles) had an HPLC ret. time=3.85 min. (condition A); LC/MS $M^{+1}$=318.2.

Preparation 2G: Mixture of 3-(4-propylphenyl)-4H-chromeno[4,3-c]isoxazole-7-carbaldehyde and 3-(4-propylphenyl)-4H-chromeno[3,4-d]isoxazole-7-carbaldehyde

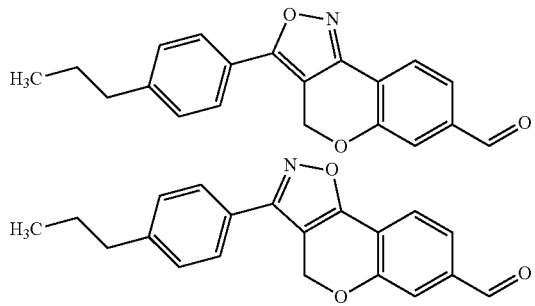

To a mixture of 3-(4-propylphenyl)-7-vinyl-4H-chromeno[4,3-c]isoxazole and 3-(4-propylphenyl)-7-vinyl-4H-chromeno[3,4-d]isoxazole (Preparation 2F, 0.040 g, 0.126 mmol) and NMO in water (0.026 mL, 0.126 mmol) in THF (1.5 mL) at room temperature was added 4% osmium tetroxide in water (0.040 mL, 5.04 μmol). The reaction mixture was stirred at room temperature over the weekend. The intermediate diol (MW 351.40) had an HPLC ret. time=3.03 min. (condition A); LC/MS $M^{+1}$=352.3. A solution of sodium periodate (0.040 g, 0.189 mmol) in water (1 mL) was added via syringe. The resulting cloudy reaction mixture was stirred for 60 min. The reaction mixture was concentrated under reduced pressure, and the residue was diluted with ethyl acetate (40 mL) and washed with water (20 mL). The organic layer was washed with brine, the combined aqueous layers were extracted with ethyl acetate (30 mL), and the combined organic layers were dried over anhydrous sodium sulfate. Concentration under reduced pressure followed by purification by flash silica gel chromatography using a 20% mixture of ethyl acetate in hexane afforded a mixture of 3-(4-propylphenyl)-4H-chromeno[4,3-c]isoxazole-7-carbaldehyde and 3-(4-propylphenyl)-7-vinyl-4H-chromeno[3,4-d]isoxazole (0.024 g, 0.075 mmol, 60% yield) as a white solid. The product had an HPLC ret. time=3.45 min. (condition A); LC/MS $M^{+1}$=320.2.

Examples 2 and 3

To a mixture of 3-(4-propylphenyl)-4H-chromeno[4,3-c]isoxazole-7-carbaldehyde and 3-(4-propylphenyl)-4H-chromeno[3,4-d]isoxazole-7-carbaldehyde (Preparation 2G, 0.023 g, 0.072 mmol) and azetidine-3-carboxylic acid (8.74 mg, 0.086 mmol) in methanol (0.5 mL) and dichloroethane (1.0 mL) at room temperature was added 3 drops of acetic acid via a Pasteur pipette. The heterogeneous reaction mixture was heated at 60° C. for 1 h. The reaction was cooled to room temperature, sodium cyanoborohydride (5.52 mg, 0.086 mmol) was added, and the mixture was stirred at room temperature for 4 h. The reaction mixture was diluted with dichloromethane, washed with water, brine, and dried over anhydrous sodium sulfate. Concentration under reduced pressure afforded a pale yellow solid (~22 mg) which was triturated with methanol with sonication and filtered. The resulting pale yellow solid (7.5 mg) was purified by preparative HPLC to give an unspecified 3:2 mixture ($^1$H NMR) of 1-((3-(4-propylphenyl)-4H-chromeno[4,3-c]isoxazol-7-yl)methyl)azetidine-3-carboxylic acid, trifluoroacetic acid salt and 1-((3-(4-propylphenyl)-4H-chromeno[3,4-d]isoxazol-7-yl)methyl)azetidine-3-carboxylic acid, trifluoroacetic acid salt (0.005 g, 9.16 μmol, 13% yield) as a white solid. The product mixture had HPLC ret. times of 2.74 and 2.80 min. (condition A); LC/MS $M^{+1}$=405.4. $^1$H NMR (500 MHz, MeOD) δ ppm 0.94-0.99 (m, 3H), 1.65-1.74 (m, 2H), 2.65-2.70 (m, 2H), 3.64-3.73 (m, 1H), 4.30-4.38 (m, 4H), 4.39-4.44 (m, 2H), [5.57 (s, 1.2H) and 5.70 (s, 0.8H)], 7.10-7.20 (m, 2H), 7.36 (d, J=8.05 Hz, 1H), 7.40 (d, J=8.32 Hz, 1H), 7.58 (d, J=8.05 Hz, 1H), 7.62 (d, J=8.32 Hz, 1H), and [7.69 (d, J=7.77 Hz, 0.6H) and 7.92 (d, J=8.32 Hz, 0.4H)].

Example 4

1-((3-(5-(1-Methylcyclopropyl)-4-(trifluoromethyl)isoxazol-3-yl)-4,5-dihydronaphtho-[1,2-c]isoxazol-7-yl)methyl)azetidine-3-carboxylic acid

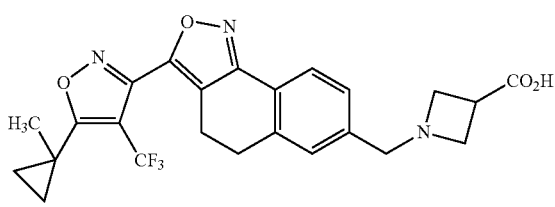

(4)

Preparation 4A:
Trimethyl((1-methylcyclopropyl)ethynyl)silane

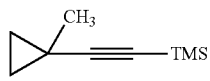

(4A)

A 2.5 M solution of n-butyllithium in hexanes (96 mL, 240 mmol) was slowly added over 30 min. to a stirred solution of (cyclopropylethynyl)trimethylsilane (16.6 g, 120 mmol) in diethyl ether (50 mL) at room temperature. After complete addition, the reaction mixture was stirred at room temperature overnight. The reaction mixture was cooled to −78° C. and dimethyl sulfate (13.6 mL, 144 mmol) was added slowly over 30 min. to the stirred solution. After complete addition, the reaction mixture was allowed to warm to room temperature and stirred at room temperature for 1 h. The reaction mixture was diluted with diethyl ether (150 mL) and quenched with a saturated aqueous solution of ammonium chloride. The organic layer was collected, dried over anhydrous sodium sulfate, and concentrated under reduced pressure. The product mixture was further distilled to remove the lower boiling diethyl ether, hexanes, and unreacted starting material to give trimethyl((1-methylcyclopropyl)ethynyl)silane (15.7 g, 86% yield) as a clear yellow liquid. $^1$H NMR (400 MHz, CDCl$_3$) δ ppm 04-0.06 (m, 9H), 0.45 (d, J=2.42 Hz, 2H), 2.78 (d, J=2.42 Hz, 2H), and 1.13 (s, 3H).

Preparation 4B: 1-Ethynyl-1-methylcyclopropane

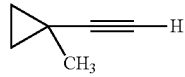

(4B)

A mixture of trimethyl((1-methylcyclopropyl)ethynyl)silane (Preparation 4A, 7.6 g, 49.9 mmol) and potassium fluoride (1.17 mL, 49.9 mmol) in dimethylformamide (20 mL) and water (2 mL) was stirred at room temperature overnight. The reaction mixture was filtered, and the filtrate was distilled. The fraction distilling over at 70-80° C. was collected to give 1-ethynyl-1-methylcyclopropane (2.33 g, 64% yield) as a clear liquid. $^1$H NMR (400 MHz, CDCl$_3$) δ ppm 0.51 (m, 2H), 0.84 (m, 2H), 1.21 (s, 3H), and 1.77 (s, 1H).

Preparation 4C: Ethyl-5-(1-methylcyclopropyl)isoxazole-3-carboxylate

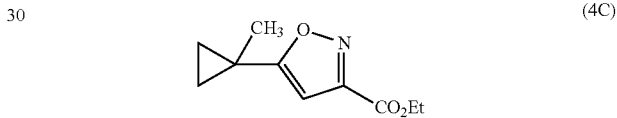

(4C)

To a mixture of 1-ethynyl-1-methylcyclopropane (Preparation 4B, 5.0 g, 62.4 mmol) and (Z)-ethyl 2-chloro-2-(hydroxyimino)acetate (4.73 g, 31.2 mmol) in diethyl ether (80 mL) was added a solution of triethylamine (8.67 mL, 62.4 mmol) in diethyl ether (20 mL) dropwise over 75 min. After complete addition, the reaction mixture was stirred at room temperature for 2 h. The reaction mixture was filtered, and the filtrate was concentrated under reduced pressure. The crude product was purified by flash silica gel chromatography using a 10% mixture of ethyl acetate in hexane to give ethyl-5-(1-methylcyclopropyl)isoxazole-3-carboxylate (3.54 g, 65% yield) as a yellow liquid. The product had an HPLC ret. time=2.23 min.-(condition B); LC/MS $M^{+1}$=196.07. $^1$H NMR (400 MHz, CDCl$_3$) δ ppm 0.79 (m, 2H), 1.13 (m, 2H), 1.26 (t, J=7.15 Hz, 3H), 1.35 (s, 3H), 4.31 (q, J=7.12 Hz, 2H), and 6.23 (s, 1H).

Preparation 4D: Ethyl-4-iodo-5-(1-methylcyclopropyl)isoxazole-3-carboxylate

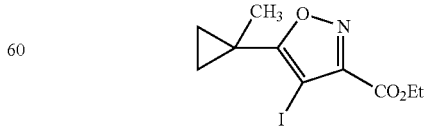

(4D)

A mixture of ethyl 5-(1-methylcyclopropyl)isoxazole-3-carboxylate (Preparation 4C, 1.5 g, 7.68 mmol) and 1-iodopyrrolidine-2,5-dione (2.07 g, 9.22 mmol) in TFA (25 mL)

was stirred at room temperature for 2 h. The reaction mixture was concentrated under reduced pressure. The residue was dissolved in ethyl acetate (50 mL) and washed sequentially with water (50 mL), 1N aqueous sodium hydroxide (50 mL), 2.5 M aqueous sodium bisulfate (50 mL), brine (50 mL), dried over anhydrous sodium sulfate, and concentrated under reduced pressure to give ethyl-4-iodo-5-(1-methylcyclopropyl)isoxazole-3-carboxylate (1.93 g, 75% yield) as a yellow liquid. The product had an HPLC ret. time=2.49 min. (condition B); LC/MS M$^{+1}$=321.9; $^1$H NMR (400 MHz, CDCl$_3$) δ ppm 0.85 (m, 2H), 1.12 (m, 2H), 1.40 (t, J=7.15 Hz, 3H), 1.42 (s, 3H), and 4.41 (q, J=7.15 Hz, 2H).

Preparation 4E: Ethyl-5-(1-methylcyclopropyl)-4-(trifluoromethyl)isoxazole-3-carboxylate

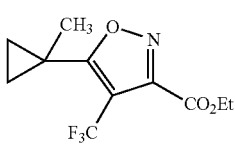

(4E)

To a mixture of ethyl 4-iodo-5-(1-methylcyclopropyl)isoxazole-3-carboxylate (Preparation 4D, 1.60 g, 4.98 mmol), copper(I) iodide (0.190 g, 0.997 mmol), and HMPA (3 mL) in anhydrous dimethylformamide (24 mL) was added methyl 2,2-difluoro-2-(fluorosulfonyl)acetate (3.17 mL, 24.9 mmol). The reaction mixture was heated at 75° C. for 6 h and then stirred overnight at room temperature. The reaction mixture was diluted with diethyl ether (50 mL), washed with saturated aqueous solution of ammonium chloride (3×50 mL), brine (50 mL), dried over anhydrous sodium sulfate, and concentrated under reduced pressure. The crude product was purified by flash silica gel chromatography using a 10% mixture of ethyl acetate in hexane to give ethyl-5-(1-methylcyclopropyl)-4-(trifluoromethyl)isoxazole-3-carboxylate (1.15 g, 83% yield) as a clear colorless liquid. (condition B); LC/MS M$^{+1}$=285.9. $^1$H NMR (400 MHz, CDCl$_3$) δ ppm 0.86 (m, 2H), 1.07 (m, J=1.10 Hz, 2H), 1.35 (t, J=7.15 Hz, 3H), 1.34 (s, 3H), and 4.39 (q, J=7.26 Hz, 2H).

Preparation 4F: 3-(5-(1-Methylcyclopropyl)-4-(trifluoromethyl)isoxazol-3-yl)-7-vinyl-4,5-dihydronaphtho-[1,2-c]isoxazole

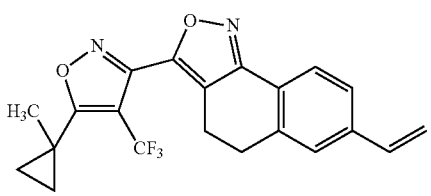

(4F)

A fresh solution of lithium diisopropylamide was made by adding n-butyllithium (0.855 mL, 2.14 mmol) to a stirred mixture of diisopropylamine (0.299 mL, 2.14 mmol) in THF (10 mL) at 0° C. After stirring for 30 min., the lithium diisopropylamide solution was added to a solution of (E)-6-vinyl-3,4-dihydronaphthalen-1(2H)-one oxime (Intermediate 1, 0.200 g, 1.068 mmol) in THF (25 mL) at 0° C. over 10 min., during which time the reaction mixture became orange in color. The reaction mixture was stirred for an additional 20 min., and then methyl 5-(1-methylcyclopropyl)-4-(trifluoromethyl)isoxazole-3-carboxylate (Preparation 4E, 0.177 g, 0.712 mmol) in THF (1 mL) was added. The resulting reaction mixture was stirred for 30 min. at 0° C., quenched with 1N aqueous hydrochloric acid (10 mL), and concentrated under reduced pressure. The crude residue was dissolved in toluene (10 mL), p-toluenesulfonic acid monohydrate (0.271 g, 1.424 mmol) was added, and the mixture was heated at 110° C. for 45 min. The reaction mixture was concentrated using methanol to azeotrope off the toluene solvent. The crude residue was taken up in ethyl acetate (25 mL), stirred, and filtered. The filtrate was concentrated to give 0.442 g of the crude product which was purified by flash silica gel chromatography using a 5% mixture of ethyl acetate in hexane. Fractions containing the product were combined and concentrated to give 3-(5-(1-methylcyclopropyl)-4-(trifluoromethyl)isoxazol-3-yl)-7-vinyl-4,5-dihydronaphtho[1,2-c]isoxazole (0.043 g, 16%) as a yellow solid. The product had an HPLC ret. time=4.35 min. (condition B); LC/MS M$^{+1}$=387.12; $^1$H NMR (500 MHz, CDCl$_3$) δ ppm 0.79-0.93 (m, 2H), 1.02-1.16 (m, 2H), 1.42 (s, 3H), 2.75-3.12 (m, 4H), 5.26 (dd, J=11.37 Hz, 1H), 5.79 (dd, J=17.48 Hz, 1H), 6.44-6.89 (m, 1H), 7.29 (s, 1H), 7.43 (m, 1H), and 7.88 (d, J=8.05 Hz, 1H).

Preparation 4G: 3-(5-(1-Methylcyclopropyl)-4-(trifluoromethyl)isoxazol-3-yl)-4,5-dihydronaphtho[1,2-c]-isoxazole-7-carbaldehyde

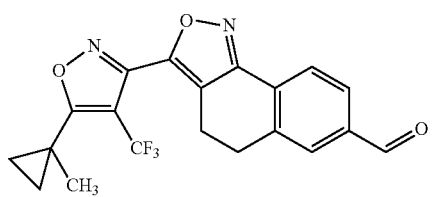

(4G)

To a solution of 3-(5-(1-methylcyclopropyl)-4-(trifluoromethyl)isoxazol-3-yl)-7-vinyl-4,5-dihydronaphtho[1,2-c]isoxazole (Preparation 4F, 0.043 g, 0.111 mmol) in dichloromethane (10 mL) at −78° C. was passed ozone from an ozone generator until the solution turned a deep blue. The reaction mixture was purged with oxygen until the blue color disappeared and then purged with nitrogen for five minutes. The reaction mixture was allowed to warm to room temperature, and triethylamine (0.046 mL, 0.334 mmol) was added. The reaction mixture was stirred at room temperature for 15 min. and then concentrated under reduced pressure to give 3-(5-(1-methylcyclopropyl)-4-(trifluoromethyl)isoxazol-3-yl)-4,5-dihydronaphthol[1,2-c]isoxazole-7-carbaldehyde (0.044 g, 96% yield) as a tan solid. The product had an HPLC ret. time=4.02 min. (condition B); LC/MS M$^{+1}$=389.09.

Example 4

To a solution of 3-(5-(1-methylcyclopropyl)-4-(trifluoromethyl)isoxazol-3-yl)-4,5-dihydronaphtho[1,2-c]isoxazole-7-carbaldehyde (Preparation 4G, 0.044 g, 0.113 mmol) in methanol (2 mL) and 1,2-dichloroethane (2 mL) was added azetidine-3-carboxylic acid (0.014 g, 0.136 mmol) followed by 5 drops of acetic acid. The reaction mixture was heated at 60° C. for 1.5 h. The reaction mixture was cooled to room temperature, and sodium cyanoborohydride (0.009 g, 0.143 mmol) was added. The reaction mixture was stirred at room temperature for 15 min. and then concentrated under reduced pressure. The crude residue was partitioned between dichloromethane and water, and the dichloromethane extract was concentrated and purified by silica gel chromatography using a 10% mixture of methanol in dichloromethane followed a 20% mixture of methanol in dichloromethane with 1% ammonium hydroxide to give the product (0.011 g). The compound was triturated with methanol and filtered to give 1-((3-(5-(1-methylcyclopropyl)-4-(trifluoromethyl)isoxazol-3-yl)-4,5-dihydronaphtho-[1,2-c]isoxazol-7-yl)methyl) azetidine-3-carboxylic acid (5.2 mg). The product had an HPLC ret. time=3.23 min. (condition B); LC/MS $M^{+1}$=474.17. $^1$H NMR (500 mhz, CD$_3$OD) δ ppm 0.63-1.02 (m, 2H), 1.00-1.23 (m, 2H), 1.39 (s, 3H), 2.68-3.13 (m, 4H), 3.50-3.80 (m, 1H), 4.10-4.32 (m, 4H), 4.36 (s, 2H), 7.10-7.44 (m, 1H), 7.40 (s, 1H), and 7.94 (d, J=7.63 Hz, 1H).

Example 5

1-((3-(5-Isobutyl-4-(trifluoromethyl)isoxazol-3-yl)-4,5-dihydronaphtho[1,2-c]isoxazol-7-yl)methyl)azetidine-3-carboxylic acid

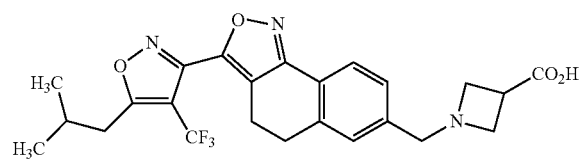

(5)

Preparation 5A: Methyl 5-isobutylisoxazole-3-carboxylate

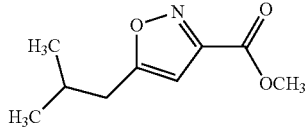

(5A)

To a solution of 5-isobutylisoxazole-3-carboxylic acid (1.0 g, 5.91 mmol) in a mixture of dichloromethane (18 mL) and methanol (6 mL) was added trimethylsilyldiazomethane (2.0 M in ether) (5.91 mL, 11.8 mmol) dropwise until the yellow color persisted and the bubbling ceased (~3.9 mL was required). The solvent was removed under reduced pressure, and the residue was diluted with dichloromethane, washed with a saturated aqueous solution of sodium bicarbonate, and dried over anhydrous sodium sulfate. Concentration under reduced pressure followed by purification by flash silica gel chromatography using a 5% mixture of ethyl acetate in hexane afforded methyl 5-isobutylisoxazole-3-carboxylate (0.925 g, 5.05 mmol, 85% yield) as a flakey, white solid. The product had an HPLC ret. time=1.83 min.–Column: (condition A); LC/MS $M^{+1}$=184.1. $^1$H NMR (500 MHz, CDCl$_3$) δ ppm [mixture of isobutyl rotomers] 0.96-1.00 (m, 6H), [1.94-2.03 (m, 0.1H) and 2.03-2.14 (m, 0.9H)], [2.62 (d, J=7.21 Hz, 0.2H) and 2.70 (d, J=7.21 Hz, 1.8H)], 3.96-3.99 (m, 3H), and [6.41-6.44 (m, 0.9H) and 6.80 (s, 0.1H)].

Preparation 5B: Methyl 4-iodo-5-isobutylisoxazole-3-carboxylate

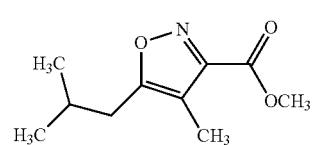

(5B)

A mixture of methyl 5-isobutylisoxazole-3-carboxylate (Preparation 5A, 0.923 g, 5.04 mmol) and N-iodosuccinimide (1.247 g, 5.54 mmol) in TFA (25 mL) was stirred at room temperature overnight. The TFA was removed under reduced pressure, and the residue was diluted with dichloromethane (100 mL), washed with a saturated aqueous solution of sodium bicarbonate (2×25 mL), 2.5% aqueous solution of sodium bisulfate (25 mL), and dried over anhydrous sodium sulfate. Concentration under reduced pressure followed by purification by flash silica gel chromatography using a 5% mixture of ethyl acetate in hexane afforded methyl 4-iodo-5-isobutylisoxazole-3-carboxylate (1.21 g, 3.91 mmol, 78% yield) as a pale yellow oil. The product had an HPLC ret. time=2.40 min. (condition A); LC/MS $M^{+1}$=310.1.

Preparation 5C: Methyl 5-isobutyl-4-(trifluoromethyl)isoxazole-3-carboxylate

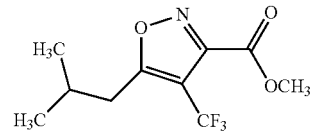

(5C)

To a solution of methyl 4-iodo-5-isobutylisoxazole-3-carboxylate (Preparation 5B, 1.21 g, 3.91 mmol), copper(I) iodide (0.149 g, 0.783 mmol), and HMPA (2.59 mL) in N,N-dimethylformamide (19 mL) was added methyl 2,2-difluoro-2-(fluorosulfonyl)acetate (1.993 mL, 15.66 mmol) over 1 min. The reaction mixture was immediately immersed in an oil bath at 75° C. and was stirred overnight. The clear, orange reaction mixture was cooled to room temperature and diluted with ether (100 mL), washed with a saturated aqueous solution of ammonium chloride (2×100 mL), washed with a 10% aqueous solution of lithium chloride (2×50 mL), and washed with brine (50 mL). The aqueous layer was back-extracted with ether (100 mL+50 mL), and the combined organic layers were dried over anhydrous sodium sulfate. Concentration under reduced pressure followed by purification by flash silica gel chromatography using a 5% mixture of ethyl acetate in hexane provided methyl 5-isobutyl-4-(trifluoromethyl) isoxazole-3-carboxylate (0.819 g, 3.26 mmol, 83% yield) as a clear, colorless oil. The product had an HPLC ret. time=2.52 min. (condition A); $^1$H NMR (500 MHz, CDCl$_3$) δ ppm 0.99 (s, 3H), 1.00 (s, 3H), 2.09-2.20 (m, 1H), 2.86 (dd, J=7.21, 1.11 Hz, 2H), and 4.01 (s, 3H).

Preparation 5D: (5-Isobutyl-4-(trifluoromethyl)isoxazol-3-yl)-7-vinyl-4,5-dihydronaphtho[1,2-c]isoxazole

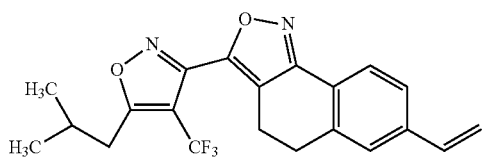

(5D)

To a fresh solution of lithium diisopropylamide made by adding n-butyllithium (2.15 mL, 5.37 mmol) to a stirred mixture of diisopropylamine (0.753 mL, 5.37 mmol) in THF (10 mL) at 0° C. was added a solution of (E)-6-vinyl-3,4-dihydronaphthalen-1(2H)-one oxime (Intermediate 1, 0.335 g, 1.79 mmol) in THF (2 mL) over ten minutes. After complete addition, the reaction mixture turned orange in colored and was stirred an additional 20 min. Methyl 5-isobutyl-4-(trifluoromethyl)isoxazole-3-carboxylate (Preparation 5C, 0.300 g, 1.19 mmol) in THF (1 mL) was added over 5 min., and the resulting reaction mixture turned dark brown-black and was stirred for 30 min. at 0° C. The reaction mixture was allowed to warm to room temperature, quenched with 1N aqueous hydrochloric acid (10 mL), and concentrated under vacuum. The residue was diluted with toluene (25 mL) and filtered. To the filtrate was added pyridine (0.5 mL) and thionyl chloride (0.261 mL, 3.58 mmol), and the reaction mixture was heated at 110° C. for about 20 min. The mixture was diluted with ethyl acetate (50 mL), stirred, and filtered. The filtrate was concentrated under reduced pressure to give 102 mg of the dark brown crude product mixture which was purified by flash silica gel chromatography using 10% ethyl acetate in hexane to give 3-(5-isobutyl-4-(trifluoromethyl)isoxazol-3-yl)-7-vinyl-4,5-dihydronaphtho[1,2-c]isoxazole (46 mg, 10% yield) as a yellow solid. The product had an HPLC ret. time=4.39 min. (condition B); LC/MS $M^{+1}$=389.20.

Preparation 5E: 3-(5-Isobutyl-4-(trifluoromethyl)isoxazol-3-yl)-4,5-dihydronaphtho[1,2-c]isoxazole-7-carbaldehyde

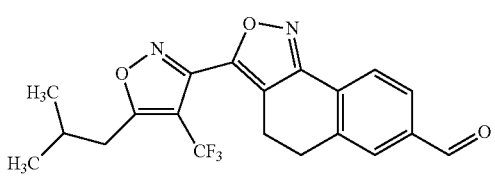

(5E)

To a solution of 3-(5-isobutyl-4-(trifluoromethyl)isoxazol-3-yl)-7-vinyl-4,5-dihydronaphtho[1,2-c]isoxazole (Preparation 5D, 0.045 g, 0.116 mmol) in dichloromethane (10 mL) at −78° C. was passed ozone from an ozone generator until the solution turned deep blue. The reaction mixture then was purged with oxygen until the blue color disappeared and then with nitrogen for 5 min. The reaction mixture was allowed to warm to room temperature, and triethylamine (0.016 mL, 0.116 mmol) was added. The reaction mixture was stirred at room temperature for 15 min. and then concentrated under pressure to give 3-(5-isobutyl-4-(trifluoromethyl)isoxazol-3-yl)-4,5-dihydronaphtho[1,2-c]isoxazole-7-carbaldehyde (0.045 g, 85% yield) as a tan solid. The product had an HPLC ret. time=4.02 min. (condition B); LC/MS $M^{+1}$=391.09.

Example 5

To a solution of 3-(5-isobutyl-4-(trifluoromethyl)isoxazol-3-yl)-4,5-dihydronaphtho[1,2-c]isoxazole-7-carbaldehyde (Preparation 5E, 0.022 g, 0.056 mmol) in methanol (2 mL) and 1,2-dichloroethane (2 mL) was added azetidine-3-carboxylic acid (6.84 mg, 0.068 mmol) followed by 2 drops of acetic acid. The reaction mixture was heated at 60° C. for 1.5 h, cooled to room temperature, and sodium cyanoborohydride (4.25 mg, 0.068 mmol) was added. The reaction mixture was then stirred at room temperature for 15 min. and concentrated under reduced pressure. The crude residue was diluted with dichloromethane, washed with water, and the organic layer was collected and concentrated. The residue was purified by flash silica gel chromatography using a 10% mixture of methanol in dichloromethane followed by a 20% mixture of methanol in dichloromethane with 1% ammonium hydroxide to give 21 mg of the product. The compound was further purified by preparative HPLC to give 1-((3-(5-isobutyl-4-(trifluoromethyl)isoxazol-3-yl)-4,5-dihydronaphtho[1,2-c]isoxazol-7-yl)methyl)azetidine-3-carboxylic acid (3.2 mg, 12% yield) as an off-white solid. The product had an HPLC ret. time=3.36 min. (condition A); LC/MS $M^{+1}$=476.29. $^1$H NMR (400 MHz, CD$_3$OD) δ ppm 0.94 (s, 6H), 2.07 (m, 1H), 2.87 (d, J=7.37 Hz, 2H), 2.92-3.11 (m, 4H), 3.56-3.77 (m, 1H), 4.14-4.30 (m, 4H), 4.37 (s, 2H), 7.39 (d, J=7.92 Hz, 1H), 7.43 (dd, 2H), and 7.95 (d, J=7.96 Hz, 1H).

Example 6

1-((3-(5-Phenyl-4-(trifluoromethyl)isoxazol-3-yl)-4,5-dihydronaphtho[1,2-c]isoxazol-7-yl)methyl)azetidine-3-carboxylic acid

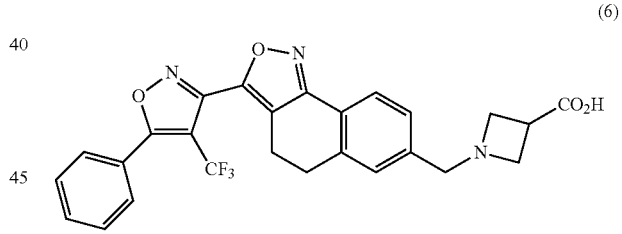

(6)

Preparation 6A: 3-(5-Phenyl-4-(trifluoromethyl)isoxazol-3-yl)-7-vinyl-4,5-dihydronaphtho[1,2-c]isoxazole

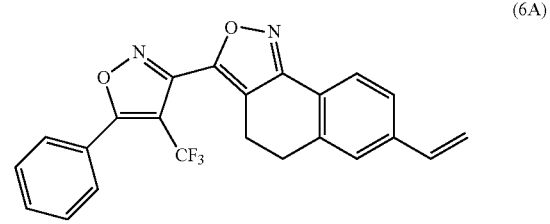 [SMILES: C=Cc1ccc2c(c1)CCc1c-2noc1-c1noc(-c2ccccc2)c1C(F)(F)F]

(6A)

To a stirred solution of diisopropylamine (2.80 mL, 19.62 mmol) in anhydrous THF (15 mL) was added n-butyllithium (7.85 mL, 19.62 mmol) (2.5 M in hexanes) dropwise at 0° C. under a nitrogen atmosphere. The yellow cloudy solution was stirred at the same temperature for 20 min before a solution of 6-vinyl-3,4-dihydronaphthalen-1(2H)-one oxime (Intermediate 1, 1.705 g, 9.11 mmol) in anhydrous THF (7 mL) was added dropwise at 0° C. under nitrogen. The mixture was stirred at 0° C. for 50 min. A solution of methyl 5-phenyl-4-(trifluoromethyl)isoxazole-3-carboxylate (Intermediate 5, 1.9 g, 7.01 mmol) in anhydrous THF (5 mL) was added dropwise at 0° C. The dark red mixture was stirred at 0° C. for 70 min., quenched with saturated aqueous ammonium chloride solution (15 mL) and water (15 mL) and extracted with ethyl acetate (2×30 mL). The ethyl acetate extracts were washed with brine (20 mL), dried over sodium sulfate, and concentrated to yield a brown foamy solid. To the solid was added anhydrous toluene (40 mL) and p-toluenesulfonic acid monohydrate (2.67 g, 14.01 mmol) and the contents were heated at 110° C. under nitrogen for 3 h. The reaction mixture was cooled to room temperature and the liquid was separated from the solid by decantation and washed with saturated aqueous sodium bicarbonate solution (5 mL). The left solid was stirred with dichloromethane (70 mL) and water (50 mL) for 1 hr with occasional sonication. The solid was filtered off and washed with dichloromethane (2×5 mL). The filtrate was basified with aqueous ammonia solution (2 mL). The aqueous layer was separated, combined with previous sodium bicarbonate solution wash, and extracted with dichloromethane (2×20 mL). The combined organic solutions were dried over sodium sulfate and concentrated under reduced pressure. Silica gel chromatography (10 to 100% dichloromethane in heptane) afforded 3-(5-phenyl-4-(trifluoromethyl)isoxazol-3-yl)-7-vinyl-4,5-dihydronaphtho[1,2-c]isoxazole (1.07 g, 2.62 mmol, 37.4% yield) as a yellow solid. LC/MS $M^{+1}$=409.4.

Preparation 6B: (3-(5-Phenyl-4-(trifluoromethyl)isoxazol-3-yl)-4,5-dihydronaphtho[1,2-c]isoxazol-7-yl)methanol (6B)

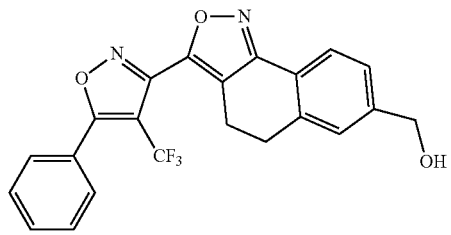

To a clear solution of 3-(5-phenyl-4-(trifluoromethyl)isoxazol-3-yl)-7-vinyl-4,5-dihydronaphtho[1,2-c]isoxazole (Preparation 6A, 1.06 g, 2.60 mmol) in chloroform (1 mL) and THF (15 mL) were sequentially added N-methylmorpholine-N-oxide in water (0.807 mL, 3.89 mmol) and osmium tetroxide in water (0.317 mL, 0.052 mmol) at room temperature. The solution was stirred at room temperature overnight. More N-methylmorpholine-N-oxide in water (0.40 mL) was added. The mixture was stirred at room temperature for 2 hr before sodium periodate (0.666 g, 3.11 mmol) in water (4 mL) was added. The mixture was stirred at room temperature under nitrogen for 2 hr. Water (30 mL) was added and the mixture was concentrated to remove THF. The solid was filtered, washed with water (1 mL), and dried to give 3-(5-phenyl-4-(trifluoromethyl)isoxazol-3-yl)-4,5-dihydronaphtho[1,2-c]isoxazole-7-carbaldehyde as a yellow solid. The filtrate was extracted with dichloromethane (3×6 mL). The combined extracts were dried over sodium sulfate and concentrated under reduced pressure to give a yellow liquid. This liquid was combined with the yellow solid obtained above with dichloromethane (5 mL), THF (5 mL), and methanol (7 mL). The suspension obtained was treated with sodium borohydride (0.147 g, 3.89 mmol) at room temperature under nitrogen. The mixture was stirred at room temperature for 1 hr before water (10 mL) and saturated aqueous ammonium chloride solution (5 mL) were added. The mixture was concentrated to remove organic solvents. The solid was filtered, washed with water (2×2 mL), and crystallized in methanol to give (3-(5-phenyl-4-(trifluoromethyl)isoxazol-3-yl)-4,5-dihydronaphtho[1,2-c]isoxazol-7-yl)methanol (500 mg, 1.213 mmol, 46.7% yield) as a yellow solid. The filtrate was extracted with dichloromethane (3×10 mL). The dichloromethane extracts were dried over sodium sulfate and combined with the mother liquor from the crystallization. Purification using silica gel chromatography (20 to 100% dichloromethane in heptane and then 20→100% ethyl acetate in heptane) afforded an additional crop of (3-(5-phenyl-4-(trifluoromethyl)isoxazol-3-yl)-4,5-dihydronaphtho[1,2-c]isoxazol-7-yl)methanol (205 mg, 0.497 mmol, 19.15% yield) as a yellow solid. LC/MS $M^{+1}$=413.1.

Preparation 6C: 7-(Bromomethyl)-3-(5-phenyl-4-(trifluoromethyl)isoxazol-3-yl)-4,5-dihydronaphtho[1,2-c]isoxazole (6C)

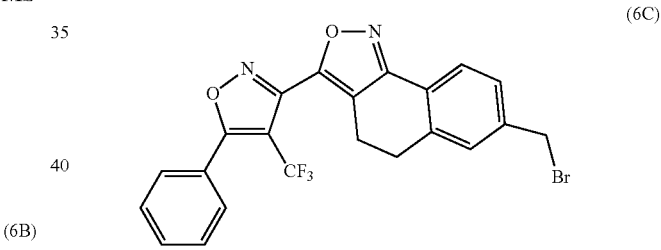

To a solution of (3-(5-phenyl-4-(trifluoromethyl)isoxazol-3-yl)-4,5-dihydronaphtho[1,2-c]isoxazol-7-yl)methanol (Preparation 6B, 700 mg, 1.698 mmol) in anhydrous dichloromethane (25 mL) was added phosphorous tribromide (0.240 mL, 2.55 mmol) slowly at 0° C. under nitrogen. The reaction mixture was then stirred at room temperature overnight. Next, 10 mL of ice water was added at 0° C. to quench the reaction. The organic layer was separated, washed with saturated aqueous sodium bicarbonate solution (20 mL) and filtered over CELITE®. The aqueous layer was separated, combined with the aqueous layer from before and extracted with dichloromethane (2×20 mL). The combined organic solutions were dried over sodium sulfate, filtered through a silica gel pad that was rinsed with dichloromethane, and concentrated under reduced pressure to give 7-(bromomethyl)-3-(5-phenyl-4-(trifluoromethyl)isoxazol-3-yl)-4,5-dihydronaphtho[1,2-c]isoxazole (580 mg, 1.220 mmol, 71.9% yield) as a yellow solid. LC/MS $M^{+1}$=477.

Example 6

To a cloudy solution of 7-(bromomethyl)-3-(5-phenyl-4-(trifluoromethyl)isoxazol-3-yl)-4,5-dihydronaphtho[1,2-c]

isoxazole (Preparation 6C, 550 mg, 1.157 mmol) and tert-butyl azetidine-3-carboxylate acetic acid (377 mg, 1.736 mmol) in anhydrous DMF (12 mL) was added triethylamine (0.645 mL, 4.63 mmol) dropwise at 0° C. under a nitrogen atmosphere. The reaction mixture was stirred at the same temperature for 1 hr before being concentrated. The solid residue was partitioned between dichloromethane (2 mL) and saturated aqueous sodium bicarbonate solution (6 mL). The aqueous layer was extracted with dichloromethane (2×2 mL). The combined dichloromethane solutions were dried over sodium sulfate, concentrated and purified by silica gel chromatography (20 to 75% ethyl acetate in heptane) to afford tert-butyl 1-((3-(5-phenyl-4-(trifluoromethyl)isoxazol-3-yl)-4,5-dihydronaphtho[1,2-c]isoxazol-7-yl)methyl)azetidine-3-carboxylate (520 mg, 0.943 mmol, 81% yield) as a solid. To the solid was added TFA (3 mL) and the mixture stirred at room temperature for 70 min before being concentrated. Dichloromethane (15 mL) was added and the mixture concentrated again. The residue was mixed with water (4 ml) and neutralized to pH=5 with an aqueous sodium acetate solution. The resulting solid was filtered and washed with water (3×1 mL). To the solid was added methanol (1 mL) and water (0.5 mL), the contents were sonicated, and filtered. To the solid was added acetonitrile (0.5 mL) and water (6 mL). Lyophilization gave 1-((3-(5-phenyl-4-(trifluoromethyl)isoxazol-3-yl)-4,5-dihydronaphtho[1,2-c]isoxazol-7-yl)methyl)azetidine-3-carboxylic acid (420 mg, 0.805 mmol, 69.6% yield) as a white solid. The compound had an HPLC retention time=3.25 min. (condition C). LC/MS $M^{+1}$=496.2. $^1$H NMR (400 MHz, MeOD+CDCl$_3$) δ ppm 8.06 (1H, d, J=7.9 Hz), 7.77 (2H, d, J=7.3 Hz), 7.59-7.71 (3H, m), 7.51 (1H, s), 7.48 (1H, d, J=7.7 Hz), 4.42 (2H, s), 4.25-4.34 (4H, m), 3.55-3.65 (1H, m), 3.14 (4H, s).

Example 7

1-((3-(3-Phenyl-4-(trifluoromethyl)isoxazol-5-yl)-4,5-dihydronaphtho[1,2-c]isoxazol-7-yl)methyl)azetidine-3-carboxylic acid

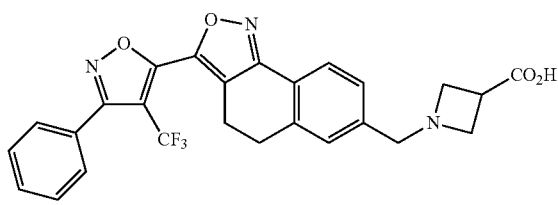

(7)

This compound was prepared employing a similar protocol to that outlined for the compound in Example 6, by substituting methyl 5-phenyl-4-(trifluoromethyl)isoxazole-3-carboxylate in step A with methyl 3-phenyl-4-(trifluoromethyl) isoxazole-5-carboxylate (intermediate 3). The compound had an HPLC retention time=3.23 min (condition C); LC/MS $M^{+1}$=496.4. $^1$H NMR (400 MHz, MeOD) δ ppm 7.96 (1H, d, J=7.9 Hz), 7.58 (2H, d, J=6.8 Hz), 7.43-7.53 (4H, m), 7.39 (1H, d, J=7.7 Hz), 4.26 (2H, s), 4.02-4.12 (4H, m), 3.28-3.37 (1H, m), 3.02-3.12 (4H, m).

Alternative Synthesis of Example 7

Preparation 7A: 3-(3-phenyl-4-(trifluoromethyl)isoxazol-5-yl)-7-vinyl-4,5-dihydronaphtho[1,2-c]isoxazole

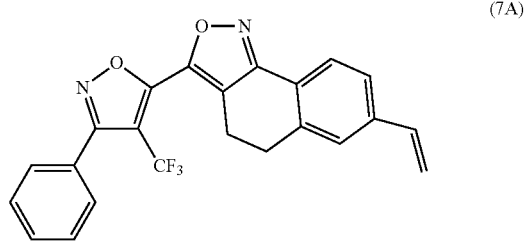 [SMILES: C=Cc1ccc2c(c1)CCc1c-2noc1-c1onc(-c2ccccc2)c1C(F)(F)F]

(7A)

Preparation of LiTMP: To a stirred solution of 2,2,6,6-tetramethylpiperidine (10.88 mL, 64.5 mmol) in anhydrous THF (25 mL) was added n-BuLi (25.8 mL, 64.5 mmol) (2.5M in hexanes) dropwise at 0° C. under nitrogen. The pale yellow solution was then stirred at the same temperature for 20 min.

To a stirred solution of 6-vinyl-3,4-dihydronaphthalen-1(2H)-one oxime (I-1, 4.03 g, 21.50 mmol) and diisopropylethylamine (6.83 mL, 39.1 mmol) in anhydrous THF (50 mL) was added TMS-Cl (2.75 mL, 21.50 mmol) dropwise at 0° C. under nitrogen. The mixture was stirred at 0° C. for 30 min. The previously prepared LiTMP solution was added dropwise at −78° C. under nitrogen. After the mixture was stirred at the same temperature for 30 min, a solution of methyl 3-phenyl-4-(trifluoromethyl)isoxazole-5-carboxylate (I-3, 5.3 g, 19.54 mmol) in anhydrous THF (10 mL) was added dropwise at −78° C. The solution was stirred at −78° C. for 30 min and then warmed to 0° C. over 30 min. The reaction was quenched with saturated aqueous ammonium chloride solution (25 mL) and water (20 mL). The mixture was mixed with EtOAc (50 mL), stirred at room temperature for 30 min and filtered through a pad of celite. The filtrate was separated. The aqueous layer was extracted with EtOAc (2×25 mL). The combined organic solutions were washed with brine (50 mL), dried over sodium sulfate and concentrated to give a liquid. Flash chromatography purification (330 g silica gel column, 15-30% ethyl acetate in hexanes) afforded 3-(3-phenyl-4-(trifluoromethyl)isoxazol-5-yl)-7-vinyl-3,3a,4,5-tetrahydronaphtho[1,2-c]isoxazol-3-ol (5 g, 11.73 mmol, 60.0% yield) as a yellow solid. The compound had an HPLC retention time=3.74 min (condition C); LC/MS $M^{+1}$=426.9.

The 3-(3-phenyl-4-(trifluoromethyl)isoxazol-5-yl)-7-vinyl-3,3a,4,5-tetrahydronaphtho[1,2-c]isoxazol-3-ol (5 g, 11.73 mmol) was mixed with thionyl chloride (1.712 mL, 23.45 mmol) and anhydrous toluene (80 mL). Pyridine (0.190 mL, 2.345 mmol) was then added dropwise. The mixture was stirred under nitrogen at room temperature for 30 min and 90° C. for 15 min. The mixture was concentrated under reduced pressure. The residue was partitioned between saturated aqueous sodium bicarbonate solution (50 mL) and dichloromethane (100 mL, 2×50 mL). The combined dichloromethane extracts were dried over sodium sulfate, filtered through a pad of silica gel and concentrated under reduced pressure. Flash chromatography purification (220 g silica gel column, 25→60% dichloromethane in hexanes) and trituration with methanol gave 3-(3-phenyl-4-(trifluoromethyl) isoxazol-5-yl)-7-vinyl-4,5-dihydronaphtho[1,2-c]isoxazole (1.96 g, 4.80 mmol, 40.9% yield) as a white solid. The compound had an HPLC retention time=4.28 min (condition C); LC/MS M$^{+1}$=408.9.

Preparation 7B: 3-(3-phenyl-4-(trifluoromethyl)isoxazol-5-yl)-4,5-dihydronaphtho[1,2-c]isoxazole-7-carbaldehyde

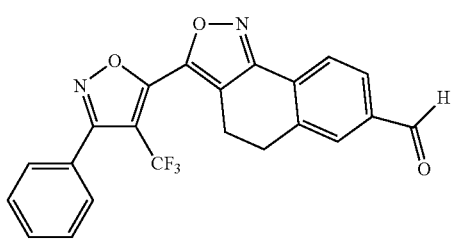

(7B)

To a stirred mixture of 3-(3-phenyl-4-(trifluoromethyl)isoxazol-5-yl)-7-vinyl-4,5-dihydronaphtho[1,2-c]isoxazole (7A, 1.96 g, 4.80 mmol) and THF (20 mL) were added NMO (50% in water, 1.493 mL, 7.20 mmol) and osmium tetroxide (4% in water, 1.173 mL, 0.192 mmol) at room temperature. The mixture was vigorously stirred at room temperature overnight. A solution of sodium periodate (1.540 g, 7.20 mmol) in water (10 mL) was added. The mixture was stirred at room temperature under nitrogen for 30 min. Water (20 mL) was then added. The solid was filtered, washed with water (2×5 mL) and ethanol (2 mL) and dried to give 3-(3-phenyl-4-(trifluoromethyl)isoxazol-5-yl)-4,5-dihydronaphtho[1,2-c]isoxazole-7-carbaldehyde (1.92 g, 4.68 mmol, 98%) as a white solid. The compound had an HPLC retention time=3.95 min (condition C); LC/MS M$^{+1}$=410.9.

Preparation 7C: tert-butyl 1-((3-(3-phenyl-4-(trifluoromethyl)isoxazol-5-yl)-4,5-dihydronaphtho[1,2-c]isoxazol-7-yl)methyl)azetidine-3-carboxylate

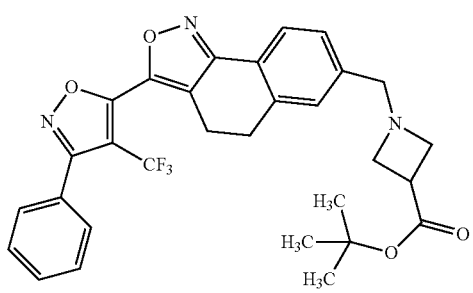

(7C)

To a stirred solution of 3-(3-phenyl-4-(trifluoromethyl)isoxazol-5-yl)-4,5-dihydronaphtho[1,2-c]isoxazole-7-carbaldehyde (7B, 2.1 g, 5.12 mmol), tert-butyl azetidine-3-carboxylate, AcOH (1.668 g, 7.68 mmol), and acetic acid (0.586 mL, 10.24 mmol) in anhydrous MeOH (10 mL) and anhydrous 1,2-dichloroethane (30 mL) was added titanium (IV) isopropoxide (3.05 mL, 10.24 mmol) dropwise at room temperature under nitrogen. The solution was stirred at room temperature for 1 hr before sodium triacetoxyborohydride (4.34 g, 20.47 mmol) was added in 10 portions over 3.5 hr. The mixture was stirred at room temperature for 2 hr. Saturated sodium bicarbonate (70 mL) was added slowly to make the mixture basic. After celite was added, the mixture was stirred at room temperature for 30 min and then filtered through a pad of celite. The aqueous filtrate was separated and extracted with dichloromethane (3×20 mL). The combined organic solutions were dried (sodium sulfate) and concentrated. Flash chromatography purification (120 g silica gel column, 25→70% ethyl acetate in hexanes) afforded tert-butyl 1-((3-(3-phenyl-4-(trifluoromethyl)isoxazol-5-yl)-4,5-dihydronaphtho[1,2-c]isoxazol-7-yl)methyl)azetidine-3-carboxylate (2.24 g, 4.06 mmol, 79% yield) as a yellow solid. The compound had an HPLC retention time=3.40 min (condition C); LC/MS M$^{+1}$=552.1.

Example 7

To a stirred solution of tert-butyl 1-((3-(3-phenyl-4-(trifluoromethyl)isoxazol-5-yl)-4,5-dihydronaphtho[1,2-c]isoxazol-7-yl)methyl)azetidine-3-carboxylate (7C, 2.24 g, 4.06 mmol) in dichloromethane (4 mL) was added TFA (4 mL) slowly at room temperature. The reaction mixture was stirred at room temperature for 2 hr. The mixture was concentrated to remove dichloromethane and TFA (6 mL) was added. The mixture was stirred at room temperature till the starting material was observed to disappear. Dichloroethane (6 mL) was added and the mixture was concentrated under reduced pressure. The residue was mixed with water (10 mL), basified with 1 N aqueous NaOH to pH=8 and acidified with 1N aqueous HCl to pH=5. The mixture was sonicated for 30 min. The solid was filtered and washed with water (4×10 mL). The wet solid was mixed with methanol (40 mL), sonicated for 30 min, filtered, washed with methanol (3×10 mL), and dried to give 1-((3-(3-phenyl-4-(trifluoromethyl)isoxazol-5-yl)-4,5-dihydronaphtho[1,2-c]isoxazol-7-yl)methyl)azetidine-3-carboxylic acid as a white solid.

Example 8

3-(3-Phenyl-4-(trifluoromethyl)isoxazol-5-yl)-4,5-dihydronaphtho[1,2-c]isoxazol-7-ol

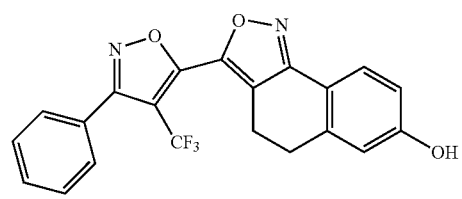

(8)

Preparation 8A: 7-Methoxy-3-(3-phenyl-4-(trifluoromethyl)isoxazol-5-yl)-4,5-dihydronaphtho[1,2-c]isoxazole

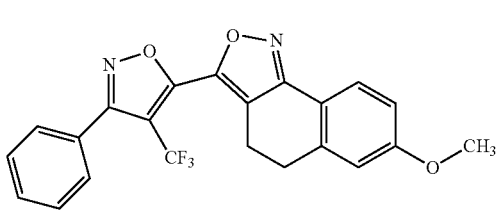

(8A)

To 6-methoxy-3,4-dihydronaphthalen-1(2H)-one oxime (Intermediate 2, 0.328 g, 1.715 mmol) in 3 mL of THF, cooled to 0° C. was added butyllithium (1.372 mL, 3.43 mmol) dropwise over a period of 3 min. The contents were stirred at 0° C. for 30 min. A solution of methyl 3-phenyl-4-(trifluoromethyl)isoxazole-5-carboxylate (Intermediate 3, 0.31 g, 1.14 mmol) dissolved in 2 mL of THF was added over a period of 3 min. The pale yellow reaction mixture was allowed to come to room temperature and stirred for 20 min. To the reaction mixture was added 0.5 mL of conc. sulfuric acid dropwise over a period of 3 min. at 0° C. and the contents were allowed to come to room temperature over a period of 10 min., then stirred at room temperature for 1.5 h. The reaction mixture was concentrated under reduced pressure. Dioxane (5 mL) was added and the contents were heated at 100° C. for 1.5 h, and at room temperature for 18 h. The reaction mixture was concentrated under reduced pressure and partitioned between ethyl acetate (25 mL) and water (10 mL). The ethyl acetate layer was washed with sat. aq. sodium bicarbonate (15 mL), dried over sodium sulfate, concentrated and purified by silica gel column chromatography using hexane/ethyl acetate to yield 7-methoxy-3-(3-phenyl-4-(trifluoromethyl)isoxazol-5-yl)-4,5-dihydronaphtho[1,2-c]isoxazole (0.125 g, 0.303 mmol, 26.5% yield) as pale yellow solid. LC/MS $M^{+1}$=413.0.

Example 8

To 7-methoxy-3-(3-phenyl-4-(trifluoromethyl)isoxazol-5-yl)-4,5-dihydronaphtho[1,2-c]isoxazole (Preparation 8A, 0.125 g, 0.303 mmol) in dichloromethane (4 mL) was added borontribromide (1.0 M in dichloromethane, 3.03 mL, 3.03 mmol) at 0° C. over a period of 3 min. The contents were allowed to come to room temperature over a period of 15 min. and stirred at room temperature for 1 h. Additional borontribromide (4 mL) was added at room temperature over a period of 2 min. and the reaction was stirred for 3 h. The reaction mixture was concentrated and kept on the high vacuum pump for 10 min. Dichloromethane (5 mL) was added followed by 3 mL of borontribromide at room temperature. The contents were stirred at room temperature for 60 h. The reaction mixture was cooled to 0° C. and quenched by the slow addition of methanol (~0 mL). The contents were stirred for 10 min. and concentrated under reduced pressure. The resulting residue was partitioned between dichloromethane (25 mL) and water (10 mL). The dichloromethane layer was washed with brine (20 mL), dried over sodium sulfate and concentrated. The resulting solid was triturated with ethyl acetate (5 mL), collected by filtration, washed with ethyl acetate (2×3 mL) and dried to yield 3-(3-phenyl-4-(trifluoromethyl)isoxazol-5-yl)-4,5-dihydronaphtho[1,2-c]isoxazol-7-ol (0.050 g, 0.119 mmol, 39.3% yield) as a white solid. The compound had an HPLC retention time=3.77 min (condition C); LC/MS $M^{+1}$=399.

Example 9

3-(4-Propylphenyl)-4,5-dihydronaphtho[1,2-c]isoxazol-7-ol (9)

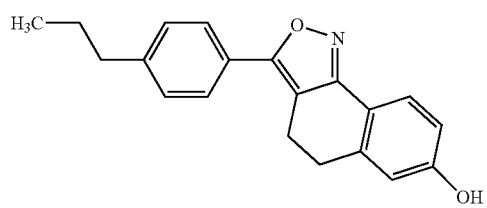

Preparation 9A: Methyl 4-propylbenzoate (9A)

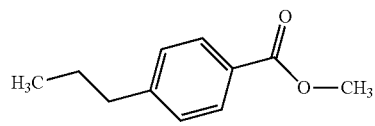

To a 0° C. solution of 4-propylbenzoic acid (2 g, 12.18 mmol) in methanol (3.00 mL) and dichloromethane (10 mL) was added trimethylsilyldiazomethane (7.92 mL, 15.83 mmol), dropwise over a period of 5 min. Towards the end of the addition, the reaction mixture was pale yellow. The reaction was stirred at 0° C. for 30 min. and the excess diazo reagent was quenched by the slow addition of acetic acid at 0° C. (~1.5 mL). The colorless solution was concentrated and partitioned between ether (20 mL) and sat. aq. sodium bicarbonate (10 mL). The ether layer was washed with brine (10 mL), dried over sodium sulfate and concentrated to yield methyl 4-propylbenzoate (2.1 g, 11.78 mmol, 97% yield) as a liquid. $^1$H NMR (400 MHz, CDCl$_3$) δ ppm 7.95 (d, J=8.28 Hz, 2H) 7.24 (d, J=8.53 Hz, 2H) 3.90 (s, 3H) 2.61-2.67 (m, 2H) 1.59-1.71 (m, 1H) 0.94 (t, J=7.40 Hz, 1H).

Preparation 9B: 7-Methoxy-3-(4-propylphenyl)-4,5-dihydronaphtho[1,2-c]isoxazole (9B)

To 6-methoxy-3,4-dihydronaphthalen-1(2H)-one oxime (Intermediate 2, 0.483 g, 2.52 mmol) in 4 mL of THF, cooled to 0° C. was added butyllithium (2.5 M, 2.020 mL, 5.05 mmol) dropwise over a period of 3 min. The contents were stirred at 0° C. for 30 min. A solution of methyl 4-propylbenzoate (Preparation 9A, 0.3 g, 1.683 mmol) dissolved in 2 mL of THF was added over a period of 3 min. The pale yellow reaction mixture was allowed to come to room temperature and stirred for 20 min. at room temperature. To the reaction mixture was added 0.5 mL of conc. H$_2$SO$_4$ dropwise over a period of 3 min. at 0° C. The reaction was allowed to come to room temperature over a period of 10 min. and stirred at room temperature for 40 min. The reaction mixture was concentrated under reduced pressure and partitioned between ethyl acetate (25 mL) and water (10 mL). The ethyl acetate layer was washed with sat. aq. sodium bicarbonate (15 mL), dried over sodium sulfate, concentrated and purified by silica gel column chromatography employing hexane/ethyl acetate. Product containing fractions were collected and concentrated to yield 7-methoxy-3-(4-propylphenyl)-4,5-dihydronaphtho[1,2-c]isoxazole (0.355 g, 1.111 mmol, 66.0% yield) as a white solid. $^1$H NMR (400 MHz, CDCl$_3$) δ ppm 7.93 (d, J=8.28 Hz, 1H) 7.69 (d, J=8.28 Hz, 2H) 7.30 (d, J=8.28 Hz, 2H) 6.83-6.91 (m, 2H) 3.86 (s, 3H) 2.95-3.06 (m, 4H) 2.61-2.68 (m, 2H) 1.62-1.74 (m, J=7.47, 7.47, 7.47, 7.47, 7.28 Hz, 2H) 0.97 (t, 3H).

Example 9

To 7-methoxy-3-(4-propylphenyl)-4,5-dihydronaphtho[1,2-c]isoxazole (Preparation 9B, 0.35 g, 1.096 mmol) in dichloromethane (10 mL) was added boron tribromide (1.425 mL, 1.425 mmol) dropwise over a period of 3 min. at 0° C.

Approximately 2 min. after the addition was complete a white solid separated out. The reaction mixture was allowed to come to room temperature over a period of 10 min. and then was stirred at room temperature for 30 min. Additional boron tribromide (2 mL) was added at room temperature and the contents were stirred at room temperature for 1.5 h. Additional boron tribromide (10 mL) was added at room temperature. The heterogeneous solution become homogenous and brown. The contents were stirred at room temperature for an additional 3 h, then cooled to 0° C. and quenched by the very slow addition of MeOH (~5 mL). The reaction mixture was concentrated under reduced pressure and partitioned between dichloromethane (50 mL) and water (20 mL). The dichloromethane layer was dried over sodium sulfate and concentrated to yield a greenish solid. Trituration with dichloromethane (2 mL) and ether (10 mL) followed by sonication for 3 min. yielded an off-white solid which was collected by filtration and washed with ether (2×5 mL) to afford 3-(4-propylphenyl)-4,5-dihydronaphtho[1,2-c]isoxazol-7-ol (0.115 g). The compound had an HPLC retention time=3.80 min (condition C); LC/MS $M^{+1}$=306. $^1$H NMR (400 MHz, MeOD) δ ppm 7.72 (dd, J=8.16, 1.38 Hz, 3H) 7.38 (d, J=8.28 Hz, 2H) 6.76-6.84 (m, 2H) 2.93-3.07 (m, 4H) 2.65-2.72 (m, 2H) 1.65-1.78 (m, 2H) 0.99 (t, 3H).

Example 10

3-(4-Propylphenyl)-4H-indeno[1,2-c]isoxazol-6-ol

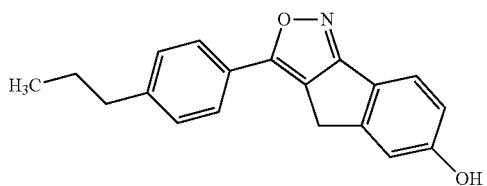
(10)

This compound was prepared using the same protocol as outlined for Example 9 by substituting 6-methoxy-3,4-dihydronaphthalen-1(2H)-one oxime in step B with 5-methoxy-2,3-dihydro-1H-inden-1-one oxime. The compound had an HPLC retention time=3.71 min (condition C); LC/MS $M^{+1}$=291.9. $^1$H NMR (400 MHz, DMSO-$d_6$) δ ppm 10.06 (s, 1H) 7.73 (d, J=8.28 Hz, 2H) 7.66 (d, J=8.28 Hz, 1H) 7.40 (d, J=8.28 Hz, 2H) 7.02 (d, J=1.76 Hz, 1H) 6.87 (dd, J=8.28, 2.26 Hz, 1H) 3.99 (s, 2H) 2.64 (t, J=7.53 Hz, 2H) 1.58-1.70 (m, 2H) 0.92 (t, 3H).

Example 11

1-((3-(4-Propylphenyl)-4,5-dihydronaphtho[1,2-c]isoxazol-7-yl)methyl)azetidine-3-carboxylic acid

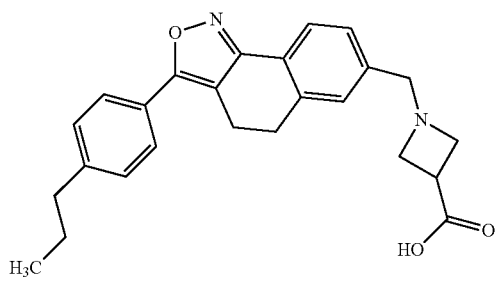
(11)

Preparation 11A: 3-(4-Propylphenyl)-4,5-dihydronaphtho[1,2-c]isoxazol-7-yl 1,1,2,2,3,3,4,4,4-nonafluorobutane-1-sulfonate

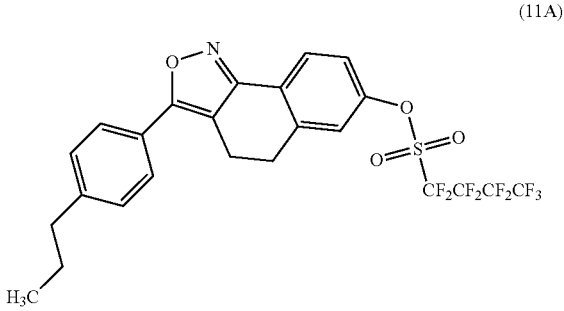
(11A)

To a solution of 3-(4-propylphenyl)-4,5-dihydronaphtho[1,2-c]isoxazol-7-ol (Example 9, 115 mg, 0.377 mmol), dimethylaminopyridine (4.60 mg, 0.038 mmol), and triethylamine (0.262 mL, 1.883 mmol) in anhydrous dichloromethane (2 mL) was added perfluoro-1-butanesulfonyl fluoride (0.102 mL, 0.565 mmol) dropwise at room temperature under nitrogen. The mixture was stirred at room temperature for 4.5 hr and allowed to stand in the freezer overnight and quenched by the addition of saturated aqueous sodium bicarbonate solution (3 mL). The dichloromethane layer was separated and the aqueous layer was re-extracted with dichloromethane (2 mL). The combined organic solutions were dried over sodium sulfate, filtered through a silica gel pad and concentrated under reduced pressure to give 3-(4-propylphenyl)-4,5-dihydronaphtho[1,2-c]isoxazol-7-yl 1,1,2,2,3,3,4,4,4-nonafluorobutane-1-sulfonate (160 mg, 0.272 mmol, 72.3% yield) as a white solid. LC/MS $M^{+1}$=588

Preparation 11B: 3-(4-Propylphenyl)-7-vinyl-4,5-dihydronaphtho[1,2-c]isoxazole

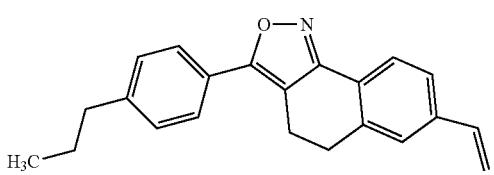
(11B)

To a mixture of 3-(4-propylphenyl)-4,5-dihydronaphtho[1,2-c]isoxazol-7-yl 1,1,2,2,3,3,4,4,4-nonafluorobutane-1-sulfonate (Preparation 11A, 160 mg, 0.272 mmol), anhydrous lithium chloride (34.6 mg, 0.817 mmol), tributyl(vinyl)tin (0.120 mL, 0.409 mmol), and anhydrous dioxane (1 mL) was bubbled nitrogen gas for 3 min before Pd(Ph$_3$P)$_4$ (62.9 mg, 0.054 mmol) was added. The reaction mixture was purged with nitrogen gas for an additional 3 min, stirred for 1 h at room temperature, and then at 110° C. for 4 h. The reaction mixture was cooled and treated with saturated aqueous sodium bicarbonate solution (1.5 mL). The biphasic mixture was extracted with ethyl acetate (2×2 mL). The combined ethyl acetate extracts were dried over sodium sulfate and concentrated under reduced pressure. The residue was dissolved in dichloromethane and filtered through a pad of silica gel and rinsed with dichloromethane. The filtrate was concentrated to give 3-(4-propylphenyl)-7-vinyl-4,5-dihydronaphtho[1,2-c]isoxazole (74 mg, 0.235 mmol, 86% yield) LC/MS $M^{+1}$=316.17.

Preparation 11C: 3-(4-Propylphenyl)-4,5-dihydronaphtho[1,2-c]isoxazole-7-carbaldehyde

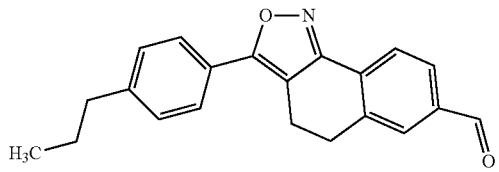

(11C)

To a solution of 3-(4-propylphenyl)-7-vinyl-4,5-dihydronaphtho[1,2-c]isoxazole (Preparation 11B, 70 mg, 0.222 mmol) dissolved in dichloromethane (5 mL) was bubbled ozone gas at −78° C., until a blue color persisted. Excess ozone was purged with air. Triethylamine (0.8 mL) was added and the mixture was stirred at room temperature under nitrogen for 1 hr. The reaction mixture was concentrated and purified by silica gel flash chromatography (0% to 50% ethyl acetate in heptanes) to afford 3-(4-propylphenyl)-4,5-dihydronaphtho[1,2-c]isoxazole-7-carbaldehyde as a solid (22 mg, 0.069 mmol, 31.2% yield). LC/MS $M^{+1}$=318.11.

Example 11

A mixture of 3-(4-propylphenyl)-4,5-dihydronaphtho[1,2-c]isoxazole-7-carbaldehyde (Preparation 11C, 22 mg, 0.069 mmol), 3-azetidinecarboxylic acid (14.02 mg, 0.139 mmol), MeOH (3 mL), and acetic acid (1 mL) was stirred for 20 min at room temperature under nitrogen before sodium cyanoborohydride (8.71 mg, 0.139 mmol) was added. The reaction mixture was stirred at room temperature overnight and concentrated. The solid residue was dissolved in methanol and purified by reverse phase preparative HPLC (PHENOMENEX® Luna Axia 5 u c18 30×100 mm, 10 min. run, solvent A: 10% MeOH: 90% H$_2$O: 0.1% TFA, solvent B: 90% MeOH, 10% H$_2$O, 0.1% TFA). Lyophilization of the product containing fractions gave 1-((3-(4-propylphenyl)-4,5-dihydronaphtho[1,2-c]isoxazol-7-yl)methyl)azetidine-3-carboxylic acid, TFA (13 mg, 0.024 mmol, 34.9% yield) as a white solid. The compound had an HPLC retention time=3.24 min (condition C); LC/MS $M^{+1}$=403.1. $^1$H NMR (500 MHz, MeOD) δ ppm 8.00 (d, J=7.77 Hz, 1H) 7.73 (d, J=8.32 Hz, 2H) 7.51 (s, 1H) 7.46 (dd, J=7.91, 1.53 Hz, 1H) 7.39 (d, J=8.32 Hz, 2H) 4.45 (s, 2H) 4.31-4.39 (m, 4H) 3.64-3.73 (m, 1H) 3.06-3.12 (m, 4H) 2.68 (t, J=7.63 Hz, 2H) 1.70 (sxt, J=7.44 Hz, 2H) 0.98 (t, J=7.35 Hz, 3H).

Example 12

(R)-3-(3-(4-Propylphenyl)-4,5-dihydronaphtho[1,2-c]isoxazol-7-yloxy)propane-1,2-diol

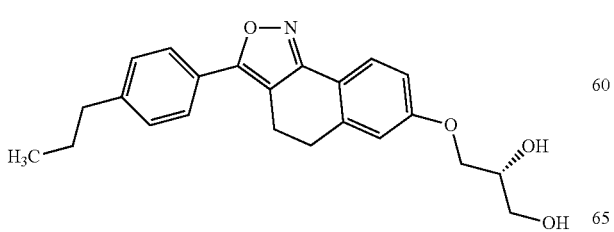

(12)

To a solution of 3-(4-propylphenyl)-4,5-dihydronaphtho[1,2-c]isoxazol-7-ol (Example 9, 0.1 g, 0.327 mmol) in acetonitrile (2 mL) was added potassium carbonate (0.100 g, 0.720 mmol) and (R)-(2,2-dimethyl-1,3-dioxolan-4-yl)methyl 4-methylbenzenesulfonate (0.094 g, 0.327 mmol) at room temperature. The heterogeneous reaction mixture was heated at 120° C. in a microwave reactor for 1 h. Next, 2 mL of methanol was added followed by additional (R)-(2,2-dimethyl-1,3-dioxolan-4-yl)methyl 4-methylbenzenesulfonate (100 mg). The contents were heated in the microwave reactor at 120° C. for 1 h. To the reaction mixture was added 1.0 mL of 2.5 M hydrochloric acid in ethanol at room temperature. The heterogeneous reaction mixture was stirred at room temperature for 1.5 h and concentrated under reduced pressure. Methanol (3 mL) was added followed by 3 drops of water and the contents were filtered. The pale yellow filtrate was subjected to Prep. HPLC (PHENOMENEX® Luna Axia 30×100 mm; 10 min. gradient; solvent A=10% MeOH, 90% H$_2$O, 0.1% TFA, solvent B=90% MeOH, 10% H$_2$O, 0.1% TFA). Fractions corresponding to the desired product were isolated and concentrated to yield (R)-3-(3-(4-propylphenyl)-4,5-dihydronaphtho[1,2-c]isoxazol-7-yloxy)propane-1,2-diol (0.016 g, 0.042 mmol, 13% yield) as a white solid. The compound had an HPLC retention time=3.73 min (condition C); LC/MS $M^{+1}$=380.1; $^1$H NMR (400 MHz, CDCl$_3$) δ ppm 7.93 (d, J=8.53 Hz, 1H) 7.69 (d, J=8.28 Hz, 2H) 7.31 (d, J=8.28 Hz, 2H) 6.85-6.92 (m, 2H) 4.08-4.15 (m, 3H) 3.74-3.91 (m, 2H) 2.96-3.05 (m, 4H) 2.55-2.68 (m, 3H) 1.97 (t, J=5.90 Hz, 1H) 1.68 (sxt, J=7.43 Hz, 2H) 0.97 (t, 3H).

Example 13

(3S)-1-(2-Hydroxy-2-(3-(5-phenyl-4-(trifluoromethyl)isoxazol-3-yl)-4,5-dihydronaphtho[1,2-c]isoxazol-7-yl)ethyl)piperidine-3-carboxylic acid

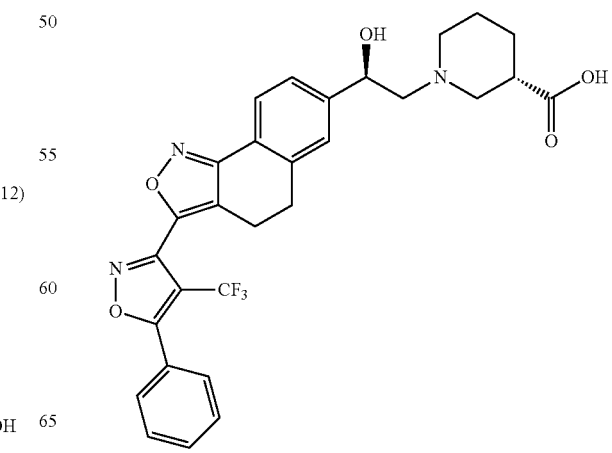

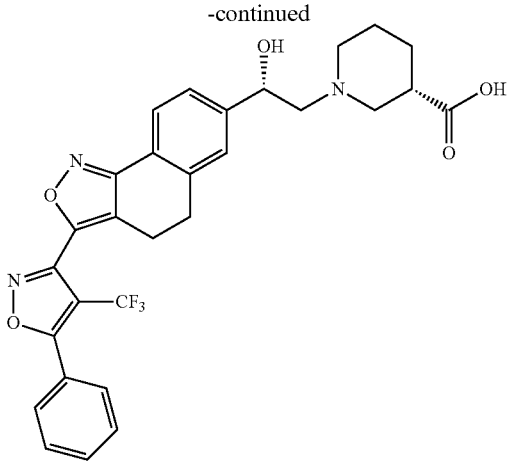

Preparation 13A: 7-(Oxiran-2-yl)-3-(5-phenyl-4-(trifluoromethyl)isoxazol-3-yl)-4,5-dihydronaphtho[1,2-c]isoxazole

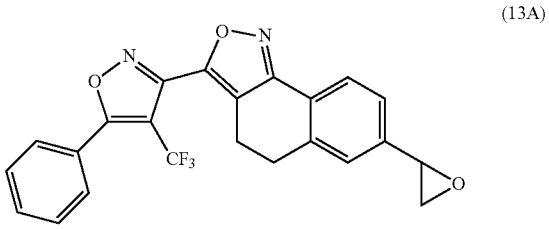 [SMILES: FC(F)(F)c1c(-c2onc3c2CCc2cc(C4CO4)ccc2-3)noc1-c1ccccc1]
(13A)

To a solution of 3-(5-phenyl-4-(trifluoromethyl)isoxazol-3-yl)-7-vinyl-4,5-dihydronaphtho[1,2-c]isoxazole (Preparation 6A, 0.09 g, 0.220 mmol) in dichloromethane (5 mL) was added 3-chlorobenzoperoxoic acid (0.109 g, 0.441 mmol) at room temperature. The reaction mixture was stirred at room temperature for 1.5 h. Next, 3 mL of 10% sodium sulfite solution was added to the reaction mixture at room temperature and the contents were stirred for 10 min. The reaction mixture was concentrated and partitioned between ethyl acetate (10 mL) and sat. aq. sodium bicarbonate (2×10 mL). The ethyl acetate layer was dried over sodium sulfate and concentrated to yield a pale yellow solid. LC/MS M$^{+1}$=425.

Example 13

A 2-dram vial was charged with 7-(oxiran-2-yl)-3-(5-phenyl-4-(trifluoromethyl)isoxazol-3-yl)-4,5-dihydronaphtho[1,2-c]isoxazole (Preparation 13A, 0.085 g, 0.200 mmol), N-methyl-2-pyrrolidinone (1 mL), (S)-ethyl piperidine-3-carboxylate (0.062 mL, 0.401 mmol) and lithium perchlorate (4.26 mg, 0.040 mmol). The vial was sealed and the contents were heated at 100° C. for 6.5 h and then left stirring at room temperature for 65 h. The reaction mixture was partitioned between ethyl acetate (20 mL) and brine (2×15 mL). The ethyl acetate layer was dried over sodium sulfate and concentrated to yield a brown oil. To the brown oil was added acetonitrile (2 mL) and 6N hydrochloric acid (2 mL) and the contents were heated at 60° C. for 5 h. The reaction mixture was concentrated under reduced pressure. To the residue was added TFA (5 drops) followed by 2 mL of MeOH and the material was purified by reverse phase preparative HPLC (PHENOMENEX® Luna Axia 30×100 mm; 10 min. gradient; solvent A=10% MeOH, 90% H$_2$O, 0.1% TFA, solvent B=90% MeOH, 10% H$_2$O, 0.1% TFA). Product containing fractions were isolated and concentrated. Acetonitrile (2 mL) and 6N hydrochloric acid (2 mL) were added to the resulting oil and the contents were heated at 60° C. for 2 h. The reaction mixture was concentrated and freeze dried to yield (3S)-1-(2-hydroxy-2-(3-(5-phenyl-4-(trifluoromethyl)isoxazol-3-yl)-4,5-dihydronaphtho[1,2-c]isoxazol-7-yl)ethyl)piperidine-3-carboxylic acid, hydrochloric acid (0.046 g, 0.074 mmol, 37.0% yield) as a pale yellow solid.

The compound had an HPLC retention time=3.11 min. (condition C); LC/MS M$^{+1}$=554.2.

The individual diastereomers were separated using a CHIRALPAK® AD-H column under SFC conditions (30% isopropyl alcohol with 0.1% diethylamine in CO$_2$). Isomer 1, retention time on chiral HPLC, 7.84 min; Isomer 2, retention time on chiral HPLC, 9.51 min. The absolute stereochemistry at the carbon anchoring the secondary alcohol, of Isomer 1 and Isomer 2 was not determined.

Example 14

1-((3-(4-Isopropoxy-3-(trifluoromethyl)phenyl)-4,5-dihydronaphtho[1,2-c]isoxazol-7-yl)methyl)azetidine-3-carboxylic acid

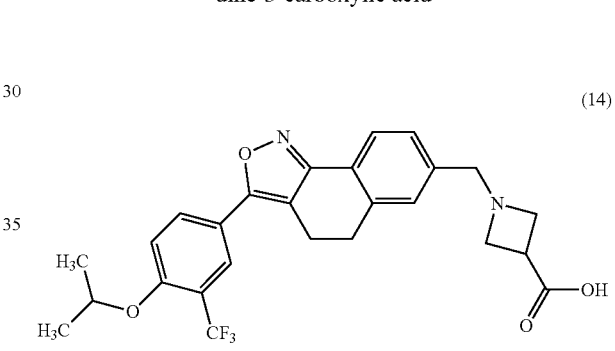
(14)

Preparation 14A: Isopropyl 4-isopropoxy-3-(trifluoromethyl)benzoate

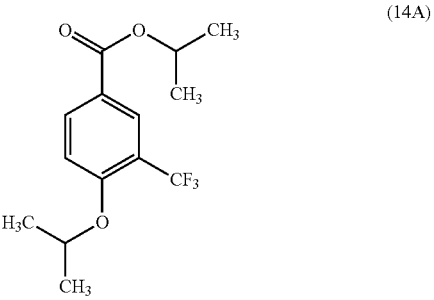 [SMILES: CC(C)OC(=O)c1ccc(OC(C)C)c(C(F)(F)F)c1]
(14A)

To a solution of 4-hydroxy-3-(trifluoromethyl)benzoic acid (0.3 g, 1.455 mmol) in dimethylformamide (1 mL) was added 2-iodopropane (0.437 mL, 4.37 mmol) and potassium carbonate (0.402 g, 2.91 mmol) at room temperature. The reaction was heated at 80° C. for 18 h. Additional 2-iodopropane (0.2 mL) was added followed by 0.15 g of potassium carbonate and the contents were heated at 80° C. for 7 h. The reaction mixture was stirred at room temperature overnight, partitioned between ethyl acetate (15 mL) and water (10 mL). The ethyl acetate layer was washed with brine (2×10 mL) dried over sodium sulfate and concentrated. The brown oil was azeotroped with THF (5 mL) and kept on the high vacuum pump for 10 min. to yield isopropyl 4-isopropoxy-3-(trifluoromethyl)benzoate (0.408 g, 1.406 mmol, 97% yield). $^1$H NMR (400 MHz, CDCl$_3$) δ ppm 8.23 (d, J=1.98 Hz, 1H) 8.15 (dd, J=8.69, 2.09 Hz, 1H) 7.01 (d, J=8.80 Hz, 1H) 5.24 (dt, J=12.54, 6.27 Hz, 1H) 4.73 (dt, J=12.10, 6.05 Hz, 1H) 1.38 (dd, 12H).

Preparation 14B: 3-(4-Isopropoxy-3-(trifluoromethyl)phenyl)-7-vinyl-4,5-dihydronaphtho[1,2-c]isoxazole

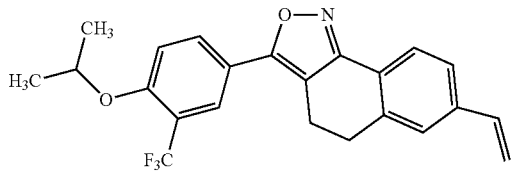

(14B)

Preparation of LDA: To a heat gun dried 50 mL 2-necked flask was added butyllithium (2.5 M in hexanes) (1.359 mL, 3.40 mmol) under a nitrogen atmosphere. The flask was cooled to 0° C. and THF (2 mL) was added followed by diisopropylamine (0.48 mL, 3.40 mmol) over a period of 1 min. The contents were stirred at 0° C. for 15 min.

To the LDA solution at 0° C. was added 6-vinyl-3,4-dihydronaphthalen-1(2H)-one oxime (Intermediate 1, 0.212 g, 1.132 mmol) as a solution in THF (1 mL), dropwise over a period of 1 min. After 15 min. isopropyl 4-isopropoxy-3-(trifluoromethyl)benzoate (Preparation 14A, 0.329 g, 1.132 mmol) dissolved in 1 mL of THF was added dropwise over a period of 1 min. at 0° C. and the contents were stirred at 0° C. for 10 min. The reaction mixture was partitioned between 1N hydrochloric acid (5 mL) and ethyl acetate (10 mL)-THF. The 1N hydrochloric acid layer was back extracted with ethyl acetate (10 mL). The combined ethyl acetate layers were dried over sodium sulfate and concentrated under reduced pressure to yield a dark oil. To this oil was added toluene (5 mL). The contents were sonicated for 2 min. and p-toluenesulfonic acid monohydrate (0.431 g, 2.265 mmol) was added at room temperature. The contents were heated at 110° C. for 25 min. The reaction mixture was concentrated and partitioned between dichloromethane (15 mL) and sat. aq. sodium bicarbonate (10 mL). The dichloromethane layer was dried over sodium sulfate, concentrated and subjected to silica gel column chromatography (hexane/ethyl acetate). Product fractions were collected and concentrated to yield 3-(4-isopropoxy-3-(trifluoromethyl)phenyl)-7-vinyl-4,5-dihydronaphtho[1,2-c]isoxazole as a semi-solid (180 mg). LC/MS M$^{+1}$=400.1.

Preparation 14C: 3-(4-Isopropoxy-3-(trifluoromethyl)phenyl)-4,5-dihydronaphtho[1,2-c]isoxazole-7-carbaldehyde

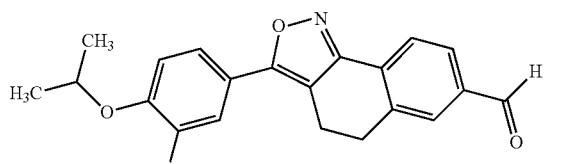

(14C)

To 3-(4-isopropoxy-3-(trifluoromethyl)phenyl)-7-vinyl-4,5-dihydronaphtho[1,2-c]isoxazole (Preparation 14B, 0.18 g, 0.451 mmol) in THF (2 mL) was added N-methylmorpholine-N-oxide (50% in water) (0.093 mL, 0.451 mmol) followed by osmium tetroxide (0.071 mL, 9.01 μmol) in one portion at room temperature. The contents were stirred at room temperature for 14 h. LCMS indicated formation of a major peak corresponding to the diol intermediate. Sodium periodate (0.145 g, 0.676 mmol) dissolved in 2 mL of water was added in one portion at room temperature. The milky heterogeneous solution was stirred at room temperature for 45 min. The reaction mixture was concentrated and partitioned between ethyl acetate (15 mL) and water (10 mL). The ethyl acetate layer was dried over sodium sulfate, concentrated and purified by silica gel column chromatography (hexane/ethyl acetate) to yield 3-(4-isopropoxy-3-(trifluoromethyl)phenyl)-4,5-dihydronaphtho[1,2-c]isoxazole-7-carbaldehyde (0.06 g, 0.149 mmol, 33.2% yield) as a white solid. LC/MS M$^{+1}$=402.1.

Example 14

To 3-(4-isopropoxy-3-(trifluoromethyl)phenyl)-4,5-dihydronaphtho[1,2-c]isoxazole-7-carbaldehyde (Preparation 14C, 0.06 g, 0.149 mmol) in methanol (2 mL) and dichloroethane (2 mL) was added azetidine-3-carboxylic acid (0.018 g, 0.179 mmol) followed by 5 drops of acetic acid. The contents were heated at 70° C. for 1 h. The reaction mixture was then cooled to room temperature and sodium cyanoborohydride (0.011 g, 0.179 mmol) was added in one portion at room temperature. The turbid reaction mixture became clear after 15 min. at room temperature. The reaction mixture was concentrated under reduced pressure and the resulting white solid was partitioned between dichloromethane (20 mL) and water (10 mL). The cloudy dichloromethane layer was separated, washed with brine (2×10 mL), dried over sodium sulfate and concentrated. To the resulting semi-solid was added methanol (3 mL) and the contents were triturated and filtered. The solid was combined with the filtrate and subjected to prep. HPLC. Fractions corresponding to the product were collected and concentrated. To the solid was added acetonitrile (2 ml) and 2 mL of 6N hydrochloric acid (aq). The contents were heated at 70° C. for 30 min. The reaction mixture was concentrated, azeotroped with THF (2×2 mL) and freeze dried using acetonitrile (0.5 mL) and water (1 mL) to yield 1-((3-(4-isopropoxy-3-(trifluoromethyl)phenyl)-4,5-dihydronaphtho[1,2-c]isoxazol-7-yl)methyl)azetidine-3-carboxylic acid, hydrochloric acid (0.017 g, 0.027 mmol, 18% yield) as a pale yellow solid. LC/MS M$^{+1}$=487.1; $^1$H NMR (400 MHz, MeOD) δ ppm 7.95-8.03 (3H, m), 7.45-7.58

(2H, m), 7.39 (1H, d, J=8.8 Hz), 4.31-4.53 (6H, m), 3.67-3.79 (1H, m), 3.04-3.15 (4H, m), 1.40 (6H, d, J=6.2 Hz).

Example 15

1-((3-(3-Cyano-4-isopropoxyphenyl)-4,5-dihydronaphtho[1,2-c]isoxazol-7-yl)methyl)azetidine-3-carboxylic acid

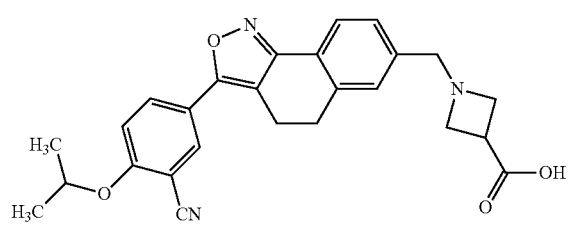

(15)

Preparation 15A: Methyl 3-cyano-4-isopropoxybenzoate

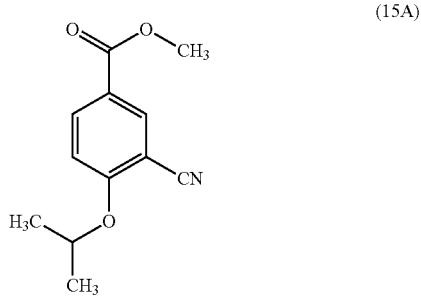 [SMILES: COC(=O)c1ccc(OC(C)C)c(C#N)c1]

(15A)

To 3-cyano-4-isopropoxybenzoic acid (0.3 g, 1.462 mmol) in a mixture of dichloromethane (4 mL) and MeOH (1.00 mL) was added trimethylsilyldiazomethane (0.950 mL, 1.9 mmol) dropwise over a period of 3 min at 0° C. The pale yellow solution was allowed to come to room temperature over a period of 15 min. and stirred at room temperature for 1.5 h. Excess trimethylsilyldiazomethane was quenched by the slow addition of acetic acid (~0.5 ml) at room temperature until the yellow color was discharged. The reaction mixture was concentrated and partitioned between ether (20 mL) and sat. aq. sodium bicarbonate (10 mL). The ether layer was washed with brine (10 mL), dried over sodium sulfate and concentrated. The resulting oil was azeotroped with THF (5 mL) and dried under high vacuum to yield methyl 3-cyano-4-isopropoxybenzoate (0.32 g, 1.460 mmol, 100% yield) as an oil. LC/MS $M^{+1}$=219.9.

Preparation 15B: 5-(7-Bromo-4,5-dihydronaphtho[1,2-c]isoxazol-3-yl)-2-isopropoxybenzonitrile

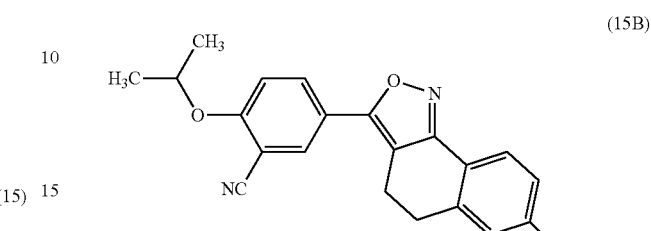

(15B)

Preparation of LDA: To a heat gun dried 50 mL 2-necked flask was added butyl lithium (2.5 M in hexanes) (0.850 mL, 2.124 mmol) under a nitrogen atmosphere. The flask was cooled to 0° C. and THF (2 mL) was added followed by diisopropylamine (0.297 mL, 2.124 mmol) dropwise over a period of 1 min. The contents were stirred at 0° C. for 15 min.

To the LDA solution was added 6-bromo-3,4-dihydronaphthalen-1(2H)-one oxime (prepared in an analogous manner as step C, intermediate 1, starting from 6-bromo-3,4-dihydronaphthalen-1(2H)-one, 0.17 g, 0.708 mmol) dissolved in 1 mL of THF dropwise over a period of 1 min. at 0° C. The orange-yellow solution was stirred at 0° C. for 15 min. Methyl 3-cyano-4-isopropoxybenzoate (Preparation 15A, 0.155 g, 0.708 mmol) dissolved in 1 mL of THF was added dropwise over a period of 1 min. at 0° C. and the contents were stirred at 0° C. for 10 min. The reaction mixture was partitioned between 1N hydrochloric acid (4 mL) and ethyl acetate (20 mL)-THF. The 1N hydrochloric acid layer was back extracted with ethyl acetate (10 mL). The combined ethyl acetate layers were dried over sodium sulfate and concentrated under reduced pressure to yield a turquoise blue semi-solid. To this semi-solid was added toluene (5 mL). The contents were sonicated for 2 min. and p-toluenesulfonic acid monohydrate (0.269 g, 1.416 mmol) was added at room temperature. The contents were heated at 110° C. for 25 min. The reaction mixture was concentrated and azeotroped with methanol (10 mL). Methanol (5 mL) was added, the contents were triturated and filtered. The solid on the filter paper was washed with additional methanol (2×2 mL) and subjected to silica gel column chromatography (hexane/ethyl acetate). Fractions corresponding to the product were collected and concentrated to yield 5-(7-bromo-4,5-dihydronaphtho[1,2-c] isoxazol-3-yl)-2-isopropoxybenzonitrile (100 mg) as a white solid.

The filtrate was also subjected to silica gel column chromatography (hexane/ethyl acetate). Fractions corresponding to the product were collected and concentrated to yield an additional 26 mgs of 5-(7-bromo-4,5-dihydronaphtho[1,2-c] isoxazol-3-yl)-2-isopropoxybenzonitrile (26 mg) as a pale yellow solid. LC/MS $M^{+1}$=411.0.

Preparation 15C: 2-Isopropoxy-5-(7-vinyl-4,5-dihydronaphtho[1,2-c]isoxazol-3-yl)benzonitrile

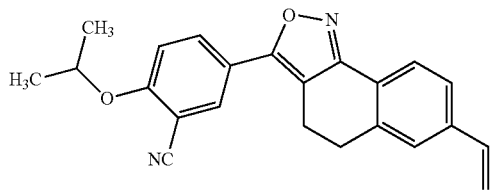

(15C)

5-(7-Bromo-4,5-dihydronaphtho[1,2-c]isoxazol-3-yl)-2-isopropoxybenzonitrile (Preparation 15B, 0.15 g, 0.367 mmol) dissolved in dioxane (3 mL) was transferred to a 15 mL sealed tube. Tributyl(vinyl)stannane (0.118 mL, 0.403 mmol) was added followed by lithium chloride (0.047 g, 1.100 mmol) and tetrakis(triphenylphosphine)palladium(0) (0.042 g, 0.037 mmol). The contents were purged with nitrogen gas for 5 min., immersed in an oil bath, and heated at 100° C. for 14 h. The reaction mixture was concentrated and to the red-brown oil was added ethyl acetate (10 mL). The contents were sonicated for 5 min. and filtered. The filter cake was washed with ethyl acetate (2×5 mL). The filtrate was concentrated under reduced pressure and the resulting oil was subjected to silica gel column chromatography (hexane/ethyl acetate). Fractions corresponding to the product were collected and concentrated to yield 2-isopropoxy-5-(7-vinyl-4,5-dihydronaphtho[1,2-c]isoxazol-3-yl)benzonitrile (0.088 g, 0.247 mmol, 67% yield) as a pale yellow solid. LC/MS $M^{+1}$=357.1.

Preparation 15D: 5-(7-Formyl-4,5-dihydronaphtho[1,2-c]isoxazol-3-yl)-2-isopropoxybenzonitrile

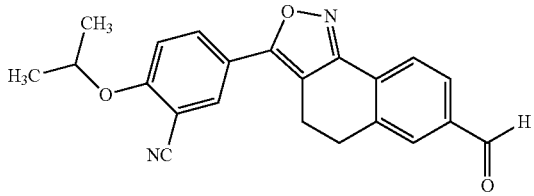

(15D)

To 2-isopropoxy-5-(7-vinyl-4,5-dihydronaphtho[1,2-c]isoxazol-3-yl)benzonitrile (Preparation 15C, 0.088 g, 0.247 mmol) in THF (1.5 mL) was added N-methylmorpholine-N-oxide (50% in water) (0.17 mL, 0.370 mmol) followed by osmium tetroxide (0.039 mL, 4.94 µmol) at room temperature. The contents were stirred at room temperature for 3.5 h. Sodium periodate (0.106 g, 0.494 mmol) dissolved in 0.5 mL of water was added over a period of 2 min. at room temperature and the contents were stirred at room temperature for 1 h. The reaction mixture was concentrated and partitioned between ethyl acetate (15 mL) and water (10 mL). The ethyl acetate layer was dried over sodium sulfate and concentrated to yield 5-(7-formyl-4,5-dihydronaphtho[1,2-c]isoxazol-3-yl)-2-isopropoxybenzonitrile (0.090 g, 0.176 mmol, 71% yield) as an orange-yellow solid. LC/MS $M^{+1}$=359.1.

Example 15

To 5-(7-formyl-4,5-dihydronaphtho[1,2-c]isoxazol-3-yl)-2-isopropoxybenzonitrile (Preparation 15D, 0.09 g, 0.251 mmol) in methanol (1.5 mL) and dichloroethane (1.5 mL) was added azetidine-3-carboxylic acid (0.030 g, 0.301 mmol) followed by 4 drops of acetic acid added via a Pasteur pipette. The contents were heated at 60° C. for 1 h. The cloudy solution was cooled to room temperature and sodium cyanoborohydride (0.019 g, 0.301 mmol) was added in one lot at room temperature and stirred at room temperature for 14 h. The reaction mixture was concentrated under reduced pressure and the resulting brown oil was obtained was partitioned between dichloromethane (20 mL) and water (10 mL). The cloudy dichloromethane layer was separated, washed with brine (10 mL), dried over sodium sulfate, and concentrated. To the resulting semi-solid was added methanol (3 mL) and the contents were triturated and filtered. The brown solid was washed with methanol (2×3 mL). LCMS of the brown solid was consistent with the desired product (14 mgs, first crop). The filtrate was concentrated and to the semi-solid was added ethanol (4 mL). The contents were triturated, filtered, and the solid was washed with ethanol (2×2 mL) to yield a light tan solid (55 mgs second crop). The compound had an HPLC retention time=2.69 min (condition C); LC/MS $M^{+1}$=444.2; $^{1}$H NMR (400 MHz, MeOD) δ ppm 8.02-8.07 (2H, m), 7.97 (1H, d, J=7.9 Hz), 7.51 (1H, s), 7.46 (1H, dd, J=7.8, 1.2 Hz), 7.38 (1H, d), 4.38 (2H, s), 4.13-4.23 (5H, m), 3.40-3.50 (1H, m), 3.04-3.13 (4H, m), 1.44 (6H, d, J=5.9 Hz).

Example 16

3-((3-(3-Cyano-4-isopropoxyphenyl)-4,5-dihydronaphtho[1,2-c]isoxazol-7-yl)methylamine)propanoic acid

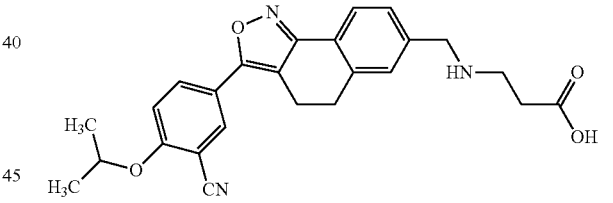

(16)

To 5-(7-formyl-4,5-dihydronaphtho[1,2-c]isoxazol-3-yl)-2-isopropoxybenzonitrile (Preparation 15D, 0.02 g, 0.056 mmol) in dichloromethane (2 mL) were added sequentially tert-butyl 3-aminopropanoate.hydrochloric acid (0.011 g, 0.061 mmol), triethylamine (8.56 mL, 0.061 mmol), and sodium triacetoxyborohydride (0.014 g, 0.067 mmol) at room temperature. The reaction mixture was stirred at room temperature for 30 min. Next, three drops of AcOH was added via a Pasteur pipette at room temperature and the contents were stirred at room temperature for 1.5 h. Powdered mol. sieves (~500 mgs) were added and the contents were stirred at room temperature for 2 h. To the reaction mixture was added sodium cyanoborohydride (3.51 mg, 0.056 mmol) in one lot at room temperature. The contents were stirred at room temperature for 30 min. The reaction mixture was filtered over a medium sintered funnel and the solid was washed with dichloromethane (2×5 mL). The filtrate was concentrated to ~3 mL and left overnight at room temperature. To the dichloromethane solution was added 6 drops of TFA via a Pasteur pipette at room temperature. The contents were stirred at room temperature for 1 h. The reaction mixture was concentrated and TFA (0.5 mL) was added at room temperature. The reaction mixture was stirred at room temperature for 30 min. The reaction mixture was concentrated, dissolved in acetonitrile (1.5 mL), and purified by prep. HPLC (PHENOMENEX® Luna Axia 30×100 mm; 10 min. gradient; solvent A=10% MeOH, 90% H$_2$O, 0.1% TFA, solvent B=90% MeOH, 10% H$_2$O, 0.1% TFA). Fractions corresponding to the product were collected and concentrated. The oily residue was dissolved in acetonitrile (0.5 mL) and water (1.5 mL) and freeze dried to yield 3-((3-(3-cyano-4-isopropoxyphenyl)-4,5-dihydronaphtho[1,2-c]isoxazol-7-yl)methylamino)propanoic acid, TFA (0.015 g, 0.027 mmol, 49.3% yield) as a white solid. The compound had an HPLC retention time=2.69 min (condition C); LC/MS M$^{+1}$=432.2; $^1$H NMR (500 MHz, CDCl$_3$) δ ppm 9.22 (2H, br. s.), 7.89 (1H, d, J=7.8 Hz), 7.81-7.87 (2H, m), 7.39 (1H, s), 7.35 (1H, d, J=8.0 Hz), 7.07 (1H, d, J=9.2 Hz), 4.73 (1H, spt, J=6.0 Hz), 4.17 (2H, br. s.), 3.21 (2H, br. s.), 2.90-3.02 (4H, m), 2.79 (2H, br. s.), 1.44 (6H, d, J=6.1 Hz).

Example 17

1-((3-(4-Isopropoxy-2-(trifluoromethyl)phenyl)-4,5-dihydronaphtho[1,2-c]isoxazol-7-yl)methyl)azetidine-3-carboxylic acid

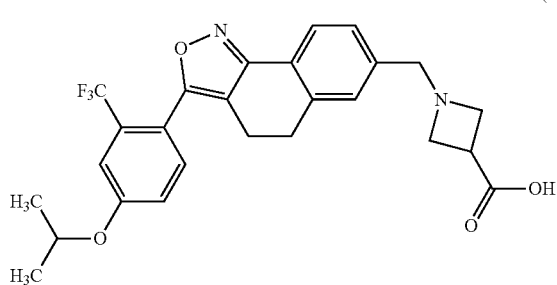

(17)

Preparation 17A: Isopropyl 4-isopropoxy-2-(trifluoromethyl)benzoate

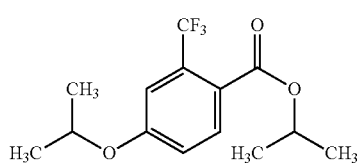

(17A)

To 4-hydroxy-2-(trifluoromethyl)benzoic acid (0.5 g, 2.426 mmol) in dimethylformamide (1.5 mL) were sequentially added potassium carbonate (0.671 g, 4.85 mmol) and 2-iodopropane (0.728 mL, 7.28 mmol) at room temperature. The reaction mixture was heated at 100° C. for 18 h. The reaction mixture was cooled to room temperature and partitioned between ethyl acetate (20 mL) and brine (2×10 mL). The ethyl acetate layer was dried over sodium sulfate, concentrated, and purified by silica gel column chromatography (hexane/ethyl acetate). Fractions corresponding to the product were collected and concentrated to yield isopropyl 4-isopropoxy-2-(trifluoromethyl)benzoate (0.344 g, 1.185 mmol, 48.9% yield) as an oil. $^1$H NMR (500 MHz, CDCl$_3$) δ ppm 7.81 (1H, d, J=8.6 Hz), 7.22 (1H, d, J=2.5 Hz), 7.02 (1H, dd, J=8.7, 2.6 Hz), 5.23 (1H, spt, J=6.3 Hz), 4.65 (1H, spt, J=6.1 Hz), 1.37 (6H, d, J=6.1 Hz), 1.36 (6H, d, J=6.1 Hz).

Preparation 17B: 3-(4-Isopropoxy-2-(trifluoromethyl)phenyl)-7-vinyl-4,5-dihydronaphtho[1,2-c]isoxazole

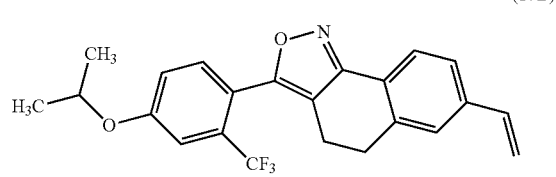

(17B)

Preparation of LDA: To a heat gun dried 50 mL 2-necked flask was added butyllithium (1.406 mL, 3.51 mmol) followed by 2 mL of anhydrous THF under a nitrogen atmosphere. The flask was cooled to 0° C. and diisopropylamine (0.49 mL, 3.51 mmol) was added dropwise over a period of 1 min. The contents were stirred at 0° C. for 15 min. To the LDA solution, 6-vinyl-3,4-dihydronaphthalen-1(2H)-one oxime (Intermediate 1, 0.219 g, 1.171 mmol) dissolved in 1 mL of THF was added dropwise over a period of 1 min. at 0° C. The orange-red solution was stirred at 0° C. for 25 min. Isopropyl 4-isopropoxy-2-(trifluoromethyl)benzoate (Preparation 17A, 0.340 g, 1.171 mmol) dissolved in 1 mL of THF was added dropwise over a period of 1 min. at 0° C. and the contents were stirred at 0° C. for 10 min. The reaction mixture was partitioned between 1N hydrochloric acid (5 mL) and ethyl acetate (10 mL)-THF. The 1N hydrochloric acid layer was back extracted with ethyl acetate (10 mL). The combined ethyl acetate layers were dried over sodium sulfate and concentrated under reduced pressure to yield a dark oil. To this oil was added toluene (5.00 mL). The contents were sonicated for 2 min. and p-toluenesulfonic acid monohydrate (0.446 g, 2.343 mmol) was added at room temperature. The contents were heated at 110° C. for 25 min. The reaction mixture was concentrated and partitioned between dichloromethane (15 mL) and saturated aqueous sodium bicarbonate (10 mL). The dichloromethane layer was dried over sodium sulfate, concentrated, and subjected to silica gel column chromatography (hexane/ethyl acetate). Fractions corresponding to the product were collected and concentrated to yield 3-(4-isopropoxy-2-(trifluoromethyl)phenyl)-7-vinyl-4,5-dihydronaphtho[1,2-c]isoxazole (0.225 g, 0.563 mmol, 48% yield) as an oil. LC/MS M$^{+1}$=400.1.

Preparation 17C: 3-(4-Isopropoxy-2-(trifluoromethyl)phenyl)-4,5-dihydronaphtho[1,2-c]isoxazole-7-carbaldehyde

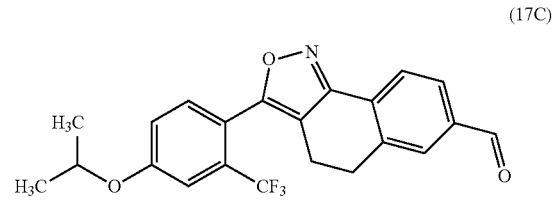 [SMILES: CC(C)Oc1ccc(-c2onc3c2CCc2cc(C=O)ccc2-3)c(C(F)(F)F)c1]

(17C)

123

To 3-(4-isopropoxy-2-(trifluoromethyl)phenyl)-7-vinyl-4,5-dihydronaphtho[1,2-c]isoxazole (Preparation 17B, 0.225 g, 0.563 mmol) in THF (2 mL) was added N-methylmorpholine-N-oxide (50% in water) (0.3 mL, 0.563 mmol) followed by osmium tetroxide (4% in water) (0.088 mL, 0.011 mmol) at room temperature. The contents were stirred at room temperature for 14 h. Sodium periodate (0.181 g, 0.845 mmol) dissolved in 1 mL of water was added at room temperature. The contents were stirred at room temperature for 30 min. The reaction mixture was partitioned between ethyl acetate (10 mL) and brine (5 mL). The dichloromethane layer was dried over sodium sulfate and concentrated to yield 3-(4-isopropoxy-2-(trifluoromethyl)phenyl)-4,5-dihydronaphtho[1,2-c]isoxazole-7-carbaldehyde (0.222 g, 0.553 mmol, 98% yield). LC/MS $M^{+1}$=402.1.

Example 17

To 3-(4-isopropoxy-2-(trifluoromethyl)phenyl)-4,5-dihydronaphtho[1,2-c]isoxazole-7-carbaldehyde (Preparation 17C, 0.22 g, 0.548 mmol) in dichloroethane (2 mL) and methanol (2.000 mL) were sequentially added azetidine-3-carboxylic acid (0.066 g, 0.658 mmol) and 8 drops of AcOH at room temperature. The contents were heated at 80° C. for 75 minutes. The reaction mixture was cooled to room temperature and sodium cyanoborohydride (0.041 g, 0.658 mmol) was added in one lot. The contents were stirred at room temperature for 30 minutes. The reaction mixture was concentrated, dissolved in acetonitrile (1.5 mL), and subjected to prep. HPLC (PHENOMENEX® Luna Axia 30×100 mm; 10 min. gradient; solvent A=10% MeOH, 90% $H_2O$, 0.1% TFA, solvent B=90% MeOH, 10% $H_2O$, 0.1% TFA). The desired fractions were concentrated and freeze dried to yield 1-((3-(4-isopropoxy-2-(trifluoromethyl)phenyl)-4,5-dihydronaphtho[1,2-c]isoxazol-7-yl)methyl)azetidine-3-carboxylic acid, TFA (0.135 g, 0.225 mmol, 41.0% yield) as a tan solid. The compound had an HPLC retention time=3.01 min (condition C); LC/MS $M^{+1}$=487.2; $^1$H NMR (500 MHz, MeOD) δ ppm 8.01 (1H, d, J=7.8 Hz), 7.55 (1H, d, J=8.6 Hz), 7.50 (1H, s), 7.48 (1H, dd, J=8.0, 1.7 Hz), 7.36 (1H, d, J=2.5 Hz), 7.31 (1H, dd, J=8.6, 2.5 Hz), 4.79 (1H, spt, J=6.1 Hz), 4.46 (2H, s), 4.32-4.41 (4H, m), 3.71 (1H, quin, J=8.3 Hz), 3.04 (2H, t, J=7.1 Hz), 2.77 (2H, t, J=7.2 Hz), 1.39 (6H, d, J=6.1 Hz).

Example 18

2-((3-(5-Phenyl-4-(trifluoromethyl)isoxazol-3-yl)-4,5-dihydronaphtho[1,2-c]isoxazol-7-yl)methyl)-2,5,7-triazaspiro[3.4]octane-6,8-dione

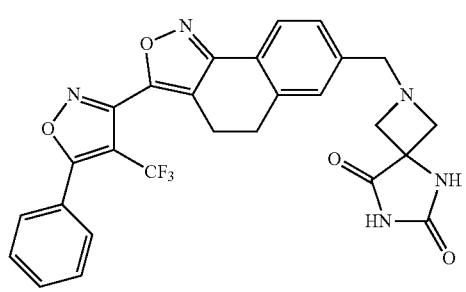

(18)

Preparation 18A: tert-Butyl 6,8-dioxo-2,5,7-triazaspiro[3.4]octane-2-carboxylate

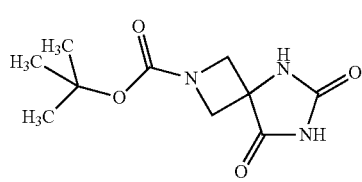

(18A)

A long sealed tube was charged with solid tert-butyl 3-oxoazetidine-1-carboxylate (2.500 g, 14.60 mmol), ammonium carbonate (9.82 g, 102 mmol), potassium cyanide (1.902 g, 29.2 mmol), and formamide (20 mL). The vessel was sealed and shaken back and forth until all of the solids were wetted and then placed in a 80° C. oil bath overnight behind a blast shield. The reaction vessel was cooled in an ice bath for 15 min and the contents of the vessel were carefully transferred to a separating funnel using ethyl acetate and saturated aq. sodium chloride to which ~3 g of ammonium chloride had been added. The aqueous layer (200 mL) was extracted with ethyl acetate, dried over magnesium sulfate, filtered, concentrated to ~10 mL of a yellow homogeneous liquid. The crude material was chromatographed on a 80 g $SiO_2$ cartridge using pure ethyl acetate. The desired fractions were collected and concentrated in vacuo to give tert-butyl 6,8-dioxo-2,5,7-triazaspiro[3.4]octane-2-carboxylate (1.54 g, 44%) as a white solid. MS (M-1)=240. $^1$H NMR (400 MHz, DMSO-$d_6$) δ ppm 10.8 (1H, s), 8.48 (1H, s), 4.05 (2H, d), 3.39 (2H, d), 1.06 (9H, s).

Preparation 18B: 2,5,7-Triazaspiro[3.4]octane-6,8-dione

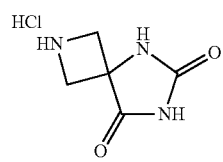

(18B)

tert-Butyl 6,8-dioxo-2,5,7-triazaspiro[3.4]octane-2-carboxylate (Preparation 18A, 620 mg, 2.57 mmol) was dissolved in 15 mL of hot dioxane until a homogeneous yellow solution formed. To this solution was added 30 mL of 4 M hydrochloric acid in dioxane. The reaction was stirred for 3 h and then concentrated in vacuo to give 2,5,7-triazaspiro[3.4]octane-6,8-dione, hydrochloric acid (420 mg, 92%). MS (M+1)=142.0. $^1$H NMR (400 MHz, DMSO-$d_6$) δ ppm 10.9 (1H, s), 9.30 (2H, br d), 8.70 (1H, s), 4.15 (1H, br s), 4.05 (1H, br s), 3.39 (2H, br s).

Example 18

To a stirred mixture of 7-(bromomethyl)-3-(5-phenyl-4-(trifluoromethyl)isoxazol-3-yl)-4,5-dihydronaphtho[1,2-c]isoxazole (Preparation 6C, 25 mg, 0.053 mmol), 2,5,7-triazaspiro[3.4]octane-6,8-dione, hydrochloric acid (Preparation 17B, 11 mg, 0.079 mmol), and anhydrous dimethylformamide (0.5 mL) was added N,N-diisopropylethylamine (0.046 mL, 0.263 mmol) dropwise at 0° C. The mixture was stirred at 0° C. for 30 min and at room temperature for 80 min. The reaction mixture was concentrated and subjected to prep HPLC conditions (PHENOMENEX® Luna Axia 30×100 mm; 10 min. gradient; solvent A=10% MeOH, 90% H$_2$O, 0.1% TFA, solvent B=90% MeOH, 10% H$_2$O, 0.1% TFA). The desired fractions were concentrated to yield an aqueous suspension of the product, to which saturated aqueous sodium bicarbonate solution (1 mL) was added to make the mixture basic. The solid was filtered and washed with water (3×1 mL) and then lyophilized to give 2-((3-(5-phenyl-4-(trifluoromethyl)isoxazol-3-yl)-4,5-dihydronaphtho[1,2-c]isoxazol-7-yl)methyl)-2,5,7-triazaspiro[3.4]octane-6,8-dione (19 mg, 0.034 mmol, 65.4% yield) as a white solid. The compound had an HPLC retention time=3.19 min (condition C); LC/MS M$^{+1}$=536.3; $^1$H NMR (400 MHz, MeOD) δ ppm 7.92 (1H, d, J=7.9 Hz), 7.77 (2H, d, J=7.3 Hz), 7.58-7.71 (3H, m), 7.40 (1H, s), 7.37 (1H, d, J=7.7 Hz), 3.78 (2H, s), 3.75 (2H, d, J=8.6 Hz), 3.48 (2H, d, J=8.8 Hz), 3.08 (4H, s).

Example 19

2-((3R)-1-(2-Hydroxy-2-(3-(5-phenyl-4-(trifluoromethyl)isoxazol-3-yl)-4,5-dihydronaphtho[1,2-c]isoxazol-7-yl)ethyl)piperidin-3-yl)acetic acid

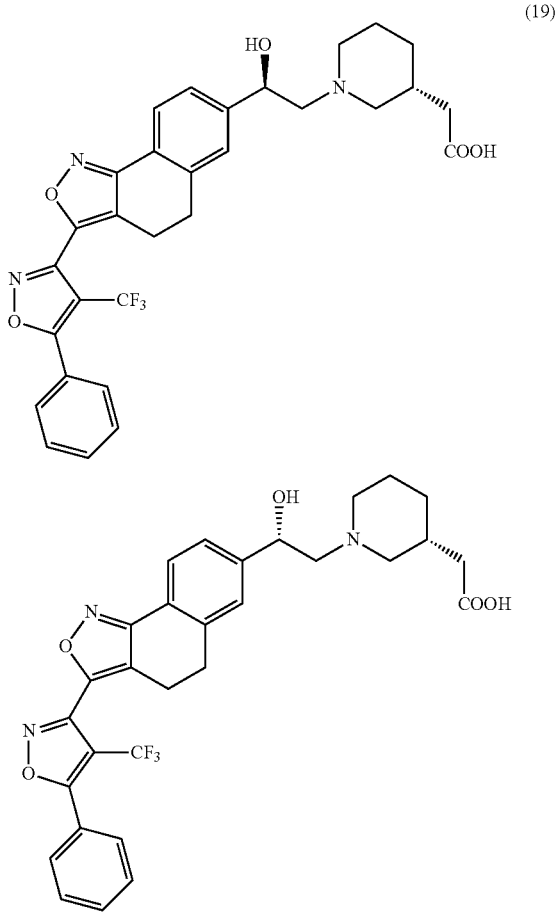 [SMILES: O=C(O)C[C@H]1CCCN(C[C@H](O)c2ccc3c(c2)CCc2c-3noc2-c2noc(-c3ccccc3)c2C(F)(F)F)C1 ; O=C(O)C[C@H]1CCCN(C[C@@H](O)c2ccc3c(c2)CCc2c-3noc2-c2noc(-c3ccccc3)c2C(F)(F)F)C1]

Preparation 19A: Ethyl 2-((3R)-1-(2-hydroxy-2-(3-(5-phenyl-4-(trifluoromethyl)isoxazol-3-yl)-4,5-dihydronaphtho[1,2-c]isoxazol-7-yl)ethyl)piperidin-3-yl)acetate

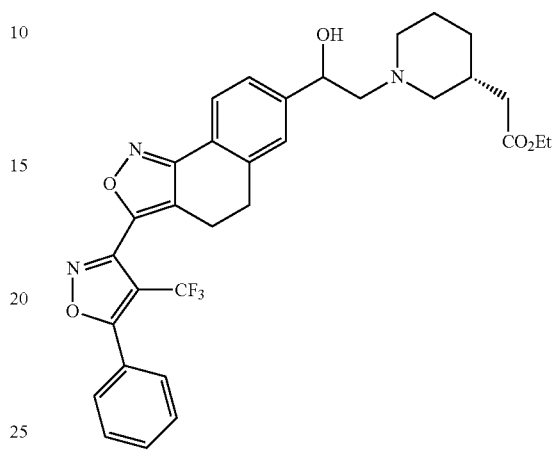

A mixture of 7-(oxiran-2-yl)-3-(5-phenyl-4-(trifluoromethyl)isoxazol-3-yl)-4,5-dihydronaphtho[1,2-c]isoxazole (Preparation 13A, 150 mg, 0.353 mmol) and (R)-ethyl 2-(piperidin-3-yl)acetate (90 mg, 0.526 mmol) in 2-propanol (5 mL) was stirred at 85° C. under a nitrogen atmosphere for 5 hr. The reaction mixture was concentrated and purified by silica gel column chromatography using ethyl acetate/heptane followed by 10% methanol in ethyl acetate to afford ethyl 2-((3R)-1-(2-hydroxy-2-(3-(5-phenyl-4-(trifluoromethyl)isoxazol-3-yl)-4,5-dihydronaphtho[1,2-c]isoxazol-7-yl)ethyl)piperidin-3-yl)acetate (125 mg, 0.210 mmol, 59.4% yield) as a yellow solid. LC/MS M$^{+1}$=596.3.

Example 19

To ethyl 2-((3R)-1-(2-hydroxy-2-(3-(5-phenyl-4-(trifluoromethyl)isoxazol-3-yl)-4,5-dihydronaphtho[1,2-c]isoxazol-7-yl)ethyl)piperidin-3-yl)acetate (Preparation 19A, 125 mg, 0.210 mmol were added acetonitrile (3 mL) and 6N hydrochloric acid (3 mL). The reaction mixture was heated at 60° C. for 4 h. The reaction mixture was concentrated under reduced pressure to yield a solid. To the solid was added acetonitrile (0.5 mL) and water (10 mL). The contents were sonicated and lyophilized to yield 2-((3R)-1-(2-hydroxy-2-(3-(5-phenyl-4-(trifluoromethyl)isoxazol-3-yl)-4,5-dihydronaphtho[1,2-c]isoxazol-7-yl)ethyl)piperidin-3-yl)acetic acid, hydrochloric acid (150 mg, 0.248 mmol, 70.3% yield) as a white solid.

The individual enantiomers were separated using a CHIRALPAK® AD-H column (250×30 mm ID, 5 μm) under SFC conditions (18% methanol with 0.2% diethylamine and TFA in CO$_2$). Each individual isomer was processed as follows:

Example 19

Isomer 1

The individual fractions were concentrated, the residue bought to neutral pH using 1N sodium hydroxide and extracted into dichloromethane. The dichloromethane layer was dried over sodium sulfate, concentrated and lyophilized to yield isomer 1 (39 mgs, 19.4%) as an yellow solid. Retention time on chiral HPLC, 9.45 min. The compound had an HPLC retention time=3.22 min (condition C); LC/MS $M^{+1}$=568.5; $^1$H NMR (400 MHz, MeOD+CDCl$_3$) δ ppm 7.99 (1H, d, J=7.9 Hz), 7.77 (2H, d, J=7.5 Hz), 7.57-7.70 (3H, m), 7.43-7.52 (2H, m), 5.12-5.20 (1H, m), 3.51 (1H, br. s.), 3.13-3.24 (3H, m), 3.11 (4H, s), 2.88-2.98 (1H, m), 2.72 (1H, br. s.), 2.18-2.41 (1H, m), 1.90-2.01 (4H, m), 1.28 (2H, br. s.).

Example 19

Isomer 2

The individual fractions were collected, concentrated, and lyophilized to yield isomer 2 (39 mgs, 16.2%. 0.5 diethyl ammonium salt based on $^1$H NMR) as a yellow solid. Retention time on chiral HPLC, 14.79 min. The compound had an HPLC retention time=3.18 min (condition C); LC/MS $M^{+1}$=568.5; $^1$H NMR (400 MHz, MeOD) δ ppm 7.94 (1H, d, J=7.9 Hz), 7.78 (2H, d, J=7.3 Hz), 7.60-7.71 (3H, m), 7.49 (1H, s), 7.45 (1H, dd, J=7.9, 1.3 Hz), 4.99-5.05 (1H, m), 3.09 (4H, s), 2.91 (2H, d, J=6.4 Hz), 2.48-2.58 (1H, m), 2.31-2.42 (1H, m), 2.04-2.29 (3H, m), 1.68-1.93 (3H, m), 1.05-1.24 (2H, m).

Example 20

1-((3-(4-Propylphenyl)-4,5-dihydronaphtho[2,1-d]isoxazol-7-yl)methyl)azetidine-3-carboxylic acid

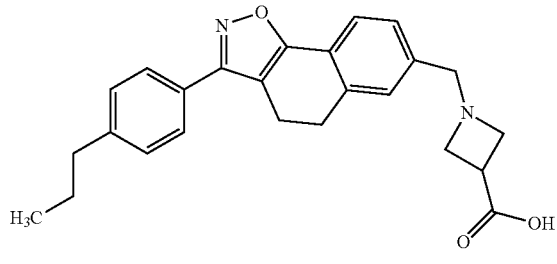

(20)

Preparation 20A:
4-(6-Bromo-3,4-dihydronaphthalen-1-yl)morpholine

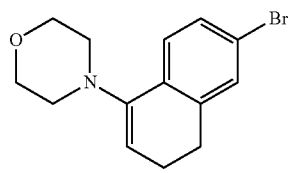

(20A)

To 6-bromo-3,4-dihydronaphthalen-1(2H)-one (0.475 g, 2.110 mmol) in toluene (5 mL) was added morpholine (0.735 mL, 8.44 mmol) at room temperature. The reaction mixture was cooled to 0° C. and titanium tetrachloride (1.0 M in toluene) (1.161 mL, 1.161 mmol) was added over a period of 3 min. The brown heterogeneous reaction mixture was allowed to come to room temperature and stirred for 20 h. The reaction mixture was diluted with 5 mL of anhydrous toluene and filtered over a thin pad of CELITE®. The filter pad was washed with addition anhydrous toluene (2×10 mL). The pale yellow filtrate was concentrated under reduced pressure to yield 4-(6-bromo-3,4-dihydronaphthalen-1-yl)morpholine (0.580 g, 1.972 mmol, 93% yield) as an oil.

Preparation 20B: N-Hydroxy-4-propylbenzimidoyl chloride

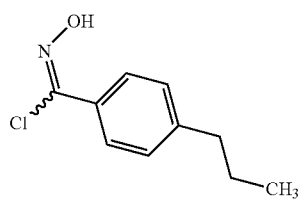

(20B)

To 4-propylbenzaldehyde oxime (1.4 g, 8.58 mmol) in dimethylformamide (3 mL) was added N-chlorosuccinamide (1.145 g, 8.58 mmol) in batches over a period of 10 min. at room temperature. The reaction mixture was stirred at that temperature for an additional 10 min., and partitioned between ethyl acetate (20 mL) and brine (2×20 mL). The ethyl acetate layer was dried over sodium sulfate and purified by silica gel column chromatography using hexane and ethyl acetate. Fractions corresponding to the desired product were collected and concentrated to yield the title compound, which was immediately used for the subsequent step. LCMS $M^{+1}$=198.

Preparation 20C: 7-Bromo-3-(4-propylphenyl)-4,5-dihydronaphtho[2,1-d]isoxazole

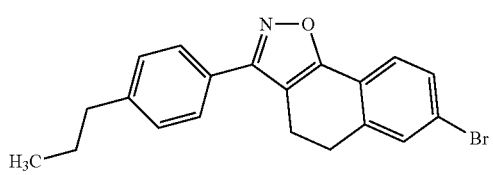

(20C)

To 4-(6-bromo-3,4-dihydronaphthalen-1-yl)morpholine (Preparation 20A, 0.36 g, 1.224 mmol) in dichloromethane (4 mL) was added N-hydroxy-4-propylbenzimidoyl chloride (Preparation 20B, 0.242 g, 1.224 mmol) dissolved in 1 mL of dichloromethane at room temperature. Next, triethylamine was added dropwise over a period of 5 min. at room temperature. The reaction mixture was stirred at room temperature for 14 h. and concentrated. The reaction mixture was partitioned between ethyl acetate (15 mL) and water (10 mL). The ethyl acetate layer was dried over sodium sulfate, filtered, and concentrated to yield an oil. To the oil was added dichloroethane (4.00 mL) followed by TFA (0.141 mL, 1.836 mmol) at room temperature. The reaction mixture was heated at 70° C. for 45 min., stirred at room temperature for 2 h, and partitioned between dichloromethane (10 mL) and sat. aq. sodium bicarbonate (10 mL). The dichloromethane layer was dried over sodium sulfate, concentrated, and purified by silica gel column chromatography employing hexane/ethyl acetate.

The desired fractions were collected and concentrated to yield 7-bromo-3-(4-propylphenyl)-4,5-dihydronaphtho[2,1-d]isoxazole (0.32 g, 0.869 mmol, 71.0% yield) as a white solid. LCMS M$^{+1}$=369.

Preparation 20D: 3-(4-Propylphenyl)-7-vinyl-4,5-dihydronaphtho[2,1-d]isoxazole

(20D)

To 7-bromo-3-(4-propylphenyl)-4,5-dihydronaphtho[2,1-d]isoxazole (Preparation 20C, 0.32 g, 0.869 mmol) in dioxane (3 mL) were added sequentially lithium chloride (0.111 g, 2.61 mmol) and tributyl(vinyl)stannane (0.251 mL, 0.869 mmol). The reaction mixture was purged with nitrogen gas for 3 min. Tetrakis(triphenylphosphine) palladium(0) (0.100 g, 0.087 mmol) was added and the resulting yellow solution was purged with nitrogen gas for 2 min., and heated at 100° C. for 2 h. The reaction mixture was concentrated under reduced pressure and the residue was subjected to silica gel column chromatography using hexane/ethyl acetate. Fractions corresponding to the desired product were collected and concentrated to yield 3-(4-propylphenyl)-7-vinyl-4,5-dihydronaphtho[2,1-d]isoxazole (0.205 g, 0.650 mmol, 74.8% yield) as a pale yellow solid. LCMS M$^{+1}$=316.2.

Preparation 20E: 3-(4-Propylphenyl)-4,5-dihydronaphtho[2,1-d]isoxazole-7-carbaldehyde

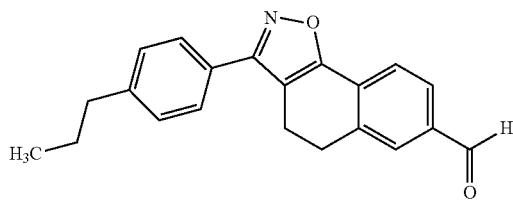

(20E)

To 3-(4-propylphenyl)-7-vinyl-4,5-dihydronaphtho[2,1-d]isoxazole (Preparation 20D, 0.205 g, 0.650 mmol) in THF (2 mL) were added sequentially N-methylmorpholine-N-oxide (0.3 mL, 0.650 mmol) and osmium tetroxide (0.102 mL, 0.013 mmol) at room temperature. The contents were stirred at room temperature for 85 h. Next, sodium periodate (0.209 g, 0.975 mmol) dissolved in 1.5 mL of water was added at room temperature and the reaction mixture was stirred at room temperature for 1 h. The reaction mixture was partitioned between ethyl acetate (20 mL) and brine (20 mL). The ethyl acetate layer was dried over sodium sulfate and concentrated to yield 3-(4-propylphenyl)-4,5-dihydronaphtho[2,1-d]isoxazole-7-carbaldehyde (0.19 g, 0.599 mmol, 92% yield) as a tan solid. LCMS M$^{+1}$=318.2.

Example 20

To 3-(4-propylphenyl)-4,5-dihydronaphtho[2,1-d]isoxazole-7-carbaldehyde (Preparation 20E, 0.191 g, 0.602 mmol) in dichloroethane (2 mL) and methanol (2.0 mL) was added azetidine-3-carboxylic acid (0.073 g, 0.722 mmol) and 8 drops of acetic acid. The reaction mixture was heated at 80° C. for 1.5 h. The reaction mixture was cooled to room temperature and sodium cyanoborohydride (0.045 g, 0.722 mmol) was added in one lot. The reaction mixture was stirred at room temperature for 20 min., and then concentrated. Acetonitrile (10 mL) was added to the resulting residue. The contents were sonicated for ~2 min. and filtered. The solid was washed with acetonitrile (2×10 mL), water (2×10 mL), acetonitrile (5 mL), and dried to yield 1-((3-(4-propylphenyl)-4,5-dihydronaphtho[2,1-d]isoxazol-7-yl)methyl)azetidine-3-carboxylic acid as a grey solid (90 mgs). The compound had an HPLC retention time=3.08 min (condition C); LC/MS M$^{+1}$=403.

Example 21

3-(3-(3-Cyano-4-isopropoxyphenyl)-4,5-dihydronaphtho[1,2-c]isoxazol-7-yl)propanoic acid

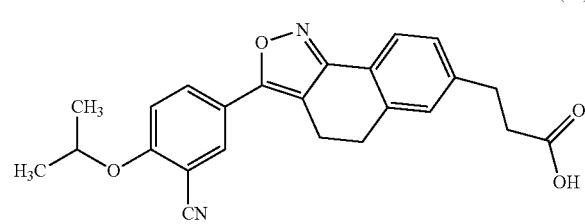

(21)

Preparation 21A: Ethyl 3-(3-(3-cyano-4-isopropoxyphenyl)-4,5-dihydronaphtho[1,2-c]isoxazol-7-yl)propanoate

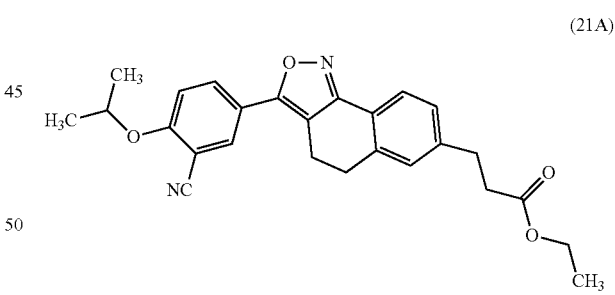

(21A)

To 5-(7-bromo-4,5-dihydronaphtho[1,2-c]isoxazol-3-yl)-2-isopropoxybenzonitrile (Preparation 15B, 0.1 g, 0.244 mmol) in a 2-dram vial was added THF (1 mL). The vial was purged with nitrogen gas for 3 min and (3-ethoxy-3-oxopropyl)zinc(II) bromide (0.5 M in THF) (0.977 mL, 0.489 mmol) was added followed by dichlorobis(tri-o-tolylphosphine)palladium(II) (1.921 mg, 2.443 µmol) at room temperature. The vial was again purged with nitrogen gas for 30 seconds and the pale yellow heterogeneous reaction mixture was stirred at room temperature for 18 h. To the reaction mixture was added potassium fluoride (60 mg) dissolved in 0.2 mL of water at room temperature. The contents were stirred for 5 min. and then filtered. The solid was washed with ethyl acetate (2×5 mL). The filtrate was concentrated under reduced pressure to yield a pale yellow solid. LC/MS M$^{+1}$=401.1.

Example 21

To ethyl 3-(3-(3-cyano-4-isopropoxyphenyl)-4,5-dihydronaphtho[1,2-c]isoxazol-7-yl)propanoate (Preparation 21A, 0.05 g, 0.116 mmol) in THF (2 mL) was added sodium hydroxide (0.058 mL, 0.348 mmol) at room temperature. The reaction mixture was heated at 60° C. for 45 min. An additional 6N sodium hydroxide (0.1 mL) was added and the reaction mixture was heated at 60° C. for an additional 3 hours. The reaction mixture was cooled to room temperature, concentrated under reduced pressure and partitioned between 1N hydrochloric acid (5 mL) and ethyl acetate (15 mL). The hydrochloric acid layer was back extracted with dichloromethane (5 mL). The combined organic layers were dried over sodium sulfate, concentrated under reduced pressure, and purified by silica gel column chromatography (hexane/ethyl acetate). Fractions corresponding to the product were collected and concentrated to yield the title compound as a white solid (23 mgs). The compound had an HPLC retention time=3.45 min (condition C); LC/MS M$^{+1}$=403.1; $^1$H NMR (400 MHz, CDCl$_3$) δ ppm 7.86-7.99 (m, 3H) 7.17-7.24 (m, 2H) 7.09 (d, J=8.80 Hz, 1H) 4.74 (dt, J=12.16, 6.13 Hz, 1H) 2.95-3.07 (m, 6H) 2.74 (t, J=7.59 Hz, 2H) 1.60 (br. s., 1H) 1.41-1.50 (m, 6H).

Example 22

1-((3-(3-Phenyl-4-(trifluoromethyl)isoxazol-5-yl)-4,5-dihydro-2H-benzo[g]indazol-7-yl)methyl)azetidine-3-carboxylic acid

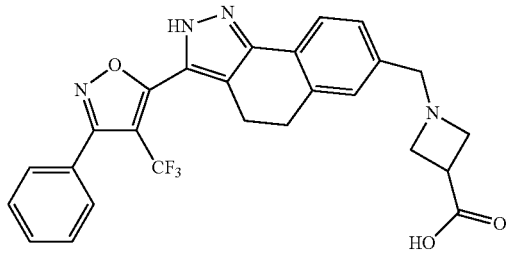

(22)

Preparation 22A: 2-(3-Phenyl-4-(trifluoromethyl)isoxazole-5-carbonyl)-6-vinyl-3,4-dihydronaphthalen-1(2H)-one

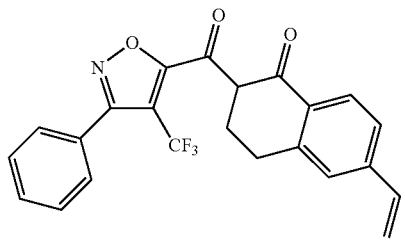

(22A)

Preparation of LDA: To a heat gun dried 50 mL 2-necked flask was added butyllithium (0.764 mL, 2.5 M in hexanes, 1.91 mmol) followed by 2 mL of anhydrous THF under a nitrogen atmosphere. The flask was cooled to 0° C. and diisopropylamine (0.272 mL, 1.910 mmol) was added dropwise over a period of 2 min. The contents were stirred at 0° C. for 20 min.

The LDA solution was cooled to −78° C. and 6-vinyl-3,4-dihydronaphthalen-1(2H)-one (Intermediate I-1B, 0.299 g, 1.736 mmol) dissolved in 1 mL of THF was added dropwise over a period of 2 min. The pale yellow reaction mixture was stirred at −78° C. for 20 min. Then, 3-phenyl-4-(trifluoromethyl)isoxazole-5-carbonyl fluoride (Intermediate 4, 0.450 g, 1.736 mmol) dissolved in 1 mL of THF was added dropwise over a period of 2 min. The reaction mixture was stirred at −78° C. for 20 min, brought to room temperature, and stirred at room temperature for 10 min. The reaction mixture was quenched with 1N hydrochloric acid (5 mL) and extracted into ethyl acetate (20 mL). The aqueous layer was re-extracted with ethyl acetate (10 mL). The combined organic layers were dried over sodium sulfate, concentrated, and purified by silica gel column chromatography (hexane/ethyl acetate). Fractions corresponding to the product were collected and concentrated to yield 2-(3-phenyl-4-(trifluoromethyl)isoxazole-5-carbonyl)-6-vinyl-3,4-dihydronaphthalen-1(2H)-one (0.25 g, 0.608 mmol, 35.0% yield) as a yellow solid. LC/MS M$^{+1}$=412.1.

Preparation 22B: 3-Phenyl-4-(trifluoromethyl)-5-(7-vinyl-4,5-dihydro-2H-benzo[g]indazol-3-yl)isoxazole

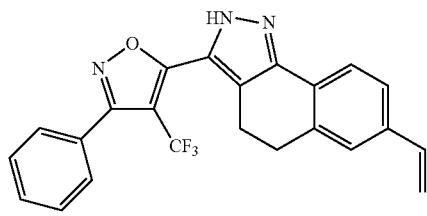

(22B)

To 2-(3-phenyl-4-(trifluoromethyl)isoxazole-5-carbonyl)-6-vinyl-3,4-dihydronaphthalen-1(2H)-one (Preparation 22A, 0.25 g, 0.608 mmol) in a 50 mL round bottom flask was added methanol (2 mL) followed by hydrazine hydrate (0.040 mL, 0.790 mmol) at room temperature. Dioxane (2 mL) was added and the homogenous reaction mixture was heated at 90° C. for 1 h. The reaction mixture was stirred at room temperature for 14 h, concentrated under reduced pressure, azeotroped with methanol (2×10 mL, water bath heated to ~60° C.) and kept under high vacuum for 15 min to yield 3-phenyl-4-(trifluoromethyl)-5-(7-vinyl-4,5-dihydro-2H-benzo[g]indazol-3-yl)isoxazole (0.24 g, 0.454 mmol, 74.6% yield) as a thick oil. LC/MS M$^{+1}$=408.1.

Preparation 22C: 3-(3-Phenyl-4-(trifluoromethyl)isoxazol-5-yl)-4,5-dihydro-2H-benzo[g]indazole-7-carbaldehyde

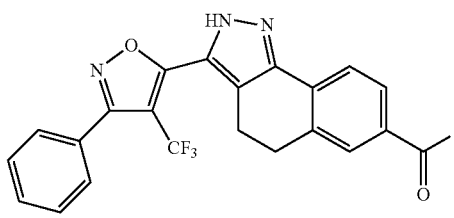

(22C)

To 3-phenyl-4-(trifluoromethyl)-5-(7-vinyl-4,5-dihydro-2H-benzo[g]indazol-3-yl)isoxazole (Preparation 22B, 0.15 g, 0.368 mmol) in THF (2 mL) were added sequentially N-methylmorpholine N-oxide (50% aq., 0.17 mL, 0.368 mmol) and osmium tetroxide (4% aq. 0.058 mL, 7.36 μmol) at room temperature under a nitrogen atmosphere. The reaction was stirred at room temperature for 45 min. and sodium periodate (0.118 g, 0.552 mmol) in water (1 mL) was added over a period of 1 min. at room temperature. The milky heterogeneous reaction mixture was stirred at room temperature for 45 min., concentrated, and partitioned between ethyl acetate (20 mL) and water (10 mL). The ethyl acetate layer was dried over sodium sulfate and concentrated to yield 3-(3-phenyl-4-(trifluoromethyl)isoxazol-5-yl)-4,5-dihydro-2H-benzo[g]indazole-7-carbaldehyde (0.164 g, 0.401 mmol, quantitative yield) as a dark brown oil. LC/MS $M^{+1}$=410.1.

Example 22

To 3-(3-phenyl-4-(trifluoromethyl)isoxazol-5-yl)-4,5-dihydro-2H-benzo[g] indazole-7-carbaldehyde (Preparation 22C, 0.15 g, 0.366 mmol) in methanol (2 mL) and dichloroethane (2 mL) was added azetidine-3-carboxylic acid (0.044 g, 0.440 mmol) at room temperature followed by 5 drops of acetic acid. The reaction mixture was heated at 60° C. for 1 h, cooled to room temperature, and sodium cyanoborohydride (0.028 g, 0.440 mmol) was added in one lot. The reaction mixture was stirred at room temperature for 14 h. The reaction mixture was concentrated under reduced pressure and the resulting brown oil was partitioned between dichloromethane (20 mL) and water (10 mL). The cloudy dichloromethane layer was separated, washed with brine (10 mL), dried over sodium sulfate, and concentrated. To the resulting semi-solid material was added methanol (5 mL) and the contents were triturated and filtered. The filtrate was concentrated under reduced pressure and purified using Prep. HPLC (PHENOMENEX® Luna Axia 30×100 mm; 10 min. gradient; solvent A=10% MeOH, 90% $H_2O$, 0.1% TFA, solvent B=90% MeOH, 10% $H_2O$, 0.1% TFA). Fractions corresponding to the product were collected and concentrated. LCMS indicated the fraction to be a mixture of the desired product and methyl ester. The pH of the residual solution was adjusted to ~5 with 1N sodium hydroxide. The resulting solid out was filtered and washed with water (2×5 mL), ethyl acetate (2×5 mL) and dried. The solid was dissolved in acetonitrile (3 mL) and 6N hydrochloric acid (3 mL) and the contents were heated at 90° C. for 2.5 h. LCMS indicated the fraction to be a mixture of the desired product and the methyl ester. The contents were heated at 90° C. for an additional 4 h. The reaction mixture was concentrated and azeotroped twice with THF (5 mL). The pale yellow solid was triturated with acetonitrile (3 mL), filtered, washed with acetonitrile (2×3 mL) and dried to yield 1-((3-(3-phenyl-4-(trifluoromethyl)isoxazol-5-yl)-4,5-dihydro-2H-benzo[g]indazol-7-yl)methyl)azetidine-3-carboxylic acid, hydrochloric acid (0.04 g, 0.075 mmol, 21% yield). The compound had an HPLC retention time=2.88 min (condition A); LC/MS $M^{+1}$=495.1.

Example 23

1-((3-(4-Isobutyl-3-(trifluoromethyl)phenyl)-4,5-dihydronaphtho[1,2-c]isoxazol-7-yl)methyl)azetidine-3-carboxylic acid

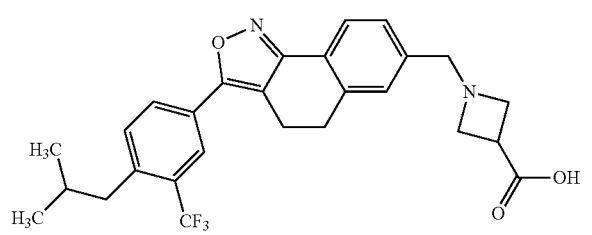

(23)

Preparation 23A:
4-Isobutyl-3-(trifluoromethyl)benzoic acid

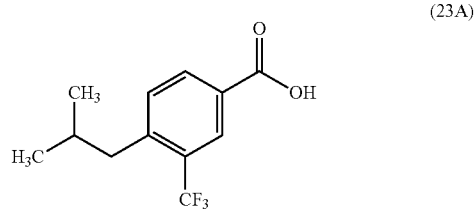 [SMILES: CC(C)Cc1ccc(C(=O)O)cc1C(F)(F)F]

(23A)

A 50 mL round bottom flask was charged with 4-bromo-3-(trifluoromethyl)benzonitrile (0.7 g, 2.80 mmol). THF (5 mL) was added and the contents were evacuated and flushed with nitrogen gas. The process was repeated twice, then isobutylzinc (II) bromide (11.20 mL, 5.60 mmol) was added over 3 min. at room temperature. Next, 1,1'-bis(diphenylphosphino)ferrocenedichloro palladium(II) dichloromethane complex (0.307 g, 0.420 mmol) was added at room temperature. The flask was evacuated and flushed with nitrogen gas. The process was repeated twice and the reaction mixture was heated at 70° C. for 3 h., cooled to room temperature, and concentrated under reduced pressure. Ethyl acetate (20 mL) was added and the contents were stirred at room temperature for 5 min. and filtered over a pad of CELITE®. The filtrate was partitioned between ethyl acetate and water (15 mL). Most of the water layer was separated and the emulsion was filtered over CELITE®. The filtrate was transferred into a separating funnel. The ethyl acetate layer was separated, dried over sodium sulfate, and concentrated. To the resulting semi-solid was added 4 mL of acetic acid, 4 mL of concentrated hydrochloric acid and 8 mL of water. The contents were heated at 110° C. for 14 h. The reaction mixture was cooled to room temperature. The solid and the pale yellow hydrochloric acid-AcOH—$H_2O$ layer were processed separately. The solid was transferred to a beaker, 20 mL of ethyl acetate was added and the contents were sonicated for 5 min. and filtered. The solid on the filter paper was washed with ethyl acetate (2×5 mL). The filtrate was concentrated under reduced pressure and ether (20 ml) was added to the resulting brown solid. The contents were triturated and filtered. The filtrate was concentrated under reduced pressure to yield 4-isobutyl-3-(trifluoromethyl)benzoic acid (0.55 g, 1.966 mmol, 70.2% yield) as a light tan solid. The hydrochloric acid-AcOH—$H_2O$ layer was extracted with ethyl acetate (15 mL). The ethyl acetate layer was washed with 10% LiCl solution (2×20 mL). The ethyl acetate layer was dried over sodium sulfate and concentrated to yield an additional 60 mgs. MS $M^{-1}$=245.4.

Preparation 23B: Methyl
4-isobutyl-3-(trifluoromethyl)benzoate

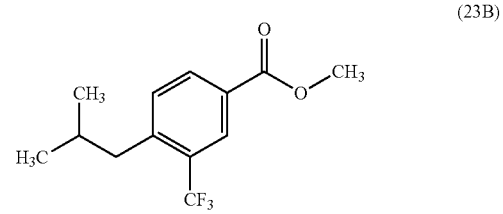 [SMILES: COC(=O)c1ccc(CC(C)C)c(C(F)(F)F)c1]

(23B)

To 4-isobutyl-3-(trifluoromethyl)benzoic acid (Preparation 23A, 0.55 g, 2.234 mmol) in dichloromethane (5 mL) and methanol (2.00 mL) was added trimethylsilyldiazomethane (1.452 mL, 2.90 mmol) at 0° C. The reaction mixture was stirred at 0° C. for 30 min. Excess trimethylsilyldiazomethane was quenched by the slow addition of acetic acid (~0.5 ml) at room temperature. The reaction mixture was concentrated and partitioned between ethyl acetate (20 mL) and sat. aq. sodium bicarbonate (10 mL). The ether layer was washed with brine (10 mL), dried over sodium sulfate, and concentrated. The resulting dark oil was subjected to silica gel column chromatography (hexane/ethyl acetate). Fractions corresponding to the product were collected and concentrated to yield an oil. The oil was azeotroped with THF (2×5 mL) and dried under high vacuum to yield methyl 4-isobutyl-3-(trifluoromethyl)benzoate (0.52 g, 1.998 mmol, 89% yield) as a clear liquid.

Preparation 23C: 3-(4-Isobutyl-3-(trifluoromethyl) phenyl)-7-vinyl-4,5-dihydronaphtho[1,2-c]isoxazole

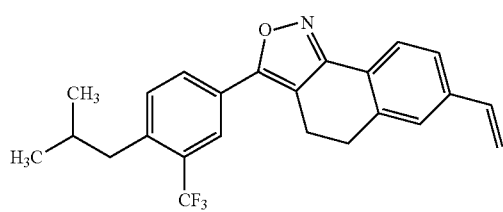

(23C)

Preparation of LDA: To a heat gun dried 50 mL 2-necked flask was added butyllithium (2.5 M in hexanes) (1.602 mL, 4.01 mmol) under a nitrogen atmosphere followed by 2 mL of anhydrous THF. The flask was cooled to 0° C., and diisopropylamine (0.0.56 mL, 4.01 mmol) was added over a period of 3 min. The contents were stirred at 0° C. for 15 min.

To the LDA solution was added 6-vinyl-3,4-dihydronaphthalen-1(2H)-one oxime (Intermediate 1, 0.25 g, 1.335 mmol) dissolved in 1 mL of THF dropwise over a period of 1 min. at 0° C. After 15 min., methyl 4-isobutyl-3-(trifluoromethyl)benzoate (Preparation 23B, 0.347 g, 1.335 mmol) dissolved in 1 mL of THF was added dropwise over a period of 1 min. at 0° C. and the contents were stirred at 0° C. for 10 min. The reaction mixture was partitioned between 1N hydrochloric acid (5 mL) and ethyl acetate (10 mL)-THF. The 1N hydrochloric acid layer was back extracted with ethyl acetate (10 mL). The combined ethyl acetate layers were dried over sodium sulfate and concentrated under reduced pressure. The resulting yellow solid was azeotroped with toluene (5 mL). To the solid was added toluene (5.00 mL), followed by thionyl chloride (0.195 mL, 2.67 mmol) and 1 drop of pyridine. The contents were heated at 110° C. for 5 min. The dark reaction mixture was concentrated and partitioned between ethyl acetate (15 mL) and water (10 mL). The ethyl acetate layer was dried over sodium sulfate, concentrated and subjected to silica gel column chromatography (hexane/ethyl acetate). Fractions corresponding to the product were collected and concentrated to yield 3-(4-isobutyl-3-(trifluoromethyl)phenyl)-7-vinyl-4,5-dihydronaphtho[1,2-c]isoxazole (0.305 g, 0.767 mmol, 57.5% yield) as a pale yellow solid.

Preparation 23D: 3-(4-Isobutyl-3-(trifluoromethyl) phenyl)-4,5-dihydronaphtho[1,2-c]isoxazole-7-carbaldehyde

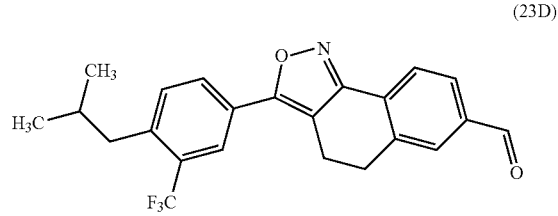 [SMILES: CC(C)Cc1ccc(-c2onc3c2CCc2cc(C=O)ccc2-3)cc1C(F)(F)F]

(23D)

To 3-(4-isobutyl-3-(trifluoromethyl)phenyl)-7-vinyl-4,5-dihydronaphtho[1,2-c]isoxazole (Preparation 23C, 0.3 g, 0.755 mmol) in THF (2 mL) was sequentially added N-methylmorpholine N-oxide (50% in water) (0.35 mL, 0.755 mmol) and osmium tetroxide (4% in water) (0.118 mL, 0.015 mmol) at room temperature. The reaction mixture was stirred at room temperature for 60 h. Next, sodium periodate (0.242 g, 1.132 mmol) dissolved in 1.5 mL of water was added at room temperature. The heterogeneous reaction mixture was stirred at room temperature for 30 min. and the reaction mixture was partitioned between ethyl acetate (10 mL) and brine (5 mL). The ethyl acetate layer was dried over sodium sulfate and concentrated to yield 3-(4-isobutyl-3-(trifluoromethyl)phenyl)-4,5-dihydronaphtho[1,2-c]isoxazole-7-carbaldehyde (0.3 g, 0.751 mmol, 100% yield) as an off-white solid. LC/MS $M^{+1}$=400.2.

Example 23

To 3-(4-isobutyl-3-(trifluoromethyl)phenyl)-4,5-dihydronaphtho[1,2-c]isoxazole-7-carbaldehyde (Preparation 23D, 0.3 g, 0.751 mmol) in dichloroethane (2 mL) and methanol (2 mL) was added azetidine-3-carboxylic acid (0.091 g, 0.901 mmol) followed by 8 drops of AcOH. The reaction mixture was heated at 80° C. for 1 h. The reaction mixture was cooled to room temperature and sodium cyanoborohydride was added in one lot. The contents were stirred at room temperature for 30 min., concentrated, dissolved in acetonitrile (1.5 mL) and subjected to prep. HPLC purification PHENOMENEX® Luna Axia 30×100 mm; 10 min. gradient; solvent A=10% MeOH, 90% $H_2O$, 0.1% TFA, solvent B=90% MeOH, 10% $H_2O$, 0.1% TFA). Fractions corresponding to the product were collected and concentrated. The oily residue was freeze dried to yield 1-((3-(4-isobutyl-3-(trifluoromethyl)phenyl)-4,5-dihydronaphtho[1,2-c]isoxazol-7-yl)methyl)azetidine-3-carboxylic acid, TFA (0.146 g, 0.244 mmol, 32.5% yield) as a tan solid. The compound had an HPLC retention time=3.55 min. (condition C); LC/MS $M^{+1}$=485.4. $^1$H NMR (500 MHz, MeOD) δ ppm 7.83-7.94 (m, 3H) 7.50 (d, J=8.32 Hz, 1H) 7.38 (s, 1H) 7.34 (dd, J=8.05, 1.66 Hz, 1H) 4.33 (s, 2H) 4.18-4.28 (m, 3H) 3.58 (qd, J=8.37, 8.18 Hz, 1H) 3.15 (1H, hidden under $CD_3OD$ peak) 2.96-3.01 (m, 4H) 2.62 (d, J=6.94 Hz, 2H) 1.85-1.94 (m, 1H) 0.84 (d, J=6.66 Hz, 6H).

Examples 24 and 25

(3-(3-(Trifluoromethyl)phenyl)-4,5-dihydronaphtho[1,2-c]isoxazol-7-yl)methanol (24) and 1-((3-(3-(Trifluoromethyl)phenyl)-4,5-dihydronaphtho[1,2-c]isoxazol-7-yl)methyl)azetidine-3-carboxylic acid (25)

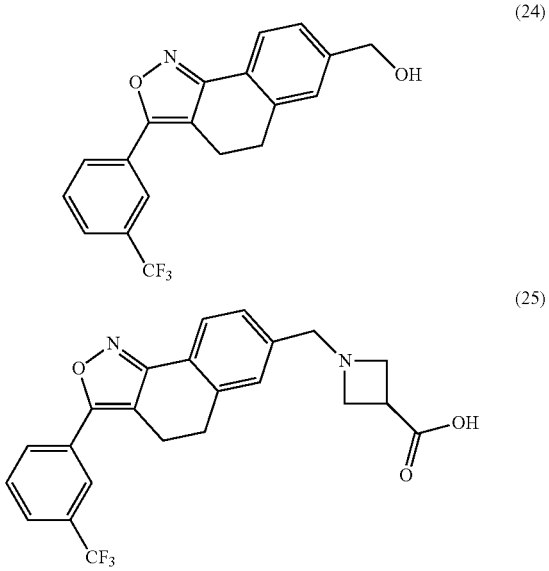

Preparation 24A: 3-(3-(Trifluoromethyl)phenyl)-7-vinyl-4,5-dihydronaphtho[1,2-c]isoxazole

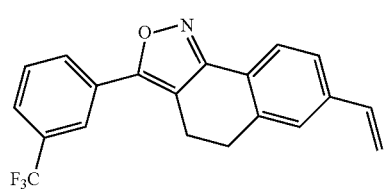

To 6-vinyl-3,4-dihydronaphthalen-1(2H)-one oxime (Intermediate 1, 0.151 g, 0.808 mmol) was added 5 mL of toluene and the contents were concentrated under reduced pressure. The resulting solid was kept under high vacuum for 10 min. The white solid was cooled to 0° C. and lithium diisopropylamide (2.0 M, 0.8 mL, 1.61 mmol) was added drop wise over a period of 3 min. The reaction mixture was stirred at 0° C. for 20 min., then methyl 3-(trifluoromethyl)benzoate (0.087 mL, 0.539 mmol) was added dropwise over a period of 1 min. at 0° C. After 10 min. at 0° C., concentrated sulfuric acid (0.2 mL) was added dropwise at 0° C. and the reaction was stirred for 20 minutes. Water (2 mL) was added and the homogenous solution was heated at 60° C. for ~2 hr. The reaction mixture was stirred overnight at room temperature. The contents were concentrated under reduced pressure. Next, 5 mL of dioxane was added and the contents were heated at 100° C. for 1.5 hr. The reaction mixture was concentrated under reduced pressure and partitioned between ethyl acetate (20 mL) and sat. aq. sodium bicarbonate (10 mL). The ethyl acetate layer was dried over sodium sulfate, concentrated under reduced pressure, and purified by silica gel column chromatography (hexane/ethyl acetate). Fractions corresponding to the product were collected and concentrated to yield 3-(3-(trifluoromethyl)phenyl)-7-vinyl-4,5-dihydronaphtho[1,2-c]isoxazole (0.15 g, 0.439 mmol, 82% yield) as a pale yellow solid. LC/MS $M^{+1}$=342.

Preparation 24B: 3-(3-(Trifluoromethyl)phenyl)-4,5-dihydronaphtho[1,2-c]isoxazole-7-carbaldehyde

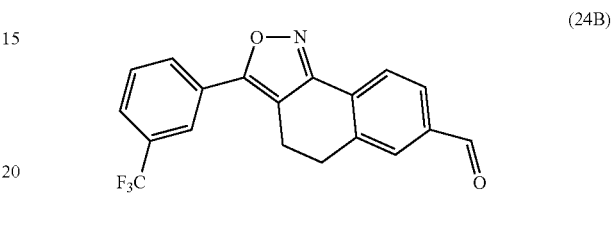

To 3-(3-(trifluoromethyl)phenyl)-7-vinyl-4,5-dihydronaphtho[1,2-c]isoxazole (Preparation 24A, 0.15 g, 0.439 mmol) was added dichloromethane (7 mL). The contents were ozonized at –78° C., until a blue color persisted (~5 min). Excess ozone was purged out using nitrogen gas. Triethylamine (0.2 mL, 1.435 mmol) was added at –78° C., and the cooling bath was removed. The color of the reaction mixture changed from yellow to green to yellow-brown on reaching room temperature. The reaction mixture was partitioned between dichloromethane (20 mL) and 1N hydrochloric acid (5 ml). The dichloromethane layer was separated, washed with brine (10 mL), dried over sodium sulfate, and concentrated to yield an orange-yellow solid (160 mgs). LC/MS $M^{+1}$=344.

Examples 24 and 25

To 3-(3-(trifluoromethyl)phenyl)-4,5-dihydronaphtho[1,2-c]isoxazole-7-carbaldehyde (Preparation 24B, 0.15 g, 0.437 mmol) in a mixture of methanol (3 mL) and acetic acid (1.00 mL) was added azetidine-3-carboxylic acid (0.066 g, 0.655 mmol) at room temperature. A minute after the addition, the reaction mixture turned dirty green. Sodium triacetoxyborohydride (0.232 g, 1.092 mmol) was added at room temperature and the heterogeneous reaction mixture was stirred at room temperature for 65 h. To the reaction mixture was added sodium cyanoborohydride (0.055 g, 0.874 mmol) at room temperature. The contents were stirred at room temperature for 6 h. The reaction mixture was concentrated under reduced pressure, methanol (3 mL) was added and the contents were triturated and filtered. The filtrate was subjected to prep. HPLC purification (PHENOMENEX® Luna Axia 30×100 mm; 10 min. gradient; solvent A=10% MeOH, 90% $H_2O$, 0.1% TFA, solvent B=90% MeOH, 10% $H_2O$, 0.1% TFA). Fractions corresponding to the Examples 24 and 25 were collected, concentrated and freeze dried using methanol (0.5 mL) and water (1 mL).

Example 24 had an HPLC retention time=2.85 min (condition C); LC/MS $M^{+1}$=429.1; $^1$H NMR (400 MHz, MeOD) δ ppm 7.86-8.06 (m, 3H) 7.60-7.76 (m, 2H) 7.33-7.48 (m, 2H) 4.36 (s, 2H) 4.19-4.31 (m, 4H) 3.54-3.69 (m, 1H) 3.02 (s, 4H).

Example 25 had an HPLC retention time=3.45 min (condition C); LC/MS $M^{+1}$=346.2; $^1$H NMR (400 MHz, MeOD)

δ ppm 7.93-8.00 (m, 2H) 7.78 (d, J=7.92 Hz, 1H) 7.63-7.73 (m, 2H) 7.23-7.32 (m, 2H) 4.55 (s, 2H) 2.95-3.03 (m, 4H).

Example 26

1-((3-(2-(1-(4-Fluorophenyl)cyclohexyl)ethyl)-4,5-dihydronaphtho[1,2-c]isoxazol-7-yl)methyl)azetidine-3-carboxylic acid (26)

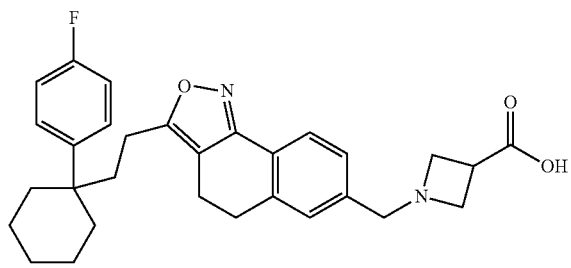

Preparation 26A: 3-(2-(1-(4-Fluorophenyl)cyclohexyl)ethyl)-7-vinyl-4,5-dihydronaphtho[1,2-c]isoxazole (26A)

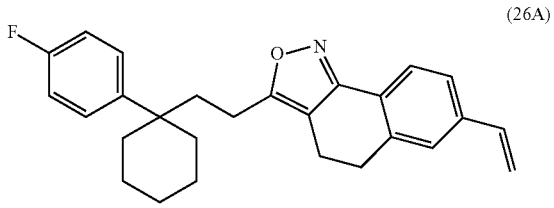 [SMILES: C=Cc1ccc2c(c1)CCc1c-2noc1CCC1(c2ccc(F)cc2)CCCCC1]

To a stirring solution of the diisopropylamine (0.230 mL, 1.617 mmol) in 2.5 mL of THF at −60° C. was added 2.5 M n-butyl lithium in hexanes (0.657 mL, 1.644 mmol) dropwise. The solution was allowed to stir with a gradual warm up to about −20° C. This freshly generated LDA solution was slowly added to a stirring solution of the 6-vinyl-3,4-dihydronaphthalen-1(2H)-one oxime (Intermediate 1, 0.151 g, 0.808 mmol) in 1 mL of THF at ice bath temperature and the reaction mixture was stirred at this temperature for 15 min. To this mixture was then slowly added a solution of ethyl 3-(1-(4-fluorophenyl)cyclohexyl)propanoate (Intermediate 7, 0.15 g, 0.539 mmol) in 2 ml of THF. The reaction was warmed to room temperature and stirred for 4 hrs. It was quenched with saturated aq ammonium chloride and partitioned between ethyl acetate and water. The organic layer was then dried over anhyd. magnesium sulfate, concentrated and dried in vacuo. The residue was taken in 3 ml of toluene and treated with p-toluenesulfonic acid monohydrate (0.205 g, 1.078 mmol) and the mixture was then heated at 60° C. for slightly over an hour. The reaction mixture was cooled and diluted with ethyl acetate and washed with saturated. aq. sodium bicarbonate and brine. It was dried over anhyd. magnesium sulfate, concentrated and chromatographed (40 g REDISEP® silica cartridge; eluted with 10% ethyl acetate-hexanes) to yield 3-(2-(1-(4-fluorophenyl)cyclohexyl)ethyl)-7-vinyl-4,5-dihydronaphtho[1,2-c]isoxazole (89.8 mg, 0.224 mmol, 41.5% yield) as a pale oil. LC/MS $M^{+1}$=402.22.

Preparation 26B: 1-(3-(2-(1-(4-Fluorophenyl)cyclohexyl)ethyl)-4,5-dihydronaphtho[1,2-c]isoxazol-7-yl)ethane-1,2-diol (26B)

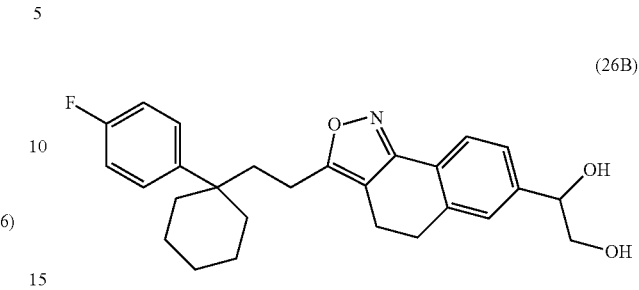

To a solution of 3-(2-(1-(4-fluorophenyl)cyclohexyl)ethyl)-7-vinyl-4,5-dihydronaphtho[1,2-c]isoxazole (Preparation 26A, 0.0898 g, 0.224 mmol) in THF (1.5 mL) was added a solution of N-methylmorpholine-N-oxide (0.039 g, 0.335 mmol) in water (1.5 mL), followed by 0.37 mL of 2.5% osmium tetroxide. The reaction mixture was stirred at room temperature for 2 hrs and quenched with aq. sodium sulfite. The reaction mixture was extracted with ethyl acetate and the aqueous layer was reextracted with ethyl acetate. The combined organic layers were then washed with brine dried over magnesium sulfate, concentrated, and purified by silica gel column chromatography to yield 1-(3-(2-(1-(4-fluorophenyl)cyclohexyl)ethyl)-4,5-dihydronaphtho[1,2-c]isoxazol-7-yl)ethane-1,2-diol as an oil. LC/MS $M^{+1}$=436.25.

Preparation 26C: 3-(2-(1-(4-Fluorophenyl)cyclohexyl)ethyl)-4,5-dihydronaphtho[1,2-c]isoxazole-7-carbaldehyde (26C)

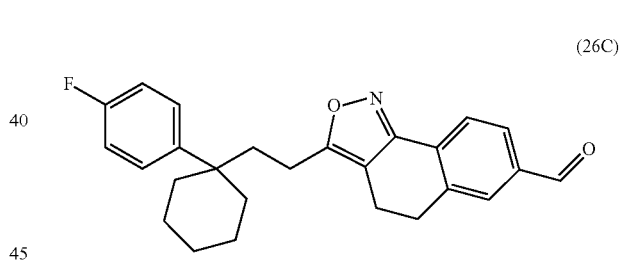

To a solution of 1-(3-(2-(1-(4-fluorophenyl)cyclohexyl)ethyl)-4,5-dihydronaphtho[1,2-c]isoxazol-7-yl)ethane-1,2-diol (Preparation 26B, 0.097 g, 0.223 mmol) in methanol (2 mL) at 0° C. was added a solution of sodium periodate (0.057 g, 0.268 mmol) in water (2 mL) dropwise. The white heterogeneous reaction mixture was stirred for 40 mins. at 0° C. and partitioned between ethyl acetate and water. The ethyl acetate layer was washed with brine, dried over sodium sulfate, concentrated, dried in vacuo to yield 3-(2-(1-(4-fluorophenyl)cyclohexyl)ethyl)-4,5-dihydronaphtho[1,2-c]isoxazole-7-carbaldehyde. LC/MS $M^{+1}$=402.23.

Example 26

To a solution of the 3-(2-(1-(4-fluorophenyl)cyclohexyl)ethyl)-4,5-dihydronaphtho[1,2-c]isoxazole-7-carbaldehyde (Preparation 26C, 89 mg, 0.22 mmol) and the azetidine-3-carboxylic acid (26.7 mg, 0.264 mmol) in methanol (1.5 mL) and dichloroethane (1.5 mL) at room temperature was added 4 to 5 drops of glacial acetic acid. The reaction mixture was heated at 60° C. for 1 hr, cooled to room temperature, and then treated with sodium cyanoborohydride (16.59 mg, 0.264 mmol). The reaction was stirred overnight at room temperature, quenched with ~1 ml of saturated. aq. sodium bicarbonate, stirred for 30 min, concentrated under reduced pressure and partitioned between dichloromethane and water. The organic layer was washed with brine, dried over anhyd. sodium sulfate, concentrated, dried in vacuo and purified by preparative HPLC using the following conditions: Column. Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation.) to yield 4.5 mgs (4.14% over three steps) of 1-((3-(2-(1-(4-fluorophenyl)cyclohexyl)ethyl)-4,5-dihydronaphtho[1,2-c]isoxazol-7-yl)methyl)azetidine-3-carboxylic acid. The compound had a HPLC retention time=2.53 min. (condition F); LC/MS M$^{+1}$=489.16; $^1$H NMR (400 MHz, MeOD) δ ppm 7.84 (1H, d, J=7.78 Hz), 7.36-7.44 (4H, m), 7.05 (2H, t, J=8.78 Hz), 4.34 (2H, s), 4.19 (2H, s), 4.17 (2H, s), 3.42 (1H, quin, J=8.34 Hz), 2.91 (2H, t, J=7.15 Hz), 2.51 (2H, t, J=7.15 Hz), 2.38-2.45 (2H, m), 2.14 (2H, br. s.), 1.92-1.99 (2H, m), 1.35-1.70 (8H, m).

Example 27

1-((3-(4-(4-Chlorophenyl)cyclohexyl)-4,5-dihydronaphtho[1,2-c]isoxazol-7-yl)methyl)azetidine-3-carboxylic acid (27)

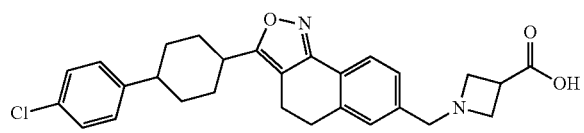

Preparation 27A: Methyl 4-(4-chlorophenyl)cyclohexanecarboxylate (27A)

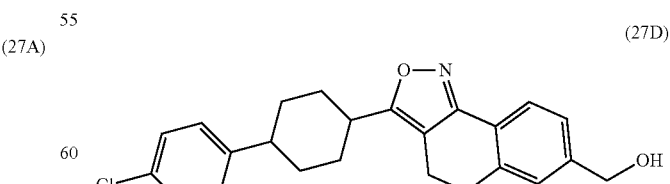

To a stirred solution of the 4-(4-chlorophenyl)cyclohexanecarboxylic acid (0.5 g, 2.095 mmol) in methanol (10 mL) was added one drop of conc. sulfuric acid. After stirring overnight at room temperature, the reaction mixture was extracted with ethyl acetate and washed with water, saturated sodium bicarbonate and brine. It was then dried over anhyd. magnesium sulfate, concentrated and dried in vacuo to yield methyl 4-(4-chlorophenyl)cyclohexanecarboxylate a white solid. $^1$H NMR (400 MHz, CDCl$_3$) δ ppm 7.23-7.30 (2H, m), 7.10-7.17 (2H, m), 3.70 (3H, s), 2.44-2.56 (1H, m), 2.36 (1H, tt, J=12.13, 3.60 Hz), 2.07-2.16 (2H, m), 1.92-2.01 (2H, m), 1.38-1.67 (4H, m).

Preparation 27B: 3-(4-(4-Chlorophenyl)cyclohexyl)-7-vinyl-4,5-dihydronaphtho[1,2-c]isoxazole (27B)

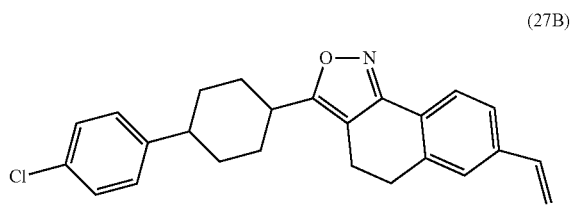 [SMILES: C=Cc1ccc2c(c1)CCc1c-2noc1C1CCC(c2ccc(Cl)cc2)CC1]

This compound was prepared according to the general procedure described for Preparation 26A, employing methyl 4-(4-chlorophenyl)cyclohexanecarboxylate as the starting material. LC/MS M$^{+1}$=390.3.

Preparation 27C: 1-(3-(4-(4-Chlorophenyl)cyclohexyl)-4,5-dihydronaphtho[1,2-c]isoxazol-7-yl)ethane-1,2-diol (27C)

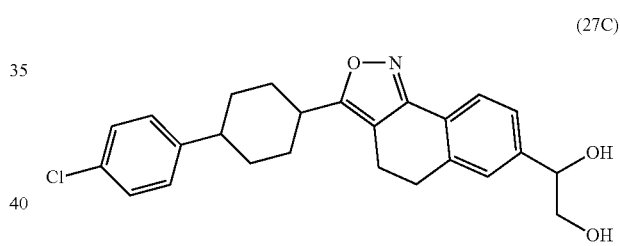

This compound was prepared according to the general procedure described for Preparation 26B employing 3-(4-(4-chlorophenyl)cyclohexyl)-7-vinyl-4,5-dihydronaphtho[1,2-c]isoxazole (Preparation 27B) as the starting material. LC/MS M$^{+1}$=424.19.

Preparation 27D: (3-(4-(4-Chlorophenyl)cyclohexyl)-4,5-dihydronaphtho[1,2-c]isoxazol-7-yl)methanol (27D)

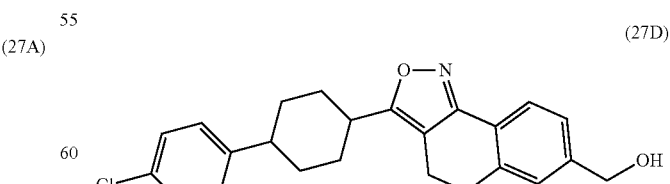

To a solution of 1-(3-(4-(4-chlorophenyl)cyclohexyl)-4,5-dihydronaphtho[1,2-c]isoxazol-7-yl)ethane-1,2-diol (Preparation 27C, 0.05 g, 0.118 mmol) in methanol (1.0 mL) at 0° C. was added a solution of sodium periodate (0.030 g, 0.142 mmol) in water (1.0 mL) dropwise. The white heterogeneous reaction mixture was stirred for 40 mins. at the same temperature and then partitioned between ethyl acetate and water. The organic layer was washed with brine, dried over anhyd. sodium sulfate and concentrated. The residue was taken in methanol (2 mL) and treated with sodium borohydride (5.35 mg, 0.142 mmol) at room temperature. After 1 h, the reaction was quenched with saturated. aq. sodium bicarbonate. After stirring for 30 min, the reaction mixture was partitioned between ethyl acetate and water. The ethyl acetate layer was washed with brine, dried over anhyd. magnesium sulfate and concentrated to yield (3-(4-(4-chlorophenyl)cyclohexyl)-4,5-dihydronaphtho[1,2-c]isoxazol-7-yl)methanol.

Preparation 27E: (3-(4-(4-Chlorophenyl)cyclohexyl)-4,5-dihydronaphtho[1,2-c]isoxazol-7-yl)methyl methanesulfonate

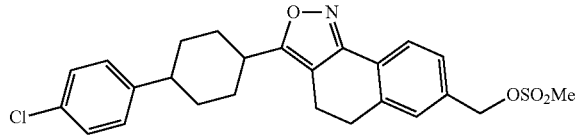

(27E)

To a stirring solution of the (3-(4-(4-chlorophenyl)cyclohexyl)-4,5-dihydronaphtho[1,2-c]isoxazol-7-yl)methanol (Preparation 27D, 0.046 g, 0.118 mmol) in dichloromethane (2.0 mL) at room temperature was added triethylamine (0.049 mL, 0.354 mmol) followed by methanesulfonyl chloride (0.014 mL, 0.177 mmol). The reaction mixture was stirred for 1 h at room temperature, concentrated under reduced pressure to yield (3-(4-(4-chlorophenyl)cyclohexyl)-4,5-dihydronaphtho[1,2-c]isoxazol-7-yl)methyl methanesulfonate.

Example 27

To a solution of 3-(4-(4-chlorophenyl)cyclohexyl)-4,5-dihydronaphtho[1,2-c]isoxazol-7-yl)methyl methanesulfonate (Preparation 27E, 0.056 g, 0.118 mmol) and acetic acid salt of tert-butyl azetidine-3-carboxylate (0.038 g, 0.177 mmol) in dimethylsulfoxide (2.5 ml) at room temperature was added cesium carbonate (0.115 g, 0.354 mmol). The mixture was stirred at room temperature overnight and partitioned between ethyl acetate and water. The ethyl acetate layer was washed with brine, dried over anhyd. sodium sulfate and concentrated under reduced pressure. To the residue was added 2 ml of TFA at room temperature and stirred for 30 min. The reaction mixture was concentrated under reduced pressure and the residue purified by preparative HPLC using the following conditions: Column: Waters XBridge C18, 19×250 mm, 5-nm particles; Guard Column: Waters XBridge C18, 19×10 mm, 5-nm particles; Mobile Phase A: 5:95 acetonitrile:water with 10-mM ammonium acetate; Mobile Phase B: 95:5 acetonitrile:water with 10-mM ammonium acetate; Gradient: 35-100% B over 25 minutes, then a 5-minute hold at 100% B; Flow: 20 mL/min. Fractions containing the desired product were combined and dried via centrifugal evaporation, to yield 0.9 mgs (1.6% yield over 5 steps) of 1-((3-(4-(4-chlorophenyl)cyclohexyl)-4,5-dihydronaphtho[1,2-c]isoxazol-7-yl)methyl)azetidine-3-carboxylic acid. The compound had an HPLC retention time=2.841 min. (condition F); LC/MS $M^{+1}$=477.22; $^1$H NMR (400 MHz, MeOD) δ ppm 8.25 (1H, d, J=8.28 Hz), 7.65-7.75 (2H, m), 7.53 (2H, d, J=8.28 Hz), 7.45 (2H, d, J=8.53 Hz), 4.70 (2H, s), 4.46 (4H, br. s.), 3.31 (2H, t, J=7.15 Hz), 3.19-3.28 (1H, m), 3.12 (2H, t, J=7.15 Hz), 2.84-2.95 (1H, m), 2.42 (2H, d, J=11.54 Hz), 2.30 (2H, d, J=11.80 Hz), 2.04-2.18 (2H, m, J=12.92, 12.80, 12.80, 3.14 Hz), 1.80-1.95 (3H, m).

Example 28

1-((3-(2-(1-(3,5-Dichlorophenyl)cyclohexyl)ethyl)-4,5-dihydronaphtho[1,2-c]isoxazol-7-yl)methyl)azetidine-3-carboxylic acid

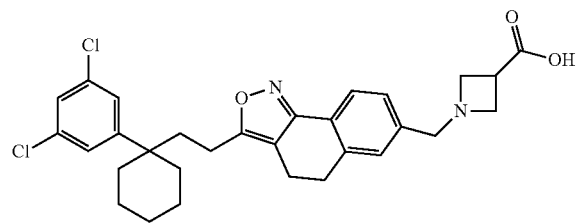

(28)

The compound was prepared according to the general procedure described in Example 27 by employing ethyl 3-(1-(3,5-dichlorophenyl)cyclohexyl)propanoate (Intermediate 8). The compound had an HPLC retention time=3.135 min. (condition F); LC/MS $M^{+1}$=539.18. $^1$H NMR (400 MHz, MeOD) δ ppm 7.93 (1H, d, J=8.28 Hz), 7.35-7.40 (3H, m), 7.20 (1H, d, J=1.76 Hz), 7.15 (1H, t, J=1.76 Hz), 4.40 (2H, s), 4.06 (4H, br. s.), 2.95 (2H, t, J=6.90 Hz), 2.55 (2H, t, J=7.15 Hz), 2.39-2.46 (1H, m), 2.06-1.32 (10H, m).

Example 29

1-((3-(3-(4-Chlorophenyl)-3-methylbutyl)-4,5-dihydronaphtho[1,2-c]isoxazol-7-yl)methyl)azetidine-3-carboxylic acid

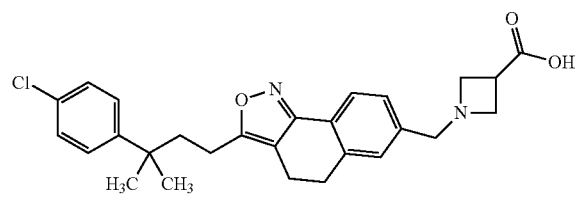

(29)

The compound was prepared according to the general procedure described in Example 26 by employing ethyl 4-(4-chlorophenyl)-4-methylpentanoate (Intermediate 9) in the synthesis of Preparation 26B. The compound had an HPLC retention time=2.088 min (Condition: Column: Sunfire C18, 4.6×50 mm; (4 min), 5 μm particles; solvent A: 10% MeOH-90% water-0.1% TFA; solvent B: 90% MeOH-10% water-0.1% TFA; Start % B=50 to Final % B=100); LC/MS $M^{+1}$=465.24; $^1$H NMR (400 MHz, MeOD) δ ppm 7.83 (1H, d, J=7.92 Hz), 7.34-7.40 (2H, m), 7.34 (2H, d, J=8.80 Hz), 7.24-7.28 (2H, m, J=8.80 Hz), 4.18 (2H, s), 3.95-4.08 (4H, m), 3.31-3.41 (1H, m), 2.92 (2H, t, J=7.15 Hz), 2.48-2.58 (4H, m), 2.04-2.11 (2H, m), 1.37 (6H, s).

Example 30

1-((3-(((1-(4-Fluorophenyl)cyclohexyl)methoxy)methyl)-4,5-dihydronaphtho[1,2-c]isoxazol-7-yl)azetidine-3-carboxylic acid

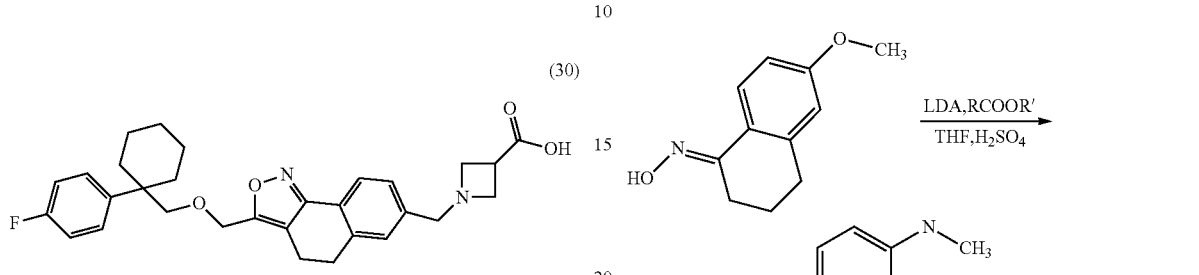

(30)

The compound was prepared according to the general procedure described in Example 26 employing ethyl 2-((1-(4-fluorophenyl)cyclohexyl)methoxy)acetate (Intermediate 10) in the synthesis of Preparation 26A. The compound had an HPLC retention time=1.213 min (Column: Waters Sunfire C18, 2.5 um; 2.1×30 mm; (2 min); solvent A: 0.1% TFA in MeOH-water (10:90); solvent B: 0.1% TFA in MeOH-water (10:90); Start % B=50 to Final % B=100); LC/MS $M^{+1}$=505.39; $^1$H NMR (400 MHz, MeOD) δ ppm 7.91 (1H, d, J=7.92 Hz), 7.45 (1H, s), 7.43 (1H, d, J=7.92 Hz), 7.38 (2H, dd, J=9.02, 5.50 Hz), 6.99 (2H, t, J=8.91 Hz), 4.48 (2H, s), 4.43 (2H, s), 4.34 (4H, d, J=7.26 Hz), 3.70 (1H, quin, J=8.31 Hz), 3.44 (2H, s), 2.91 (2H, t, J=7.15 Hz), 2.55 (2H, t, J=7.15 Hz), 2.06-2.16 (2H, m), 1.64-1.74 (2H, m), 1.47-1.58 (3H, m), 1.30-1.39 (3H, m).

Example 31

1-((3-(3-(1-(4-Fluorophenyl)cyclohexyl)propyl)-4,5-dihydronaphtho[1,2-c]isoxazol-7-yl)methyl)azetidine-3-carboxylic acid

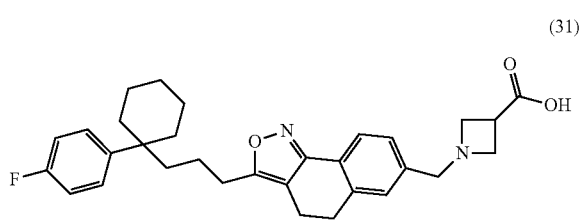 [SMILES: O=C(O)C1CN(Cc2ccc3c(c2)CCc2c-3noc2COCC2(c3ccc(F)cc3)CCCCC2)C1]

(31)

The compound was prepared according to the general procedure described in Example 26 employing ethyl 4-(1-(4-fluorophenyl)cyclohexyl)butanoate (Intermediate 11) in the synthesis of Preparation 26A. The compound had an HPLC retention time of 10.38 min (Condition: Column: Sunfire C18 3.5 um, 3.0×150 mm; (15 min); solvent A: 95/5 water/MeCN with 0.05% TFA; solvent B: 5/95 water/MeCN with 0.05% TFA; Start % B=10 to Final % B=100; Wavelength=220 nm) LC/MS $M^{+1}$=503.3; $^1$H NMR (400 MHz, CDCl$_3$) δ ppm 7.92 (1H, d, J=7.70 Hz), 7.40 (1H, s), 7.35 (1H, d, J=8.58 Hz), 7.24 (2H, dd, J=8.69, 5.39 Hz), 6.98 (2H, t, J=8.69 Hz), 4.32 (2H, s), 4.36 (2H, br. s.), 4.12 (2H, br. s.), 3.70 (1H, m), 3.46-3.50 (2H, m), 3.38 (2H, d, J=1.10 Hz), 2.91 (2H, t, J=6.93 Hz), 2.49-2.63 (4H, m), 2.05 (2H, d, J=5.50 Hz), 1.18-1.64 (8H, m).

Examples 32 to 34

General Reaction Sequence

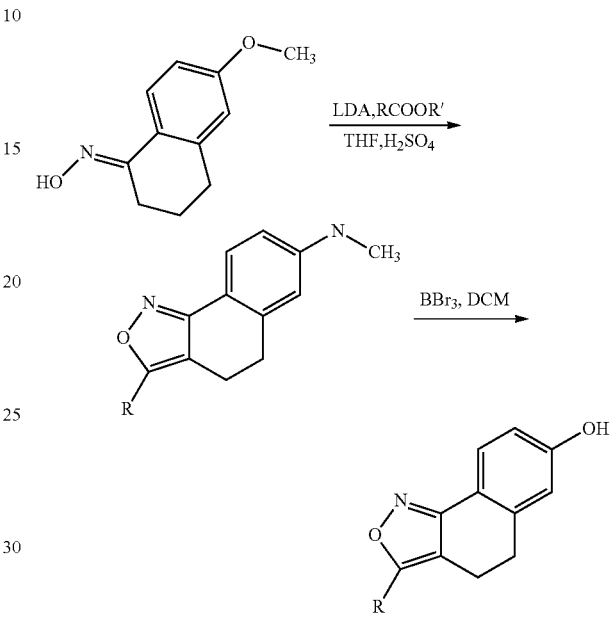

To diisopropylamine (0.04 mL, 0.314 mmol) in THF was added a solution of butyllithium (2.6 M in hexanes, 0.12 mL, 0.314 mmol) at 0° C. and stirred for 30 mins. at 0° C. To the reaction mixture was added 6-methoxy-3,4-dihydronaphthalen-1(2H)-one oxime (Intermediate 2) (30 mg, 0.157 mmol) dissolved in 0.5 mL of THF at 0° C. and stirred for 30 mins. The corresponding ester (0.102 mmol, 0.65 eqv.) in 0.5 mL of THF was added at 0° C. and stirred at room temperature for 40 mins. To the reaction mixture was then added 0.1 mL of concentrated sulfuric acid at 0° C. and stirred for 1 h at room temperature. The reaction was monitored by LCMS and when complete conversion to the product was observed, the reaction mixture was concentrated, water added (2 mL) and extracted with ethyl acetate. The ethyl acetate layer was dried over anhydrous sodium sulphate and concentrated to give the crude isoxazole derivative.

To the crude isoxazole derivative was added 0.5 mL of dichloromethane followed by 3 mL of boron tribromide in dichloromethane at 0° C. and stirred for 5 h at room temperature. The reaction mixture was quenched with methanol (2 mL) and concentrated. The residue was purified by Prep HPLC (XBridge, 19×100, 5 u, 20 min. gradient; Solvent A: 10 mM NH$_4$OAc, Solvent B: MeOH) to afford products shown in Table 1. The following esters were employed in the synthesis of final products employing this protocol.

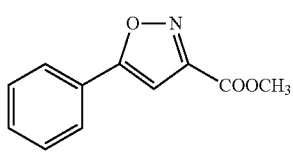

-continued

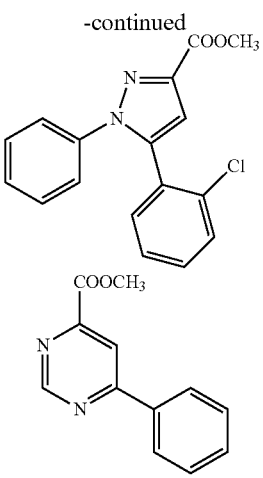

Representative ¹H NMR for compound 32 (Table 1): (400 MHz, CDCl₃) δ ppm 7.80-7.98 (m, 3H) 7.43-7.61 (m, 3H) 7.00 (s, 1H) 6.77-6.89 (m, 2H) 3.08-3.22 (m, 2H) 2.93-3.08 (m, 2H).

Examples 35 to 41

General Reaction Sequence

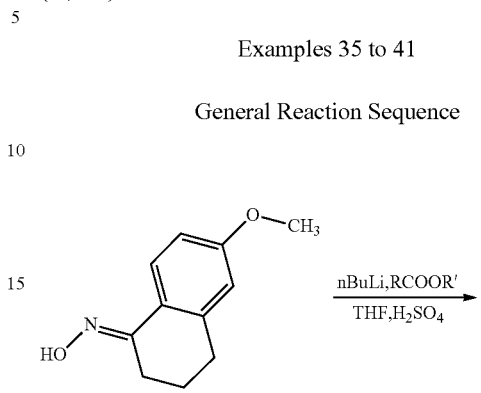

TABLE 1

| Ex. No. | R | | MW | HPLC ret. time (min.)* | MS (M⁺¹) |
|---|---|---|---|---|---|
| 32 | | 3-(5-Phenylisoxazol-3-yl)-4,5-dihydronaphtho[1,2-c]isoxazol-7-ol | 330 | 2.62 | 331 |
| 33 | | 3-(5-(2-Chlorophenyl)-1-phenyl-1H-pyrazol-3-yl)-4,5-dihydronaphtho[1,2-c]isoxazol-7-ol | 439 | 2.91 | 440 |
| 34 | | 3-(6-Phenylpyrimidin-4-yl)-4,5-dihydronaphtho[1,2-c]isoxazol-7-ol | 341 | 2.58 | 342 |

*Ascentis Express C18 4.6 × 50 mm 2.7 μM (4 min. Gradient) Solvent A: 5% acetonitrile, 95% water, 10 mM NH₄OAc; Solvent B: 95% acetonitrile, 5% water, 10 mM NH₄OAc.

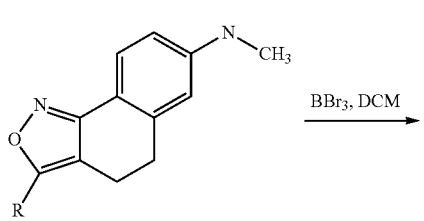

BBr₃, DCM →

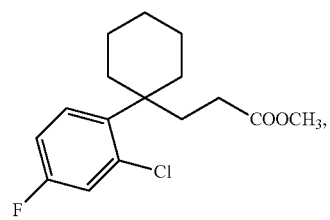

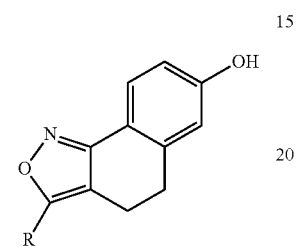

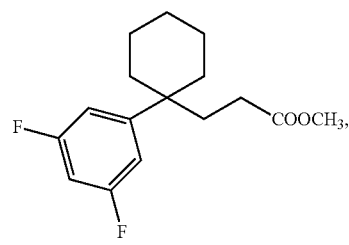

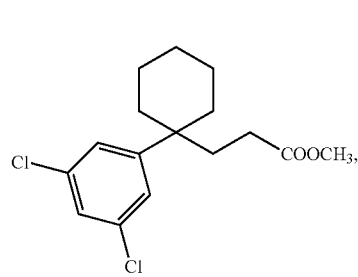

To 6-methoxy-3,4-dihydronaphthalen-1(2H)-one oxime (intermediate 2) (30 mg, 0.157 mmol) in 0.5 mL THF was added a solution of butyllithium (2.6 M in hexanes, 0.12 mL, 0.314 mmol) at 0° C. The reaction mixture was stirred for 15 min. at 0° C., warmed to room temperature and stirred at room temperature for 30 mins. The corresponding ester (0.102 mmol) in 0.5 mL of THF was added at room temperature and stirred for 40 mins. The reaction mixture was cooled to 0° C. and conc. sulfuric acid (0.1 mL) was added. The reaction mixture was stirred for 1 h at room temperature, concentrated under reduced pressure, and partitioned between water (2 mL) and ethyl acetate. The ethyl acetate layer was dried over anhydrous sodium sulphate and concentrated to afford the isoxazole.

To the crude product was added 0.5 mL of dichloromethane and 3 mL of boron tribromide in dichloromethane at 0° C. The reaction mixture was stirred at 0° C. for 5 hrs. The reaction mixture was quenched with methanol (2 mL), concentrated and purified by Prep HPLC (XBridge, 19×100, 5 u, 20 min. gradient; Solvent A: 10 mM NH₄OAc, Solvent B: MeOH) to afford products shown in Table 2. The following esters were employed in the synthesis of final products employing this protocol.

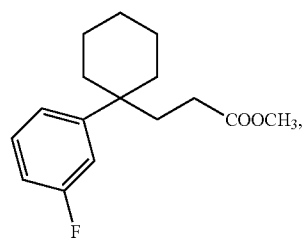

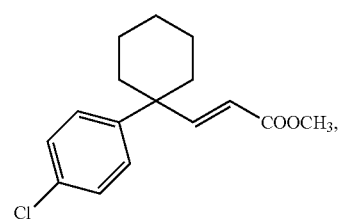

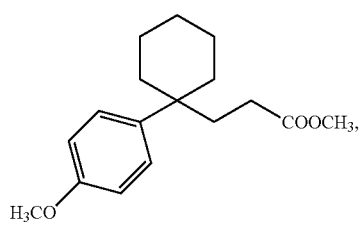

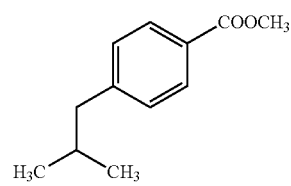

TABLE 2

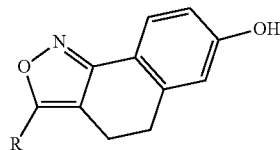

| Ex. No. | X | | MW | HPLC ret. time (min.)* | MS (M+1) |
|---|---|---|---|---|---|
| 35 | [4-hydroxyphenyl cyclohexyl ethyl group] | 3-(2-(1-(4-Hydroxyphenyl) cyclohexyl)ethyl)-4,5-dihydronaphtho[1,2-c]isoxazol-7-ol | 389 | 2.64 | 390 |
| 36 | [2-chloro-4-fluorophenyl cyclohexyl ethyl group] | 3-(2-(1-(2-Chloro-4-fluorophenyl)cyclohexyl)ethyl)-4,5-dihydronaphtho[1,2-c]isoxazol-7-ol | 425 | 3.4 | 426 |
| 37 | [3,5-difluorophenyl cyclohexyl ethyl group] | 3-(2-(1-(3,5-Difluorophenyl) cyclohexyl)ethyl)-4,5-dihydronaphtho[1,2-c]isoxazol-7-ol | 409 | 3.22 | 410 |
| 38 | [3,5-dichlorophenyl cyclohexyl ethyl group] | 3-(2-(1-(3,5-Dichlorophenyl) cyclohexyl)ethyl)-4,5-dihydronaphtho[1,2-c]isoxazol-7-ol | 442 | 3.56 | 442 |
| 39 | [3-fluorophenyl cyclopentyl ethyl group] | 3-(2-(1-(3-Fluorophenyl) cyclopentyl)ethyl)-4,5-dihydronaphtho[1,2-c]isoxazol-7-ol | 377 | 3.05 | 378 |

TABLE 2-continued

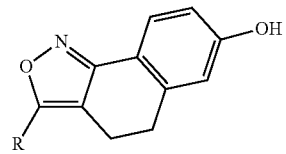

| Ex. No. | X | | MW | HPLC ret. time (min.)* | MS (M+1) |
|---|---|---|---|---|---|
| 40 | (structure: 4-chlorophenyl cyclohexyl vinyl) | (E)-3-(2-(1-(4-Chlorophenyl)cyclohexyl)vinyl)-4,5-dihydronaphtho[1,2-c]isoxazol-7-ol | 405 | 3.4 | 406 |
| 41 | (structure: 4-isobutylphenyl methyl) | 3-(4-Isobutylphenyl)-4,5-dihydronaphtho[1,2-c]isoxazol-7-ol | 319 | 3.09 | 320 |

*Ascentis Express C18 4.6 × 50 mm 2.7 μM (4 min. Gradient) Solvent A: 5% acetonitrile, 95% water, 10 mM NH₄OAc; Solvent B: 95% acetonitrile, 5% water, 10 mM NH₄OAc.

Example 42

1-((2-(2-(1-(4-Fluorophenyl)cyclohexyl)ethyl)naphtho[1,2-d]oxazol-7-yl)methyl)azetidine-3-carboxylic acid

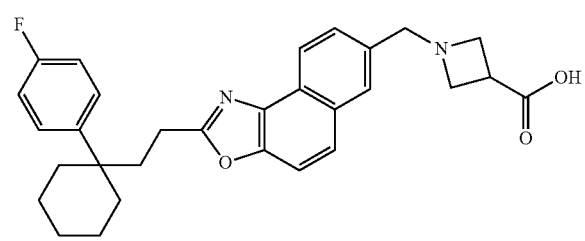

(42)

Preparation 42A:
3-(1-(4-Fluorophenyl)cyclohexyl)propanoic acid

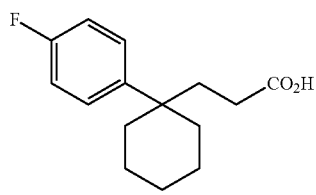

(42A)

To a solution of ethyl 3-(1-(4-fluorophenyl)cyclohexyl)propanoate (Intermediate 7, 1.347 g, 4.84 mmol) in methanol (20 mL) was added 1N sodium hydroxide (9.68 mL, 9.68 mmol), and the mixture was stirred at 60° C. for 7 hrs. After cooling, methanol was evaporated off and the residue was acidified with 12 mL of 1N HCl. The product was extracted with ethyl acetate (2×) and the combined extracts were washed with brine, dried over sodium sulfate and evaporated to give the desired 3-(1-(4-fluorophenyl)cyclohexyl)propanoic acid (1.183 g, 4.73 mmol, 98% yield) as a white solid. $^1$H NMR (400 MHz, CDCl$_3$) δ ppm 7.26 (2H, dd, J=8.80, 5.28 Hz), 7.01 (2H, t, J=8.69 Hz), 2.01-2.10 (2H, m), 1.95-2.01 (2H, m), 1.82-1.88 (2H, m), 1.31-1.62 (8H, m).

Preparation 42B:
3-(1-(4-Fluorophenyl)cyclohexyl)propanoyl chloride

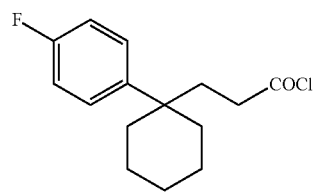

(42B)

To a solution of 3-(1-(4-fluorophenyl)cyclohexyl)propanoic acid (Preparation 42A, 209 mg, 0.835 mmol) in dichloromethane (3 mL) at 0° C. was added oxalyl chloride (0.146 mL, 1.670 mmol) followed by a couple of drops of N,N-dimethylformamide, and the mixture was stirred at the same temperature for 20 mins and warmed up to room temperature. The volatiles were evaporated off and the residue was used for next reaction without further purification.

Preparation 42C: 2-(2-(1-(4-Fluorophenyl)cyclohexyl)ethyl)-7-vinyl-4,5-dihydronaphtho[1,2-d]oxazole

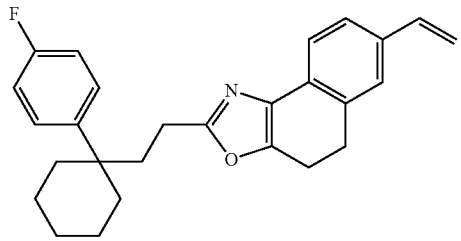

(42C)

To a solution of 3-(1-(4-fluorophenyl)cyclohexyl)propanoyl chloride (Preparation 42B, 215 mg, 0.799 mmol) and 6-vinyl-3,4-dihydronaphthalen-1(2H)-one oxime (Intermediate 1, 224 mg, 1.199 mmol) in 1,2-dichlorobenzene (2 mL) was added 4-(dimethylamino)pyridine (6.15 mg, 0.050 mmol), and the mixture was microwaved at 180° C. for 10 mins. The mixture of was purified by Combiflash (silica gel, 24 g) eluting with 5:95 followed by 2:8 ethyl acetate-hexane to give the desired 2-(2-(1-(4-fluorophenyl)cyclohexyl)ethyl)-7-vinyl-4,5-dihydronaphtho[1,2-d]oxazole (47 mg, 14.6% yield) as an oil. LC/MS $M^{+1}$=402.26.

Preparation 42D: 1-(2-(2-(1-(4-Fluorophenyl)cyclohexyl)ethyl)naphtho[1,2-d]oxazol-7-yl)ethane-1,2-diol

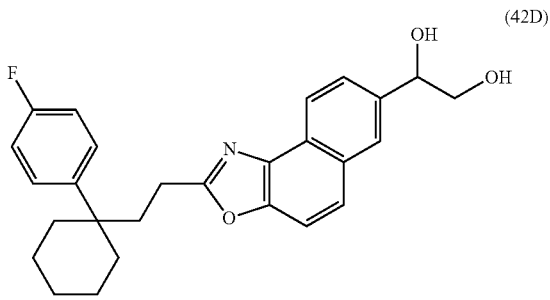 [SMILES: OCC(O)c1ccc2c(ccc3oc(CCC4(c5ccc(F)cc5)CCCCC4)nc32)c1]

(42D)

To a solution of 2-(2-(1-(4-fluorophenyl)cyclohexyl)ethyl)-7-vinyl-4,5-dihydronaphtho[1,2-d]oxazole (Preparation 42C, 47 mg, 0.117 mmol) and N-methylmorpholine-N-oxide (20.57 mg, 0.176 mmol) in THF (1 mL) and water (1.000 mL) was added 4% osmium tetroxide (0.018 mL, 2.341 μmol) in water and the mixture was stirred at room temperature for 18 hrs. Next, an aq. solution of sodium bisulfate was added and the mixture was stirred at room temperature for 30 mins. The mixture was extracted with ethyl acetate (2x), and the combined extracts were washed with brine and dried over sodium sulfate. Solvent was evaporated off to give the desired 1-(2-(2-(1-(4-fluorophenyl)cyclohexyl)ethyl)naphtho[1,2-d]oxazol-7-yl)ethane-1,2-diol as an oil. LC/MS $M^{+1}$=434.24.

Preparation 42E: 2-(2-(1-(4-Fluorophenyl)cyclohexyl)ethyl)naphtho[1,2-d]oxazole-7-carbaldehyde

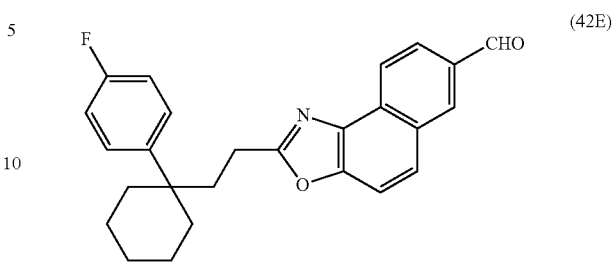

(42E)

To a solution of 1-(2-(2-(1-(4-fluorophenyl)cyclohexyl)ethyl)naphtho[1,2-d]oxazol-7-yl)ethane-1,2-diol (Preparation 42D, 0.051 g, 0.117 mmol) in methanol (1 mL) at 0° C. was added a solution of sodium periodate (0.038 g, 0.176 mmol) in water (1.000 mL) dropwise and the mixture was stirred for 30 mins at the same temp. Next, about 5 mL of ethyl acetate was added and the mixture was stirred for an addition 1 hr at 0-10° C. The mixture was extracted with EtOAc, washed with brine, dried over sodium sulfate, and evaporated to give the desired 2-(2-(1-(4-fluorophenyl)cyclohexyl)ethyl)naphtho[1,2-d]oxazole-7-carbaldehyde as an oil. $^1$H NMR (400 MHz, CDCl$_3$) δ ppm 10.17 (1H, s), 8.51 (1H, d, J=8.58 Hz), 8.44 (1H, s), 8.09 (1H, dd, J=8.58, 1.32 Hz), 7.89 (1H, d, J=9.02 Hz), 7.68 (1H, d, J=9.02 Hz), 7.35 (2H, dd, J=9.02, 5.28 Hz), 7.02 (2H, t, J=8.69 Hz), 2.66-2.72 (2H, m), 2.15-2.22 (2H, m), 1.17-1.92 (10H, m).

Example 42

To a solution of 2-(2-(1-(4-fluorophenyl)cyclohexyl)ethyl)naphtho[1,2-d]oxazole-7-carbaldehyde (Preparation 42E, 47.0 mg, 0.117 mmol) in dichloroethane (1 mL) and methanol (1 mL) was added azetidine-3-carboxylic acid (23.66 mg, 0.234 mmol) followed by 2 drops of acetic acid. Next, the reaction mixture was stirred in a 60° C. in an oil bath for 1 hr. After cooling to room temp sodium cyanoborohydride (14.71 mg, 0.234 mmol) was added, and the mixture was stirred at room temperature overnight. Next, the reaction mixture was placed on a Combiflash column (12 g silica gel) filled with 7:93 methanol-dichloromethane, and eluted with 2:8 followed by 3:7 and 1:1 MeOH—CH$_2$Cl$_2$ to give the 1-((2-(2-(1-(4-fluorophenyl)cyclohexyl)ethyl)naphtho[1,2-d]oxazol-7-yl)methyl)azetidine-3-carboxylic acid as a brown solid. LC/MS $M^{+1}$=487.31; $^1$H NMR (400 MHz, CDCl$_3$) δ ppm 8.31 (1H, d, J=8.36 Hz), 7.81 (1H, s), 7.58 (1H, d, J=9.02 Hz), 7.50 (1H, d, J=9.02 Hz), 7.46 (1H, d, J=9.02 Hz), 7.24-7.31 (2H, m), 6.98 (2H, t, J=8.69 Hz), 4.03 (2H, br. s.), 3.79-3.96 (4H, m), 3.31 (1H, br. s.), 2.51-2.60 (2H, m), 2.00-2.14 (4H, m), 1.29-1.65 (8H, m).

Example 43

(S)-3-(2-(3-Phenyl-4-(trifluoromethyl)isoxazol-5-yl)-4,5-dihydronaphtho[2,1-d]oxazol-7-yloxy)propane-1,2-diol

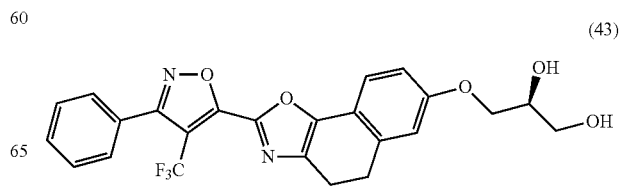

(43)

Preparation 43A: N-(6-Methoxy-1-oxo-1,2,3,4-tetrahydronaphthalen-2-yl)-3-phenyl-4-(trifluoromethyl)isoxazole-5-carboxamide

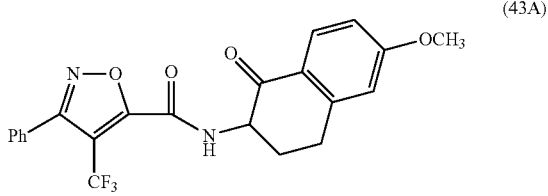 [SMILES: COc1ccc2c(c1)CCC(NC(=O)c1onc(-c3ccccc3)c1C(F)(F)F)C2=O]

(43A)

To a solution of 3-phenyl-4-(trifluoromethyl)isoxazole-5-carboxylic acid (Intermediate I-3D, 300 mg, 1.167 mmol) in dichloromethane (4 mL) at 0° C. was added oxalyl chloride (0.204 mL, 2.333 mmol) and a few drops of N,N-dimethylformamide, and the mixture was stirred at the same temperature for 20 min. Next, the reaction mixture was stirred for 5 min at room temperature, and the solvent and excess oxalyl chloride were evaporated off. The residue was dissolved in anhydrous dichloromethane and evaporated to give an oily residue which became solid upon drying under vacuum. The solid material was dissolved in 5 mL of dichloromethane and 2-amino-6-methoxy-3,4-dihydronaphthalen-1(2H)-one hydrochloride (223 mg, 1.167 mmol, J. Heterocyclic Chem., 29:1245 (1992)), diisopropylethylamine (0.61 mL, 3.50 mmol), and 4-(dimethylamino)pyridine (7.13 mg, 0.058 mmol) were added. The reaction mixture was stirred at room temperature for 2 hrs. The reaction mixture was extracted with ethyl acetate, washed with 1N HCl, saturated sodium bicarbonate and brine. The ethyl acetate layer was dried over sodium sulfate and evaporated to give a dark green solid residue. The product was crystallized from ethyl acetate and hexane to give 317 mg of the desired N-(6-methoxy-1-oxo-1,2,3,4-tetrahydronaphthalen-2-yl)-3-phenyl-4-(trifluoromethyl)isoxazole-5-carboxamide. The mother liquor was purified by Combiflash (40 g silica gel) eluting with 2:8 ethyl acetate-hexane to give additional 119 mg of the product (87% yield). $^1$H NMR (400 MHz, CDCl$_3$) δ ppm 8.05 (1H, d, J=8.80 Hz), 7.82 (1H, br. s.), 7.61 (2H, d, J=6.82 Hz), 7.47-7.58 (3H, m), 6.89 (1H, dd, J=8.80, 2.42 Hz), 6.75 (1H, d, J=2.20 Hz), 4.77 (1H, ddd, J=13.31, 4.84, 4.73 Hz), 3.90 (3H, s), 3.23-3.36 (1H, m), 3.02-3.10 (1H, m), 2.94-3.02 (1H, m), 1.96-2.10 (1H, m).

Preparation 43B: 7-Methoxy-2-(3-phenyl-4-(trifluoromethyl)isoxazol-5-yl)-4,5-dihydronaphtho[2,1-d]oxazole

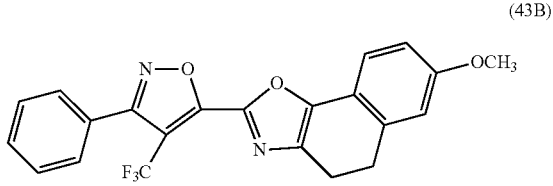 [SMILES: COc1ccc2c(c1)CCc1nc(-c3onc(-c4ccccc4)c3C(F)(F)F)oc1-2]

(43B)

A solution of N-(6-methoxy-1-oxo-1,2,3,4-tetrahydronaphthalen-2-yl)-3-phenyl-4-(trifluoromethyl)isoxazole-5-carboxamide (Preparation 43A, 135.6 mg, 0.315 mmol) and phosphorous oxychloride (1.468 mL, 15.75 mmol) in anhydrous dichloroethane (5 mL) was heated under an argon atmosphere at 85° C. for 13 hrs. The solvent and excess phosphorous oxychloride were evaporated off and the residue was purified by Combiflash (12 g silica gel) eluting with 2:8 ethyl acetate-hexane to give the desired 7-methoxy-2-(3-phenyl-4-(trifluoromethyl)isoxazol-5-yl)-4,5-dihydronaphtho[2,1-d]oxazole (126 mg, 97% yield) as an oil. $^1$H NMR (400 MHz, MeOD) δ ppm 7.62-7.66 (2H, m), 7.53-7.60 (3H, m), 7.48 (1H, d, J=8.14 Hz), 6.94 (1H, d, J=2.20 Hz), 6.89-6.93 (1H, m), 3.84 (3H, s), 3.18 (2H, t, J=8.03 Hz), 2.95-3.01 (2H, m).

Preparation 43C: 2-(3-Phenyl-4-(trifluoromethyl)isoxazol-5-yl)-4,5-dihydronaphtho[2,1-d]oxazol-7-ol

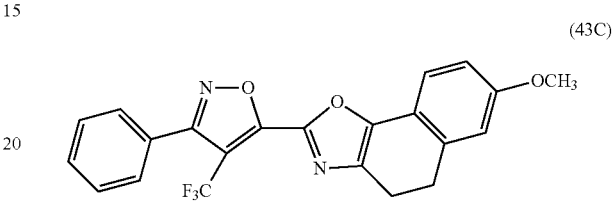

(43C)

To solution of 7-methoxy-2-(3-phenyl-4-(trifluoromethyl)isoxazol-5-yl)-4,5-dihydronaphtho[2,1-d]oxazole (Preparation 43B, 123 mg, 0.298 mmol) in dichloromethane (3 mL) was added 1 M boron tribromide (1.491 mL, 1.491 mmol) in dichloromethane dropwise, and the reaction mixture was stirred at room temperature overnight. The reaction mixture was quenched by the slow addition of saturated ammonium chloride, extracted with dichloromethane, washed with water and brine. The combined aq. layers were back extracted with dichloromethane. The combined organic layers were dried over magnesium sulfate and evaporated to give a yellow crystalline solid (quantitative yield). $^1$H NMR (400 MHz, CDCl$_3$ mixed with methanol-d$_4$) δ ppm 7.66 (2H, d, J=6.82 Hz), 7.49-7.59 (4H, m), 7.46 (1H, d, J=8.58 Hz), 6.76-6.83 (2H, m), 3.14 (2H, t, J=7.70 Hz), 3.03 (2H, t, J=7.59 Hz).

Example 43

Nitrogen was bubbled to a solution of 2-(3-phenyl-4-(trifluoromethyl)isoxazol-5-yl)-4,5-dihydronaphtho[2,1-d]oxazol-7-ol (Preparation 43C, 0.021 ml, 0.169 mmol) and (R)-(−)-2,2-dimethyl-1,3-dioxolane-4-methanol (0.021 ml, 0.169 mmol) in THF (2.5 ml) at room temperature for two min. To this mixture was added triphenylphosphine (0.044 g, 0.169 mmol) in one portion. Nitrogen was bubbled for two more minutes followed by the addition of diethyl azodicarboxylate (0.027 ml, 0.169 mmol) dropwise. The reaction vessel was immersed in a preheated oil bath held at 65° C., heated for 3 h., cooled, and concentrated under reduced pressure. The residue was extracted with ether and washed with water. The aqueous layer was re-extracted with ether and the combined organic layers were washed with brine, dried over magnesium sulfate, concentrated, and dried in vacuo. The residue was taken in 2 ml of acetic acid, cooled to 0° C. and treated with 1 ml 1N HCl. The reaction mixture was stirred at 0° C. for 30 min., concentrated under reduced pressure, and purified by silica gel column chromatography using hexane/ethyl acetate (0 to 30%) to yield (S)-3-(2-(3-phenyl-4-(trifluoromethyl)isoxazol-5-yl)-4,5-dihydronaphtho[2,1-d]oxazol-7-yloxy)propane-1,2-diol (4.3 mg, 8.92 μmol, 11.84% yield) as a clear oil. The compound had an HPLC retention time of 9.39 min (Condition: Column: Sunfire C18 3.5 um, 3.0×150 mm; (15 min); solvent A: 95/5 water/MeCN with 0.05% TFA; solvent B: 5/95 water/MeCN with 0.05% TFA; Start % B=10 to Final % B=100; Wavelength=220 nm). LC/MS M$^{+1}$=473.27. $^1$H NMR (400 MHz, DMSO-d$_6$) δ ppm 7.58-7.68 (5H, m), 7.45 (1H, d, J=8.36 Hz), 7.02 (1H, d, J=2.42 Hz), 6.94 (1H, dd, J=8.36, 2.42 Hz), 4.99 (1H, d, J=5.06 Hz), 4.70 (1H, t, J=5.61 Hz), 4.02-4.09 (1H, m), 3.88-3.95 (1H, m), 3.74-3.84 (1H, m), 3.42-3.50 (2H, m), 3.14 (2H, t, J=7.92 Hz), 2.90-3.00 (2H, m).

Example 44

1-((3-(3-Phenyl-4-(trifluoromethyl)isoxazol-5-yl)-4,5-dihydronaphtho[2,1-d]isoxazol-7-yl)methyl)azetidine-3-carboxylic acid, TFA salt

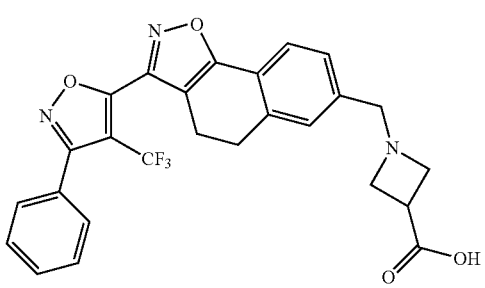
(44)

The compound was prepared according to the general procedures described in Example 20 by substituting N-hydroxy-4-propylbenzimidoyl chloride in step B with N-hydroxy-3-phenyl-4-(trifluoromethyl)isoxazole-5-carbimidoyl chloride (Intermediate 12). The compound had an HPLC retention time=3.15 min (condition C); LC/MS M+1=496.6.

Example 45

1-((3-(2,2-Diphenylethylcarbamoyl)-4,5-dihydronaphtho[2,1-d]isoxazol-7-yl)methyl)azetidine-3-carboxylic acid, TFA salt

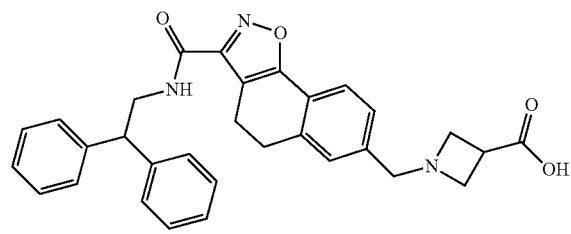
(45)

Preparation 45A: Methyl 2-oxo-2-(1-oxo-6-vinyl-1,2,3,4-tetrahydronaphthalen-2-yl)acetate

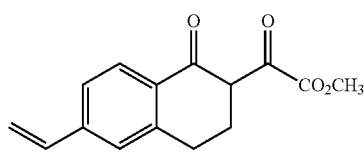
(45A)

To a 250 mL round bottom flask charged with a solution of 6-vinyl-3,4-dihydronaphthalen-1(2H)-one (intermediate 1, 400 mg, 2.323 mmol) and diethyl oxalate (0.630 mL, 4.65 mmol) in methanol (20 mL) was added sodium methoxide (25% wt in MeOH) (2008 mg, 9.29 mmol) via syringe. After the addition was complete, the dark reaction mixture was heated at reflux for 10 h. The reaction was quenched with 50% HCl aq. solution and then evaporated to remove the methanol. The aqueous residue was diluted with water (80 mL) and extracted with dichloromethane (2×100 ml). The organic layers were combined, concentrated, and purified by silica gel chromatography, (40 g Isco column, 0% to 25% ethyl acetate in hexane gradient) to yield the title compound. The compound had an HPLC ret. time=1.05/2.0 min. (condition E); MS:(M+H)=259.1.

Preparation 45B: Methyl 7-vinyl-4,5-dihydronaphtho[2,1-d]isoxazole-3-carboxylate

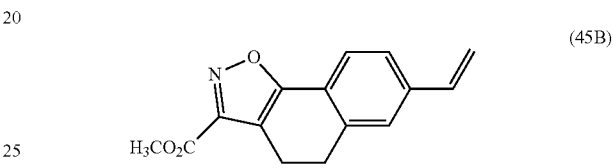
(45B)

A mixture of methyl 2-oxo-2-(1-oxo-6-vinyl-1,2,3,4-tetrahydronaphthalen-2-yl)acetate (Preparation 45A, 180 mg, 0.697 mmol) and hydroxylamine hydrochloride (145 mg, 2.091 mmol) in methanol (3 mL) was stirred at reflux for 60 min. The reaction mixture was allowed to stir at room temperature overnight. The product crystallized from solution upon stirring at room temperature. The solid was collected by vacuum filtration and dried to give methyl 7-vinyl-4,5-dihydronaphtho[2,1-d]isoxazole-3-carboxylate (65 mg, 0.244 mmol, 35.1% yield over two steps) as yellow solid. The compound had an HPLC ret. time=1.05/2.0 min. (condition E); MS:(M+H)=256.2.

Preparation 45C: Methyl 7-formyl-4,5-dihydronaphtho[2,1-d]isoxazole-3-carboxylate

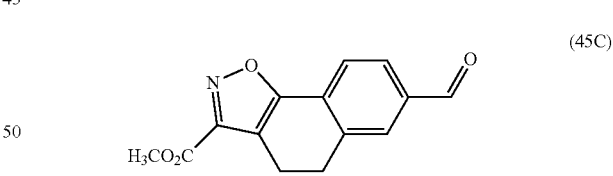
(45C)

To a clear solution of methyl 7-vinyl-4,5-dihydronaphtho[2,1-d]isoxazole-3-carboxylate (Preparation 45B, 65 mg, 0.255 mmol) in THF (4 mL) were sequentially added N-methylmorpholine-N-oxide in water (0.084 mL, 0.407 mmol) and osmium tetroxide in water (0.062 mL, 10.19 µmol) at room temperature. The solution was stirred vigorously at room temperature overnight. Sodium periodate (109 mg, 0.509 mmol) in water (1 mL) was added and the mixture was stirred at room temperature under nitrogen for two hours. Water (2 mL) was then added and the mixture was concentrated to remove THF. The resulting solid was filtered, washed with water (2×2 mL), and dried to give 72 mg of product as a yellow solid. The compound had an HPLC ret. time=0.88/2.0 min. (condition E).

Preparation 45D: Methyl 7-((3-(tert-butoxycarbonyl)azetidin-1-yl)methyl)-4,5-dihydronaphtho[2,1-d]isoxazole-3-carboxylate

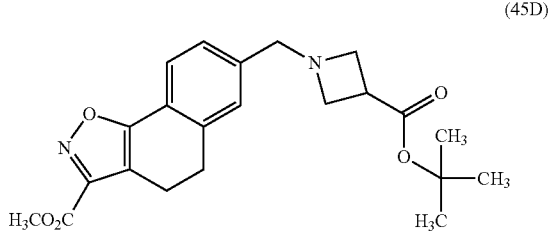 [SMILES: COC(=O)c1noc2c1CCc1cc(CN3CC(C(=O)OC(C)(C)C)C3)ccc1-2]

(45D)

To a solution of methyl 7-formyl-4,5-dihydronaphtho[2,1-d]isoxazole-3-carboxylate (Preparation 45C, 72 mg, 0.280 mmol) in methanol (5 mL) and 1,2-dichloroethane (1 mL) was added acetic acid (0.1 mL) and tert-butyl azetidine-3-carboxylate acetic acid salt (73.0 mg, 0.336 mmol). The contents were allowed to stir at room temperature for 40 min. and then sodium triacetoxyborohydride (178 mg, 0.840 mmol) was added. The reaction mixture was allowed to stir at room temperature overnight. Additional sodium triacetoxyborohydride (2 eq) was added and the reaction mixture was allowed to stir at room temperature for 2 hours. Additional sodium triacetoxyborohydride (4 eq) was added and the reaction mixture was allowed to stir at room temperature for 3 days. Additional amine (0.5 eq.), followed by additional triacetoxyborohydride (3 eq.) was added and the reaction mixtures was stirred at room temperature for 6 more hours to drive the reaction to about 90% conversion. The solvents were evaporated and the residue was re-dissolved into 80 ml ethyl acetate, washed twice with sat. sodium bicarbonate, dried over sodium sulfate, and concentrated to give 95 mg of product. The compound had an HPLC ret. time=0.75/2.0 min. (condition E); MS:(M+H)=399.3.

Preparation 45E: 7-((3-(tert-Butoxycarbonyl)azetidin-1-yl)methyl)-4,5-dihydronaphtho[2,1-d]isoxazole-3-carboxylic acid

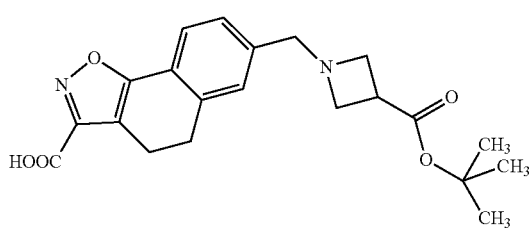

(45E)

A mixture of methyl 7-((3-(tert-butoxycarbonyl)azetidin-1-yl)methyl)-4,5-dihydronaphtho[2,1-d]isoxazole-3-carboxylate (Preparation 45D, 95 mg, 0.238 mmol) and lithium hydroxide monohydrate (12.01 mg, 0.286 mmol) in THF (3 mL) and water (1.500 mL) was allowed to stir at room temperature overnight. The THF was evaporated and the residue diluted with 5 ml of water. The pH was adjusted to 5-6 and extracted with ethyl acetate six times. The organic layers were combined, dried over sodium sulfate and concentrated to afford 110 mg of product (HPLC purity 75-80%). The compound had an HPLC ret. time=0.67/2.0 min. (condition E); MS:(M+H)=385.3.

Example 45

A solution of 7-((3-(tert-butoxycarbonyl)azetidin-1-yl)methyl)-4,5-dihydronaphtho[2,1-d]isoxazole-3-carboxylic acid (Preparation 45E, 30 mg, 0.078 mmol), EDC (22.44 mg, 0.117 mmol) and HOBT (17.93 mg, 0.117 mmol) in dichloromethane (2 mL) and N,N-dimethylformamide (1.000 mL) was stirred at room temperature for 30 min. 2,2-diphenylethanamine (30.8 mg, 0.156 mmol) was added and the mixtures were allowed to stir at room temperature overnight. The solvent was evaporated and the residue re-dissolved into 1 ml dichloromethane. TFA (1 mL) was added and the contents were stirred at room temperature overnight. The mixture was purified on preparative reverse phase HPLC (YMC S5 ODS 30×75 mm; 9 min. gradient; solvent A=10% MeOH, 90% $H_2O$, 0.1% TFA, solvent B=90% MeOH, 10% $H_2O$, 0.1% TFA) and the product containing fractions were concentrated to afford the product as a white solid (1.0 TFA salt, 7.8 mg, 0.0126 mmol). The compound had an HPLC ret. time=0.85/2.0 min. (condition E); MS:(M+H)=508.3; $^1$H NMR (400 MHz, MeOD) ppm 7.72 (1H, d, J=7.70 Hz), 7.40-7.48 (2H, m), 7.26-7.37 (8H, m), 7.16-7.24 (2H, m), 4.39-4.47 (3H, m), 4.30-4.38 (4H, m), 4.02 (2H, dd, J=8.14, 5.94 Hz), 3.64-3.75 (1H, m), 3.06 (2H, d, J=7.92 Hz), 2.86-2.96 (2H, m).

The Examples in Table 3 below were prepared according to the general procedure described above, substituting the appropriate amine.

TABLE 3

| Ex. No. | R | MW | HPLC ret. time (min.)* | MS (M$^{+1}$) |
|---|---|---|---|---|
| 46 | 1-((3-(2-Chlorobenzyl-carbamoyl)-4,5-dihydronaphtho[2,1-d]isoxazol-7-yl)methyl)azetidine-3-carboxylic acid | 451.91 | 0.76 | 452.2 |
| 47 | 1-((3-(Neopentyl-carbamoyl)-4,5-dihydronapltho[2,1-d]isoxazol-7-yl)methyl)azetidine-3-carboxylic acid | 397.47 | 0.74 | 398.3 |

Example 48

1-((2-(3-Phenyl-4-(trifluoromethyl)isoxazol-5-yl)-4,5-dihydronaphtho[2,1-d]oxazol-7-yl)methyl)azetidine-3-carboxylic acid (48)

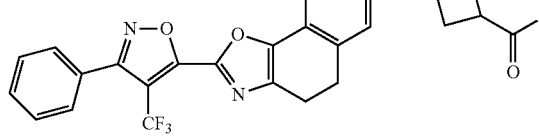

Preparation 48A: 2-(3-Phenyl-4-(trifluoromethyl)isoxazol-5-yl)-4,5-dihydronaphtho[2,1-d]oxazol-7-yl trifluoromethanesulfonate (48A)

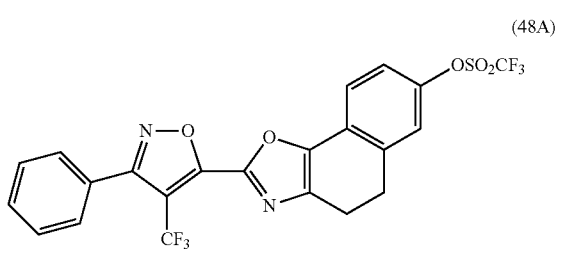

To a solution of 2-(3-phenyl-4-(trifluoromethyl)isoxazol-5-yl)-4,5-dihydronaphtho[2,1-d]oxazol-7-ol (Step C of Example 43, 119 mg, 0.299 mmol) in pyridine (1 mL) at 0° C. was added triflicanhydride (0.061 mL, 0.358 mmol) dropwise over a period of 3 mins. The mixture was stirred at 0° C. for 30 mins and at room temperature for 2 hrs. Most of the pyridine was removed by evaporation under reduced pressure, and the residue was partitioned between ethyl acetate and water. The ethyl acetate layer was washed with water, 1N hydrochloric acid, saturated sodium bicarbonate, and brine. The water washings and 1N hydrochloric acid washing were combined and back extracted with ethyl acetate. The extract was washed with saturated sodium bicarbonate and brine. The combined ethyl acetate extracts were dried over sodium sulfate and evaporated to give a solid residue which was purified by Combiflash (12 g silica gel) eluting with 5:95 followed by 2:8 EtOAc-hexane to provide 2-(3-phenyl-4-(trifluoromethyl)isoxazol-5-yl)-4,5-dihydronaphtho[2,1-d]oxazol-7-yl trifluoromethanesulfonate (142 mg, 0.268 mmol, 90% yield) as a solid. $^1$H NMR (400 MHz, CDCl$_3$) δ ppm 7.65-7.69 (2H, m), 7.63 (1H, d, J=8.36 Hz), 7.50-7.60 (3H, m), 7.20-7.27 (2H, m), 3.25 (2H, t), 3.07-3.14 (2H, m).

Preparation 48 B: 2-(3-Phenyl-4-(trifluoromethyl)isoxazol-5-yl)-7-vinyl-4,5-dihydronaphtho[2,1-d]oxazole (48B)

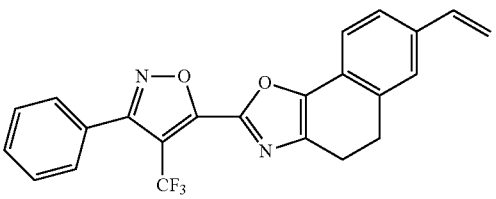

To a solution of 2-(3-phenyl-4-(trifluoromethyl)isoxazol-5-yl)-4,5-dihydronaphtho[2,1-d]oxazol-7-yl trifluoromethanesulfonate (Preparation 48A, 140 mg, 0.264 mmol) in dioxane (1 mL) in a 150 mL sealed tube were sequentially added tributyl(vinyl)tin (0.085 mL, 0.290 mmol), lithium chloride (33.6 mg, 0.792 mmol), and tetrakis(triphenylphosphine)palladium(0) (30.5 mg, 0.026 mmol). The solution was purged with argon for 5 mins. It was stirred for 20 hrs in a 100° C. oil bath. After cooling, the solution was diluted with ~20 mL of ether and filtered thru CELITE® and evaporated to give an oily residue. The residue was purified by Combiflash (24 g silica gel) eluting with 1:9 followed by 2:8 EtOAc-hexane to give 2-(3-phenyl-4-(trifluoromethyl)isoxazol-5-yl)-7-vinyl-4,5-dihydronaphtho[2,1-d]oxazole (49.4 mg, 46% yield). LC/MS M$^{+1}$=409.25.

Preparation 48C: 2-(3-Phenyl-4-(trifluoromethyl)isoxazol-5-yl)-4,5-dihydronaphtho[2,1-d]oxazole-7-carbaldehyde (48C)

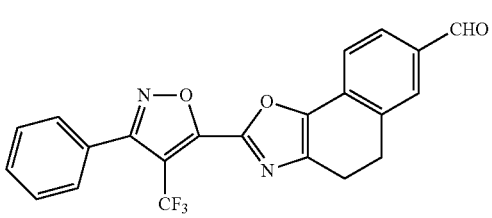

To a stirred solution of 2-(3-phenyl-4-(trifluoromethyl)isoxazol-5-yl)-7-vinyl-4,5-dihydronaphtho[2,1-d]oxazole (Preparation 48B, 26.2 mg, 0.064 mmol) in 0.5 mL of THF were added 0.113 mL of 10% N-methyl-morpholine-1-oxide in water and 0.04 mL of 4% OsO$_4$ in water, and 0.2 mL of water. The heterogeneous mixture was stirred at room temperature for 18 hrs. To the homogenous reaction mixture was added 0.14 mL of 10% sodium periodate in water, and the mixture was stirred for 3 hrs. The reaction mixture was extracted with EtOAc, washed with water, brine dried over Na$_2$SO$_4$ and evaporated to give a solid residue which was purified by Combiflash (24 g silica gel) eluting with 1:9 followed by 3:7 EtOAc-hexane to give 2-(3-phenyl-4-(trifluoromethyl)isoxazol-5-yl)-4,5-dihydronaphtho[2,1-d]oxazole-7-carbaldehyde (20.2 mg, 77% yield). $^1$H NMR (400 MHz, CDCl$_3$) δ ppm 9.69 (1H, s), 7.51-7.61 (2H, m), 7.44 (1H, d, J=7.70 Hz), 7.36 (2H, d, J=7.70 Hz), 7.22-7.30 (3H, m), 2.99-3.05 (2H, m), 2.83 (2H, t, J=8.03 Hz).

Example 48

To a stirring solution of the 2-(3-phenyl-4-(trifluoromethyl)isoxazol-5-yl)-4,5-dihydronaphtho[2,1-d]oxazole-7-carbaldehyde (Preparation 48C, 20.2 mg, 0.049 mmol) and azetidine-3-carboxylic acid (5.97 mg, 0.059 mmol) in methanol (1.5 mL) and dichloroethane (1.5 mL) was added at room temperature about 5 drops of acetic acid. The reaction mixture was immersed in an oil bath and heated at 80° C. for 1 h. It was cooled to room temperature and then treated with sodium cyanoborohydride (3.71 mg, 0.059 mmol) in one portion. The reaction mixture was concentrated under reduced pressure and the residue purified by preparative HPLC using the following conditions: Column: PHENOMENEX® Luna C18 5 micron column (250×30 mm); 25-100% CH$_3$CN/water (0.1% TFA); 25 minute gradient; 30 mL/min. $^1$H NMR (400 MHz, methanol-d) δ ppm 7.66-7.71 (3H, m), 7.59-7.66 (3H, m), 7.47-7.51 (2H, m), 4.44 (2H, s), 4.34 (2H, d, J=2.42 Hz), 4.32 (2H, s), 3.63 (1H, quin, J=8.36 Hz), 3.31 (2H, t, J=8.14 Hz), 3.07-3.12 (2H, m).

Example 49

1-((2-(5-Phenyl-4-(trifluoromethyl)isoxazol-3-yl)-4,5-dihydronaphtho[2,1-d]oxazol-7-yl)methyl)azetidine-3-carboxylic acid

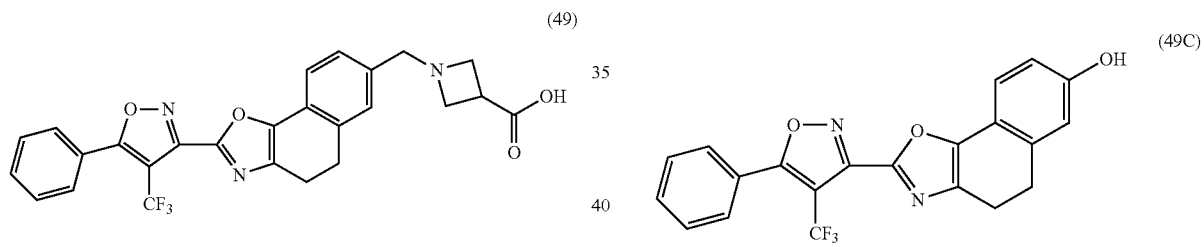

(49)

Preparation 49A: N-(6-Methoxy-1-oxo-1,2,3,4-tetrahydronaphthalen-2-yl)-5-phenyl-4-(trifluoromethyl)isoxazole-3-carboxamide

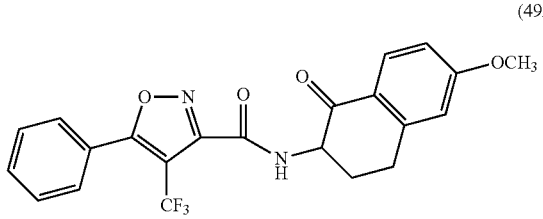

(49A)

The titled compound was prepared using the experimental protocol described for Preparation 43A employing 5-phenyl-4-(trifluoromethyl)isoxazole-3-carboxylic acid (Step D of Intermediate 5). $^1$H NMR (400 MHz, CDCl$_3$) δ ppm 8.04 (1H, d, J=8.80 Hz), 7.85 (1H, d, J=5.28 Hz), 7.70 (2H, d, J=7.48 Hz), 7.52-7.62 (3H, m), 6.88 (1H, dd, J=8.80, 2.42 Hz), 6.74 (1H, d, J=2.20 Hz), 4.78 (1H, ddd, J=13.53, 4.95, 4.84 Hz), 3.89 (3H, s), 3.29 (1H, ddd, J=17.11, 12.93, 4.29 Hz), 2.93-3.08 (2H, m), 1.97-2.10 (1H, m).

Preparation 49B: 7-Methoxy-2-(5-phenyl-4-(trifluoromethyl)isoxazol-3-yl)-4,5-dihydronaphtho[2,1-d]oxazole

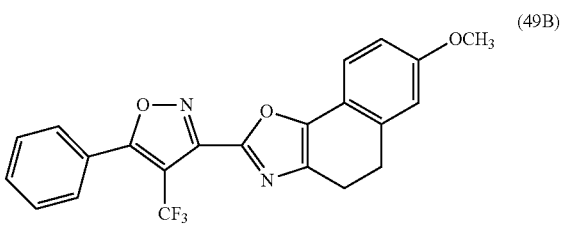 [SMILES: COc1ccc2c(c1)CCc1nc(-c3noc(-c4ccccc4)c3C(F)(F)F)oc1-2]

(49B)

The titled compound was prepared using the experimental protocol described for Preparation 43B employing N-(6-methoxy-1-oxo-1,2,3,4-tetrahydronaphthalen-2-yl)-5-phenyl-4-(trifluoromethyl)isoxazole-3-carboxamide (Preparation 49A). $^1$H NMR (400 MHz, CDCl$_3$) δ ppm 7.73 (2H, d, J=7.26 Hz), 7.51-7.60 (3H, m), 7.48 (1H, d, J=9.02 Hz), 6.78-6.84 (2H, m), 3.82 (3H, s), 3.08-3.17 (2H, m), 2.95-3.03 (2H, m).

Preparation 49C: 2-(5-Phenyl-4-(trifluoromethyl)isoxazol-3-yl)-4,5-dihydronaphtho[2,1-d]oxazol-7-ol

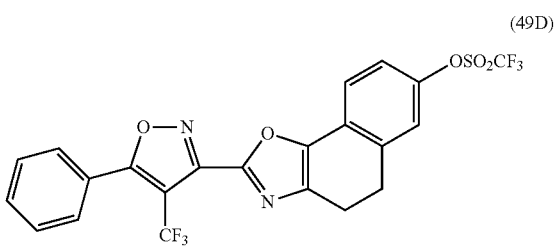

(49C)

The titled compound was made using the experimental protocol described for Preparation 43C employing 7-methoxy-2-(5-phenyl-4-(trifluoromethyl)isoxazol-3-yl)-4,5-dihydronaphtho[2,1-d]oxazole (Preparation 49B). LC/MS M$^{+1}$=399.03.

Preparation 49D: 2-(5-Phenyl-4-(trifluoromethyl)isoxazol-3-yl)-4,5-dihydronaphtho[2,1-d]oxazol-7-yl trifluoromethanesulfonate (49D)

The titled compound was made using the experimental protocol described for the compound in the Preparation 48A employing 2-(5-phenyl-4-(trifluoromethyl)isoxazol-3-yl)-4,5-dihydronaphtho[2,1-d]oxazol-7-ol (Preparation 49C). ¹H NMR (400 MHz, CDCl₃) δ ppm 7.75 (2H, d, J=7.48 Hz), 7.55-7.65 (4H, m), 7.19-7.24 (2H, m), 3.23 (2H, t, J=8.03 Hz), 3.08 (2H, t).

Preparation 49E: 2-(5-Phenyl-4-(trifluoromethyl)isoxazol-3-yl)-7-vinyl-4,5-dihydronaphtho[2,1-d]oxazole

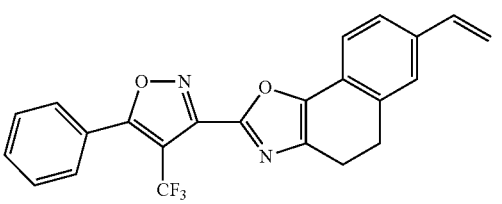

(49E)

The titled compound was made using the experimental protocol described for the compound in the Preparation 48B employing 2-(5-phenyl-4-(trifluoromethyl)isoxazol-3-yl)-4,5-dihydronaphtho[2,1-d]oxazol-7-yl trifluoromethanesulfonate (Preparation 49D). LC/MS M⁺¹=409.05.

Preparation 49F: 2-(5-Phenyl-4-(trifluoromethyl)isoxazol-3-yl)-4,5-dihydronaphtho[2,1-d]oxazole-7-carbaldehyde

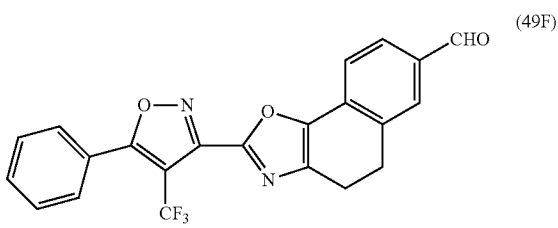 [SMILES: O=Cc1ccc2c(c1)CCc1nc(-c3noc(-c4ccccc4)c3C(F)(F)F)oc1-2]

(49F)

The titled compound was prepared using the experimental protocol described for Preparation 48C employing 2-(5-phenyl-4-(trifluoromethyl)isoxazol-3-yl)-7-vinyl-4,5-dihydronaphtho[2,1-d]oxazole (Preparation 48E). LC/MS M⁺¹=411.1.

Example 49

Example 49 was prepared using the experimental protocol described for Example 48 employing 2-(5-phenyl-4-(trifluoromethyl)isoxazol-3-yl)-4,5-dihydronaphtho[2,1-d]oxazole-7-carbaldehyde (Preparation 49F). The product was purified by preparative HPLC using the following conditions: Column: PHENOMENEX® Luna C18 5 micron column (250× 30 mm); 25-100% CH₃CN/water (0.1% TFA); 25 minute gradient; 30 mL/min. LC/MS M⁺¹=496.02; ¹H NMR (400 MHz, MeOD) δ ppm 7.80 (2H, d, J=7.26 Hz), 7.72 (1H, d, J=7.26 Hz), 7.63-7.70 (3H, m), 7.47 (2H, d, J=4.40 Hz), 4.44 (2H, s), 4.30-4.40 (4H, m), 3.61-3.72 (1H, m), 3.29 (2H, t, J=8.03 Hz), 3.07 (2H, t, J=8.03 Hz).

Example 50

2-Amino-2-methyl-4-(3-(1-phenyl-5-(trifluoromethyl)-1H-pyrazol-4-yl)-4,5-dihydronaphtho[1,2-c]isoxazol-7-yl)butan-1-ol

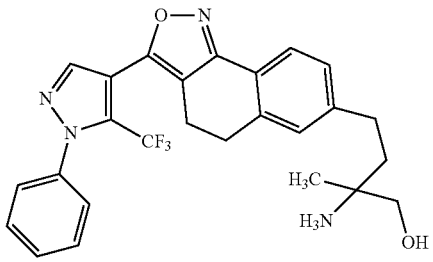

(50)

Preparation 50A: 3-(1-Phenyl-5-(trifluoromethyl)-1H-pyrazol-4-yl)-7-vinyl-4,5-dihydronaphtho[1,2-c]isoxazole

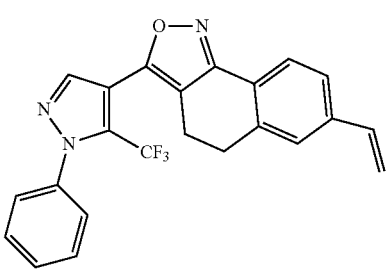

(50A)

Preparation of LDA: To stirred solution of diisopropylamine (1.103 mL, 7.74 mmol) in anhydrous THF (8 mL) was added n-butyllithium (3.10 mL, 7.74 mmol) (2.5 M in hexanes) dropwise at 0° C. under nitrogen. The pale yellow solution was stirred at the same temperature for 20 min before a solution of 6-vinyl-3,4-dihydronaphthalen-1(2H)-one oxime (intermediate 1, 0.659 g, 3.52 mmol) in anhydrous THF (4 mL) was added dropwise at 0° C. under nitrogen. The mixture was stirred at 0° C. for 1 hour and then transferred to a dry-ice bath. A solution of ethyl 1-phenyl-5-(trifluoromethyl)-1H-pyrazole-4-carboxylate (1 g, 3.52 mmol) in anhydrous THF (3 mL) was added dropwise over 4 min. The solution was stirred with dry-ice cooling for 40 min and at 0° C. for 45 min. The reaction mixture was quenched with saturated aqueous ammonium chloride solution (5 mL) and water (3 mL) extracted with ethyl acetate (2×20 mL), washed with brine (10 mL), dried over sodium sulfate, and concentrated to yield a yellow foamy solid. The solid was mixed with anhydrous toluene (20 mL), thionyl chloride (0.514 mL, 7.04 mmol), and pyridine (0.057 mL, 0.704 mmol) was added at room temperature under nitrogen. The reaction mixture was stirred at room temperature for 5 min and at 100° C. for 25 min., concentrated and quenched with saturated aqueous sodium bicarbonate solution (20 mL) and water (10 mL). The reaction mixture was extracted with dichloromethane (20 mL, then 2×10 mL), dried over sodium sulfate, concentrated and chromatographed (40 g silica gel column, 20→100% dichloromethane in n-heptane and then 20%→50% ethyl acetate in n-heptane) to yield 3-(1-phenyl-5-(trifluoromethyl)-1H-pyrazol-4-yl)-7-vinyl-4,5-dihydronaphtho[1,2-c]

isoxazole (560 mg, 1.375 mmol, 39.1% yield) as a green solid. The compound had an HPLC retention time=3.98 min (condition C); LC/MS $M^{+1}$=407.8.

Preparation 50B: Ethyl 2-(diphenylmethylene-amino)-4-(3-(1-phenyl-5-(trifluoromethyl)-1H-pyrazol-4-yl)-4,5-dihydronaphtho[1,2-c]isoxazol-7-yl)butanoate

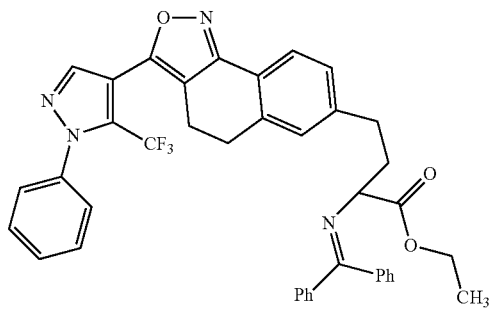

(50B)

A solution of ethyl 2-(diphenylmethyleneamino)acetate (315 mg, 1.178 mmol) in anhydrous dimethylsulfoxide (1 mL) was purged with nitrogen for 10 min before cesium carbonate (192 mg, 0.589 mmol) was added. The mixture was purged with nitrogen for 5 min. and stirred at room temperature for 30 min. Next, 3-(1-phenyl-5-(trifluoromethyl)-1H-pyrazol-4-yl)-7-vinyl-4,5-dihydronaphtho[1,2-c]isoxazole (Preparation 50A, 100 mg, 0.245 mmol) was added, the mixture was purged with nitrogen for 5 min and then stirred at 40° C. for 5 hr. The reaction mixture was cooled, diluted with water (10 mL), and extracted with ethyl acetate (3×5 mL). The ethyl acetate extracts were dried over sodium sulfate and concentrated under reduced pressure. Flash chromatography purification using an ISCO setup (4 g silica gel column, 10→100% ethyl acetate in hexanes) afforded ethyl 2-(diphenylmethyleneamino)-4-(3-(1-phenyl-5-(trifluoromethyl)-1H-pyrazol-4-yl)-4,5-dihydronaphtho[1,2-c]isoxazol-7-yl)butanoate (160 mg, 0.237 mmol, 97% yield) as a glassy solid. LC/MS $M^{+1}$=675.4.

Preparation 50C: Ethyl 2-(diphenylmethylene-amino)-2-methyl-4-(3-(1-phenyl-5-(trifluoromethyl)-1H-pyrazol-4-yl)-4,5-dihydronaphtho[1,2-c]isoxazol-7-yl)butanoate

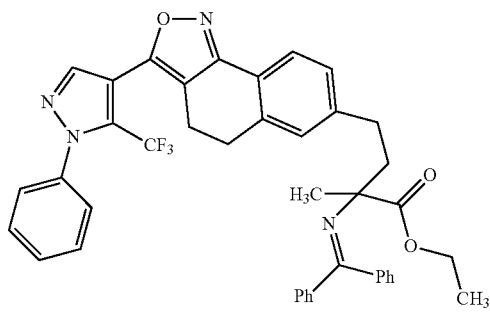

(50C)

To a stirred clear solution of ethyl 2-(diphenylmethylene-amino)-4-(3-(1-phenyl-5-(trifluoromethyl)-1H-pyrazol-4-yl)-4,5-dihydronaphtho[1,2-c]isoxazol-7-yl)butanoate (Preparation 50B, 150 mg, 0.222 mmol) in anhydrous THF (5 mL) was added a 1 M THF solution of lithium bis(trimethylsilyl)amide (333 µL, 0.333 mmol) dropwise at 0° C. under nitrogen. The reaction mixture was stirred at the same temperature for 30 min before iodomethane (50 µL, 0.800 mmol) was added. The reaction mixture was stirred at 0° C. for 30 min and at room temperature for 1 hr. The reaction was not complete. Anhydrous DMF (2 mL) was added, followed by lithium bis(trimethylsilyl)amide (2 mL, 2 mmol) at 0° C. The reaction mixture was stirred at the same temperature for 30 min before iodomethane (0.2 mL) was added. The mixture was stirred at 0° C. for 1 hr and quenched using saturated aqueous ammonium chloride solution (5 mL), ethyl acetate (10 mL), and water (10 mL). The aqueous solution was separated and re-extracted with ethyl acetate (2×5 mL). The combined ethyl acetate extracts were dried over sodium sulfate and concentrated under reduced pressure. Flash chromatography purification using ISCO (4 g silica gel column, 10→100% ethyl acetate in hexanes) afforded ethyl 2-(diphenylmethyleneamino)-2-methyl-4-(3-(1-phenyl-5-(trifluoromethyl)-1H-pyrazol-4-yl)-4,5-dihydronaphtho[1,2-c]isoxazol-7-yl)butanoate (120 mg, 0.174 mmol, 78% yield) as a solid. LC/MS $M^{+1}$=689.5.

Preparation 50D: Ethyl 2-amino-2-methyl-4-(3-(1-phenyl-5-(trifluoromethyl)-1H-pyrazol-4-yl)-4,5-dihydronaphtho[1,2-c]isoxazol-7-yl)butanoate

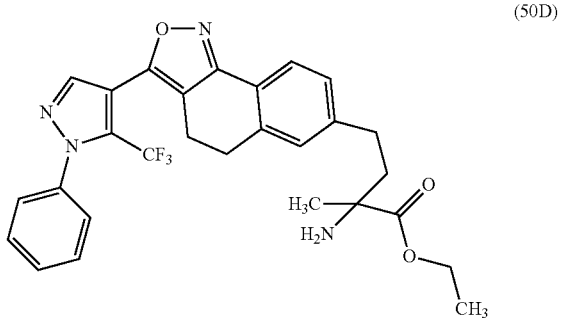 [SMILES: CCOC(=O)C(C)(N)CCc1ccc2c(c1)CCc1c-2noc1-c1cnn(-c2ccccc2)c1C(F)(F)F]

(50D)

To a stirred clear solution of ethyl 2-(diphenylmethylene-amino)-2-methyl-4-(3-(1-phenyl-5-(trifluoromethyl)-1H-pyrazol-4-yl)-4,5-dihydronaphtho[1,2-c]isoxazol-7-yl)butanoate (Preparation 50C, 120 mg, 0.174 mmol) in diethyl ether (3 mL) was added 4 N aqueous HCl (0.261 mL, 1.045 mmol) dropwise at room temperature. The reaction mixture was stirred at room temperature for 30 min. The ether layer was separated and the aqueous layer re-extracted with ether (2 mL). The aqueous solutions were basified with solid potassium carbonate and extracted with ethyl acetate (3×2 mL). The combined ethyl acetate extracts were dried over sodium sulfate and concentrated under reduced pressure to give ethyl 2-amino-2-methyl-4-(3-(1-phenyl-5-(trifluoromethyl)-1H-pyrazol-4-yl)-4,5-dihydronaphtho[1,2-c]isoxazol-7-yl)butanoate (86 mg, 0.164 mmol, 94% yield) as an yellow oil. The compound had an HPLC retention time=3.22 min (condition C); LC/MS $M^{+1}$=525.5.

Example 50

To a stirred solution of ethyl 2-amino-2-methyl-4-(3-(1-phenyl-5-(trifluoromethyl)-1H-pyrazol-4-yl)-4,5-dihydronaphtho[1,2-c]isoxazol-7-yl)butanoate (Preparation 50D, 80 mg, 0.153 mmol) in ethanol (1 mL) was added sodium borohydride (30 mg, 0.793 mmol) at room temperature. The reaction mixture was stirred at room temperature for 19 hr before ethyl acetate (4 mL) and water (2 ml) were added followed by the addition of saturated aqueous ammonium chloride solution (3 mL). The aqueous layer was separated and extracted with ethyl acetate (3×2 mL). The combined ethyl acetate solutions were dried over sodium sulfate and concentrated under reduced pressure to give a white solid. The solid was triturated with ethyl acetate to give 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol (32 mg, 0.066 mmol, 43.5% yield) as a white solid.

The mother liquor was concentrated. Purification using reverse phase HPLC (PHENOMENEX® Luna Axia 5 u c18 30×100 mm, 10 min. run, solvent A: 10% MeOH: 90% H$_2$O: 0.1% TFA, solvent B: 90% MeOH, 10% H$_2$O, 0.1% TFA), concentration, and lyophilization gave an additional batch of 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol, TFA (23 mg, 0.037 mmol, 24.02% yield) as a white solid. The compound had an HPLC retention time=3.03 min (condition C); LC/MS M$^{+1}$=483.3; $^1$H NMR (400 MHz, MeOD) δ ppm 8.14 (1H, s), 7.85 (1H, d, J=7.7 Hz), 7.54-7.64 (5H, m), 7.25-7.34 (2H, m), 3.67 (1H, d, J=11.5 Hz), 3.56 (1H, d, J=11.5 Hz), 3.03 (2H, t, J=6.9 Hz), 2.90 (2H, t, J=6.9 Hz), 2.66-2.81 (2H, m), 1.86-2.07 (2H, m), 1.37 (3H, s).

Example 51

(2S)-2-Amino-2-methyl-4-(3-(1-phenyl-5-(trifluoromethyl)-1H-pyrazol-4-yl)-4,5-dihydronaphtho[1,2-c]isoxazol-7-yl)butanoic acid

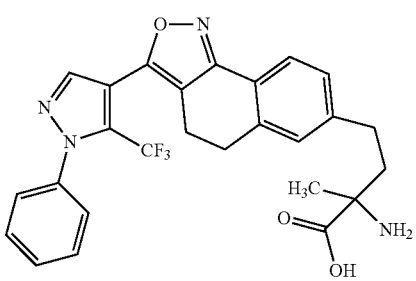

(51)

A solution of ethyl 2-amino-2-methyl-4-(3-(1-phenyl-5-(trifluoromethyl)-1H-pyrazol-4-yl)-4,5-dihydronaphtho[1,2-c]isoxazol-7-yl)butanoate (Preparation 50D, 4 mg, 7.63 µmol) and 10% aqueous sodium hydroxide (0.2 mL) in methanol (0.2 mL) was stirred under nitrogen at 60° C. for 1.5 hr and then room temperature overnight. Purification using reverse phase HPLC (PHENOMENEX® Luna Axia 5 u c18 30×100 mm, 10 min. run, solvent A: 10% MeOH: 90% H$_2$O: 0.1% TFA, solvent B: 90% MeOH, 10% H$_2$O, 0.1% TFA), concentration, and lyophilization gave (2S)-2-amino-2-methyl-4-(3-(1-phenyl-5-(trifluoromethyl)-1H-pyrazol-4-yl)-4,5-dihydronaphtho[1,2-c]isoxazol-7-yl)butanoic acid, TFA (3 mg, 4.82 µmol, 63.1% yield) as a white solid. The compound had an HPLC retention time=3.07 min (condition C); LC/MS M+1=497.3; $^1$H NMR (400 MHz, MeOD) δ ppm 8.14 (1H, s), 7.86 (1H, d, J=7.7 Hz), 7.54-7.64 (5H, m), 7.22-7.30 (2H, m), 3.03 (2H, t, J=7.0 Hz), 2.90 (2H, t, J=7.0 Hz), 2.83 (1H, td, J=13.1, 5.0 Hz), 2.65 (1H, td, J=13.0, 5.0 Hz), 2.26 (1H, td, J=13.5, 4.7 Hz), 2.10 (1H, td, J=13.5, 4.7 Hz), 1.62 (3H, s).

Example 52

2-Amino-2-methyl-4-(3-(1-phenyl-5-(trifluoromethyl)-1H-pyrazol-4-yl)-4,5-dihydronaphtho[1,2-c]isoxazol-7-yl)butyl dihydrogen phosphate

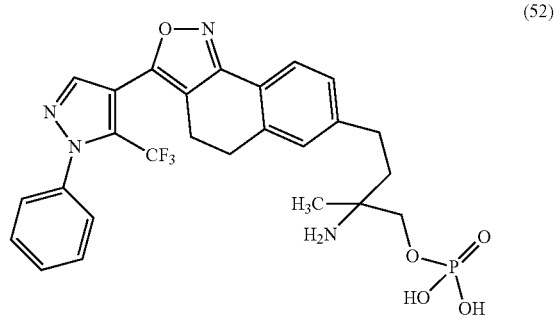 [SMILES: CC(N)(CCc1ccc2c(c1)CCc1c-2noc1-c1cnn(-c2ccccc2)c1C(F)(F)F)COP(=O)(O)O]

(52)

A mixture of phosphorus pentoxide (300 mg, 1.057 mmol) and 85% phosphoric acid (0.3 mL, 0.021 mmol) was stirred at 100° C. under nitrogen for 1 hr before 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol (Example 50, 10 mg, 0.021 mmol) was added. The clear solution was stirred at the same temperature for 2 hr before ice (~2 gram) was added. The reaction mixture was stirred at room temperature for 3 hour and dissolved in a minimum amount of methanol and dichloromethane. Purification using reverse phase HPLC (PHENOMENEX® Luna Axia 5 u c18 30×100 mm, 10 min. run, solvent A: 10% MeOH: 90% H$_2$O: 0.1% TFA, solvent B: 90% MeOH, 10% H$_2$O, 0.1% TFA), concentration, and lyophilization gave 2-amino-2-methyl-4-(3-(1-phenyl-5-(trifluoromethyl)-1H-pyrazol-4-yl)-4,5-dihydronaphtho[1,2-c]isoxazol-7-yl)butyl dihydrogen phosphate, 0.4 TFA (8 mg, 0.012 mmol, 60.3% yield) as a white solid. The compound had an HPLC retention time=3.16 min (condition C); LC/MS M$^{+1}$=563.4; $^1$H NMR (400 MHz, MeOD+CDCl$_3$) δ ppm 8.07 (1H, s), 7.86 (1H, d, J=7.7 Hz), 7.52-7.63 (5H, m), 7.24-7.33 (2H, m), 3.98 (1H, dd, J=11.5, 5.5 Hz), 3.89 (1H, dd, J=11.5, 5.5 Hz), 3.04 (2H, t, J=6.9 Hz), 2.90 (2H, t, J=6.9 Hz), 2.65-2.85 (2H, m), 2.08 (1H, td, J=13.1, 4.7 Hz), 1.94 (1H, td, J=13.1, 4.7 Hz), 1.41 (3H, s).

Example 53

1-((3-(5-Phenyl-4-(trifluoromethyl)isoxazol-3-yl)-4H-chromeno[3,4-d]isoxazol-7-yl)methyl)azetidine-3-carboxylic acid

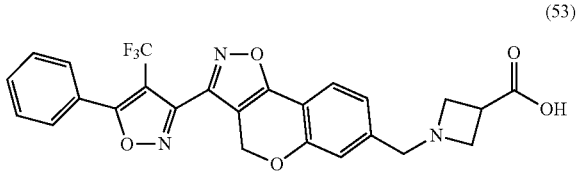 [SMILES: O=C(O)C1CN(Cc2ccc3c(c2)OCc2c(-c4noc(-c5ccccc5)c4C(F)(F)F)noc2-3)C1]

(53)

Preparation 53A: 4-(7-Vinyl-2H-chromen-4-yl)morpholine

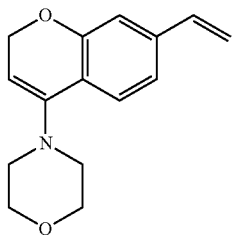

(53A)

To a mixture of 7-vinylchroman-4-one (Preparation 2D, 0.370 g, 2.12 mmol) and morpholine (0.925 mL, 10.6 mmol) in toluene (8 mL) at 0° C. was added titanium(IV) chloride (1.0 M in toluene) (1.17 mL, 1.17 mmol) dropwise. The ice-bath was removed, and the orange, heterogeneous reaction mixture was stirred at room temperature overnight. The reaction mixture was filtered under reduced pressure through a pad of CELITE®, which was rinsed with toluene (3×10 mL). The pale yellow filtrate was concentrated under reduced pressure to give 4-(7-vinyl-2H-chromen-4-yl)morpholine (0.448 g, 1.84 mmol, 87% yield) as a yellow oil. $^1$H NMR (500 MHz, CDCl$_3$) δ ppm 2.85-2.90 (m, 4), 3.84-3.89 (m, 4), 4.71 (d, J=4.16 Hz, 2), 5.10 (t, J=4.16 Hz, 1), 5.27 (d, J=11.37 Hz, 1), 5.76 (d, J=17.48 Hz, 1), 6.67 (dd, J=17.62, 10.96 Hz, 1), 6.98-7.03 (m, 2H), and 7.29 (s, 1H).

Preparation 53B: 3-(5-Phenyl-4-(trifluoromethyl)isoxazol-3-yl)-7-vinyl-4H-chromeno[3,4-d]isoxazole

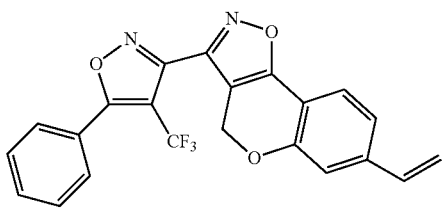

(53B)

To a mixture of (Z)—N-hydroxy-5-phenyl-4-(trifluoromethyl)isoxazole-3-carbimidoyl chloride (Intermediate 13, 0.221 g, 0.646 mmol) and 4-(7-vinyl-2H-chromen-4-yl)morpholine (Preparation 53A, 0.535 M in dichloromethane, 1.21 mL, 0.646 mmol) at 0° C. was added triethylamine (0.108 mL, 0.776 mmol) dropwise over 3 min. The ice-bath was removed, and the reaction mixture was stirred at room temperature for 30 min. The reaction mixture was diluted with dichloromethane (30 mL), washed with water (15 mL), dried over anhydrous sodium sulfate, and concentrated to give a foamy solid. The product mixture was dissolved in dichloroethane (3 mL), TFA (0.075 mL, 0.970 mmol) was added, and the resulting solution was heated at 80° C. for ~60 min. The reaction mixture was diluted with dichloromethane (30 mL), washed with a saturated aqueous solution of sodium bicarbonate (15 mL), and dried over anhydrous sodium sulfate. Concentration under reduced pressure followed by purification by flash silica gel chromatography using a mixture of ethyl acetate in hexane (5%-12%-20%) afforded 3-(5-phenyl-4-(trifluoromethyl)isoxazol-3-yl)-7-vinyl-4H-chromeno[3,4-d]isoxazole (0.033 g, 0.078 mmol, 12% yield) as a white solid. The product had an HPLC ret. time=3.93 min. (condition A); LC/MS M+1=411.0.

Preparation 53C: 3-(5-Phenyl-4-(trifluoromethyl)isoxazol-3-yl)-4H-chromeno[3,4-d]isoxazole-7-carbaldehyde

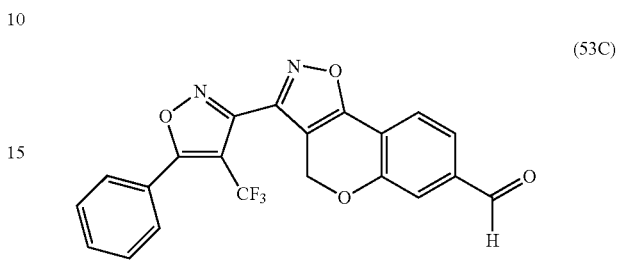

(53C)

To a mixture of 3-(5-phenyl-4-(trifluoromethyl)isoxazol-3-yl)-7-vinyl-4H-chromeno[3,4-d]isoxazole (Preparation 53B, 0.033 g, 0.080 mmol) and N-methylmorpholine-N-oxide (50% in water, 0.017 mL, 0.080 mmol) in THF (1 mL) at room temperature was added osmium tetroxide (4% in water, 0.025 mL, 3.22 µmol). The reaction mixture was stirred at room temperature overnight. To the reaction mixture was added sodium periodate (0.026 g, 0.121 mmol) and water (0.05 mL), and the reaction mixture was stirred overnight. By HPLC, the reaction still contained ~50% of the diol. Due to a significant amount of solid floating in the reaction mixture, additional THF (1 ml) was added to solubilize. After ~60 min., the reaction had progressed some. An additional 10 mg of sodium periodate was added, and the reaction mixture was stirred overnight. By HPLC, the reaction was complete. The reaction mixture was diluted with ethyl acetate (30 mL) and washed with water (10 mL). The organic layer was washed with brine (10 mL), the combined aqueous layers were extracted with ethyl acetate (30 mL), and the combined organic layers were dried over anhydrous sodium sulfate. Concentration under reduced pressure afforded the product as an off-white solid. The compound was further purified by methanol trituration to give 3-(5-phenyl-4-(trifluoromethyl)isoxazol-3-yl)-4H-chromeno[3,4-d]isoxazole-7-carbaldehyde (0.022 g, 0.053 mmol, 66% yield) as a white solid. The compound had an HPLC ret. time=4.13 min. (condition C); LC/MS M+1=413.1.

Example 53

To a mixture of 3-(5-phenyl-4-(trifluoromethyl)isoxazol-3-yl)-4H-chromeno[3,4-d]isoxazole-7-carbaldehyde (Preparation 53C, 0.022 g, 0.053 mmol) and azetidine-3-carboxylic acid (6.47 mg, 0.064 mmol) in a mixture of methanol (0.4 mL) and dichloroethane (0.8 mL) at room temperature was added 3 drops of acetic acid via a Pasteur pipette. The heterogeneous reaction mixture was heated at 70° C. for 1.75 h. The reaction mixture became homogeneous within the first minute. The reaction mixture was cooled to room temperature, and sodium cyanoborohydride (4.09 mg, 0.064 mmol) was added in one portion. The reaction mixture was stirred overnight at room temperature. The reaction mixture was diluted with dichloromethane, washed with water, 10% aqueous solution of lithium chloride, and dried over anhydrous sodium sulfate. Concentration under reduced pressure followed by purification using reverse phase preparative HPLC (PHENOMENEX® Luna Axia 5 u c18 30×100 mm, 10 min.

run, solvent A: 10% MeOH: 90% H₂O: 0.1% TFA, solvent B: 90% MeOH, 10% H₂O, 0.1% TFA) afforded the TFA salt of the product (14 mg). By HPLC, there was ~10% of the azetidine methyl ester present. The mixture was suspended in a mixture of acetonitrile (0.5 mL) and 6N aqueous hydrochloric acid (0.5 mL) and heated at 75° C. for 5 h and then at 90° C. for 30 min. The compound was purified by flash silica gel chromatography using a mixture of methanol, dichloromethane, and ammonium hydroxide (10:90:0-20:80:1), followed by trituration with methanol to give 1-((3-(5-phenyl-4-(trifluoromethyl)isoxazol-3-yl)-4H-chromeno[3,4-d]isoxazol-7-yl)methyl)azetidine-3-carboxylic acid (0.004 g, 8.03 μmol, 15% yield) as a white solid. The product had an HPLC ret. time=2.90 min. (condition A); LC/MS M$^{+1}$=498.2. $^1$H NMR (500 MHz, DMSO-d₆) δ ppm 3.16-3.43 (m, 5H), 3.55 (s, 2H), 5.62 (s, 2H), 6.96 (s, 1H), 7.03 (dd, J=7.77, 1.39 Hz, 1H), 7.61 (d, J=7.77 Hz, 1H), 7.64-7.69 (m, 2H), 7.70-7.74 (m, 1H), and 7.78 (d, J=7.21 Hz, 2H).

Example 54

1-((3-(5-Phenyl-4-(trifluoromethyl)isoxazol-3-yl)-4,5-dihydroisoxazolo[5,4-f]quinolin-7-yl)methyl)azetidine-3-carboxylic acid

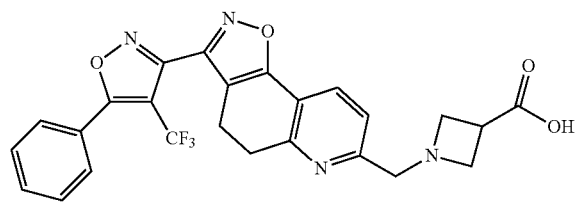

(54)

Example 54A 7,8-Dihydroquinoline-2,5(1H,6H)-dione

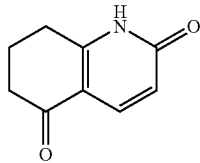

(54A)

A mixture of 3-aminocyclohex-2-enone (5.00 g, 45.0 mmol) and methyl propiolate (5.00 mL, 59.8 mmol) was heated without stirring at 100-105° C. for 2 h. The reflux condenser was removed, and the brown, homogeneous reaction mixture was heated to 170° C. to remove any excess methyl propiolate. At ~165° C., the product started to crystallize. The resulting dark brown solidified reaction mixture was triturated quickly with dichloromethane (2×5 mL)). The solid was then suspended in methanol and sonicated for 60 min., collected by vacuum filtration, washed with methanol, and dried to give 7,8-dihydroquinoline-2,5(1H,6H)-dione (1.49 g, 9.13 mmol, 20% yield) as a yellow solid. The compound had an HPLC ret. time=0.638 min. (condition A); LC/MS M$^{+1}$=163.9. $^1$H NMR (500 MHz, DMSO-d₆) δ ppm 1.99 (quin, J=6.38 Hz, 2H), 2.39-2.44 (m, 2H), 2.78 (t, J=6.24 Hz, 2H), 6.23 (d, J=9.43 Hz, 1H), 7.76 (d, J=9.43 Hz, 1H), and 12.07 (br. s., 1H).

Preparation 54B:
5-Oxo-5,6,7,8-tetrahydroquinolin-2-yl trifluoromethanesulfonate

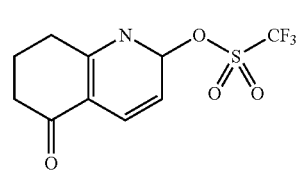

(54B)

To a heterogeneous mixture of 7,8-dihydroquinoline-2,5 (1H,6H)-dione (Preparation 54A, 1.27 g, 7.78 mmol) in pyridine (7 mL) immersed in a water bath was added trifluoromethanesulfonic anhydride (1.578 mL, 9.34 mmol) over 10 min. The water bath was removed, and the reaction mixture was stirred at room temperature for 10 min. The dark, homogeneous reaction mixture was concentrated under reduced pressure, and the residue was diluted with dichloromethane (100 mL), washed with 1N aqueous hydrochloric acid, saturated aqueous solution of sodium bicarbonate, dried over anhydrous sodium sulfate, and concentrated under reduced pressure. The crude compound was purified by flash silica gel chromatography using a mixture of ethyl acetate in hexane (5%-12%) to afford 5-oxo-5,6,7,8-tetrahydroquinolin-2-yl trifluoromethanesulfonate (2.21 g, 7.49 mmol, 96% yield) as a pale yellow solid. The compound had an HPLC ret. time=2.18 min. (condition A); LC/MS M$^{+1}$=295.8.

Preparation 54C:
2-Vinyl-7,8-dihydroquinolin-5(6H)-one

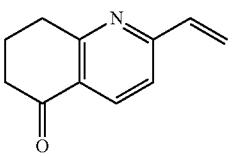

(54C)

To a solution of 5-oxo-5,6,7,8-tetrahydroquinolin-2-yl trifluoromethanesulfonate (Preparation 54B, 2.21 g, 7.49 mmol) in dioxane (12 mL) in a sealed tube was added sequentially tributyl(vinyl)stannane (2.418 mL, 8.23 mmol) and lithium chloride (0.952 g, 22.46 mmol). The mixture was degassed under reduced pressure and charged with nitrogen (3×). To the mixture was added tetrakis(triphenylphosphine)palladium(0) (0.865 g, 0.749 mmol), and the mixture was stirred under a strong stream of nitrogen for 5 min. The reaction mixture was sealed, immersed in an oil bath at 100° C., and stirred overnight. The reaction mixture was filtered and the solid was rinsed with ethyl acetate (150 mL). The filtrate was concentrated under reduced pressure, and the resulting residue was diluted with ether (150 mL). The resulting solid was removed by vacuum filtration and rinsed with ether (150 mL). The filtrate was concentrated under reduced pressure and purified by flash silica gel chromatography using a mixture of ethyl acetate in hexane (5%-12.5%-20%)

to give 2-vinyl-7,8-dihydroquinolin-5(6H)-one (1.09 g, 6.29 mmol, 84% yield) as a pale yellow solid. The compound had an HPLC ret. time=0.738 min. (condition A); LC/MS M$^{+1}$=273.8; $^1$H NMR (500 MHz, CDCl$_3$) δ ppm 2.21 (quin, 2H), 2.67-2.73 (m, 2H), 3.15 (t, J=6.10 Hz, 2H), 5.65 (d, J=10.82 Hz, 1H), 6.35 (d, J=17.48 Hz, 1H), 6.86 (dd, J=17.48, 10.54 Hz, 1H), 7.34 (d, J=8.05 Hz, 1H), and 8.25 (d, J=8.05 Hz, 1H).

Preparation 54D: 2-(1,2-Dihydroxyethyl)-7,8-dihydroquinolin-5(6H)-one

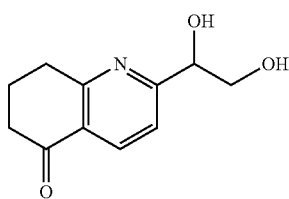

(54D)

To a mixture of 2-vinyl-7,8-dihydroquinolin-5(6H)-one (Preparation 54C, 0.400 g, 2.31 mmol) and N-methylmorpholine-N-oxide (50% in water, 0.479 mL, 2.31 mmol) in THF (11 mL) at room temperature was added osmium tetroxide (4% in water, 0.725 mL, 0.092 mmol). The reaction mixture was stirred at room temperature overnight. The reaction mixture was diluted with ethyl acetate (100 mL) and washed with water (50 mL). The organic layer was washed with brine (50 mL), the combined aqueous layers were extracted with ethyl acetate (100 mL), dried over anhydrous sodium sulfate and concentrated under reduced pressure to afford 2-(1,2-dihydroxyethyl)-7,8-dihydroquinolin-5(6H)-one (0.226 g, 1.09 mmol, 47% yield) as a yellow oil. The compound had an HPLC ret. time=0.330 min. (condition A); LC/MS M$^{+1}$=207.9.

Preparation 54E: 2-(2,2-Dimethyl-1,3-dioxolan-4-yl)-7,8-dihydroquinolin-5(6H)-one

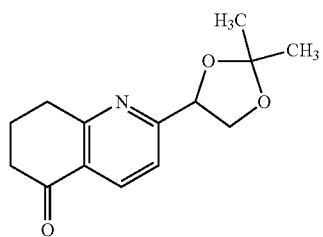

(54E)

A mixture of 2-(1,2-dihydroxyethyl)-7,8-dihydroquinolin-5(6H)-one (Preparation 54D, 0.226 g, 1.09 mmol), 2,2-dimethoxypropane (0.402 mL, 3.27 mmol), and (1R)-(−)-camphorsulfonic acid (0.051 g, 0.22 mmol) in acetone (6 mL) was stirred at room temperature overnight. The reaction mixture was quenched with a saturated aqueous solution of sodium bicarbonate and concentrated under reduced pressure. The aqueous residue was diluted with ethyl acetate, washed with a saturated aqueous solution of sodium bicarbonate and brine. The organic layer was collected, and the aqueous layer was extracted with ethyl acetate. The combined organic layers were dried over anhydrous sodium sulfate and concentrated and purified by flash silica gel chromatography using a mixture of ethyl acetate in hexane (50%) to afford 2-(2,2-dimethyl-1,3-dioxolan-4-yl)-7,8-dihydroquinolin-5 (6H)-one (0.182 g, 0.736 mmol, 68% yield) as a clear, colorless oil. The product had an HPLC ret. time=1.75 min. (condition A); LC/MS M$^{+1}$=247.9.

Preparation 54F: 4-(2-(2,2-Dimethyl-1,3-dioxolan-4-yl)-7,8-dihydroquinolin-5-yl)morpholine

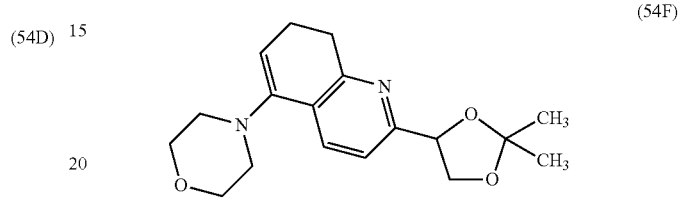

(54F)

To a mixture of 2-(2,2-dimethyl-1,3-dioxolan-4-yl)-7,8-dihydroquinolin-5(6H)-one (0.182 g, 0.736 mmol) and morpholine (0.321 mL, 3.68 mmol) in toluene (3 mL) at 0° C. was added titanium(IV) chloride (1.0 M in toluene) (0.405 mL, 0.405 mmol) dropwise. The ice-bath was removed, and the orange, heterogeneous reaction mixture was stirred at room temperature overnight. The reaction mixture was filtered through a pad of CELITE®, which was then rinsed with toluene (3×10 mL). The pale yellow filtrate was concentrated under reduced pressure to give 4-(2-(2,2-dimethyl-1,3-dioxolan-4-yl)-7,8-dihydroquinolin-5-yl)morpholine (0.194 g, 0.613 mmol, 83% yield) as a yellow oil.

Preparation 54G: 1-(3-(5-Phenyl-4-(trifluoromethyl) isoxazol-3-yl)-4,5-dihydroisoxazolo[5,4-f]quinolin-7-yl)ethane-1,2-diol

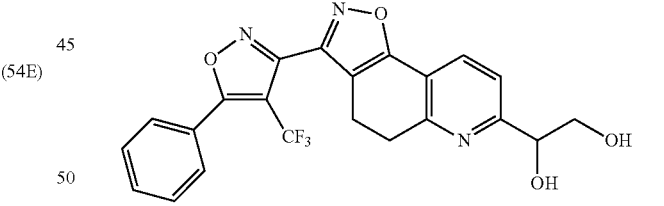

(54G)

To a solution of 4-(2-(2,2-dimethyl-1,3-dioxolan-4-yl)-7, 8-dihydroquinolin-5-yl)morpholine (Preparation 15F, 0.194 g, 0.613 mmol) in dichloromethane (2 mL) was added a solution of (Z)—N-hydroxy-5-phenyl-4-(trifluoromethyl) isoxazole-3-carbimidoyl chloride (Intermediate 13, 0.210 g, 0.613 mmol) in dichloromethane (1 mL). The reaction mixture was cooled to 0° C., and triethylamine (0.093 mL, 0.674 mmol) was added dropwise over 2 min. The ice-bath was removed, and the resulting cloudy solution was stirred at room temperature for 30 min. The reaction mixture was diluted with dichloromethane (30 mL), washed with water (15 mL), dried over anhydrous sodium sulfate, and concentrated to give the morpholino-intermediate, 7-(2,2-dimethyl-1,3-dioxolan-4-yl)-9b-morpholino-3-(5-phenyl-4-(trifluoromethyl)-isoxazol-3-yl)-3a,4,5,9b-tetrahydroisoxazolo[5, 4-f]quinoline, as an orange oil. To the oil was added dichloroethane (3 mL) and TFA (0.071 mL, 0.920 mmol), and the reaction mixture was heated at 80° C. for 60 min. The reaction mixture was stirred overnight at room temperature. Additional TFA (0.071 mL, 0.920 mmol) was added, and the reaction mixture was heated at 80° C. for 6 h. The reaction mixture was diluted with dichloromethane (30 mL), washed with a saturated aqueous solution of sodium bicarbonate (15 mL), and dried over anhydrous sodium sulfate. Concentration under reduced pressure followed by trituration with methanol with sonication afforded 44 mg of a 3:7 mixture of 1-(3-(5-phenyl-4-(trifluoromethyl)isoxazol-3-yl)-4,5-dihydroisoxazolo[5,4-f]quinolin-7-yl)ethane-1,2-diol and 7-(oxiran-2-yl)-3-(5-phenyl-4-(trifluoromethyl)isoxazol-3-yl)-4,5-dihydroisoxazolo[5,4-f]quinoline as a light brown solid.

The filtrate was purified by flash silica gel chromatography using a 20% mixture of ethyl acetate in hexane followed by a 5% mixture of methanol in dichloromethane to give 80 mg of the product (plus other polar material) as reddish oil. The oil was triturated with methanol to give a solid which was collected by vacuum filtration, rinsed with methanol, and dried well to afford 20 mg of the product as a yellow solid. The filtrate was concentrated and purified by reverse phase preparative HPLC to give after neutralization an additional 10 mg of the product as an off-white solid. The two samples were combined to give 1-(3-(5-phenyl-4-(trifluoromethyl)isoxazol-3-yl)-4,5-dihydroisoxazolo[5,4-f]quinolin-7-yl)ethane-1,2-diol (30 mg) as a yellow solid. The compound had an HPLC ret. time=2.82 min. (condition A); LC/MS M$^{+1}$=444.2.

Preparation 54H: 3-(5-Phenyl-4-(trifluoromethyl)isoxazol-3-yl)-4,5-dihydroisoxazolo[5,4-f]quinoline-7-carbaldehyde

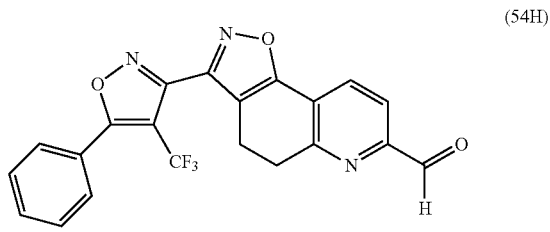 [SMILES: O=Cc1ccc2c(n1)CCc1c(-c3noc(-c4ccccc4)c3C(F)(F)F)noc1-2]

(54H)

To a solution of 1-(3-(5-phenyl-4-(trifluoromethyl)isoxazol-3-yl)-4,5-dihydroisoxazolo[5,4-f]quinolin-7-yl)ethane-1,2-diol (Preparation 54G, 0.030 g, 0.068 mmol) in THF (1 mL) at room temperature was added sodium periodate (0.022 g, 0.101 mmol) followed by water (0.05 mL). The reaction mixture was stirred at room temperature for 2.5 h. The reaction mixture was diluted with ethyl acetate (30 mL), washed with water (10 mL), and brine (10 mL). The combined aqueous layers were extracted with ethyl acetate (30 mL), dried over and anhydrous sodium sulfate and concentrated to give 3-(5-phenyl-4-(trifluoromethyl)isoxazol-3-yl)-4,5-dihydroisoxazolo[5,4-f]quinoline-7-carbaldehyde (0.029 g, 0.071 mmol, quantitative yield) as a tan solid. The compound had an HPLC ret. time=3.08 min. (condition A); LC/MS M$^{+1}$=412.1.

Example 54

A mixture of 3-(5-phenyl-4-(trifluoromethyl)isoxazol-3-yl)-4,5-dihydroisoxazolo[5,4-f]quinoline-7-carbaldehyde (step H, 0.029 g, 0.071 mmol) and azetidine-3-carboxylic acid (8.55 mg, 0.085 mmol) in a mixture of methanol (0.4 mL) and dichloroethane (0.8 mL) was heated at 67° C. for 1.75 h. The reaction mixture was cooled to room temperature, and sodium cyanoborohydride (5.40 mg, 0.085 mmol) was added in one portion. After 1 h, the reaction mixture was concentrated under reduced pressure, and the residue was purified by reverse phase preparative HPLC (PHENOMENEX® Luna Axia 5 u c18 30×100 mm, 10 min. run, solvent A: 10% MeOH: 90% H$_2$O: 0.1% TFA, solvent B: 90% MeOH, 10% H$_2$O, 0.1% TFA). The desired fraction was collected and concentrated under reduced pressure to give 14.6 mg of the product. The compound was diluted with dichloromethane and triethylamine, and the homogeneous solution was concentrated. The residue was purified by flash silica gel chromatography using a mixture of methanol, dichloromethane, and ammonium hydroxide (10:90:0-80:20:1) to give 11.8 mg of the product as an off-white solid. The solid was then triturated with methanol with sonication, filtered, rinsed with methanol, and dried well to give 1-((3-(5-phenyl-4-(trifluoromethyl)isoxazol-3-yl)-4,5-dihydroisoxazolo[5,4-f]quinolin-7-yl)methyl)azetidine-3-carboxylic acid (0.008 g, 0.016 mmol, 23% yield) as a white solid. The compound had an HPLC ret. time=2.74 min. (condition A); LC/MS M$^{+1}$=497.2. $^1$H NMR (500 MHz, DMSO-d$_6$) δ ppm 3.05-3.10 (m, 2H), 3.16-3.34 (m, 5H), 3.49 (t, J=7.63 Hz, 2H), 3.70 (s, 2H), 5.75 (s, 2H), 7.36 (d, J=8.05 Hz, 1H), 7.64-7.69 (m, 2H), 7.70-7.74 (m, 1H), 7.80 (d, J=7.21 Hz, 2H), and 8.06 (d, J=8.05 Hz, 1H).

Example 55

1-((3-(5-Phenyl-4-(trifluoromethyl)isoxazole-3-yl)-2,3-dihydrobenzo[b]oxepino-[4,5-d]isoxazol-8-yl)methyl)-azetidine-3-carboxylic acid

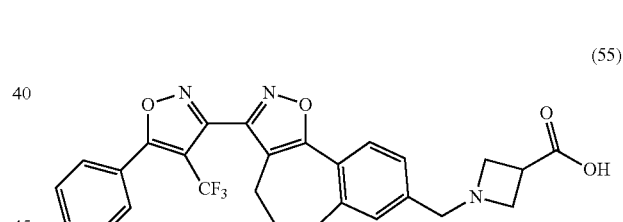

(55)

Preparation 55A: Ethyl 4-(3-bromophenoxy)butanoate

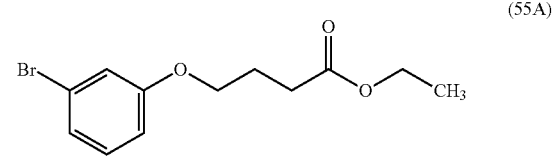 [SMILES: CCOC(=O)CCCOc1cccc(Br)c1]

(55A)

To a solution of 3-bromophenol (2 g, 11.56 mmol) in dimethylformamide (10 mL) was added sequentially cesium carbonate (11.30 g, 34.7 mmol) and ethyl 4-bromobutanoate (1.66 mL, 11.6 mmol) at room temperature. The heterogeneous reaction mixture was stirred at room temperature for 2.5 h. The reaction mixture was partitioned between ether (75 mL) and water (50 mL). The ether layer was collected, washed with brine (50 mL), dried over sodium sulfate, and concentrated to yield ethyl 4-(3-bromophenoxy)butanoate (3.3 g, 11.5 mmol, 99% yield) as an oil. $^1$H NMR (400 MHz, CDCl$_3$) δ ppm 1.25-1.29 (m, 3H), 2.07-2.15 (m, 2H), 2.48-2.54 (m, 2H), 3.99 (t, J=6.16 Hz, 2H), 4.13-4.15 (m, 1H), 4.16-4.19 (m, 1H), 6.80-6.84 (m, 1H), 7.05 (t, J=1.98 Hz, 1H), 7.06-7.09 (m, 1H), and 7.11-7.16 (m, 1H).

Preparation 55B: 4-(3-Bromophenoxy)butanoic acid

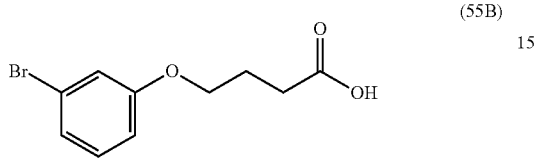

(55B)

To a solution of ethyl 4-(3-bromophenoxy)butanoate (Preparation 55A, 3.3 g, 11.5 mmol) in THF (5 mL) was added lithium hydroxide (0.550 g, 23.0 mmol) dissolved in water (5 mL) at room temperature. The reaction mixture was heated at 50° C. for 3 h. The reaction mixture was concentrated and partitioned between ethyl acetate (50 mL) and 1N aqueous hydrochloric acid (20 mL) (pH of aqueous layer ~3). The organic layer was washed with brine (20 mL), dried over sodium sulfate, and concentrated under reduced pressure to yield 4-(3-bromophenoxy)butanoic acid (2.9 g, 11.2 mmol, 97% yield) as an oil. $^1$H NMR (400 MHz, CDCl$_3$) δ ppm 2.10-2.15 (m, 2H), 2.59 (t, J=7.26 Hz, 2H), 4.01 (t, J=6.05 Hz, 2H), 6.82 (ddd, J=8.14, 2.42, 1.10 Hz, 1H), 7.04-7.06 (m, 1H), 7.07-7.10 (m, 1H), and 7.14 (t, J=8.03 Hz, 1H).

Preparation 55C:
8-Bromo-3,4-dihydrobenzo[b]oxepin-5(2H)-one

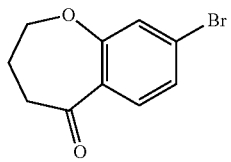

(55C)

To 4-(3-bromophenoxy)butanoic acid (Preparation 55B, 2.9 g, 11.19 mmol) was added PPA (13.6 mL, 11.2 mmol) at room temperature. The reaction mixture was heated at 100° C. for 14 h. To the dark reaction mixture was added ice cubes over a period of 5 min. (~5 g). The mixture was brought to room temperature, and stirred for 20 min. The dark reaction mixture was partitioned between ethyl acetate (120 mL) and water (50 mL). The organic layer was washed with brine (20 mL), dried over sodium sulfate, concentrated under reduced pressure, and purified by silica gel column chromatography using a mixture of ethyl acetate and hexane (4.5:0.5) to yield 8-bromo-3,4-dihydrobenzo[b]oxepin-5(2H)-one (0.170 g, 0.705 mmol, 6.3% yield) as a yellow oil. $^1$H NMR (400 MHz, CDCl$_3$) δ ppm 2.22 (quin, 2H) 2.89 (t, J=6.90 Hz, 2H), 4.25 (t, J=6.65 Hz, 2H), 7.25 (dd, J=8.28, 2.01 Hz, 1H), 7.28 (d, J=2.01 Hz, 1H), and 7.64 (d, J=8.53 Hz, 1H).

Preparation 55D: (E)-4-(8-Bromo-2,3-dihydrobenzo [b]oxepin-5-yl)morpholine

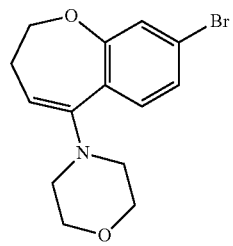

(55D)

To a mixture of 8-bromo-3,4-dihydrobenzo[b]oxepin-5 (2H)-one (0.170 g, 0.705 mmol) and morpholine (0.307 mL, 3.53 mmol) in toluene (3 mL) at 0° C. was added titanium(IV) chloride (1.0 M in toluene) (0.388 mL, 0.388 mmol) dropwise. The ice-bath was removed, and the orange, heterogeneous reaction mixture was stirred at room temperature overnight. The reaction mixture was filtered under reduced pressure through a pad of CELITE®, which was then rinsed with toluene (3×10 mL). The pale yellow filtrate was concentrated under reduced pressure to give (E)-4-(8-bromo-2,3-dihydrobenzo[b]oxepin-5-yl)morpholine (0.182 g, 0.587 mmol, 83% yield) as a yellow oil.

Preparation 55E: 3-(5-Phenyl-4-(trifluoromethyl) isoxazole-3-yl)-8-bromo-2,3-dihydrobenzo[b]oxepino-[4,5-d]isoxazole

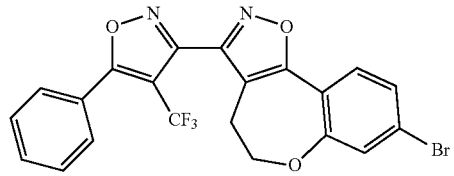

(55E)

To a solution of (E)-4-(8-bromo-2,3-dihydrobenzo[b]oxepin-5-yl)morpholine (Preparation 55D, 0.182 g, 0.587 mmol) in dichloromethane (2 mL) was added a solution of (Z)—N-hydroxy-5-phenyl-4-(trifluoromethyl)isoxazole-3-carbimidoyl chloride (Intermediate 13, 0.201 g, 0.587 mmol) in dichloromethane (1 mL). The reaction mixture was cooled to 0° C., and triethylamine (0.089 mL, 0.645 mmol) was added dropwise over 2 min. The ice-bath was removed, and the resulting cloudy solution was stirred at room temperature for 30 min. The mixture was diluted with dichloromethane, washed with water, dried over anhydrous sodium sulfate, and concentrated to give an orange oil. To the oil was added dichloroethane (3 mL) and TFA (0.068 mL, 0.880 mmol), and the reaction mixture was heated at 80° C. for 60 min. The reaction mixture was diluted with dichloromethane (30 mL), washed with an aqueous solution of sodium bicarbonate (15 mL), and dried over anhydrous sodium sulfate. Concentration under reduced pressure followed by trituration with methanol with sonication afforded 3-(5-phenyl-4-(trifluoromethyl) isoxazole-3-yl)-8-bromo-2,3-dihydrobenzo[b]oxepino[4,5-d]isoxazole (0.110 g, 0.230 mmol, 39% yield) as a tan solid. The compound had an HPLC ret. time=3.81 min. (condition A); LC/MS M+1=479.

Preparation 55F: 3-(5-Phenyl-4-(trifluoromethyl)isoxazole-3-yl)-8-vinyl-2,3-dihydrobenzo[b]oxepino-[4,5-d]isoxazole

(55F)

To a heterogeneous solution of 3-(5-phenyl-4-(trifluoromethyl)isoxazole-3-yl)-8-bromo-2,3-dihydrobenzo[b]oxepino[4,5-d]isoxazole (Preparation 55E, 0.110 g, 0.230 mmol) in dioxane (2 mL) in a sealed tube was added sequentially tributyl(vinyl)stannane (0.074 mL, 0.254 mmol) and lithium chloride (0.029 g, 0.691 mmol). The mixture was degassed under reduced pressure and charged with nitrogen. To the mixture was added tetrakis(triphenylphosphine)palladium(0) (0.027 g, 0.023 mmol), and the mixture was stirred under a strong stream of nitrogen for 5 min. The reaction mixture was sealed, immersed in an oil bath at 100° C. and stirred overnight. As it reached 100° C., the solution became near homogeneous. The reaction mixture was concentrated under reduced pressure, and the residue was diluted with dichloromethane (10 mL), filtered through a pad of CELITE®, and rinsed with dichloromethane (10 mL). The filtrate was concentrated, and the residue was purified by flash silica gel chromatography using a 5% mixture of ethyl acetate in hexane to give 3-(5-phenyl-4-(trifluoromethyl)isoxazole-3-yl)-8-vinyl-2,3-dihydrobenzo[b]oxepino-[4,5-d]isoxazole (0.052 g, 0.123 mmol, 53% yield) as a pale yellow solid. The compound had an HPLC ret. time=3.75 min. (condition A); LC/MS M$^{+1}$=425.1.

Preparation 55G: 3-(5-Phenyl-4-(trifluoromethyl)isoxazole-3-yl)-2,3-dihydrobenzo[b]oxepino-[4,5-d]isoxazole-8-carbaldehyde

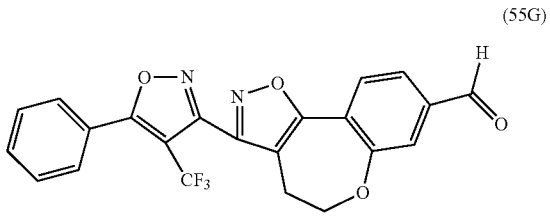 [SMILES: O=Cc1ccc2c(c1)OCCc1c(-c3noc(-c4ccccc4)c3C(F)(F)F)noc1-2]

(55G)

To a mixture of 2-(5-phenyl-4-(trifluoromethyl)isoxazole-3-yl)-8-vinyl-2,3-dihydrobenzo[b]oxepino-[4,5-d]isoxazole (Preparation 55F, 0.052 g, 0.123 mmol) and N-methylmorpholine-N-oxide (50% in water, 0.025 mL, 0.123 mmol) in THF (1 mL) at room temperature was added osmium tetroxide (4% in water, 0.038 mL, 4.90 μmol). The reaction mixture was stirred at room temperature overnight. To the reaction mixture was added sodium periodate (0.039 g, 0.184 mmol) and water (0.05 mL), and the contents stirred for 4 hour at room temperature. The reaction mixture was diluted with ethyl acetate (30 mL) and washed with water (10 mL). The organic layer was washed with brine (10 mL), the combined aqueous layers were extracted with ethyl acetate (30 mL) and dried over anhydrous sodium sulfate. Concentration under reduced pressure afforded the aldehyde as an off-white solid. The compound was further purified by methanol trituration to give 3-(5-phenyl-4-(trifluoromethyl)isoxazole-3-yl)-2,3-dihydrobenzo[b]oxepino-[4,5-d]isoxazole-8-carbaldehyde (0.036 g, 0.084 mmol, 69% yield) as a white solid. The compound had an HPLC ret. time=3.44 min. (condition A).

Example 55

To a mixture of 3-(5-phenyl-4-(trifluoromethyl)isoxazole-3-yl)-2,3-dihydrobenzo[b]oxepino-[4,5-d]isoxazole-8-carbaldehyde (Preparation 55G, 0.036 g, 0.084 mmol) and azetidine-3-carboxylic acid (10.24 mg, 0.101 mmol) in a mixture of methanol (0.4 mL) and dichloroethane (0.8 mL) was added one drop of acetic acid from a Pasteur pipette. The reaction mixture was heated at 67° C. for 2.0 h. The reaction mixture was then cooled to room temperature, and sodium cyanoborohydride (6.47 mg, 0.101 mmol) was added in one portion. The reaction mixture was concentrated under reduced pressure, and the residue suspended in water (5 mL) with sonication. The solid was collected by vacuum filtration, rinsed well with water, and dried over the weekend to give 33 mg of the product mixture as a white solid. The solid was triturated with methanol with sonication to give 20 mg of the product of as a white solid. The compound was further purified by flash silica gel chromatography using a mixture of methanol, dichloromethane, and ammonium hydroxide (10:90:0-80:20:1) to give 6.9 mg of the product as a white solid, which was then triturated with methanol with sonication, filtered, rinsed with methanol, and dried well to give 1-((3-(5-phenyl-4-(trifluoromethyl)isoxazole-3-yl)-2,3-dihydrobenzo[b]oxepino-[4,5-d]isoxazol-8-yl)methyl)-azetidine-3-carboxylic acid (0.0042 g, 8.05 μmol, 9.5% yield) as a white solid. The compound had an HPLC ret. time=2.85 min. (condition A); LC/MS M$^{+1}$=512.5. $^1$H NMR (400 MHz, DMSO-d$_6$) δ ppm 3.14 (t, J=4.95 Hz, 2H), 3.16-3.46 (m, 5H), 3.58 (s, 2H), 4.37 (t, J=4.84 Hz, 2H), 7.05 (d, J=1.10 Hz, 1H), 7.17 (dd, J=8.25, 1.43 Hz, 1H), 7.64-7.76 (m, 3H), 7.80 (d, J=7.26 Hz, 2H), and 7.95 (d, J=7.92 Hz, 1H).

Example 56

1-((2-(3-phenyl-4-(trifluoromethyl)isoxazol-5-yl)-4,5-dihydronaphtho[2,1-d]thiazol-7-yl)methyl)azetidine-3-carboxylic acid

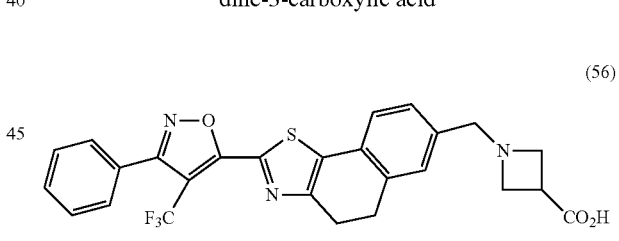

(56)

Preparation 56A: N-(6-Methoxy-1-oxo-1,2,3,4-tetrahydronaphthalen-2-yl)-3-phenyl-4-(trifluoromethyl)isoxazole-5-carboxamide

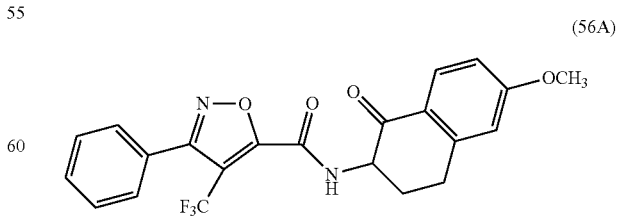

(56A)

Preparation 56A was made using 3-phenyl-4-(trifluoromethyl)isoxazole-5-carboxylic acid (Intermediate I-3D) and 2-amino-6-methoxy-3,4-dihydronaphthalen-1(2H)-one hydrochloride according to the procedure outlined for Preparation 43A. $^1$H NMR (400 MHz, CDCl$_3$) δ ppm 8.06 (1H, d, J=8.80 Hz), 7.82 (1H, d, J=4.40 Hz), 7.59-7.64 (2H, m), 7.49-7.57 (2H, m), 6.90 (1H, dd, J=8.80, 2.42 Hz), 6.75 (1H, d, J=2.20 Hz), 4.77 (1H, dt, J=13.42, 4.84 Hz), 3.90 (3H, s), 3.30 (1H, ddd, J=17.28, 13.09, 4.62 Hz), 3.05 (1H, ddd, J=17.22, 4.24, 2.31 Hz), 2.95-3.02 (2H, m). (M+H)$^+$=431.1.

Preparation 56B: 5-(7-methoxy-4,5-dihydronaphtho[2,1-d]thiazol-2-yl)-3-phenyl-4-(trifluoromethyl)isoxazole

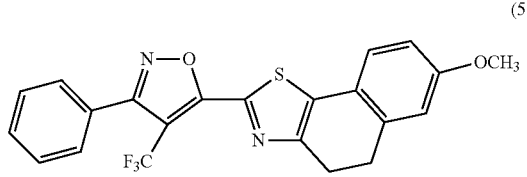

(56B)

A mixture of N-(6-methoxy-1-oxo-1,2,3,4-tetrahydronaphthalen-2-yl)-3-phenyl-4-(trifluoromethyl)isoxazole-5-carboxamide (Preparation 56A, 337 mg, 0.783 mmol) and Lawesson's reagent (2,4-Bis-[4-methoxyphenyl]-1,3-dithia-2,4-diphosphetane 2,4-disulfide) (475 mg, 1.175 mmol) in THF (4.0 ml) was heated for 33 min at 140° C. on a microwave which resulted in an incomplete reaction. The reaction mixture was then microwaved for 15 min more at 140° C. The crude reaction mixture was loaded onto a 40 g silica gel Redisep® cartridge which was presaturated with 10% EtOAc-hexanes and eluted with the same. The 5-(7-methoxy-4,5-dihydronaphtho[2,1-d]thiazol-2-yl)-3-phenyl-4-(trifluoromethyl)isoxazole (0.365 g, 0.852 mmol, quant. yield) was isolated as a yellow solid. The product had an LC ret. time=2.62 min. (condition: Start % B=0; Final % B=100; Gradient Time=2 min; Flow Rate=5 ml/min; Wavelength=220; Solvent Pair=MeOH/H$_2$O/TFA; Solvent A=0.1% TFA in MeOH: H$_2$O (10:90); Solvent B=0.1% TFA in; MeOH: H$_2$O (10:90); Column 1=Waters Sunfire C18 5 um 4.6×30 mm); LC/MS M$^{+1}$=429.04.

Preparation 56C: 2-(3-phenyl-4-(trifluoromethyl)isoxazol-5-yl)-4,5-dihydronaphtho[2,1-d]thiazol-7-ol

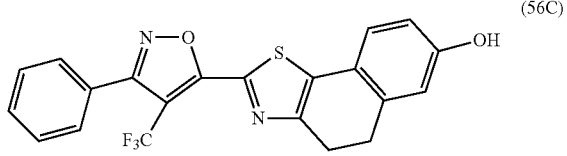 [SMILES: Oc1ccc2c(c1)CCc1nc(-c3onc(-c4ccccc4)c3C(F)(F)F)sc1-2]

(56C)

To a solution of 5-(7-methoxy-4,5-dihydronaphtho[2,1-d]thiazol-2-yl)-3-phenyl-4-(trifluoromethyl)isoxazole (Preparation 56B, 0.448 g, 1.046 mmol) in dichloromethane (13.07 mL) was added 1M BBr$_3$ (5.23 mL, 5.23 mmol) in dichloromethane dropwise, and the mixture was stirred at room temperature for 4.5 h. The reaction was slowly quenched with sat. NaHCO$_3$. After stirring for 5 min, sat. NH$_4$Cl was added. It was then partitioned between dichloromethane and water. The aqueous layer was extracted with dichloromethane. The combined organic layers were then washed with brine, dried over anhydrous MgSO$_4$, concentrated and chromatographed to give the 2-(3-phenyl-4-(trifluoromethyl)isoxazol-5-yl)-4,5-dihydronaphtho[2,1-d]thiazol-7-ol (0.388 g, 0.936 mmol, 90% yield) as a yellow solid. $^1$H NMR (400 MHz, CDCl$_3$) δ ppm 7.63-7.69 (2H, m), 7.46-7.58 (3H, m), 7.31 (1H, d, J=8.14 Hz), 6.80 (1H, d, J=2.42 Hz), 6.76 (1H, dd, J=8.25, 2.53 Hz), 3.15-3.23 (2H, m), 3.05-3.14 (2H, m).

Preparation 56D: 2-(3-phenyl-4-(trifluoromethyl)isoxazol-5-yl)-4,5-dihydronaphtho[2,1-d]thiazol-7-yl trifluoromethanesulfonate

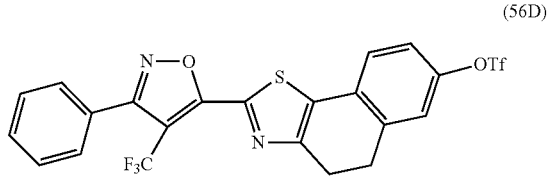 [SMILES: O=S(=O)(Oc1ccc2c(c1)CCc1nc(-c3onc(-c4ccccc4)c3C(F)(F)F)sc1-2)C(F)(F)F]

(56D)

To a solution of 2-(3-phenyl-4-(trifluoromethyl)isoxazol-5-yl)-4,5-dihydronaphtho[2,1-d]thiazol-7-ol (Preparation 56C, 0.388 g, 0.936 mmol) in pyridine (15 mL) at 0° C. was added triflic anhydride (0.190 mL, 1.124 mmol). After 30 min, the cooling bath was removed. After 2 h at room temperature, the reaction mixture was concentrated. The residue was partitioned between ether and 1N HCl. The organic layer was washed with sat. NaHCO$_3$, brine and dried over anhydrous Na$_2$SO$_4$, concentrated, and chromatographed (40 g Redisep® cartridge, which was presaturated with 5% EtOAc-hexanes and eluted with the same followed by 10% of the same). The 2-(3-phenyl-4-(trifluoromethyl)isoxazol-5-yl)-4,5-dihydronaphtho[2,1-d]thiazol-7-yl trifluoromethanesulfonate (0.451 g, 0.825 mmol, 88% yield) was obtained as a fluffy white solid. The product had an LC ret. time=4.343 min. (condition: Start % B=0, Final % B=100, Gradient Time=4 min, Flow Rate=4 ml/min, Wavelength=220, Solvent Pair=MeOH–H$_2$O–TFA; Solvent A=10% MeOH–90% H$_2$O–0.1% TFA; Solvent B=90% MeOH–10% H$_2$O–0.1% TFA; Column 1=1: Waters Sunfire C18 4.6×50 mm (4 min. grad)); LC/MS M$^{+1}$=547.03. $^1$H NMR (400 MHz, CDCl$_3$) δ ppm 7.64-7.68 (2H, m), 7.50-7.59 (3H, m), 7.47 (1H, d, J=8.14 Hz), 7.24 (1H, d, J=2.20 Hz), 7.21 (1H, dd, J=8.14, 2.42 Hz), 3.23-3.28 (2H, m), 3.17-3.23 (2H, m).

Preparation 56E: 3-phenyl-4-(trifluoromethyl)-5-(7-vinyl-4,5-dihydronaphtho[2,1-d]thiazol-2-yl)isoxazole

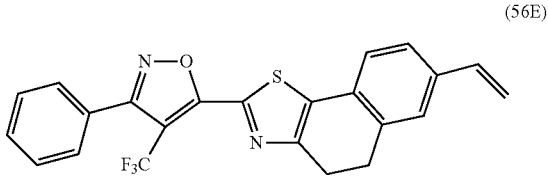 [SMILES: C=Cc1ccc2c(c1)CCc1nc(-c3onc(-c4ccccc4)c3C(F)(F)F)sc1-2]

(56E)

A mixture of 2-(3-phenyl-4-(trifluoromethyl)isoxazol-5-yl)-4,5-dihydronaphtho[2,1-d]thiazol-7-yl trifluoromethanesulfonate (Preparation 56D, 0.451 g, 0.825 mmol), tributyl (vinyl)tin (0.265 mL, 0.908 mmol), and lithium chloride (0.105 g, 2.476 mmol) in dioxane (5.0 mL) was placed in a microwave reaction vessel. To this was added tetrakis(triphenylphosphine)palladium(0) (0.095 g, 0.083 mmol) and argon was bubbled into the mixture for 3 min. The vessel was capped and the reddish brown mixture was immersed in a 100° C. oil bath. After 6 h of stirring, the reaction mixture was cooled to room temperature. EtOAc was added and the contents were stirred for 30 min. It was then filtered through a plug of Celite. The filter cake was washed with EtOAc (2×). The combined organic layers were then concentrated in vacuo. The residue was suspended in ether and stirred vigorously for another 30 min., filtered through a plug of celite and the filter cake washed with ether (2×). The combined organic layers were concentrated and chromatographed. The product had an LC ret. time=3.996 min. (condition: Start % B=50, Final % B=100, Gradient Time=4 min, Flow Rate=4 ml/min, Wavelength=220, Solvent Pair=MeOH–H$_2$O–TFA; Solvent A=10% MeOH—90% H$_2$O–0.1% TFA; Solvent B=90% MeOH–10% H$_2$O–0.1% TFA; Column 1=1: Waters Sunfire C18 4.6×50 mm (4 min. grad)); LC/MS M$^{+1}$=425.07.

Preparation 56F: 2-(3-phenyl-4-(trifluoromethyl)isoxazol-5-yl)-4,5-dihydronaphtho[2,1-d]thiazole-7-carbaldehyde

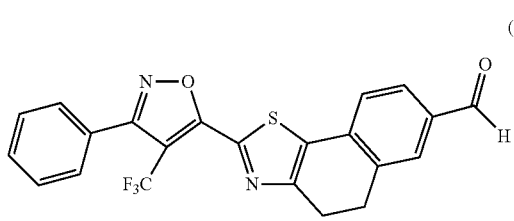

(56F)

To a solution of 3-phenyl-4-(trifluoromethyl)-5-(7-vinyl-4,5-dihydronaphtho[2,1-d]thiazol-2-yl)isoxazole (Preparation 56E, 0.350 g, 0.825 mmol) in THF (7.5 ml) at room temperature, was added a solution of osmium tetroxide, (2.5% in butanol, 1.7 ml, 0.017 mmol) followed by sodium periodate (0.265 g, 1.238 mmol) as a solution in 7.5 ml of water. After stirring for 90 min it was quenched with a saturated solution of sodium bisulfate. The dark colored suspension was filtered through Celite. The filter cake was washed with EtOAc. The combined EtOAc layers were washed with water, dried over anhydrous MgSO$_4$, concentrated, and chromatographed to yield the 2-(3-phenyl-4-(trifluoromethyl)isoxazol-5-yl)-4,5-dihydronaphtho[2,1-d]thiazole-7-carbaldehyde as an orange colored solid. The product had an LC ret. time=3.136 min. (condition: Start % B=50, Final % B=100, Gradient Time=4 min, Flow Rate=4 ml/min, Wavelength=220, Solvent Pair=MeOH–H$_2$O–TFA; Solvent A=10% MeOH–90% H$_2$O–0.1% TFA; Solvent B=90% MeOH–10% H$_2$O–0.1% TFA; Column 1=1: Waters Sunfire C18 4.6×50 mm (4 min. grad)); LC/MS M$^{+1}$=427.03.

Example 56

To a stirring solution of 2-(3-phenyl-4-(trifluoromethyl)isoxazol-5-yl)-4,5-dihydronaphtho[2,1-d]thiazole-7-carbaldehyde (Preparation 56F, 352 mg, 0.825 mmol) and azetidine-3-carboxylic acid (100 mg, 0.990 mmol) in MeOH (5 mL) and 1,2-dichloroethane (5.00 mL) was added at room temperature about 3-4 drops of AcOH. The reaction mixture was immersed in an oil bath heated at 80° C. and stirred for 1 h. It was cooled to room temperature and was treated with sodium cyanoborohydride (62.2 mg, 0.990 mmol), which was added in one portion. The reaction mixture was stirred at room temperature for 1 h, concentrated, and half of the material was purified by prep. HPLC (HPLC conditions: Phenomenex Luna C18 5 micron column (250×30 mm); 25-100% CH$_3$CN/water (0.1% TFA); 25 minute gradient; 30 mL/min.) to yield 1-((2-(3-phenyl-4-(trifluoromethyl)isoxazol-5-yl)-4,5-dihydronaphtho[2,1-d]thiazol-7-yl)methyl)azetidine-3-carboxylic acid, TFA (12 mg, 0.019 mmol, 2.279% yield) as a fluffy light yellow solid. The product had an LC ret. time=3.155 min. (condition: Start % B=0, Final % B=100, Gradient Time=4 min, Flow Rate=4 ml/min, Wavelength=220, Solvent Pair=MeOH–H$_2$O–TFA; Solvent A=10% MeOH–90% H$_2$O–0.1% TFA; Solvent B=90% MeOH–10% H$_2$O–0.1% TFA; Column 1=1: Waters Sunfire C18 4.6×50 mm (4 min. grad)); LC/MS M$^{+1}$=512.12. $^1$H NMR (400 MHz, CD$_3$OD) δ ppm 7.65 (1H, s), 7.63 (1H, d, J=1.32 Hz), 7.53-7.62 (4H, m), 7.46 (1H, s), 7.41 (1H, dd, J=7.92, 1.76 Hz), 4.42 (2H, s), 4.34 (2H, d, J=3.08 Hz), 4.32 (2H, d, J=1.10 Hz), 3.60-3.70 (1H, m), 3.21 (4H, s).

Examples 57-58

The Examples in Table 4 below were prepared according to the general procedure described above, substituting with the appropriate acid.

TABLE 4

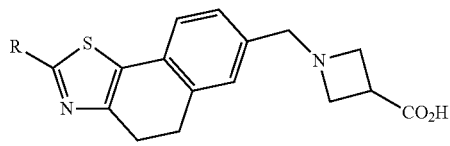

| Ex. No. | R | | MW | HPLC ret. time (min.) | MS (M$^{+1}$) |
|---|---|---|---|---|---|
| 57 | 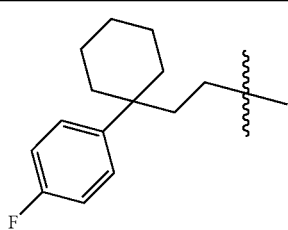 | 1-((2-(2-(1-(4-fluorophenyl)cyclohexyl)ethyl)-4,5-dihydronaphtho [2,1-d] thiazol-7-yl)methyl) azetidine-3-carboxylic acid, TFA | 504.66 | 2.482 (*) | 505.03 |

TABLE 4-continued

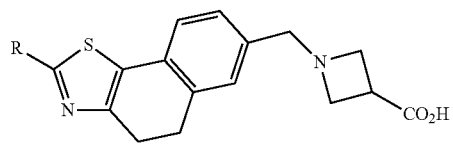

| Ex. No. | R | | MW | HPLC ret. time (min.) | MS (M⁺¹) |
|---|---|---|---|---|---|
| 58 | 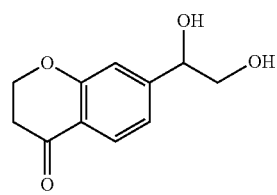 | 1-((2-(4-(4-chlorophenyl) cyclohexyl)-4,5-dihydronaphtho[2,1-d] thiazol-7-yl)methyl) azetidine-3-carboxylic acid, TFA | 493.06 | 2.472 (*) | 492.95 |

(*) Conditions: Start % B = 50, Final % B = 100, Gradient Time = 4 min, Flow Rate = 4 ml/min, Wavelength = 220, Solvent Pair = MeOH—H₂O-TFA; Solvent A = 10% MeOH-90% H₂O-0.1% TFA; Solvent B = 90% MeOH-10% H₂O-0.1% TFA; Column 1 = 1: Waters Sunfire C18 4.6 × 50 mm (4 min. grad).

Example 59

1-((2-(5-phenyl-4-(trifluoromethyl)isoxazol-3-yl)-4,5-dihydronaphtho[2,1-d]thiazol-7-yl)methyl)azetidine-3-carboxylic acid (59)

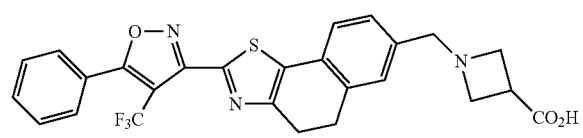

Example 59 was prepared according to the same protocol as outlined for Example 56, except that the final reductive amination reaction in the sequence, which is described below.

Example 59

To a stirring solution of 2-(5-phenyl-4-(trifluoromethyl)isoxazol-3-yl)-4,5-dihydronaphtho[2,1-d]thiazole-7-carbaldehyde (0.106 g, 0.249 mmol) in 1,2-dichloroethane (2.0 ml) at room temperature, was added azetidine-3-carboxylic acid (0.075 g, 0.746 mmol). The resulting pale suspension was stirred for 15 min after which tetraisopropyl titanate (0.222 ml, 0.746 mmol) was added dropwise. The reaction mixture turned light orange. Stirring was continued for 4 h after which sodium cyanoborohydride (0.023 g, 0.373 mmol) was added in one portion. After 90 min, the reaction mixture was diluted with MeOH and filtered through Celite. The filter cake was washed with MeOH (2×), and the filtrate was concentrated in vacuo. The crude product was purified by flash chromatography (24 g Redisep® cartridge, eluting with 5%-MeOH in dichloromethane followed by 10% (10%-Ammonia-MeOH in dichloromethane) to yield 57 mg of the desired 1-((2-(5-phenyl-4-(trifluoromethyl)isoxazol-3-yl)-4,5-dihydronaphtho[2,1-d]thiazol-7-yl)methyl)azetidine-3-carboxylic acid as an off white solid. The product had an LC ret. time=1.927 min. (condition: Start % B=0; Final % B=100; Gradient Time=2 min; Flow Rate=5 ml/min; Wavelength=254; Solvent Pair=MeOH/H₂O/TFA; Solvent A=0.1% TFA in MeOH: H₂O (10:90); Solvent B=0.1% TFA in; MeOH: H₂O (10:90); Column 1=Waters Sunfire C18 5 um 4.6×30 mm); LC/MS M⁺¹=512.08. ¹H NMR (400 MHz, CD₃OD) δ ppm 7.75 (2H, d, J=7.48 Hz), 7.59-7.68 (3H, m), 7.53 (1H, d, J=7.70 Hz), 7.43 (1H, s), 7.38 (1H, dd, J=7.92, 1.54 Hz), 4.34 (2H, s), 4.16-4.23 (4H, m), 3.42 (1H, quin, J=8.36 Hz), 3.12-3.23 (4H, m).

Example 60

1-((3-(3-Phenyl-4-(trifluoromethyl)isoxazol-5-yl)-4H-chromeno[3,4-d]isoxazol-7-yl)methyl)-azetidine-3-carboxylic acid (60)

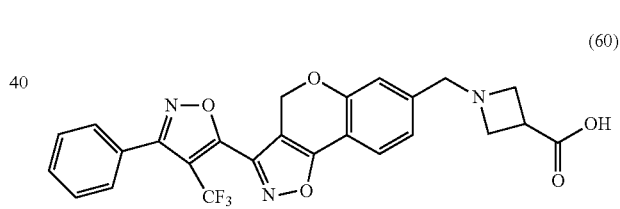

Preparation 60A:
7-(1,2-Dihydroxyethyl)chroman-4-one (60A)

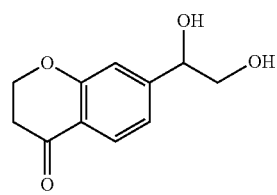

To a mixture of 7-vinylchroman-4-one (Preparation 2D, 0.801 g, 4.60 mmol) and a 50% solution of NMO in water (0.953 mL, 4.60 mmol) in THF (11 mL) at room temperature was added a 4% aqueous solution of osmium tetroxide in water (1.44 mL, 0.184 mmol). The reaction mixture was stirred at room temperature overnight. The reaction mixture was diluted with dichloromethane (200 mL) and washed with water (40 mL). The organic layer was collected and was washed with brine (40 mL). The combined aqueous layers were extracted with dichloromethane (200 mL), and the combined organic layers were dried over anhydrous sodium sulfate. Concentration under reduced pressure afforded 7-(1,2-dihydroxyethyl)chroman-4-one (0.950 g, 4.56 mmol, 99% yield) as a dark yellow oil. The product had an HPLC ret. time=0.587 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=209.0.

Preparation 60B:
7-(2,2-Dimethyl-1,3-dioxolan-4-yl)chroman-4-one

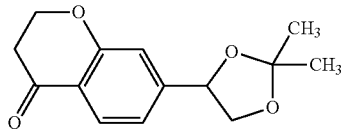

(60B)

To a mixture of 7-(1,2-dihydroxyethyl)chroman-4-one (Preparation 60A, 0.950 g, 4.56 mmol) and 2,2-dimethoxypropane (1.68 mL, 13.7 mmol) in acetone (20 mL) at room temperature was added (1R)-(−)-camphorsulfonic acid (0.212 g, 0.913 mmol). The reaction mixture was stirred at room temperature overnight. The reaction mixture was quenched with a saturated aqueous solution of sodium bicarbonate and concentrated under reduced pressure. The aqueous residue was diluted with ethyl acetate, washed with a saturated aqueous solution of sodium bicarbonate, and brine. The organic layer was collected, and the aqueous layer was extracted with ethyl acetate. The combined organic layers were dried over anhydrous sodium sulfate and concentrated to give the crude product as a dark oil, which was purified by flash silica gel chromatography using a 20% mixture of ethyl acetate and hexane to afford 7-(2,2-dimethyl-1,3-dioxolan-4-yl)chroman-4-one (0.657 g, 2.65 mmol, 58% yield) as a clear, colorless oil. The product had an HPLC ret. time=2.14 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=248.9.

Preparation 60C: 4-(7-(2,2-Dimethyl-1,3-dioxolan-4-yl)-2H-chromen-4-yl)morpholine

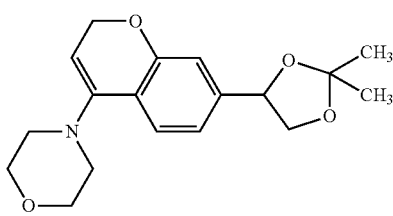

(60C)

To a mixture of 7-(8C,2,2-dimethyl-1,3-dioxolan-4-yl) chroman-4-one (Preparation 60C, 0.657 g, 2.65 mmol) and morpholine (1.15 mL, 13.2 mmol) in toluene (12 mL) at 0° C. was added a 1.0 M solution of titanium(IV) chloride in toluene (1.46 mL, 1.46 mmol) dropwise. The ice-bath was removed, and the orange, heterogeneous reaction mixture was stirred at room temperature overnight. The reaction mixture was filtered through a pad of Celite and rinsed with toluene (3×20 mL). The pale yellow filtrate was concentrated under reduced pressure to give 4-(7-(2,2-dimethyl-1,3-dioxolan-4-yl)-2H-chromen-4-yl)morpholine (0.751 g, 2.37 mmol, 89% yield) as a yellow oil.

Preparation 60D: 7-(2,2-Dimethyl-1,3-dioxolan-4-yl)-9b-morpholino-3-(3-phenyl-4-(trifluoromethyl)-isoxazol-5-yl)-4,9b-dihydro-3aH-chromeno[3,4-d] isoxazole

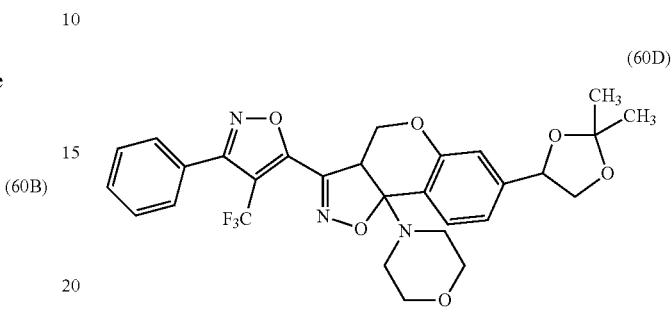

(60D)

To a solution of the N-hydroxy-3-phenyl-4-(trifluoromethyl)isoxazole-5-carbimidoyl chloride (Intermediate 1-12, 0.340 g, 1.170 mmol) in dichloromethane (3.5 mL) was added 4-(7-(2,2-dimethyl-1,3-dioxolan-4-yl)-2H-chromen-4-yl) morpholine (Preparation 60C, 0.473 M in dichloromethane) (2.47 mL, 1.17 mmol). The reaction mixture was cooled to 0° C., and triethylamine (0.324 mL, 2.34 mmol) was added dropwise over 10 min. The ice-bath was removed, and the resulting cloudy solution was stirred at room temperature for 1.5 h. The reaction mixture was diluted with dichloromethane (50 mL), washed with water (25 mL), dried over anhydrous sodium sulfate, concentrated under reduced pressure to afford the crude product as an orange oil. The compound was purified by flash silica gel chromatography using a mixture of ethyl acetate and hexane (5%-12%-20%) to give 7-(2,2-dimethyl-1,3-dioxolan-4-yl)-9b-morpholino-3-(3-phenyl-4-(trifluoromethyl)isoxazol-5-yl)-4,9b-dihydro-3aH-chromeno [3,4-d]isoxazole (0.080 g, 0.140 mmol, 12% yield) as a yellow solid. The product had an HPLC ret. time=3.25 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=572.1.

Preparation 60E: 1-(9b-Morpholino-3-(3-phenyl-4-(trifluoromethyl)isoxazol-5-yl)-4,9b-dihydro-3aH-chromeno[3,4-d]isoxazol-7-yl)ethane-1,2-diol

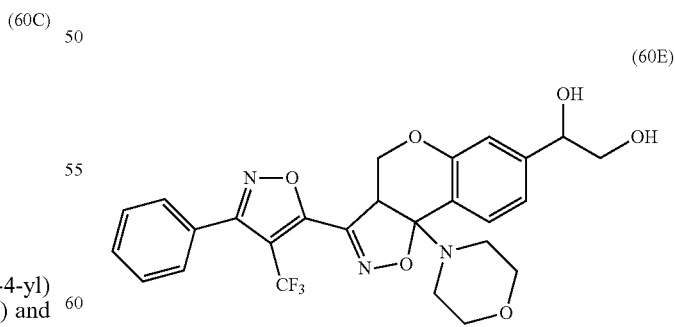

(60E)

A mixture of 7-(2,2-dimethyl-1,3-dioxolan-4-yl)-9b-morpholino-3-(3-phenyl-4-(trifluoromethyl)isoxazol-5-yl)-4, 9b-dihydro-3aH-chromeno[3,4-d]isoxazole (Preparation 60D, 0.080 g, 0.140 mmol) and TFA (3.00 ml, 38.9 mmol) was stirred at room temperature for 60 min. The TFA was removed under reduced pressure, and the residue was diluted with dichloromethane, washed with a saturated aqueous solution of sodium bicarbonate, and dried over anhydrous sodium sulfate. Concentration under reduced pressure afforded a quantitative yield of 1-(9b-morpholino-3-(3-phenyl-4-(trifluoromethyl)isoxazol-5-yl)-4,9b-dihydro-3aH-chromeno[3,4-d]isoxazol-7-yl)ethane-1,2-diol as a yellow oil. The product had an HPLC ret. time=2.63 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=532.0.

Preparation 60F: 9b-Morpholino-3-(3-phenyl-4-(trifluoromethyl)isoxazol-5-yl)-4,9b-dihydro-3aH-chromeno[3,4-d]isoxazole-7-carbaldehyde

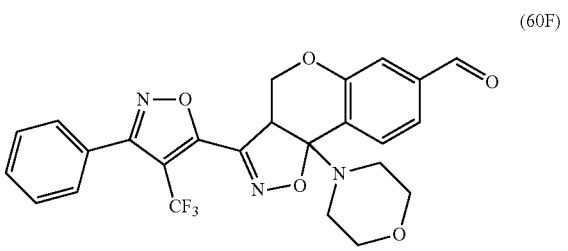 [SMILES: O=Cc1ccc2c(c1)OCC1C(c3onc(-c4ccccc4)c3C(F)(F)F)=NOC21N1CCOCC1]

(60F)

To a homogeneous solution of 1-(9b-morpholino-3-(3-phenyl-4-(trifluoromethyl)isoxazol-5-yl)-4,9b-dihydro-3aH-chromeno[3,4-d]isoxazol-7-yl)ethane-1,2-diol (Preparation 60E, 0.074 g, 0.139 mmol) in a mixture of THF (2.0 mL) and water (0.13 mL) at room temperature was added sodium periodate (0.045 g, 0.209 mmol). The reaction mixture was stirred for 60 min. The solvent was removed under reduced pressure, and the residue was diluted with ethyl acetate, washed with water, and washed with brine. The organic layer was collected, and the combined aqueous layers were extracted with ethyl acetate. The combined organic layers were dried over anhydrous sodium sulfate and concentrated to afford a quantitative yield of 9b-morpholino-3-(3-phenyl-4-(trifluoromethyl)isoxazol-5-yl)-4,9b-dihydro-3aH-chromeno[3,4-d]isoxazole-7-carbaldehyde as a yellow oil. The product had an HPLC ret. time=3.02 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=499.9.

Preparation 60G: (9b-Morpholino-3-(3-phenyl-4-(trifluoromethyl)isoxazol-5-yl)-4,9b-dihydro-3aH-chromeno[3,4-d]isoxazol-7-yl)methanol

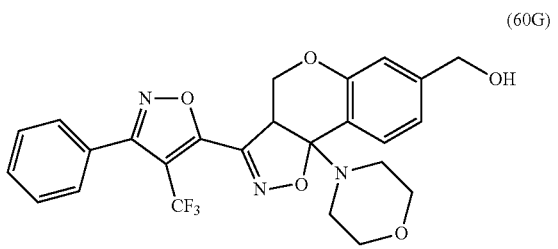 [SMILES: OCc1ccc2c(c1)OCC1C(c3onc(-c4ccccc4)c3C(F)(F)F)=NOC21N1CCOCC1]

(60G)

To a solution of 9b-morpholino-3-(3-phenyl-4-(trifluoromethyl)isoxazol-5-yl)-4,9b-dihydro-3aH-chromeno[3,4-d]isoxazole-7-carbaldehyde (Preparation 60F, 0.070 g, 0.140 mmol) in methanol (1.0 mL) at room temperature was added sodium borohydride (1.43 mg, 0.038 mmol). The reaction mixture was stirred at room temperature for 30 min. Methanol was removed under reduce pressure, and the residue was diluted with dichloromethane, washed with water, and dried over anhydrous sodium sulfate. Concentration under reduced pressure afforded (9b-morpholino-3-(3-phenyl-4-(trifluoromethyl)isoxazol-5-yl)-4,9b-dihydro-3aH-chromeno[3,4-d]isoxazol-7-yl)methanol as a yellow oil. The product had an HPLC ret. time=2.83 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=502.0.

Preparation 60H: (3-(3-Phenyl-4-(trifluoromethyl)isoxazol-5-yl)-4H-chromeno[3,4-d]isoxazol-7-yl)methanol

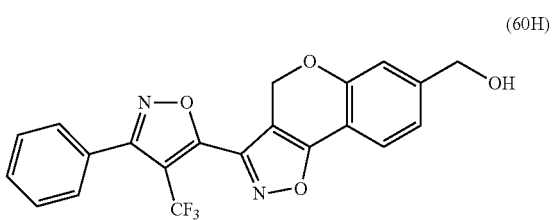 [SMILES: OCc1ccc2c(c1)OCc1c(-c3onc(-c4ccccc4)c3C(F)(F)F)noc1-2]

(60H)

To a solution of (9b-morpholino-3-(3-phenyl-4-(trifluoromethyl)isoxazol-5-yl)-4,9b-dihydro-3aH-chromeno[3,4-d]isoxazol-7-yl)methanol (Preparation 60G 0.070 g, 0.140 mmol) in dichloroethane (1.0 mL) at room temperature was added TFA (0.016 mL, 0.209 mmol). The reaction mixture was heated at 80° C. for 60 min. The reaction mixture was diluted with dichloromethane, washed with a saturated aqueous solution of sodium bicarbonate, and dried over anhydrous sodium sulfate. Concentration under reduced pressure afforded a pale yellow solid which was triturated with methanol with sonication and dried to give (3-(3-phenyl-4-(trifluoromethyl)isoxazol-5-yl)-4H-chromeno[3,4-d]isoxazol-7-yl)methanol (0.027 g, 0.065 mmol, 47% yield) as a white solid. The product had an HPLC ret. time=3.18 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=414.9.

Preparation 60I: 3-(3-Phenyl-4-(trifluoromethyl)isoxazol-5-yl)-4H-chromeno[3,4-d]isoxazole-7-carbaldehyde

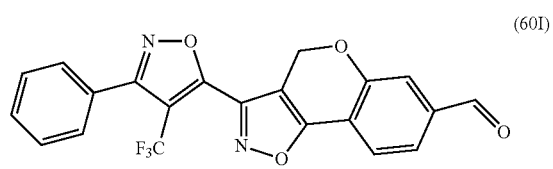 [SMILES: O=Cc1ccc2c(c1)OCc1c(-c3onc(-c4ccccc4)c3C(F)(F)F)noc1-2]

(60I)

To a solution of (3-(3-phenyl-4-(trifluoromethyl)isoxazol-5-yl)-4H-chromeno[3,4-d]isoxazol-7-yl)methanol (Preparation 60H, 0.027 g, 0.065 mmol) in dichloromethane (2.0 mL) at room temperature was added Dess-Martin Periodinane (0.030 g, 0.072 mmol). The reaction mixture was stirred for 30 min. The reaction was quenched with a 1:1 mixture of saturated aqueous sodium thiosulfate and saturated aqueous sodium bicarbonate (~2.0 mL), extracted with dichloromethane (2×), and the combined organic layers were dried over anhydrous sodium sulfate and filtered through a pad of Celite. The filtrate was concentrated under reduced pressure to afford 3-(3-phenyl-4-(trifluoromethyl)isoxazol-5-yl)-4H-chromeno[3,4-d]isoxazole-7-carbaldehyde (0.027 g, 0.065 mmol, 100% yield) as a white solid. The product had an HPLC ret. time=3.31 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA.

Preparation 60J: tert-Butyl 1-((3-(3-phenyl-4-(trifluoromethyl)isoxazol-5-yl)-4H-chromeno[3,4-d]isoxazol-7-yl)methyl)azetidine-3-carboxylate

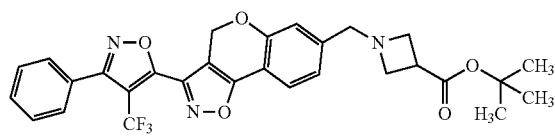

(60J)

To a mixture of 3-(3-phenyl-4-(trifluoromethyl)isoxazol-5-yl)-4H-chromeno[3,4-d]isoxazole-7-carbaldehyde (Preparation 60I, 0.027 g, 0.065 mmol), tert-butyl azetidine-3-carboxylate, acetic acid salt (0.021 g, 0.098 mmol), and acetic acid (7.50 µl, 0.131 mmol) in methanol (0.3 mL) and dichloroethane (0.900 mL) at room temperature was added titanium (IV) isopropoxide (0.038 mL, 0.131 mmol) dropwise. The resulting homogeneous reaction mixture was stirred for 80 min. To the reaction mixture was added sodium triacetoxyborohydride (0.042 g, 0.196 mmol) in one portion, and the reaction mixture was stirred at room temperature for 60 min. HPLC analysis indicated that there was still some starting material remaining. An additional small amount of the sodium triacetoxyborohydride was added, and the reaction mixture was stirred for an additional ~3 h. HPLC analysis indicated that the reaction was complete. The reaction was quenched with a saturated aqueous solution of sodium bicarbonate until the pH was slightly basic. The resulting emulsion was extracted with dichloromethane (3×). The organic layers were combined, dried over anhydrous sodium sulfate, and concentrated to give a pale yellow solid. The crude product was purified by flash silica gel chromatography using a mixture of ethyl acetate in hexane (20%-35%) to provide tert-butyl 1-((3-(3-phenyl-4-(trifluoromethyl)isoxazol-5-yl)-4H-chromeno[3,4-d]isoxazol-7-yl)methyl)azetidine-3-carboxylate (0.030 g, 0.054 mmol, 83% yield) as a white solid. The product had an HPLC ret. time=2.96 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=554.0.

Example 60

A mixture of tert-butyl 1-((3-(3-phenyl-4-(trifluoromethyl)isoxazol-5-yl)-4H-chromeno[3,4-d]isoxazol-7-yl)methyl)azetidine-3-carboxylate (Preparation 60J, 0.030 g, 0.054 mmol) and TFA (1.00 ml, 13.0 mmol) was left standing at room temperature for 45 min. The TFA was removed under reduced pressure, and the residue was suspended in water. The pH was adjusted to ~5 with 1N aqueous sodium hydroxide with sonication, and the resulting suspension was stirred for 20 min. The pH remained steady. The solid was collected by vacuum filtration, washed well with water, and dried to give the product as a white solid. The compound was suspended in methanol with sonication, concentrated, and resuspended in methanol with sonication. The solid was collected by vacuum filtration and dried well under reduced pressure to provide 1-((3-(3-phenyl-4-(trifluoromethyl)isoxazol-5-yl)-4H-chromeno[3,4-d]isoxazol-7-yl)methyl)azetidine-3-carboxylic acid (0.027 g, 0.052 mmol, 97% yield) as a white solid. The product had an HPLC ret. time=2.67 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=498.0. $^1$H NMR (500 MHz, DMSO-$d_6$) δ ppm 3.19-3.44 (m, 5H), 3.56 (br. s., 2H), 5.65 (s, 2H), 6.98 (s, 1H), 7.04 (d, J=7.49 Hz, 1H), and 7.59-7.69 (m, 6H).

Example 61

1-((3-(3-phenyl-4-(trifluoromethyl)isoxazol-5-yl)-4H-chromeno[4,3-c]isoxazol-7-yl)methyl)-azetidine-3-carboxylic acid

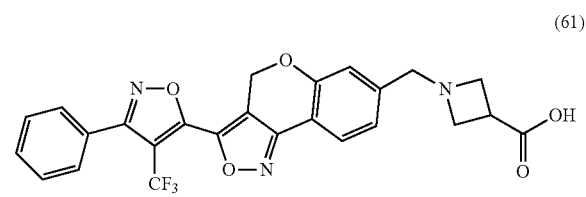 [SMILES: O=C(O)C1CN(Cc2ccc3c(c2)OCc2c-3noc2-c2onc(-c3ccccc3)c2C(F)(F)F)C1]

(61)

Preparation 61A: 7-(2,2-Dimethyl-1,3-dioxolan-4-yl)-3-(3-phenyl-4-(trifluoromethyl)isoxazol-5-yl)-3a,4-dihydro-3H-chromeno[4,3-c]isoxazol-3-ol

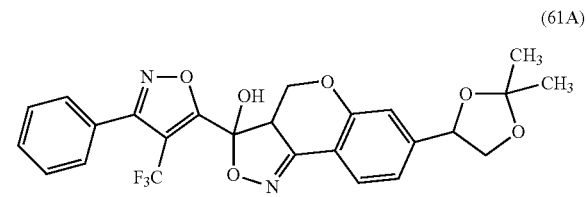 [SMILES: CC1(C)OCC(c2ccc3c(c2)OCC2C3=NOC2(O)c2onc(-c3ccccc3)c2C(F)(F)F)O1]

(61A)

To a homogeneous solution of 4-(7-(2,2-dimethyl-1,3-dioxolan-4-yl)-2H-chromen-4-yl)morpholine (Preparation 60C, 0.266 g, 0.838 mmol) and triethylamine (0.232 mL, 1.68 mmol) in anhydrous acetonitrile (3.0 mL) at 0° C. was added a solution of 3-phenyl-4-(trifluoromethyl)isoxazole-5-carbonyl fluoride (Intermediate I-4, 0.217 g, 0.838 mmol) in acetonitrile (1.0 mL). The reaction mixture was stirred at 0° C. for 30 min. and then at room temperature for 60 min. A homogeneous solution of hydroxylamine hydrochloride (0.233 g, 3.35 mmol) and sodium acetate (0.275 g, 3.35 mmol) in water (0.544 mL, 30.2 mmol) was added, and the reaction mixture was heated at 45° C. for 60 min. The reaction mixture was diluted with dichloromethane, washed with water, and dried over anhydrous sodium sulfate. Concentration under reduced pressure followed by purification by flash silica gel chromatography using a mixture of ethyl acetate in hexane (5%-12%-

20%) afforded 240 mg of the product mixture. The product was further purified by reverse phase preparative HPLC (2×120 mg) to give, after neutralization, 7-(2,2-dimethyl-1,3-dioxolan-4-yl)-3-(3-phenyl-4-(trifluoromethyl)isoxazol-5-yl)-3a,4-dihydro-3H-chromeno[4,3-c]isoxazol-3-ol (0.070 g, 0.139 mmol, 17% yield) as a white solid. The product had an HPLC ret. time=3.08 min. Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=502.9.

Preparation 61B: 7-(2,2-Dimethyl-1,3-dioxolan-4-yl)-3-(3-phenyl-4-(trifluoromethyl)isoxazol-5-yl)-4H-chromeno[4,3-c]isoxazole

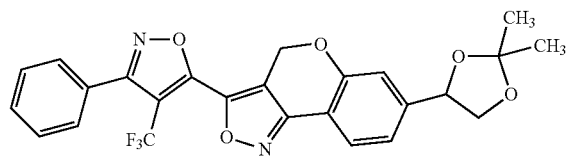

(61B)

To a stirred suspension of 7-(2,2-dimethyl-1,3-dioxolan-4-yl)-3-(3-phenyl-4-(trifluoromethyl)isoxazol-5-yl)-3a,4-dihydro-3H-chromeno[4,3-c]isoxazol-3-ol (Preparation 61A, 0.035 g, 0.070 mmol) in anhydrous toluene (1.0 mL) at room temperature was added pyridine (0.012 mL, 0.153 mmol) followed by thionyl chloride (8.64 µl, 0.118 mmol). The reaction mixture was stirred at room temperature for 15 min. and then at 80° C. for 15 min. The reaction mixture was cooled to room temperature and concentrated. The solid residue was diluted with dichloromethane, washed with a saturated aqueous solution of sodium bicarbonate, and dried over anhydrous sodium sulfate. Concentration under reduced pressure afforded a yellow film. The combined crude products were triturated with methanol with sonication. The solid was collected to provide 7-(2,2-dimethyl-1,3-dioxolan-4-yl)-3-(3-phenyl-4-(trifluoromethyl)isoxazol-5-yl)-4H-chromeno[4,3-c]isoxazole (0.042 g, 0.087 mmol, 62% yield) as an off-white solid. The product had an HPLC with a ret. time=3.63 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=484.9.

Preparation 61C: 1-(3-(3-Phenyl-4-(trifluoromethyl)isoxazol-5-yl)-4H-chromeno[4,3-c]isoxazol-7-yl)ethane-1,2-diol

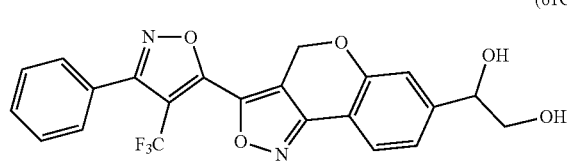

(61C)

A solution of 7-(2,2-dimethyl-1,3-dioxolan-4-yl)-3-(3-phenyl-4-(trifluoromethyl)isoxazol-5-yl)-4H-chromeno[4,3-c]isoxazole (Preparation 61B, 0.042 g, 0.087 mmol) in TFA (1.00 ml, 13.0 mmol) was left standing at room temperature for 45 min. The TFA was removed under reduced pressure, and the residue was diluted with dichloromethane, washed with a saturated aqueous solution of sodium bicarbonate, and dried over anhydrous sodium sulfate. Concentration under reduced pressure afforded 1-(3-(3-phenyl-4-(trifluoromethyl)isoxazol-5-yl)-4H-chromeno[4,3-c]isoxazol-7-yl)ethane-1,2-diol (0.039 g, 0.088 mmol, 100% yield) as an off-white solid. The product had an HPLC ret. time=3.00 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=444.9.

Preparation 61D: 3-(3-Phenyl-4-(trifluoromethyl)isoxazol-5-yl)-4H-chromeno[4,3-c]isoxazole-7-carbaldehyde

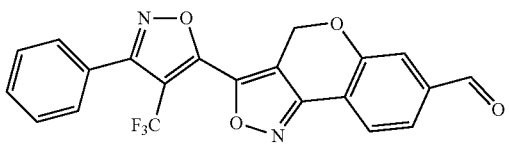

(61D)

To a homogeneous solution of 1-(3-(3-phenyl-4-(trifluoromethyl)isoxazol-5-yl)-4H-chromeno[4,3-c]isoxazol-7-yl)ethane-1,2-diol (Preparation 61C, 0.039 g, 0.088 mmol) in a mixture of THF (1.0 mL) and water (0.065 mL) at room temperature was added sodium periodate (0.028 g, 0.132 mmol). The reaction mixture was stirred for 30 min. The solvent was removed under reduced pressure, and the residue was diluted with dichloromethane, washed with water, and dried over anhydrous sodium sulfate. Concentration under reduced pressure afforded 36 mg of a ~1:1 mixture of 3-(3-phenyl-4-(trifluoromethyl)isoxazol-5-yl)-4H-chromeno[4,3-c]isoxazole-7-carbaldehyde and 7-(2,2-dimethyl-1,3-dioxolan-4-yl)-3-(3-phenyl-4-(trifluoromethyl)isoxazol-5-yl)-4H-chromeno[4,3-c]isoxazole as a yellow oil. As a result of a very tight separation, as indicated by TLC, the product was used in the next step without any further purification. The product had an HPLC ret. time=3.35 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=412.9.

Preparation 61E: tert-Butyl 1-((3-(3-phenyl-4-(trifluoromethyl)isoxazol-5-yl)-4H-chromeno[4,3-c]isoxazol-7-yl)methyl)azetidine-3-carboxylate (61E)

To the mixture of 3-(3-phenyl-4-(trifluoromethyl)isoxazol-5-yl)-4H-chromeno[4,3-c]isoxazole-7-carbaldehyde (Preparation 61D, 0.036 g, 0.087 mmol) and 7-(2,2-dimethyl-1,3-dioxolan-4-yl)-3-(3-phenyl-4-(trifluoromethyl)isoxazol-5-yl)-4H-chromeno[4,3-c]isoxazole from the previous reaction in methanol (0.333 mL) and dichloromethane (1.0 mL) at room temperature was added the tert-butyl azetidine-3-carboxylate, acetic acid salt (0.028 g, 0.131 mmol), acetic acid (10.00 μl, 0.175 mmol), and titanium(IV) isopropoxide (0.051 mL, 0.175 mmol) dropwise. The resulting homogeneous reaction mixture was stirred for 60 min. To the reaction mixture was added sodium triacetoxyborohydride (0.056 g, 0.262 mmol) in one portion, and the reaction mixture was stirred at room temperature for 30 min. The reaction was quenched with a saturated aqueous solution of sodium bicarbonate until the pH was slightly basic (~5 mL). The resulting emulsion was extracted with dichloromethane (3×). and the organic layers were combined, dried over anhydrous sodium sulfate, and concentrated to give a pale yellow solid. The crude product was purified by flash silica gel chromatography using a mixture of ethyl acetate in hexane (20%-35%-50%) to afford tert-butyl 1-((3-(3-phenyl-4-(trifluoromethyl)isoxazol-5-yl)-4H-chromeno[4,3-c]isoxazol-7-yl)methyl)azetidine-3-carboxylate (0.031 g, 0.056 mmol, 64% yield) as an off-white solid. The desired product had an HPLC ret. time=3.01 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=553.9.

Example 61

A mixture of tert-butyl 1-((3-(3-phenyl-4-(trifluoromethyl)isoxazol-5-yl)-4H-chromeno[4,3-c]isoxazol-7-yl)methyl)azetidine-3-carboxylate (Preparation 61E, 0.031 g, 0.056 mmol) and TFA (2.58 ml, 33.5 mmol) was left standing at room temperature for 45 min. The TFA was removed under reduced pressure, and the residue was suspended in water, the pH was adjusted to a value of 5 with sonication, and the resulting suspension was stirred for 1 h. The pH remained at 5, so the solid was collected by vacuum filtration, washed with water, and dried under reduced pressure to give a quantitative yield of the product as a white solid. The solid material was suspended in methanol and sonicated for 15 min. The product was collected by vacuum filtration, washed with methanol, and dried under reduced pressure to provide 1-((3-(3-phenyl-4-(trifluoromethyl)isoxazol-5-yl)-4H-chromeno [4,3-c]isoxazol-7-yl)methyl)azetidine-3-carboxylic acid (0.029 g, 0.058 mmol, 100% yield) as a white solid. The product had an HPLC ret. time=2.72 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=498.0. $^1$H NMR (500 MHz, DMSO-$d_6$) δ ppm 3.20-3.46 (m, 5H), 3.58 (s, 2H), 5.61 (s, 2H), 7.04 (s, 1H), 7.09 (d, J=7.77 Hz, 1H), 7.59-7.69 (m, 5H), and 7.79 (d, J=7.77 Hz, 1H).

Example 62

1-((3-(5-Phenyl-4-(trifluoromethyl)isoxazol-3-yl)-4H-chromeno[4,3-c]isoxazol-7-yl)methyl)-azetidine-3-carboxylic acid (62)

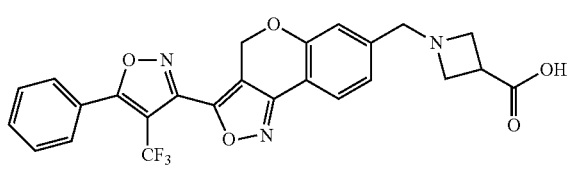

Preparation 62A: 3-(2,2-Dibromovinyl)-5-phenyl-4-(trifluoromethyl)isoxazole (62A)

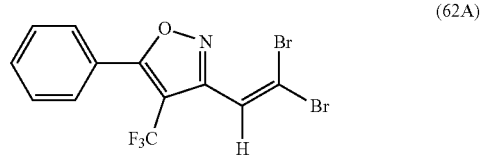 [SMILES: FC(F)(F)c1c(C=C(Br)Br)noc1-c1ccccc1]

To a solution of carbon tetrabromide (12.24 g, 36.9 mmol) in dichloromethane (10 mL) at 0° C. was added a solution of triphenylphosphine (4.84 g, 18.5 mmol) in dichloromethane (10 mL), and the resulting mixture was stirred at 0° C. for 5 min. A solution of 5-phenyl-4-(trifluoromethyl)isoxazole-3-carbaldehyde (Intermediate I-13B, 1.59 g, 4.62 mmol) in dichloromethane (10 mL) was added via syringe, and the reaction mixture was stirred at 0° C. for 20 min. The reaction mixture was diluted with dichloromethane and washed with water. A white precipitate formed in the organic and was removed by vacuum filtrating. The filtrate was washed with a saturated aqueous solution of sodium bicarbonate, washed with a saturated aqueous solution of ammonium chloride, dried over anhydrous sodium sulfate, and concentrated. The residue was purified by flash silica gel chromatography using a mixture of ethyl acetate in hexane (1%-3%) to give 3-(2,2-dibromovinyl)-5-phenyl-4-(trifluoromethyl)isoxazole (1.21 g, 3.05 mmol, 66.0% yield) as a white solid. The product had an HPLC ret. time=3.10 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=397.9. $^1$H NMR (500 MHz, CDCl$_3$) δ ppm 7.43 (s, 1H), 7.52-7.56 (m, 2H), 7.56-7.61 (m, 1H), and 7.74 (d, J=7.49 Hz, 2H).

Preparation 62B: 3-(5-Phenyl-4-(trifluoromethyl) isoxazol-3-yl)prop-2-yn-1-ol (62B)

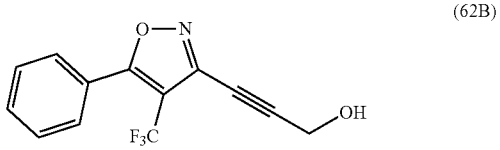 [SMILES: OCC#Cc1noc(-c2ccccc2)c1C(F)(F)F]

To a solution of 3-(2,2-dibromovinyl)-5-phenyl-4-(trifluoromethyl)isoxazole (Preparation 62A, 0.496 g, 1.19 mmol) in THF (6.0 mL) at −78° C. was slowly added a 2.5 M solution of butyl lithium in hexane (1.05 mL, 2.61 mmol). The reaction mixture was stirred at −78° C. for 25 min. and then warmed to room temperature gently with a heat gun. Once at room temperature, paraformaldehyde (0.713 g, 23.74 mmol) was added, and the reaction mixture was stirred for 5 min. The mixture was diluted with ether, washed with water (2×), and washed with brine. The combined aqueous layers were extracted with ether, and the combined organics layers were dried over anhydrous sodium sulfate and concentrated. The residue was purified by flash silica gel chromatography using a mixture of ethyl acetate in hexane (1%-5%-20%) to give 3-(5-phenyl-4-(trifluoromethyl)isoxazol-3-yl)prop-2-yn-1-ol (0.199 g, 0.745 mmol, 63% yield) as a yellowish-orange solid. The product had an HPLC ret. time=2.39 min.–Col- Preparation 62C: 3-(3-Bromoprop-1-ynyl)-5-phenyl-4-(trifluoromethyl)isoxazole

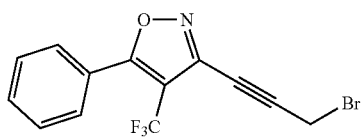

To a solution of 3-(5-phenyl-4-(trifluoromethyl)isoxazol-3-yl)prop-2-yn-1-ol (Preparation 62B, 0.465 g, 1.740 mmol) in dichloromethane (9.0 mL) at 0° C. was added a 1.0 M solution of tribromophosphine in dichloromethane (2.09 mL, 2.09 mmol). After 5 min., the ice-bath was removed, and the reaction mixture was stirred at room temperature overnight. HPLC and LCMS analysis indicated that there was still significant starting material remaining. Additional tribromophosphine (1.0 M in dichloromethane) (2.09 mL, 2.09 mmol) was added, and the reaction mixture was stirred at room temperature for 4.5 h. Additional tribromophosphine (1.0 M in dichloromethane) (2.09 mL, 2.09 mmol) was added, and the reaction mixture was stirred at room temperature over the weekend. The reaction mixture was diluted with dichloromethane, washed with a saturated aqueous solution of sodium bicarbonate, and dried over anhydrous sodium sulfate. Concentration under reduced pressure provided the crude product, which was loaded with a minimum amount of dichloromethane on a fitted funnel containing a layer of Celite topped with a layer of silica gel. The plug column was eluted with a mixture of ethyl acetate and hexane (1%-3%) to give 3-(3-bromoprop-1-ynyl)-5-phenyl-4-(trifluoromethyl)isoxazole (0.219 g, 0.663 mmol, 38% yield) as a clear, colorless oil. The product had an HPLC ret. time=2.95 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=331.93.

Preparation 62D: 4-Bromo-2-(3-(5-phenyl-4-(trifluoromethyl)isoxazol-3-yl)prop-2-ynyloxy)benzaldehyde

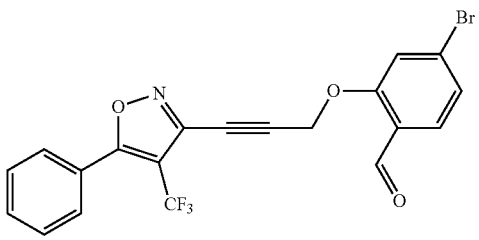

To a mixture of 3-(3-bromoprop-1-ynyl)-5-phenyl-4-(trifluoromethyl)isoxazole (Preparation 62C, 0.219 g, 0.663 mmol) and 4-bromo-2-hydroxybenzaldehyde (0.133 g, 0.663 mmol) in dimethylformamide (2.0 mL) at room temperature was added potassium carbonate (0.115 g, 0.829 mmol). The reaction mixture was stirred at room temperature for 3 h, diluted with ethyl acetate (75 mL), washed with a 10% aqueous solution of lithium chloride (2×25 mL), and washed with brine (25 mL). The organic layer was collected, and the combined aqueous phases were extracted with ethyl acetate (2×25 mL). The combined organic layers were dried over anhydrous sodium sulfate. Concentration under reduced pressure afforded a tan solid which was triturated with methanol with sonication to give 4-bromo-2-(3-(5-phenyl-4-(trifluoromethyl)isoxazol-3-yl)prop-2-ynyloxy)benzaldehyde (0.223 g, 0.495 mmol, 75% yield) as a white solid. The product had an HPLC ret. time=3.28 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=451.92. $^1$H NMR (500 MHz, CDCl$_3$) δ ppm 5.12 (s, 2H), 7.28 (d, J=8.32 Hz, 1H), 7.34 (d, J=1.66 Hz, 1H), 7.51-7.55 (m, 2H), 7.56-7.61 (m, 1H), 7.72 (d, J=7.21 Hz, 2H), 7.75 (d, J=8.32 Hz, 1H), and 10.44 (s, 1H).

Preparation 62E: (E)-4-Bromo-2-(3-(5-phenyl-4-(trifluoromethyl)isoxazol-3-yl)prop-2-ynyloxy)-benzaldehyde oxime

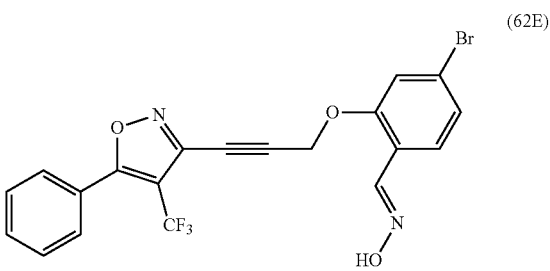 [SMILES: O/N=C/c1ccc(Br)cc1OCC#Cc1noc(-c2ccccc2)c1C(F)(F)F]

A mixture of 4-bromo-2-(3-(5-phenyl-4-(trifluoromethyl)isoxazol-3-yl)prop-2-ynyloxy)benzaldehyde (Preparation 62D, 0.050 g, 0.111 mmol), hydroxylamine hydrochloride (9.26 mg, 0.133 mmol), and sodium acetate (0.018 g, 0.222 mmol) in methanol (2.0 mL) was heated at reflux for 30 min. The solvent was removed under reduce pressure, and the residue was diluted with dichloromethane, washed with water, and dried over anhydrous sodium sulfate. Concentration under reduced pressure afforded (E)-4-bromo-2-(3-(5-phenyl-4-(trifluoromethyl)isoxazol-3-yl)prop-2-ynyloxy)benzaldehyde oxime (0.050 g, 0.107 mmol, 97% yield) as a white solid. The product had an HPLC with a ret. time=3.26 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=466.8.

Preparation 62F: 7-Bromo-3-(5-phenyl-4-(trifluoromethyl)isoxazol-3-yl)-4H-chromeno[4,3-c]isoxazole

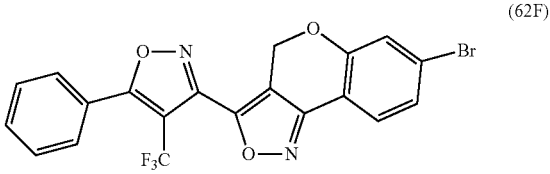 [SMILES: FC(F)(F)c1c(-c2onc3c2COc2cc(Br)ccc2-3)noc1-c1ccccc1]

To a mixture of sodium hypochlorite (23 mL), triethylamine (Preparation 62E, 0.021 mL, 0.155 mmol), and dichloromethane (1.0 mL) at 0° C. was added dropwise a solution of (E)-4-bromo-2-(3-(5-phenyl-4-(trifluoromethyl)isoxazol-3-yl)prop-2-ynyloxy)benzaldehyde oxime (0.036 g, 0.077 mmol) in dichloromethane (3 mL). The reaction mixture was stirred at 0° C. for 30 min. and then at room temperature for 1.5 h. The reaction mixture was diluted with dichloromethane, and the organic layer was collected. The aqueous layer was extracted with dichloromethane (2×), and the combined organic layers were washed with brine and dried over anhydrous sodium sulfate. Concentration under reduced pressure followed by trituration with methanol with sonication afforded 7-bromo-3-(5-phenyl-4-(trifluoromethyl)isoxazol-3-yl)-4H-chromeno[4,3-c]isoxazole (0.026 g, 0.056 mmol, 73% yield) as a white solid. The product had an HPLC ret. time=3.91 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=464.9. $^1$H NMR (500 MHz, $CDCl_3$) δ ppm 5.49 (s, 2H), 7.23-7.27 (m, 2H), 7.55-7.59 (m, 2H), 7.60-7.65 (m, 1H), 7.73 (d, J=7.49 Hz, 2H), and 7.78 (d, J=8.05 Hz, 1H).

Alternative Synthesis of Preparation 62F

To a solution of (E)-4-bromo-2-(3-(5-phenyl-4-(trifluoromethyl)isoxazol-3-yl)prop-2-ynyloxy)benzaldehyde oxime (Preparation 62E, 0.142 g, 0.305 mmol) in N,N-dimethylformamide (1.5 mL) at 0° C. was added N-bromosuccinimide (0.081 g, 0.458 mmol) followed by triethylamine (0.085 mL, 0.610 mmol). The resulting homogeneous reaction mixture was stirred at 0° C. for 10 min. and then at room temperature for 50 min. HPLC and LCMS analysis indicated that ~65% of the starting material remained. The reaction mixture was then stirred at 75° C. for 60 min. HPLC analysis indicated that the reaction had progressed to ~1:1 starting material to product. Additional N-bromosuccinimide (0.081 g, 0.458 mmol) and triethylamine (0.085 mL, 0.610 mmol) were added, and the reaction was heated for an additional 60 min. Very little change was noted upon HPLC analysis. The reaction mixture was stirred overnight at room temperature. The reaction mixture was diluted with ethyl acetate, washed with a 10% aqueous solution of lithium chloride (2×), and washed with brine. The organic layer was collected, and the aqueous layers were sequentially extracted with ethyl acetate. The combined organic layers were dried over anhydrous sodium sulfate and concentrated. The solid residue was triturated with methanol with sonication to afford 7-bromo-3-(5-phenyl-4-(trifluoromethyl)isoxazol-3-yl)-4H-chromeno[4,3-c]isoxazole (0.063 g, 0.136 mmol, 45% yield) as a white solid.

Preparation 62G: 3-(5-Phenyl-4-(trifluoromethyl)isoxazol-3-yl)-7-vinyl-4H-chromeno[4,3-c]isoxazole

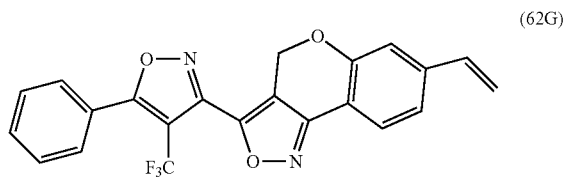 [SMILES: C=Cc1ccc2c(c1)OCc1c-2noc1-c1noc(-c2ccccc2)c1C(F)(F)F]

(62G)

To a heterogeneous solution of 7-bromo-3-(5-phenyl-4-(trifluoromethyl)isoxazol-3-yl)-4H-chromeno[4,3-c]isoxazole (Preparation 62F, 0.105 g, 0.227 mmol) in dioxane (2.0 mL) in a sealed tube was added sequentially tributyl(vinyl)stannane (0.073 mL, 0.249 mmol) and lithium chloride (0.029 g, 0.680 mmol). The mixture was degassed under reduced pressure and charged with nitrogen (3×). To the mixture was added tetrakis(triphenylphosphine)palladium(0) (0.026 g, 0.023 mmol), and the mixture was stirred under a strong stream of nitrogen for 5 min. The reaction mixture was sealed, immersed in an oil bath at 100° C., and stirred overnight. As it reached 100° C., the solution became near homogeneous. The reaction mixture was concentrated under reduced pressure, and the residue was diluted with dichloromethane (10 mL), filtered through a pad of Celite, and rinsed with dichloromethane (10 mL). The filtrate was concentrated, and the residue was purified by flash silica gel chromatography using a 5% mixture of ethyl acetate in hexane to give 3-(5-phenyl-4-(trifluoromethyl)isoxazol-3-yl)-7-vinyl-4H-chromeno[4,3-c]isoxazole (0.062 g, 0.151 mmol, 67% yield) as a white solid. The product had an HPLC ret. time=3.84 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=411.0.

Preparation 62H: 3-(5-Phenyl-4-(trifluoromethyl)isoxazol-3-yl)-4H-chromeno[4,3-c]isoxazole-7-carbaldehyde

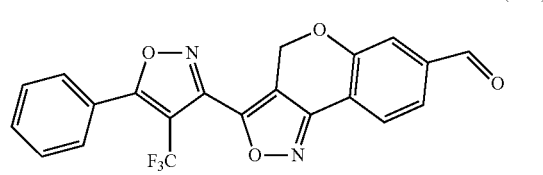

(62H)

To a mixture of 3-(5-phenyl-4-(trifluoromethyl)isoxazol-3-yl)-7-vinyl-4H-chromeno[4,3-c]isoxazole (Preparation 62G, 0.060 g, 0.146 mmol) and a 50% aqueous solution of NMO (0.030 mL, 0.146 mmol) at room temperature was added a 4% aqueous solution of osmium tetroxide (0.046 mL, 5.85 µmol). The reaction mixture was stirred at room temperature for 5 h. The intermediate diol had an HPLC ret. time=3.09 min and an LCMS $M^{+1}$=445.0. Sodium periodate (0.047 g, 0.219 mmol) was added to the homogeneous mixture followed by water (0.10 mL), and the reaction was stirred for 60 min. at room temperature. Concentration under reduced pressure afforded a tan solid residue that was then diluted with ethyl acetate (40 mL), washed with the water (10 mL), and washed with brine (10 mL). The organic layer was collected, and the aqueous layer was washed with ethyl acetate (40 mL). The combined organic layers were dried over anhydrous sodium sulfate. Concentration under reduced pressure afforded 3-(5-phenyl-4-(trifluoromethyl)isoxazol-3-yl)-4H-chromeno[4,3-c]isoxazole-7-carbaldehyde (0.057 g, 0.138 mmol, 95% yield) as a pale yellow solid. The product had an HPLC ret. time=3.49 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA.

Preparation 62I: tert-Butyl 1-((3-(5-phenyl-4-(trifluoromethyl)isoxazol-3-yl)-4H-chromeno[4,3-c]isoxazol-7-yl)methyl)azetidine-3-carboxylate

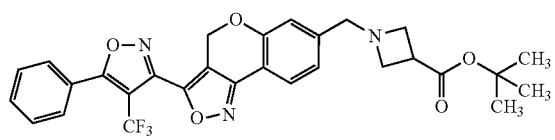

(62I)

To a mixture of 3-(5-phenyl-4-(trifluoromethyl)isoxazol-3-yl)-4H-chromeno[4,3-c]isoxazole-7-carbaldehyde (Preparation 62H, 0.057 g, 0.138 mmol), tert-butyl azetidine-3-carboxylate, acetic acid salt (0.045 g, 0.207 mmol), and acetic acid (0.016 mL, 0.276 mmol) in methanol (3.0 mL) and dichloroethane (0.900 mL) at room temperature was added titanium(IV) isopropoxide (0.081 mL, 0.276 mmol) dropwise. The resulting homogeneous reaction mixture was stirred for 90 min. To the reaction mixture was added sodium triacetoxyborohydride (0.088 g, 0.415 mmol) in one portion, and the reaction mixture was stirred at room temperature for 2 h. The reaction mixture was quenched with a saturated aqueous solution of sodium bicarbonate until the pH was slightly basic (~5 mL). The resulting emulsion was extracted with dichloromethane (3×). The organic layers were combined, dried over anhydrous sodium sulfate, and concentrated to give a pale yellow solid. The crude product was purified by flash silica gel chromatography using a mixture of ethyl acetate in hexane (20%-35%-50%) to afford tert-butyl 1-((3-(5-phenyl-4-(trifluoromethyl)isoxazol-3-yl)-4H-chromeno[4,3-c]isoxazol-7-yl)methyl)azetidine-3-carboxylate (0.044 g, 0.079 mmol, 58% yield) as an off-white solid. The product had an HPLC ret. time=3.06 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=554.2.

Example 62

A mixture of tert-butyl 1-((3-(5-phenyl-4-(trifluoromethyl)isoxazol-3-yl)-4H-chromeno[4,3-c]isoxazol-7-yl)methyl)azetidine-3-carboxylate (Preparation 62I, 0.044 g, 0.079 mmol) and TFA (3.00 mL, 39.0 mmol) was left standing at room temperature for 60 min. The TFA was removed under reduced pressure, and the residue was suspended in water, the pH was adjusted to 5 with sonication, and the resulting suspension was stirred overnight. The pH remained at 5, so the solid was collected by vacuum filtration, washed with water, and dried under reduced pressure to give a quantitative yield of the product as a white solid. The compound was suspended in methanol and sonicated for 15 min. and then stirred overnight. The product was collected by vacuum filtration, washed with methanol, and dried under reduced pressure to provide 1-((3-(5-phenyl-4-(trifluoromethyl)isoxazol-3-yl)-4H-chromeno[4,3-c]isoxazol-7-yl)methyl)azetidine-3-carboxylic acid (0.026 g, 0.052 mmol, 65% yield) as a white solid. The product had an HPLC ret. time=2.83 min.–Column: Chromolith SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=498.1. $^1$H NMR (500 MHz, DMSO-$d_6$) δ ppm 3.22 (br. s., 3H), 3.42 (br. s., 2H), 3.58 (s, 2H), 5.51 (s, 2H) 7.03 (s, 1H), 7.08 (d, J=7.77 Hz, 1H), 7.64-7.70 (m, 2H), 7.70-7.75 (m, 1H), and 7.78 (dd, J=7.21, 5.83 Hz, 3H).

Example 63

1-((3-(3-(Pyridin-2-yl)-4-(trifluoromethyl)isoxazol-5-yl)-4,5-dihydronaphtho[1,2-c]isoxazol-7-yl)methyl)azetidine-3-carboxylic acid

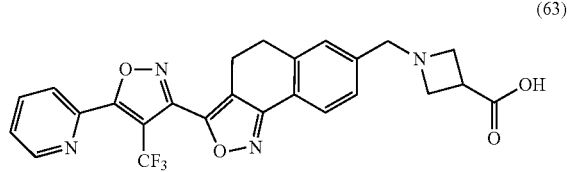 [SMILES: O=C(O)C1CN(Cc2ccc3c(c2)CCc2c-3noc2-c2noc(-c3ccccn3)c2C(F)(F)F)C1]

(63)

Preparation 63A: (Z)—N-Hydroxypicolinimidoyl chloride

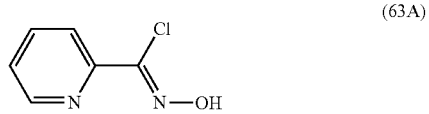

(63A)

To a solution of (E)-picolinaldehyde oxime (10.0 g, 82.0 mmol) in DMF (30 mL) at room temperature was slowly added over 30 minutes N-chlorosuccinamide (10.9 g, 82.0 mmol). An exotherm was noted during the addition. The reaction mixture was stirred overnight at room temperature, diluted with diethyl ether (300 mL), washed with water, dried over magnesium sulfate, and concentrated under reduced pressure. The residue was triturated with dichloromethane, and the resulting solid was collected by vacuum filtration and dried to give (Z)—N-hydroxypicolinimidoyl chloride (12.8 g, 51.1 mmol, 62% yield). $^1$H NMR (400 MHz, DMSO-$d_6$) δ ppm 7.49 (ddd, 1H), 7.83-7.95 (m, 2H), 8.66 (ddd, J=4.73, 1.43, 1.32 Hz, 1H), and 12.64 (s, 1H).

Preparation 63B: Ethyl 3-(pyridin-2-yl)isoxazole-5-carboxylate

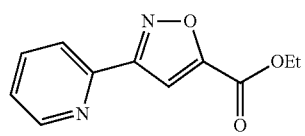

(63B)

To a suspension of the (Z)—N-hydroxypicolinimidoyl chloride (Preparation 63A, 8.00 g, 51.1 mmol) in dichloromethane (75 mL) in a three neck 1000 mL flask immersed in water and equipped with an addition funnel and thermometer was added ethyl propiolate (5.21 mL, 51.1 mmol). A mixture of triethylamine (8.55 mL, 61.3 mmol) and dichloromethane (20 mL) were added to the addition funnel and then slowly added to the reaction dropwise so that the temperature remained between 20 and 28° C. (by adding ice to the water bath). After the triethylamine was completely added, the reaction was stirred at room temperature for 2 h. The reaction mixture was diluted with ethyl acetate (350 mL), washed with water, and washed with brine. The combined aqueous layers were extracted with ethyl acetate, and the combined organic layers were dried over anhydrous magnesium sulfate. Concentration under reduced pressure followed by purification on silica gel using a 20% mixture of ethyl acetate in hexane afforded ethyl 3-(pyridin-2-yl)isoxazole-5-carboxylate (9.90 g, 45.4 mmol, 89% yield) as an off white solid. $^1$H NMR (400 MHz, CDCl$_3$) δ ppm 1.44 (t, 3H), 4.47 (q, J=7.26 Hz, 2H), 7.39 (ddd, J=7.59, 4.84, 1.21 Hz, 1H), 7.59 (s, 1H), 7.83 (td, J=7.81, 1.76 Hz, 1H), 8.13 (dt, J=7.92, 1.10 Hz, 1H), and 8.71 (ddd, J=4.84, 1.76, 0.88 Hz, 1H).

Preparation 63C: Ethyl 4-iodo-3-(pyridin-2-yl)isoxazole-5-carboxylate

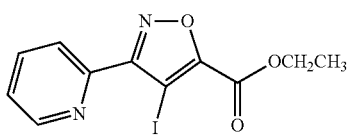

(63C)

A suspension of ethyl 3-(pyridin-2-yl)isoxazole-5-carboxylate (Preparation 63B, 6.25 g, 28.6 mmol), Palladium(II) acetate (1.61 g, 7.16 mmol) and 1-iodopyrrolidine-2,5-dione (12.9 g, 57.3 mmol) in acetonitrile (20 mL) was heated in the microwave for 30 minutes at 120° C. LC/MS analysis indicated that approximately 50% conversion had occurred. Additional 1-iodopyrrolidine-2,5-dione (12.9 g, 57.3 mmol) was added, and the reaction mixture heated for an additional 30 min. at 120° C. The reaction mixture was diluted with acetonitrile (25 mL) and filtered through a plug of Celite. The filtrate was concentrated and purified by silica gel column chromatography using an ISCO setup to afford ethyl 4-iodo-3-(pyridin-2-yl)isoxazole-5-carboxylate (4.00 g, 11.6 mmol, 41%). $^1$H NMR (400 MHz, CDCl$_3$) δ ppm 1.48 (t, 3H), 4.51 (q, J=7.04 Hz, 2H), 7.44 (ddd, J=7.48, 4.84, 1.32 Hz, 1H), 7.82-7.88 (m, 1H), 7.89-7.94 (m, 1H), and 8.81 (ddd, J=4.18, 1.32, 1.10 Hz, 1H).

Preparation 63D: Ethyl 3-(pyridin-2-yl)-4-(trifluoromethyl)isoxazole-5-carboxylate

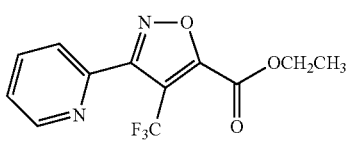

(63D)

To a stirred solution of ethyl 4-iodo-3-(pyridin-2-yl)isoxazole-5-carboxylate (Preparation 63C, 4.00 g, 11.6 mmol) in dimethylformamide (20 mL) and HMPA (5.0 mL) was added copper(I) iodide (0.443 g, 2.33 mmol) followed by methyl 2,2-difluoro-2-(fluorosulfonyl)acetate (7.40 mL, 58.1 mmol). The reaction mixture was heated at 85° C. After a few minutes at 85° C., the reaction mixture began to evolve gas and the reaction mixture turned from a pale orange solution to a dark reddish solution. The reaction mixture was diluted with ethyl acetate and washed with brine (2×). The organic layer was dried over anhydrous magnesium sulfate, concentrated, and purified by silica gel column chromatography using an ISCO setup to give ethyl 3-(pyridin-2-yl)-4-(trifluoromethyl)isoxazole-5-carboxylate (1.40 g, 4.89 mmol, 42% yield) as a yellow oil. $^1$H NMR (400 MHz, CDCl$_3$) δ ppm 1.46 (t, 3H), 4.54 (q, J=7.26 Hz, 2H), 7.45 (ddd, J=7.70, 4.84, 1.32 Hz, 1H), 7.76-7.81 (m, 1H), 7.82-7.89 (m, 1H), and 8.78 (d, J=4.18 Hz, 1H).

Preparation 63E: 3-(3-(Pyridin-2-yl)-4-(trifluoromethyl)isoxazol-5-yl)-7-vinyl-3,3a,4,5-tetrahydronaphtho[1,2-c]isoxazol-3-ol

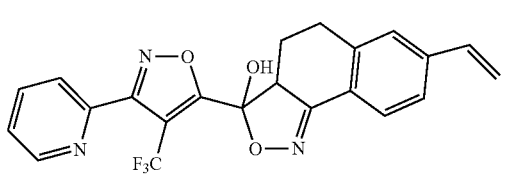

(63E)

To a stirred solution of 2,2,6,6-tetramethylpiperidine (Preparation 63D, 0.354 mL, 2.096 mmol) in anhydrous THF (1 mL) in a flame-dried flask at 0° C. was added a 2.5 M solution of butyl lithium in hexane (0.839 mL, 2.10 mmol) dropwise. The resulting dark yellowish reaction mixture was stirred for 30 min. at 0° C. To a solution of (E)-6-vinyl-3,4-dihydronaphthalen-1(2H)-one oxime (Intermediate I-1, 0.131 g, 0.699 mmol) and Hunig's Base (0.220 mL, 1.258 mmol) in anhydrous THF (2.0 mL) at 0° C. was added TMS-Cl (0.089 mL, 0.699 mmol) dropwise. The resulting off-white suspension was stirred for 60 min. at 0° C. The reaction mixture was cooled to −78° C., the above LiTMP solution was added dropwise, and the mixture was stirred for 30 min. at −78° C. To the reaction mixture was added ethyl 3-(pyridin-2-yl)-4-(trifluoromethyl)isoxazole-5-carboxylate (0.69 M in THF) (1.01 mL, 0.699 mmol), and the resulting orange mixture was then stirred at −78° C. for 30 min. The dry-ice bath was removed, and the reaction mixture was slowly warmed to 0° C. over 25 min. The reaction was quenched with a saturated aqueous solution of sodium bicarbonate (~4.0 mL), and the mixture was diluted with dichloromethane (40 mL), washed with a 1:1 mixture of saturated aqueous solution of ammonium chloride and water, dried over anhydrous sodium sulfate, and concentrated to give a dark red residue, which was purified by flash silica gel chromatography using a mixture of ethyl acetate and hexane (5%-12%-20%) to give 3-(3-(pyridin-2-yl)-4-(trifluoromethyl)isoxazol-5-yl)-7-vinyl-3,3a,4,5-tetrahydronaphtho[1,2-c]isoxazol-3-ol (0.080 g, 0.187 mmol, 26.8% yield) as a yellow oil. The product had an HPLC ret. time=2.76 min.−Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=427.9.

Preparation 63F: 3-(3-(Pyridin-2-yl)-4-(trifluoromethyl)isoxazol-5-yl)-7-vinyl-4,5-dihydronaphtho[1,2-c]isoxazole

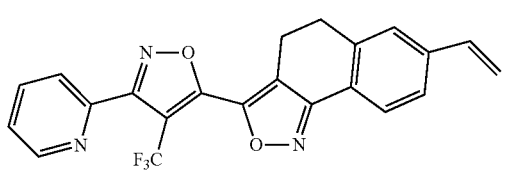

(63F)

To a stirred suspension of 3-(3-(pyridin-2-yl)-4-(trifluoromethyl)isoxazol-5-yl)-7-vinyl-3,3a,4,5-tetrahydronaphtho[1,2-c]isoxazol-3-ol (Preparation 63E, 0.081 g, 0.190 mmol) in anhydrous toluene (2.0 mL) at room temperature was added thionyl chloride (0.028 mL, 0.379 mmol) followed by pyridine (3.07 µl, 0.038 mmol). The reaction mixture was stirred at room temperature for 30 min. and then at 80° C. for 15 min. The reaction mixture was cooled to room temperature and concentrated. The solid residue was diluted with dichloromethane (30 mL), washed with a saturated aqueous solution of sodium bicarbonate (10 mL), and dried over anhydrous sodium sulfate. Concentration under reduced pressure afforded a tan solid. The crude products were combined and triturated with methanol with sonication. The solid was collected to provide 3-(3-(pyridin-2-yl)-4-(trifluoromethyl)isoxazol-5-yl)-7-vinyl-4,5-dihydronaphtho[1,2-c]isoxazole (0.098 g, 0.239 mmol, 64% yield) as a tan solid. The product had an HPLC with a ret. time=3.36 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=409.9.

Preparation 63G: 3-(3-(Pyridin-2-yl)-4-(trifluoromethyl)isoxazol-5-yl)-4,5-dihydronaphtho[1,2-c]isoxazole-7-carbaldehyde (63G)

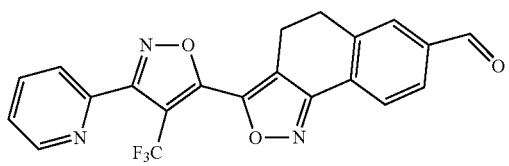

To a mixture of 3-(3-(pyridin-2-yl)-4-(trifluoromethyl)isoxazol-5-yl)-7-vinyl-4,5-dihydronaphtho[1,2-c]isoxazole (Preparation 63F, 0.098 g, 0.239 mmol) and a 50% aqueous solution of NMO (0.050 mL, 0.239 mmol) at room temperature was added a 4% aqueous solution of osmium tetroxide (0.075 mL, 9.58 µmol). The reaction mixture was stirred at room temperature over the weekend. The intermediate diol had an HPLC ret. time=2.66 min and an LCMS M$^{+1}$=443.8. Sodium periodate (0.077 g, 0.359 mmol) was added to the homogeneous mixture followed by water (0.15 mL), and the reaction was stirred for 60 min. at room temperature. Concentration under reduced pressure afforded a tan solid residue that was then diluted with ethyl acetate (40 mL), washed with the water (10 mL), and washed with brine (10 mL). The organic layer was collected, and the aqueous layer was washed with ethyl acetate (40 mL). The combined organic layers were dried over anhydrous sodium sulfate. Concentration under reduced pressure afforded 3-(3-(pyridin-2-yl)-4-(trifluoromethyl)isoxazol-5-yl)-4,5-dihydronaphtho[1,2-c]isoxazole-7-carbaldehyde (0.096 g, 0.233 mmol, 97% yield) as a pale yellow solid. The product had an HPLC ret. time=3.00 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=411.9.

Preparation 63H: tert-Butyl 1-((3-(3-(pyridin-2-yl)-4-(trifluoromethyl)isoxazol-5-yl)-4,5-dihydro-naphtho[1,2-c]isoxazol-7-yl)methyl)azetidine-3-carboxylate (63H)

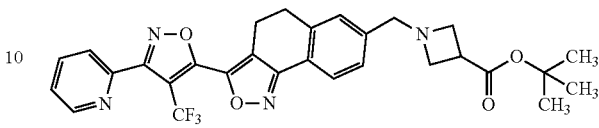

To a mixture of 3-(3-(pyridin-2-yl)-4-(trifluoromethyl)isoxazol-5-yl)-4,5-dihydronaphtho[1,2-c]isoxazole-7-carbaldehyde (Preparation 63G, 0.096 g, 0.233 mmol), tert-butyl azetidine-3-carboxylate, acetic acid salt (0.076 g, 0.350 mmol), and acetic acid (0.027 mL, 0.467 mmol) in methanol (0.6 mL) and dichloroethane (1.8 mL) at room temperature was added titanium(IV) isopropoxide (0.137 mL, 0.467 mmol) dropwise. The resulting homogeneous reaction mixture was stirred for 80 min. To the reaction mixture was added sodium triacetoxyborohydride (0.148 g, 0.700 mmol) in one portion, and the reaction mixture was stirred at room temperature for 60 min. The reaction was quenched with a saturated aqueous solution of sodium bicarbonate until the pH was slightly basic (~5 mL). The resulting emulsion was extracted with dichloromethane (3×). The organic layers were combined, dried over anhydrous sodium sulfate, and concentrated to give a pale yellow solid. The crude product was purified by flash silica gel chromatography using a mixture of ethyl acetate in hexane (20%-35%-50%) to afford tert-butyl 1-((3-(3-(pyridin-2-yl)-4-(trifluoromethyl)isoxazol-5-yl)-4,5-dihydronaphtho[1,2-c]isoxazol-7-yl)methyl) azetidine-3-carboxylate (0.096 g, 0.174 mmol, 74% yield) as an off-white solid. The product had an HPLC ret. time=2.70 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=553.0.

Example 63

A mixture of tert-butyl 1-((3-(3-(pyridin-2-yl)-4-(trifluoromethyl)isoxazol-5-yl)-4,5-dihydronaphtho[1,2-c]isoxazol-7-yl)methyl)azetidine-3-carboxylate (Preparation 63H, 0.095 g, 0.172 mmol) and TFA (3.01 ml, 39.0 mmol) was left standing at room temperature for 45 min. The TFA was removed under reduced pressure, and the residue was diluted with toluene and re-concentrated. The residue was suspended in water, the pH was adjusted to 5 with sonication, and the resulting suspension was stirred for 3.5 h. The pH remained at 5, so the solid was collected by vacuum filtration, washed with water, and dried under reduced pressure to give a quantitative yield of the product as a white solid. The compound was suspended in methanol and sonicated for 15 min. The product was collected by vacuum filtration, washed with water, and dried overnight under reduced pressure to provide 1-((3-(3-(pyridin-2-yl)-4-(trifluoromethyl)isoxazol-5-yl)-4,5-dihydronaphtho[1,2-c]isoxazol-7-yl)methyl)azetidine-3-carboxylic acid (0.067 g, 0.134 mmol, 78% yield) as a white solid. The product had an HPLC ret. time=2.41 min.–Column: Chromolith SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=497.0. $^1$H NMR (400 MHz, DMSO-d$_6$) δ ppm 3.05 (d, 2H), 3.08 (d, J=5.50 Hz, 2H), 3.23 (br. s., 3H), 3.42 (br. s., 2H), 3.60 (s, 2H), 7.33 (d, J=7.92 Hz, 1H), 7.37 (s, 1H), 7.65 (dd, J=6.71, 4.95 Hz, 1H), 7.85 (d, J=7.92 Hz, 1H), 7.95 (d, J=7.70 Hz, 1H), 8.07 (td, J=7.65, 1.43 Hz, 1H), and 8.81 (d, J=4.40 Hz, 1H).

Example 64

1-((8-Methyl-3-(5-phenyl-4-(trifluoromethyl)isoxazol-3-yl)-4,5-dihydronaphtho[1,2-c]isoxazol-7-yl)methyl)azetidine-3-carboxylic acid

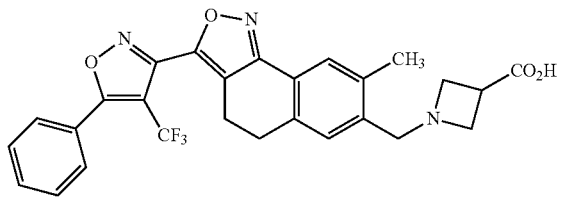

(64)

Preparation 64A: (E)-6-Methoxy-7-methyl-3,4-dihydronaphthalen-1(2H)-one oxime

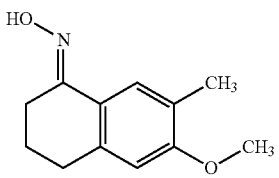

(64A)

To 6-methoxy-7-methyl-3,4-dihydronaphthalen-1(2H)-one (0.500 g, 2.63 mmol) in methanol (10 mL) were sequentially added hydroxylamine hydrochloride (0.292 g, 4.21 mmol) and sodium acetate (0.345 g, 4.21 mmol) at room temperature. The reaction mixture was heated at 60° C. for 2 h. The reaction mixture was concentrated under vacuum. The residue was dissolved in 25 mL ethyl acetate, transferred to a separating funnel and washed with water (2×10 mL). The ethyl acetate layer was dried over sodium sulfate and concentrated to give (E)-6-methoxy-7-methyl-3,4-dihydronaphthalen-1(2H)-one oxime as viscous orange-colored liquid (0.498 g, 2.43 mmol, 92%). The product had an HPLC ret. time=3.10 min (condition B). LC/MS $M^{+1}$=206.0.

Preparation 64B: 7-Methoxy-8-methyl-3-(5-phenyl-4-(trifluoromethyl)isoxazol-3-yl)-4,5-dihydronaphtho[1,2-c]isoxazole

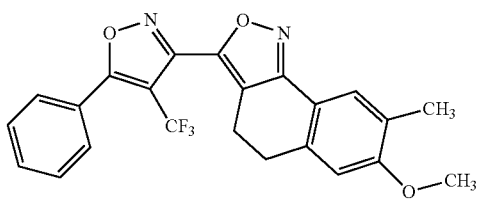

(64B)

To a fresh solution of lithium diisopropylamide made by adding butyllithium (2.92 mL, 7.30 mmol) to a stirred mixture of diisopropylamine (1.023 mL, 7.30 mmol) in 10 mL THF at 0° C. was added a solution of (E)-6-methoxy-7-methyl-3,4-dihydronaphthalen-1(2H)-one oxime (Preparation 64A, 0.500 g, 2.434 mmol) in 2 mL THF over ten minutes. After complete addition, the reaction mixture turned orange-colored and was stirred an additional 20 minutes. Methyl 5-phenyl-4-(trifluoromethyl)isoxazole-3-carboxylate (Intermediate 1-5, 0.440 g, 1.622 mmol) in 1 mL THF was then added over 5 minutes. The resulting reaction mixture turned dark brown and was stirred for 30 minutes at 0° C. The reaction mixture was allowed to warm to room temperature, quenched with methanol, and concentrated. The residue was chromatographed on silica gel eluting with 10% ethyl acetate:90% hexane. Fractions containing intermediate product were combined and concentrated under vacuum to give 0.157 g of solid material. The material was taken up in 15 mL of toluene, filtered, and dried. To the filtrate in a round-bottomed flask under nitrogen was added 1.5 mL pyridine and thionyl chloride (0.355 mL, 4.87 mmol). The mixture was heated at 110° C. for about 10 minutes. The residue was taken up in 50 mL ethyl acetate, stirred, and filtered. The filtrate was washed with 1N aqueous HCl, washed with water, dried over sodium sulfate, and concentrated in vacuo to give 7-methoxy-8-methyl-3-(5-phenyl-4-(trifluoromethyl)isoxazol-3-yl)-4,5-dihydronaphtho[1,2-c]isoxazole as an off-white solid. (0.130 g, 0.305 mmol, 19%). The product had an HPLC ret. time=4.44 min (condition B). LC/MS $M^{+1}$=427.07.

Preparation 64C: 8-Methyl-3-(5-phenyl-4-(trifluoromethyl)isoxazol-3-yl)-4,5-dihydronaphtho[1,2-c]isoxazol-7-ol

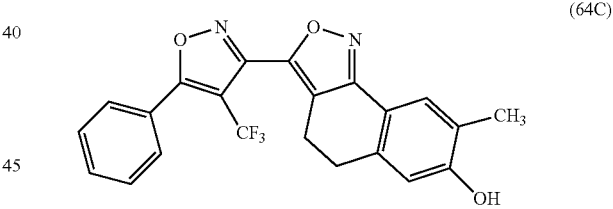

(64C)

To a stirred solution of 7-methoxy-8-methyl-3-(5-phenyl-4-(trifluoromethyl)isoxazol-3-yl)-4,5-dihydronaphtho[1,2-c]isoxazole (Preparation 64B, 0.130 g, 0.305 mmol) in dichloromethane (5 mL) at 0° C. was added boron tribromide (1.52 mL, 1.52 mmol). The reaction mixture was stirred at 0° C. for 1 h and then allowed to warm to room temperature and stirred overnight. The reaction mixture was partitioned between dichloromethane (25 mL) and water (25 mL). The dichloromethane extract was washed with a saturated aqueous solution of sodium bicarbonate (2×25 mL), washed with brine, dried over sodium sulfate, and concentrated. This crude product was filtered through a short silica gel pad, and the filtrate was concentrated to give 8-methyl-3-(5-phenyl-4-(trifluoromethyl)isoxazol-3-yl)-4,5-dihydronaphtho[1,2-c]isoxazol-7-ol (0.121 g, 0.293 mmol, 96%) as a tan solid. The product had an HPLC ret. time=4.08 min (condition B). LC/MS $M^{+1}$=413.30.

Preparation 64D: 8-Methyl-3-(5-phenyl-4-(trifluoromethyl)isoxazol-3-yl)-4,5-dihydronaphtho[1,2-c]isoxazol-7-yl trifluoromethanesulfonate

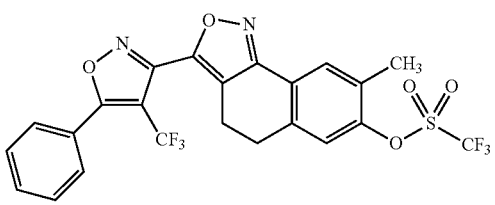

(64D)

Trifluoromethanesulfonic anhydride (0.074 mL, 0.440 mmol) was added to a solution of 8-methyl-3-(5-phenyl-4-(trifluoromethyl)isoxazol-3-yl)-4,5-dihydronaphtho[1,2-c]isoxazol-7-ol (Preparation 64C, 0.121 g, 0.293 mmol) in pyridine (5 mL) at 0° C. over a period of 5 min. The reaction mixture was stirred at 0° C. for ten minutes and then at room temperature overnight. The reaction mixture was concentrated, and the yellowish-brown residue was partitioned between ethyl acetate (10 mL) and water (10 mL). The ethyl acetate layer was washed sequentially with 1N aqueous HCl (10 mL), saturated aqueous NaHCO$_3$ (10 mL), and brine (10 mL). The organic layer was collected, dried over sodium sulfate, and concentrated. The residue was purified by silica gel column chromatography eluting with a mixture of 15% ethyl acetate:85% hexane to yield 8-methyl-3-(5-phenyl-4-(trifluoromethyl)isoxazol-3-yl)-4,5-dihydronaphtho[1,2-c]isoxazol-7-yl trifluoromethanesulfonate as a tan solid (0.123 g, 0.226 mmol, 77%). The product had an HPLC ret. time=4.52 min (condition B). LC/MS M$^{+1}$=545.2.

Preparation 64E: 8-Methyl-3-(5-phenyl-4-(trifluoromethyl)isoxazol-3-yl)-7-vinyl-4,5-dihydronaphtho[1,2-c]isoxazole

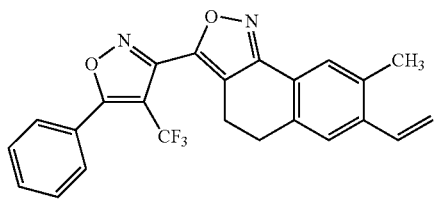

(64E)

A mixture of 8-methyl-3-(5-phenyl-4-(trifluoromethyl)isoxazol-3-yl)-4,5-dihydronaphtho[1,2-c]isoxazol-7-yl trifluoromethanesulfonate (Preparation 64D, 0.120 g, 0.220 mmol) and lithium chloride (0.014 mL, 0.661 mmol) in dioxane (15 mL) was degassed with nitrogen for 15 minutes. Tributyl(vinyl)stannane (0.077 g, 0.242 mmol) was added followed by the addition of tetrakis(triphenylphosphine) palladium(0) (0.025 g, 0.022 mmol) at room temperature. The resulting reaction mixture was heated at 100° C. overnight. The reaction mixture was cooled to room temperature and filtered. The brownish residue was washed with ethyl acetate (3×10 mL), and the combined filtrates were concentrated under reduce pressure. The residue was chromatographed on silica gel eluting with a mixture of 10% ethyl acetate and 90% hexane to yield 8-methyl-3-(5-phenyl-4-(trifluoromethyl)isoxazol-3-yl)-7-vinyl-4,5-dihydronaphtho[1,2-c]isoxazole (0.088 g, 0.137 mmol, 62% yield) as a tan viscous liquid. The product had an HPLC ret. time=4.58 min (condition B). LC/MS M$^{+1}$=423.30.

Preparation 64F: 8-Methyl-3-(5-phenyl-4-(trifluoromethyl)isoxazol-3-yl)-4,5-dihydronaphtho[1,2-c]isoxazole-7-carbaldehyde

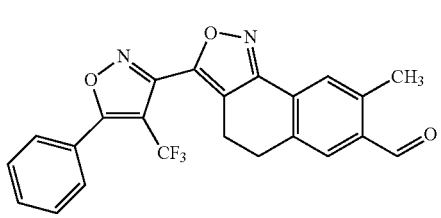

(64F)

To a solution of 8-methyl-3-(5-phenyl-4-(trifluoromethyl)isoxazol-3-yl)-7-vinyl-4,5-dihydronaphtho[1,2-c]isoxazole (Preparation 64E, 0.058 g, 0.137 mmol) in dichloromethane (10 mL) at −78° C. was passed ozone from an ozone generator until the solution turned a deep blue. The reaction mixture then was purged with oxygen until the blue color disappeared, then with nitrogen for five minutes. The reaction mixture was allowed to warm to room temperature and triethylamine (0.019 mL, 0.137 mmol) was added. The reaction mixture was stirred at room temperature for fifteen minutes and then concentrated under vacuum to give 8-methyl-3-(5-phenyl-4-(trifluoromethyl)isoxazol-3-yl)-4,5-dihydronaphtho[1,2-c]isoxazole-7-carbaldehyde as a tan solid (0.043, 0.101 mmol, 74%). The product had an HPLC ret. time=3.43 min (condition B). LC/MS M$^{+1}$=425.10.

Example 64

To a solution of 8-methyl-3-(5-phenyl-4-(trifluoromethyl)isoxazol-3-yl)-4,5-dihydronaphtho[1,2-c]isoxazole-7-carbaldehyde (Preparation 64F, 0.043 g, 0.101 mmol) in MeOH (5.00 mL) and 1,2-dichloroethane (5 mL) was added azetidine-3-carboxylic acid (0.012 g, 0.122 mmol) followed by 2 drops of acetic acid (5.37 mg, 0.089 mmol). The reaction mixture was heated at 60° C. for one and a half hours. The reaction mixture was cooled to room temperature, and sodium cyanotrihydroborate (7.64 mg, 0.122 mmol) was added. The reaction mixture was then stirred at room temperature for 15 minutes. The reaction mixture was concentrated under reduced pressure. The crude residue was partitioned between dichloromethane and water. The dichloromethane extract was concentrated, and the crude product residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 24 mg of the product as a white solid which was further triturated with methanol and diethyl ether to give 1-((8-methyl-3-(5-phenyl-4-(trifluoromethyl)isoxazol-3-yl)-4,5-dihydronaphtho[1,2-c]isoxazol-7-yl)methyl)azetidine-3-carboxylic acid as a white solid. (8.0 mg, 0.016 mmol, 15%). The product had an HPLC ret. time=3.47 min (condition B). LC/MS M$^{+1}$=510.20. $^1$H NMR (400 MHz, CD$_3$OD) δ ppm 7.91 (1H, s), 7.80 (2H, d, J=7.26

Hz), 7.58-7.75 (3H, m), 7.44 (1H, s), 4.43 (2H, br. s.), 4.21 (4H, br. s.), 3.40-3.63 (1H, m), 3.10 (4H, s), and 2.51 (3H, s).

Example 65

(3S)-1-(2-Hydroxy-2-(8-methyl-3-(5-phenyl-4-(trifluoromethyl)isoxazol-3-yl)-4,5-dihydronaphtho[1,2-c]isoxazol-7-yl)ethyl)piperidine-3-carboxylic acid (65)

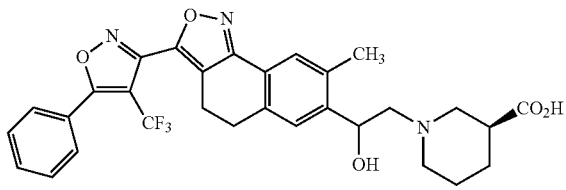

Preparation 65A: 8-Methyl-7-(oxiran-2-yl)-3-(5-phenyl-4-(trifluoromethyl)isoxazol-3-yl)-4,5-dihydronaphtho[1,2-c]isoxazole (65A)

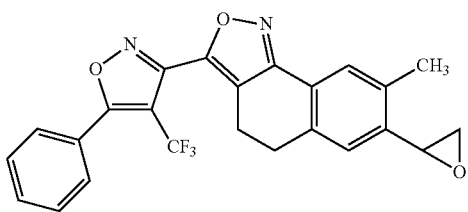

3-Chloroperoxybenzoic acid (0.163 g, 0.947 mmol) was added slowly to a stirred solution of 8-methyl-3-(5-phenyl-4-(trifluoromethyl)isoxazol-3-yl)-7-vinyl-4,5-dihydronaphtho[1,2-c]isoxazole (Preparation 64E, 0.200 g, 0.473 mmol) in dichloromethane at room temperature. The reaction mixture was stirred at room temperature under a nitrogen atmosphere overnight, concentrated under vacuum, and the residue chromatographed using flash silica gel chromatography eluting with a 10-20% mixture of ethyl acetate and hexane (10%-20%) to give 8-methyl-7-(oxiran-2-yl)-3-(5-phenyl-4-(trifluoromethyl)isoxazol-3-yl)-4,5-dihydronaphtho[1,2-c]isoxazole as a white solid (0.156 g, 0.397 mmol, 75%). The product had an HPLC ret. time=4.57 min. (condition B). LC/MS $M^{+1}$=439.90.

Preparation 65B: (3S)-Ethyl-1-(2-hydroxy-2-(8-methyl-3-(5-phenyl-4-(trifluoromethyl)isoxazol-3-yl)-4,5-dihydronaphthol[1,2-c]isoxazol-7-yl)ethyl)piperidine-3-carboxylate (65B)

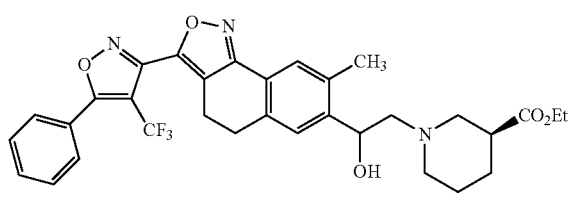

A stirred mixture of 8-methyl-7-(oxiran-2-yl)-3-(5-phenyl-4-(trifluoromethyl)isoxazol-3-yl)-4,5-dihydronaphtho[1,2-c]isoxazole (Preparation 65A, 0.200 g, 0.456 mmol), (S)-ethyl piperidine-3-carboxylate (0.072 g, 0.456 mmol), and 4-dimethylaminopyridine (0.011 g, 0.091 mmol) in 2-propanol (5.0 mL) and dioxane (1.0 mL) was heated at 50° C. for 24 hours. The reaction mixture was concentrated under vacuum, and the residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give (3S)-ethyl-1-(2-hydroxy-2-(8-methyl-3-(5-phenyl-4-(trifluoromethyl)isoxazol-3-yl)-4,5-dihydronaphthol[1,2-c]isoxazol-7-yl)ethyl)piperidine-3-carboxylate as a viscous tan liquid (0.025 g, 0.042 mmol, 9%). The product had an HPLC ret. time=3.68 min. (condition B). LC/MS $M^{+1}$=596.07.

Example 65

A mixture of (3S)-ethyl 1-(2-hydroxy-2-(8-methyl-3-(5-phenyl-4-(trifluoromethyl)isoxazol-3-yl)-4,5-dihydronaphtho[1,2-c]isoxazol-7-yl)ethyl)piperidine-3-carboxylate (Preparation 65B, 0.025 g, 0.042 mmol) and 6N aqueous hydrochloric acid (1.40 mL, 8.39 mmol) in dioxane (5.0 mL) was stirred overnight at 50° C. The reaction mixture was concentrated in vacuo. The residue was dissolved in ethyl acetate, and the ethyl acetate solution washed with saturated sodium bicarbonate solution, water and brine. The ethyl acetate extract was separated, dried over sodium sulfate, filtered, concentrated and dried under vacuum to give 0.018 g product as an off-white solid. The crude product was sonicated with methanol and left to stand overnight. A solid precipitated out of the methanol solution. The supernatant was filtered off, and the residue was dried to give (3S)-1-(2-hydroxy-2-(8-methyl-3-(5-phenyl-4-(trifluoromethyl)isoxazol-3-yl)-4,5-dihydronaphthol[1,2-c]isoxazol-7-yl)ethyl)piperidine-3-carboxylic acid as an off-white solid. [0.010 g, 0.018 mmol, 42%]. The product had an HPLC ret. time=3.55 min. (condition B). LC/MS $M^{+1}$=568.01. $^1$H NMR (400 MHz, CD$_3$OD) δ ppm 7.85-8.12 (1H, m), 7.75-7.87 (1H, m), 7.53-7.73 (5H, m), 4.18-4.30 (1H, m), 3.42-3.88 (4H, m), 3.19-3.50 (4H, m), 3.09 (3H, s), 2.27-2.63 (1H, m), and 1.54-1.88 (6H, m).

Example 66

1-((5,5-Difluoro-3-(5-phenyl-4-(trifluoromethyl)isoxazol-3-yl)-4,5-dihydronaphtho[1,2-c]isoxazol-7-yl)methyl)azetidine-3-carboxylic acid (66)

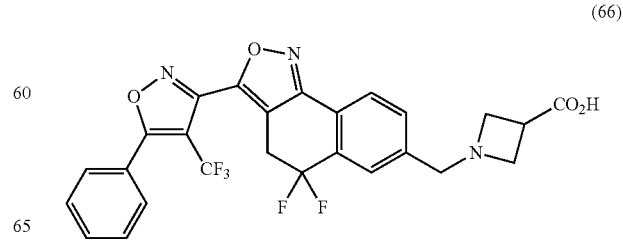

Preparation 66A: 7-Methoxy-3-(5-phenyl-4-(trifluoromethyl)isoxazol-3-yl)-4,5-dihydronaphtho[1,2-c]isoxazole

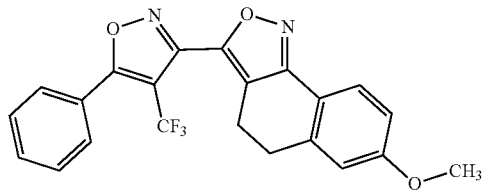

(66A)

To a fresh solution of lithium diisopropylamide made by adding butyllithium (6.64 mL, 16.6 mmol) to a stirred mixture of diisopropylamine (2.33 mL, 16.6 mmol) in THF (10 mL) at 0° C. was added a solution of (E)-6-methoxy-3,4-dihydronaphthalen-1(2H)-one oxime (I-2, 1.06 g, 5.53 mmol) in THF (4 mL) over 2 minutes. After complete addition, the reaction mixture turned orange-colored and was stirred for an additional 20 minutes. Methyl 5-phenyl-4-(trifluoromethyl)isoxazole-3-carboxylate (I-5, 1.00 g, 3.69 mmol) in THF (4 mL) was then added over 5 minutes. The resulting reaction mixture turned dark brown and was stirred for thirty minutes at 0° C. The reaction mixture was allowed to warm to room temperature, quenched with conc. sulfuric acid (1.0 mL), and concentrated under vacuum. The residue was taken up in toluene (25 mL), filtered, and dried. To the filtrate was added pyridine (1.5 mL) and thionyl chloride (0.234 mL, 3.20 mmol), and the reaction mixture was heated at 110° C. for about 20 minutes. The residue was taken up in ethyl acetate (50 mL), stirred, and filtered. The filtrate was concentrated in vacuo to give a dark brown crude product mixture. This crude product was chromatographed on silica gel eluting with a 10% mixture of ethyl acetate in hexane to give 7-Methoxy-3-(5-phenyl-4-(trifluoromethyl)isoxazol-3-yl)-4,5-dihydronaphtho[1,2-c]isoxazole (416 mg, 3.69 mmol, 27%) as a yellowish solid. The product had an HPLC ret. time=4.32 min (condition B). LC/MS $M^{+1}$=413.15.

Preparation 66B: 7-Methoxy-3-(5-phenyl-4-(trifluoromethyl)isoxazol-3-yl)naphtho[1,2-c]isoxazol-5(4H)-one

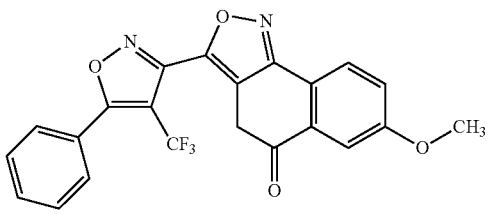

(66B)

To a stirred solution of 7-methoxy-3-(5-phenyl-4-(trifluoromethyl)isoxazol-3-yl)-4,5-dihydronaphtho[1,2-c]isoxazole (Preparation 66A, 0.103 g, 0.250 mmol) and cuprous iodide (0.476 mg, 0.0025 mmol) in acetonitrile (2.0 mL) at room temperature [note: the reactant was sparingly soluble in acetonitrile, so dimethyl formamide (0.5 ml) was added to solubilize the reactant] was added t-butyl hydroperoxide (0.250 mL, 1.50 mmoL). The reaction mixture was heated at 50° C. overnight. An additional aliquot of t-butyl hydroperoxide (0.250 mL, 1.50 mmol) was added, and the reaction was heated at 50° C. overnight. A small change in the amount of product was noted, so an additional aliquot of t-butyl hydroperoxide (0.250 mL, 1.50 mmol) was added. The reaction mixture was heated at 50° C. overnight. The reaction mixture was concentrated in vacuo, and the crude mixture was chromatographed using reverse-phase preparative HPLC to give the product [39 mg, 0.094 mmol, 36% yield] as a tan solid. The product had an HPLC ret. time=3.90 min. (condition B). LC/MS $M^{+1}$=427.10.

Preparation 66C: 5,5-Difluoro-7-Methoxy-3-(5-phenyl-4-(trifluoromethyl)isoxazol-3-yl)-4,5-naphtho[1,2-c]isoxazole

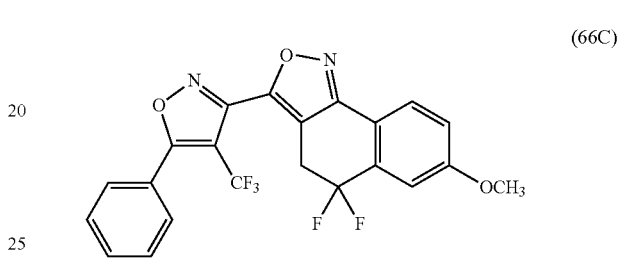

(66C)

(Diethylamino)sulfur trifluoride (9.30 mL, 0.70 mmol) was slowly added to a stirred solution of 7-methoxy-3-(5-phenyl-4-(trifluoromethyl)isoxazol-3-yl)naphtho[1,2-c]isoxazol-5(4H)-one (Preparation 66B, 0.10 g, 0.23 mmol) in 1,2-dichloroethane (25 mL) at room temperature. The reaction mixture was heated at 60° C. for 24 h. The reaction mixture was cooled, diluted with dichloromethane (100 mL), and poured into ice-water with vigorous stirring. The dichloromethane extract was washed with saturated aqueous sodium bicarbonate solution (100 mL), brine (100 mL), dried over sodium sulfate, and concentrated. The residue was triturated with methanol and filtered to give 44 g of a brown viscous liquid. The crude product was chromatographed using reverse-phase preparative HPLC (Column: LUNA 5 u C18, 21×100 mm:Solvent MeOH(B)—H₂O(A), 0.1% TFA: 0% B-100% B, Gradient Time 12 min, Stop Time 20 min, Flow Rate 20 ml/min, Wavelength 220 nM) to give 5,5-difluoro-7-methoxy-3-(5-phenyl-4-(trifluoromethyl)isoxazol-3-yl)-4,5-naphtho[1,2-c]isoxazole (32 mg, 0.230 mmol, 30%) as a tan viscous liquid. The product had an HPLC ret. time=3.66 min. (condition B). LC/MS $M^{+1}$=449.30.

Preparation 66D: 5,5-Difluoro-3-(5-phenyl-4-(trifluoromethyl)isoxazol-3-yl)-4,5-naphtho[1,2-c]isoxazol-7-ol

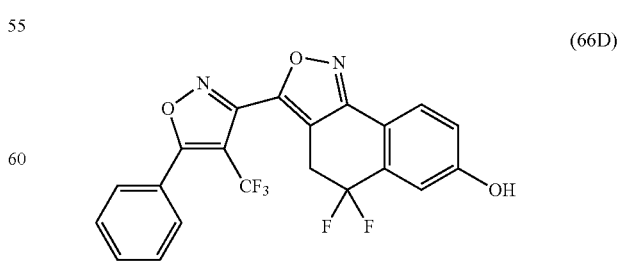

(66D)

To a stirred solution of 5,5-difluoro-7-methoxy-3-(5-phenyl-4-(trifluoromethyl)isoxazol-3-yl)-4,5-dihydronaphtho

[1,2-c]isoxazole (66C, 0.032 g, 0.071 mmol) in dichloromethane (5.0 mL) at 0° C. was added boron tribromide (0.357 mL, 0.357 mmol). The reaction mixture was stirred at 0° C. for 1 h, warmed to room temperature, and stirred overnight. The reaction mixture was partitioned between dichloromethane (25 mL) and water (25 mL). The dichloromethane extract was washed with a saturated aqueous sodium bicarbonate solution (2×25 mL), washed with brine (25 mL), dried over sodium sulfate, and concentrated to give 25 mg of the crude product. The product was filtered through a short silica gel pad, and the filtrate was concentrated to give 5,5-difluoro-3-(5-phenyl-4-(trifluoromethyl)isoxazol-3-yl)-4,5-naphtho[1,2-c]isoxazol-7-ol as a tan solid [23 mg, 0.053 mmol, 74%]. The product had an HPLC ret. time=2.67 min (condition B). LC/MS $M^{+1}$=435.30.

Preparation 66E: 5,5-Difluoro-3-(5-phenyl-4-(trifluoromethyl)isoxazol-3-yl)-4,5-naphtho[1,2-c]isoxazol-7-yl trifluoromethanesulfonate

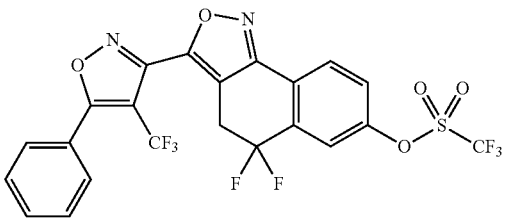

(66E)

Trifluoromethanesulfonic anhydride (0.012 mL, 0.069 mmol) was added to a solution of 5,5-difluoro-3-(5-phenyl-4-(trifluoromethyl)isoxazol-3-yl)-4,5-dihydronaphtho[1,2-c]isoxazol-7-ol (Preparation 66D, 0.020 g, 0.046 mmol) in pyridine (5.0 mL) at 0° C. over a period of 5 min. The reaction mixture was stirred at 0° C. for ten minutes, warmed to room temperature, and stirred overnight. The reaction mixture was concentrated, and the yellowish-brown residue was partitioned between ethyl acetate (10 mL) and water (10 mL). The ethyl acetate layer was collected, washed with 1N aqueous Hydrochloric acid (10 mL), saturated aqueous solution of sodium bicarbonate (10 mL), brine (10 mL), and dried over sodium sulfate. Concentration followed by purification by silica gel chromatography eluting with a mixture of ethyl acetate and hexane (10%-20%) afforded 5,5-difluoro-3-(5-phenyl-4-(trifluoromethyl)isoxazol-3-yl)-4,5-dihydronaphtho[1,2-c]isoxazol-7-yl trifluoromethanesulfonate (0.024 g, 0.042 mmol, 92% yield) as a viscous liquid. The product had an HPLC ret. time=3.34 min. (condition B). LC/MS $M^{+1}$=566.3, 568.4.

Preparation 66F: 5,5-Difluoro-3-(5-phenyl-4-(trifluoromethyl)isoxazol-3-yl)-7-vinyl-4,5-naphtho[1,2-c]isoxazole

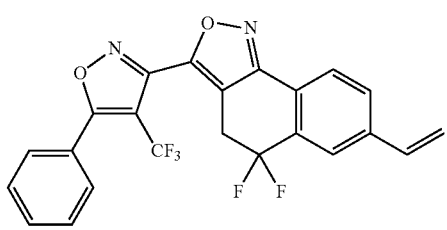

(66F)

A mixture of 5,5-difluoro-3-(5-phenyl-4-(trifluoromethyl)isoxazol-3-yl)-4,5-dihydronaphtho[1,2-c]isoxazol-7-yl trifluoromethanesulfonate (Preparation 66E, 0.024 g, 0.042 mmol) and lithium chloride (2.60 μL, 0.127 mmol) in dioxane (5.0 mL) was degassed with nitrogen for 15 minutes. To the reaction mixture was added tributyl(vinyl)stannane (0.015 g, 0.047 mmol) followed by tetrakis(triphenylphosphine)palladium(0) (4.90 mg, 4.24 μmol) at room temperature. The resulting reaction mixture was heated at 100° C. overnight. The reaction mixture was cooled to room temperature and filtered. The brownish residue was washed with ethyl acetate (3×10 mL), and the combined filtrates were concentrated in vacuo. The residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to yield 5,5-difluoro-3-(5-phenyl-4-(trifluoromethyl)isoxazol-3-yl)-7-vinyl-4,5-dihydronaphtho[1,2-c]isoxazole (0.012 g, 0.027 mmol, 63.7% yield) as a tan viscous liquid. The product had an HPLC ret. time=3.77 min. (condition B). LC/MS $M^{+1}$=444.20. $^1$H NMR (500 MHz, CD$_3$OD) δ ppm 7.75 (1H, d, J=7.93 Hz), 7.55-7.68 (2H, m), 7.38-7.57 (4H, m), 7.18-7.38 (1H, m), 6.63 (1H, dd, J=17.70, 10.99 Hz), 5.75 (1H, d, J=17.70 Hz), 5.19 (1H, d, J=10.99 Hz), and 2.85-3.02 (2H, m).

Preparation 66G: 5,5-Difluoro-3-(5-phenyl-4-(trifluoromethyl)isoxazol-3-yl)-4,5-naphtho[1,2-c]isoxazole-7-carbaldehyde

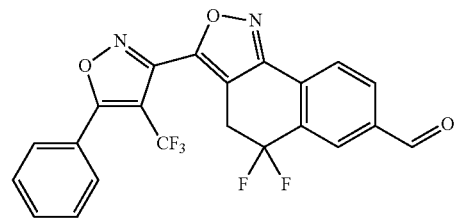

(66G)

To a solution of 5,5-difluoro-3-(5-phenyl-4-(trifluoromethyl)isoxazol-3-yl)-7-vinyl-4,5-dihydronaphtho[1,2-c]isoxazole (Preparation 66F, 0.012 g, 0.027 mmol) in dichloromethane (10 mL) at −78° C. was passed ozone from an ozone generator until the solution turned a deep blue. The reaction mixture then was purged with oxygen until the blue color disappeared and then with nitrogen for five minutes. The reaction mixture was allowed to warm to room temperature and triethylamine (3.78 μL, 0.027 mmol) was added. The reaction mixture was stirred at room temperature for fifteen minutes and then concentrated under vacuum to give 5,5-difluoro-3-(5-phenyl-4-(trifluoromethyl)isoxazol-3-yl)-4,5-naphtho[1,2-c]isoxazole-7-carbaldehyde [0.011 g, 0.025 mmol, 95%] as a tan solid. The product had an HPLC ret. time=3.15 min. (condition B). LC/MS $M^{+1}$=447.26.

Example 66

1-((5,5-Difluoro-3-(5-phenyl-4-(trifluoromethyl)isoxazol-3-yl)-4,5-dihydronaphtho[1,2-c]isoxazol-7-yl)methyl)azetidine-3-carboxylic acid To a solution of 5,5-difluoro-3-(5-phenyl-4-(trifluoromethyl)isoxazol-3-yl)-4,5-dihydronaphtho[1,2-c]isoxazole-7-carbaldehyde (66G, 0.015 g, 0.034 mmol) in methanol (2.0 mL) and 1,2-dichloroethane (2.0 mL) was added azetidine- 3-carboxylic acid (4.08 mg, 0.040 mmol) followed by 2 drops of acetic acid (1.78 mg, 0.030 mmol). The reaction mixture was heated at 60° C. for 1.5 h. The reaction mixture was cooled to room temperature, and sodium cyanotrihydroborate (2.53 mg, 0.040 mmol) was added. The reaction mixture was then stirred at room temperature for 15 minutes. The reaction mixture was concentrated in vacuo, and the crude residue was partitioned between dichloromethane and water. The dichloromethane extract was concentrated, and the residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 1-((5,5-difluoro-3-(5-phenyl-4-(trifluoromethyl)isoxazol-3-yl)-4,5-naphtho[1,2-c]isoxazol-7-yl)methyl)azetidine-3-carboxylic acid TFA [2.5 mg, 0.500 mmol, 14%] as a tan solid. The product had an HPLC ret. time=3.44 min (condition B). LC/MS M$^{+1}$=630.30. $^1$H NMR (500 MHz, CD$_3$OD) δ ppm 7.95 (1H, d, J=7.93 Hz), 7.57-7.79 (3H, m), 7.49-7.64 (1H, m), 7.27-7.62 (3H, m), 4.45 (2H, s), 4.14-4.40 (4H, m), 3.84-4.14 (2H, m), and 3.62 (1H, t, J=8.24 Hz).

Example 67

1-((8-Fluoro-3-(3-phenyl-4-(trifluoromethyl)isoxazol-5-yl)-4,5-dihydronaphtho[1,2-c]isoxazol-7-yl)azetidine-3-carboxylic acid (67)

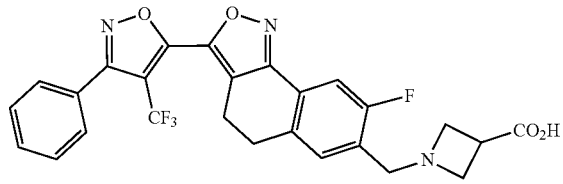

Preparation 67A: Methyl 3fluoro-5-morpholino-7,8-dihydronaphthalene-2-carboxylate (67A)

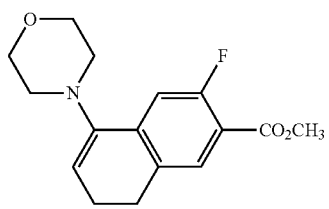

To a mixture of methyl 3fluoro-5-oxo-5,6,7,8-tetrahydronaphthalene-2-carboxylate (0.155 g, 0.698 mmol) and morpholine (0.304 mL, 3.49 mmol) in toluene (5.0 mL) at 0° C. was added titanium(IV) chloride (1M in toluene) (0.384 mL, 0.384 mmol) dropwise. The ice-bath was removed, and the orange, heterogeneous reaction mixture was stirred at room temperature for 16 hours. The heterogeneous, orange reaction mixture was filtered under reduced pressure through a pad of Celite which was then rinsed with toluene (3×10 mL). The pale yellow filtrate was concentrated under reduced pressure to give methyl 3fluoro-5-morpholino-7,8-dihydronaphthalene-2-carboxylate (0.122 g, 0.419 mmol, 60.0% yield). The product had an LC/MS M$^{+1}$=292.2.

Preparation 67B: Methyl 8-fluoro-3-hydroxy-3-(3-phenyl-4-(trifluoromethyl)isoxazol-5-yl)-3,3a,4,5-dihydronaphtho[1,2-c]isoxazole-7-carboxylate (67B)

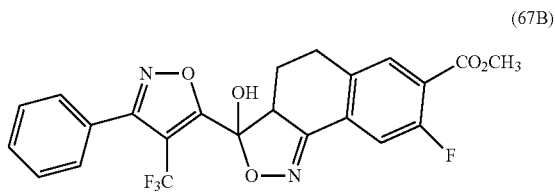 [SMILES: COC(=O)c1cc2c(cc1F)C1=NOC(O)(c3onc(-c4ccccc4)c3C(F)(F)F)C1CC2]

To a homogeneous solution of methyl 3fluoro-5-morpholino-7,8-dihydronaphthalene-2-carboxylate (Preparation 67A, 0.122 g, 0.419 mmol) and triethylamine (0.116 mL, 0.838 mmol) in acetonitrile (5.0 mL) at 0° C. was added a solution of 3-phenyl-4-(trifluoromethyl)isoxazole-5-carbonyl fluoride (I-4, 0.109 g, 0.419 mmol) in acetonitrile (1.0 mL). The reaction mixture was stirred at 0° C. for 2.5 hours, at room temperature for 2 hours, and then overnight at room temperature. A homogeneous solution of hydroxylamine hydrochloride (0.116 g, 1.68 mmol) and sodium acetate (0.137 g, 1.675 mmol) in water (0.272 mL, 15.1 mmol) was added, and the reaction mixture was heated at 45° C. for 60 min. The reaction mixture was diluted with dichloromethane, washed with water, and dried over anhydrous sodium sulfate. Concentration followed by purification by silica gel chromatography eluting with a 10% mixture of ethyl acetate in hexane afforded Methyl 8-fluoro-3-hydroxy-3-(3-phenyl-4-(trifluoromethyl)isoxazol-5-yl)-3,3a,4,5-dihydronaphtho[1,2-c]isoxazole-7-carboxylate (0.055 g, 0.115 mmol, 27%) as a white solid. The product had an LC/MS M$^{+1}$=477.07.

Preparation 67C: Methyl 8-fluoro-3-(3-phenyl-4-(trifluoromethyl)isoxazol-5-yl)-4,5-dihydronaphtho[1,2-c]isoxazole-7-carboxylate (67C)

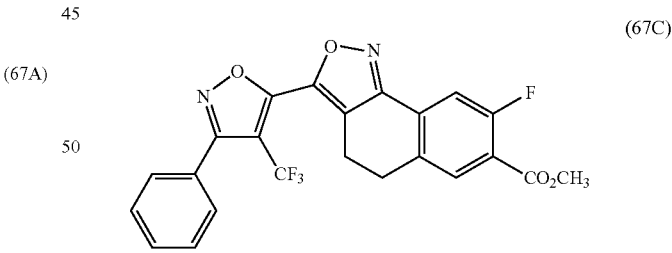

To a stirred suspension of methyl 8-fluoro-3-hydroxy-3-(3-phenyl-4-(trifluoromethyl)isoxazol-5-yl)-3,3a,4,5-tetrahydronaphtho[1,2-c]isoxazole-7-carboxylate (Preparation 67B, 0.055 g, 0.115 mmol) in anhydrous toluene (1.0 mL) at room temperature was added pyridine (0.2 mL) followed by thionyl chloride (0.014 mL, 0.196 mmol). The reaction mixture was stirred at room temperature for 15 min. and then at 80° C. for 15 min. The reaction mixture was cooled to room temperature and concentrated. The solid residue was partitioned between dichloromethane and a saturated aqueous solution of sodium bicarbonate. The dichloromethane extract was collected and dried over anhydrous sodium sulfate. Concentration under reduced pressure afforded methyl 8-fluoro-3-(3-phenyl-4-(trifluoromethyl)isoxazol-5-yl)-4,5-dihydronaphtho[1,2-c]isoxazole-7-carboxylate [0.050 g, 0.109 mmol, 94%] as an off white solid product. The product had an HPLC ret. time=3.28 min. (condition B). LC/MS M$^{+1}$=459.1.

Preparation 67D: 8-Fluoro-3-(3-phenyl-4-(trifluoromethyl)isoxazol-5-yl)-4,5-dihydronaphtho[1,2-c]isoxazole-7-carboxylic acid

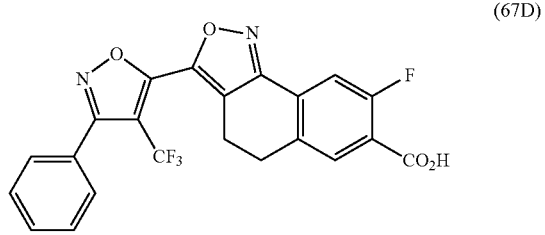 [SMILES: O=C(O)c1cc2c(cc1F)-c1noc(-c3onc(-c4ccccc4)c3C(F)(F)F)c1CC2]

(67D)

A mixture of methyl 8-fluoro-3-(3-phenyl-4-(trifluoromethyl)isoxazol-5-yl)-4,5-dihydronaphtho[1,2-c]isoxazole-7-carboxylate (Preparation 67C, 0.050 g, 0.109 mmol) and lithium hydroxide monohydrate (0.005 g, 0.119 mmol) in THF (4.0 mL) and water (4 mL) was stirred at room temperature for 4 h. An additional amount of lithium hydroxide monohydrate (0.005 g, 0.119 mmol) was added and the contents stirred at room temperature for 2 h. The reaction mixture was concentrated under vacuum and the residue was partitioned between ethyl acetate (3×10 mL) and water (5.0 mL). The ethyl acetate extracts were combined, dried, and concentrated to give 8-fluoro-3-(3-phenyl-4-(trifluoromethyl)isoxazol-5-yl)-4,5-dihydronaphtho[1,2-c]isoxazole-7-carboxylic acid as a white solid. [40 mg, 0.090 mmol, 83%]. The product had an HPLC ret. time=4.15 min. (condition B). LC/MS M$^{+1}$=445.0.

Preparation 67E: 8-Fluoro-3-(3-phenyl-4-(trifluoromethyl)isoxazol-5-yl)-4,5-dihydronaphtho[1,2-c]isoxazol-7-yl)methanol

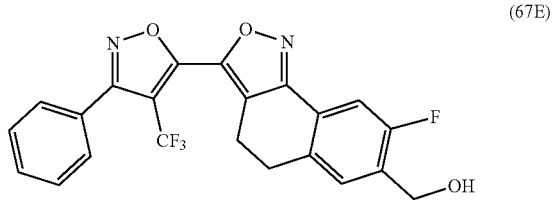 [SMILES: OCc1cc2c(cc1F)-c1noc(-c3onc(-c4ccccc4)c3C(F)(F)F)c1CC2]

(67E)

To a solution of 8-fluoro-3-(3-phenyl-4-(trifluoromethyl)isoxazol-5-yl)-4,5-dihydronaphtho[1,2-c]isoxazole-7-carboxylic acid (Preparation 67D, 0.040 g, 0.090 mmol) in THF (5.0 mL) at 0° C. was added 4-methylmorpholine (0.015 mL, 0.135 mmol) followed by isobutyl chloroformate (0.018 mL, 0.135 mmol) over 5 min. The resulting suspension was stirred at 0° C. for 15 min. The suspension was then added to a suspension of sodium borohydride (6.13 mg, 0.162 mmol) in THF (10 mL) and methanol (3 mL) at −78° C. via a 10 mL syringe. The reaction mixture was stirred at −78° C. for 120 min. The reaction mixture was slowly warmed to ~−20° C. and quenched with a 1:9 mixture of acetic acid in water. The reaction mixture was then stirred at room temperature for 60 min. The solvent was removed under reduced pressure, and the residue was diluted with ethyl acetate (120 mL), washed with water (20 mL), saturated aqueous solution of sodium bicarbonate (2×20 mL), and brine (20 mL). The organic layer was collected, the aqueous layers were back-extracted with ethyl acetate (100 mL), and the combined organic layers were dried over anhydrous sodium sulfate. The organic layer was concentrated in vacuo to give 53 mgs of the crude product mixture. This mixture was chromatographed on silica gel eluting with ethyl acetate and hexane (10%-15%) to give 8-fluoro-3-(3-phenyl-4-(trifluoromethyl)isoxazol-5-yl)-4,5-dihydronaphtho[1,2-c]isoxazol-7-yl)methanol (30 mg, 0.070 mmol, 37%) as a viscous clear film. The product had an HPLC ret. time=4.046 min. (condition B). LC/MS M$^{+1}$ 431.05.

Preparation 67F: 8-Fluoro-3-(3-phenyl-4-(trifluoromethyl)isoxazol-5-yl)-4,5-dihydronaphtho[1,2-c]isoxazol-7-yl)isoxazole-7-carbaldehyde

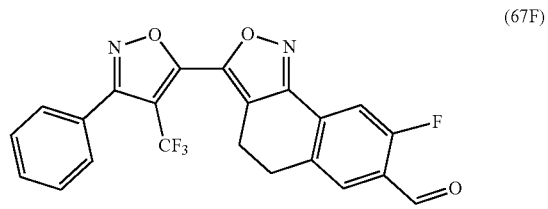 [SMILES: O=Cc1cc2c(cc1F)-c1noc(-c3onc(-c4ccccc4)c3C(F)(F)F)c1CC2]

(67F)

Dess-Martin reagent (0.065 g, 0.153 mmol) was added to a stirred mixture of (8-fluoro-3-(3-phenyl-4-(trifluoromethyl)isoxazol-5-yl)-4,5-dihydronaphtho[1,2-c]isoxazol-7-yl)methanol (Preparation 67E, 0.030 g, 0.070 mmol) in dichloromethane (5.0 mL) at 0° C. After complete addition, the reaction mixture was stirred for 15 minutes at 0° C. and then at room temperature for 30 minutes. The reaction mixture was quenched with a 1:1 mixture of aqueous sodium thiosulfate and saturated sodium bicarbonate and extracted with dichloromethane. The dichloromethane extract was dried over sodium sulfate and concentrated to give 8-fluoro-3-(3-phenyl-4-(trifluoromethyl)isoxazol-5-yl)-4,5-dihydronaphtho[1,2-c]isoxazol-7-yl)isoxazole-7-carbaldehyde (0.026 g, 0.061 mmol, 87%) as a white solid. The product had an HPLC ret. time=4.12 min. (condition B). LC/MS M$^{+1}$=429.2.

Example 67

To a mixture of 8-fluoro-3-(3-phenyl-4-(trifluoromethyl)isoxazol-5-yl)-4,5-dihydronaphtho[1,2-c]isoxazole-7-carbaldehyde (Preparation 67F, 0.023 g, 0.054 mmol), tert-butyl azetidine-3-carboxylate.acetic acid salt (0.012 g, 0.054 mmol) and acetic acid (6.15 µl, 0.107 mmol) in MeOH (1.0 mL) and dichloromethane (3.0 mL) at room temperature was added tetraisopropyl titanate (0.096 mL, 0.324 mmol) dropwise. The resulting homogeneous reaction mixture was stirred for 80 min. To the reaction mixture was added sodium triacetoxyborohydride (0.034 g, 0.161 mmol) in one portion, and the reaction mixture was stirred at room for 60 min. Additional sodium triacetoxyborohydride (0.034 g, 0.161 mmol) was added, and the reaction stirred at room temperature for an additional hour. The reaction was quenched with a saturated aqueous solution of sodium bicarbonate, and the resulting emulsion was extracted with dichloromethane (3×). The organic layers were combined, dried over anhydrous sodium sulfate, and concentrated to give 33 mg of the crude product as a tan, viscous film, which was purified by silica gel chromatography eluting with a 30% mixture of ethyl acetate in hexane to afford tert-butyl ester-1-((8-fluoro-3-(3-phenyl-4-(trifluoromethyl)isoxazol-5-yl)-4,5-dihydronaphtho[1,2-c]isoxazol-7-yl)methyl)azetidine-3-carboxylic acid (0.008 g, 0.016 mmol, 29.0% yield) as a tan, viscous film. The t-butyl ester product had an HPLC ret. time=3.70 min. (condition B). LC/MS M$^{+1}$=570.07.

The product was taken up in dichloromethane (3.0 mL) and TFA (1.0 mL) and was stirred for 3 hours at room temperature. The reaction mixture was concentrated and dried under vacuum. The crude product was taken up in 0.5 mL water and basified to approximately a pH of 5 with 0.5 N aqueous sodium hydroxide, and the water layer was decanted. The remaining solid was triturated with methanol (0.2 mL) with sonication and the methanol supernatant was decanted. The resulting solid was dried overnight under vacuum give 1-((8-fluoro-3-(3-phenyl-4-(trifluoromethyl)isoxazol-5-yl)-4,5-dihydronaphtho[1,2-c]isoxazol-7-yl)azetidine-3-carboxylic acid [0.010 g, 0.016 mmol, 29%] as a tan solid. The product had an HPLC ret. time=3.54 min. (condition B). LC/MS M$^{+1}$=514.07. $^1$H NMR (400 MHz, CD$_3$OD) δ ppm 7.70-7.93 (1H, m), 7.37-7.81 (6H, m), 4.51 (2H, s), 4.31 (4H, br. s.), 2.92-3.27 (4H, m), and 2.31 (1H, s).

Example 68

3-(Methyl((3-(5-phenyl-4-(trifluoromethyl)isoxazol-3-yl)-4,5-dihydronaphtho[1,2-c]isoxazol-7-yl)methyl)amino)propanoic acid (68)

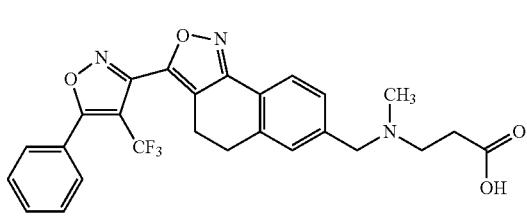

To a mixture of 3-(5-phenyl-4-(trifluoromethyl)isoxazol-3-yl)-4,5-dihydronaphtho[1,2-c]isoxazole-7-carbaldehyde (Preparation 88A, 0.054 g, 0.132 mmol), tert-butyl 3-(methylamino)propanoate (0.031 g, 0.197 mmol) and acetic acid (0.016 g, 0.263 mmol) in methanol (1.0 mL) and dichloromethane (3.0 mL) at room temperature was added tetraisopropyl titanate (0.096 mL, 0.324 mmol) dropwise. The resulting homogeneous reaction mixture was stirred for 80 min at room temperature. To the reaction mixture was added sodium triacetoxyborohydride (0.084 g, 0.395 mmol) in one portion, and the reaction mixture was stirred at room temperature for 60 min. The reaction was quenched with a saturated aqueous solution of sodium bicarbonate, and the resulting emulsion was extracted with dichloromethane (3×). The organic layers were combined, dried over anhydrous sodium sulfate, and concentrated to give 68 mg of the product as a pale brown solid. The crude product was purified by silica gel chromatography eluting with a 10% mixture of ethyl acetate in hexane.

The intermediate ester was treated with TFA for 1 h, then neutralized with 1N aqueous sodium hydroxide to afford after drying 3-(methyl((3-(5-phenyl-4-(trifluoromethyl)isoxazol-3-yl)-4,5-dihydronaphtho[1,2-c]isoxazol-7-yl)methyl)amino)propanoic acid [0.024 g, 0.048 mmol, 37%] as an off-white solid. The product had an HPLC ret. time=3.43 min. (condition B). LC/MS M$^{+1}$=498.1. $^1$H NMR (400 MHz, CD$_3$OD) δ ppm 8.12 (1H, d, J=7.92 Hz), 7.81 (2H, d, J=7.48 Hz), 7.37-7.77 (5H, m), 4.48 (2H, br. s.), 3.07-3.29 (4H, m), and 2.58-3.09 (7H, m).

Example 69

3-((3-(5-Phenyl-4-(trifluoromethyl)isoxazol-3-yl)-4,5-dihydronaphtho[1,2-c]isoxazol-7-yl)methyl)amino)propanoic acid (69)

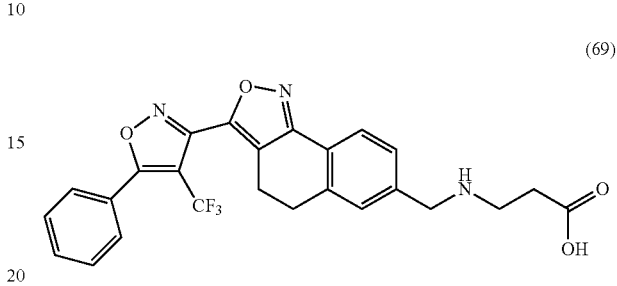

Triethylamine (0.018 mL, 0.126 mmol) was added to a stirred mixture of 7-(bromomethyl)-3-(5-phenyl-4-(trifluoromethyl)isoxazol-3-yl)-4,5-dihydronaphtho[1,2-c]isoxazole (6C, 0.020 g, 0.042 mmol) in dimethyl formamide (5.0 mL). Next, tert-butyl 3-aminopropanoate (9.17 mg, 0.063 mmol) was added at room temperature, and the reaction mixture was stirred at room temperature overnight. The reaction mixture was diluted with ethyl acetate (20 mL), washed with water (3×10 mL), and dried over sodium sulfate. Concentration under vacuum afforded 38 mg of the tert-butyl ester intermediate, which was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 15 mg of the tert-butyl ester.

The tert-butyl intermediate was stirred with TFA (0.2 mL) in dichloromethane (5 mL) overnight, and then neutralized to a pH of 5 with 1 N aqueous sodium hydroxide. The resulting product was vacuum dried to give 3-((3-(5-phenyl-4-(trifluoromethyl)isoxazol-3-yl)-4,5-dihydronaphtho[1,2-c]isoxazol-7-yl)methyl)amino)propanoic acid [0.008 g, 0.017 mmol, 41%] as a tan solid. The product had an HPLC ret. time=3.49 min. (condition B). LC/MS M$^{+1}$=484.07. $^1$H NMR (400 MHz, CD$_3$OD) δ ppm 8.12 (1H, d, J=7.92 Hz), 7.81 (2H, d, J=7.48 Hz), 7.37-7.77 (5H, m), 4.48 (2H, br. s.), 3.07-3.29 (4H, m), and 2.58-3.09 (4H, m).

Example 70

(3S)-1-((3-(5-Phenyl-4-(trifluoromethyl)isoxazol-3-yl)-4,5-dihydronaphtho[1,2-c]isoxazol-7-yl)methyl)piperidine-3-carboxylic acid (70)

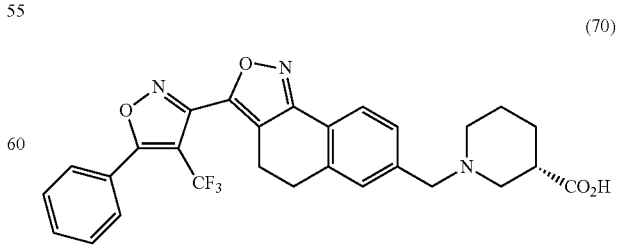

Triethylamine (0.018 mL, 0.126 mmol) was added to a stirred mixture of 7-(bromomethyl)-3-(5-phenyl-4-(trifluoromethyl)isoxazol-3-yl)-4,5-dihydronaphtho[1,2-c]isoxazole (Preparation 6C, 0.020 g, 0.042 mmol) in dimethyl formamide (5.0 mL) at room temperature. (S)-tert-Butyl piperidine-3-carboxylate was added, and the reaction mixture was stirred at room temperature overnight. The reaction mixture was diluted with ethyl acetate (20 mL) and washed with water (3×10 mL), dried, and concentrated. The crude intermediate tert-butyl ester (54 mg) was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 19 mg of the tert-butyl ester intermediate.

The intermediate ester was stirred with TFA (0.2 mL) in dichloromethane (5 mL) overnight and then neutralized to pH 5 with 1 N aqueous sodium hydroxide. The product was vacuum dried to give (3S)-1-((3-(5-phenyl-4-(trifluoromethyl)isoxazol-3-yl)-4,5-dihydronaphtho[1,2-c]isoxazol-7-yl)methyl)piperidine-3-carboxylic acid (0.009 g, 0.017 mmol, 41%) as a white solid. The product had an HPLC ret. time=3.59 min. (condition B). LC/MS M$^{+1}$=524.07. $^1$H NMR (400 MHz, CD$_3$OD) δ ppm 7.99-8.26 (1H, m), 7.78 (2H, d, J=7.26 Hz), 7.27-7.71 (5H, m), 4.43 (2H, d, J=2.64 Hz), 3.66-3.83 (1H, m), 3.60 (2H, s), 2.80-3.23 (6H, m), 2.00-2.39 (2H, m), and 1.64 (2H, br. s.).

Example 71

2-((3-(5-Phenyl-4-(trifluoromethyl)isoxazol-3-yl)-4,5-dihydronaphtho[1,2-c]isoxazol-7-yl)methylamino)acetic acid (71)

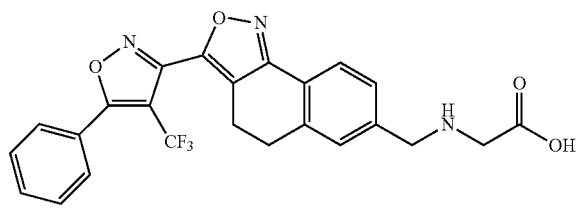

A mixture of 7-(bromomethyl)-3-(5-phenyl-4-(trifluoromethyl)isoxazol-3-yl)-4,5-dihydronaphtho[1,2-c]isoxazole (0.025 g, 0.053 mmol), tert-butyl 2-aminoacetate (Preparation 6C, 6.90 mg, 0.053 mmol) and triethylamine (7.33 mL, 0.053 mmol) in dimethyl formamide (3.0 mL) was stirred at room temperature overnight. The reaction mixture was diluted with ethyl acetate (15 mL) and washed with water (3×1.0 mL) water. The ethyl acetate extract was concentrated, and the residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 5.1 mg the intermediate tert-butyl ester.

The ester was treated with TFA (1.0 mL) for 30 minutes. The excess TFA was evaporated, the residue neutralized with 1 N aqueous NaOH to pH 5, and the precipitate was collected by vacuum filtration and dried to give 2-((3-(5-phenyl-4-(trifluoromethyl)isoxazol-3-yl)-4,5-dihydronaphtho[1,2-c]isoxazol-7-yl)methylamino)acetic acid [0.012 g, 0.500 mmol, 50%] as a white solid. The product had an HPLC ret. time=4.45 min. (condition B). LC/MS M$^{+1}$=470.07. $^1$H NMR (400 MHz, CD$_3$OD) δ ppm 8.12 (1H, d, J=7.92 Hz), 7.81 (2H, d, J=7.48 Hz), 7.37-7.77 (5H, m), 4.48 (2H, br. s.), 3.07-3.29 (4H, m), and 2.58-3.09 (2H, m).

Example 72

3-Hydroxy-2-((3-(5-phenyl-4-(trifluoromethyl)isoxazol-3-yl)-4,5-dihydronaphtho[1,2-c]isoxazol-7-yl)methylamino)propanoic acid (72)

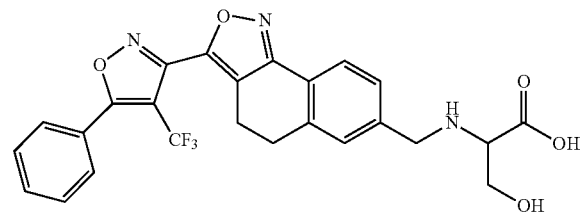

A mixture of 7-(bromomethyl)-3-(5-phenyl-4-(trifluoromethyl)isoxazol-3-yl)-4,5-dihydronaphtho[1,2-c]isoxazole (6C, 0.025 g, 0.053 mmol), tert-butyl 2-amino-3-hydroxypropanoate (8.48 mg, 0.053 mmol) and triethylamine (7.33 mL, 0.053 mmol) in DMF (3.0 mL) was stirred at room temperature overnight. The reaction mixture was diluted with ethyl acetate (15 mL) and washed with water (3×1.0 mL). The ethyl acetate extract was concentrated, and the residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 0.0015 g of the intermediate tert-butyl ester.

The ester was treated with TFA (1.0 mL) for 30 minutes. The excess TFA was removed, and the residue was neutralized to pH 5 with 1 N aqueous sodium hydroxide. The precipitate was collected by vacuum filtration and dried to afford 3-hydroxy-2-((3-(5-phenyl-4-(trifluoromethyl)isoxazol-3-yl)-4,5-dihydronaphtho[1,2-c]isoxazol-7-yl)methylamino)propanoic acid (0.013 g, 0.500 mmol, 50%) as a white solid. The product had an HPLC ret. time=4.09 min. (condition B). LC/MS M$^{+1}$=500.1. $^1$H NMR (400 MHz, CD$_3$OD) δ ppm 8.12 (1H, d, J=7.70 Hz), 7.79 (2H, d, J=7.48 Hz), 7.34-7.77 (5H, m), 4.54 (2H, s), 3.25-3.42 (3H, m), and 2.82-3.25 (4H, m).

Example 73

3-(Methyl((3-(5-phenyl-4-(trifluoromethyl)isoxazol-3-yl)-4,5-dihydronaphtho[1,2-c]isoxazol-7-yl)methyl)amino)propanamide (73)

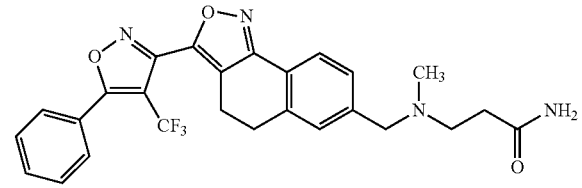

A mixture of 7-(bromomethyl)-3-(5-phenyl-4-(trifluoromethyl)isoxazol-3-yl)-4,5-dihydronaphtho[1,2-c]isoxazole (6C, 0.025 g, 0.053 mmol), 3-(methylamino)propanamide (5.37 mg, 0.053 mmol) and triethylamine (7.33 mL, 0.053 mmol) in DMF (3.0 mL) was stirred at room temperature overnight. The reaction mixture was diluted with ethyl acetate (15 mL) and washed with water (3×1.0 mL). The ethyl acetate extract was concentrated, and the residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 3-(methyl((3-(5-phenyl-4-(trifluoromethyl)isoxazol-3-yl)-4,5-dihydronaphtho[1,2-c]isoxazol-7-yl)methyl)amino)propanamide TFA (0.012 g., 0.493 mmol, 48%) as a viscous tan liquid. The product had an HPLC ret. time=4.02 min. (condition B). LC/MS M$^{+1}$=497.07. $^1$H NMR (400 MHz, CD$_3$OD) δ ppm 8.09 (1H, d, J=7.92 Hz), 7.79 (2H, d, J=7.26 Hz), 7.32-7.77 (5H, m), 4.54 (2H, s), 3.23-3.44 (4H, m), 2.98-3.21 (4H, m), and 2.89 (3H, s).

Example 74

4-((3-(5-Phenyl-4-(trifluoromethyl)isoxazol-3-yl)-4,5-dihydronaphtho[1,2-c]isoxazol-7-yl)methyl)morpholino-3-yl)methanol

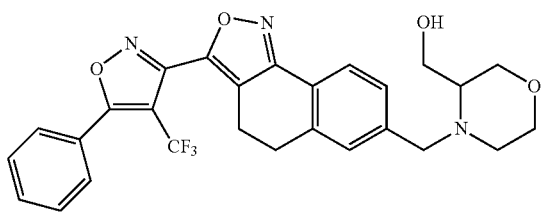

(74)

A mixture of 7-(bromomethyl)-3-(5-phenyl-4-(trifluoromethyl)isoxazol-3-yl)-4,5-dihydronaphtho[1,2-c]isoxazole (6C, 0.025 g, 0.053 mmol), morpholin-3-ylmethanol (6.16 mg, 0.053 mmol) and triethylamine (7.33 mL, 0.053 mmol) in DMF (3.0 mL) was stirred at room temperature overnight. The reaction mixture was diluted with ethyl acetate (15 mL) and washed with water (3×1.0 mL). The ethyl acetate extract was concentrated, and the residue was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 Nm) to give 4-((3-(5-phenyl-4-(trifluoromethyl)isoxazol-3-yl)-4,5-dihydronaphtho[1,2-c]isoxazol-7-yl)methyl)morpholino-3-yl)methanol TFA [0.013 g, 0.500 mmol, 50%] as a viscous tan film. The product had an HPLC ret. time=4.02 min. (condition B). LC/MS M$^{+1}$=512.1. $^1$H NMR (400 MHz, CD$_3$OD) δ ppm 7.97-8.14 (1H, m), 7.78 (2H, d, J=7.48 Hz), 7.44-7.73 (5H, m), 4.20 (2H, br. s.), 3.76 (6H, br. s.), and 2.96-3.25 (7H, m).

Example 75

1-((3-(5-Cyclohexyl-4-(trifluoromethyl)isoxazol-3-yl)-4,5-dihydronaphtho[1,2-c]isoxazol-7-yl)methyl)azetidine-3-carboxylic acid

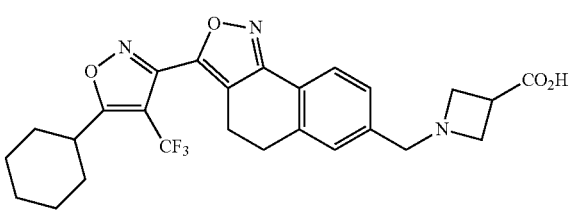

(75)

Preparation 75A: 3-(5-Cyclohexyl-4-(trifluoromethyl)isoxazol-3-yl)-7-vinyl-4,5-dihydronaphtho[1,2-c]isoxazole

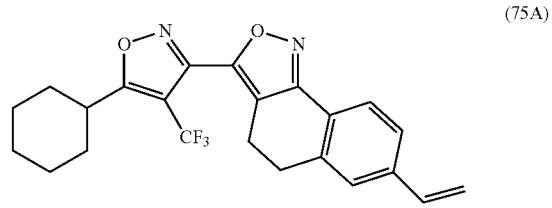 [SMILES: C=Cc1ccc2c(c1)CCc1c-2noc1-c1noc(C2CCCCC2)c1C(F)(F)F]

(75A)

To a fresh solution of lithium diisopropylamide made by adding butyllithium (0.404 mL, 1.01 mmol) to a stirred mixture of diisopropylamine (0.142 mL, 1.01 mmol) in THF (10 mL) at 0° C. was added a solution of (E)-6-vinyl-3,4-dihydronaphthalen-1(2H)-one oxime (I-A, 0.057 g, 0.303 mmol) in THF (2 mL) over 10 minutes. After complete addition, the reaction mixture turned orange-colored and was stirred an additional 20 minutes. Methyl 5-cyclohexyl-4-(trifluoromethyl)isoxazole-3-carboxylate (0.070 g, 0.252 mmol) in THF (1.0 mL) was added over 5 minutes. The resulting dark brown-black reaction mixture was stirred for 30 minutes at 0° C. The reaction mixture was quenched with methanol (10 mL) plus 3 drops concentrated sulfuric acid, concentrated, and chromatographed on silica gel eluting with a 10% mixture of ethyl acetate in hexane to give 195 mg of the intermediate, 3-(5-cyclohexyl-4-(trifluoromethyl)isoxazol-3-yl)-7-vinyl-3,3a,4,5-tetrahydronaphtho[1,2-c]isoxazol-3-ol.

A stirred mixture of 3-(5-cyclohexyl-4-(trifluoromethyl)isoxazol-3-yl)-7-vinyl-3,3a,4,5-tetrahydronaphtho[1,2-c]isoxazol-3-ol and thionyl chloride (0.030 g, 0.252 mmol) in toluene (5.0 mL) and pyridine (1.5 mL) was heated at 110° C. for 10 minutes. The reaction mixture was cooled, diluted with 1 N aqueous hydrochloric acid (5.0 mL), and extracted with ethyl acetate (3×20 mL). The ethyl acetate extracts were combined and concentrated to give 3-(5-cyclohexyl-4-(trifluoromethyl)isoxazol-3-yl)-7-vinyl-4,5-dihydronaphtho[1,2-c]isoxazole [0.016 g, 0.039 mmol, 16%] as an orange solid. The product had an HPLC ret. time=4.916 min. (condition B). LC/MS M$^{+1}$=415.08.

Preparation 75B: 3-(5-Cyclohexyl-4-(trifluoromethyl)isoxazol-3-yl)-4,5-dihydronaphtho[1,2-c]isoxazole-7-carbaldehyde

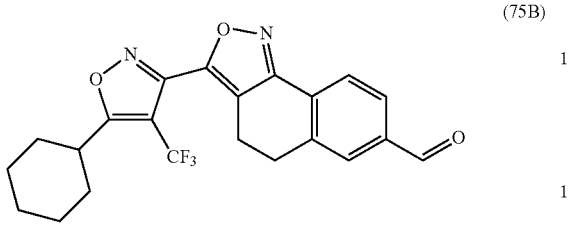

(75B)

To a solution of 3-(5-cyclohexyl-4-(trifluoromethyl)isoxazol-3-yl)-7-vinyl-4,5-dihydronaphtho[1,2-c]isoxazole (Preparation 75A, 0.015 g, 0.036 mmol) in dichloromethane (5.0 mL) at −78° C. was passed ozone from an ozone generator until the solution turned a deep blue. The reaction mixture was then purged with oxygen until the blue color disappeared and then with nitrogen for 5 minutes. The reaction mixture was allowed to warm to room temperature, and triethylamine (5.07 µl, 0.036 mmol) was added. The reaction mixture was stirred at room temperature for 15 minutes. Concentration under vacuum provided 3-(5-cyclohexyl-4-(trifluoromethyl)isoxazol-3-yl)-4,5-dihydronaphtho[1,2-c]isoxazole-7-carbaldehyde [0.014 g, 0.0036 mmol, 98%] as a tan solid. The product had an HPLC ret. time=4.44 min. (condition B). LC/MS $M^{+1}$=417.07.

Example 75

To a solution of 3-(5-cyclohexyl-4-(trifluoromethyl)isoxazol-3-yl)-4,5-dihydronaphtho[1,2-c]isoxazole-7-carbaldehyde (0.015 g, 0.036 mmol) in methanol (2.0 mL) and 1,2-dichloroethane (2.0 mL) was added azetidine-3-carboxylic acid (3.64 mg, 0.036 mmol) followed by 3 drops of acetic acid (2.16 mg, 0.036 mmol). The reaction mixture was heated at 60° C. for 1.5 h. The reaction mixture was cooled to room temperature, and sodium cyanoborohydride (4.83 mg, 0.077 mmol) was added. The reaction mixture was then stirred at room temperature for 15 minutes, concentrated under vacuum, and the crude residue was partitioned between dichloromethane and water. The dichloromethane extract was concentrated, and the residue was chromatographed using reverse-phase preparative HPLC (Column: LUNA 5 u C18, 21×100 mm:Solvent MeOH(B)—H₂O(A), 0.1% TFA: 0% B-100% B, Gradient Time 12 min, Stop Time 20 min, Flow Rate 20 ml/min, Wavelength 220 nM) to give 1-((3-(5-cyclohexyl-4-(trifluoromethyl)isoxazol-3-yl)-4,5-dihydronaphtho[1,2-c]isoxazol-7-yl)methyl)azetidine-3-carboxylic acid TFA (0.008 g, 0.016 mmol, 44%) as a white solid. The product had an HPLC ret. time=3.78 min. (condition B). LC/MS $M^{+1}$=502.07. ¹H NMR (400 MHz, CD₃OD) δ ppm 8.04 (1H, d, J=7.70 Hz), 7.52 (2H, m), 4.41 (2H, s), 4.05-4.34 (4H, m), 3.43-3.62 (1H, m), 2.90-3.21 (4H, m), 2.71 (1H, s), 2.01 (2H, br. s.), 1.76 (4H, br. s.), and 1.28-1.57 (4H, m).

Example 76

3-(5-Cyclohexyl-4-(trifluoromethyl)isoxazol-3-yl)-4,5-dihydronaphtho[1,2-c]isoxazole-7-carboxylic acid

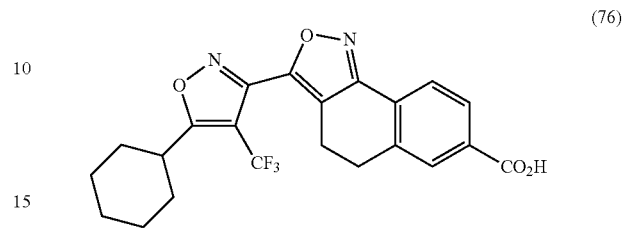

(76)

A bi-product formed in the final reaction of Example 75 was isolated by reverse-phase preparative HPLC and determined to be 3-(5-cyclohexyl-4-(trifluoromethyl)isoxazol-3-yl)-4,5-dihydronaphtho[1,2-c]isoxazole-7-carboxylic acid [0.008 g, 0.016 mmol, 15%] as a white solid. The product had an HPLC ret. time=4.43 min. (condition B). LC/MS $M^{+1}$=433.07. ¹H NMR (400 MHz, CD₃OD) δ ppm 8.04 (1H, d, J=7.70 Hz), 7.21-7.53 (2H, m), 4.07-4.36 (4H, m), 3.63 (1H, t, J=8.47 Hz), 1.68-2.09 (6H, m), and 1.28-1.62 (4H, m).

Example 77

1-((5-Methyl-3-(3-phenyl-4-(trifluoromethyl)isoxazol-5-yl)-4,5-dihydroisoxazolo[4,3-c]quinolin-7-yl)methyl)azetidine-3-carboxylic acid (77)

Preparation 77A: tert-Butyl 7-bromo-4-morpholinoquinoline-1(2H)-carboxylate (77A)

To a mixture of tert-butyl 7-bromo-4-oxo-3,4-dihydroquinoline-1(2H)-carboxylate (0.500 g, 1.53 mmol) and morpholine (0.668 mL, 7.66 mmol) in toluene (10 mL) at 0° C. was added titanium(IV) chloride [1M in toluene] (0.843 mL, 0.843 mmol) dropwise. The ice-bath was removed, and the orange, heterogeneous reaction mixture was stirred at room temperature overnight. The heterogeneous, orange reaction mixture was filtered under reduced pressure through a pad of Celite which was then rinsed with toluene (3×10 mL). The pale yellow filtrate was concentrated under reduced pressure to give tert-butyl 7-bromo-4-morpholinoquinoline-1(2H)-carboxylate (0.598 g, 1.513 mmol, 99% yield) as a yellow oil. The product had LC/MS M$^{+1}$=395.1 and 397.1.

Preparation 77B: tert-Butyl 7-bromo-3-hydroxy-3-(3-phenyl-4-(trifluoromethyl)isoxazol-5-yl)-3a,4-dihydroisoxazolo[4,3-c]quinoline-5(3H)-carboxylate

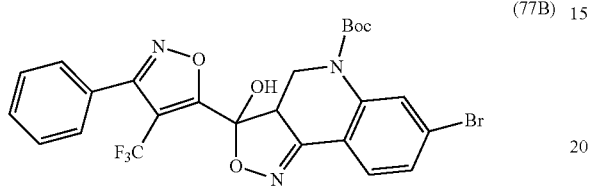

(77B)

To a homogeneous solution of tert-butyl 7-bromo-4-morpholinoquinoline-1(2H)-carboxylate (Preparation 77A, 0.598 g, 1.513 mmol) and triethylamine (0.419 mL, 3.03 mmol) in acetonitrile (20 mL) at 0° C. was added a solution of 3-phenyl-4-(trifluoromethyl)isoxazole-5-carbonyl fluoride (I-4, 0.392 g, 1.51 mmol) in acetonitrile (1.0 mL). The reaction mixture was stirred at 0° C. for 2.5 hours and then overnight at room temperature. A homogeneous solution of hydroxylamine hydrochloride (0.421 g, 6.05 mmol) and sodium acetate (0.496 g, 6.05 mmol) in water (0.981 mL, 54.5 mmol) was added, and the reaction mixture was heated at 45° C. for 60 min. The reaction mixture was diluted with dichloromethane, washed with water, and dried over anhydrous sodium sulfate. Concentration under vacuum afforded the crude product which was chromatographed using silica gel chromatography eluting with a 10% mixture of ethyl acetate in hexane to give tert-butyl 7-bromo-3-hydroxy-3-(3-phenyl-4-(trifluoromethyl)isoxazol-5-yl)-3a,4-dihydroisoxazolo[4,3-c]quinoline-5(3H)-carboxylate (0.050 g, 0.086 mmol, 6% yield) as a yellowish solid. The product had LC/MS M$^{+1}$=636.2 and 637.2.

Preparation 77C: tert-Butyl 7-bromo-3-(3-phenyl-4-(trifluoromethyl)isoxazol-5-yl)isoxazolo[4,3-c]quinoline-5(4H)-carboxylate

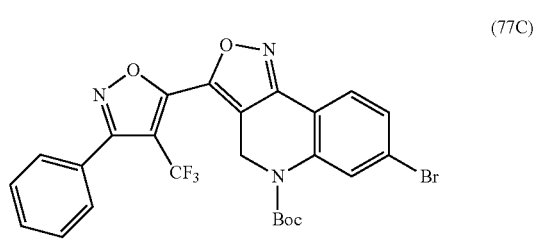 [SMILES: CC(C)(C)OC(=O)N1Cc2c(noc2-c2onc(-c3ccccc3)c2C(F)(F)F)-c2ccc(Br)cc21]

(77C)

To a stirred suspension of tert-butyl 7-bromo-3-hydroxy-3-(3-phenyl-4-(trifluoromethyl)isoxazol-5-yl)-3a,4-dihydroisoxazolo[4,3-c]quinoline-5(3H)-carboxylate (Preparation 77B, 0.050 g, 0.086 mmol) in anhydrous toluene (1.0 mL) at room temperature was added pyridine (0.2 mL) followed by thionyl chloride (10.7 µl, 0.146 mmol). The reaction mixture was stirred at room temperature for 15 min. and then at 80° C. for 15 min. The reaction mixture was cooled to room temperature and concentrated. The solid residue was partitioned between dichloromethane and a saturated aqueous solution of sodium bicarbonate, and the dichloromethane extracts were combined, dried over anhydrous sodium sulfate, and concentrated under reduced pressure. The crude product mixture was chromatographed using silica gel flash chromatography eluting with a 15% mixture of ethyl acetate in hexane to give 42.7 mg of a yellowish solid. The compound was triturated with methanol and filtered to give tert-butyl 7-bromo-3-(3-phenyl-4-(trifluoromethyl)isoxazol-5-yl)isoxazolo[4,3-c]quinoline-5(4H)-carboxylate [0.031 g, 0.053 mmol, 62%] as a white solid. The product had an HPLC ret. time=4.65 min. (condition B). LC/MS M$^{+1}$=562.07 and 564.07.

Preparation 77D: 7-Bromo-3-(3-phenyl-4-(trifluoromethyl)isoxazol-5-yl)-4,5-dihydroisoxazolo[4,3-c]quinoline

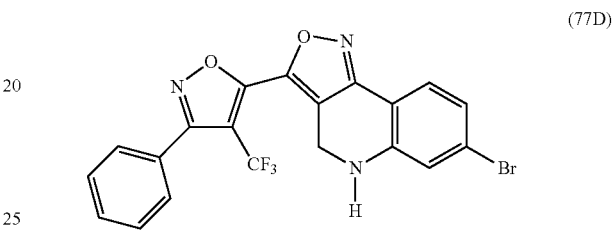

(77D)

A mixture of tert-butyl 7-bromo-3-(3-phenyl-4-(trifluoromethyl)isoxazol-5-yl)isoxazolo[4,3-c]quinoline-5(4H)-carboxylate (Preparation 77C, 0.030 g, 0.053 mmol) and 6 N aqueous hydrochloric acid (0.107 mL, 0.640 mmol) in THF (5.0 mL) was stirred at room temperature overnight. The reaction mixture was concentrated, dissolved in dichloromethane (3 mL) and treated with TFA (0.5 mL) for 2 h. The reaction mixture was concentrated under vacuum, dissolved in 5 ml dichloromethane and carefully neutralized with 1N NaOH to approx. pH=7, filtered and the filtrate concentrated to give 7-bromo-3-(3-phenyl-4-(trifluoromethyl)isoxazol-5-yl)-4,5-dihydroisoxazolo[4,3-c]quinoline (0.025 g, 0.054 mmol, 100%) as a yellowish solid. The product had an HPLC ret. time=4.43 min. (condition B). LC/MS M$^{+1}$=463.4 and 465.2.

Preparation 77E: 7-Bromo-5-methyl-3-(3-phenyl-4-(trifluoromethyl)isoxazol-5-yl)-4,5-dihydroisoxazolo[4,3-c]quinoline

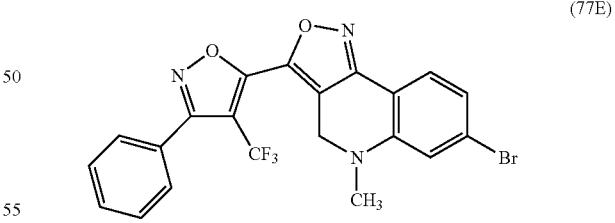

(77E)

Iodomethane (0.020 mL, 0.325 mmol) was slowly added to a stirred mixture of 7-bromo-3-(3-phenyl-4-(trifluoromethyl)isoxazol-5-yl)-4,5-dihydroisoxazolo[4,3-c]quinoline (Preparation 77D, 0.050 g, 0.108 mmol) and sodium hydride (2.60 mg, 0.108 mmol) in THF (5.0 mL) at room temperature. The reaction mixture was stirred at room temperature overnight. The reaction mixture was quenched with 1 N aqueous hydrochloric acid (10 mL) and extracted with ethyl acetate (3×25 mL). The ethyl acetate extract was dried over sodium sulfate and concentrated to give 7-bromo-5-methyl-3-(3-phenyl-4-(trifluoromethyl)isoxazol-5-yl)-4,5-dihydroisoxazolo

[4,3-c]quinoline (0.041 g, 0.084 mmol, 78%) as an orange solid. The product had an HPLC ret. time=4.45 min. (condition B). LC/MS M$^{+1}$ 478.0.

Preparation 77F: 5-Methyl-3-(3-phenyl-4-(trifluoromethyl)isoxazol-5-yl)-7-vinyl-4,5-dihydroisoxazolo[4,3-c]quinoline

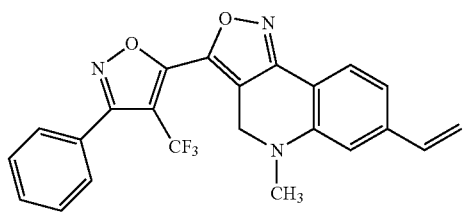

(77F)

To a heterogeneous solution of 7-bromo-5-methyl-3-(3-phenyl-4-(trifluoromethyl)isoxazol-5-yl)-4,5-dihydroisoxazolo[4,3-c]quinoline (Preparation 77E, 0.040 g, 0.084 mmol) in dioxane (5.0 mL) in a sealed tube was added sequentially tributyl(vinyl)stannane (0.027 mL, 0.092 mmol) and lithium chloride (10.7 mg, 0.252 mmol). The reaction mixture was degassed with nitrogen for 5 minutes. Tetrakis(triphenylphosphine)palladium(0) (9.71 mg, 8.40 μmol) was added, and the stirred reaction mixture was heated in an oil bath at 100° C. for 4 h overnight. The reaction mixture was concentrated under reduced pressure, and the residue was diluted with dichloromethane (10 mL), filtered through a pad of Celite, and rinsed with dichloromethane (10 mL). The filtrate was concentrated, and the solid residue was purified by flash silica gel chromatography using a 5% mixture of ethyl acetate in hexane to give the crude product mixture. The crude mixture was chromatographed using reverse-phase preparative HPLC (Column: LUNA 5 u C18, 21×100 mm:Solvent MeOH(B)—H$_2$O(A), 0.1% TFA: 0% B-100% B, Gradient Time 12 min, Stop Time 20 min, Flow Rate 20 ml/min, Wavelength 220 nM) to give 5-methyl-3-(3-phenyl-4-(trifluoromethyl)isoxazol-5-yl)-7-vinyl-4,5-dihydroisoxazolo[4,3-c]quinoline [0.020 g, 0.047 mmol, 56%] as a viscous, tan film. The product had an HPLC ret. time=3.85 min. (condition B); LC/MS M$^{+1}$=424.1.

Preparation 77G: 5-Methyl-3-(3-phenyl-4-(trifluoromethyl)isoxazol-5-yl)-4,5-dihydroisoxazolo[4,3-c]quinoline-7-carbaldehyde

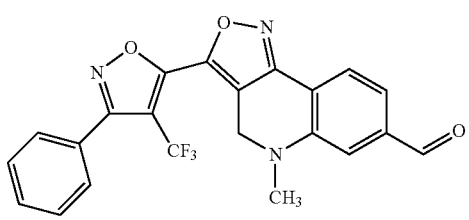

(77G)

To a solution of 5-methyl-3-(3-phenyl-4-(trifluoromethyl)isoxazol-5-yl)-7-vinyl-4,5-dihydroisoxazolo[4,3-c]quinoline (Preparation 77F, 0.020 g, 0.047 mmol) in Dichloromethane (5 mL) at −78° C. was passed ozone from an ozone generator until the solution turned a deep blue. The reaction mixture then was purged with oxygen until the blue color disappeared, then with nitrogen for five minutes. The reaction mixture was allowed to warm to room temperature and triethylamine (5.07 μl, 0.036 mmol) was added. The reaction mixture was stirred at room temperature for fifteen minutes, and then concentrated under vacuum to give 5-methyl-3-(3-phenyl-4-(trifluoromethyl)isoxazol-5-yl)-4,5-dihydroisoxazolo[4,3-c]quinoline-7-carbaldehyde as a tan solid. (0.015 mg, 0.035 mmol, 74%). The product had an HPLC ret. time=3.61 min. (condition B). LC/MS M$^{+1}$=426.1 min Example 77

To a mixture of 5-methyl-3-(3-phenyl-4-(trifluoromethyl)isoxazol-5-yl)-4,5-dihydroisoxazolo[4,3-c]quinoline-7-carbaldehyde (77G, 0.020 g, 0.047 mmol), tert-butyl azetidine-3-carboxylate (7.39 mg, 0.047 mmol) and acetic acid (5.38 μl, 0.094 mmol) in methanol (1.0 mL) and dichloromethane (3.0 mL) at room temperature was added tetraisopropoxytitanium (0.028 mL, 0.094 mmol) dropwise. The resulting homogeneous reaction mixture was stirred for 80 min. at room temperature. To the reaction mixture was added sodium triacetoxyhydroborate (0.030 g, 0.141 mmol) in one portion, and the reaction mixture was stirred at room temperature overnight. Additional sodium triacetoxyhydroborate (0.030 g, 0.141 mmol) was added, and the reaction stirred at room temperature for an additional hour. The reaction was quenched with a saturated aqueous solution of sodium bicarbonate, and the resulting emulsion was extracted with dichloromethane (3×). The organic layers were combined, dried over anhydrous sodium sulfate, and concentrated to give 33 mg of a pale tan viscous film. The crude product was purified by silica gel chromatography eluting with a 30% mixture of ethyl acetate in hexane to afford 8-mg of tert-butyl ester 1-((5-methyl-3-(3-phenyl-4-(trifluoromethyl)isoxazol-5-yl)-4,5-dihydroisoxazolo[4,3-c]quinolin-7-yl)methyl)azetidine-3-carboxylic acid as a tan viscous film.

The tert-butyl intermediate was stirred with TFA (1.0 mL) for 1 h, and then concentrated under vacuum, neutralized with 1 N aqueous sodium hydroxide to a pH 5, and concentrated. The residue was diluted with dichloromethane, filtered, and the filtrate was concentrated and dried to give 1-((5-methyl-3-(3-phenyl-4-(trifluoromethyl)isoxazol-5-yl)-4,5-dihydroisoxazolo[4,3-c]quinolin-7-yl)methyl)azetidine-3-carboxylic acid (0.0025 g, 0.005 mmol, 10%) as an off-white solid. The product had an HPLC ret. time=3.60 min. (condition B). LC/MS M$^{+1}$=511.07. $^1$H NMR (400 MHz, CD$_3$OD) δ ppm 8.09 (1H, d, J=7.92 Hz), 7.78 (2H, d, J=7.26 Hz), 7.32-7.77 (5H, m), 4.44 (2H, s), 3.47 (2H, s), 3.09-3.21 (4H, m), and 2.78-3.01 (4H, m).

Examples 78 and 79

1-((1-methyl-3-(5-phenyl-4-(trifluoromethyl)isoxazol-3-yl)-4,5-dihydro-1H-benzo[g]indazol-7-yl)methyl)azetidine-3-carboxylic acid, TFA (78) and 1-((2-methyl-3-(5-phenyl-4-(trifluoromethyl)isoxazol-3-yl)-4,5-dihydro-2H-benzo[g]indazol-7-yl)methyl)azetidine-3-carboxylic acid, TFA (79)

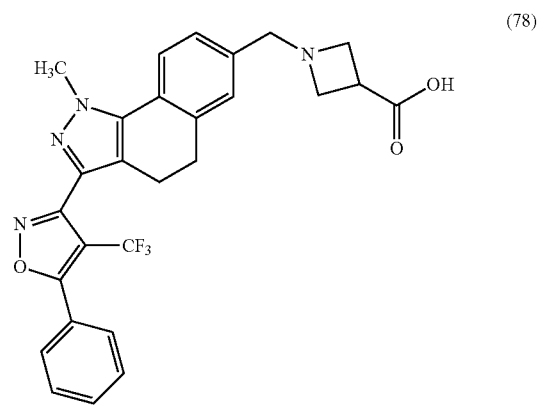

(78)

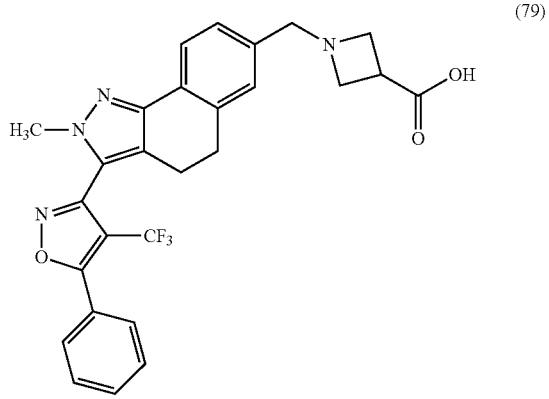

(79)

Preparation 78A: 2-(5-phenyl-4-(trifluoromethyl)
isoxazole-3-carbonyl)-6-vinyl-3,4-dihydronaphtha-
len-1(2H)-one

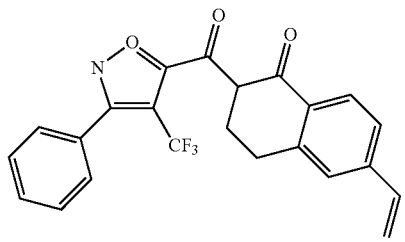

(78A)

To a heat gun dried 100 mL 2-necked flask was added diisopropylamine (0.910 mL, 6.39 mmol) under a nitrogen atmosphere followed by THF (5 mL). The flask was cooled to 0° C. and n-BuLi (2.55 mL, 6.39 mmol) was added dropwise over a period of 2 min. The contents were stirred at 0° C. for 20 min., cooled to −78° C. and 6-vinyl-3,4-dihydronaphtha-len-1(2H)-one (I-1B, 1 g, 5.81 mmol) dissolved in 2 mL of THF was added dropwise over a period of 3 min. The pale yellow reaction mixture was stirred at −78° C. for 20 min. Then 5-phenyl-4-(trifluoromethyl)isoxazole-3-carbonyl fluoride (I-14, 1.505 g, 5.81 mmol) dissolved in 2 mL of THF was added dropwise over a period of 2 min. The reaction mixture was stirred at −78° C. for 20 min, bought to room temperature and stirred at room temperature for 10 min. The reaction mixture was quenched with 1N HCl (5 mL) and extracted into EtOAc (20 mL). The aqueous layer was re-extracted with EtOAc (10 mL). The combined organic layers were dried over sodium sulfate concentrated and purified by column chromatography using an ISCO setup (80 g, RediSep® silica gel column). The desired fractions were collected and concentrated to yield 2-(5-phenyl-4-(trifluo-romethyl)isoxazole-3-carbonyl)-6-vinyl-3,4-dihydronaph-thalen-1(2H)-one (1.55 g, 3.77 mmol, 64.9% yield) as a yellow solid. LC/MS M$^{+1}$=412.12.

Preparation 78B and 79B: 3-(1-methyl-7-vinyl-4,5-
dihydro-1H-benzo[g]indazol-3-yl)-5-phenyl-4-(trif-
luoromethyl)isoxazole (78B) and 3-(2-methyl-7-
vinyl-4,5-dihydro-2H-benzo[g]indazol-3-yl)-5-
phenyl-4-(trifluoromethyl)isoxazole (78B)

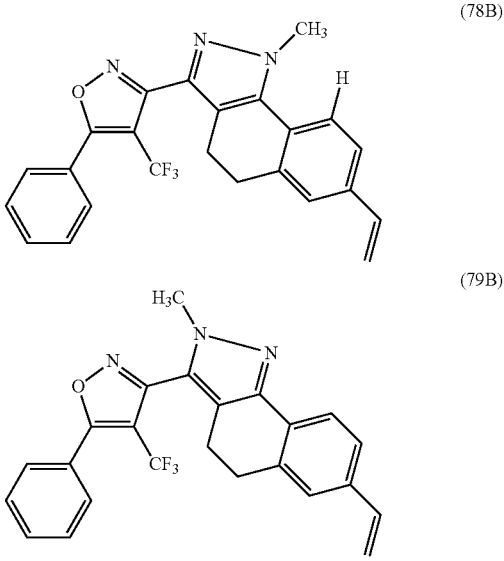

To 2-(5-phenyl-4-(trifluoromethyl)isoxazole-3-carbonyl)-6-vinyl-3,4-dihydronaphthalen-1(2H)-one (Preparation 78A, 0.7 g, 1.702 mmol) in MeOH (3.00 mL) and Dioxane (3 mL) was added methyl hydrazine (0.109 mL, 2.042 mmol) at room temperature. The reaction mixture was heated at 100° C. for 4 h., stirred at room temperature overnight, concentrated under reduced pressure and partitioned between 1N HCl (10 mL) and EtOAc (30 mL). The EtOAc layer was washed with brine (20 mL), dried over sodium sulfate, concentrated and subjected to column chromatography using an ISCO setup (40 g, RediSep® silica gel column). Fractions corresponding to B1 and B2 (were collected and concentrated to yield 50 mgs of 78B and 244 mgs of 79B. 78B1-LC/MS M$^{+1}$=422.2 and 78B2-LC/MS M$^{+1}$=422.1

Preparation 78C: 1-methyl-3-(5-phenyl-4-(trifluo-
romethyl)isoxazol-3-yl)-4,5-dihydro-1H-benzo[g]
indazole-7-carbaldehyde

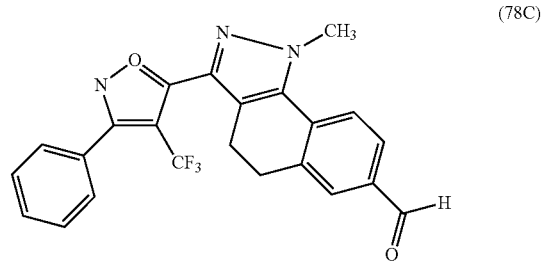

This compound was prepared according to the general procedure described for Preparation 23D, employing 50 mgs of 3-(1-methyl-7-vinyl-4,5-dihydro-1H-benzo[g]indazol-3-yl)-5-phenyl-4-(trifluoromethyl)isoxazole (78B). Yield: 48 mgs (96%); LC/MS M$^{+1}$=424.2.

Preparation 79C: 2-methyl-3-(5-phenyl-4-(trifluoromethyl)isoxazol-3-yl)-4,5-dihydro-2H-benzo[g]indazole-7-carbaldehyde

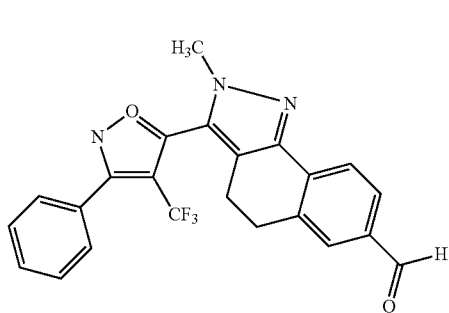

(79C)

This compound was prepared according to the general procedure described for Preparation 23D, employing 240 mgs of 3-(2-methyl-7-vinyl-4,5-dihydro-2H-benzo[g]indazol-3-yl)-5-phenyl-4-(trifluoromethyl)isoxazole (79B). Yield: 235 mgs (97%); LC/MS $M^{+1}$=424.2.

Example 78

This compound was prepared according to the general procedure described for Preparation 23, employing 48 mgs of 1-methyl-3-(5-phenyl-4-(trifluoromethyl)isoxazol-3-yl)-4,5-dihydro-1H-benzo[g]indazole-7-carbaldehyde (78C). Yield: 20 mgs (23%); The compound had a HPLC retention time=3.03 min. (condition C); LC/MS $M^{+1}$=509.2 $^1$H NMR (400 MHz, MeOD) δ ppm 7.35-7.85 (m, 8H) 4.3-4.6 (hidden under broad $CD_3OD$ peak, 9H) 3.7-3.9 (m, 1H) 2.85-3.2 (m, 4H).

Example 79

This compound was prepared according to the general procedure described for Preparation 23, employing 100 mgs of 2-methyl-3-(5-phenyl-4-(trifluoromethyl)isoxazol-3-yl)-4,5-dihydro-2H-benzo[g]indazole-7-carbaldehyde (79C). Yield: 66 mgs (40%); The compound had a HPLC retention time=2.96 min. (condition C); LC/MS $M^{+1}$=509.2 $^1$H NMR (400 MHz, $CD_3OD$) δ ppm 7.90 (1H, d, J=8.1 Hz), 7.82-7.87 (2H, m), 7.61-7.72 (3H, m), 7.40 (2H, dd, J=4.1, 2.3 Hz), 4.41 (2H, s), 4.30-4.38 (4H, m), 3.91 (3H, s), 3.71 (1H, quin, J=8.4 Hz), 3.02 (2H, t, J=7.3 Hz), 2.76 (2H, t, J=7.3 Hz).

Example 80

1-((3-(3,4-diethoxyphenyl)-4,5-dihydronaphtho[1,2-c]isoxazol-7-yl)methyl)azetidine-3-carboxylic acid

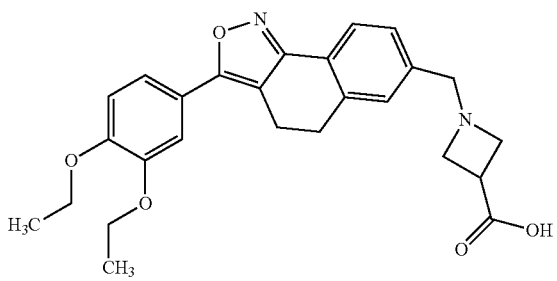 [SMILES: CCOc1ccc(-c2onc3c2CCc2cc(CN4CC(C(=O)O)C4)ccc2-3)cc1OCC]

Preparation 80A: 3-(3,4-diethoxyphenyl)-7-vinyl-4,5-dihydronaphtho[1,2-c]isoxazole

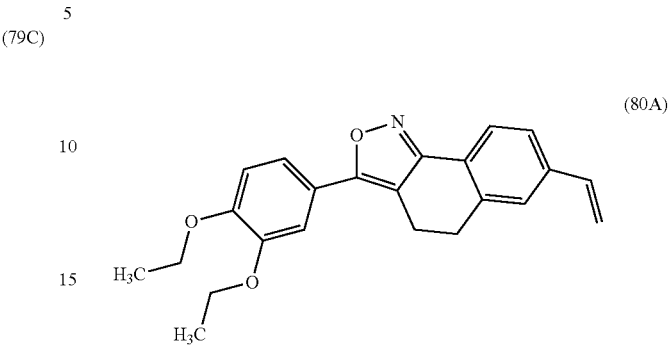

(80A)

This compound was prepared according to the general procedure described for Preparation 23C, employing 200 mgs of 6-vinyl-3,4-dihydronaphthalen-1(2H)-one oxime (I-1) and methyl 3,4-diethoxybenzoate (1 eq). Yield: 217 mgs (25%); LC/MS $M^{+1}$=362.1.

Preparation 80B (3-(3,4-diethoxyphenyl)-4,5-dihydronaphtho[1,2-c]isoxazole-7-carbaldehyde

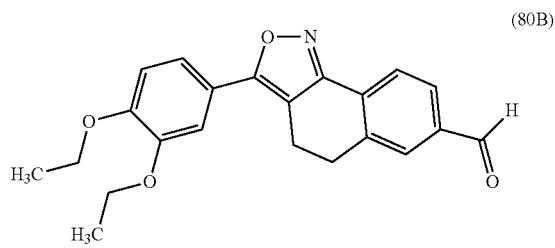 [SMILES: CCOc1ccc(-c2onc3c2CCc2cc(C=O)ccc2-3)cc1OCC]

(80B)

This compound was prepared according to the general procedure described for Preparation 23D, employing 67 mgs of 3-(3,4-diethoxyphenyl)-7-vinyl-4,5-dihydronaphtho[1,2-c]isoxazole (80A). Yield: 67 mgs (99%); LC/MS $M^{+1}$=364.

Example 80

This compound was prepared according to the general procedure described for Preparation 23, employing 75 mgs of 3-(3,4-diethoxyphenyl)-4,5-dihydronaphtho[1,2-c]isoxazole-7-carbaldehyde (81B). Yield: 66 mgs (28%); The compound had an HPLC retention time=6.8 min. (condition D); LC/MS $M^{+1}$=449; $^1$H NMR (500 MHz, $CD_3OD$) δ ppm 7.96 (1H, d, J=7.8 Hz), 7.48 (1H, s), 7.44 (1H, dd, J=7.9, 1.5 Hz), 7.32-7.38 (2H, m), 7.10 (1H, d, J=8.0 Hz), 4.36 (2H, s), 4.12-4.21 (8H, m), 3.37-3.46 (1H, m), 3.01-3.12 (4H, m), 1.42-1.49 (6H, m).

Example 81

(3S)-1-(2-(3-(3,4-diethoxyphenyl)-4,5-dihydronaphtho[1,2-c]isoxazol-7-yl)-2-hydroxyethyl)piperidine-3-carboxylic acid, HCl

Preparation of 81B: (3S)-ethyl 1-(2-(3-(3,4-diethoxyphenyl)-4,5-dihydronaphtho[1,2-c]isoxazol-7-yl)-2-hydroxyethyl)piperidine-3-carboxylate

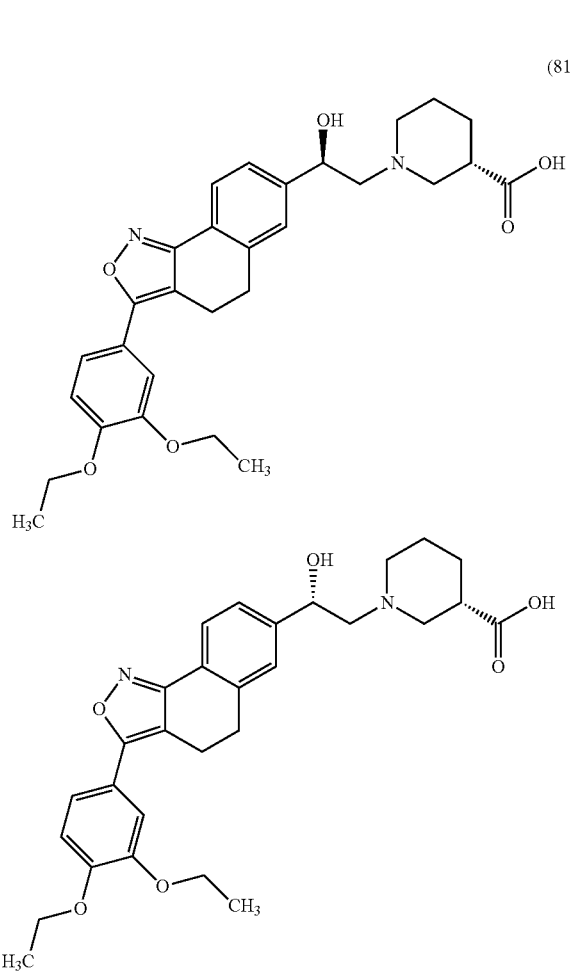

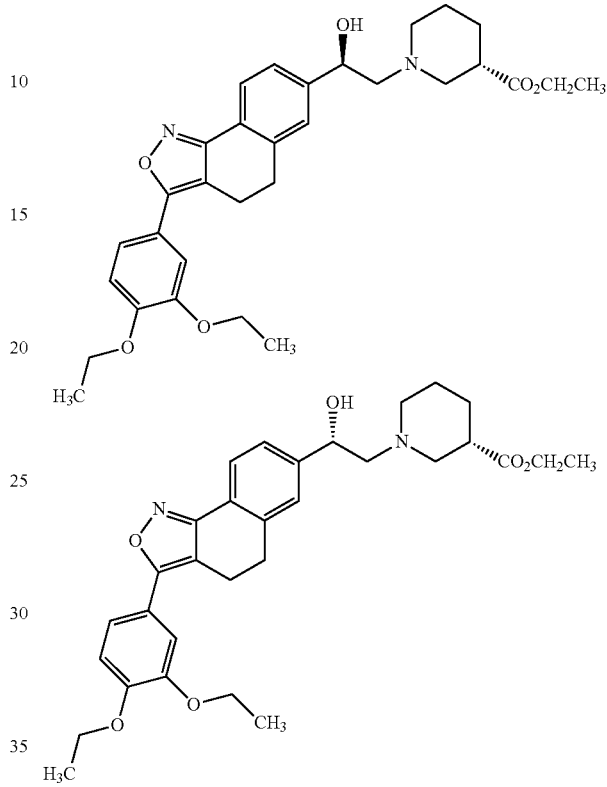

Preparation 81A: 3-(3,4-diethoxyphenyl)-7-(oxiran-2-yl)-4,5-dihydronaphtho[1,2-c]isoxazole

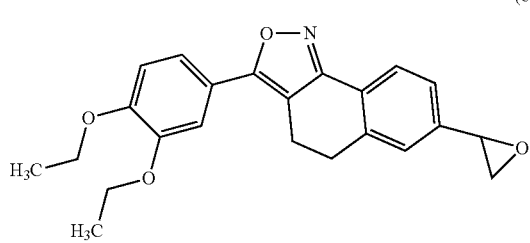

This compound was prepared according to the procedure described for Preparation 13A, employing 70 mgs of 3-(3,4-diethoxyphenyl)-7-vinyl-4,5-dihydronaphtho[1,2-c]isoxazole (80A). Yield: 80 mgs (25%); LC/MS M$^{+1}$=378.1.

To 3-(3,4-diethoxyphenyl)-7-(oxiran-2-yl)-4,5-dihydronaphtho[1,2-c]isoxazole (Preparation 81A, 0.08 g, 0.212 mmol) in a mixture of 2-propanol (1 mL) and dioxane (1.000 mL) was added DMAP (5.18 mg, 0.042 mmol) followed by (S)-ethyl piperidine-3-carboxylate (0.033 mL, 0.212 mmol) at room temperature. The reaction mixture was heated at 60° C. (oil bath temp.) for 26 h, concentrated under reduced pressure, and purified by column chromatography using an ISCO setup (12 g, RediSep® silica gel column). The desired fractions were collected and concentrated to yield (0.03 g, 0.056 mmol, 26.5% yield) of the product as a diastereomeric mixture. The individual diastereomers were separated using a CHIRALCE1® OJ-H column under SFC conditions (25% MeOH with 0.1% diethylamine in CO$_2$). Isomer 1 (7.7 mgs), retention time on chiral HPLC, 4.39 min; Isomer 2 (9 mgs), retention time on chiral HPLC, 6.15 min. The absolute stereochemistry at the carbon anchoring the secondary alcohol, of Isomer 1 and Isomer 2 was not determined.

Example 81

Isomer 1

To (3S)-ethyl 1-(2-(3-(3,4-diethoxyphenyl)-4,5-dihydronaphtho[1,2-c]isoxazol-7-yl)-2-hydroxyethyl)piperidine-3-carboxylate (X—B, isomer 1, 7.7 mg, 0.014 mmol) in dioxane (0.5 mL) was added HCl (6N aq.) (0.5 mL, 3.00 mmol) at room temperature and the contents heated at 60° C. for 15 h. The reaction mixture was concentrated and freeze dried to yield (3S)-1-(2-(3-(3,4-diethoxyphenyl)-4,5-dihydronaphtho[1,2-c]isoxazol-7-yl)-2-hydroxyethyl)piperidine-3-carboxylic acid, HCl (0.008 g, 0.013 mmol, 94% yield) as a pale yellow solid. The compound had an HPLC retention time=2.75 min. (condition C); LC/MS $M^{+1}$=507.1.

Example 81

Isomer 2

To (3S)-ethyl 1-(2-(3-(3,4-diethoxyphenyl)-4,5-dihydronaphtho[1,2-c]isoxazol-7-yl)-2-hydroxyethyl)piperidine-3-carboxylate (X—B, isomer 2, 9 mg, 0.017 mmol) in dioxane (0.5 mL) was added HCl (6N aq.) (0.5 mL, 3.00 mmol) at room temperature and the contents heated at 60° C. for 15 h. The reaction mixture was concentrated and freeze dried to yield (3S)-1-(2-(3-(3,4-diethoxyphenyl)-4,5-dihydronaphtho[1,2-c]isoxazol-7-yl)-2-hydroxyethyl)piperidine-3-carboxylic acid, HCl (0.009 g, 0.013 mmol, 94% yield) as a pale yellow solid. The compound had an HPLC retention time=2.74 min. (condition C); LC/MS $M^{+1}$=507.1.

Example 82

(3S)-1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylic acid, HCl (82)

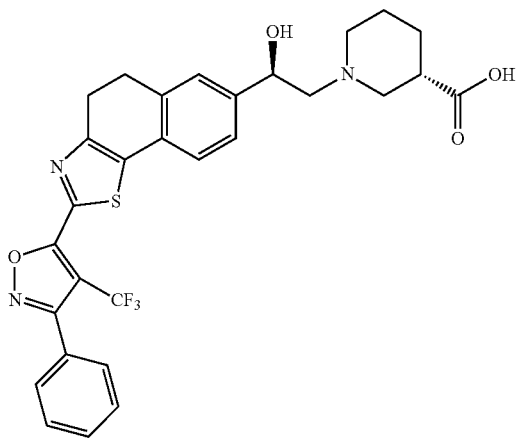

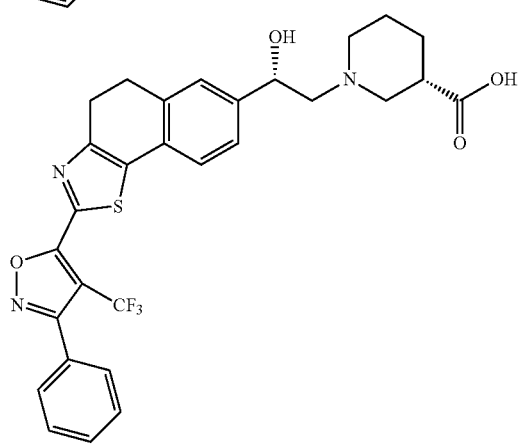

Preparation of 82A:
6-bromo-3,4-dihydronaphthalen-1(2H)-one O-tosyl oxime (82A)

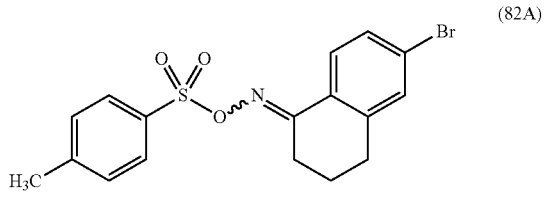 [SMILES: Cc1ccc(S(=O)(=O)ON=C2CCCc3cc(Br)ccc32)cc1]

To 6-bromo-3,4-dihydronaphthalen-1(2H)-one oxime (2.5 g, 10.41 mmol) in pyridine (5 mL) was added p-toluenesulfonyl chloride (2.184 g, 11.45 mmol) in one lot at room temperature. The reaction mixture was stirred at room temperature for 20 h. Ice cubes (~10 g) were added to the flask and the contents stirred at room temperature for 30 min. The solid that separated out was filtered and washed with water (3×20 mL), dried over sodium sulfate and concentrated to yield 6-bromo-3,4-dihydronaphthalen-1(2H)-one O-tosyl oxime (3.92 g, 9.94 mmol, 95% yield) as light pink solid. The solid was azeotroped once with toluene (10 mL) and used for the subsequent reaction. MS $M^{+1}$=395.

Preparation of 82B:
2-amino-6-bromo-3,4-dihydronaphthalen-1(2H)-one, HCl (82B)

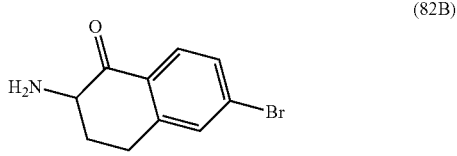 [SMILES: NC1CCc2cc(Br)ccc2C1=O]

Toluene (25 mL) was added to a 200 mL RB flask followed by the addition of ethanol (8.0 mL). Sodium (0.297 g, 12.92 mmol) metal was added at room temperature to the toluene/EtOH mixture under a nitrogen atmosphere and the contents were stirred at room temperature for 30 min. Most of the sodium had dissolved. Next, 6-bromo-3,4-dihydronaphthalen-1(2H)-one O-tosyl oxime (Preparation 82A, 3.92 g, 9.94 mmol) dissolved in toluene (20 mL) was added over a period of 3 min. at room temperature. The dirty green reaction mixture was stirred at room temperature for 60 h. The reaction mixture was filtered to remove sodium p-toluenesulfonate and the filter cake was washed with toluene (2×15 mL). To the filtrate was added 10% HCl (40 mL) in one lot at room temperature. The contents were transferred into a separating funnel and the aqueous layer was separated. The aqueous layer was washed once with EtOAc (20 mL) and concentrated using the high vacuum pump (water bath heated to ~40° C.). The resulting solid was azeotroped with toluene (30 mL). To the solid was added acetonitrile (20 mL), the contents sonicated for 5 min, filtered, and dried to yield 2-amino-6-bromo-3,4-dihydronaphthalen-1(2H)-one, HCl (2.52 g, 9.11 mmol, 92% yield) as a white solid. LC/MS $M^{+1}$=241.

Preparation of 82C: N-(6-bromo-1-oxo-1,2,3,4-tetrahydronaphthalen-2-yl)-3-phenyl-4-(trifluoromethyl)isoxazole-5-carboxamide

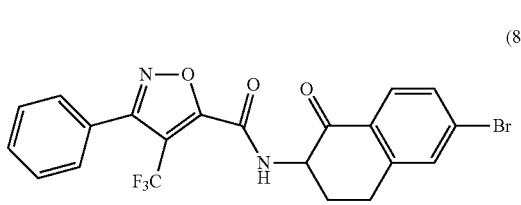

(82C)

To 3-phenyl-4-(trifluoromethyl)isoxazole-5-carboxylic acid (Intermediate I-3D, 0.465 g, 1.808 mmol) in dichloromethane (5 mL) was added pyridine (0.175 ml, 2.170 mmol) followed by cyanuric fluoride (0.188 ml, 2.172 μmol) at room temperature. The reaction mixture was stirred at room temperature for 20 h., and partitioned between dichloromethane (30 mL) and cold 0.5N HCl (15 mL). The dichloromethane layer was separated, dried over sodium sulfate, and concentrated to afford an orange-red solid. The solid was dissolved in dichloromethane (5 mL) and added dropwise over a period of 2 min. to 2-amino-6-bromo-3,4-dihydronaphthalen-1(2H)-one hydrochloride (Preparation 82B, 0.5 g, 1.808 mmol) in dichloromethane (5.00 mL) and diisopropylethylamine (0.789 ml, 4.52 mmol) at 0° C. The reaction mixture was allowed to come to room temperature over a period of 20 min., stirred at room temperature for 2 h., and partitioned between dichloromethane (30 mL) and cold 0.5N HCl (10 mL). The dichloromethane layer was separated, dried over sodium sulfate, and concentrated. The resulting solid was triturated with ether (15 mL), sonicated for 5 min. and filtered to yield N-(6-bromo-1-oxo-1,2,3,4-tetrahydronaphthalen-2-yl)-3-phenyl-4-(trifluoromethyl)isoxazole-5-carboxamide (0.640 g, 1.335 mmol, 73.9% yield) as a light tan solid. LC/MS $M^{+1}$=480.

Preparation of 82D: 5-(7-bromo-4,5-dihydronaphtho[2,1-d]thiazol-2-yl)-3-phenyl-4-(trifluoromethyl)isoxazole

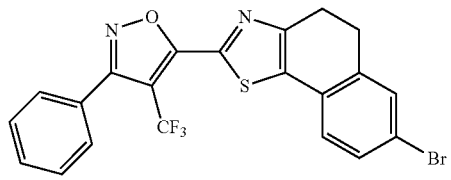

(82D)

To Lawesson's Reagent (1.393 g, 3.44 mmol) was added N-(6-bromo-1-oxo-1,2,3,4-tetrahydronaphthalen-2-yl)-3-phenyl-4-(trifluoromethyl)isoxazole-5-carboxamide (Preparation 82C, 1.1 g, 2.295 mmol) followed by toluene (10 mL). The reaction mixture was heated at 140° C. behind a safety shield for 15 h. The reaction mixture was cooled to room temperature, loaded onto a silica gel column (with toluene) and purified using hexane/EtOAc (9.25:0.75, 600 mL). The desired fractions were collected and concentrated to yield a pale yellow solid. The solid was triturated with acetonitrile (20 mL), filtered and washed with acetonitrile (2×5 mL) to yield 5-(7-bromo-4,5-dihydronaphtho[2,1-d]thiazol-2-yl)-3-phenyl-4-(trifluoromethyl)isoxazole (0.935 g, 1.959 mmol, 85% yield) as a pale yellow solid. LC/MS $M^{+1}$=478.

Preparation of 82E: 3-phenyl-4-(trifluoromethyl)-5-(7-vinyl-4,5-dihydronaphtho[2,1-d]thiazol-2-yl)isoxazole

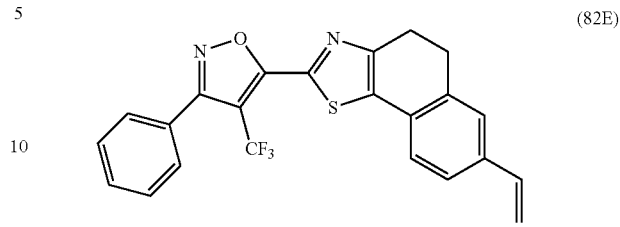

(82E)

To 5-(7-bromo-4,5-dihydronaphtho[2,1-d]thiazol-2-yl)-3-phenyl-4-(trifluoromethyl)isoxazole (Preparation 82D), 0.4 g, 0.838 mmol) in toluene (2 mL) was added tributyl(vinyl)stannane (0.294 mL, 1.00 mmol), followed by bis(triphenylphosphine)palladium(II)chloride (0.029 g, 0.042 mmol) at room temperature. The reaction mixture was heated at 110° C. for 3 h. The reaction mixture was loaded onto a silica gel column and purified using hexane/EtOAc (9.25:0.75, 300 mL). The desired fractions were collected and concentrated to yield 0.35 mgs of a yellow solid. The solid was triturated with acetonitrile (5 mL), filtered and washed with acetonitrile (2×5 mL) to yield 200 mgs of a pale yellow solid (I crop). The mother liquor was concentrated to yield another 100 mgs of greenish-yellow solid (II crop). LC/MS $M^{+1}$=425.

Preparation of 82F: 5-(7-(oxiran-2-yl)-4,5-dihydronaphtho[2,1-d]thiazol-2-yl)-3-phenyl-4-(trifluoromethyl)isoxazole

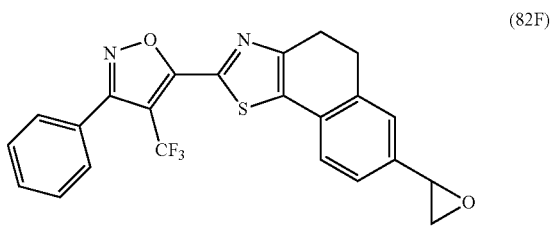 [SMILES: FC(F)(F)c1c(-c2ccccc2)noc1-c1nc2c(s1)-c1ccc(C3CO3)cc1CC2]

(82F)

This compound was prepared according to the procedure described for Preparation 13A, employing 100 mgs of 3-phenyl-4-(trifluoromethyl)-5-(7-vinyl-4,5-dihydronaphtho[2,1-d]thiazol-2-yl)isoxazole (82E). Yield: 100 mgs (96%)

Preparation of 82G: (3S)-ethyl 1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylate

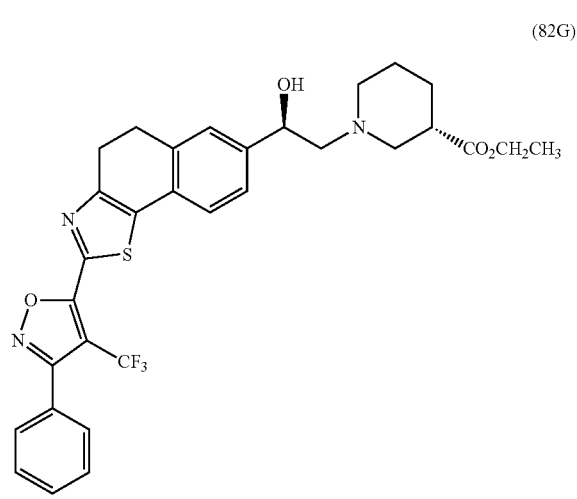

(82G)

-continued

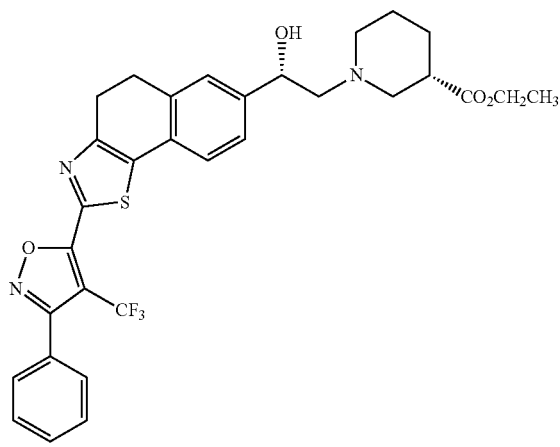

This compound was prepared according to the procedure described for Preparation 81B, employing 90 mgs of 5-(7-(oxiran-2-yl)-4,5-dihydronaphtho[2,1-d]thiazol-2-yl)-3-phenyl-4-(trifluoromethyl)isoxazole (Preparation 82F). Yield: 50 mgs (41%). The individual diastereomers were separated using a CHIRALCE1® OJ-H column under SFC conditions (27% MeOH with 0.25% diethylamine in $CO_2$). Isomer 1 (20 mgs), retention time on chiral HPLC, 4.91 min; LC/MS $M^{+1}$=598.3; Isomer 2 (18 mgs), retention time on chiral HPLC, 6.44 min.; LC/MS $M^{+1}$=598.2 The absolute stereochemistry at the carbon anchoring the secondary alcohol, of Isomer 1 and Isomer 2 was not determined.

Example 82

Isomer 1

This compound was prepared according to the procedure described for Preparation 81, employing 20 mgs of (3S)-ethyl 1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylate (82, isomer 1). Yield: (17 mgs, 80%); The compound had an HPLC retention time=3.25 min. (condition C); LC/MS $M^{+1}$=570.1.

Example 82

Isomer 2

This compound was prepared according to the procedure described for Preparation 81, employing 18 mgs of (3S)-ethyl 1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylate (82, isomer 2). Yield: (18 mgs, 94%); The compound had an HPLC retention time=3.24 min. (condition C); LC/MS $M^{+1}$=570.1.

Example 83

(±)1-(2-(3-phenyl-4-(trifluoromethyl)isoxazol-5-yl)-4,5-dihydronaphtho[2,1-d]thiazol-7-yl)ethane-1,2-diol

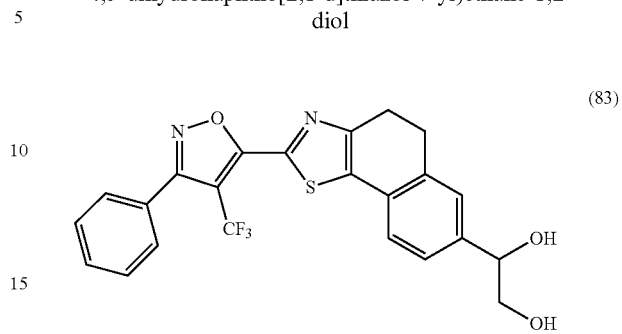

(83)

To 3-phenyl-4-(trifluoromethyl)-5-(7-vinyl-4,5-dihydronaphtho[2,1-d]thiazol-2-yl)isoxazole (Preparation 82E, 0.2 g, 0.471 mmol) in THF (3 mL) were sequentially added osmium tetroxide (4% aq.) (0.148 mL, 0.019 mmol) and NMO (50% aq.) (0.22 mL, 0.471 mmol) at room temperature and the contents were stirred overnight under a nitrogen atmosphere. The same reaction was setup in a different flask. The reaction mixtures from both flasks were combined and concentrated. The residue was partitioned between dichloromethane (40 mL) and water (10 mL). The dichloromethane layer was separated, dried over sodium sulfate and concentrated. To the solid was added acetonitrile (10 mL), the contents were triturated, sonicated and filtered. The solid was washed with acetonitrile (2×3 mL) and dried to yield 240 mgs of a pale yellow solid. The filtrate was concentrated and purified by silica gel column chromatography using an ISCO setup. (24 g, RediSep® silica gel column). The desired fractions were collected and concentrated to yield another 55 mgs of a pale yellow solid. The compound had an HPLC retention time=3.69 min. (condition C); LC/MS $M^{+1}$=459; $^1$H NMR (400 MHz, $CDCl_3$) δ ppm 7.66 (2H, d, J=6.6 Hz), 7.48-7.58 (3H, m), 7.41 (1H, d, J=7.7 Hz), 7.28-7.36 (2H, m), 4.82-4.90 (1H, m), 3.83 (1H, ddd, J=11.0, 7.3, 3.5 Hz), 3.71 (1H, td, J=7.5, 4.0 Hz), 3.13-3.25 (4H, m), 2.63 (1H, OH, d, J=3.3 Hz).

Example 84

2-hydroxy-N-(2-hydroxyethyl)-2-(2-(3-phenyl-4-(trifluoromethyl)isoxazol-5-yl)-4,5-dihydronaphtho[2,1-d]thiazol-7-yl)acetamide

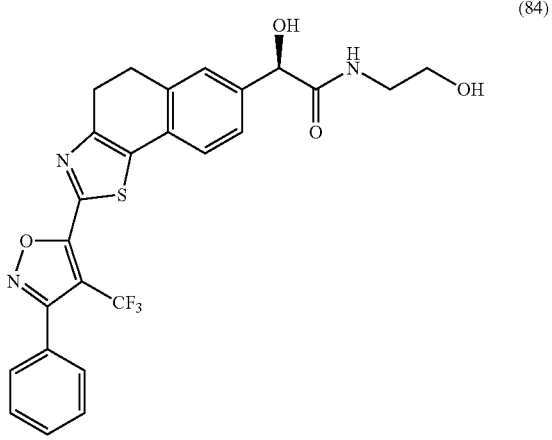

(84)

-continued

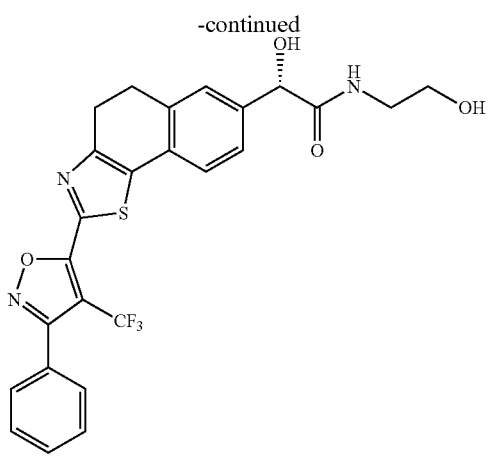

Preparation of 84A: 2-(3-phenyl-4-(trifluoromethyl) isoxazol-5-yl)-4,5-dihydronaphtho[2,1-d]thiazole-7-carbaldehyde

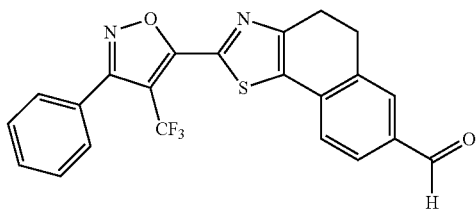
(84A)

To 1-(2-(3-phenyl-4-(trifluoromethyl)isoxazol-5-yl)-4,5-dihydronaphtho[2,1-d]thiazol-7-yl)ethane-1,2-diol (Example 83, 0.233 g, 0.508 mmol) in THF (3 mL) was added sodium periodate (0.163 g, 0.762 mmol) in 2 mL of water over a period of 2 min. at room temperature and the contents stirred at room temperature for 30 min. The reaction mixture was partitioned between EtOAc (60 mL) and water (20 mL). The EtOAc layer was concentrated, the yellow solid that was obtained was azeotroped with acetonitrile (20 mL), dried under a high vacuum. Yield: (183 mgs, 83%); LC/MS $M^{+1}$=427.

Preparation of 84B: 2-hydroxy-2-(2-(3-phenyl-4-(trifluoromethyl)isoxazol-5-yl)-4,5-dihydronaphtho[2,1-d]thiazol-7-yl)acetonitrile

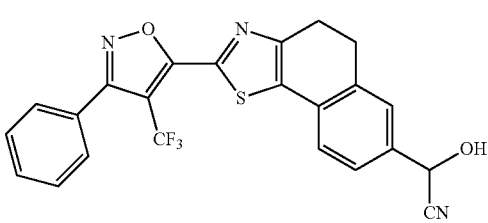
(84B)

To 2-(3-phenyl-4-(trifluoromethyl)isoxazol-5-yl)-4,5-dihydronaphtho[2,1-d]thiazole-7-carbaldehyde (Preparation 84A, 0.175 g, 0.410 mmol) in dichloromethane (5 mL) was added zinc iodide (0.039 g, 0.123 mmol) followed by trimethylsilyl cyanide (0.083 mL, 0.616 mmol) over a period of 1 min. at room temperature. The reddish-brown reaction mixture was stirred at room temperature for 1 h. The reaction mixture was cooled to 0° C. and conc. HCl (0.068 mL, 0.821 mmol) was added over a period of 1 min. and the contents stirred at room temperature for 5 min. The reaction mixture was partitioned between dichloromethane (2×20 mL) and 10% aq. $Na_2S_2O_3$ (10 mL). The dichloromethane layer was dried over sodium sulfate and concentrated to yield 2-hydroxy-2-(2-(3-phenyl-4-(trifluoromethyl)isoxazol-5-yl)-4,5-dihydronaphtho[2,1-d]thiazol-7-yl)acetonitrile (0.185 g, 0.408 mmol, 99% yield) as a yellow solid. LC/MS $M^{+1}$=454.

Preparation of 84C: 2-hydroxy-2-(2-(3-phenyl-4-(trifluoromethyl)isoxazol-5-yl)-4,5-dihydronaphtho[2,1-d]thiazol-7-yl)acetic acid

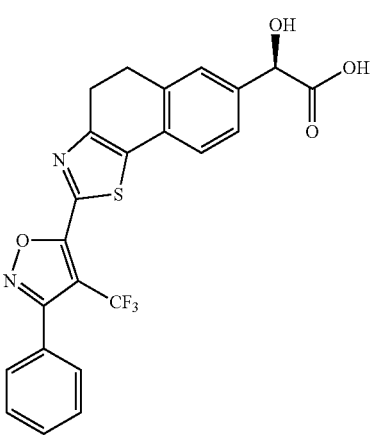
(84C)

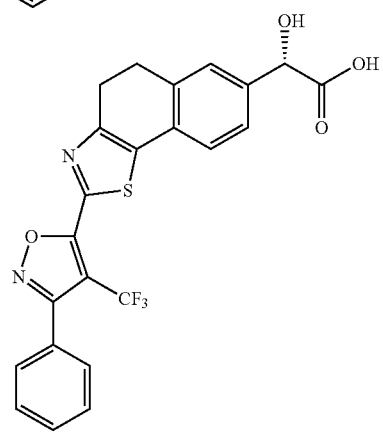

To 2-hydroxy-2-(2-(3-phenyl-4-(trifluoromethyl)isoxazol-5-yl)-4,5-dihydronaphtho[2,1-d]thiazol-7-yl)acetonitrile (Preparation 84B, 0.185 g, 0.408 mmol) in dioxane (5 mL) was added HCl (6N aq.) (3 ml, 18.00 mmol) at room temperature and the contents heated at 100° C. for 70 h. The reaction mixture was concentrated under reduced pressure and the resulting solid was azeotroped with acetonitrile (3×10 mL) and freeze dried to yield 2-hydroxy-2-(2-(3-phenyl-4-(trifluoromethyl)isoxazol-5-yl)-4,5-dihydronaphtho[2,1-d]thiazol-7-yl)acetic acid (0.2 g) as a pale yellow solid. The individual enantiomers were separated using a CHIRAL-PAK® AD-H column under SFC conditions (20% MeOH with 0.1% TFA in $CO_2$). Isomer 1 (69 mgs), retention time on chiral HPLC, 9.11 min; LC/MS $M^{+1}$=473.1; Isomer 2 (72 mgs), retention time on chiral HPLC, 10.36 min.; LC/MS $M^{+1}$=473.1. The absolute stereochemistry at the carbon anchoring the secondary alcohol, of Isomer 1 and Isomer 2 was not determined.

Example 84

Isomer 1

To 2-hydroxy-2-(2-(3-phenyl-4-(trifluoromethyl)isoxazol-5-yl)-4,5-dihydronaphtho[2,1-d]thiazol-7-yl)acetic acid (Preparation 84C, isomer 1, 0.033 g, 0.070 mmol) in DMF (1 mL) were sequentially added N-methylmorpholine (0.031 mL, 0.279 mmol), 2-aminoethanol (5.48 µl, 0.091 mmol) and HATU (0.040 g, 0.105 mmol) at room temperature. The reaction mixture was stirred at room temperature for 18 h. The reaction mixture was diluted with 0.5 mL of MeOH and subjected to preparative. HPLC (Waters Xbridge C18 19×100 mm; solvent A: 10% MeOH, 90% $H_2O$, 0.1% TFA; Solvent B: 90% MeOH, 10% $H_2O$, 0.1% TFA). The desired fractions were collected, concentrated and freeze dried using MeOH (0.3 mL) and water (0.7 mL) to yield 2-hydroxy-N-(2-hydroxyethyl)-2-(2-(3-phenyl-4-(trifluoromethyl)isoxazol-5-yl)-4,5-dihydronaphtho[2,1-d]thiazol-7-yl)acetamide (0.013 g, 0.024 mmol, 34.3% yield) as a pale yellow solid. The compound had an HPLC retention time=3.54 min. (condition C); LC/MS $M^{+1}$=516; $^1$H NMR (500 MHz, CDCl$_3$) δ ppm 7.65 (2H, d, J=6.9 Hz), 7.48-7.58 (3H, m), 7.33-7.44 (3H, m), 6.72 (1H, br. s.), 5.12 (1H, s), 3.76 (2H, t, J=4.9 Hz), 3.46-3.53 (2H, m), 3.12-3.25 (4H, m).

Example 84

Isomer 2

To 2-hydroxy-2-(2-(3-phenyl-4-(trifluoromethyl)isoxazol-5-yl)-4,5-dihydronaphtho[2,1-d]thiazol-7-yl)acetic acid (Preparation 84C, isomer 2, 0.035 g, 0.074 mmol) in DMF (1 mL) were sequentially added N-methylmorpholine (0.033 mL, 0.296 mmol), 2-aminoethanol (5.81 µl, 0.096 mmol) and HATU (0.042 g, 0.111 mmol) at room temperature. The reaction mixture was stirred at room temperature for 18 h. The reaction mixture was diluted with 0.5 mL of MeOH and subjected to preparative. HPLC (Waters Xbridge C18 19×100 mm; Solvent A: 10% MeOH, 90% $H_2O$, 0.1% TFA; Solvent B: 90% MeOH, 10% $H_2O$, 0.1% TFA). The desired fractions were collected, concentrated and freeze dried using MeOH (0.3 mL) and water (0.7 mL) to yield 2-hydroxy-N-(2-hydroxyethyl)-2-(2-(3-phenyl-4-(trifluoromethyl)isoxazol-5-yl)-4,5-dihydronaphtho[2,1-d]thiazol-7-yl)acetamide (0.014 g, 0.024 mmol, 35% yield) as a pale yellow solid. The compound had an HPLC retention time=3.53 min. (condition C); LC/MS $M^{+1}$=516; $^1$H NMR (500 MHz, C$_3$D$_6$O) δ ppm 6.91-6.97 (2H, m), 6.82-6.90 (4H, m), 6.69-6.77 (2H, m), 4.62 (1H, d, J=4.4 Hz), 4.36 (1H, d, J=3.9 Hz), 3.18 (1H, OH, br. s.), 2.87 (2H, m.), 2.57-2.65 (2H, m).

Example 85

N-(1-cyanocyclopropyl)-2-hydroxy-2-(2-(3-phenyl-4-(trifluoromethyl)isoxazol-5-yl)-4,5-dihydronaphtho[2,1-d]thiazol-7-yl)acetamide

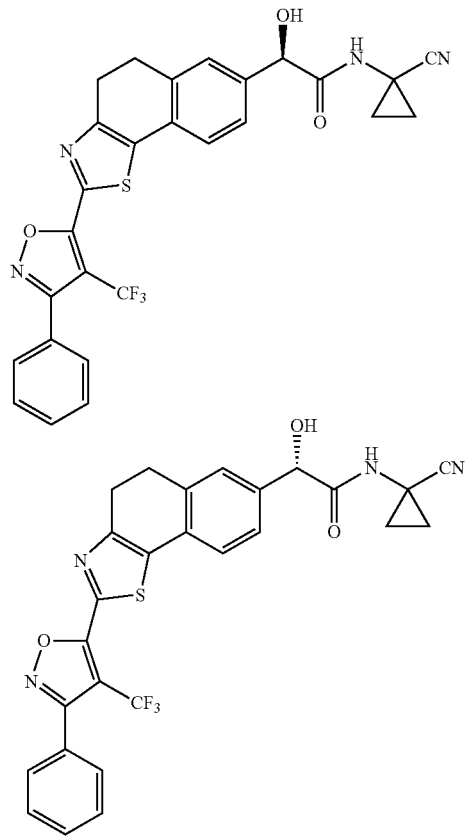

(85)

Example 85

Isomer 1

This compound was prepared according to the procedure described for Preparation 84, employing 33 mgs of 2-hydroxy-2-(2-(3-phenyl-4-(trifluoromethyl)isoxazol-5-yl)-4,5-dihydronaphtho[2,1-d]thiazol-7-yl)acetic acid (Preparation 84C, isomer 1). Yield: (2 mgs, 6%); The compound had an HPLC retention time=3.59 min. (condition C); LC/MS $M^{+1}$=537. $^1$H NMR (400 MHz, C$_3$D$_6$O) δ ppm 8.43 (1H, s), 7.69 (2H, d, J=5.5 Hz), 7.57-7.65 (3H, m), 7.40-7.54 (3H, m), 5.14 (1H, s), 3.14-3.21 (4H, m), 1.44-1.51 (2H, m), 1.18-1.35 (2H, m).

Example 85

Isomer 2

This compound was prepared according to the procedure described for Preparation 84, employing 35 mgs of 2-hydroxy-2-(2-(3-phenyl-4-(trifluoromethyl)isoxazol-5-yl)-4,5-dihydronaphtho[2,1-d]thiazol-7-yl)acetic acid (Preparation 84C, isomer 2). Yield: (7 mgs, 17%); The compound had an HPLC retention time=3.59 min. (condition C); LC/MS $M^{+1}$=537. $^1$H NMR (400 MHz, C$_3$D$_6$O) δ ppm 8.40 (1H, s), 7.66-7.72 (2H, m), 7.57-7.65 (3H, m), 7.41-7.54 (3H, m), 5.14 (1H, s), 3.14-3.20 (4H, m), 1.44-1.53 (2H, m), 1.18-1.34 (2H, m).

Example 86

1-((2-pentyl-4,5-dihydronaphtho[2,1-d]thiazol-7-yl)methyl)azetidine-3-carboxylic acid, TFA (86)

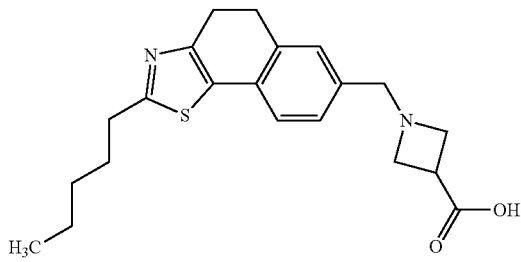

Preparation of 86A: N-(6-bromo-1-oxo-1,2,3,4-tetrahydronaphthalen-2-yl)hexanamide (86A)

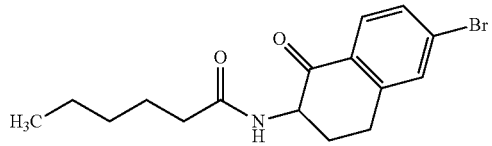

To 2-amino-6-bromo-3,4-dihydronaphthalen-1(2H)-one hydrochloride (Preparation 82B, 1.1 g, 3.98 mmol) in dichloromethane (5 mL) was added diisopropylethylamine (1.737 mL, 9.94 mmol) at 0° C. under a nitrogen atmosphere. To the homogenous solution was added hexanoyl chloride (0.602 mL, 4.38 mmol) dropwise over a period of 3 min. The reaction mixture was allowed to come to room temperature (~5 min.) and was stirred at room temperature for 3 h. The reaction mixture was partitioned between dichloromethane (30 mL) and 1N HCl (10 mL). The dichloromethane layer was separated, washed with sat. aq. NaHCO$_3$ (20 mL), dried over sodium sulfate and concentrated to yield N-(6-bromo-1-oxo-1,2,3,4-tetrahydronaphthalen-2-yl)hexanamide (1.2 g, 3.55 mmol, 89% yield) as an off-white solid. LC/MS M$^{+1}$ 339.

Preparation of 86B:
7-bromo-2-pentyl-4,5-dihydronaphtho[2,1-d]thiazole (86B)

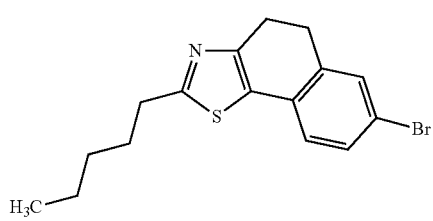

This compound was prepared according to the procedure described for Preparation 82D, employing 1.25 g of N-(6-bromo-1-oxo-1,2,3,4-tetrahydronaphthalen-2-yl)hexanamide (86A). Yield: (415 mgs, 33%). LC/MS M$^{+1}$=337.

Preparation of 86C:
2-pentyl-7-vinyl-4,5-dihydronaphtho[2,1-d]thiazole (86C)

This compound was prepared according to the procedure described for Preparation 82E, employing 270 mgs of 7-bromo-2-pentyl-4,5-dihydronaphtho[2,1-d]thiazole (Preparation 86B). Yield: (193 mgs, 85%). LC/MS M$^{+1}$=337.

Preparation of 86D: 2-pentyl-4,5-dihydronaphtho[2,1-d]thiazole-7-carbaldehyde (86D)

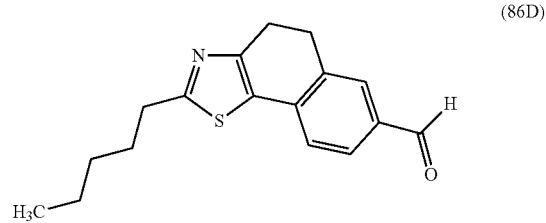 [SMILES: CCCCCc1nc2c(s1)-c1ccc(C=O)cc1CC2]

This compound was prepared according to the procedure described for Preparation 23D, employing 192 mgs of 2-pentyl-7-vinyl-4,5-dihydronaphtho[2,1-d]thiazole (86C). Yield: (190 mgs, 98%). LC/MS M$^{+1}$=286.

Example 86

This compound was prepared according to the general procedure described for Preparation 23, employing 195 mgs of 2-pentyl-4,5-dihydronaphtho[2,1-d]thiazole-7-carbaldehyde (Preparation 86D). Yield: 50 mgs (14%); The compound had an HPLC retention time=2.72 min. (condition C); LC/MS M$^{+1}$=371 $^1$H NMR (400 MHz, CD$_3$CN) δ ppm 7.22-7.34 (3H, m), 4.27 (6H, s), 3.67 (1H, br. s.), 2.92-3.11 (6H, m), 1.73-1.84 (2H, m), 1.32-1.45 (4H, m), 0.91 (3H, t, J=7 Hz).

Example 87

1-((3-(5-phenyl-4-(trifluoromethyl)isoxazol-3-yl)-4H-indeno[1,2-c]isoxazol-6-yl)methyl)azetidine-3-carboxylic acid (87)

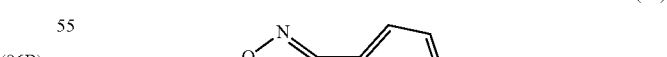
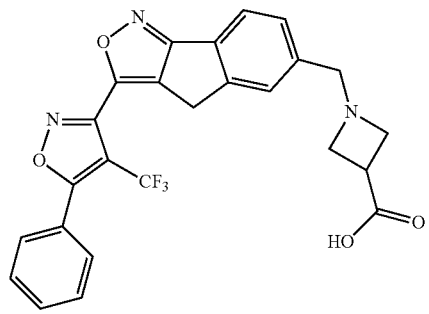

Preparation 87A:
5-vinyl-2,3-dihydro-1H-inden-1-one

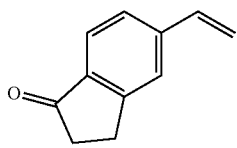
(87A)

To a mixture of 5-bromo-2,3-dihydro-1H-inden-1-one (2 g, 9.48 mmol), tributyl(vinyl)stannane (3.32 mL, 11.37 mmol) and toluene (30 mL) in a sealed tube was added Pd(Ph$_3$P)$_4$ (0.548 g, 0.474 mmol). Nitrogen was bubbled through the reaction for 5 min., the vessel was sealed and heated at 100° C. for 20 hr. After cooling the reaction mixture to room temperature, ethyl acetate (20 mL), water (30 mL) and celite were added. The mixture was stirred at room temperature for 30 min. and filtered. The EtOAc layer was separated and the aqueous layer was re-extracted with ethyl acetate (3×10 mL). The combined organic extracts were dried (sodium sulfate) and concentrated under reduced pressure. Flash chromatography purification (40 g silica gel column, 5→50% ethyl acetate in hexanes) afforded 5-vinyl-2,3-dihydro-1H-inden-1-one (1.2 g, 7.59 mmol, 80% yield) as a yellow solid. The product had an HPLC ret. time=2.50 min. (condition C); LC/MS M$^{+1}$=159.2.

Preparation 87B:
(E)-5-vinyl-2,3-dihydro-1H-inden-1-one oxime

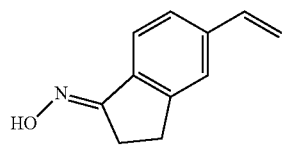
(87B)

To a mixture of 5-vinyl-2,3-dihydro-1H-inden-1-one (Preparation 87A, 1.05 g, 6.64 mmol), hydroxylamine hydrochloride (0.553 g, 7.96 mmol) and methanol (20 mL) at room temperature was added sodium acetate (0.653 g, 7.96 mmol). The reaction mixture was stirred at 60° C. for 1 hr and at room temperature overnight. The heterogeneous mixture was concentrated and water (20 mL) was added. The mixture was heated to ~60° C. and then cooled. The solid was filtered, washed with a mixture of water and ethanol (1:1) and dried to give (E)-5-vinyl-2,3-dihydro-1H-inden-1-one oxime (1.13 g, 6.52 mmol, 98% yield) as a yellow solid. The product had an HPLC ret. time=2.72 min. (condition C); LC/MS M$^{+1}$=174.3.

Preparation 87C: 3-(5-phenyl-4-(trifluoromethyl)isoxazol-3-yl)-6-vinyl-4H-indeno[1,2-c]isoxazole

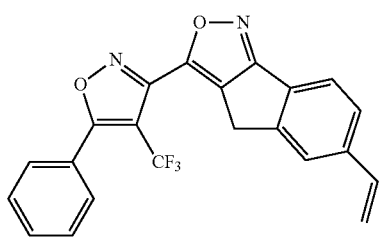
(87C)

To a stirred solution of diisopropylamine (0.441 mL, 3.10 mmol) in anhydrous THF (2 mL) was added n-BuLi (1.239 mL, 3.10 mmol) (2.5M solution in hexanes) dropwise at 0° C. under nitrogen. The pale yellow solution was then stirred at the same temperature for 20 min. before a solution of (E)-5-vinyl-2,3-dihydro-1H-inden-1-one oxime (Preparation 87B, 0.249 g, 1.438 mmol) in anhydrous THF (1 mL) was added dropwise at 0° C. under nitrogen. The mixture was stirred at 0° C. for 1 h and then a solution of methyl 5-phenyl-4-(trifluoromethyl)isoxazole-3-carboxylate (Intermediate 1-5, 0.3 g, 1.106 mmol) in anhydrous THF (1 mL) was added dropwise at 0° C. The mixture was stirred at 0° C. for 70 min before being quenched with saturated aqueous ammonium chloride solution (3 mL) and water (3 mL). The mixture was extracted with EtOAc (2×30 mL). The EtOAc extracts were washed with brine (20 mL), dried over sodium sulfate and concentrated to yield a brown foamy solid. Flash chromatography purification (12 g silica gel column, 10→50% ethyl acetate in n-heptane) afforded 3-(5-phenyl-4-(trifluoromethyl)isoxazol-3-yl)-6-vinyl-3a,4-dihydro-3H-indeno[1,2-c]isoxazol-3-ol as a brown solid.

The solid was mixed with anhydrous toluene (5 mL), thionyl chloride (0.073 mL, 1 mmol) and pyridine (0.016 mL, 0.2 mmol). The mixture was heated at 100° C. under nitrogen for 20 min. before being cooled. Saturated aqueous sodium bicarbonate solution (6 mL) was added. The aqueous layer was separated and extracted with dichloromethane (3×3 mL). The combined organic solutions were dried (sodium sulfate) and concentrated. Flash chromatography purification (12 g silica gel column, 10→100% dichloromethane in n-heptane) afforded 3-(5-phenyl-4-(trifluoromethyl)isoxazol-3-yl)-6-vinyl-4H-indeno[1,2-c]isoxazole (25 mg, 0.063 mmol, 5.73% yield) as a yellow solid. The compound had an HPLC retention time=4.20 min. (condition C); LC/MS M$^{+1}$=395.1.

Example 87

To a clear solution of 3-(5-phenyl-4-(trifluoromethyl)isoxazol-3-yl)-6-vinyl-4H-indeno[1,2-c]isoxazole (Preparation 87C, 25 mg, 0.063 mmol) in THF (1 mL) were sequentially added NMO (50% in water, 0.016 mL, 0.076 mmol) and osmium tetroxide (4% in water, 0.012 mL, 1.902 µmol) at room temperature. The solution was vigorously stirred at room temperature for 1 hr before more osmium tetroxide (4% in water, 0.02 mL) was added. The mixture was stirred at room temperature overnight. Sodium periodate (17.63 mg, 0.082 mmol) in water (0.1 mL) was added. After the mixture was stirred vigorously at room temperature under nitrogen for 1 hr, water (2 mL) was added. The mixture was concentrated, the solid was filtered, washed with water (1×0.5 mL) and dried to give 3-(5-phenyl-4-(trifluoromethyl)isoxazol-3-yl)-4H-indeno[1,2-c]isoxazole-6-carbaldehyde as a yellow solid.

The solid was mixed with 3-azetidinecarboxylic acid (12.82 mg, 0.127 mmol), anhydrous sodium sulfate (900 mg, 6.34 mmol), anhydrous 1,2-dichloroethane (1.5 mL), anhydrous MeOH (1.5 mL), and acetic acid (0.018 mL, 0.317 mmol). The mixture was stirred at 60° C. under nitrogen for 1 hr and then cooled. Sodium cyanoborohydride (7.97 mg, 0.127 mmol) was added. After being stirred at room temperature for 2 hr, the mixture was filtered and the filtrate was concentrated. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 1-((3-(5-phenyl-4-(trifluoromethyl)isoxazol-3-yl)-4H-indeno[1,2-c]isoxazol-6-yl)methyl)azetidine-3-carboxylic acid, TFA (15 mg, 0.024 mmol, 37.4% yield) (80592-029-01) as a yellow solid. The compound had an HPLC retention time=3.10 min. (condition C)); LC/MS M$^{+1}$=482.4. $^1$H NMR (400 MHz, MeOD) δ ppm 8.04 (1H, d, J=7.9 Hz), 7.75-7.81 (3H, m), 7.59-7.73 (4H, m), 4.54 (2H, s), 4.33-4.44 (4H, m), 4.10 (2H, s), 3.72 (1H, quin, J=8.3 Hz).

Example 88

2-(methyl((3-(5-phenyl-4-(trifluoromethyl)isoxazol-3-yl)-4,5-dihydronaphtho[1,2-c]isoxazol-7-yl)methyl)amino)acetic acid

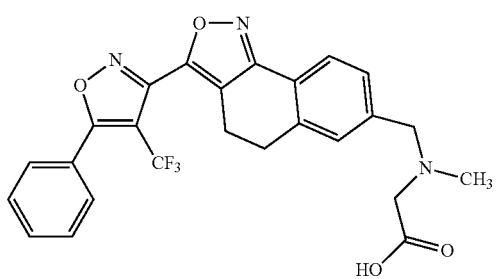

(88)

Preparation 88A: 3-(5-phenyl-4-(trifluoromethyl)isoxazol-3-yl)-4,5-dihydronaphtho[1,2-c]isoxazole-7-carbaldehyde

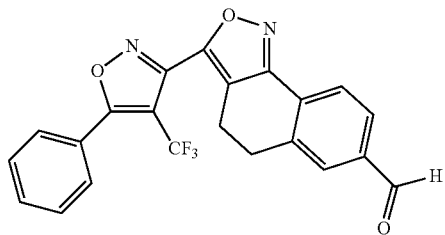

(88A)

To a clear solution of 3-(5-phenyl-4-(trifluoromethyl)isoxazol-3-yl)-7-vinyl-4,5-dihydronaphtho[1,2-c]isoxazole (Preparation 6A, 1.6 g, 3.92 mmol) in THF (15 mL) were sequentially added NMO (50% in water, 1.219 mL, 5.88 mmol) and osmium tetroxide (4% in water, 0.958 mL, 0.157 mmol) at room temperature. The solution was vigorously stirred at room temperature overnight. A cloudy solution of sodium periodate (1.425 g, 6.66 mmol) in water (14 mL) was added. The mixture was stirred at room temperature under nitrogen for 0.5 hr. Water (20 mL) was then added and the mixture was stirred at room temperature for 30 min. The solid was filtered, washed with water (2×2 mL) and methanol (2 mL) and dried to give 3-(5-phenyl-4-(trifluoromethyl)isoxazol-3-yl)-4,5-dihydronaphtho[1,2-c]isoxazole-7-carbaldehyde (1.6 g, 3.90 mmol, 100% yield) as a white solid. The compound had an HPLC retention time=4.02 min. (condition C); LC/MS M$^{+1}$=410.9.

Example 88

A stirred mixture of 3-(5-phenyl-4-(trifluoromethyl)isoxazol-3-yl)-4,5-dihydronaphtho[1,2-c]isoxazole-7-carbaldehyde (Preparation 88A, 28 mg, 0.068 mmol), sarcosine hydrochloride (42.8 mg, 0.341 mmol), sodium acetate (28.0 mg, 0.341 mmol), anhydrous sodium sulfate (1 g), anhydrous MeOH (1 mL), and anhydrous 1,2-dichloroethane (3 mL) was stirred at 60° C. under nitrogen for 1 hr. After the mixture was cooled to room temperature, sodium cyanoborohydride (8.58 mg, 0.136 mmol) was added. The reaction mixture was stirred at room temperature for 30 min and then filtered. The filtrate was concentrated. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 2-(methyl((3-(5-phenyl-4-(trifluoromethyl)isoxazol-3-yl)-4,5-dihydronaphtho[1,2-c]isoxazol-7-yl)methyl)amino)acetic acid, TFA (25 mg, 0.041 mmol, 60.7% yield) as a white solid. The compound had an HPLC retention time=3.39 min. (condition C); LC/MS M$^{+1}$=484.4. $^1$H NMR (400 MHz, MeOD) δ ppm 8.08 (1H, d, J=7.9 Hz), 7.77 (2H, d, J=7.3 Hz), 7.54-7.72 (5H, m), 4.45 (2H, s), 4.08 (2H, s), 3.07-3.19 (4H, m), 2.94 (3H, s).

Example 89

(±) 2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid

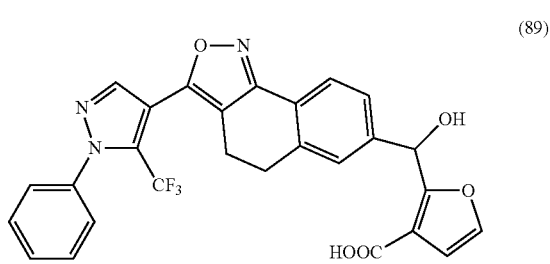 [SMILES: O=C(O)c1ccoc1C(O)c1ccc2c(c1)CCc1c-2noc1-c1cnn(-c2ccccc2)c1C(F)(F)F]

(89)

Preparation 89A: 3-(1-phenyl-5-(trifluoromethyl)-1H-pyrazol-4-yl)-7-vinyl-4,5-dihydronaphtho[1,2-c]isoxazole

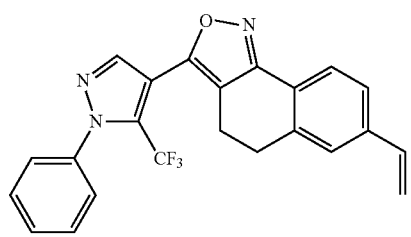

(89A)

To a stirred solution of diisopropylamine (1.103 mL, 7.74 mmol) in anhydrous THF (8 mL) was added n-BuLi (2.5M in hexanes, 3.10 mL, 7.74 mmol) dropwise at 0° C. under nitrogen. The pale yellow solution was then stirred at the same temperature for 20 min. before a solution of 6-vinyl-3,4-dihydronaphthalen-1(2H)-one oxime (I-1, 0.659 g, 3.52 mmol) in anhydrous THF (4 mL) was added dropwise at 0° C. under nitrogen. The mixture was stirred at 0° C. for 1 h. A solution of ethyl 1-phenyl-5-(trifluoromethyl)-1H-pyrazole-4-carboxylate (1 g, 3.52 mmol) in anhydrous THF (3 mL) was added dropwise while the mixture was cooled down with dry ice. The solution was stirred with dry ice cooling for 40 min. The temperature was raised to 0° C. over 15 min. After stirring at 0° C. for 45 min., the reaction mixture was quenched with saturated aqueous ammonium chloride solution (5 mL) and water (3 mL). The mixture was extracted with EtOAc (2×20 mL). The EtOAc extracts were washed with brine (10 mL), dried over sodium sulfate and concentrated to yield a yellow foam solid.

The solid was mixed with anhydrous toluene (20 mL). Thionyl chloride (0.514 mL, 7.04 mmol) in pyridine (0.057 mL, 0.704 mmol) was added at room temperature under nitrogen. The mixture was stirred at room temperature for 5 min. and at 100° C. for 25 min. After the mixture was concentrated, saturated aqueous sodium bicarbonate solution (20 mL) and water (10 mL) were added. The mixture was extracted with dichloromethane (20 mL, then 2×10 mL). The combined dichloromethane extracts were dried (sodium sulfate) and concentrated. Flash chromatograph (40 g silica gel column, 20→100% dichloromethane in n-heptane and then 20%→50% ethyl acetate in n-heptane) and trituration with ethyl acetate and n-heptane afforded 3-(1-phenyl-5-(trifluoromethyl)-1H-pyrazol-4-yl)-7-vinyl-4,5-dihydronaphtho[1,2-c]isoxazole (560 mg, 1.375 mmol, 39.1% yield) as a green solid. The compound had an HPLC retention time=3.98 min. (condition C); LC/MS $M^{+1}$=407.8.

Preparation 89B: 3-(1-phenyl-5-(trifluoromethyl)-1H-pyrazol-4-yl)-4,5-dihydronaphtho[1,2-c]isoxazole-7-carbaldehyde

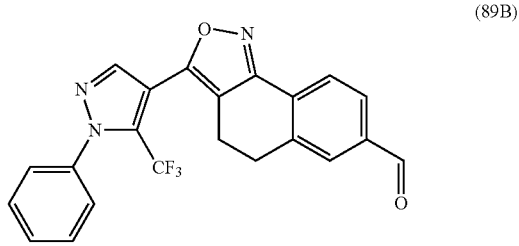 [SMILES: O=Cc1ccc2c(c1)CCc1c-2noc1-c1cnn(-c2ccccc2)c1C(F)(F)F]

(89B)

To a clear solution of 3-(1-phenyl-5-(trifluoromethyl)-1H-pyrazol-4-yl)-7-vinyl-4,5-dihydronaphtho[1,2-c]isoxazole (Preparation 89A, 0.15 g, 0.368 mmol) in THF (1.5 mL) were added NMO (50% in water, 0.092 mL, 0.442 mmol) and osmium tetroxide (4% in water, 0.068 mL, 0.011 mmol) at room temperature. The solution was vigorously stirred at room temperature overnight. Sodium periodate (0.102 g, 0.479 mmol) in water (0.5 mL) was added. The mixture was stirred vigorously at room temperature under nitrogen for 30 min. Water (5 mL) was added and the mixture was extracted with ethyl acetate (3×2 mL). The combined ethyl acetate extracts were dried (sodium sulfate), filtered through a pad of silica gel which was then rinsed with ethyl acetate and concentrated to give 3-(1-phenyl-5-(trifluoromethyl)-1H-pyrazol-4-yl)-4,5-dihydronaphtho[1,2-c]isoxazole-7-carbaldehyde (0.15 g, 0.366 mmol, 100% yield) as a green solid. The compound had an HPLC retention time=3.64 min. (condition C); LC/MS $M^{+1}$=409.9.

Example 89

To a stirred solution of diisopropylamine (0.072 mL, 0.508 mmol) in anhydrous THF (0.5 mL) was added a 2.5 M THF solution of n-BuLi (0.203 mL, 0.508 mmol) dropwise at 0° C. under nitrogen. The mixture was stirred at the same temperature for 15 min. before being cooled to −78° C. A solution of furan-3-carboxylic acid (28.5 mg, 0.254 mmol) in anhydrous THF (1 mL) was added. The reaction mixture was stirred at −78° C. for 30 min. before a solution of 3-(1-phenyl-5-(trifluoromethyl)-1H-pyrazol-4-yl)-4,5-dihydronaphtho[1,2-c]isoxazole-7-carbaldehyde (Preparation 89B, 80 mg, 0.195 mmol) in anhydrous THF (1 mL) was added at the same temperature. The mixture was then allowed to warm to room temperature over 30 min. The reaction was quenched with water (3 mL). The mixture was concentrated and the aqueous residue was acidified with 10% aqueous citric acid solution to pH=3. The mixture was extracted with ethyl acetate (2×3 mL). The combined organic solutions were dried (sodium sulfate) and concentrated to give 2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid (110 mg, 0.211 mmol, 108% yield) as green foam solid. Next, 48 mg of the solid was purified by reverse phase preparative HPLC (Phenomenex Luna AXIA 5 u c18 30×100 mm, 10 min. run, solvent A: 10% MeOH: 90% $H_2O$: 0.1% TFA, solvent B: 90% MeOH, 10% $H_2O$, 0.1% TFA) to give 2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid, TFA (32 mg) as white solid. The compound had an HPLC retention time=3.42 min. (condition C); LC/MS $M^{+1}$=522.2; $^1$H NMR (400 MHz, MeOD) δ ppm 8.14 (1H, s), 7.88 (1H, d, J=7.9 Hz), 7.54-7.63 (6H, m), 7.48-7.52 (2H, m), 7.47 (1H, d, J=7.9 Hz), 6.72 (1H, d, J=2.0 Hz), 6.56 (1H, s), 3.03 (2H, t, J=6.9 Hz), 2.89 (2H, t, J=6.9 Hz).

Example 90

(±) 2-(amino(3-(1-phenyl-5-(trifluoromethyl)-1H-pyrazol-4-yl)-4,5-dihydronaphtho[1,2-c]isoxazol-7-yl)methyl)furan-3-carboxylic acid

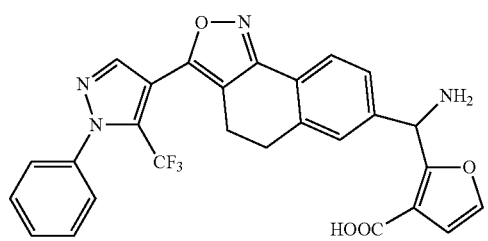

(90)

To a stirred solution of 2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid (Example 89, 50 mg, 0.096 mmol) in anhydrous dichloromethane (1 mL) was added thionyl chloride (0.1 mL, 1.370 mmol) dropwise at room temperature under nitrogen. The resulting mixture was stirred at room temperature overnight. The volatiles were removed and the residue was dissolved in dichloromethane (2 mL) and treated with concentrated aqueous ammonia (1.5 mL). The mixture was stirred at room temperature for 1 hr before being diluted with water (2 mL) and extracted with dichloromethane (3×2 mL). The combined dichloromethane extracts were dried (sodium sulfate) and concentrated. The residue was mixed with 48% aq. HBr (0.5 mL). The mixture was stirred at 100° C. for 4 hr under nitrogen before being cooled and neutralized with concentrated aqueous ammonia. The solid was filtered and purified using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA) to give 2-(amino(3-(1-phenyl-5-(trifluoromethyl)-1H-pyrazol-4-yl)-4,5-dihydronaphtho[1,2-c]isoxazol-7-yl)methyl)furan-3-carboxylic acid, 1.5 TFA (4 mg, 5.44 μmol, 5.67% yield) as a white solid. The compound had an HPLC retention time=3.02 min. (condition C); LC/MS M$^{-1}$=519.4; $^1$H NMR (400 MHz, MeOD) δ ppm 8.14 (1H, s), 8.01 (1H, d, J=7.9 Hz), 7.73 (1H, d, J=2.0 Hz), 7.51-7.64 (7H, m), 6.86 (1H, d, J=2.0 Hz), 6.36 (1H, s), 3.08 (2H, t, J=7.0 Hz), 2.92 (2H, t, J=7.0 Hz).

Example 91

(±) 2-amino-4-(3-(5-phenyl-4-(trifluoromethyl)isoxazol-3-yl)-4,5-dihydronaphtho[1,2-c]isoxazol-7-yl)butanoic acid (91)

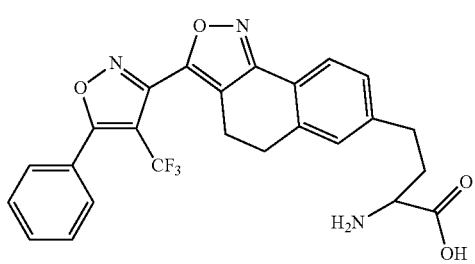

Preparation 91A: Ethyl 2-(diphenylmethyleneamino)-4-(3-(5-phenyl-4-(trifluoromethyl)isoxazol-3-yl)-4,5-dihydronaphtho[1,2-c]isoxazol-7-yl)butanoate (91A)

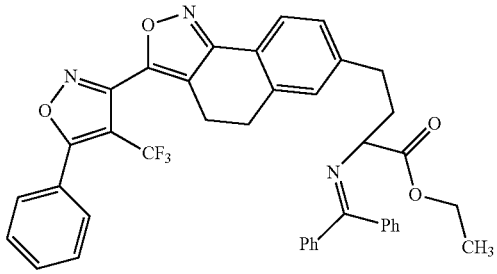

A mixture of ethyl 2-(diphenylmethyleneamino)acetate (236 mg, 0.882 mmol), Cs$_2$CO$_3$ (144 mg, 0.441 mmol), 3-(5-phenyl-4-(trifluoromethyl)isoxazol-3-yl)-7-vinyl-4,5-dihydronaphtho[1,2-c]isoxazole (Preparation 6A, 100 mg, 0.245 mmol), and anhydrous DMSO (0.6 mL) was purged with nitrogen for 5 min. and then sealed in a 1 dram vial. The mixture was stirred at 50° C. for 2 h. The mixture was cooled, diluted with water (15 mL) and extracted with ethyl acetate (3×5 mL). The combined ethyl acetate extracts were dried (sodium sulfate) and concentrated under reduced pressure. Flash chromatography purification (12 g silica gel column, 10→100% ethyl acetate in hexanes) afforded ethyl 2-(diphenylmethyleneamino)-4-(3-(5-phenyl-4-(trifluoromethyl)isoxazol-3-yl)-4,5-dihydronaphtho[1,2-c]isoxazol-7-yl)butanoate (140 mg, 0.207 mmol, 85% yield) as a sticky liquid. The compound had an LC/MS M$^{+1}$=676.2.

Example 91

To a stirred solution of ethyl 2-(diphenylmethyleneamino)-4-(3-(5-phenyl-4-(trifluoromethyl)isoxazol-3-yl)-4,5-dihydronaphtho[1,2-c]isoxazol-7-yl)butanoate (Preparation 91A, 34 mg, 0.050 mmol) and water (0.025 mL) in diethyl ether (1.5 mL) was added 6 N aqueous HCl (50 μL, 0.300 mmol). The mixture was stirred at room temperature for 30 min. The ether layer was removed and the residue was mixed with MeOH (0.5 mL) and 2 N aqueous sodium hydroxide (0.5 mL, 1.000 mmol). After being stirred at room temperature for 30 min, the mixture was acidified with TFA to get a clear solution. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 2-amino-4-(3-(5-phenyl-4-(trifluoromethyl)isoxazol-3-yl)-4,5-dihydronaphtho[1,2-c]isoxazol-7-yl)butanoic acid, TFA (10 mg, 0.015 mmol, 30.6% yield) as a white solid. The compound had an HPLC retention time=3.40 min. (condition C); LC/MS M$^{+1}$=484.1; $^1$H NMR (400 MHz, MeOD) δ ppm 7.91 (1H, d, J=7.7 Hz), 7.78 (2H, d, J=8.1 Hz), 7.59-7.72 (3H, m), 7.33 (1H, s), 7.30 (1H, dd, J=8.0, 1.7 Hz), 4.00 (1H, t, J=6.3 Hz), 3.04-3.10 (4H, m), 2.74-2.95 (2H, m), 2.12-2.36 (2H, m).

Example 92

2-amino-2-(2-(3-(5-phenyl-4-(trifluoromethyl)isoxazol-3-yl)-4,5-dihydronaphtho[1,2-c]isoxazol-7-yl)ethyl)propane-1,3-diol (92)

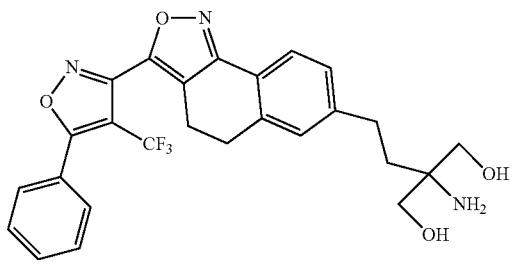

Preparation 92A: Diethyl 2-(tert-butoxycarbonylamino)-2-(2-(3-(5-phenyl-4-(trifluoromethyl)isoxazol-3-yl)-4,5-dihydronaphtho[1,2-c]isoxazol-7-yl)ethyl)malonate (92A)

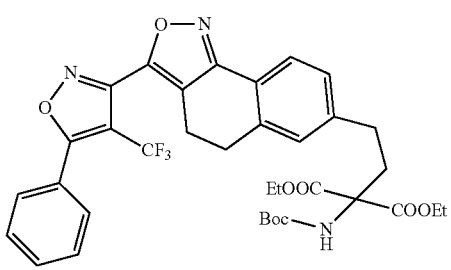

The titled compound was prepared using the experimental protocol described for Preparation 91A employing diethyl 2-(tert-butoxycarbonylamino)malonate as a starting material. The reaction was heated at 70° C. for 7 hr. The compound had an LC/MS [M-Boc]$^{+1}$=584.5.

Example 92

To a stirred solution of diethyl 2-(tert-butoxycarbonylamino)-2-(2-(3-(5-phenyl-4-(trifluoromethyl)isoxazol-3-yl)-4,5-dihydronaphtho[1,2-c]isoxazol-7-yl)ethyl)malonate (Preparation 92A, 80 mg, 0.117 mmol) in ethanol (2 mL) was added sodium borohydride (50 mg, 1.322 mmol) at room temperature. The mixture was stirred at room temperature overnight. Saturated aqueous ammonium chloride solution (2 mL) was added slowly, to quench the reaction. The mixture was concentrated and extracted with ethyl acetate (3×2 mL). The combined ethyl acetate extracts were dried (sodium sulfate) and concentrated under reduced pressure. The residue was mixed with TFA (0.5 mL). After being stirred at room temperature for 30 min, the mixture was concentrated. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave a white solid. The solid was further purified by SFC (Lux-cellulose-2 (3×25 cm), 35% MeOH/DEA (100/0.1) in CO$_2$, 220 nm, 120 ml/min, 35° C.) to give 2-amino-2-(2-(3-(5-phenyl-4-(trifluoromethyl)isoxazol-3-yl)-4,5-dihydronaphtho[1,2-c]isoxazol-7-yl)ethyl)propane-1,3-diol, TFA (12 mg, 0.019 mmol, 16.05% yield) as a white solid. The compound had an HPLC retention time=3.32 min. (condition C); LC/MS M$^{+1}$=500.2. $^1$H NMR (400 MHz, MeOD) δ ppm 7.87 (1H, d, J=7.7 Hz), 7.77 (2H, d, J=7.5 Hz), 7.59-7.71 (3H, m), 7.32 (1H, s), 7.29 (1H, d, J=7.9 Hz), 3.67 (4H, s), 3.02-3.10 (4H, m), 2.69-2.78 (2H, m), 1.89-1.98 (2H, m).

Example 93

2-amino-2-methyl-4-(3-(5-phenyl-4-(trifluoromethyl)isoxazol-3-yl)-4,5-dihydronaphtho[1,2-c]isoxazol-7-yl)butan-1-ol (93)

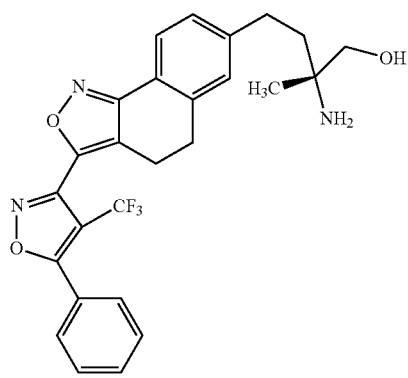

-continued

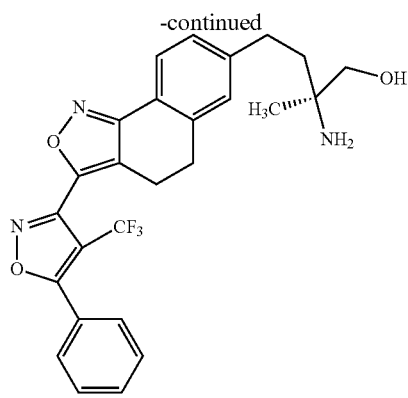

Preparation 93A: Ethyl 2-(diphenylmethyleneamino)-2-methyl-4-(3-(5-phenyl-4-(trifluoromethyl)isoxazol-3-yl)-4,5-dihydronaphtho[1,2-c]isoxazol-7-yl)butanoate (93A)

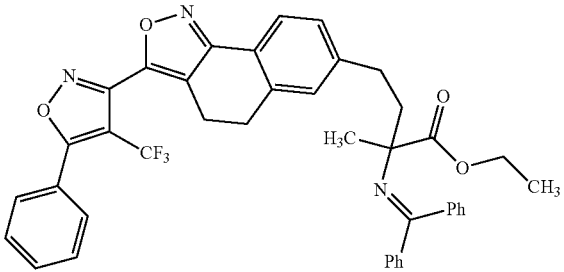

To a clear solution of ethyl 2-(diphenylmethyleneamino)-4-(3-(5-phenyl-4-(trifluoromethyl)isoxazol-3-yl)-4,5-dihydronaphtho[1,2-c]isoxazol-7-yl)butanoate (Preparation 91A, 560 mg, 0.829 mmol) in anhydrous THF (20 mL) was added 1 M THF solution of lithium bis(trimethylsilyl)amide (4 mL, 4.00 mmol) dropwise at 0° C. under nitrogen. The mixture was stirred at the same temperature for 60 min. before half the amount of the required iodomethane (0.25 mL, 4.00 mmol) was added. The mixture was stirred at 0° C. for 20 min. before the rest of the iodomethane was added. The mixture was stirred at 0° C. for an additional 50 min. and saturated aqueous ammonium chloride solution (5 mL) and water (2 mL) were added. The mixture was extracted with ethyl acetate (10 mL and then 2×5 mL). The combined ethyl acetate extracts were dried (sodium sulfate) and concentrated under reduced pressure. Flash chromatography purification (24 g silica gel column, 5→50% ethyl acetate in hexanes) afforded ethyl 2-(diphenylmethyleneamino)-2-methyl-4-(3-(5-phenyl-4-(trifluoromethyl)isoxazol-3-yl)-4,5-dihydronaphtho[1,2-c]isoxazol-7-yl)butanoate (300 mg, 0.435 mmol, 52.5% yield) as a glassy solid. The compound had an LC/MS M$^{+1}$=690.4.

Example 93

To a stirred solution of ethyl 2-(diphenylmethyleneamino)-2-methyl-4-(3-(5-phenyl-4-(trifluoromethyl)isoxazol-3-yl)-4,5-dihydronaphtho[1,2-c]isoxazol-7-yl)butanoate (Preparation 93A, 200 mg, 0.290 mmol) and water (0.025 mL) in diethyl ether (6 mL) was added 6 N aqueous HCl (0.290 mL, 1.740 mmol). The mixture was stirred at room temperature for 2 h. The diethyl ether layer was decanted and the residue was washed with diethyl ether (2 mL). The combined diethyl ether solutions were extracted with water (1 mL). The aqueous extract and the above residue were combined. The mixture was basified with potassium carbonate solid and extracted with ethyl acetate (3×2 mL). The combined ethyl acetate extracts were dried (sodium sulfate) and concentrated under reduced pressure to give a liquid. The liquid was mixed with EtOH (3 mL) and sodium borohydride (54.9 mg, 1.450 mmol). The mixture was stirred at room temperature overnight. Saturated aqueous ammonium chloride solution (10 mL) was added slowly, to quench the reaction. Ethyl acetate (20 mL) and water (10 mL) were then added. The solid was filtered through a pad of celite. The filtrate was separated and the aqueous layer was extracted with ethyl acetate (4×5 mL). The combined ethyl acetate solutions were washed with water (2×5 mL) and 2N aqueous sodium hydroxide (10 mL), dried (sodium sulfate) and concentrated under reduced pressure to give an oily product (30 mg). The solid on the celite was washed with 1:1 dichloromethane/methanol (40 mL). The filtrate was concentrated and dissolved in dichloromethane (30 mL). The mixture was washed with 2N aqueous sodium hydroxide (10 mL) and water (10 mL), dried (sodium sulfate) and concentrated to give a solid product (53 mg). The solid and the oily products were combined and separated into individual enantiomers using a Lux-Cellulose-2 column under SFC conditions (35% MeOH with 0.1% EA in $CO_2$). Example 93, Isomer 1 (28 mg), retention time on chiral HPLC, 10.61 min; LC/MS $M^{+1}$=484.1; Example 93, Isomer 2 (26 mg), retention time on chiral HPLC, 14.05 min; LC/MS $M^{+1}$=484.2. The absolute stereochemistry at the carbon anchoring the secondary alcohol, of Isomer 1 and Isomer 2, was not determined. $^1$H NMR (400 MHz, $CDCl_3$) δ ppm 7.95 (1H, d, J=7.7 Hz), 7.76 (2H, d, J=7.3 Hz), 7.53-7.66 (3H, m), 7.22 (1H, d, J=7.7 Hz), 7.19 (1H, s), 3.34-3.47 (2H, m), 2.98-3.14 (4H, m), 2.70 (2H, t, J=8.7 Hz), 1.64-1.85 (2H, m), 1.18 (3H, s).

Example 94

2-amino-2-methyl-4-(3-(5-phenyl-4-(trifluoromethyl)isoxazol-3-yl)-4,5-dihydronaphtho[1,2-c]isoxazol-7-yl)butanoic acid (94)

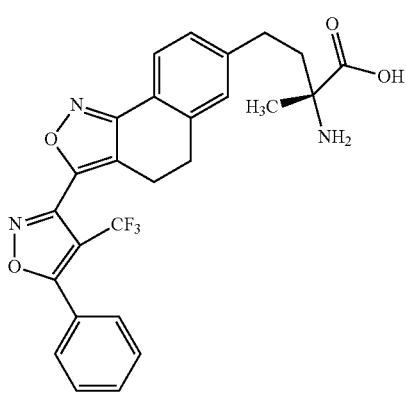

Preparation 94A: Ethyl 2-amino-2-methyl-4-(3-(5-phenyl-4-(trifluoromethyl)isoxazol-3-yl)-4,5-dihydronaphtho[1,2-c]isoxazol-7-yl)butanoate (94A)

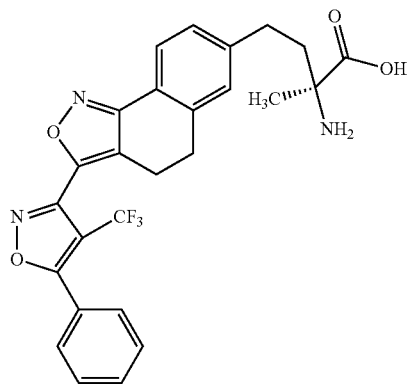

To a stirred solution of ethyl 2-(diphenylmethyleneamino)-2-methyl-4-(3-(5-phenyl-4-(trifluoromethyl)isoxazol-3-yl)-4,5-dihydronaphtho[1,2-c]isoxazol-7-yl)butanoate (Preparation 93A, 36 mg, 0.052 mmol) in diethyl ether (3 mL) was added 4 M aqueous solution of HCl (120 μL, 0.480 mmol). The mixture was stirred at room temperature for 30 min. The ether layer was separated and extracted with water (1 mL). The aqueous extract was combined with the aqueous layer in the reaction. The mixture was basified with solid potassium carbonate and extracted with ethyl acetate (4×1.5 ml). The combined ethyl acetate extracts were dried (sodium sulfate) and concentrated under reduced pressure to give a glassy solid. The individual enantiomers were separated using a Lux-Cellulose-2 column under SFC conditions (20% IPA with 0.1% EA in $CO_2$). Isomer 1 (Preparation 94A, 8 mg), retention time on chiral HPLC, 8.3 min; Isomer 2 (Preparation 94A, 6 mg), retention time on chiral HPLC, 9.3 min. The

Example 94

Isomer 1

A mixture of ethyl 2-amino-2-methyl-4-(3-(5-phenyl-4-(trifluoromethyl)isoxazol-3-yl)-4,5-dihydronaphtho[1,2-c]isoxazol-7-yl)butanoate (Preparation 94A, isomer 1, 8 mg, 0.015 mmol), 2 M aqueous solution of sodium hydroxide (0.015 mL, 0.030 mmol), water (0.1 mL) and methanol (0.2 mL) was stirred at 66° C. under nitrogen for 30 min. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 2-amino-2-methyl-4-(3-(5-phenyl-4-(trifluoromethyl)isoxazol-3-yl)-4,5-dihydronaphtho[1,2-c]isoxazol-7-yl)butanoic acid, TFA (6 mg, 9.42 µmol, 61.9% yield) as a white solid. The compound had an HPLC retention time=3.45 min. (condition C); LC/MS M$^{+1}$=498.5.

Example 94

Isomer 2

In the same fashion, the second enantiomer (Preparation 94A, isomer 2, 6 mg) was converted to (2-amino-2-methyl-4-(3-(5-phenyl-4-(trifluoromethyl)isoxazol-3-yl)-4,5-dihydronaphtho[1,2-c]isoxazol-7-yl)butanoic acid, TFA (6 mg, 9.32 µmol, 61.2% yield) as a white solid. The compound had an HPLC retention time=3.46 min. (condition C); LC/MS M$^{+1}$=498.4. $^1$H NMR (400 MHz, MeOD) δ ppm 7.90 (1H, d, J=7.7 Hz), 7.78 (2H, d, J=7.5 Hz), 7.60-7.72 (3H, m), 7.29 (1H, s), 7.27 (1H, d, J=8.1 Hz), 3.07 (4H, s), 2.84 (1H, td, J=13.0, 4.8 Hz), 2.66 (1H, td, J=13.0, 5.1 Hz), 2.26 (1H, td, J=13.6, 4.5 Hz), 2.10 (1H, td, J=13.2, 5.0 Hz), 1.62 (3H, s).

Example 95

2-amino-2-methyl-4-(3-(5-phenyl-4-(trifluoromethyl)isoxazol-3-yl)-4,5-dihydronaphtho[1,2-c]isoxazol-7-yl)butyl dihydrogen phosphate

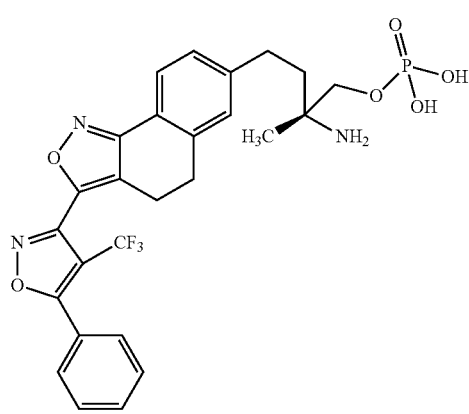

(95)

-continued

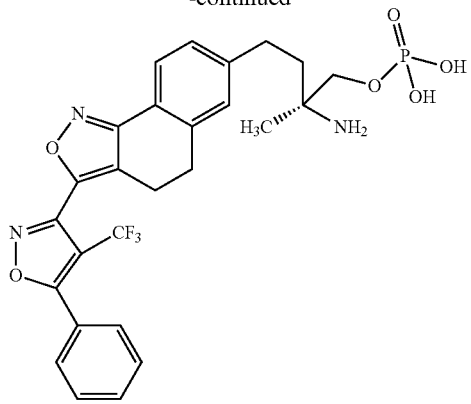

Example 95

Isomer 1

A mixture of phosphorus pentoxide (150 mg, 0.528 mmol) and 85% phosphoric acid (0.15 mL, 0.017 mmol) was stirred at 100° C. under nitrogen for 1 hr before 2-amino-2-methyl-4-(3-(5-phenyl-4-(trifluoromethyl)isoxazol-3-yl)-4,5-dihydronaphtho[1,2-c]isoxazol-7-yl)butan-1-ol (Isomer 1 of Example 93, 8 mg, 0.017 mmol) was added. The clear solution was stirred at the same temperature for 3 hr before being cooled. Water (0.4 mL) was added while the mixture was cooled with ice. The mixture was stirred at room temperature for 30 min. The mixture was dissolved in methanol and a little dichloromethane. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 2-amino-2-methyl-4-(3-(5-phenyl-4-(trifluoromethyl)isoxazol-3-yl)-4,5-dihydronaphtho[1,2-c]isoxazol-7-yl)butyl dihydrogen phosphate (5 mg, 8.6 µmol, 52% yield) as a white solid. The compound had an HPLC retention time=3.55 min. (condition C); LC/MS M$^{+1}$=564.6. $^1$H NMR (400 MHz, MeOD) δ ppm 7.88 (1H, d, J=7.9 Hz), 7.76 (2H, d, J=7.3 Hz), 7.57-7.69 (3H, m), 7.31 (1H, s), 7.28 (1H, d, J=7.9 Hz), 3.82-3.99 (2H, m), 3.04-3.10 (4H, m), 2.67-2.83 (2H, m), 1.89-2.10 (2H, m), 1.40 (3H, s).

Example 95

Isomer 2

The titled compound was prepared in the same way employing Isomer 2 of Example 93. The compound had an HPLC retention time=3.54 min. (condition C); LC/MS M$^{+1}$=564.5.

The compounds in the following table were prepared in the same fashion employing the corresponding alcohols.

| Ex. No. | Structure | Name | MW | HPLC ret. time (min)* | MS (M⁺¹) |
|---|---|---|---|---|---|
| 96 | 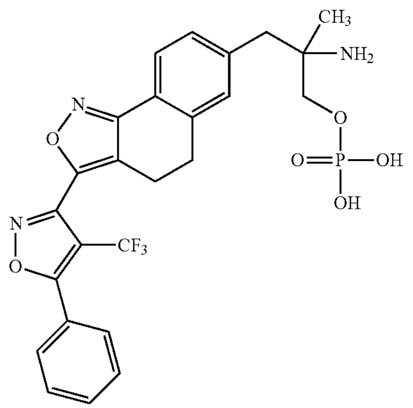 [SMILES: CC(N)(COP(=O)(O)O)Cc1ccc2c(c1)CCc1c-2noc1-c1noc(-c2ccccc2)c1C(F)(F)F] | (±) 2-amino-2-methyl-3-(3-(5-phenyl-4-(trifluoromethyl)isoxazol-3-yl)-4,5-dihydronaphtho[1,2-c]isoxazol-7-yl)propyl dihydrogen phosphate | 549 | 3.53 | 549.9 |
| 97 | 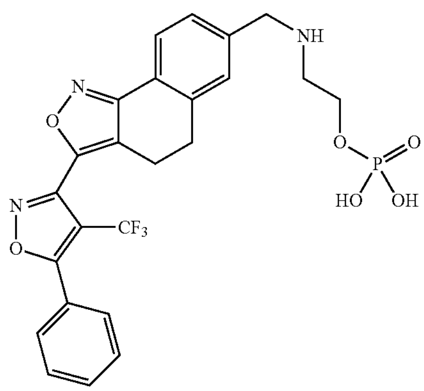 [SMILES: O=P(O)(O)OCCNCc1ccc2c(c1)CCc1c-2noc1-c1noc(-c2ccccc2)c1C(F)(F)F] | 2-((3-(5-phenyl-4-(trifluoromethyl)isoxazol-3-yl)-4,5-dihydronaphtho[1,2-c] isoxazol-7-yl)methylamino)ethyl dihydrogen phosphate | 535 | 3.48 | 535.9 |
| 98 Isomer 1 | 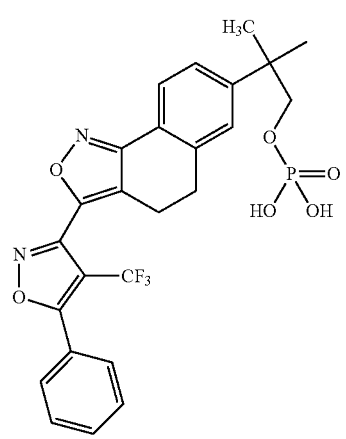 [SMILES: CC(C)(COP(=O)(O)O)c1ccc2c(c1)CCc1c-2noc1-c1noc(-c2ccccc2)c1C(F)(F)F] | 2-amino-2-(3-(5-phenyl-4-(trifluoromethyl)isoxazol-3-yl)-4,5-dihydronaphtho[1,2-c]isoxazol-7-yl)propyl dihydrogen phosphate | 535 | 3.30 | 536 |
| 98 Isomer 2 | | | 535 | 3.31 | 536 |

-continued

| Ex. No. | Structure | Name | MW | HPLC ret. time (min)* | MS (M+1) |
|---|---|---|---|---|---|
| 99 Isomer 1 | 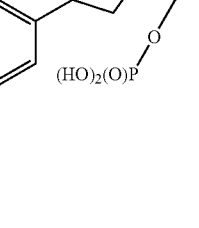 | (1-amino-3-(5-phenyl-4-(trifluoromethyl) isoxazol-3-yl)-4,5-dihydronaphtho[1,2-c] isoxazol-7-yl) cyclopentyl)methyl dihydrogen phosphate | 575 | 3.61 | 576 |
| 99 Isomer 2 | | | 575 | 3.59 | 576 |
| 99 Isomer 3 | | | 575 | 3.59 | 576 |
| 99 Isomer 4 | | | 575 | 3.60 | 576 |
| 100 Isomer 1 | 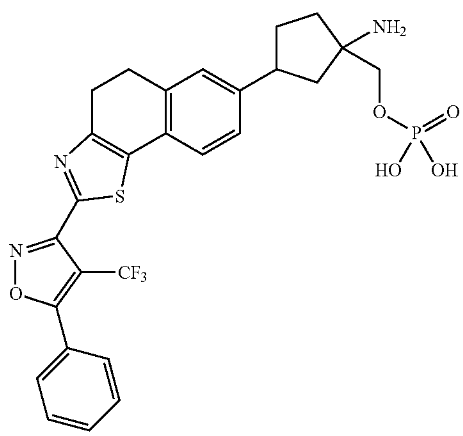 [SMILES: NC1(COP(=O)(O)O)CCC(c2ccc3c(c2)CCc2nc(-c4noc(-c5ccccc5)c4C(F)(F)F)sc2-3)C1] | (1-amino-3-(2-(3-phenyl-4-(trifluoromethyl) isoxazol-5-yl)-4,5-dihydronaphtho[2,1-d] thiazol-7-yl)cyclopentyl) methyl dihydrogen phosphate | 591 | 3.76 | 592 |
| 100 Isomer 2 | | | 591 | 3.76 | 592 |
| 100 Isomer 3 | | | 591 | 3.75 | 592 |
| 100 Isomer 4 | | | 591 | 3.75 | 592 |
| 101 Isomer 1 | 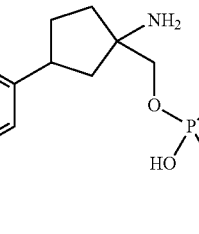 | 2-(1-amino-3-(2-(3-phenyl-4-(trifluoromethyl)isoxazol-5-yl)-4,5-dihydronaphtho[2,1-d]thiazol-7-yl)cyclopentyl)ethyl dihydrogen phosphate | 605 | 3.83 | 606 |
| 101 Isomer 2 & 3 | | | 605 | 3.82 | 606 |

*Condition C

Example 102

1-(3-(5-phenyl-4-(trifluoromethyl)isoxazol-3-yl)-4,5-dihydronaphtho[1,2-c]isoxazol-7-yl)ethane-1,2-diol

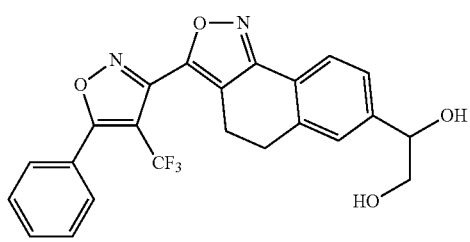
(102)

To a clear solution of 3-(5-phenyl-4-(trifluoromethyl)isoxazol-3-yl)-7-vinyl-4,5-dihydronaphtho[1,2-c]isoxazole (Preparation 6A, 0.4 g, 0.979 mmol) in THF (3 mL) were added NMO (50% in water, 0.305 mL, 1.469 mmol) and osmium tetroxide (4% in water, 0.239 mL, 0.039 mmol) at room temperature. The solution was vigorously stirred at room temperature overnight. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 1-(3-(5-phenyl-4-(trifluoromethyl)isoxazol-3-yl)-4,5-dihydronaphtho[1,2-c]isoxazol-7-yl)ethane-1,2-diol as a white solid. The compound had an HPLC retention time=3.61 min. (condition C); LC/MS M$^{+1}$=443.2. $^1$H NMR (400 MHz, MeOD) δ ppm 7.92 (1H, d, J=7.9 Hz), 7.77 (2H, d, J=7.5 Hz), 7.58-7.72 (3H, m), 7.45 (1H, s), 7.42 (1H, d, J=7.9 Hz), 4.74 (1H, dd, J=6.8, 4.8 Hz), 3.61-3.72 (2H, m), 3.08 (4H, s).

Example 103

1-((3-(3-phenyl-4-(trifluoromethyl)isothiazol-5-yl)-4,5-dihydronaphtho[1,2-c]isoxazol-7-yl)methyl)azetidine-3-carboxylic acid

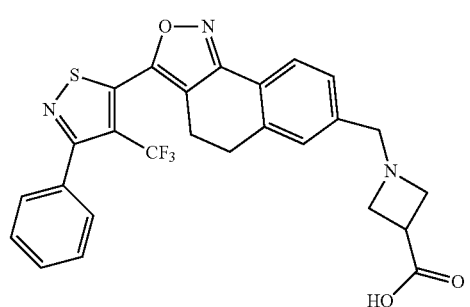
(103)

Preparation 103A: (Z)—N-hydroxybenzimidoyl cyanide

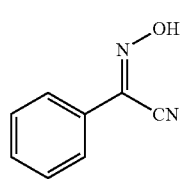
(103A)

A solution of isopentyl nitrite (16.00 g, 137 mmol) in EtOH (30 mL) was added dropwise to a solution of 2-phenylacetonitrile (16 g, 137 mmol) and sodium hydroxide (5.46 g, 137 mmol) while cooling in an ice bath. Once the addition was complete, the mixture was allowed to warm to room temperature. After stirring at room temperature for 2 h, the reaction was diluted with diethyl ether. The resultant precipitate was filtered and washed with diethyl ether. The solid was air dried and then vacuum dried to yield the titled compound (10 g, 68.9 mmol, 50.4% yield) as a light yellow solid.

Preparation 103B: (Z)—N-(tosyloxy)benzimidoyl cyanide

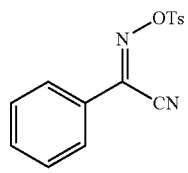
(103B)

A mixture of (Z)—N-hydroxybenzimidoyl cyanide (Preparation 103A, 8 g, 55.1 mmol) and 4-methylbenzene-1-sulfonyl chloride (10.51 g, 55.1 mmol) in toluene (70 mL) was heated to reflux. After refluxing for 2 h, the reaction was cooled, diluted with EtOAc (100 mL) and washed with water (50 mL) and brine (50 mL). The organic layer was dried over anhydrous sodium sulfate and concentrated to yield (Z)—N-(tosyloxy)benzimidoyl cyanide (10 g, 33.3 mmol, 60.4% yield) as a light yellow solid.

Preparation 103C: Methyl 4-amino-3-phenylisothiazole-5-carboxylate

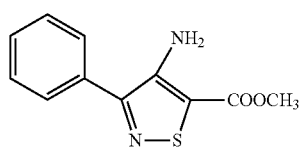
(103C)

Triethylamine (5.39 g, 53.3 mmol) was added dropwise to a stirred solution of (Z)—N-(tosyloxy)benzimidoyl cyanide (Preparation 103B, 8 g, 26.6 mmol) and methyl 2-mercaptoacetate (2.86 mL, 32.0 mmol) in MeOH (70 mL) at room temperature. After stirring at room temperature for 3 h, the reaction was cooled and treated with 100 mL ice/water. The resultant solid was filtered and washed with water. The solid was vacuum dried to yield 6 g brown colored solid. Recrystallization from hexane/ethyl acetate yielded the titled compound (3 g) as a beige colored needles. The compound had an LC/MS M$^{+1}$=235.2.

Preparation 103D: Methyl 4-iodo-3-phenylisothiazole-5-carboxylate

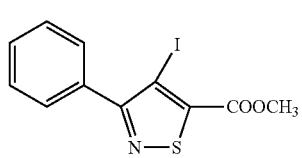
(103D)

To a solution of methyl 4-amino-3-phenylisothiazole-5-carboxylate (Preparation 103C, 700 mg, 2.99 mmol) in chloroform (80 mL) were added iodine (4019 mg, 15.84 mmol) and amyl nitrite (0.602 mL, 4.48 mmol). The resulting mixture was heated to reflux for 30 min. The reaction mixture was cooled to room temperature and washed with aqueous sodium thiosulfate and then water. The organic layer was dried over sodium sulfate. Removal of the solvent in vacuo and crystallization from ethanol yielded methyl 4-iodo-3-phenylisothiazole-5-carboxylate (600 mg, 1.738 mmol, 58.2% yield) as a pale yellow solid. The compound had an LC/MS $M^{+1}$=346.0.

Preparation 103E: Methyl 3-phenyl-4-(trifluoromethyl)isothiazole-5-carboxylate

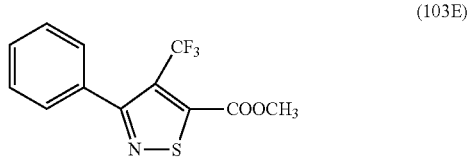 [SMILES: COC(=O)c1snc(-c2ccccc2)c1C(F)(F)F]

(103E)

To a solution of methyl 4-iodo-3-phenylisothiazole-5-carboxylate (Preparation 103D, 700 mg, 2.028 mmol) in dry DMF (2 mL) under a nitrogen flow was added copper(I) iodide (772 mg, 4.06 mmol) and methyl 2,2-difluoro-2-(fluorosulfonyl)acetate (0.519 mL, 4.06 mmol). The resulting mixture was heated to 85° C. overnight. LC-MS indicates the reaction was not complete. The reaction was re-subjected to copper iodide (400 mg) and methyl 2,2-difluoro-2-(fluorosulfonyl)acetate (0.25 mL) at 85° C. in a sealed tube for 3 h. The mixture was cooled to room temperature, diluted with EtOAc (40 mL) and filtered through celite. The filtrate was washed with water (3×20 mL) and brine (30 mL), dried over sodium sulfate, and concentrated. Flash chromatography yielded methyl 3-phenyl-4-(trifluoromethyl)isothiazole-5-carboxylate (350 mg, 1.218 mmol, 60.1% yield) as an oil. The compound had an LC/MS $M^{+1}$=288.1.

Preparation 103F: 3-(3-phenyl-4-(trifluoromethyl)isothiazol-5-yl)-7-vinyl-4,5-dihydronaphtho[1,2-c]isoxazole

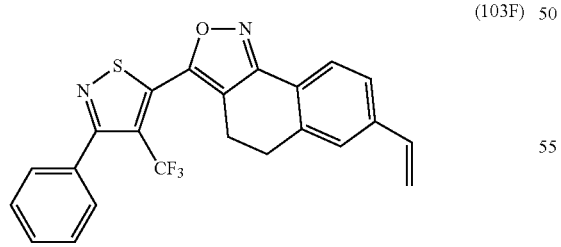

(103F)

The titled compound was prepared using the experimental protocol described for Preparation 89A employing 6-vinyl-3,4-dihydronaphthalen-1(2H)-one oxime (Intermediate 1) and methyl 3-phenyl-4-(trifluoromethyl)isothiazole-5-carboxylate (Preparation 103E) as starting materials. The compound had an HPLC retention time=4.25 min. (condition C); LC/MS $M^{+1}$=424.8.

Example 103

To a clear solution of 3-(3-phenyl-4-(trifluoromethyl)isothiazol-5-yl)-7-vinyl-4,5-dihydronaphtho[1,2-c]isoxazole (Preparation 103F, 40 mg, 0.094 mmol) in THF (3 mL) were sequentially added NMO (50% in water, 0.029 mL, 0.141 mmol) and osmium tetroxide (4% in water, 0.023 mL, 3.77 µmol) at room temperature. The solution was vigorously stirred at room temperature for 3 hr before additional NMO (0.05 mL) and osmium tetroxide (0.05 mL) was added. The mixture was stirred at room temperature overnight. Sodium periodate (28.2 mg, 0.132 mmol) in water (0.5 mL) was added. The mixture was stirred at room temperature under nitrogen for 0.5 h. The mixture was mixed with water (2 mL) and concentrated. The solid was filtered, washed with water (3×1 mL) and dried. The solid was mixed with MeOH (1 mL), 1,2-dichloroethane (1 mL), azetidine-3-carboxylic acid (19.06 mg, 0.188 mmol) and acetic acid (0.032 mL, 0.565 mmol). The reaction mixture was heated at 60° C. (oil bath temp.) for 1.5 h under nitrogen and then cooled to room temperature. Sodium cyanoborohydride (11.84 mg, 0.188 mmol) was added in one lot. The mixture was stirred at room temperature till the reaction was complete. The mixture was concentrated. The residue was dissolved in MeOH with some dichloromethane and TFA. Purification using reverse phase HPLC (Phenomenex Luna AXIA 5 u c18 30×100 mm, 10 min. run, solvent A: 10% MeOH: 90% H₂O: 0.1% TFA, solvent B: 90% MeOH, 10% H₂O, 0.1% TFA), concentration, neutralization with aqueous NaOAc, filtration gave a white solid. The solid was triturated with a mixture of methanol and ethyl acetate to give 1-((3-(3-phenyl-4-(trifluoromethyl)isothiazol-5-yl)-4,5-dihydronaphtho[1,2-c]isoxazol-7-yl)methyl)azetidine-3-carboxylic acid (14 mg, 0.026 mmol, 27.9% yield) as a white solid. The compound had an HPLC retention time=3.19 min. (condition C); LC/MS $M^{+1}$=512.0. ¹H NMR (500 MHz, DMSO-d₆) δ ppm 7.84 (1H, d, J=7.8 Hz), 7.60-7.65 (2H, m), 7.53-7.58 (3H, m), 7.35 (1H, s), 7.32 (1H, d, J=7.8 Hz), 3.59 (2H, s), 3.42 (2H, s), 3.16-3.25 (3H, m), 3.02 (2H, t, J=6.9 Hz), 2.93 (2H, t, J=6.9 Hz).

Example 104

2-amino-2-methyl-4-(3-(1-phenyl-5-(trifluoromethyl)-1H-pyrazol-4-yl)-4,5-dihydronaphtho[1,2-c]isoxazol-7-yl)butyl dihydrogen phosphate

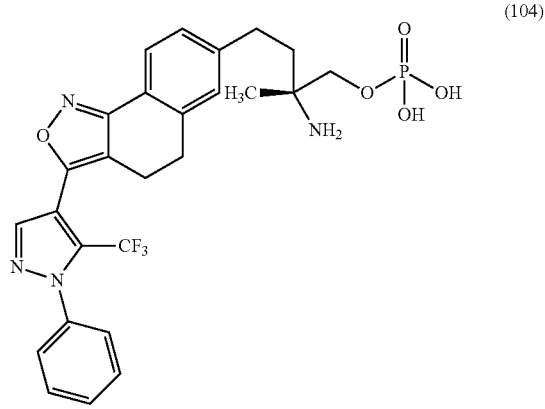

(104)

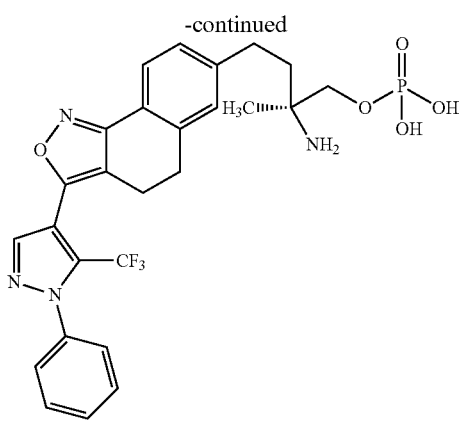

Preparation 104A: 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol (104A)

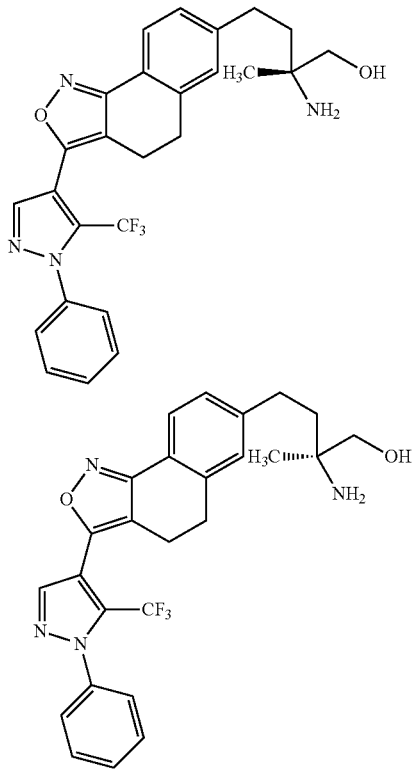

The titled compound was prepared using the experimental protocols described for Preparation 91A, and Example 93 employing 3-(1-phenyl-5-(trifluoromethyl)-1H-pyrazol-4-yl)-7-vinyl-4,5-dihydronaphtho[1,2-c]isoxazole (89A) as a starting material. The compound had an HPLC retention time=3.03 min. (condition C); LC/MS $M^{+1}$=483.3; $^1$H NMR (400 MHz, MeOD) δ ppm 8.14 (1H, s), 7.85 (1H, d, J=7.7 Hz), 7.53-7.65 (5H, m), 7.30 (1H, s), 7.28 (1H, d, J=7.9 Hz), 3.67 (1H, d, J=11.5 Hz), 3.56 (1H, d, J=11.5 Hz), 3.03 (2H, t, J=6.9 Hz), 2.90 (2H, t, J=6.9 Hz), 2.66-2.81 (2H, m), 1.86-2.07 (2H, m), 1.37 (3H, s).

The individual enantiomers were separated using a CHIRALPAK® AD-H column under SFC conditions (25% MeOH with 0.1% DEA in $CO_2$). Isomer 1 (Preparation 104A, 9 mgs), retention time on chiral HPLC, 4.95 min; LC/MS $M^{+1}$=483.3; Isomer 2 (Preparation 104A, 11 mgs), retention time on chiral HPLC, 7.46 min.; LC/MS $M^{+1}$=483.3. The absolute stereochemistry at the carbon anchoring the chiral centers of Isomer 1 and Isomer 2 was not determined.

Example 104

Isomer 1

The titled compound was prepared using the experimental protocol described for Example 95 employing 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol (Preparation 104A, isomer 1) as a starting material. The compound had an HPLC retention time=3.15 min. (condition C); LC/MS $M^{+1}$=563.2. $^1$H NMR (400 MHz, MeOD) δ ppm 8.09 (1H, s), 7.84 (1H, d, J=7.9 Hz), 7.50-7.65 (5H, m), 7.24-7.31 (2H, m), 3.85-4.04 (2H, m), 3.02 (2H, t, J=6.9 Hz), 2.90 (2H, d, J=7.3 Hz), 2.65-2.84 (2H, m), 1.88-2.13 (2H, m), 1.41 (3H, s).

Example 104

Isomer 2

The titled compound was prepared using the experimental protocol described for Example 95 employing 2-amino-2-methyl-4-(3-(1-phenyl-5-(trifluoromethyl)-1H-pyrazol-4-yl)-4,5-dihydronaphtho[1,2-c]isoxazol-7-yl)butan-1-ol (Preparation 104A, isomer 2) as a starting material. The compound had an HPLC retention time=3.15 min. (condition C); LC/MS $M^{+1}$=563.2. $^1$H NMR (400 MHz, MeOD) δ ppm 8.09 (1H, s), 7.84 (1H, d, J=7.9 Hz), 7.51-7.82 (5H, m), 7.24-7.31 (2H, m), 3.85-4.04 (2H, m), 3.02 (2H, t, J=6.9 Hz), 2.90 (2H, d, J=7.3 Hz), 2.65-2.84 (2H, m), 1.88-2.13 (2H, m), 1.41 (3H, s).

Example 105

1-((3-(5-phenyl-4-(trifluoromethyl)isothiazol-3-yl)-4,5-dihydronaphtho[1,2-c]isoxazol-7-yl)methyl)azetidine-3-carboxylic acid (105)

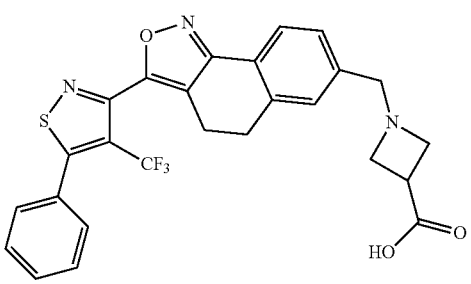

Preparation 105A: methyl 4-iodo-5-phenylisothiazole-3-carboxylate

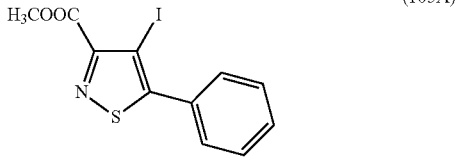
(105A)

To methyl 5-phenylisothiazole-3-carboxylate (500 mg, 2.280 mmol) in a tube were added iodine (579 mg, 2.280 mmol) and nitric acid (2.280 mmol). The resulting mixture was heated to 80° C. for 1 h. After the reaction was cooled to room temperature, EtOAc (50 mL) was added. The resulting mixture was washed with saturated $Na_2S_2O_3$ solution until the brown color disappeared. The organic layer was concentrated. HPLC and flash chromatography yielded methyl 4-iodo-5-phenylisothiazole-3-carboxylate (168 mg, 0.487 mmol, 21.34% yield). The compound had an LC/MS $M^{+1}$=345.9.

Preparation 105B: methyl 5-phenyl-4-(trifluoromethyl)isothiazole-3-carboxylate

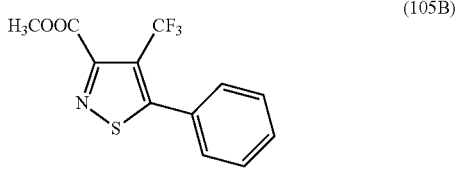
(105B)

Copper(I) iodide (177 mg, 0.927 mmol), methyl 2,2-difluoro-2-(fluorosulfonyl)acetate (0.117 mL, 0.927 mmol) and methyl 4-iodo-5-phenylisothiazole-3-carboxylate (Preparation 105A, 160 mg, 0.464 mmol) were added to a 2-dram vial under nitrogen. The contents were heated to 85° C. for 6 h. The reaction mixture was diluted with EtOAc (20 mL), washed with brine (2×10 mL) and concentrated. Flash chromatography yielded methyl 5-phenyl-4-(trifluoromethyl)isothiazole-3-carboxylate (84 mg, 0.292 mmol, 63.1% yield) as a clear oil. The compound had an LC/MS $M^{+1}$=288.0.

Preparation 105C: 3-(5-phenyl-4-(trifluoromethyl)isothiazol-3-yl)-7-vinyl-4,5-dihydronaphtho[1,2-c]isoxazole

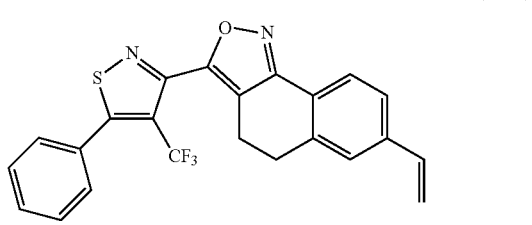
(105C)

The titled compound was prepared using the experimental protocol described for Preparation 89A employing 6-vinyl-3,4-dihydronaphthalen-1(2H)-one oxime (Intermediate I-1) and methyl 5-phenyl-4-(trifluoromethyl)isothiazole-3-carboxylate (Preparation 105B) as starting materials. The compound had an HPLC retention time=4.30 min. (condition C); LC/MS $M^{+1}$=424.9.

Example 105

To a clear solution of 3-(5-phenyl-4-(trifluoromethyl)isothiazol-3-yl)-7-vinyl-4,5-dihydronaphtho[1,2-c]isoxazole (Preparation 105C, 42 mg, 0.099 mmol) in THF (2.5 mL) were added NMO (50% in water, 0.041 mL, 0.198 mmol) and osmium tetroxide (4% in water, 0.060 mL, 9.90 µmol) at room temperature. The solution was vigorously stirred at room temperature for 1.5 h. More osmium tetroxide (4% in water, 0.060 mL, 9.90 µmol) was added and the mixture was stirred at room temperature for 4 h. Sodium periodate (29.6 mg, 0.139 mmol) in water (0.5 mL) was added. The mixture was stirred at room temperature under nitrogen for 0.5 h before being concentrated. The solid was filtered, washed with water (3×1 mL) and dried.

The solid was mixed with MeOH (1 mL), 1,2-dichloroethane (1 mL), azetidine-3-carboxylic acid (20.01 mg, 0.198 mmol), acetic acid (0.034 mL, 0.594 mmol). The reaction mixture was heated at 60° C. (oil bath temp.) for 2 h under nitrogen and then cooled to room temperature. After sodium cyanoborohydride (12.44 mg, 0.198 mmol) was added, the mixture was stirred at room temperature till the starting material disappeared. The mixture was concentrated. Purification using reverse phase HPLC (Phenomenex Luna AXIA 5 u c18 30×100 mm, 10 min. run, solvent A: 10% MeOH: 90% $H_2O$: 0.1% TFA, solvent B: 90% MeOH, 10% $H_2O$, 0.1% TFA), concentration and lyophilization gave 1-((3-(5-phenyl-4-(trifluoromethyl)isothiazol-3-yl)-4,5-dihydronaphtho[1,2-c]isoxazol-7-yl)methyl)azetidine-3-carboxylic acid, TFA (35 mg, 0.052 mmol, 52.6% yield) as a white solid. The compound had an HPLC retention time=3.22 min. (condition C); LC/MS $M^{+1}$=512.1. $^1$H NMR (400 MHz, MeOD) δ ppm 8.05 (1H, d, J=7.9 Hz), 7.55-7.63 (5H, m), 7.53 (1H, s), 7.49 (1H, dd, J=7.9, 1.8 Hz), 4.47 (2H, s), 4.32-4.43 (4H, m), 3.67-3.78 (1H, m), 3.11 (4H, s).

Example 106

1-((3-(4-cyano-3-phenylisothiazol-5-yl)-4,5-dihydronaphtho[1,2-c]isoxazol-7-yl)methyl)azetidine-3-carboxylic acid

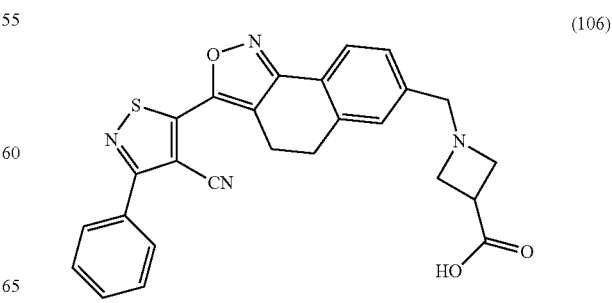
(106)

Preparation 106A: methyl 4-cyano-3-phenylisothiazole-5-carboxylate

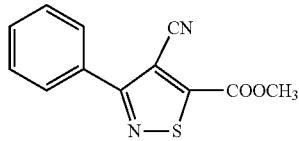

(106A)

To a solution of methyl 4-iodo-3-phenylisothiazole-5-carboxylate (Preparation 103D, 600 mg, 1.738 mmol) in NMP (2 mL) was added copper cyanide (311 mg, 3.48 mmol). The resulting mixture was heated at 100° C. in a microwave reactor for 45 min. The reaction mixture was diluted with EtOAc (40 mL), filtered, washed with water (2×20 mL), brine (10 mL) and concentrated. Flash chromatography gave methyl 4-cyano-3-phenylisothiazole-5-carboxylate (360 mg, 1.474 mmol, 85% yield) as a white solid. The compound had an LC/MS $M^{+1}$=245.1.

Preparation 106B: 3-phenyl-5-(7-vinyl-4,5-dihydronaphtho[1,2-c]isoxazol-3-yl)isothiazole-4-carbonitrile

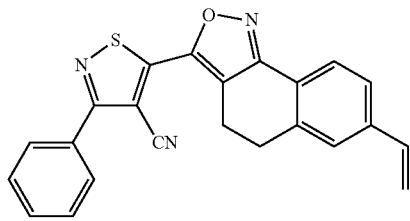

(106B)

The titled compound was prepared using the experimental protocol described for Preparation 89A employing 6-vinyl-3,4-dihydronaphthalen-1(2H)-one oxime (Intermediate 1) and methyl 4-cyano-3-phenylisothiazole-5-carboxylate (Preparation 106A) as starting materials. The compound had an HPLC retention time=4.30 min. (condition C); LC/MS $M^{+1}$=424.9.

Example 106

The titled compound was prepared using the experimental protocol described for Example 105 employing 3-phenyl-5-(7-vinyl-4,5-dihydronaphtho[1,2-c]isoxazol-3-yl)isothiazole-4-carbonitrile (Preparation 106B) as a starting material. The compound had an HPLC retention time=3.09 min. (condition C); LC/MS $M^{+1}$=469.1. $^1$H NMR (400 MHz, MeOD) δ ppm 8.02-8.08 (3H, m), 7.53-7.59 (3H, m), 7.48 (1H, s), 7.46 (1H, d, J=7.7 Hz), 4.41 (2H, s), 4.23-4.35 (4H, m), 3.59-3.68 (1H, m), 3.14 (4H, s).

Example 107

2-amino-2-methyl-3-(3-(5-phenyl-4-(trifluoromethyl)isoxazol-3-yl)-4,5-dihydronaphtho[1,2-c]isoxazol-7-yl)propan-1-ol

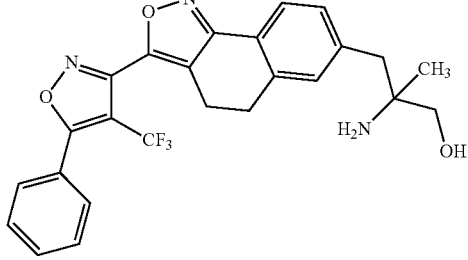

(107)

To a clear solution of ethyl 2-(diphenylmethyleneamino)propanoate (89 mg, 0.316 mmol) in anhydrous THF (2 mL) was added 1 M THF solution of lithium bis(trimethylsilyl)amide (0.358 mL, 0.358 mmol) at −78° C. under nitrogen. The solution was stirred at the same temperature for 40 min. before 7-(bromomethyl)-3-(5-phenyl-4-(trifluoromethyl)isoxazol-3-yl)-4,5-dihydronaphtho[1,2-c]isoxazole (6C, 50 mg, 0.105 mmol) was added. The mixture was stirred at −78° C. for 30 min. and at 0° C. for 70 min. before being quenched with saturated aqueous ammonium chloride solution (3 mL) and water (1 mL). The mixture was extracted with ethyl acetate (3×3 mL). The combined organic solutions were dried (sodium sulfate) and concentrated under reduced pressure.

The residue was mixed with diethyl ether (3 mL) and treated with 4N aqueous HCl (0.3 mL, 1.200 mmol). The mixture was stirred at room temperature for 30 min. The ether layer was extracted with water (2×0.2 mL). The aqueous extractions and the solid from the reaction mixture were combined, basified with $Na_2CO_3$ solid and extracted with ethyl acetate (3×1 mL). The combined ethyl acetate extracts were dried (sodium sulfate) and concentrated under reduced pressure. Purification using reverse phase HPLC (Phenomenex Luna AXIA 5 u c18 30×100 mm, 10 min. run, solvent A: 10% MeOH: 90% $H_2O$: 0.1% TFA, solvent B: 90% MeOH, 10% $H_2O$, 0.1% TFA), concentration and neutralization gave ethyl 2-amino-2-methyl-3-(3-(5-phenyl-4-(trifluoromethyl)isoxazol-3-yl)-4,5-dihydronaphtho[1,2-c]isoxazol-7-yl)propanoate (11 mg, 0.022 mmol) as a glassy solid. The solid was dissolved in EtOH (2 mL) and treated with sodium borohydride (20 mg). The mixture was stirred at room temperature overnight. The reaction was quenched with acetone and concentrated. Purification using reverse phase HPLC (Phenomenex Luna AXIA 5 u c18 30×100 mm, 10 min. run, solvent A: 10% MeOH: 90% $H_2O$: 0.1% TFA, solvent B: 90% MeOH, 10% $H_2O$, 0.1% TFA), concentration, neutralization with saturated aqueous sodium bicarbonate solution, extraction with ethyl acetate and concentration gave 2-amino-2-methyl-3-(3-(5-phenyl-4-(trifluoromethyl)isoxazol-3-yl)-4,5-dihydronaphtho[1,2-c]isoxazol-7-yl)propan-1-ol (6 mg, 0.012 mmol, 11.54% yield) as a white solid. The compound had an HPLC retention time=3.34 min. (condition C); LC/MS $M^{+1}$=470.0; $^1$H NMR (400 MHz, CHLOROFORM-d) δ ppm 7.98 (1H, d, J=7.7 Hz), 7.76 (2H, d, J=7.0 Hz), 7.52-7.66 (3H, m), 7.31-7.42 (1H, m), 7.23 (1H, d, J=7.7 Hz), 7.20 (1H, s), 3.39 (2H, q, J=10.8 Hz), 3.01-3.13 (4H, m), 2.77 (2H, s), 1.11 (3H, s).

Example 108

2-((3-(5-phenyl-4-(trifluoromethyl)isoxazol-3-yl)-4,5-dihydronaphtho[1,2-c]isoxazol-7-yl)methylamino)ethanol

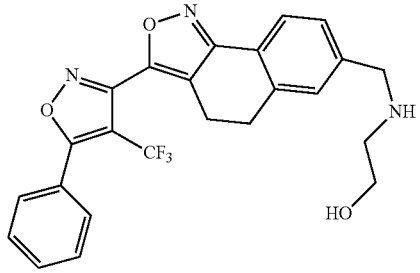

(108)

A mixture of 3-(5-phenyl-4-(trifluoromethyl)isoxazol-3-yl)-4,5-dihydronaphtho[1,2-c]isoxazole-7-carbaldehyde (Preparation 88A, 40 mg, 0.097 mmol), Ethanolamine (0.059 mL, 0.975 mmol), 1,2-dichloroethane (3 mL) and sodium triacetoxyborohydride (62.0 mg, 0.292 mmol) was stirred at room temperature overnight. Sodium cyanoborohydride (20 mg, 0.318 mmol) was then added. The mixture was stirred at room temperature for 1 h before water (1 mL) was added. The aqueous layer was extracted with ethyl acetate (3×1 mL). The combined organic solutions were concentrated under reduced pressure. Purification using reverse phase HPLC (Phenomenex Luna AXIA 5 u c18 30×100 mm, 10 min. run, solvent A: 10% MeOH: 90% H₂O: 0.1% TFA, solvent B: 90% MeOH, 10% H₂O, 0.1% TFA), concentration, neutralization with saturated aqueous sodium bicarbonate solution, and extraction with ethyl acetate gave 2-((3-(5-phenyl-4-(trifluoromethyl)isoxazol-3-yl)-4,5-dihydronaphtho[1,2-c]isoxazol-7-yl)methylamino)ethanol (28 mg, 0.060 mmol, 61.8% yield) as a white solid.

Example 109

(±)4-hydroxy-4-(3-(5-phenyl-4-(trifluoromethyl)isoxazol-3-yl)-4,5-dihydronaphtho[1,2-c]isoxazol-7-yl)butanoic acid

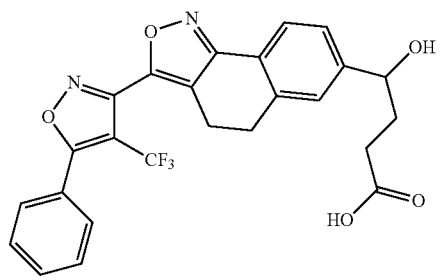

(109)

Preparation of 109A: methyl 4-oxo-4-(3-(5-phenyl-4-(trifluoromethyl)isoxazol-3-yl)-4,5-dihydronaphtho[1,2-c]isoxazol-7-yl)butanoate

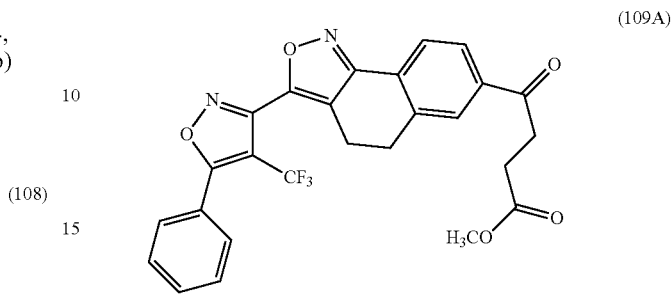

(109A)

To a mixture of 3-(5-phenyl-4-(trifluoromethyl)isoxazol-3-yl)-4,5-dihydronaphtho[1,2-c]isoxazole-7-carbaldehyde (Preparation 88A, 80 mg, 0.195 mmol), 5-(2-hydroxyethyl)-3,4-dimethylthiazolium iodide (11.12 mg, 0.039 mmol), 1,2-dichloroethane (1 mL), EtOH (1.000 mL), triethylamine (0.082 mL, 0.585 mmol) and methyl acrylate (0.053 mL, 0.585 mmol) was bubbled with nitrogen for 1 min. and then sealed in a 1-dram vial. The mixture was heated at 75° C. for 15 h. Additional 5-(2-hydroxyethyl)-3,4-dimethylthiazolium iodide (30 mg) and methyl acrylate (0.053 mL, 0.585 mmol) were added and the mixture was stirred at 75° C. for 7 h. The solvents were removed under reduced pressure. The residue was treated with water (2 mL) and extracted with dichloromethane. The combined dichloromethane extracts were dried (sodium sulfate) and concentrated. Flash chromatography purification (4 g silica gel column, 20→100% dichloromethane in heptanes) afforded methyl 4-oxo-4-(3-(5-phenyl-4-(trifluoromethyl)isoxazol-3-yl)-4,5-dihydronaphtho[1,2-c]isoxazol-7-yl)butanoate (23 mg, 0.046 mmol, 23.76% yield) as a glassy solid.

Example 109

A mixture of methyl 4-oxo-4-(3-(5-phenyl-4-(trifluoromethyl)isoxazol-3-yl)-4,5-dihydronaphtho[1,2-c]isoxazol-7-yl)butanoate (Preparation 109A, 22 mg, 0.044 mmol), THF (2 mL), MeOH (0.5 mL), water (0.5 mL) and 2N aqueous sodium hydroxide (0.2 mL, 0.400 mmol) was stirred at room temperature under nitrogen for 70 h. The reaction mixture was concentrated and the residue was acidified with 10% citric acid (1.5 mL) and extracted with dichloromethane (4×2 mL). The combined dichloromethane extracts were dried (sodium sulfate) and concentrated under reduced pressure to give 4-oxo-4-(3-(5-phenyl-4-(trifluoromethyl)isoxazol-3-yl)-4,5-dihydronaphtho[1,2-c]isoxazol-7-yl)butanoic acid (20 mg, 0.041 mmol, 94% yield) as a yellow solid.

The solid was mixed with anhydrous methanol (4 mL) and sodium cyanoborohydride (13.92 mg, 0.222 mmol). The mixture was stirred at room temperature overnight before being concentrated. Purification using reverse phase HPLC (Phenomenex Luna AXIA 5 u c18 30×100 mm, 10 min. run, solvent A: 10% MeOH: 90% H₂O: 0.1% TFA, solvent B: 90% MeOH, 10% H₂O, 0.1% TFA) and concentration gave a solid. The solid was crystallized in ethanol-water mixture to give a solid. The solid was recrystallized in EtOAc-heptanes mixture to give 4-hydroxy-4-(3-(5-phenyl-4-(trifluoromethyl)isoxazol-3-yl)-4,5-dihydronaphtho[1,2-c]isoxazol-7-yl)butanoic acid (4 mg, 7.68 µmol, 17.33% yield) as a white solid.

The compound had an HPLC retention time=3.66 min. (condition C); LC/MS M$^{+1}$=484.8. $^1$H NMR (400 MHz, MeOD) δ ppm 7.93 (1H, d, J=7.9 Hz), 7.78 (2H, d, J=7.3 Hz), 7.59-7.71 (3H, m), 7.44 (1H, s), 7.40 (1H, d, J=7.9 Hz), 4.74 (1H, t, J=6.6 Hz), 3.08 (4H, s), 2.39 (2H, t, J=7.4 Hz), 1.99-2.07 (2H, m).

Example 110

2,2'-((3-(5-phenyl-4-(trifluoromethyl)isoxazol-3-yl)-4,5-dihydronaphtho[1,2-c]isoxazol-7-yl)methylazanediyl)diethanol

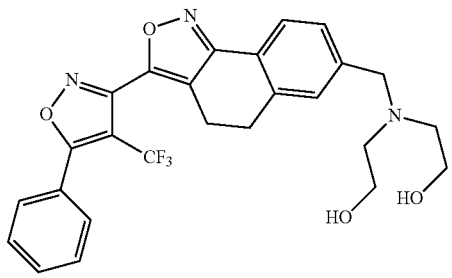

(110)

A mixture of 3-(5-phenyl-4-(trifluoromethyl)isoxazol-3-yl)-4,5-dihydronaphtho[1,2-c]isoxazole-7-carbaldehyde (Preparation 88A, 20 mg, 0.049 mmol), diethanolamine (18.68 mL, 0.195 mmol), 1,2-dichloroethane (1 mL) and sodium triacetoxyborohydride (31.0 mg, 0.146 mmol) was stirred at room temperature under nitrogen for 2 days. Sodium cyanoborohydride (20 mg, 0.318 mmol) was then added. The mixture was stirred at room temperature for 1 hr before water (1 mL) was added. The aqueous layer was extracted with dichloromethane (2×1 mL). The combined organic solutions were concentrated under reduced pressure. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 2,2'-((3-(5-phenyl-4-(trifluoromethyl)isoxazol-3-yl)-4,5-dihydronaphtho[1,2-c]isoxazol-7-yl)methylazanediyl)diethanol, TFA (15.6 mg, 0.025 mmol, 51.6% yield) as a white solid. The compound had an HPLC retention time=3.20 min. (condition C); LC/MS M$^{+1}$=500.1; $^1$H NMR (400 MHz, MeOD) δ ppm 8.06 (1H, d, J=7.9 Hz), 7.77 (2H, d, J=7.5 Hz), 7.56-7.72 (5H, m), 4.55 (2H, s), 3.94 (4H, t, J=5.2 Hz), 3.39 (4H, t, J=4.8 Hz), 3.07-3.18 (4H, m).

The compounds in the following table were prepared in the same fashion employing the corresponding alcohols.

| Ex. No. | Structure | Name | MW | HPLC ret. time (min) (condition C) | MS (M$^{+1}$) |
|---|---|---|---|---|---|
| 111 | 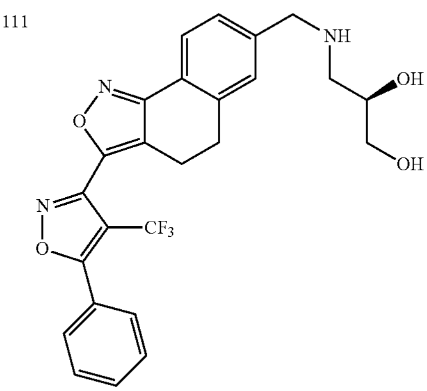 | (2R)-3-((3-(5-phenyl-4-(trifluoromethyl)isoxazol-3-yl)-4,5-dihydronaphtho[1,2-c]isoxazol-7-yl)methylamino)propane-1,2-diol | 485 | 3.19 | 486.1 |
| 112 | 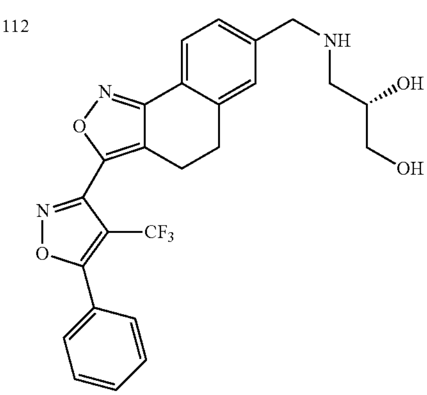 | (2S)-3-((3-(5-phenyl-4-(trifluoromethyl)isoxazol-3-yl)-4,5-dihydronaphtho[1,2-c]isoxazol-7-yl)ethylamino)propane-1,2-diol | 485 | 3.19 | 486.1 |

-continued

| Ex. No. | Structure | Name | MW | HPLC ret. time (min) (condition C) | MS (M+1) |
|---|---|---|---|---|---|
| 113 | 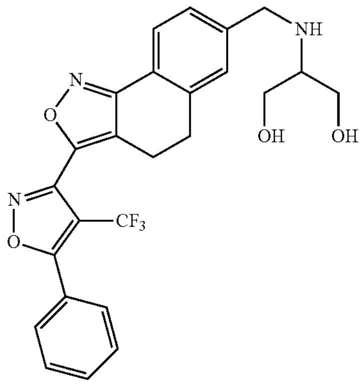 [SMILES: OCC(CO)NCc1ccc2c(c1)CCc1c-2noc1-c1noc(-c2ccccc2)c1C(F)(F)F] | 2-((3-(5-phenyl-4-(trifluoromethyl)isoxazol-3-yl)-4,5-dihydronaphtho[1,2-c]soxazol-7-yl)ethylamino)propane-1,3-diol | 485 | 3.20 | 486.1 |

Example 114

(3R)-1-((3-(5-phenyl-4-(trifluoromethyl)isoxazol-3-yl)-4,5-dihydronaphtho[1,2-c]isoxazol-7-yl)methyl)pyrrolidin-3-ol

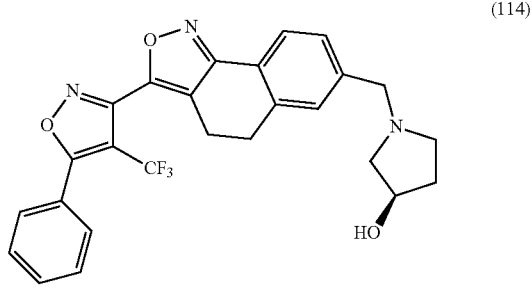 [SMILES: O[C@@H]1CCN(Cc2ccc3c(c2)CCc2c-3noc2-c2noc(-c3ccccc3)c2C(F)(F)F)C1]

(114)

A mixture of 3-(5-phenyl-4-(trifluoromethyl)isoxazol-3-yl)-4,5-dihydronaphtho[1,2-c]isoxazole-7-carbaldehyde (Preparation 88A, 20 mg, 0.049 mmol), 3R-Pyrrolidinol (21.23 mg, 0.244 mmol), sodium triacetoxyborohydride (31.0 mg, 0.146 mmol) and dichloromethane (1 mL) was stirred at room temperature overnight. The mixture was concentrated and dissolved in methanol. HPLC purification (Column: Waters XBridge C18, 19×250 mm, 5-nm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min) and concentration gave the titled compound (18.8 mg, 0.039 mmol, 80% yield) as a solid. The compound had an HPLC retention time=2.15 min. (Column: Supelco Ascentis Express C-18, 4.6×50 mm, 2.7 um; Solvent A=0.05% TFA in $H_2O$:MeCN (95:5); Solvent B=0.05% TFA in $H_2O$:MeCN (5:95)); LC/MS $M^{+1}$=482.1; $^1$H NMR (400 MHz, MeOD) δ ppm 7.95 (1H, d, J=7.7 Hz), 7.73 (2H, d, J=7.3 Hz), 7.53-7.66 (3H, m), 7.36-7.43 (2H, m), 4.39-4.47 (1H, m), 3.87-4.01 (2H, m), 2.97-3.14 (6H, m), 2.83 (2H, d, J=19.6 Hz), 2.14-2.27 (1H, m), 1.81-1.93 (1H, m, J=13.6 Hz).

The compounds in the following table were prepared and analyzed in the same fashion employing the corresponding amines

| Ex. No. | Structure | Name | MW | HPLC ret. time (min) | MS (M+1) |
|---|---|---|---|---|---|
| 115 | 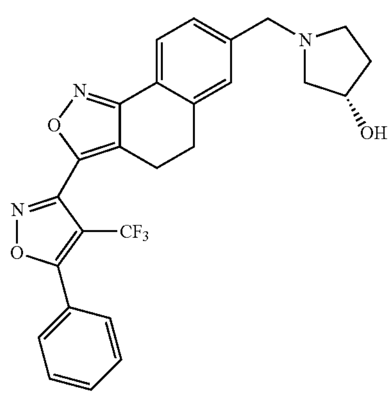 [SMILES: O[C@H]1CCN(Cc2ccc3c(c2)CCc2c-3noc2-c2noc(-c3ccccc3)c2C(F)(F)F)C1] | (3S)-1-((3-(5-phenyl-4-(trifluoromethyl)isoxazol-3-yl)-4,5-dihydronaphtho[1,2-c]isoxazol-7-yl)methyl)pyrrolidin-3-ol | 481 | 2.15 | 482.1 |

-continued

| Ex. No. | Structure | Name | MW | HPLC ret. time (min) | MS (M$^{+1}$) |
|---|---|---|---|---|---|
| 116 | 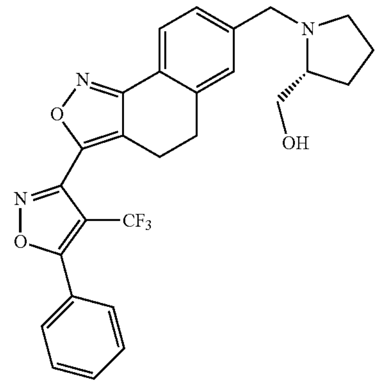 [SMILES: OC[C@H]1CCCN1Cc1ccc2c(c1)CCc1c-2noc1-c1noc(-c2ccccc2)c1C(F)(F)F] | ((2R)-1-((3-(5-phenyl-4-(trifluoromethyl)isoxazol-3-yl)-4,5-dihydronaphtho[1,2-c]isoxazol-7-yl)methyl)pyrrolidin-2-yl) | 495 | 2.20 | 496.0 |
| 117 | 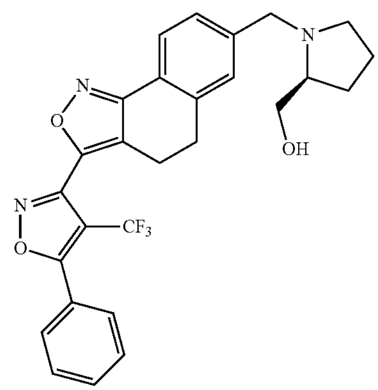 [SMILES: OC[C@@H]1CCCN1Cc1ccc2c(c1)CCc1c-2noc1-c1noc(-c2ccccc2)c1C(F)(F)F] | ((2S)-1-((3-(5-phenyl-4-(trifluoromethyl)isoxazol-3-yl)-4,5-dihydronaphtho[1,2-c]isoxazol-7-yl)methyl)pyrrolidin-2-yl)methanol | 495 | 2.20 | 496 |

Example 118

1-((3-(4-cyclohexyl-3-(trifluoromethyl)phenyl)-4,5-dihydronaphtho[1,2-c]isoxazol-7-yl)methyl)azetidine-3-carboxylic acid

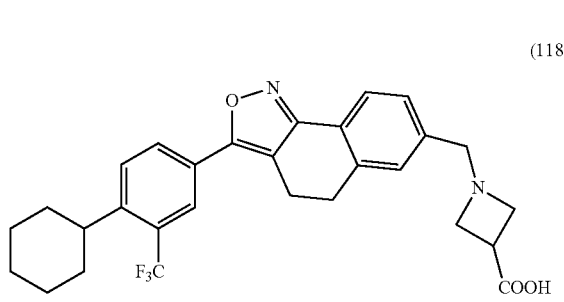
(118)

Preparation 118A:
4-Cyclohexyl-3-(trifluoromethyl)benzonitrile

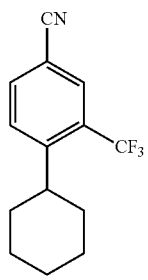
(118A)

A mixture of 4-bromo-3-(trifluoromethyl)benzonitrile (6 g, 24.00 mmol), DMA (30 mL), cuprous iodide (0.914 g, 4.80 mmol) and 1,1'-bis(diphenylphosphino) ferrocenedichloro palladium(II) dichloromethane complex (1.756 g, 2.400 mmol) was bubbled with nitrogen for 5 min. before 0.5 M THF solution of cyclohexylzinc bromide (100 mL, 50.0 mmol) was added over 20 min. via cannula at room temperature. The black reaction mixture was stirred at 60° C. overnight. The reaction mixture was concentrated under reduced pressure. EtOAc (50 mL), water (100 mL) and saturated aqueous ammonium chloride solution (30 mL) were added. The solid was filtered off over a celite pad and washed with ethyl acetate (3×20 mL). The aqueous layer was separated and extracted with ethyl acetate (50 mL). The combined organic solutions were washed with 1 N aqueous HCl (2×40 mL) and then brine (40 mL), dried (sodium sulfate) and concentrated under reduced pressure. Flash chromatography purification (silica gel column, 20→100% ethyl acetate in hexanes) afforded 4-cyclohexyl-3-(trifluoromethyl)benzonitrile (2.77 g, 10.94 mmol, 45.6% yield) as a solid. The compound had an HPLC retention time=3.44 min. (condition C); LC/MS [M+H$_2$O]$^{+1}$=272.2.

Preparation 118B:
4-Cyclohexyl-3-(trifluoromethyl)benzoic acid

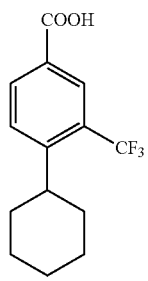
(118B)

A mixture of 4-cyclohexyl-3-(trifluoromethyl)benzonitrile (Preparation 118A, 8 g, 31.6 mmol), acetic acid (30 mL), conc. hydrochloric acid, 37% (30 mL) and water (60 mL) was stirred at 110° C. under nitrogen (oil bath temp.) for 20 h. After water (100 mL) was added, the mixture was cooled. The solid was filtered, washed with water (3×15 mL) and dried to give 4-cyclohexyl-3-(trifluoromethyl)benzoic acid (7 g, 25.7 mmol, 81% yield) as a brownish solid. The compound had an HPLC retention time=3.80 min. (condition C); LC/MS M$^{+1}$=273.1.

Preparation 118C: Methyl
4-cyclohexyl-3-(trifluoromethyl)benzoate

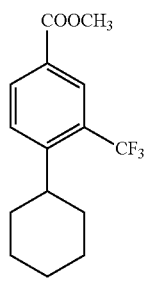
(118C)

To a stirred solution of 4-cyclohexyl-3-(trifluoromethyl) benzoic acid (Preparation 118B, 0.5 g, 1.836 mmol) in dichloromethane (2 mL) and MeOH (2 mL) was added 2M diethyl ether solution of TMS-diazomethane (1.836 mL, 3.67 mmol) dropwise at 0° C. till no gas evolved. The mixture was stirred at room temperature for 1 hr before AcOH (0.210 mL, 3.67 mmol) was added at 0° C. to quench the reaction. The mixture was concentrated. To the residue was added saturated aqueous sodium bicarbonate solution (5 mL) and extracted with dichloromethane (3×3 mL). The combined dichloromethane extracts were dried (sodium sulfate) and concentrated under reduced pressure to give a liquid. Flash chromatography purification (silica gel column, 10→40% dichloromethane in n-heptane) afforded methyl 4-cyclohexyl-3-(trifluoromethyl)benzoate (0.5 g, 1.746 mmol, 95% yield) as a colorless liquid. The compound had an HPLC retention time=4.03 min. (condition C); LC/MS M$^{+1}$=287.2.

Preparation 118D: 3-(4-cyclohexyl-3-(trifluoromethyl)phenyl)-7-vinyl-4,5-dihydronaphtho[1,2-c]
isoxazole

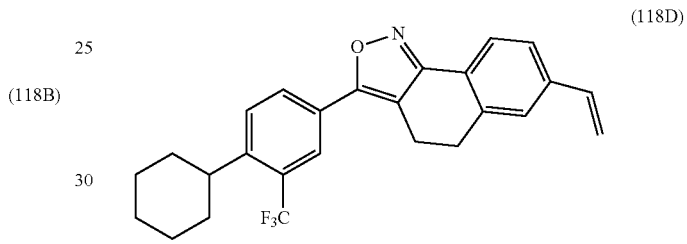
(118D)

The titled compound was prepared using the experimental protocol described for Preparation 89A employing 6-vinyl-3,4-dihydronaphthalen-1(2H)-one oxime (Intermediate 1) and methyl 4-cyclohexyl-3-(trifluoromethyl)benzoate (Preparation 118C) as starting materials. The compound had an HPLC retention time=4.83 min. (condition C); LC/MS M$^{+1}$=424.3.

Preparation 118E: 3-(4-cyclohexyl-3-(trifluoromethyl)phenyl)-4,5-dihydronaphtho[1,2-c]isoxazole-7-
carbaldehyde

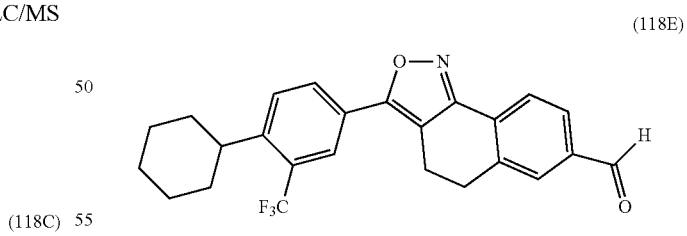
(118E)

The titled compound was prepared using the experimental protocol described for Preparation 89B employing 3-(4-cyclohexyl-3-(trifluoromethyl)phenyl)-7-vinyl-4,5-dihydronaphtho[1,2-c]isoxazole (118D) as a starting material. The compound had an HPLC retention time=4.43 min. (condition C); LC/MS M$^{+1}$=426.2.

Example 118

A mixture of 3-(4-cyclohexyl-3-(trifluoromethyl)phenyl)-4,5-dihydronaphtho[1,2-c]isoxazole-7-carbaldehyde (Preparation 118E, 20 mg, 0.047 mmol), 1,2-dichloroethane (0.4 mL), MeOH (0.4 mL), azetidine-3-carboxylic acid (14.26 mg, 0.141 mmol) and acetic acid (0.016 mL, 0.282 mmol) was heated at 50° C. (oil bath temp.) for 1 h under nitrogen. The mixture was cooled to room temperature and sodium triacetoxyborohydride (29.9 mg, 0.141 mmol) was added in one lot. The contents were stirred at room temperature for 3 hr. The mixture was concentrated and dissolved in methanol (1.8 mL) and dichloromethane (0.2 mL). Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 1-((3-(4-cyclohexyl-3-(trifluoromethyl)phenyl)-4,5-dihydronaphtho[1,2-c]isoxazol-7-yl)methyl)azetidine-3-carboxylic acid, TFA (16 mg, 0.025 mmol, 52.3% yield) as a white solid. The compound had an HPLC retention time=3.77 min. (condition C); LC/MS M$^{+1}$=511.2; $^1$H NMR (400 MHz, MeOD) δ ppm 7.99-8.05 (3H, m), 7.78 (1H, d, J=8.6 Hz), 7.51 (1H, d, J=1.1 Hz), 7.47 (1H, dd, J=7.9, 1.8 Hz), 4.46 (2H, s), 4.33-4.38 (4H, m), 3.63-3.74 (1H, m), 3.09-3.15 (4H, m), 3.00 (1H, t, J=11.7 Hz), 1.77-1.96 (5H, m), 1.54-1.67 (2H, m, J=12.0, 12.0, 11.9, 2.1 Hz), 1.35-1.53 (3H, m).

Example 119

2-amino-2-methyl-4-(2-(3-phenyl-4-(trifluoromethyl)isoxazol-5-yl)-4,5-dihydronaphtho[2,1-d]thiazol-7-yl)butan-1-ol (119)

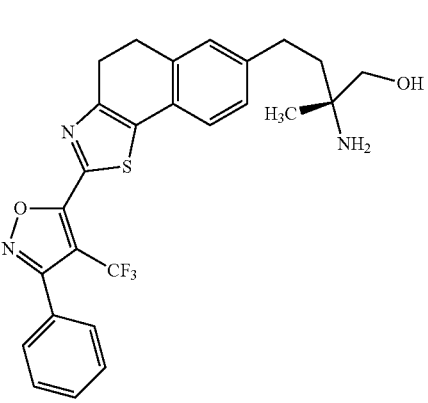

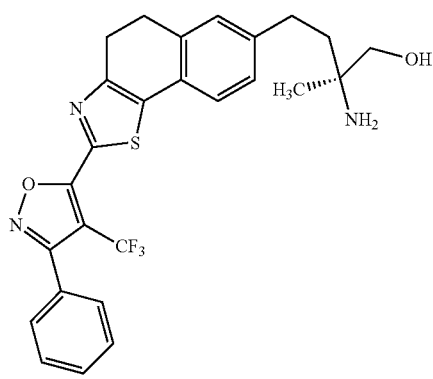

Preparation 119A: Ethyl 2-(diphenylmethyleneamino)-4-(2-(3-phenyl-4-(trifluoromethyl)isoxazol-5-yl)-4,5-dihydronaphtho[2,1-d]thiazol-7-yl)butanoate (119A)

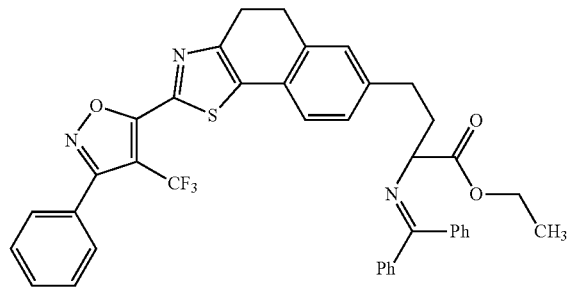

The titled compound was prepared using the experimental protocol described for Preparation 91A employing 3-phenyl-4-(trifluoromethyl)-5-(7-vinyl-4,5-dihydronaphtho[2,1-d]thiazol-2-yl)isoxazole (Preparation 82E) as a starting material. The reaction was heated at 70° C. for 7 hr. The compound had an LC/MS M$^{+1}$=692.4.

Preparation 119B: Ethyl 2-(diphenylmethyleneamino)-2-methyl-4-(2-(3-phenyl-4-(trifluoromethyl)isoxazol-5-yl)-4,5-dihydronaphtho[2,1-d]thiazol-7-yl)butanoate (119B)

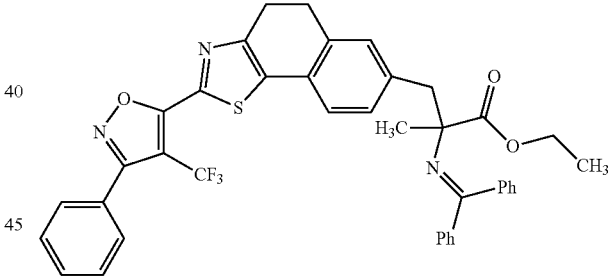

The titled compound was prepared using the experimental protocol described for Preparation 93A employing ethyl 2-(diphenylmethyleneamino)-4-(2-(3-phenyl-4-(trifluoromethyl)isoxazol-5-yl)-4,5-dihydronaphtho[2,1-d]thiazol-7-yl)butanoate (Preparation 119A) as a starting material. The compound had an LC/MS M$^{+1}$=706.4.

Example 119

The titled compound was prepared using the experimental protocol described for Example 93 employing ethyl 2-(diphenylmethyleneamino)-2-methyl-4-(2-(3-phenyl-4-(trifluoromethyl)isoxazol-5-yl)-4,5-dihydronaphtho[2,1-d]thiazol-7-yl)butanoate (Preparation 119B) as a starting material.

The individual enantiomers were separated using a CHIRALPAK® AD-H column under SFC conditions (25% MeOH with 0.1% DEA in CO$_2$). Isomer 1 had retention time on chiral HPLC, 13.5 min; LC/MS M$^{+1}$=499.7; Isomer 2 had retention time on chiral HPLC, 15.2 min.; LC/MS $M^{+1}$=499.7. The absolute stereochemistry at the carbon chiral center, of Isomer 1 and Isomer 2, was not determined.

Example 120

2-amino-2-methyl-4-(2-(3-phenyl-4-(trifluoromethyl)isoxazol-5-yl)-4,5-dihydronaphtho[2,1-d]thiazol-7-yl)butyl dihydrogen phosphate

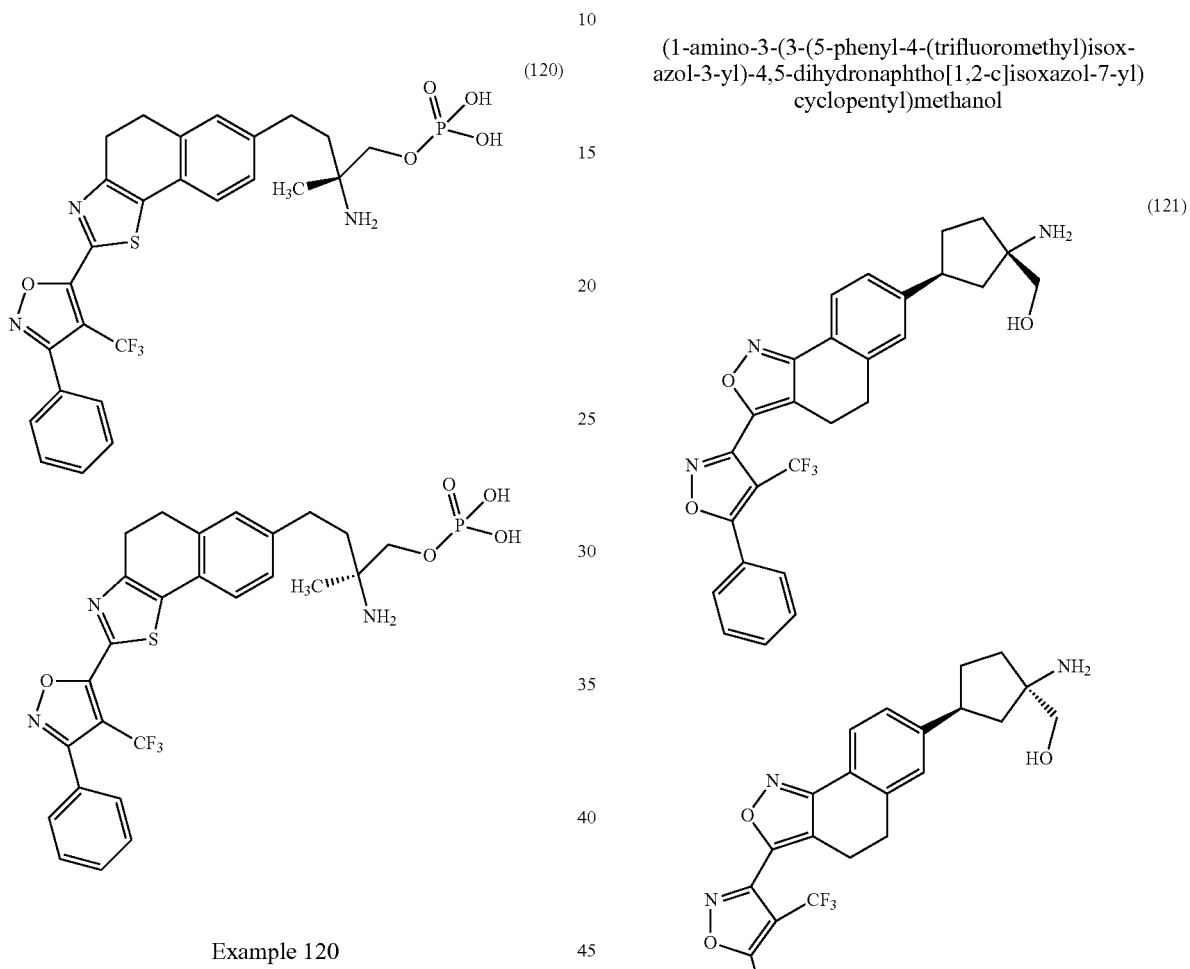

Example 120

Isomer 1

The titled compound was prepared using the experimental protocol described for Example 95 employing 2-amino-2-methyl-4-(2-(3-phenyl-4-(trifluoromethyl)isoxazol-5-yl)-4,5-dihydronaphtho[2,1-d]thiazol-7-yl)butan-1-ol (Example 119, isomer 1) as a starting material. The compound had an HPLC retention time=3.70 min. (condition C); LC/MS $M^{+1}$=580.0; $^1$H NMR (400 MHz, MeOD) δ ppm 7.59-7.64 (2H, m), 7.47-7.57 (3H, m), 7.37 (1H, d, J=7.7 Hz), 7.14-7.22 (2H, m), 3.79-3.96 (2H, m), 3.09-3.18 (4H, m), 2.58-2.79 (2H, m), 1.83-2.09 (2H, m), 1.37 (3H, s).

Example 120

Isomer 2

The titled compound was prepared using the experimental protocol described for Example 95 employing 2-amino-2-methyl-4-(2-(3-phenyl-4-(trifluoromethyl)isoxazol-5-yl)-4,5-dihydronaphtho[2,1-d]thiazol-7-yl)butan-1-ol (Example 119, isomer 2) as a starting material. The compound had an HPLC retention time=3.70 min. (condition C); LC/MS $M^{+1}$=579.9; $^1$H NMR (400 MHz, MeOD) δ ppm 7.59-7.64 (2H, m), 7.47-7.57 (3H, m), 7.37 (1H, d, J=7.7 Hz), 7.14-7.22 (2H, m), 3.79-3.96 (2H, m), 3.09-3.18 (4H, m), 2.58-2.79 (2H, m), 1.83-2.09 (2H, m), 1.37 (3H, s).

Example 121

(1-amino-3-(3-(5-phenyl-4-(trifluoromethyl)isoxazol-3-yl)-4,5-dihydronaphtho[1,2-c]isoxazol-7-yl)cyclopentyl)methanol

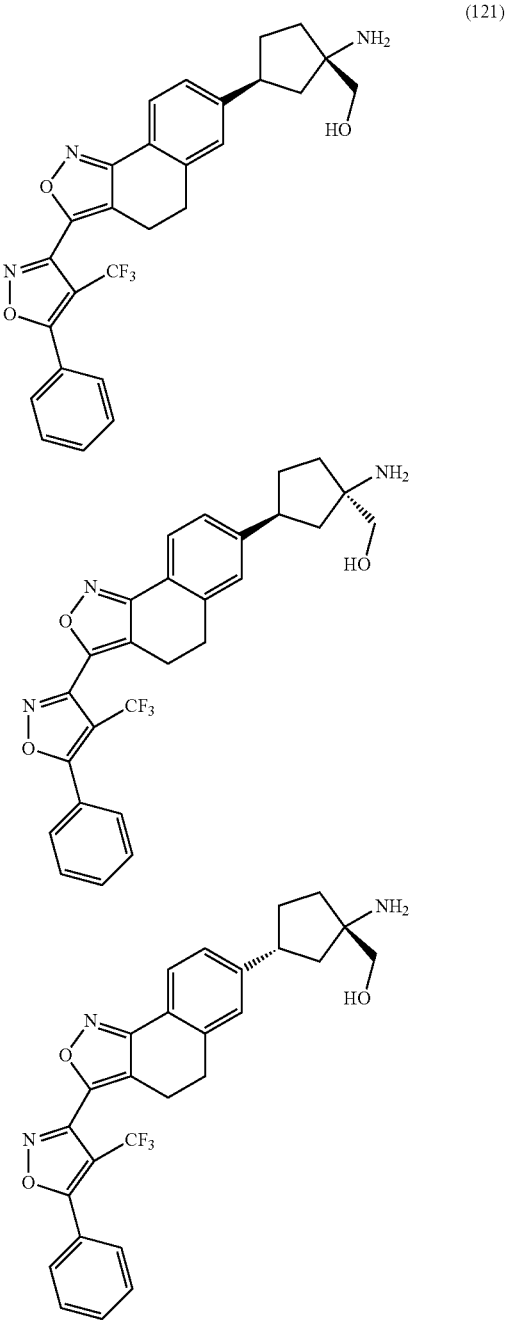

-continued

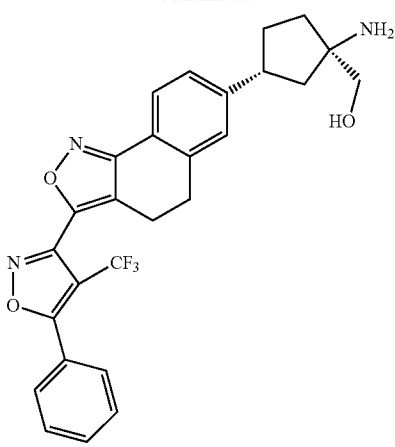 [SMILES: N[C@]1(CO)CC[C@@H](c2ccc3c(c2)CCc2c-3noc2-c2noc(-c3ccccc3)c2C(F)(F)F)C1]

Preparation 121A: (E)-6-iodo-3,4-dihydronaphthalen-1(2H)-one oxime

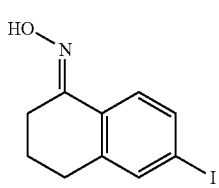

(121A)

The titled compound was prepared using the experimental protocol described for Preparation 87B employing 6-iodo-3,4-dihydronaphthalen-1(2H)-one as a starting material. The compound had an HPLC retention time=3.28 min. (condition C); LC/MS M$^{+1}$=288.1.

Preparation 121B: 7-iodo-3-(5-phenyl-4-(trifluoromethyl)isoxazol-3-yl)-4,5-dihydronaphtho[1,2-c]isoxazole

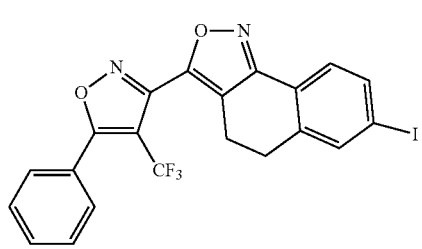

(121B)

The titled compound was prepared using the experimental protocol described for Preparation 89A employing (E)-6-iodo-3,4-dihydronaphthalen-1(2H)-one oxime (121A) and methyl 5-phenyl-4-(trifluoromethyl)isoxazole-3-carboxylate (Intermediate I-5) as starting materials. The compound had an HPLC retention time=4.42 min. (condition C); LC/MS M$^{+1}$=509.0.

Preparation 121C: 3-(3-(5-phenyl-4-(trifluoromethyl)isoxazol-3-yl)-4,5-dihydronaphtho[1,2-c]isoxazol-7-yl)cyclopentanone

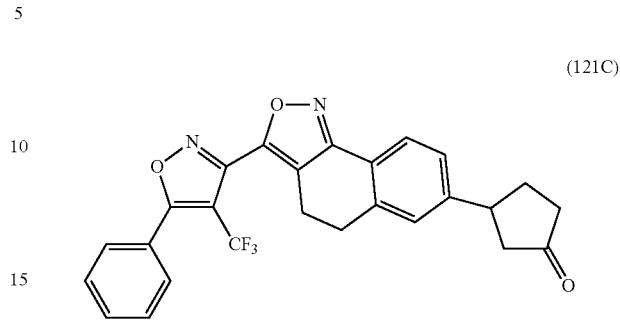

(121C)

To a mixture of 7-iodo-3-(5-phenyl-4-(trifluoromethyl)isoxazol-3-yl)-4,5-dihydronaphtho[1,2-c]isoxazole (Preparation 121B, 370 mg, 0.728 mmol), tetrabutylammonium chloride (202 mg, 0.728 mmol), potassium acetate (214 mg, 2.184 mmol), and anhydrous DMF (2 mL) was bubbled with nitrogen for 3 min. before palladium (II) acetate (16.34 mg, 0.073 mmol) and cyclopent-2-enol (122 mg, 1.456 mmol) were added. The mixture was bubbled for 2 min. and sealed in a 2-dram vial. The mixture was stirred at 75° C. for 3 h. The mixture was cooled, diluted with water (30 ml) and extracted with ethyl acetate (3×10 mL). The combined ethyl acetate extracts were dried (sodium sulfate) and concentrated under reduced pressure. Flash chromatography purification (silica gel column, 5→50% ethyl acetate in n-heptane) afforded 3-(3-(5-phenyl-4-(trifluoromethyl)isoxazol-3-yl)-4,5-dihydronaphtho[1,2-c]isoxazol-7-yl)cyclopentanone (230 mg, 0.495 mmol, 68.0% yield). The compound had an HPLC retention time=4.04 min. (condition C); LC/MS M$^{+1}$=465.2.

Preparation 121D: 1-amino-3-(3-(5-phenyl-4-(trifluoromethyl)isoxazol-3-yl)-4,5-dihydronaphtho[1,2-c]isoxazol-7-yl)cyclopentanecarbonitrile

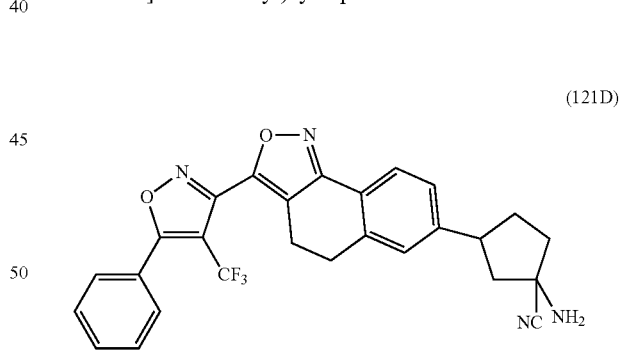

(121D)

A mixture of 3-(3-(5-phenyl-4-(trifluoromethyl)isoxazol-3-yl)-4,5-dihydronaphtho[1,2-c]isoxazol-7-yl)cyclopentanone (Preparation 121C, 230 mg, 0.495 mmol), ammonium chloride (79 mg, 1.486 mmol), sodium cyanide (72.8 mg, 1.486 mmol), 7 M methanol solution of ammonia (4.95 mL, 34.7 mmol) and dichloromethane (2 mL) was stirred at room temperature for 1 day. Additional 7 M methanol solution of ammonia (2 mL) was added and the mixture was stirred at room temperature for 2.5 days. The mixture was concentrated. The residue was partitioned between ethyl acetate (10 mL) and saturated aqueous sodium bicarbonate solution (3 mL). The aqueous layer was separated and extracted with ethyl acetate (2×1.5 mL). The combined ethyl acetate extracts were dried (sodium sulfate) and concentrated under reduced pressure to give 1-amino-3-(3-(5-phenyl-4-(trifluoromethyl)isoxazol-3-yl)-4,5-dihydronaphtho[1,2-c]isoxazol-7-yl)cyclopentanecarbonitrile (245 mg, 0.500 mmol, 100% yield) as a glassy solid. The compound had an HPLC retention time=3.51 min. (condition C); LC/MS M$^{+1}$=491.2.

Preparation 121E: 1-amino-3-(3-(5-phenyl-4-(trifluoromethyl)isoxazol-3-yl)-4,5-dihydronaphtho[1,2-c]isoxazol-7-yl)cyclopentanecarboxylic acid

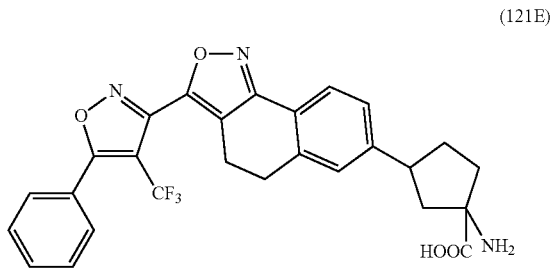 [SMILES: NC1(C(=O)O)CCC(c2ccc3c(c2)CCc2c-3noc2-c2noc(-c3ccccc3)c2C(F)(F)F)C1]

(121E)

A mixture of 1-amino-3-(3-(5-phenyl-4-(trifluoromethyl)isoxazol-3-yl)-4,5-dihydronaphtho[1,2-c]isoxazol-7-yl)cyclopentanecarbonitrile (Preparation 123D, 245 mg, 0.500 mmol), AcOH (1 mL), dioxane (1 mL), conc. HCl (1.7 mL, 56.0 mmol) and water (0.85 mL, 47.2 mmol) was stirred at 100° C. under nitrogen for 9 hr and then cooled to room temperature. The solid was filtered, washed with water (3×1 mL) and dried to give 1-amino-3-(3-(5-phenyl-4-(trifluoromethyl)isoxazol-3-yl)-4,5-dihydronaphtho[1,2-c]isoxazol-7-yl)cyclopentanecarboxylic acid, HCl (245 mg, 0.449 mmol, 90% yield) as a grey solid. The compound had an HPLC retention time=3.53 min. (condition C); LC/MS M$^{+1}$=510.3.

Preparation 121F: methyl 1-amino-3-(3-(5-phenyl-4-(trifluoromethyl)isoxazol-3-yl)-4,5-dihydronaphtho[1,2-c]isoxazol-7-yl)cyclopentanecarboxylate

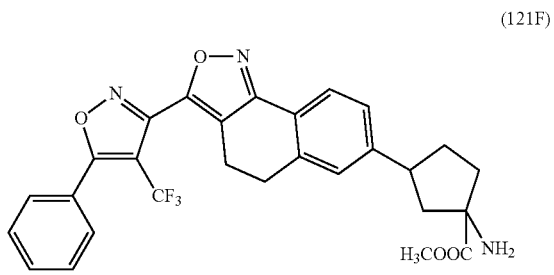

(121F)

To a stirred mixture of 1-amino-3-(3-(5-phenyl-4-(trifluoromethyl)isoxazol-3-yl)-4,5-dihydronaphtho[1,2-c]isoxazol-7-yl)cyclopentanecarboxylic acid, HCl (Intermediate 121E, 244 mg, 0.447 mmol) in anhydrous MeOH (13 mL) was added thionyl chloride (0.065 mL, 0.894 mmol) dropwise at 0° C. The reaction mixture was then stirred at 70° C. for 6 hr and room temperature overnight. More thionyl chloride (0.2 mL) was added dropwise at 0° C., followed by anhydrous MeOH (7 mL). The reaction mixture was then stirred at 70° C. for 6 hr and room temperature overnight. The mixture was concentrated. The residue was mixed with saturated aqueous sodium bicarbonate solution (20 mL) and ethyl acetate (20 mL). The aqueous layer was separated and extracted with ethyl acetate (2×10 mL). The combined ethyl acetate solutions were dried (sodium sulfate) and concentrated. Flash chromatography purification (silica gel column, 20→100% ethyl acetate in heptane; 0-10% MeOH in EtOAc) afforded methyl 1-amino-3-(3-(5-phenyl-4-(trifluoromethyl)isoxazol-3-yl)-4,5-dihydronaphtho[1,2-c]isoxazol-7-yl)cyclopentanecarboxylate (160 mg, 0.306 mmol, 68.4% yield) as a glassy solid. The compound had an HPLC retention time=3.55 min. (condition C); LC/MS M$^{+1}$=524.3.

Example 121

Methyl 1-amino-3-(3-(5-phenyl-4-(trifluoromethyl)isoxazol-3-yl)-4,5-dihydronaphtho[1,2-c]isoxazol-7-yl)cyclopentanecarboxylate (Preparation 121F, 160 mg, 0.306 mmol) was mixed with EtOH (2 mL), dichloromethane (1 mL) and sodium borohydride (57.8 mg, 1.528 mmol). The mixture was stirred at room temperature overnight. Next, 2N aqueous sodium hydroxide solution (5 mL) was added. The mixture was stirred at 40° C. for 30 min. and cooled. Water (10 mL) was added. The mixture was extracted with EtOAc (10 mL, 2×5 mL). The combined ethyl acetate extracts were dried (sodium sulfate) and concentrated under reduced pressure to give a (1-amino-3-(3-(5-phenyl-4-(trifluoromethyl)isoxazol-3-yl)-4,5-dihydronaphtho[1,2-c]isoxazol-7-yl)cyclopentyl)methanol (151 mg, 0.305 mmol, 100% yield) as a foam solid.

The four diastereomers were separated using a CHIRALPAK® AD-H column under SFC conditions (30% MeOH with 0.5% DEA in CO$_2$) into two fractions. The first fraction was then separated using a CHIRALPAK® AS-H column under SFC conditions (15% MeOH-MeCN (1:1) with 0.5% DEA in CO$_2$) into two peaks [F1A (9 mg, ret time=15.5 min) and F1B (12 mg, ret. time=18 min)] The second fraction was separated using a CHIRALPAK® AD-H column under SFC conditions (30% MeOH-MeCN (1:1) with 0.5% DEA in CO$_2$) into two peaks [F2A (13 mg, ret. time=4.6 min) and F2B (9 mg, ret. time=7.2 min)] The absolute stereochemistry at the carbon chiral centers was not determined. They all had LC/MS M$^{+1}$=496.0.

Example 122

1-((3-(1-(5-fluoropyridin-2-yl)-5-(trifluoromethyl)-1H-pyrazol-4-yl)-4,5-dihydronaphtho[1,2-c]isoxazol-7-yl)methyl)azetidine-3-carboxylic acid

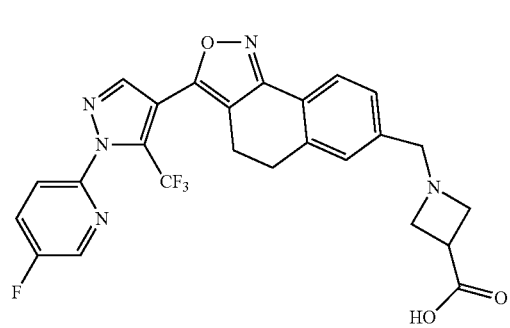

(122)

Preparation 122A: Ethyl 1-(5-fluoropyridin-2-yl)-5-(trifluoromethyl)-1H-pyrazole-4-carboxylate

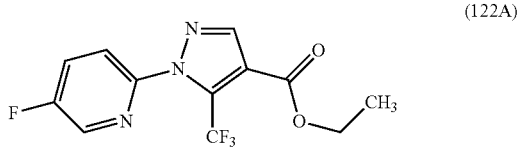 [SMILES: CCOC(=O)c1cnn(-c2ccc(F)cn2)c1C(F)(F)F]
(122A)

To (E)-ethyl 2-(ethoxymethylene)-4,4,4-trifluoro-3-oxobutanoate (0.441 g, 1.835 mmol) in ethanol (2 mL) was added diisopropylethylamine (0.427 mL, 2.447 mmol) followed by 5-fluoro-2-hydrazinylpyridine, hydrofluoride (0.3 g, 2.039 mmol) dissolved in 1 mL of ethanol (slightly exothermic). The reaction mixture was heated at 80° C. for 1 h. The reaction mixture was concentrated under reduced pressure, dissolved in dichloromethane (2 mL) and subjected to column chromatography using an ISCO setup (40 g, RediSep® silica gel column). The desired fractions were collected and concentrated to yield ethyl 1-(5-fluoropyridin-2-yl)-5-(trifluoromethyl)-1H-pyrazole-4-carboxylate (0.165 g, 27%) as a white solid. LC/MS $M^{+1}=304$.

Preparation 122B: 3-(1-(5-fluoropyridin-2-yl)-5-(trifluoromethyl)-1H-pyrazol-4-yl)-7-vinyl-4,5-dihydronaphtho[1,2-c]isoxazole

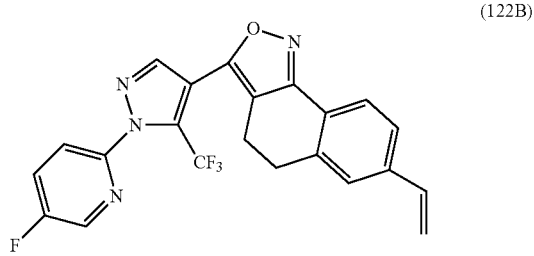 [SMILES: C=Cc1ccc2c(c1)CCc1c-2noc1-c1cnn(-c2ccc(F)cn2)c1C(F)(F)F]
(122B)

The titled compound was prepared using the experimental protocol described for Preparation 89A employing 6-vinyl-3,4-dihydronaphthalen-1(2H)-one oxime (I-1) and ethyl 1-(5-fluoropyridin-2-yl)-5-(trifluoromethyl)-1H-pyrazole-4-carboxylate (Preparation 122A) as starting materials. The compound had an HPLC retention time=3.93 min. (condition C); LC/MS $M^{+1}=426.9$.

Preparation 122C: 3-(1-(5-fluoropyridin-2-yl)-5-(trifluoromethyl)-1H-pyrazol-4-yl)-4,5-dihydronaphtho[1,2-c]isoxazole-7-carbaldehyde

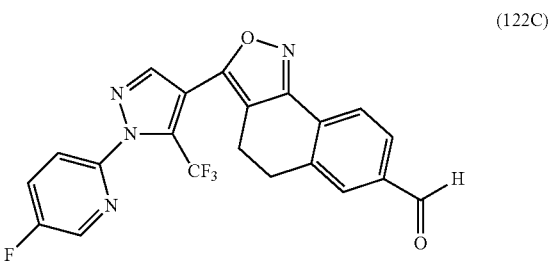 [SMILES: O=Cc1ccc2c(c1)CCc1c-2noc1-c1cnn(-c2ccc(F)cn2)c1C(F)(F)F]
(122C)

The titled compound was prepared using the experimental protocol described for Preparation 89B employing 3-(1-(5-fluoropyridin-2-yl)-5-(trifluoromethyl)-1H-pyrazol-4-yl)-7-vinyl-4,5-dihydronaphtho[1,2-c]isoxazole (122B) as a starting material. The compound had an HPLC retention time=3.56 min. (condition C); LC/MS $M^{+1}=428.9$.

Example 122

To a stirred mixture of 3-(1-(5-fluoropyridin-2-yl)-5-(trifluoromethyl)-1H-pyrazol-4-yl)-4,5-dihydronaphtho[1,2-c]isoxazole-7-carbaldehyde (Preparation 122C, 40 mg, 0.093 mmol), dichloromethane (4 mL) and MeOH (1 mL) was added azetidine-3-carboxylic acid (28.3 mg, 0.280 mmol) at room temperature followed by DBU (0.028 mL, 0.187 mmol). The reaction mixture was stirred at room temperature for 5 min. before sodium triacetoxyborohydride (59.4 mg, 0.280 mmol) was added in one lot. The mixture was stirred at room temperature overnight. More sodium triacetoxyborohydride (30 mg) was added and the mixture was stirred at room temperature for 4 hr. The mixture was concentrated and dissolved in methanol and dichloromethane. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave 1-((3-(1-(5-fluoropyridin-2-yl)-5-(trifluoromethyl)-1H-pyrazol-4-yl)-4,5-dihydronaphtho[1,2-c]isoxazol-7-yl)methyl)azetidine-3-carboxylic acid, TFA (51 mg, 0.079 mmol, 84% yield) as a white solid. The compound had an HPLC retention time=2.77 min. (condition C); LC/MS $M^{+1}=513.9$; $^1$H NMR (400 MHz, MeOD) δ ppm 8.49 (1H, s), 8.18 (1H, s), 8.02 (1H, d, J=7.7 Hz), 7.89-7.93 (2H, m), 7.52 (1H, s), 7.49 (1H, d, J=7.7 Hz), 4.46 (2H, s), 4.31-4.42 (4H, m), 3.70 (1H, quin, J=8.3 Hz), 3.09 (2H, t, J=6.9 Hz), 2.93 (2H, t, J=7.0 Hz).

Example 123

(1-amino-3-(2-(3-phenyl-4-(trifluoromethyl)isoxazol-5-yl)-4,5-dihydronaphtho[2,1-d]thiazol-7-yl)cyclopentyl)methanol

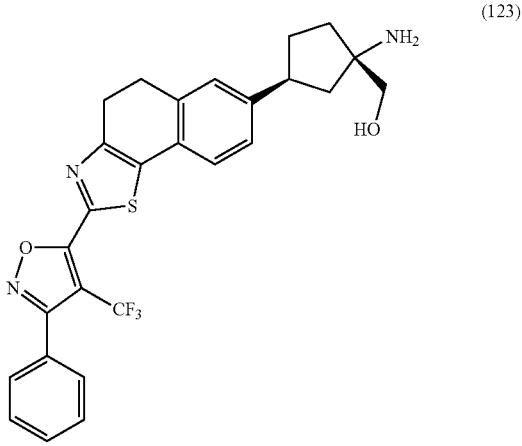
(123)

-continued

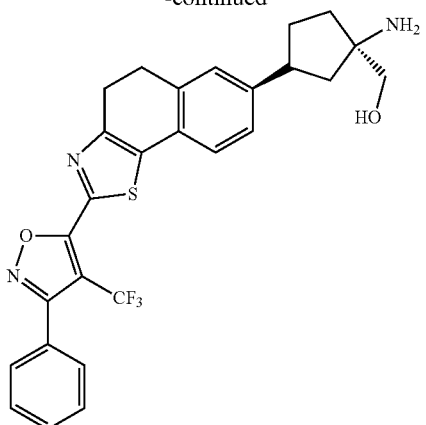

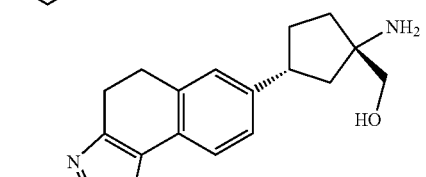

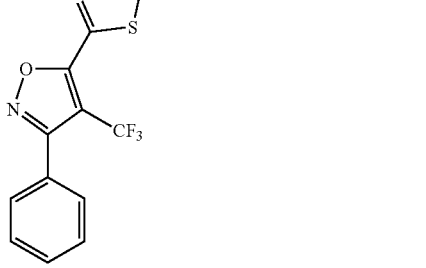

Preparation 123A: 5-(7-iodo-4,5-dihydronaphtho[2,1-d]thiazol-2-yl)-3-phenyl-4-(trifluoromethyl)isoxazole (123A)

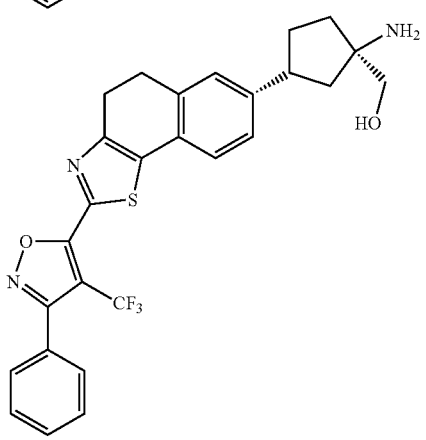

This compound was prepared according to the procedure described for example 82A-D, starting from 6-iodo-3,4-dihydronaphthalen-1(2H)-one oxime (121A). LC/MS M$^{+1}$=525.

Example 123

The titled compound was prepared using the general experimental protocol described for Preparation 121C through F and Example 121 employing (Preparation 123A) as a starting material. The compound had an HPLC retention time=3.55 min. (condition C); LC/MS M$^{+1}$=512.1.

The four diastereomers were separated using a CHIRALPAK® AD-H column under SFC conditions (30% MeOH with 0.5% DEA in CO$_2$) into three fractions. The third fraction was then separated using a CHIRALPAK® AD-H column under SFC conditions (25% MeOH-MeCN (1:1) with 0.5% DEA in CO$_2$) into two peaks [F3A (13 mg, ret. time=11.2 min) and F3B (9 mg, ret. time=13 min)]. The absolute stereochemistry at the carbon chiral centers was not determined. Each diastereomer had a LC/MS M$^{+1}$=512.

Example 124

2-(1-amino-3-(2-(3-phenyl-4-(trifluoromethyl)isoxazol-5-yl)-4,5-dihydronaphtho[2,1-d]thiazol-7-yl)cyclopentyl)ethanol (124)

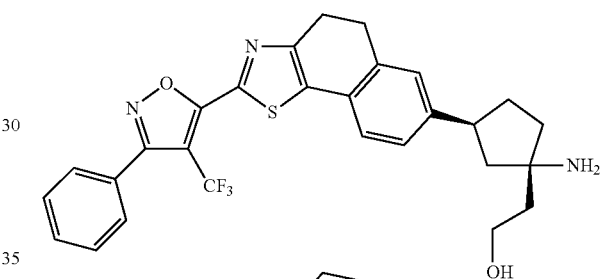

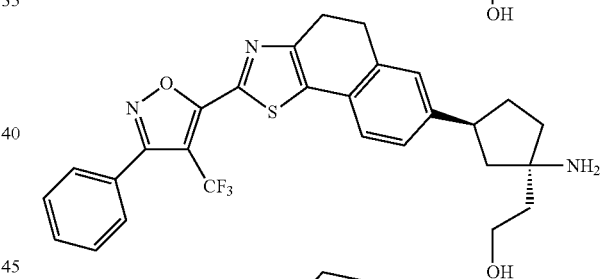

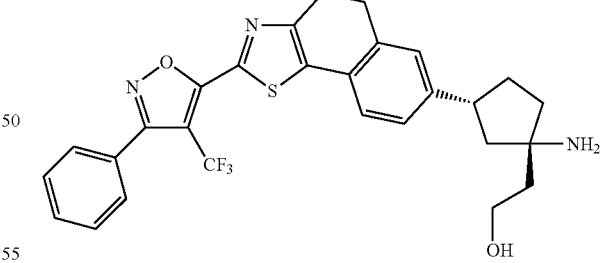

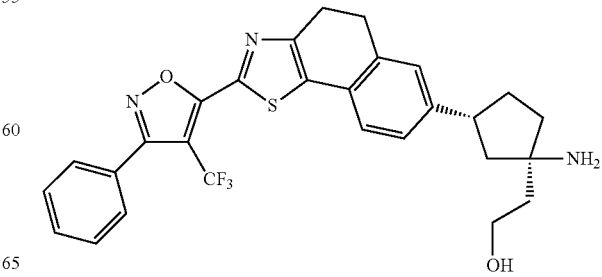

Preparation 124A: 1-allyl-3-(2-(3-phenyl-4-(trifluoromethyl)isoxazol-5-yl)-4,5-dihydronaphtho[2,1-d]thiazol-7-yl)cyclopentanamine

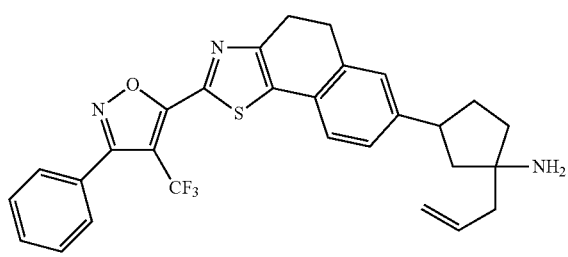

(124A)

To a stirred mixture of 3-(2-(3-phenyl-4-(trifluoromethyl)isoxazol-5-yl)-4,5-dihydronaphtho[2,1-d]thiazol-7-yl)cyclopentanone (prepared according to Preparation 121C from 5-(7-iodo-4,5-dihydronaphtho[2,1-d]thiazol-2-yl)-3-phenyl-4-(trifluoromethyl)isoxazole (Preparation 123A), 200 mg, 0.416 mmol), 7 M methanol solution of ammonia (2 mL, 14.00 mmol), and anhydrous dichloromethane (1.5 mL) was added allylboronic acid pinacol ester (0.117 mL, 0.624 mmol). The mixture was stirred at room temperature overnight. More allylboronic acid pinacol ester (0.1 mL) was added. The mixture was stirred at room temperature for 5 h before being concentrated. The residue was mixed with water (5 mL) and extracted with dichloromethane (4×2 mL). The combined dichloromethane extracts were dried (sodium sulfate) and concentrated under reduced pressure. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration, neutralization with saturated aqueous sodium bicarbonate solution and extraction with dichloromethane gave 1-allyl-3-(2-(3-phenyl-4-(trifluoromethyl)isoxazol-5-yl)-4,5-dihydronaphtho[2,1-d]thiazol-7-yl)cyclopentanamine (103 mg, 0.197 mmol, 47.4% yield) as a glassy solid. The compound had an HPLC retention time=3.75 min. (condition C); LC/MS M$^{+1}$=521.9.

Preparation 124B: tert-butyl 1-allyl-3-(2-(3-phenyl-4-(trifluoromethyl)isoxazol-5-yl)-4,5-dihydronaphtho[2,1-d]thiazol-7-yl)cyclopentylcarbamate

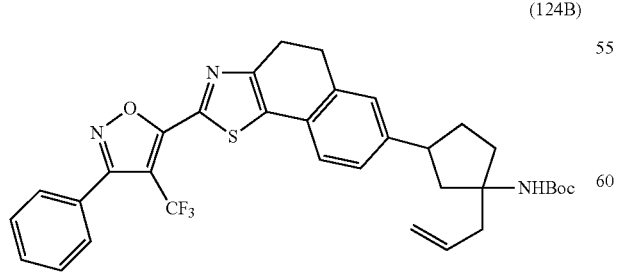

(124B)

A solution of 1-allyl-3-(2-(3-phenyl-4-(trifluoromethyl)isoxazol-5-yl)-4,5-dihydronaphtho[2,1-d]thiazol-7-yl)cyclopentanamine (Preparation 124A, 103 mg, 0.197 mmol), Boc$_2$O (0.069 mL, 0.296 mmol) and Et$_3$N (0.083 mL, 0.592 mmol) in anhydrous dichloromethane (3 mL) was stirred at room temperature for 1 day. The mixture was concentrated. The residue was dissolved in dichloromethane (8 mL). The solution was washed with 1N aqueous HCl (1 mL), water (1 mL) and then brine (2 mL). The solution was dried (sodium sulfate) and concentrated to give tert-butyl 1-allyl-3-(2-(3-phenyl-4-(trifluoromethyl)isoxazol-5-yl)-4,5-dihydronaphtho[2,1-d]thiazol-7-yl)cyclopentylcarbamate (137 mg, 0.220 mmol, 112% yield) as a glassy solid. The compound had an HPLC retention time=4.68 min. (condition C); LC/MS M$^{+1}$=622.3.

Example 124

The Boc protected titled compound was prepared using the experimental protocol described for Preparation 6B employing tert-butyl 1-allyl-3-(2-(3-phenyl-4-(trifluoromethyl)isoxazol-5-yl)-4,5-dihydronaphtho[2,1-d]thiazol-7-yl)cyclopentyl carbamate (Preparation 124B) as a starting material. TFA deprotection gave the titled compound. The compound had an HPLC retention time=3.59 min. (condition C); LC/MS M$^{+1}$=526.0. The individual diastereomers were separated using a CHIRALPAK® AD-H column under SFC conditions (30% MeOH with 0.5% DEA in CO$_2$). Isomer 1 had retention time on chiral HPLC, 5.3 min; LC/MS M$^{+1}$=525.9; Isomer 2 & 3 had retention time on chiral HPLC, 7 min.; LC/MS M$^{+1}$=525.9; Isomer 4 had retention time on chiral HPLC, 10.9 min.; LC/MS M$^{+1}$=526.1. The absolute stereochemistry at the carbon chiral centers was not determined.

Example 125

2-amino-2-(3-(5-phenyl-4-(trifluoromethyl)isoxazol-3-yl)-4,5-dihydronaphtho[1,2-c]isoxazol-7-yl)propan-1-ol

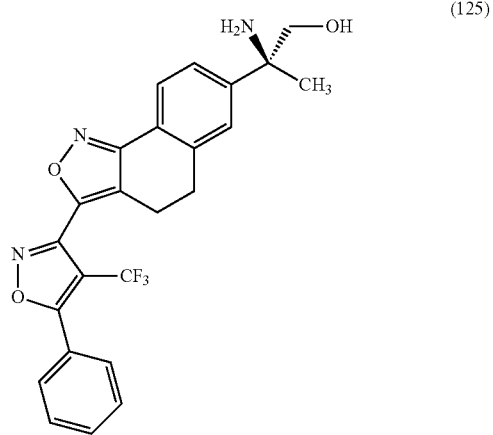

(125)

-continued

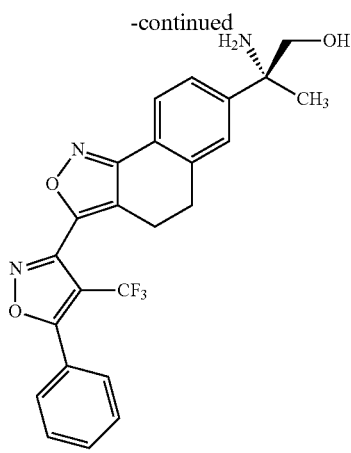

Preparation 124A: 1-(3-(5-phenyl-4-(trifluoromethyl)isoxazol-3-yl)-4,5-dihydronaphtho[1,2-c]isoxazol-7-yl)ethanol

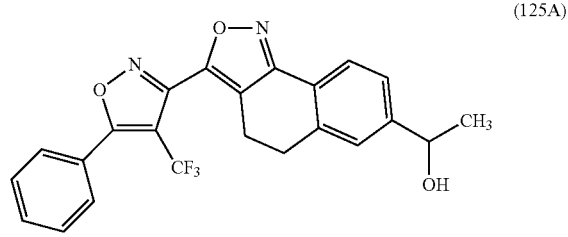 [SMILES: CC(O)c1ccc2c(c1)CCc1c-2noc1-c1noc(-c2ccccc2)c1C(F)(F)F]
(125A)

To 3-(5-phenyl-4-(trifluoromethyl)isoxazol-3-yl)-4,5-dihydronaphtho[1,2-c]isoxazole-7-carbaldehyde (Preparation 88A, 0.425 g, 1.036 mmol) in THF (5 mL), cooled to −50° C. was added methylmagnesium bromide (3.0M in diethyl ether) (0.380 mL, 1.139 mmol) over a period of 2 min. The contents were allowed to come to room temperature over a period of 30 min. The reaction mixture was re-cooled to −50° C. and 0.15 mL of methylmagnesium bromide was added and the contents allowed to come to room temperature over a period of 10 min. The reaction mixture was quenched by the slow addition of sat. aq ammonium chloride (3 mL) and extracted into EtOAc (2×15 mL). The EtOAc layer was dried over sodium sulfate and concentrated to yield 1-(3-(5-phenyl-4-(trifluoromethyl)isoxazol-3-yl)-4,5-dihydronaphtho[1,2-c]isoxazol-7-yl)ethanol (0.44 g, 1.032 mmol, 100% yield) as a tan colored solid. LC/MS $M^{+1}$=427.

Preparation 125B: 1-(3-(5-phenyl-4-(trifluoromethyl)isoxazol-3-yl)-4,5-dihydronaphtho[1,2-c]isoxazol-7-yl)ethanone

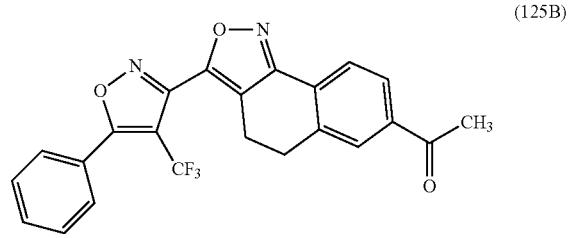 [SMILES: CC(=O)c1ccc2c(c1)CCc1c-2noc1-c1noc(-c2ccccc2)c1C(F)(F)F]
(125B)

To 1-(3-(5-phenyl-4-(trifluoromethyl)isoxazol-3-yl)-4,5-dihydronaphtho[1,2-c]isoxazol-7-yl)ethanol (Preparation 125A 0.44 g, 1.032 mmol) in dichloromethane (5 mL) was added Dess-Martin Periodinane (0.481 g, 1.135 mmol) in batches, over 2 min. at room temperature. The reaction mixture was stirred at room temperature for 1.5 h. A 1:1 mixture of saturated aqueous sodium thiosulfate and saturated aqueous bicarbonate (3.6 mL) was added slowly to the reaction mixture at room temperature and the contents stirred for 15 min. The organic layer was separated and the aqueous layer was extracted with dichloromethane (2×10 mL). The combined organic layers were dried over sodium sulfate, filtered through a pad of Celite and concentrated under reduce pressure to yield 1-(3-(5-phenyl-4-(trifluoromethyl)isoxazol-3-yl)-4,5-dihydronaphtho[1,2-c]isoxazol-7-yl)ethanone (0.415 g, 0.978 mmol, 95% yield) as a tan colored solid. LC/MS $M^{+1}$=425.

Example 125

The titled compound was prepared using the experimental protocol described for Preparation 121D through F and Example 121 employing 1-(3-(5-phenyl-4-(trifluoromethyl)isoxazol-3-yl)-4,5-dihydronaphtho[1,2-c]isoxazol-7-yl)ethanone (Preparation 125B) as a starting material. The compound had an HPLC retention time=3.19 min. (condition C); LC/MS $M^{+1}$=456.2; $^{1}$H NMR (400 MHz, CDCl$_3$) δ ppm 8.01 (1H, d, J=8.6 Hz), 7.75 (2H, d, J=7.3 Hz), 7.54-7.66 (3H, m), 7.44-7.50 (2H, m), 3.58-3.76 (2H, m), 3.03-3.14 (4H, m), 1.47-1.53 (3H, m). The individual enantiomers were separated using a CHIRALPAK® AD-H column under SFC conditions (30% MeOH with 0.1% DEA in CO$_2$). The absolute stereochemistry at the carbon chiral center, of Isomer 1 and Isomer 2, was not determined.

Example 126

N-(methylsulfonyl)-1-((3-(3-phenyl-4-(trifluoromethyl)isoxazol-5-yl)-4,5-dihydronaphtho[1,2-c]isoxazol-7-yl)methyl)azetidine-3-carboxamide

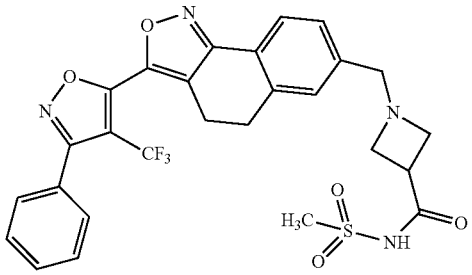
(126)

To a stirred mixture of 1-((3-(3-phenyl-4-(trifluoromethyl)isoxazol-5-yl)-4,5-dihydronaphtho[1,2-c]isoxazol-7-yl)methyl)azetidine-3-carboxylic acid (Example 7, 80 mg, 0.161 mmol), methanesulfonamide (77 mg, 0.807 mmol), DMAP (3.95 mg, 0.032 mmol), triethylamine (0.113 mL, 0.807 mmol), and anhydrous dichloromethane (5 mL) was added O-(7-azabenzotriazol-1-yl)-N,N,N',N'-tetramethyluronium hexafluorophosphate (92 mg, 0.242 mmol) under nitrogen. The reaction mixture was stirred at room temperature for 5 h before being concentrated. The residue was dissolved in MeOH and a little dichloromethane. Purification using reverse phase HPLC (Phenomenex Luna AXIA 5 u c18 30×100 mm, 10 min. run, solvent A: 10% MeOH: 90% H$_2$O: 0.1% TFA, solvent B: 90% MeOH, 10% H$_2$O, 0.1% TFA), concentration and lyophilization gave N-(methylsulfonyl)-1-((3-(3-phenyl-4-(trifluoromethyl)isoxazol-5-yl)-4,5-dihydronaphtho[1,2-c]isoxazol-7-yl)methyl)azetidine-3-carboxamide, TFA (15 mg, 0.020 mmol, 12.58% yield) as a white solid. The compound had an HPLC retention time=3.21 min (condition C); LC/MS M$^{+1}$=573.1. $^1$H NMR (400 MHz, MeOD) δ ppm 8.08 (1H, d, J=7.9 Hz), 7.64-7.69 (2H, m), 7.54-7.64 (4H, m), 7.51 (1H, dd, J=7.9, 1.8 Hz), 4.48 (2H, s), 4.36 (4H, d, J=7.9 Hz), 3.68 (1H, quin, J=8.0 Hz), 3.27 (3H, s), 3.11-3.22 (4H, m).

Example 127

(±)-2-Hydroxy-2-(3-(4-propylphenyl)-4,5-dihydronaphtho[1,2-c]isoxazol-7-yl)acetic acid

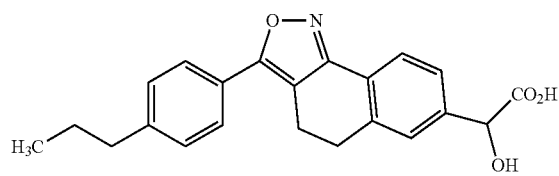

(127)

Preparation 127A: 2-Hydroxy-2-(3-(4-propylphenyl)-4,5-dihydronaphtho[1,2-c]isoxazol-7-yl)acetonitrile

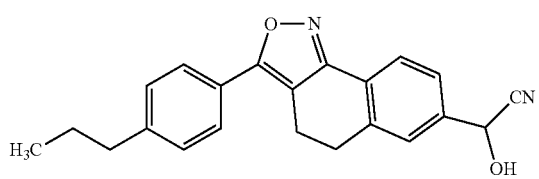

(127A)

To a solution of 3-(4-propylphenyl)-4,5-dihydronaphtho[1,2-c]isoxazole-7-carbaldehyde (Preparation 11C, 250 mg, 0.78 mmol) in dichloromethane (4 mL) at 0° C. was added trimethylsilyl cyanide (0.13 mL, 0.94 mmol) and titanium (IV) isopropoxide (0.46 mL, 1.6 mmol). The reaction mixture was stirred for 1 h before 1 N HCl (aq) was added along with additional dichloromethane. The organic layer was dried (over magnesium sulfate), filtered, and concentrated to give crude 2-hydroxy-2-(3-(4-propylphenyl)-4,5-dihydronaphtho[1,2-c]isoxazol-7-yl)acetonitrile (Preparation 127A, 265 mg, 0.77 mmol, 98% yield): LC/MS M$^{+1}$=345.1.

Example 127

To a solution of 2-hydroxy-2-(3-(4-propylphenyl)-4,5-dihydronaphtho[1,2-c]isoxazol-7-yl)acetonitrile (Preparation 127A, 120 mg, 0.35 mmol) in glacial AcOH (1.5 mL) was added concentrated HCl (0.5 mL). The reaction mixture was stirred at 70° C. for 8 h. After cooling, the solution was poured into water and was extracted with ethyl acetate. The organic layer was dried (over magnesium sulfate), filtered, and concentrated. The resulting residue was purified by preparative HPLC (Phenomenex Luna 5 u C18 21.2×100 mm, Solvent A: 90% water with 10% MeOH and 0.1% TFA, Solvent B: 90% MeOH with 10% water and 0.1% TFA, Gradient: 0% B to 100% B over 10 min, 20 mL/min, 220 nM, product retention time=12.1 min) to give 2-hydroxy-2-(3-(4-propylphenyl)-4,5-dihydronaphtho[1,2-c]isoxazol-7-yl)acetic acid (20 mg, 0.049 mmol, 13% yield): product HPLC ret. time=9.59 min. (condition G); LC/MS M$^{+1}$=364.1; $^1$H NMR (400 MHz, CD$_3$OD) δ ppm 7.87 (1H, d, J=7.92 Hz), 7.70 (2H, d, J=8.14 Hz), 7.41-7.57 (2H, m), 7.35 (2H, d, J=8.14 Hz), 5.19 (1H, s), 3.04 (4H, s), 2.66 (2H, t, J=7.59 Hz), 1.60-1.77 (2H, m), 0.97 (3H, t, J=7.26 Hz).

Example 128

(±)-N-(cyanomethyl)-2-hydroxy-2-(3-(4-propylphenyl)-4,5-dihydronaphtho[1,2-c]isoxazol-7-yl)acetamide

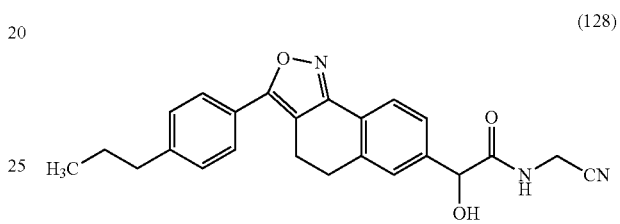

(128)

To a solution of 2-hydroxy-2-(3-(4-propylphenyl)-4,5-dihydronaphtho[1,2-c]isoxazol-7-yl)acetic acid (Example 127, 20 mg, 0.055 mmol) in DMF (1 mL) was added 4-methylmorpholine (0.036 mL, 0.33 mmol), 2-aminoacetonitrile (5.55 mg, 0.1 mmol) and BOP (43.8 mg, 0.1 mmol). The reaction mixture was stirred overnight and was then purified by preparative HPLC (Phenomenex Luna 5 u C18 21.2×100 mm, Solvent A: 90% water with 10% MeOH and 0.1% TFA, Solvent B: 90% MeOH with 10% water and 0.1% TFA, Gradient: 0% B to 100% B over 10 min, 20 mL/min, 220 nM, product retention time=11.9 min) to give N-(cyanomethyl)-2-hydroxy-2-(3-(4-propylphenyl)-4,5-dihydronaphtho[1,2-c]isoxazol-7-yl)acetamide (11.2 mg, 0.026 mmol, 46.9% yield): product HPLC ret. time=9.89 min. (condition G); LC/MS M$^{+1}$=402.1; $^1$H NMR (400 MHz, CD$_3$OD) δ ppm 7.88 (1H, d, J=7.92 Hz), 7.72 (2H, d, J=8.36 Hz), 7.43-7.53 (2H, m), 7.37 (2H, d, J=8.36 Hz), 5.13 (1H, s), 4.19 (2H, d, J=1.76 Hz), 3.06 (4H, s), 2.67 (2H, t, J=7.59 Hz), 1.62-1.77 (2H, m), 0.97 (3H, t, J=7.37 Hz).

Example 129

(±)-2-Hydroxy-N-(2-hydroxyethyl)-2-(3-(4-propylphenyl)-4,5-dihydronaphtho[1,2-c]isoxazol-7-yl)acetamide

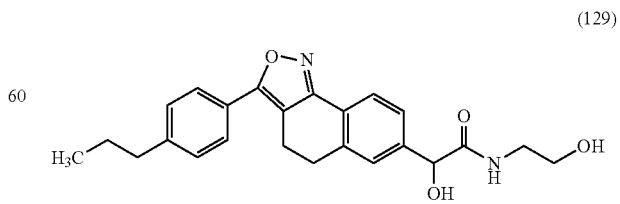

(129)

To a solution of 2-hydroxy-2-(3-(4-propylphenyl)-4,5-dihydronaphtho[1,2-c]isoxazol-7-yl)acetic acid (Example 127, 18 mg, 0.050 mmol) in DMF (1 mL) was added 2-aminoethanol (5.45 mg, 0.089 mmol), 4-methylmorpholine (0.033 mL, 0.29 mmol) and BOP (39.4 mg, 0.089 mmol). The reaction mixture was stirred overnight and was then purified by preparative HPLC (Phenomenex Luna 5 u C18 21.2×100 mm, Solvent A: 90% water with 10% MeOH and 0.1% TFA, Solvent B: 90% MeOH with 10% water and 0.1% TFA, Gradient: 0% B to 100% B over 10 min, 20 mL/min, 220 nM, product retention time=11.9 min) to give 2-hydroxy-N-(2-hydroxyethyl)-2-(3-(4-propylphenyl)-4,5-dihydronaphtho[1,2-c]isoxazol-7-yl)acetamide (14.5 mg, 0.033 mmol, 67.4% yield): product HPLC ret. time=8.79 min. (condition G); LC/MS $M^{+1}$=407.1; $^1$H NMR (400 MHz, $CD_3OD$) δ ppm 7.87 (1H, d, J=7.92 Hz), 7.72 (2H, d, J=8.36 Hz), 7.44-7.55 (2H, m), 7.37 (2H, d, J=8.36 Hz), 5.07 (1H, s), 3.58-3.69 (2H, m), 3.34-3.43 (2H, m), 3.05 (4H, s), 2.59-2.74 (2H, m), 1.61-1.80 (2H, m), 0.97 (3H, t, J=7.37 Hz).

Example 130

(±)-2-Hydroxy-N-(2-(methylsulfonyl)ethyl)-2-(3-(4-propylphenyl)-4,5-dihydronaphtho[1,2-c]isoxazol-7-yl)acetamide

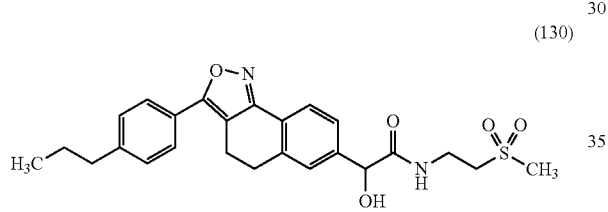

(130)

To a solution of 2-hydroxy-2-(3-(4-propylphenyl)-4,5-dihydronaphtho[1,2-c]isoxazol-7-yl)acetic acid (example 127, 35 mg, 0.096 mmol) in DMF (1 mL) was added 4-methylmorpholine (0.064 mL, 0.58 mmol), 2-aminoethylmethylsulfone hydrochloride (27.7 mg, 0.17 mmol), and BOP (77 mg, 0.17 mmol). The reaction mixture was stirred overnight and was then purified by preparative HPLC (Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min). Fractions containing the desired product were combined and dried via centrifugal evaporation to give 2-hydroxy-N-(2-(methylsulfonyl)ethyl)-2-(3-(4-propylphenyl)-4,5-dihydronaphtho[1,2-c]isoxazol-7-yl)acetamide (8.3 mg, 0.018 mmol, 18.4% yield): product HPLC ret. time=2.54 min. (condition F); LC/MS $M^{+1}$=468; $^1$H NMR (400 MHz, 1:1 $CD_3OD$ and $CDCl_3$) δ ppm 7.87 (1H, d, J=8.36 Hz), 7.67 (2H, d, J=8.14 Hz), 7.40-7.50 (2H, m), 7.31 (2H, d, J=8.36 Hz), 5.06 (1H, s), 3.73 (2H, t, J=6.49 Hz), 3.19-3.30 (2H, m), 2.94 (3H, s), 2.57-2.70 (2H, m), 1.60-1.77 (2H, m), 0.94 (3H, t, J=7.37 Hz).

Example 131

2-Hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)acetamide

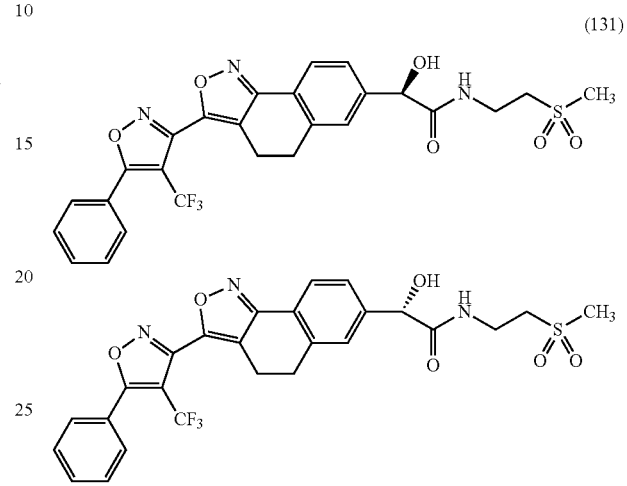

(131)

Preparation 131A: (±)-2-hydroxy-2-(3-(5-phenyl-4-(trifluoromethyl)isoxazol-3-yl)-4,5-dihydronaphtho[1,2-c]isoxazol-7-yl)acetonitrile

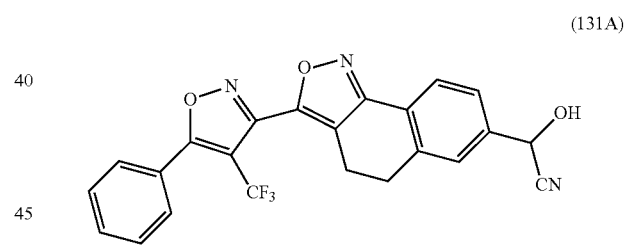

(131A)

To 3-(5-phenyl-4-(trifluoromethyl)isoxazol-3-yl)-4,5-dihydronaphtho[1,2-c]isoxazole-7-carbaldehyde (Preparation 88A, 1 g, 2.4 mmol) in acetonitrile (75 mL) was added trimethylsilyl cyanide (0.49 mL, 3.7 mmol) and zinc iodide (0.79 g, 2.4 mmol). The reaction mixture was stirred for 70 min. at room temperature. After being cooled in ice-water bath, the mixture was acidified by addition of aqueous hydrochloric acid (1N, 4.4 mL, 4.4 mmol). Ethyl acetate (100 mL) was added and the layers were separated. The organic phase was washed with saturated sodium thiosulfate solution (5 mL×2). The organic phase was then dried, filtered, and concentrated to provide the product (±)-2-hydroxy-2-(3-(5-phenyl-4-(trifluoromethyl)isoxazol-3-yl)-4,5-dihydronaphtho[1,2-c]isoxazol-7-yl)acetonitrile (1.1 g, 2.4 mmol, 99% yield); LC/MS $M^{+1}$=438.00; $^1$H NMR (400 MHz, $CDCl_3$) δ ppm 8.09 (1H, d, J=7.92 Hz), 7.76 (2H, d, J=7.26 Hz), 7.50-7.68 (5H, m), 5.62 (1H, s), 3.11 (4H, s).

Preparation of 131B: 2-hydroxy-2-(3-(5-phenyl-4-(trifluoromethyl)isoxazol-3-yl)-4,5-dihydronaphtho[1,2-c]isoxazol-7-yl)acetic acid

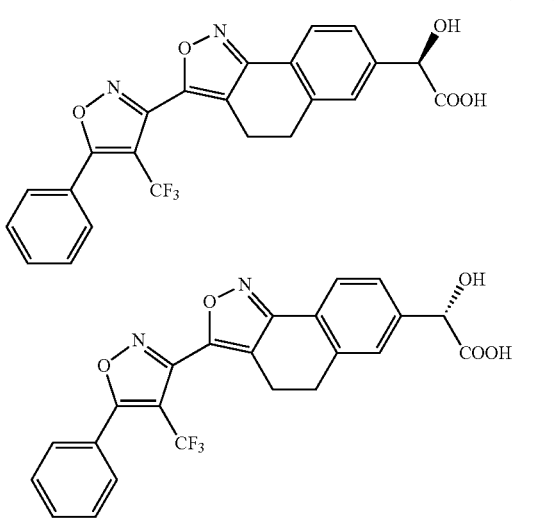

(131B)

To (±)-2-hydroxy-2-(3-(5-phenyl-4-(trifluoromethyl)isoxazol-3-yl)-4,5-dihydronaphtho[1,2-c]isoxazol-7-yl)acetonitrile (Preparation 131A, 1.1 g, 2.5 mmol) in dioxane (18.0 mL) was added water (12.0 mL) and hydrochloric acid, 37% (12 mL). The reaction mixture was heated at 100° C. for 3 h. After cooling, it was concentrated to provide the product as a racemic mixture. LC/MS M$^{+1}$=458.0. The individual enantiomers were separated using a chiral preparative column under SFC conditions (Chiralcel OJ-H 5×25 cm, column temperature 20° C., isocratic elution with mobile phase 35% acetonitrile+0.1 TFA in CO$_2$, 280 mL/min, 250 nM). Isomer 1 (500 mgs), retention time on chiral HPLC, 7.26 min; Isomer 2 (600 mgs), retention time on chiral HPLC, 9.88 min. The absolute stereochemistry at the carbon anchoring the secondary alcohol, of Isomer 1 and Isomer 2 was not determined.

Example 131

Isomer 1

To 2-hydroxy-2-(3-(5-phenyl-4-(trifluoromethyl)isoxazol-3-yl)-4,5-dihydronaphtho[1,2-c]isoxazol-7-yl)acetic acid (Preparation 131B, isomer 1, 30 mg, 0.066 mmol) in DMF (1 mL) was added 2-(methylsulfonyl)ethanamine, HCl (15.74 mg, 0.099 mmol), HATU (32.5 mg, 0.085 mmol) and 4-methylmorpholine (39.9 mg, 0.394 mmol). The reaction mixture was stirred for 1 h. Methanol was added and it was purified by prep HPLC (Phenomenex 21×250 mm Solvent A: 90% water with 10% MeOH and 0.1% TFA, Solvent B: 90% MeOH with 10% water and 0.1% TFA, Gradient: 0% B to 100% B over 30 min, 20 mL/min, 220 nM) to yield 2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)acetamide (23 mg, 0.041 mmol, 62.3% yield) as a white solid: product HPLC ret. time=9.2 min (condition G); LC/MS M$^{+1}$=562.10; $^1$H NMR (400 MHz, CD$_3$OD) δ ppm 7.93 (1H, d, J=7.92 Hz), 7.77 (2H, d, J=7.48 Hz), 7.59-7.72 (3H, m), 7.49-7.57 (2H, m), 5.09 (1H, s), 3.73 (2H, q, J=6.38 Hz), 3.34 (2H, q, J=6.38 Hz), 3.08 (4H, s), 2.97 (3H, s).

Example 131

Isomer 2

To 2-hydroxy-2-(3-(5-phenyl-4-(trifluoromethyl)isoxazol-3-yl)-4,5-dihydronaphtho[1,2-c]isoxazol-7-yl)acetic acid (Preparation 131B, isomer 2, 30 mg, 0.066 mmol) in DMF (1 mL) was added 2-(methylsulfonyl)ethanamine, HCl (15.7 mg, 0.1 mmol), HATU (32.5 mg, 0.085 mmol), and 4-methylmorpholine (39.9 mg, 0.39 mmol). The reaction mixture was stirred for 1 h. Methanol was added and it was purified by prep HPLC (Phenomenex 21×250 mm, Solvent A: 90% water with 10% MeOH and 0.1% TFA, Solvent B: 90% MeOH with 10% water and 0.1% TFA, Gradient: 0% B to 100% B over 30 min, 20 mL/min, 220 nM) to yield 2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)acetamide (23 mg, 0.041 mmol, 62.3% yield) as a white solid: product HPLC ret. time=9.23 min (condition G); LC/MS M$^{+1}$=562.1; $^1$H NMR (400 MHz, CD$_3$OD) δ ppm 7.94 (1H, d, J=7.92 Hz), 7.78 (2H, d, J=7.48 Hz), 7.59-7.71 (3H, m), 7.49-7.56 (2H, m), 5.09 (1H, s), 3.73 (2H, q, J=6.24 Hz), 3.34 (2H, q, J=6.24 Hz), 3.08 (4H, s), 2.97 (3H, s).

Example 132

N-(1-cyanocyclopropyl)-2-hydroxy-2-(3-(5-phenyl-4-(trifluoromethyl)isoxazol-3-yl)-4,5-dihydronaphtho[1,2-c]isoxazol-7-yl)acetamide

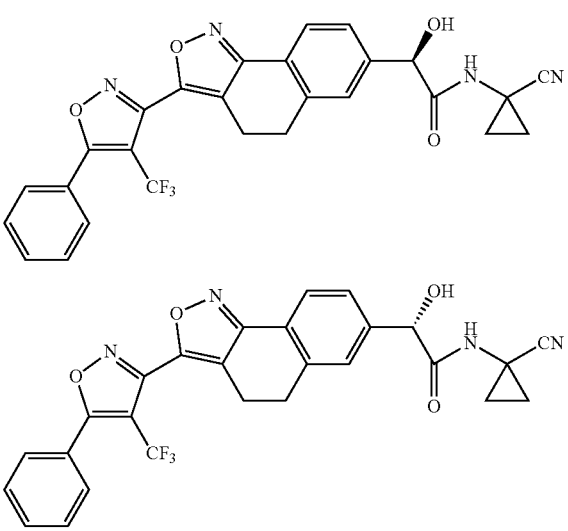

(132)

Example 132

Isomer 2

To 2-hydroxy-2-(3-(5-phenyl-4-(trifluoromethyl)isoxazol-3-yl)-4,5-dihydronaphtho[1,2-c]isoxazol-7-yl)acetic acid (Preparation 131B, Isomer 2, 25 mg, 0.055 mmol) in DMF (1 mL) was added 1-aminocyclopropanecarbonitrile, HCl (9.74 mg, 0.082 mmol), HATU (24.99 mg, 0.066 mmol), and N-methylmorpholine (0.036 mL, 0.329 mmol). The reaction mixture was stirred for 1 h at room temperature. Methanol was added and it was purified by prep HPLC (Phenomenex 21.2×250 mm, Solvent A: 90% water with 10% MeOH and 0.1% TFA, Solvent B: 90% MeOH with 10% water and 0.1% TFA, Gradient: 0% B to 100% B over 30 min, 20 mL/min, 220 nM) to yield N-(1-cyanocyclopropyl)-2-hydroxy-2-(3-(5-phenyl-4-(trifluoromethyl)isoxazol-3-yl)-4,5-dihydronaphtho[1,2-c]isoxazol-7-yl)acetamide (11 mg, 0.021 mmol, 38.2% yield) as a white solid: product HPLC ret. time=9.96 min (condition G); LC/MS $M^{+1}$=521.06; $^1$H NMR (400 MHz, DMSO-$d_6$) δ ppm 9.06 (1H, s), 7.89 (1H, d, J=7.92 Hz), 7.80 (2H, d, J=7.26 Hz), 7.63-7.76 (3H, m), 7.41-7.51 (2H, m), 6.43 (1H, d, J=4.18 Hz), 5.02 (1H, d, J=3.74 Hz), 3.05 (4H, s), 1.46 (2H, q, J=2.79 Hz), 1.07-1.24 (2H, m).

Example 132

Isomer 1

To 2-hydroxy-2-(3-(5-phenyl-4-(trifluoromethyl)isoxazol-3-yl)-4,5-dihydronaphtho[1,2-c]isoxazol-7-yl)acetic acid (Preparation 131B, isomer 1, 40 mg, 0.088 mmol) in DMF (1 mL) was added 1-aminocyclopropanecarbonitrile, HCl (15.59 mg, 0.131 mmol), HATU (40.0 mg, 0.105 mmol), and N-methylmorpholine (0.058 mL, 0.526 mmol). The reaction mixture was stirred for 1 h. Methanol was added and it was purified by prep HPLC (Phenomenex 21.2×250 mm, Solvent A: 90% water with 10% MeOH and 0.1% TFA, Solvent B: 90% MeOH with 10% water and 0.1% TFA, Gradient: 0% B to 100% B over 30 min, 20 mL/min, 220 nM) to yield N-(1-cyanocyclopropyl)-2-hydroxy-2-(3-(5-phenyl-4-(trifluoromethyl)isoxazol-3-yl)-4,5-dihydronaphtho[1,2-c]isoxazol-7-yl)acetamide (16 mg, 0.029 mmol, 33.4% yield): product HPLC ret. time=9.95 min (condition G); LC/MS $M^{+1}$=521.06; $^1$H NMR (400 MHz, DMSO-$d_6$) δ ppm 9.06 (1H, s), 7.89 (1H, d, J=7.92 Hz), 7.80 (2H, d, J=7.26 Hz), 7.63-7.76 (3H, m), 7.42-7.50 (2H, m), 6.43 (1H, d, J=4.40 Hz), 5.02 (1H, d, J=4.40 Hz), 3.05 (4H, s), 1.46 (2H, q, J=2.79 Hz), 1.07-1.24 (2H, m).

Example 133

2-Hydroxy-N-(2-hydroxyethyl)-2-(3-(5-phenyl-4-(trifluoromethyl)isoxazol-3-yl)-4,5-dihydronaphtho[1,2-c]isoxazol-7-yl)acetamide (133)

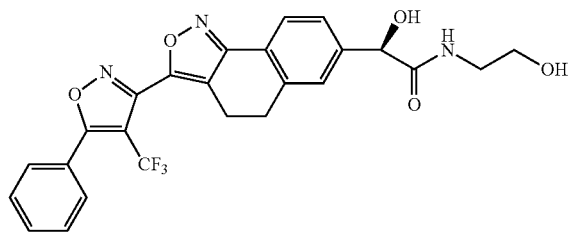

-continued

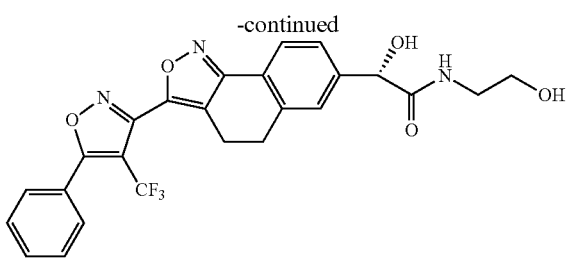

Example 133

Isomer 2

To 2-hydroxy-2-(3-(5-phenyl-4-(trifluoromethyl)isoxazol-3-yl)-4,5-dihydronaphtho[1,2-c]isoxazol-7-yl)acetic acid (Preparation 131B, isomer 2, 25 mg, 0.055 mmol) in DMF (1 mL) was added 2-aminoethanol (5.02 mg, 0.082 mmol), BOP (31.5 mg, 0.071 mmol), and 4-methylmorpholine (33.2 mg, 0.329 mmol). The reaction mixture was stirred for 30 min. Methanol was added and it was purified by prep HPLC (Phenomenex 21.2×250 mm, Solvent A: 90% water with 10% MeOH and 0.1% TFA, Solvent B: 90% MeOH with 10% water and 0.1% TFA, Gradient: 0% B to 100% B over 30 min, 20 mL/min, 220 nM) to yield 2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)acetamide (18 mg, 0.036 mmol, 65.3% yield) as a white solid: product HPLC ret. time=8.66 min (condition G); LC/MS $M^{+1}$=500.04; $^1$H NMR (400 MHz, DMSO-$d_6$) δ ppm 7.96 (1H, t, J=5.72 Hz), 7.87 (1H, d, J=7.92 Hz), 7.80 (2H, d, J=7.26 Hz), 7.63-7.76 (3H, m), 7.44-7.53 (2H, m), 6.34 (1H, d, J=4.84 Hz), 4.98 (1H, d, J=4.62 Hz), 4.71 (1H, t, J=5.50 Hz), 3.43 (2H, q, J=5.94 Hz), 3.11-3.24 (2H, m), 3.04 (4H, s).

Example 133

Isomer 1

To 2-hydroxy-2-(3-(5-phenyl-4-(trifluoromethyl)isoxazol-3-yl)-4,5-dihydronaphtho[1,2-c]isoxazol-7-yl)acetic acid (Preparation 131B, isomer 1, 40 mg, 0.088 mmol) in DMF (1 mL) was added 2-aminoethanol (8.03 mg, 0.131 mmol), BOP (46.5 mg, 0.105 mmol), and 4-methylmorpholine (53.2 mg, 0.526 mmol). The reaction mixture was stirred for 1 h. Methanol was added and it was purified by prep HPLC (Phenomenex 21.2×250 mm, Solvent A: 90% water with 10% acetonitrile and 0.1% TFA, Solvent B: 90% acetonitrile with 10% water and 0.1% TFA, Gradient: 0% B to 100% B over 30 min, 20 mL/min, 220 nM) to yield 2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)acetamide (23 mg, 0.045 mmol, 51.5% yield) as a white solid: product HPLC ret. time=8.83 min (condition G); LC/MS $M^{+1}$=500.04; $^1$H NMR (400 MHz, DMSO-$d_6$) δ ppm 7.96 (1H, t, J=5.83 Hz), 7.87 (1H, d, J=7.92 Hz), 7.80 (2H, d, J=7.26 Hz), 7.63-7.75 (3H, m), 7.45-7.52 (2H, m), 6.34 (1H, d, J=4.84 Hz), 4.99 (1H, d, J=4.62 Hz), 4.71 (1H, t, J=5.28 Hz), 3.43 (2H, q, J=5.94 Hz), 3.12-3.24 (2H, m), 3.04 (4H, s).

Example 134

2-Hydroxy-N-(2-hydroxyethyl)-2-(3-(5-phenyl-4-(trifluoromethyl)isoxazol-3-yl)-4,5-dihydronaphtho[1,2-c]isoxazol-7-yl)propanamide

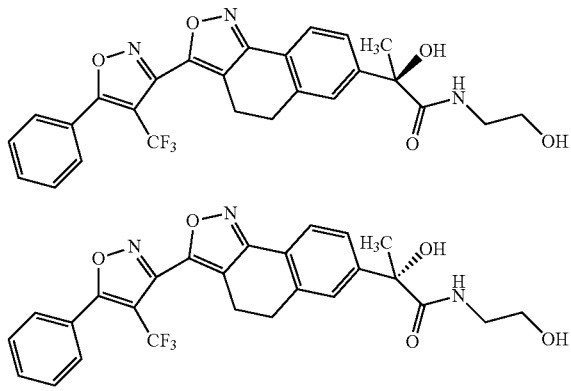

(134)

(134A)

Preparation 134A: Methyl 2-hydroxy-2-(3-(5-phenyl-4-(trifluoromethyl)isoxazol-3-yl)-4,5-dihydronaphtho[1,2-c]isoxazol-7-yl)acetate To a stirred solution of 2-hydroxy-2-(3-(5-phenyl-4-(trifluoromethyl)isoxazol-3-yl)-4,5-dihydronaphtho[1,2-c]isoxazol-7-yl)acetic acid (Preparation 131B isomer 1, 230 mg, 0.50 mmol) in dichloromethane (5 mL) and MeOH (5 mL) was added (trimethylsilyl)diazomethane (0.42 mL, 0.84 mmol) dropwise at 0° C. The excess reagent was quenched by the slow addition of glacial AcOH (0.02 mL, 0.34 mmol) at 0° C. and the solution was concentrated. The resulting residue was mixed with ethyl acetate (30 mL). The ethyl acetate solution was washed with sat. aq. sodium bicarbonate (10 mL) and brine (10 mL), dried (sodium sulfate), filtered through a pad of silica gel, and concentrated. The resulting residue was purified by silica gel flash chromatography (ethyl acetate:hexane 45%) to yield methyl 2-hydroxy-2-(3-(5-phenyl-4-(trifluoromethyl)isoxazol-3-yl)-4,5-dihydronaphtho[1,2-c]isoxazol-7-yl)acetate (230 mg, 0.489 mmol, 97% yield) as an oil: LC/MS $M^{+1}$=471.09; $^1$H NMR (400 MHz, CDCl$_3$) δ ppm 8.04 (1H, d, J=8.58 Hz), 7.76 (2H, d, J=7.26 Hz), 7.50-7.67 (3H, m), 7.41-7.49 (2H, m), 5.23 (1H, d, J=5.28 Hz), 3.82 (3H, s), 3.03-3.15 (4H, m).

Preparation 134B: Methyl 2-oxo-2-(3-(5-phenyl-4-(trifluoromethyl)isoxazol-3-yl)-4,5-dihydronaphtho[1,2-c]isoxazol-7-yl)acetate

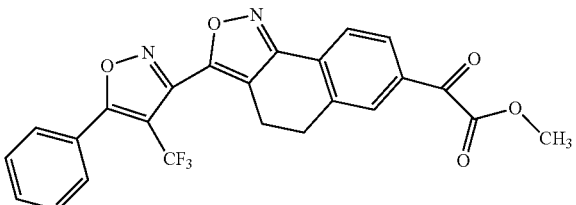

(134B)

To methyl 2-hydroxy-2-(3-(5-phenyl-4-(trifluoromethyl)isoxazol-3-yl)-4,5-dihydronaphtho[1,2-c]isoxazol-7-yl)acetate (Preparation 134A, 260 mg, 0.55 mmol) in dichloromethane (5 mL) was added 1,3,5-trichloro-1,3,5-triazinane-2,4,6-trione (193 mg, 0.83 mmol). The reaction mixture was stirred for 5 min. at room temperature. The reaction mixture was cooled to 0° C. and TEMPO (12.95 mg, 0.083 mmol) was added. The reaction mixture was warmed up to room temperature and was stirred for 1 h. The layers were separated and the organic phase was washed with sat. aq. sodium bicarbonate (5 mL) followed by 1N hydrochloric acid (5 mL) and brine (5 mL). The organic layer was dried and concentrated to provide methyl 2-oxo-2-(3-(5-phenyl-4-(trifluoromethyl)isoxazol-3-yl)-4,5-dihydronaphtho[1,2-c]isoxazol-7-yl)acetate (250 mg, 0.53 mmol, 97% yield): LC/MS $M^{+1}$=470.02; $^1$H NMR (400 MHz, CDCl$_3$) δ ppm 8.16-8.22 (1H, m), 8.01-8.08 (2H, m), 7.77 (2H, d, J=7.48 Hz), 7.53-7.68 (3H, m), 4.03 (3H, s), 3.15 (4H, s).

Preparation 134C: methyl 2-hydroxy-2-(3-(5-phenyl-4-(trifluoromethyl)isoxazol-3-yl)-4,5-dihydronaphtho[1,2-c]isoxazol-7-yl)propanoate

(134C)

To methyl 2-oxo-2-(4-(5-(3-phenyl-4-(trifluoromethyl)isoxazol-5-yl)-1,2,4-oxadiazol-3-yl)phenyl)acetate (Preparation 134B, 1.89 g, 4.26 mmol) in dichloroethane (40 mL) at -10° C. was added trimethylaluminum (5.3 mL, 10.7 mmol). The reaction mixture was stirred at -10° C. for 10 min before it was quenched with 1N hydrochloric acid. The resulting solution was washed with 1N hydrochloric acid (10 mL×2), sat. aq. sodium bicarbonate (10 mL) and brine (10 mL). The organic layer was dried and concentrated to provide racemic methyl 2-hydroxy-2-(3-(5-phenyl-4-(trifluoromethyl)isoxazol-3-yl)-4,5-dihydronaphtho[1,2-c]isoxazol-7-yl)propanoate (280 mg, 97%): LC/MS $M^{+1}$=485.16. The individual enantiomers were separated using a chiral preparative column under SFC conditions (Chiralpak AD-H 25×3 cm—5 µm, column temperature 35° C., isocratic elution with mobile phase $CO_2$/MeOH=90/10, 180 mL/min, 262 nM) Isomer 1 (90 mgs), retention time on chiral HPLC, 4.28 min; Isomer 2 (90 mgs), retention time on chiral HPLC, 5.18 min. The absolute stereochemistry at the carbon anchoring the secondary alcohol, of Isomer 1 and Isomer 2 was not determined.

Preparation 134D: 2-hydroxy-2-(3-(5-phenyl-4-(trifluoromethyl)isoxazol-3-yl)-4,5-dihydronaphtho[1,2-c]isoxazol-7-yl)propanoic acid

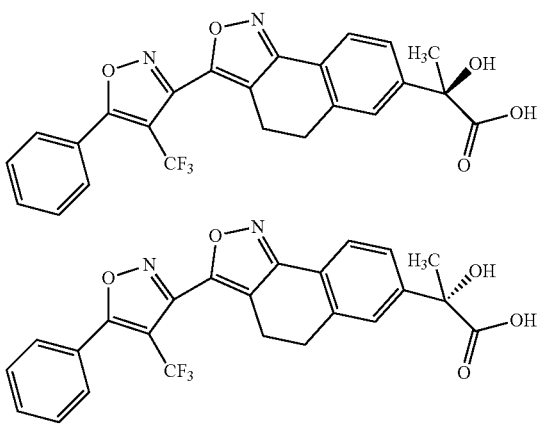

(134D)

Methyl 2-hydroxy-2-(3-(5-phenyl-4-(trifluoromethyl)isoxazol-3-yl)-4,5-dihydronaphtho[1,2-c]isoxazol-7-yl)propanoate (Preparation 134C, isomer 1, 85 mg, 0.175 mmol) was dissolved in 4 N hydrochloric acid in dioxane (1 mL). The reaction mixture stirred at 60° C. for 48 h before it was concentrated to yield 2-hydroxy-2-(3-(5-phenyl-4-(trifluoromethyl)isoxazol-3-yl)-4,5-dihydronaphtho[1,2-c]isoxazol-7-yl)propanoic acid (80 mg, 0.17 mmol, 97% yield): LC/MS $M^{+1}$=472.03. Isomer 2: Methyl 2-hydroxy-2-(3-(5-phenyl-4-(trifluoromethyl)isoxazol-3-yl)-4,5-dihydronaphtho[1,2-c]isoxazol-7-yl)propanoate (Preparation 134C, isomer 2, 83 mg, 0.171 mmol) was dissolved in 4 N hydrochloric acid in dioxane (1 mL). The reaction mixture was stirred at 60° C. for 48 h before it was concentrated to yield 2-hydroxy-2-(3-(5-phenyl-4-(trifluoromethyl)isoxazol-3-yl)-4,5-dihydronaphtho[1,2-c]isoxazol-7-yl)propanoic acid (80 mg, 0.17 mmol, 99% yield): LC/MS $M^{+1}$=472.03.

Example 134

Isomer 2

To 2-hydroxy-2-(3-(5-phenyl-4-(trifluoromethyl)isoxazol-3-yl)-4,5-dihydronaphtho[1,2-c]isoxazol-7-yl)propanoic acid (Preparation 134D, isomer 2, 15 mg, 0.032 mmol) in DMF (1 mL) was added 2-aminoethanol (2.9 mg, 0.048 mmol), 4-methylmorpholine (12.9 mg, 0.13 mmol) and BOP (18.3 mg, 0.041 mmol). The reaction mixture was stirred for 1 h. Methanol was added and it was purified by prep HPLC (Phenomenex Luna 5 u 21.2×100 mm, Solvent A: 90% water with 10% acetonitrile and 0.1% TFA, Solvent B: 90% acetonitrile with 10% water and 0.1% TFA, Gradient: 0% B to 100% B over 10 min, 20 mL/min, 220 nM) to yield 2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)propanamide (5 mg, 9.52 µmol, 29.9% yield) as a white solid: product HPLC ret. time=9.15 min. (condition G); LC/MS $M^{+1}$=514.06; $^1$H NMR (400 MHz, $CD_3OD$) δ ppm 8.09-8.20 (1H, m), 7.91 (1H, d, J=7.92 Hz), 7.77 (2H, d, J=7.48 Hz), 7.51-7.72 (5H, m), 3.60 (2H, td, J=5.72, 3.08 Hz), 3.36-3.40 (2H, m), 3.07 (4H, s), 1.78 (3H, s).

Example 134

Isomer 1

To 2-hydroxy-2-(3-(5-phenyl-4-(trifluoromethyl)isoxazol-3-yl)-4,5-dihydronaphtho[1,2-c]isoxazol-7-yl)propanoic acid (Preparation 134D, isomer 1, 15 mg, 0.032 mmol) in DMF (1 mL) was added 2-aminoethanol (2.9 mg, 0.048 mmol), BOP (18.3 mg, 0.041 mmol) and 4-methylmorpholine (12.9 mg, 0.13 mmol). The reaction mixture was stirred for 1 h. Methanol was added and it was purified by prep HPLC (Phenomenex Luna 5 u 21.2×100 mm, Solvent A: 90% water with 10% acetonitrile and 0.1% TFA, Solvent B: 90% acetonitrile with 10% water and 0.1% TFA, Gradient: 0% B to 100% B over 10 min, 20 mL/min, 220 nM) to yield 2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)propanamide (5 mg, 9.45 µmol, 29.6% yield): product HPLC ret. time=9.07 min (condition G); LC/MS $M^{+1}$=514.16; $^1$H NMR (400 MHz, $CD_3OD$) δ ppm 7.91 (1H, d, J=7.92 Hz), 7.77 (2H, d, J=7.26 Hz), 7.58-7.71 (5H, m), 3.60 (2H, td, J=5.72, 3.30 Hz), 3.33-3.41 (2H, m), 3.07 (4H, s), 1.78 (3H, s).

Example 135

2-Hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)propanamide

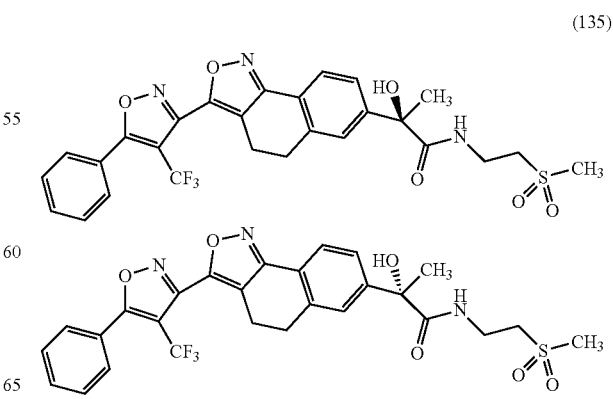

(135)

Example 135

Isomer 2

To 2-hydroxy-2-(3-(5-phenyl-4-(trifluoromethyl)isoxazol-3-yl)-4,5-dihydronaphtho[1,2-c]isoxazol-7-yl)propanoic acid (Preparation 134D, isomer 2, 15 mg, 0.032 mmol) in DMF (1 mL) was added 2-(methylsulfonyl)ethanamine, HCl (5.09 mg, 0.032 mmol), HATU (15.8 mg, 0.041 mmol) and 4-methylmorpholine (12.9 mg, 0.13 mmol). The reaction mixture was stirred for 1 h. Methanol was added and it was purified by prep HPLC (Phenomenex Luna 5 u 21.2× 100 mm, Solvent A: 90% water with 10% acetonitrile and 0.1% TFA, Solvent B: 90% acetonitrile with 10% water and 0.1% TFA, Gradient: 0% B to 100% B over 10 min, 20 mL/min, 220 nM) to yield 2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)propanamide (5 mg, 8.04 µmol, 25.2% yield) as a white solid: product HPLC ret. time=9.65 min (condition G); LC/MS $M^{+1}$=576.03; $^1$H NMR (400 MHz, CD$_3$OD) δ ppm 8.45 (1H, t, J=5.94 Hz), 7.91 (1H, d, J=8.14 Hz), 7.77 (2H, d, J=7.48 Hz), 7.58-7.71 (5H, m), 3.63-3.73 (2H, m), 3.24-3.30 (2H, m), 3.07 (4H, s), 2.94 (3H, s), 1.78 (3H, s).

Example 135

Isomer 1

To 2-hydroxy-2-(3-(5-phenyl-4-(trifluoromethyl)isoxazol-3-yl)-4,5-dihydronaphtho[1,2-c]isoxazol-7-yl)propanoic acid (Preparation 134D, isomer 1, 40 mg, 0.08 mmol) in DMF (1 mL) was added 2-(methylsulfonyl)ethanamine, HCl (20.4 mg, 0.13 mmol), HATU (42.0 mg, 0.11 mmol) and 4-methylmorpholine (34.4 mg, 0.34 mmol). The reaction mixture was stirred for 1 h. Methanol was added and it was purified by prep HPLC (Phenomenex Luna 5 u 21×250 mm, Solvent A: 90% water with 10% acetonitrile and 0.1% TFA, Solvent B: 90% acetonitrile with 10% water and 0.1% TFA, Gradient: 0% B to 100% B over 32 min, 20 mL/min, 220 nM) to yield 2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)propanamide (29 mg, 0.05 mmol, 55.4% yield) as a white solid: product HPLC ret. time=9.66 min (condition G); LC/MS $M^{+1}$=514.06; $^1$H NMR (400 MHz, CD$_3$OD) δ ppm 8.44 (1H, t, J=5.94 Hz), 7.90 (1H, d, J=8.14 Hz), 7.76 (2H, d, J=7.26 Hz), 7.58-7.70 (5H, m), 3.65-3.72 (2H, m), 3.35 (1H, s), 3.27-3.30 (2H, m), 3.06 (4H, s), 2.94 (3H, s), 1.78 (3H, s).

Example 136

1-((3-(4-propylphenyl)-4,5-dihydro-3H-benzo[e]indazol-7-yl)methyl)azetidine-3-carboxylic acid

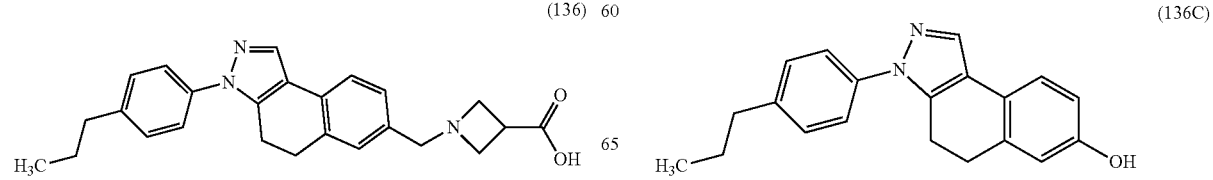

(136)

Preparation 136A: (E)-1-((dimethylamino)methylene)-6-methoxy-3,4-dihydronaphthalen-2(1H)-one

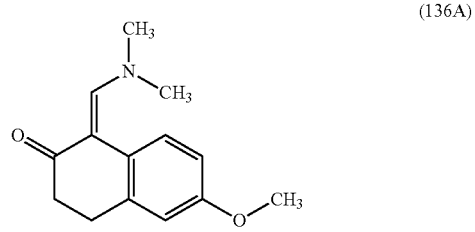 [SMILES: COc1ccc2c(c1)CCC(=O)/C2=C/N(C)C]

(136A)

6-methoxy-3,4-dihydronaphthalen-2(1H)-one (460 mg, 2.61 mmol) was dissolved in N,N-dimethylformamide dimethyl acetal (8 mL, 26.1 mmol) at room temperature. Within 5 minutes the solution had turned dark green in color. Next, p-toluenesulfonic acid (10 mg, 0.053 mmol) was added and the reaction mixture was stirred at room temperature for 2 hours. The reaction mixture was concentrated under reduced pressure and dried under vacuum to afford the title compound as a dark red oil. LC/MS M+1=232.2. The material was used for subsequent reactions without further purification.

Preparation 136B: 7-methoxy-3-(4-propylphenyl)-4,5-dihydro-3H-benzo[e]indazole

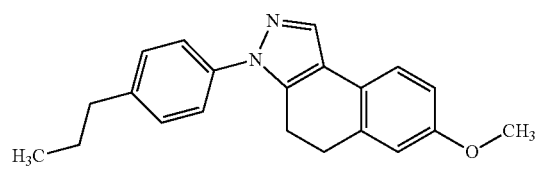

(136B)

(E)-1-((dimethylamino)methylene)-6-methoxy-3,4-dihydronaphthalen-2(1H)-one (Preparation 136A, 0.6 g, 2.59 mmol) was dissolved in ethanol (10 mL) and (4-propylphenyl)hydrazine, HCl (0.726 g, 3.89 mmol) was added. The reaction mixture was stirred at 70° C. for 4 hours, concentrated under reduced pressure and partitioned between dichloromethane (100 mL), and sat. aq. NaHCO$_3$. The dichloromethane layer was concentrated and purified on 80 g silica gel column (0-20% ethyl acetate in Hexane gradient) to yield 570 mg (58%) of the title compound. LC/MS $M^{+1}$=319.2.

Preparation 136C: 3-(4-propylphenyl)-4,5-dihydro-3H-benzo[e]indazol-7-ol

To 7-methoxy-3-(4-propylphenyl)-4,5-dihydro-3H-benzo[e]indazole (Preparation 136B, 570 mg, 1.790 mmol) in dichloromethane (8 mL), cooled to 0° C. was added borontribromide (7.16 mL, 7.16 mmol) dropwise. The reaction mixture was allowed to warm to room temperature slowly and was stirred at room temperature overnight. The reaction mixture was slowly quenched with 1 ml of MeOH. The dark colored solid that formed was filtered and dried under high vacuum to yield 370 mg of product. (yield: 62%). LC/MS $M^{+1}=305.1$.

Preparation 136D: (3-(4-propylphenyl)-4,5-dihydro-3H-benzo[e]indazol-7-yl trifluoromethanesulfonate

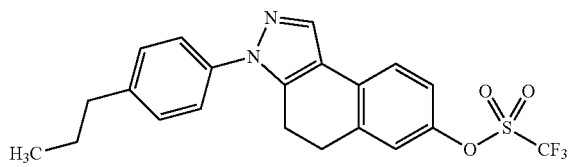

(136D)

To 3-(4-propylphenyl)-4,5-dihydro-3H-benzo[e]indazol-7-ol (Preparation 136C, 170 mg, 0.559 mmol) in pyridine (8 mL) was added trifluoromethanesulfonic anhydride (0.113 mL, 0.670 mmol) at 0° C. over a period of 5 min. The mixture was allowed to stir at 0° C. for 30 mins. The reaction mixture was concentrated under reduced pressure using a high vacuum pump. The brownish red residue that was obtained was partitioned between ether (60 mL) and water (40 mL). The ether layer was sequentially washed with sat. aq. NaHCO₃ (40 mL) and brine. The organic layer was then concentrated and purified by silica gel column chromatography using an ISCO system (40 g column; 10-40% Solvent B gradient. Solvent A: hexane; Solvent B: ethyl acetate). The desired fractions were collected and concentrated to give 240 mg of the title compound. (yield: 96%). LC/MS $M^{+1}=437.1$.

Preparation 136E: 3-(4-propylphenyl)-7-vinyl-4,5-dihydro-3H-benzo[e]indazole

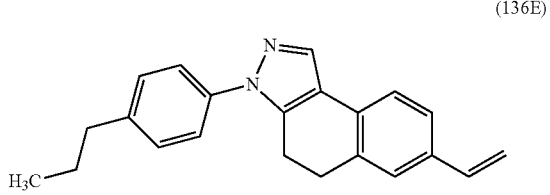 [SMILES: C=Cc1ccc2c(c1)CCc1c-2cnn1-c1ccc(CCC)cc1]

(136E)

To 3-(4-propylphenyl)-4,5-dihydro-3H-benzo[e]indazol-7-yl trifluoromethanesulfonate (Preparation 136D, 240 mg, 0.550 mmol) in dioxane was sequentially added tributyl(vinyl)stannane (0.178 mL, 0.605 mmol), lithium chloride (69.9 mg, 1.650 mmol) and tetrakis(triphenylphosphine)palladium (0) (38.1 mg, 0.033 mmol). Contents were purged with nitrogen gas for 5 min. and heated at 100° C. for 16 h.

The reaction mixture was cooled to room temperature and filtered over a coarse sintered glass funnel. The yellow residue was washed with EtOAc (3×20 ml). The filtrate was concentrated under reduced pressure and purified by silica gel column chromatography using an ISCO setup, (Column 40 g, 10-35% Solvent B gradient. Solvent A: hexane; Solvent B: ethyl acetate) to yield 170 mg of product and some inseparable impurities as yellow solid. LC/MS M+1=315.2.

Preparation 136F: 3-(4-propylphenyl)-4,5-dihydro-3H-benzo[e]indazole-7-carbaldehyde

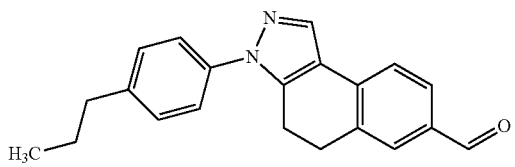

(136F)

To a clear solution of 3-(4-propylphenyl)-7-vinyl-4,5-dihydro-3H-benzo[e]indazole (Preparation 136E, 85 mg, 0.270 mmol) in THF (5 mL) were sequentially added NMO in water (0.090 mL, 0.433 mmol) and osmium tetroxide in water (0.066 mL, 10.81 μmol) at room temperature. The solution was vigorously stirred at room temperature overnight. Sodium periodate (116 mg, 0.541 mmol) in water (2 mL) was added. The mixture was stirred at room temperature under nitrogen for 2 hours. A white solid precipitated out. Water (2 mL) was then added and the solid was filtered, washed with water (2×2 mL) and dried to give 65 mg crude product which was used directly for the next step. LC/MS $M^{+1}=317.1$. The product had an HPLC retention time=3.92 min. (condition A);

Example 136

To the solution of 3-(4-propylphenyl)-4,5-dihydro-3H-benzo[e]indazole-7-carbaldehyde (Preparation 136F, 40 mg, 0.126 mmol) in methanol (3 mL) and 1,2-dichloroethane (3.00 mL), were added tert-butyl azetidine-3-carboxylate and AcOH (35.7 mg, 0.164 mmol). The reaction mixture was allowed to stir at room temperature for 40 min. and then sodium triacetoxyborohydride (161 mg, 0.759 mmol) was added in portions at room temperature and the reaction mixture was allowed to stir at room temperature overnight. The reaction mixture was concentrated, re-dissolved into 60 ml ethyl acetate, washed with sat. NaHCO₃, dried over Na₂SO₄ and concentrated. The residue was re-dissolved into dichloromethane (2 ml), then TFA (0.5 ml) was added and the contents allowed to stir at room temperature for 3 hours. The contents were concentrated under reduced pressure and purified using prep. HPLC (Luna 5 u C18 21.2*100 mm column; 15-100% 10mins gradient; Solvent A: 10% MeOH-90% H₂O-0.1% TFA; Solvent B: 90% MeOH-90% H₂O-0.1% TFA). The desired fractions were collected and concentrated under reduced pressure, dried under vacuum to yield 5 mg of product. LC/MS $M^{+1}=402.1$. The product had an HPLC retention time=8.23 min. (condition B). ¹H NMR (400 MHz, MeOD) δ ppm 8.03 (1H, s), 7.61 (1H, d, J=7.5 Hz), 7.28-7.48 (6H, m), 4.26-4.41 (6H, m), 3.73 (1H, s), 3.03 (4H, dd, J=16.2, 6.5 Hz), 2.68 (2H, t, J=7.6 Hz), 1.70 (2H, d, J=7.5 Hz), 0.98 (3H, t, J=7.4 Hz).

Example 137

(1-amino-3-(2-pentyl-4,5-dihydronaphtho[2,1-d]thiazol-7-yl)cyclopentyl)methanol

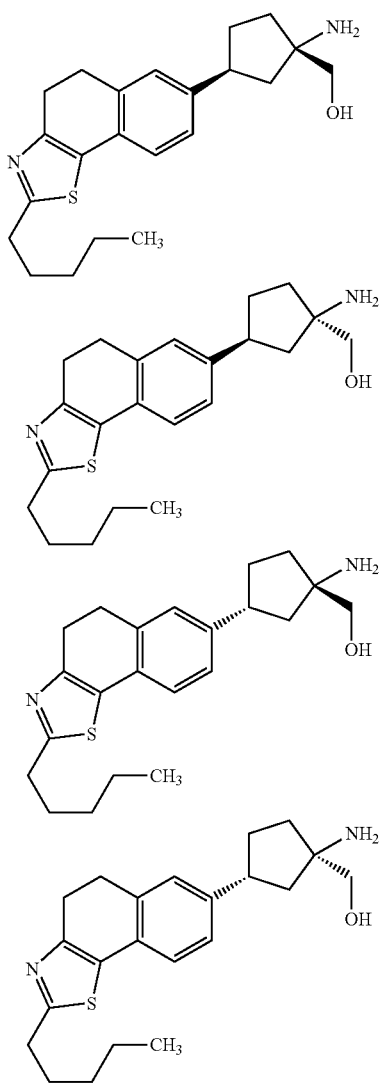

Preparation 137A:
7-iodo-2-pentyl-4,5-dihydronaphtho[2,1-d]thiazole

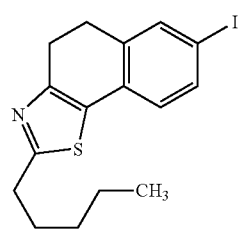

This compound was prepared according to the general procedure described for Preparations 82A-D starting from 6-iodo-3,4-dihydronaphthalen-1(2H)-one oxime (Preparation 121A) and substituting 3-phenyl-4-(trifluoromethyl)isoxazole-5-carboxylic acid in Step 82C with hexanoyl chloride. $^1$H NMR (400 MHz, CDCl$_3$-d) δ ppm 7.56 (1H, s), 7.49-7.56 (1H, m), 6.93 (1H, d, J=7.9 Hz), 2.95-3.05 (6H, m), 1.76-1.87 (2H, m), 1.63 (1H, s), 1.34-1.47 (4H, m), 1.27 (2H, t, J=7.0 Hz).

Examples 137

The titled compounds was prepared according to the general procedure described for Example 121 employing 7-iodo-2-pentyl-4,5-dihydronaphtho[2,1-d]thiazole (Preparation 137A) as a starting material. The compounds had LC/MS M$^{+1}$=371.

Example 138

(1-amino-3-(2-pentyl-4,5-dihydronaphtho[2,1-d]thiazol-7-yl)cyclopentyl)methyl dihydrogen phosphate

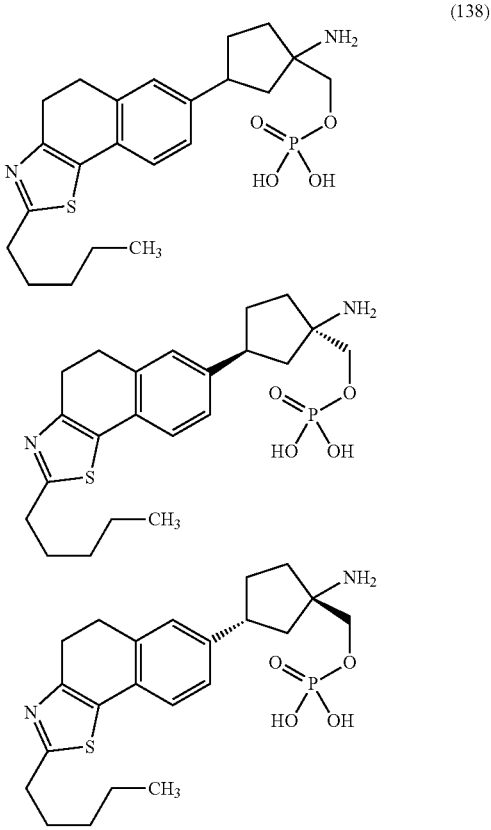

The titled compounds were prepared using the experimental protocol described for Example 95 employing (1-amino- 3-(2-pentyl-4,5-dihydronaphtho[2,1-d]thiazol-7-yl)cyclopentyl)methanol (Example 137) as a starting material. The compounds had LC/MS M+1=451.

Example 139

(R)-3-(2-amino-4,5-dihydronaphthol[1,2-d]thiazol-7-yloxy)propane-1,2-diol

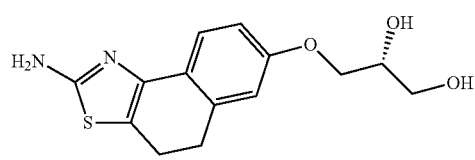

(139)

Preparation of 139A:
2-amino-4,5-dihydronaphtho[1,2-d]thiazol-7-ol

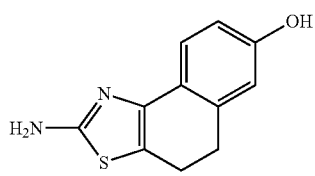

(139A)

To 7-methoxy-4,5-dihydronaphtho[1,2-d]thiazol-2-amine (15 mg, 0.065 mmol) into dichloromethane (2 mL), cooled to 0° C. was added borontribromide (0.258 mL, 0.258 mmol) slowly at 0° C. The reaction mixture was allowed to warm to room temperature and stirred at room temperature overnight. The reaction mixture was quenched by the slow addition of a few drops of MeOH and purified by prep. HPLC (Luna 5 u C18 21.2*100 mm column; 0%-100% 10mins gradient; Solvent A: 10% MeOH-90% H₂O-0.1% TFA; Solvent B: 90% MeOH-90% H₂O-0.1% TFA). The desired fractions were collected, concentrated and dried under vacuum to provide 13.5 mg of the title compound as a white solid. LC/MS M+1=219.1. The product had an HPLC retention time=1.51 min. (condition A). ¹H NMR (400 MHz, CD₃OD) δ ppm 7.35 (1H, d, J=8.36 Hz), 6.71-6.83 (2H, m), 3.04 (2H, d, J=8.14 Hz), 2.78-2.90 (2H, m).

Example 139

To 2-amino-4,5-dihydronaphtho[1,2-d]thiazol-7-ol (Preparation 139A, 7 mg, 0.032 mmol) was added ethanol (2 mL) followed by K₂CO₃ (17.73 mg, 0.128 mmol) and (R)-(2,2-dimethyl-1,3-dioxolan-4-yl)methyl 4-methylbenzenesulfonate (55.1 mg, 0.192 mmol) at room temperature. The reaction mixture was heated in a microwave oven at 120° C. for 45 mins. The reaction mixture was cooled to room temperature and the K₂CO₃ was removed by filtration. To the filtrate was added 2.0 mL of 2.5 M HCl in EtOH at room temperature (pH<1.0). The reaction mixture was allowed to stir at room temperature for overnight and purified using prep. HPLC. (Column LUNA 5 u C18 21.20*100 mm. Solvent A: 10% MeOH-90% H₂O-0.1% TFA; Solvent B: 90% MeOH-10% H₂O-0.1% TFA). The desired fractions were collected, concentrated and dried overnight to provide 3.1 mg (23%) of the title compound as white solid. LC/MS M+1=293.1. The product had an HPLC retention time=1.57 min. (condition A). ¹H NMR (400 MHz, MeOD) δ ppm 7.37-7.46 (1H, m), 6.93-6.97 (1H, m), 6.87-6.92 (1H, m), 4.06-4.15 (1H, m), 3.94-4.05 (2H, m), 3.62-3.73 (2H, m), 3.01-3.10 (2H, m), 2.78-2.86 (2H, m).

Example 140

N-(7-hydroxy-4,5-dihydronaphtho[1,2-d]thiazol-2-yl)benzamide

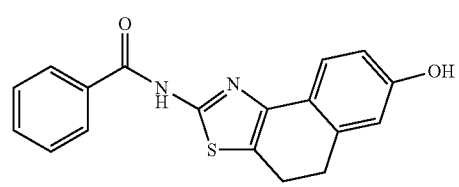

(140)

To 7-methoxy-4,5-dihydronaphtho[1,2-d]thiazol-2-amine (17 mg, 0.073 mmol) in dichloroethane (2 mL) and pyridine (17.37 mg, 0.220 mmol) was added benzoyl chloride (0.015 mL, 0.132 mmol) at room temperature. The reaction mixture was heated to 45° C. and stirred for 2 hours. The reaction mixture was cooled to room temperature, 3 ml of dichloromethane was added, and the contents were washed with sat. NaHCO₃. The organic layer was dried over Na₂SO₄ and concentrated and dried under vacuum overnight. The residue was dissolved into 2 ml dichloromethane, cooled to 0° C. using an ice bath. Borontribromide (0.293 mL, 0.293 mmol) was added slowly at 0° C. The reaction mixture was allowed to warm to room temperature slowly and stirred at room temperature for 4 hours. The reaction mixture was quenched with a few drops of MeOH and purified on prep. HPLC (Luna 5 u C18 21.2*100 mm column; 0%-100% 10mins gradient; Solvent A: 10% MeOH-90% H₂O-0.1% TFA; Solvent B: 90% MeOH-90% H₂O-0.1% TFA). The desired fractions were collected, concentrated and dried overnight to provide 3.5 mg of product. (two-step yield: 11%). LC/MS M+1=323.1. The product had an HPLC retention time=3.31 min. (condition A). ¹H NMR (400 MHz, CD₃OD) δ ppm 7.99-8.07 (2H, m), 7.63 (2H, d, J=7.48 Hz), 7.57 (2H, d, J=7.70 Hz), 6.70 (2H, s), 2.98 (4H, d, J=4.84 Hz).

The following three analogs were synthesized using the general protocol outlined for Example 140.

| Ex. No. | G₂ | MW | MS (M+1) | HPLC ret. time (Condition D) (min.) |
|---|---|---|---|---|
| 141 | ![phenylacetamide group] | 336.41 | 336.1 | 2.15 |

-continued

| Ex. No. | G₂ | MW | MS (M⁺¹) | HPLC ret. time (Condition D) (min.) |
|---|---|---|---|---|
| 142 | (O)C(NH)-CH₂CH₂-phenyl | 350.44 | 350.96 | 2.38 |
| 143 | (O)C(NH)-CH₂CH₂CH₂CH₂-CH₃ (hexanoyl, H₃C terminal) | 316.42 | 317.07 | 2.33 |

Examples 144-169

Synthesis Procedure

Diversity reagents (0.1 mmol, 2 eq) were weighed into 16 mm×100 mm vials. Carboxylic acid core (intermediate 45E) was dissolved in 0.2M DMF. EDC and HOBt were dissolved in 0.2 M DMF. To each vial containing pre-weighed reagent was added 0.25 mL core solution (50 μmol per reaction, 1 eq) and 0.25 mL EDC/HOBt solution (75 μmol each reagent per reaction, 1.5 eq). Reactions were sealed using a Teflon cap mat and agitated at room temperature for 16 hours. Upon completion of the reaction, vials were concentrated under a stream of nitrogen at 45° C. for 3 hours. Samples were then reconstituted in 1 mL dichloromethane and treated with 1 mL TFA. Reactions were sealed using a Teflon cap mat and agitated at room temperature for 16 hours. Upon completion of reaction, reactions were concentrated in a SpeedVac at 45° C. for 3 hours.

Purification Procedure: Samples in DMF were purified by prep LCMS on a Waters Xbridge 19×100 mm 5 um C18 column over a 15 minute gradient (0-100% B over gradient, A=5:95 methanol:water, B=95:5 methanol:water, modifier=10 mM NH₄OAc) using a 19×10 mm 5 um C18 guard column. Fractions collection was triggered using UV and mass. Samples were visualized at 220 nm and ionized using ESI positive mode. After purification, samples were dried on a Genevac HT-12 at a vacuum pressure of 8 mbar at 45° C. for approximately 15 hours.

Analytical Procedure: Samples in 1:1 MeOH:DCE were characterized by LCMS on a Mac-Mod Halo 4.6×50×2.7 uM column at 45° C. over a 4 minute gradient from 0-100% B (A=5:95 acetonitrile:water, B=90:10 acetonitrile:water, modifier=10 mM NH₄OAc), with a 1 minute hold at 100% B. Samples were detected by UV at 220 nm and ionized with ESI positive mode.

| Ex. No. | R | MW | HPLC ret. time (min.) | MS (M⁺¹) |
|---|---|---|---|---|
| 144 | 2-OCH₃-benzyl-HN- | 447.49 | 1.60 | 448.03 |
| 145 | 2-OCH₂CH₃-benzyl-HN- | 461.52 | 1.78 | 462.03 |
| 146 | 2-CH₃-benzyl-HN- | 431.49 | 1.64 | 432.05 |
| 147 | 4-Cl-benzyl-HN- | 451.91 | 1.72 | 452.03 |
| 148 | (diphenyl)(CH₃)C-CH₂-HN- | 521.61 | 2.16 | 522.04 |
| 149 | phenyl-CH(CH₃)-CH₂-NH- | 445.52 | 1.73 | 446.06 |
| 150 | phenyl-CH₂CH₂-NH- | 431.49 | 1.60 | 432.05 |
| 151 | 2-Cl-phenyl-CH₂CH₂-NH- | 465.94 | 1.76 | 465.99 |

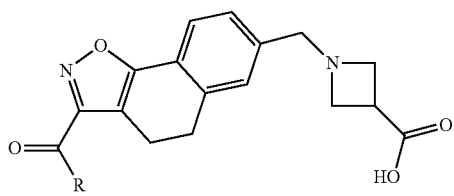

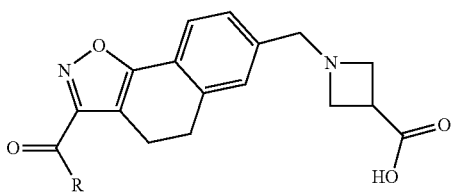

| Ex. No. | R | MW | HPLC ret. time (min.) | MS (M+1) |
|---|---|---|---|---|
| 152 | ![phenylpropyl-NH] | 445.52 | 1.74 | 446.06 |
| 153 | ![benzyl-N(CH3)] | 431.49 | 1.54 | 432.05 |
| 154 | ![3-Cl-benzyl-NH] | 451.91 | 1.71 | 451.97 |
| 155 | ![3-Cl-phenethyl-NH] | 465.94 | 1.78 | 465.97 |
| 156 | ![3-phenylpyrrolidinyl] | 457.53 | 1.72 | 458.08 |
| 157 | ![3-benzylpyrrolidinyl] | 471.55 | 1.81 | 472.05 |
| 158 | ![3-phenethylpyrrolidinyl] | 485.58 | 1.94 | 486.05 |
| 159 | ![4-MeO-phenyl-phenyl-CH-CH2-NH] | 537.61 | 1.99 | 538.04 |

| Ex. No. | R | MW | HPLC ret. time (min.) | MS (M+1) |
|---|---|---|---|---|
| 160 | ![1-naphthyl-piperidinyl] | 521.61 | 2.04 | 522.03 |
| 161 | ![3-phenyl-piperidinyl] | 471.55 | 1.80 | 472.06 |
| 162 | ![tetrahydronaphthyl-CH2-NH] | 471.55 | 1.94 | 472.03 |
| 163 | ![4-F-phenyl-pyrrolidinyl] | 475.52 | 1.76 | 476.03 |
| 164 | ![2-Cl-phenyl-pyrrolidinyl] | 491.97 | 1.88 | 491.99 |
| 165 | ![3-MeO-phenyl-pyrrolidinyl] | 487.55 | 1.72 | 488.05 |

333
-continued

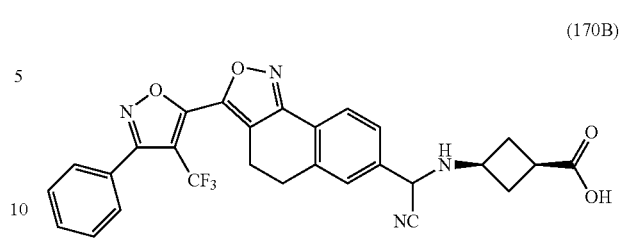

| Ex. No. | R | MW | HPLC ret. time (min.) | MS (M$^{+1}$) |
|---|---|---|---|---|
| 166 | (isopropoxy-phenyl-CH2-NH-) | 475.54 | 1.90 | 476.06 |
| 167 | (phenoxy-phenyl-CH2-NH-) | 509.56 | 2.01 | 510.03 |
| 168 | (3-methylphenyl-CH2-NH-) | 431.49 | 1.67 | 432.04 |
| 169 | (4-methylphenyl-CH2-NH-) | 431.49 | 1.68 | 432.06 |

Example 170A and 170B (1S,3S)-3-((3-(3-phenyl-4-(trifluoromethyl)isoxazol-5-yl)-4,5-dihydronaphtho[1,2-c]isoxazol-7-yl)methylamino)cyclobutanecarboxylic acid and (1S,3S)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid (170A)

334
-continued (170B)

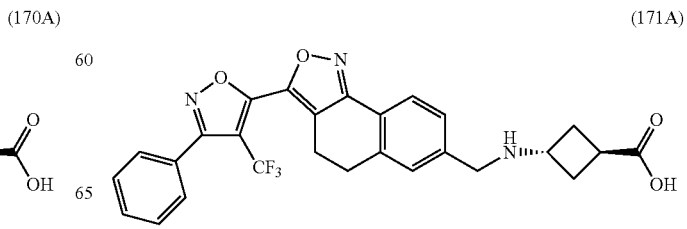

To (1S,3S)-3-aminocyclobutanecarboxylic acid, TFA (31.3 mg, 0.136 mmol), in MeOH (1.5 mL) was added Et$_3$N (0.036 mL, 0.256 mmol) and 3-(3-phenyl-4-(trifluoromethyl)isoxazol-5-yl)-4,5-dihydronaphtho[1,2-c]isoxazole-7-carbaldehyde (Intermediate 7B, 35 mg, 0.085 mmol) at room temperature. The reaction mixture was allowed to stir at 50° C. for 50 mins, then cooled down to room temperature before sodium cyanoborohydride (16.08 mg, 0.256 mmol) was added. The reaction mixture was stirred at room temperature overnight. LC-MS showed that the reaction was complete. Example 170A was the major peak and Example 170B was the minor peak. The reaction mixture was concentrated, redissolved in MeOH filtered and purified using reverse phase HPLC (Luna 5 u C18 21.2*100 mm column; 0%-100% 10 mins gradient; Solvent A: 10% MeOH-90% H$_2$O-0.1% TFA; Solvent B: 90% MeOH-90% H$_2$O-0.1% TFA). Fractions corresponding to Examples 170A and 170B were collected and concentrated.

Example 170A: LC/MS M$^{+1}$=510.2. The product had an HPLC retention time=3.39 min. (condition A). $^1$H NMR (400 MHz, CD$_3$OD) δ ppm 8.08 (1H, d, J=7.9 Hz), 7.80 (2H, d, J=7.3 Hz), 7.62-7.76 (3H, m), 7.50-7.61 (2H, m), 4.21 (2H, s), 3.84 (1H, s), 3.15 (4H, s), 3.00-3.12 (1H, m), 2.67 (2H, dd, J=10.1, 2.4 Hz), 2.46 (2H, d, J=2.6 Hz).

Example 170B: LC/MS M$^{+1}$=535.2. The product had an HPLC retention time=4.18 min. (condition A) HPLC purity 85%.

Examples 171A and 171B (1R,3R)-3-((3-(3-phenyl-4-(trifluoromethyl)isoxazol-5-yl)-4,5-dihydronaphtho[1,2-c]isoxazol-7-yl)methylamino)cyclobutanecarboxylic acid and (1R,3R)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid (171A)

-continued (171B)

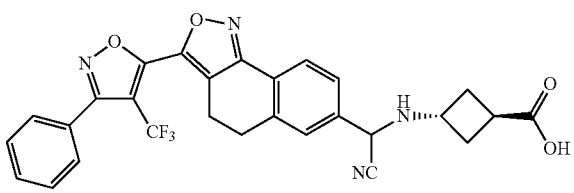

To (1R,3R)-3-aminocyclobutanecarboxylic acid, TFA (18.15 mg, 0.079 mmol) in MeOH (1.5 mL) was added Et$_3$N (0.025 mL, 0.183 mmol) and 3-(3-phenyl-4-(trifluoromethyl) isoxazol-5-yl)-4,5-dihydronaphtho[1,2-c]isoxazole-7-carbaldehyde (7B, 25 mg, 0.061 mmol) at room temperature. The reaction mixture was allowed to stir at 50° C. for 50 mins. The reaction mixture was cooled to room temperature before sodium cyanoborohydride (11.49 mg, 0.183 mmol) was added. The reaction mixture was stirred at room temperature overnight. LC-MS showed that the reaction was completed. Example 171A was the major peak and Example 171B was the minor peak. The reaction mixture was concentrated, redissolved in MeOH filtered and purified using reverse phase HPLC (Luna 5 u C18 21.2*100 mm column; 0%-100% 10mins gradient; Solvent A: 10% MeOH-90% H$_2$O-0.1% TFA; Solvent B: 90% MeOH-90% H$_2$O-0.1% TFA). Fractions corresponding to Example 171A and Example 171B were collected and concentrated.

Example 171A: LC/MS M$^{+1}$=510.2. The product had an HPLC retention time=3.37 min. (condition A). $^1$H NMR (400 MHz, CD$_3$OD) δ ppm 8.06-8.14 (1H, m), 7.77-7.85 (2H, m), 7.67 (3H, d, J=7.48 Hz), 7.58 (2H, s), 4.22 (2H, s), 4.01-4.13 (1H, m), 3.11-3.28 (5H, m), 2.64-2.77 (2H, m), 2.51-2.63 (2H, m).

Example 171B: LC/MS M$^{+1}$=535.3. The product had an HPLC retention time=4.17 min. (condition A). HPLC purity 87%.

Biological Assays

S1P$_1$ Binding Assay:

Membranes were prepared from CHO cells expressing human S1P$_1$. Cells pellets (1×10$^8$cells/pellet) were suspended in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM MgCl$_2$, 2 mM EDTA and stored in aliquots at −80° C. after protein concentration determination.

Membranes (2 μg/well) and 0.03 nM final concentration of $^{33}$P-S1P ligand (1 mCi/ml, American Radiolabeled Chemicals) diluted in assay buffer (50 mM HEPES, pH7.4, 5 mM MgCl$_2$, 1 mM CaCl$_2$, 0.5% fatty acid free BSA, 1 mM NaF) were added to the compound plates (384 Falcon v-bottom plate (0.5 μl/well in a 11 point, 3-fold dilution). Binding was performed for 45 minutes at room temperature, terminated by collecting the membranes onto 384-well Millipore FB filter plates, and radioactivity was measured by TopCount. The competition data of the test compounds over a range of concentrations was plotted as percentage inhibition of radioligand specific binding. The IC$_{50}$ is defined as the concentration of competing ligand needed to reduce specific binding by 50%.

Table A below lists S1P$_1$ Binding IC$_{50}$ values from the following examples of this invention measured in the S1P$_1$ binding assay described hereinabove. The results in Table A were rounded to two digits.

TABLE A

| Ex. | S1P$_1$ Binding IC$_{50}$ (nM) |
|---|---|
| 2 | 1.2 |
| 3 | 1.3 |
| 5 | 0.57 |
| 6 | 0.66 |
| 7 | 57 |
| 12 | 390 |
| 14 | 6.7 |
| 16 | 24 |
| 20 | 56 |
| 22 | 980 |
| 23 | 0.98 |
| 24 | 3200 |
| 25 | 94 |
| 32 | 15000 |
| 33 | 250 |
| 41 | 1600 |
| 61 | 1.6 |
| 67 | 5.6 |
| 70 | 22 |
| 74 | 600 |
| 93 | 22 |
| 94 | 16 |
| 132 | 4.1 |

Receptor [35S] GTPγS Binding Assays

Compounds were loaded in a 384 Falcon v-bottom plate (0.5 μl/well in a 11 point, 3-fold dilution). Membranes prepared from S1P$_1$/CHO cells or EDG3-Ga15-bla HEK293T cells were added to the compound plate (40 μl/well, final protein 3 μg/well) with multidrop. [$^{35}$S]GTP (1250 Ci/mmol, Perkin Elmer) was diluted in assay buffer: 20 mM HEPES, pH7.5, 10 mM MgCl$_2$, 150 mM NaCl, 1 mM EGTA, 1 mM DTT, 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to Millipore 384-well FB filter plates via the Velocity11 Vprep liquid handler. The filter plate was washed with water 4 times by using the manifold Embla plate washer and dried at 60° C. for 45 min. MicroScint 20 scintillation fluid (30 μl) was added to each well for counting on the Packard TopCount. EC$_{50}$ is defined as the agonist concentration that corresponds to 50% of the Ymax (maximal response) obtained for each individual compound tested. The results in Table B were rounded to two digits.

TABLE B

| Ex. | GTPγS S1P$_1$ EC$_{50}$ (nM) | GTPγS S1P$_3$ EC$_{50}$ (nM) |
|---|---|---|
| 2 | 1.2 | 8,200 |
| 3 | 1.3 | 1,300 |
| 5 | 0.74 | 1,500 |
| 6 | 0.59 | 4,400 |
| 7 | 57 | >31,000 |
| 12 | 6,300 | >31,000 |
| 14 | 11 | >31,000 |
| 16 | 24 | 11,000 |
| 20 | 220 | >31,000 |
| 22 | 980 | >63,000 |
| 23 | 0.73 | 3,500 |

TABLE B-continued

| Ex. | GTPγS S1P$_1$ EC$_{50}$ (nM) | GTPγS S1P$_3$ EC$_{50}$ (nM) |
|---|---|---|
| 24 | 3,200 | >31,000 |
| 25 | 330 | >31,000 |
| 32 | 15,000 | >63,000 |
| 33 | 250 | >31,000 |
| 41 | 1,600 | >63,000 |
| 61 | 0.32 | >31,000 |
| 67 | 0.76 | 14,700 |
| 70 | 49 | 4,660 |
| 74 | 410 | >63,000 |
| 93 | 40 | >63,000 |
| 94 | 12 | 16,200 |
| 132 | 1.7 | 8,500 |

A smaller value for GTPγS S1P$_1$ EC$_{50}$ value indicated greater activity for the compound in the GTPγS S1P$_1$ binding assay. A larger value for the GTPγS S1P$_3$ EC$_{50}$ value indicated less activity in the GTPγS S1P$_3$ binding assay. The compounds of the present invention, as exemplified by examples in Table B showed GTPγS S1P$_1$ EC$_{50}$ values of 5 µM or lower.

The compounds of the present invention possess activity as agonists of S1P$_1$ and are selective over S1P$_3$, and thus may be used in treating, preventing, or curing various S1P$_1$ receptor-related conditions while reducing or minimizing the side effects due to S1P$_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, or psoriasis, while reducing or minimizing possible cardiovascular side effects such as bradycardia and hypertension. Other potential uses of the compounds of the present invention include minimizing or reducing rejection of transplanted organs, while reducing or minimizing side effects due to S1P$_3$ activity.

Blood Lymphocyte Reduction Assay (BLR) in Rodents

Lewis rats were dosed orally with test article (as a solution or suspension in the vehicle) or vehicle alone (polyethylene glycol 300, "PEG300"). Blood was drawn at 4 hr and 24 h by retro-orbital bleeding. Blood lymphocyte counts were determined on an ADVIA 120 Hematology Analyzer (Siemens Healthcare Diagnostics). The results were measured as a reduction in the percentage of circulating lymphocytes as compared to the vehicle treated group at the 4 hr and 24 hr measurement. The results represent the average results of all animals within each treatment group (n=3-4).

The following examples were tested in the Blood Lymphocyte Reduction assay (BLR) described hereinabove and the results are shown in Table C for rats.

TABLE C

| Example | Dose (mg/kg) | % Reduction in Lymphocytes at 4 hr. |
|---|---|---|
| 2 | 1.0 | 65 |
| 3 | 1.0 | 85 |
| 5 | 1.0 | 83 |
| 6 | 1.0 | 86 |
| 23 | 3.0 | 76 |

What is claimed is:

1. A compound of Formula (I):

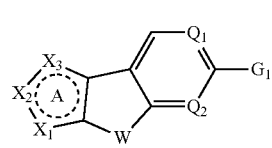

or a stereoisomer or a salt thereof, wherein:

(i) $X_1$ is C-G$_2$, one of $X_2$ and $X_3$ is N, and the other of $X_2$ and $X_3$ is O or S;

(ii) $X_2$ is C-G$_2$, one of $X_1$ and $X_3$ is N, and the other of $X_1$ and $X_3$ is O or S;

(iii) $X_1$ is C-G$_2$, one of $X_2$ and $X_3$ is N, and the other of $X_2$ and $X_3$ is NH or NCH$_3$; or (iv) $X_1$ is N-G$_2$, $X_2$ is N, and $X_3$ is CH;

wherein the broken circle represents two non-adjacent double bonds within Ring A;

Q$_1$ is CH, C(CH$_3$), or CF;

Q$_2$ is CH;

W is —CH$_2$—, —CH$_2$CH$_2$—, —CH$_2$C(CH$_3$)$_2$—, —CH$_2$CF$_2$—, —CH=CH—, —CH$_2$N(CH$_3$)—, —CH$_2$O—, or —CH$_2$CH$_2$O—;

G$_1$ is —OH, —CH$_2$OH, —CH(OH)CH$_2$OH, —(CH$_2$)$_{0-2}$COOH, —CH(OH)(CH$_2$)$_{0-2}$COOH, —CH$_2$NH(CH$_2$)$_{1-2}$OH, —CH$_2$NR$_g$(CH$_2$)$_{1-2}$COOH, —CH$_2$NR$_g$(CH$_2$)$_{1-2}$C(O)NH$_2$, —CH$_2$NR$_g$(CH$_2$)$_{1-2}$OP(O)(OH)$_2$, —OCH$_2$CH(OH)CH$_2$OH, —(CH$_2$)$_{0-2}$C(NH$_2$)(CH$_3$)CH$_2$OH, —(CH$_2$)$_{0-2}$CR$_g$(NH$_2$)C(O)OH, —(CH$_2$)$_{0-2}$C(NH$_2$)(CH$_3$)(CH$_2$)$_{1-2}$OP(O)(OH)$_2$, —CH$_2$CH$_2$C(NH$_2$)(CH$_2$OH)$_2$, —CH$_2$NHCH(CH$_2$OH)$_2$, —CH$_2$N(CH$_2$CH$_2$OH)$_2$, —CH$_2$NHCH$_2$CH(OH)CH$_2$OH, —CH(OH)C(O)NHCH$_2$CN, —CH(OH)C(O)NHCH$_2$S(O)$_2$CH$_3$, —CR$_g$(OH)C(O)NHCH$_2$CH$_2$OH, —CH$_2$(hydroxy pyrrolidinyl), —CH$_2$(hydroxymethyl pyrrolidinyl),

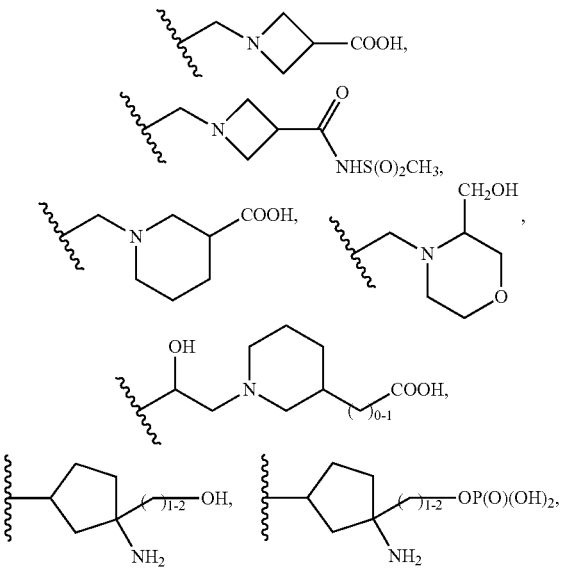

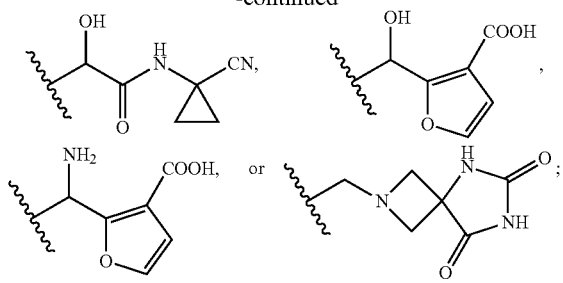

$G_2$ is:
(i) pentyl;
(ii) phenyl substituted with one or two substituents independently selected from propyl, butyl, —CN, —CF$_3$, cyclohexyl, —OCH$_2$CH$_3$, and/or —OCH(CH$_3$)$_2$;
(iii) pyrazolyl, isoxazolyl, isothiazolyl, or pyrimidinyl substituted with one or two substituents independently selected from —CF$_3$, —CN, butyl, methyl cyclopropyl, cyclohexyl, phenyl, chlorophenyl, pyridinyl, and/or fluoropyridinyl;
(iv) cyclohexyl substituted with chlorophenyl;
(v) —NHC(O)—(CH$_2$)$_{0-2}$-(phenyl) or —NHC(O)(pentyl);
(vi) —C(O)NHCH$_2$C(CH$_3$)$_3$, —C(O)NR$_g$—(CHR$_g$)$_{0-3}$-A$_1$, —C(O)NR$_g$—CH$_2$C(R$_g$)(A$_1$)(A$_1$), or —C(O)NHCH$_2$(tetrahydronaphthalenyl), wherein A$_1$ is phenyl substituted with zero to 2 substituents independently selected from Cl, —CH$_3$, —OCH$_3$, —OCH$_2$CH$_3$, —OCH(CH$_3$)$_2$, and/or phenoxy;
(vii)

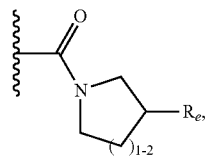

wherein R$_e$ is naphthalenyl or —(CH$_2$)$_{0-2}$(phenyl) and said phenyl is substituted with zero to 1 substituents selected from F, Cl, or OCH$_3$; or
(viii) —(CR$_5$R$_5$)$_a$CR$_e$R$_e$B$_4$, —CH═CH—CR$_e$R$_e$B$_4$, or —(CR$_5$R$_5$)$_a$O(CR$_5$R$_5$)$_a$CR$_e$R$_e$B$_4$, wherein B$_4$ is phenyl substituted with zero to 2 substituents independently selected from F, Cl, —OH, and/or butyl; and each R$_e$ is independently H and/or —CH$_3$, or two geminal R$_e$ along with the carbon atom to which they are attached form a C$_{4-6}$spirocycloalkyl ring;
each a is independently zero, 1, 2, 3, 4, and/or 5;
each R$_5$ is H; and
each R$_g$ is independently H and/or —CH$_3$.

2. The compound according to claim 1 or a stereoisomer or a salt thereof, wherein: X$_1$ is C-G$_2$, one of X$_2$ and X$_3$ is N, and the other of X$_2$ and X$_3$ is O or S.

3. The compound according to claim 1 or a stereoisomer or a salt thereof, wherein: X$_2$ is C-G$_2$, one of X$_1$ and X$_3$ is N, and the other of X$_1$ and X$_3$ is O or S.

4. The compound according to claim 1 or a stereoisomer or a salt thereof, wherein: X$_1$ is C-G$_2$, one of X$_2$ and X$_3$ is N, and the other of X$_2$ and X$_3$ is NH or NCH$_3$.

5. The compound according to claim 1 or a stereoisomer or a salt thereof, wherein: X$_1$ is N-G$_2$, X$_2$ is N and X$_3$ is CH.

6. A pharmaceutical composition comprising a compound according to claim 1 or stereoisomers or pharmaceutically acceptable salts thereof, and a pharmaceutically acceptable carrier.

7. The compound according to claim 1 or a stereoisomer or a salt thereof, wherein:
X$_1$ is C-G$_2$, one of X$_2$ and X$_3$ is N, and the other of X$_2$ and X$_3$ is O;
W is —CH$_2$CH$_2$—, —CH$_2$C(CH$_3$)$_2$—, or —CH$_2$CF$_2$—;
Q$_1$ is CH or C(CH$_3$); and
Q$_2$ is CH.

8. The compound according to claim 1 or a stereoisomer or a salt thereof, wherein:
X$_2$ is C-G$_2$, one of X$_1$ and X$_3$ is N, and the other of X$_1$ and X$_3$ is S;
W is —CH$_2$CH$_2$—, —CH$_2$C(CH$_3$)$_2$—, or —CH$_2$CF$_2$—;
Q$_1$ is CH or C(CH$_3$); and
Q$_2$ is CH.

9. The compound according to claim 1 or a stereoisomer or a salt thereof, wherein G$_1$ is: —OH, —CH$_2$OH, —CH(OH)CH$_2$OH, —(CH$_2$)$_{0-2}$COOH, —CH(OH)(CH$_2$)$_{0-2}$COOH, —CH$_2$NH(CH$_2$)$_{1-2}$OH, —CH$_2$NR$_g$(CH$_2$)$_{1-2}$COOH, —CH$_2$NR$_g$(CH$_2$)$_{1-2}$C(O)NH$_2$, —CH$_2$NR$_g$(CH$_2$)$_{1-2}$OP(O)(OH)$_2$, —OCH$_2$CH(OH)CH$_2$OH, —(CH$_2$)$_{0-2}$CNH$_2$)(CH$_3$)CH$_2$OH, —(CH$_2$)$_{0-2}$CR$_g$(NH$_2$)C(O)OH, —(CH$_2$)$_{0-2}$C(NH$_2$)(CH$_3$)(CH$_2$)$_{1-2}$OP(O)(OH)$_2$, —CH$_2$CH$_2$C(NH$_2$)(CH$_2$OH)$_2$, —CH$_2$NHCH(CH$_2$OH)$_2$, —CH$_2$N(CH$_2$CH$_2$OH)$_2$, —CH$_2$NHCH$_2$CH(OH)CH$_2$OH, —CH(OH)C(O)NHCH$_2$CN, —CH(OH)C(O)NHCH$_2$CH$_2$S(O)$_2$CH$_3$, —CR$_g$(OH)C(O)NHCH$_2$CH$_2$OH, —CH$_2$(hydroxy pyrrolidinyl), or —CH$_2$(hydroxymethyl pyrrolidinyl).

10. The compound according to claim 1 or a stereoisomer or a salt thereof, wherein G$_1$ is:

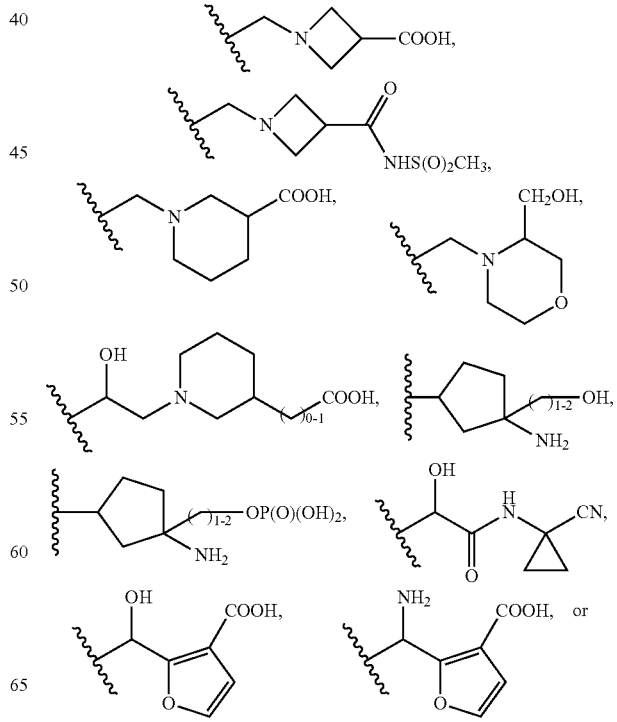

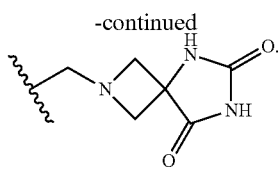

11. The compound according to claim 1 or a stereoisomer or a salt thereof, wherein $G_2$ is:
  (i) phenyl substituted with one or two substituents independently selected from propyl, butyl, —CN, —CF$_3$, cyclohexyl, —OCH$_2$CH$_3$, and/or —OCH(CH$_3$)$_2$;
  (ii) pyrazolyl, isoxazolyl, isothiazolyl, or pyrimidinyl substituted with one or two substituents independently selected from —CF$_3$, —CN, butyl, methyl cyclopropyl, cyclohexyl, phenyl, chlorophenyl, pyridinyl, and/or fluoropyridinyl; or
  (iii) cyclohexyl substituted with chlorophenyl.

12. The compound according to claim 1 or a stereoisomer or a salt thereof, wherein $G_2$ is:
  (i) —NHC(O)—(CH$_2$)$_{0-2}$-(phenyl) or —NHC(O)(pentyl);
  (ii) —C(O)NHCH$_2$C(CH$_3$)$_3$, —C(O)NR$_g$—(CHR$_g$)$_{0-3}$-A$_1$, —C(O)NR$_g$—CH$_2$C(R$_g$)(A$_1$)(A$_1$), or —C(O)NHCH$_2$(tetrahydronaphthalenyl), wherein A$_1$ is phenyl substituted with zero to 2 substituents independently selected from Cl, —CH$_3$, —OCH$_3$, —OCH$_2$CH$_3$, —OCH(CH$_3$)$_2$, and/or phenoxy; or
  (iii)

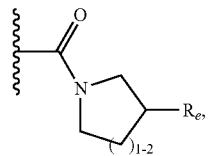

wherein R$_e$ is naphthalenyl or —(CH$_2$)$_{0-2}$(phenyl) and said phenyl is substituted with zero to 1 substituents selected from F, Cl, or OCH$_3$.

13. The compound according to claim 1 or a stereoisomer or a salt thereof, wherein $G_2$ is: —(CR$_5$R$_5$)$_a$CR$_e$R$_e$B$_4$, —CH=CH—CR$_e$R$_e$B$_4$, or —(CR$_5$R$_5$)$_a$O(CR$_5$R$_5$)$_a$CR$_e$R$_e$B$_4$, wherein B$_4$ is phenyl substituted with zero to 2 substituents independently selected from F, Cl, —OH, and/or butyl; and each R$_e$ is independently H and/or —CH$_3$, or two geminal R$_e$ along with the carbon atom to which they are attached form a C$_{4-6}$spirocycloalkyl ring.

14. The compound according to claim 1 or a stereoisomer or a salt thereof, wherein said compound is selected from:
1-((5,5-dimethyl-3-(3-phenyl-4-(trifluoromethyl)isoxazol-5-yl)-4,5-dihydronaphtho[1,2-c]isoxazol-7-yl)methyl)azetidine-3-carboxylic acid;
1-((3-(4-propylphenyl)-4H-chromeno[4,3-c]isoxazol-7-yl)methyl)azetidine-3-carboxylic acid, trifluoroacetic acid salt;
1-((3-(4-propylphenyl)-4H-chromeno[3,4-d]isoxazol-7-yl)methyl)azetidine-3-carboxylic acid, trifluoroacetic acid salt;
1-(3-(5-(1-methylcyclopropyl)-4-(trifluoromethyl)isoxazol-3-yl)-4,5-dihydronaphtho-[1,2-c]isoxazol-7-yl)methyl)azetidine-3-carboxylic acid;
1-((3-(5-isobutyl-4-(trifluoromethyl)isoxazol-3-yl)-4,5-dihydronaphtho[1,2-c]isoxazol-7-yl)methyl)azetidine-3-carboxylic acid;
1-((3-(5-phenyl-4-(trifluoromethyl)isoxazol-3-yl)-4,5-dihydronaphtho[1,2-c]isoxazol-7-yl)methyl)azetidine-3-carboxylic acid;
1-((3-(3-phenyl-4-(trifluoromethyl)isoxazol-5-yl)-4,5-dihydronaphtho[1,2-c]isoxazol-7-yl)methyl)azetidine-3-carboxylic acid;
3-(3-phenyl-4-(trifluoromethyl)isoxazol-5-yl)-4,5-dihydronaphtho[1,2-c]isoxazol-7-ol;
3-(4-propylphenyl)-4,5-dihydronaphtho[1,2-c]isoxazol-7-ol;
3-(4-propylphenyl)-4H-indeno[1,2-c]isoxazol-6-ol;
1-((3-(4-propylphenyl)-4,5-dihydronaphtho[1,2-c]isoxazol-7-yl)methyl)azetidine-3-carboxylic acid;
(R)-3-(3-(4-propylphenyl)-4,5-dihydronaphtho[1,2-c]isoxazol-7-yloxy)propane-1,2-diol;
(3S)-1-(2-hydroxy-2-(3-(5-phenyl-4-(trifluoromethyl)isoxazol-3-yl)-4,5-dihydronaphtho[1,2-c]isoxazol-7-yl)ethyl)piperidine-3-carboxylic acid;
1-((3-(4-isopropoxy-3-(trifluoromethyl)phenyl)-4,5-dihydronaphtho[1,2-c]isoxazol-7-yl)methyl) azetidine-3-carboxylic acid;
1-((3-(3-cyano-4-isopropoxyphenyl)-4,5-dihydronaphtho[1,2-c]isoxazol-7-yl)methyl)azetidine-3-carboxylic acid;
3-((3-(3-cyano-4-isopropoxyphenyl)-4,5-dihydronaphtho[1,2-c]isoxazol-7-yl)methylamine) propanoic acid;
1-((3-(4-isopropoxy-2-(trifluoromethyl)phenyl)-4,5-dihydronaphtho[1,2-c]isoxazol-7-yl)methyl) azetidine-3-carboxylic acid;
2-((3-(5-phenyl-4-(trifluoromethyl)isoxazol-3-yl)-4,5-dihydronaphtho[1,2-c]isoxazol-7-yl)methyl)-2,5,7-triazaspiro[3.4]octane-6,8-dione;
2-((3R)-1-(2-hydroxy-2-(3-(5-phenyl-4-(trifluoromethyl)isoxazol-3-yl)-4,5-dihydronaphtho [1,2-c]isoxazol-7-yl)ethyl)piperidin-3-yl)acetic acid;
1-((3-(4-propylphenyl)-4,5-dihydronaphtho[2,1-d]isoxazol-7-yl)methyl)azetidine-3-carboxylic acid;
3-(3-(3-cyano-4-isopropoxyphenyl)-4,5-dihydronaphtho[1,2-c]isoxazol-7-yl)propanoic acid;
1-((3-(3-phenyl-4-(trifluoromethyl)isoxazol-5-yl)-4,5-dihydro-2H-benzo[g]indazol-7-yl)methyl) azetidine-3-carboxylic acid;
1-((3-(4-isobutyl-3-(trifluoromethyl)phenyl)-4,5-dihydronaphtho[1,2-c]isoxazol-7-yl)methyl) azetidine-3-carboxylic acid;
(3-(3-(trifluoromethyl)phenyl)-4,5-dihydronaphtho[1,2-c]isoxazol-7-yl)methanol;
1-((3-(3-(trifluoromethyl)phenyl)-4,5-dihydronaphtho[1,2-c]isoxazol-7-yl)methyl)azetidine-3-carboxylic acid;
1-((3-(2-(1-(4-fluorophenyl)cyclohexyl)ethyl)-4,5-dihydronaphtho[1,2-c]isoxazol-7-yl)methyl) azetidine-3-carboxylic acid;
1-((3-(4-(4-chlorophenyl)cyclohexyl)-4,5-dihydronaphtho[1,2-c]isoxazol-7-yl)methyl)azetidine-3-carboxylic acid;
1-((3-(2-(1-(3,5-dichlorophenyl)cyclohexyl)ethyl)-4,5-dihydronaphtho[1,2-c]isoxazol-7-yl)methyl)azetidine-3-carboxylic acid;
1-((3-(3-(4-chlorophenyl)-3-methylbutyl)-4,5-dihydronaphtho[1,2-c]isoxazol-7-yl)methyl) azetidine-3-carboxylic acid;
1-((3-(((1-(4-fluorophenyl)cyclohexyl)methoxy)methyl)-4,5-dihydronaphtho[1,2-c]isoxazol-7-yl)azetidine-3-carboxylic acid;
1-((3-(3-(1-(4-fluorophenyl)cyclohexyl)propyl)-4,5-dihydronaphtho[1,2-c]isoxazol-7-yl)methyl) azetidine-3-carboxylic acid;

3-(5-phenylisoxazol-3-yl)-4,5-dihydronaphtho[1,2-c]isoxazol-7-ol;
3-(5-(2-chlorophenyl)-1-phenyl-1H-pyrazol-3-yl)-4,5-dihydronaphtho[1,2-c]isoxazol-7-ol;
3-(6-phenylpyrimidin-4-yl)-4,5-dihydronaphtho[1,2-c]isoxazol-7-ol;
3-(2-(1-(4-hydroxyphenyl)cyclohexyl)ethyl)-4,5-dihydronaphtho[1,2-c]isoxazol-7-ol;
3-(2-(1-(2-chloro-4-fluorophenyl)cyclohexyl)ethyl)-4,5-dihydronaphtho[1,2-c]isoxazol-7-ol;
3-(2-(1-(3,5-difluorophenyl)cyclohexyl)ethyl)-4,5-dihydronaphtho[1,2-c]isoxazol-7-ol;
3-(2-(1-(3,5-dichlorophenyl)cyclohexyl)ethyl)-4,5-dihydronaphtho[1,2-c]isoxazol-7-ol;
3-(2-(1-(3-fluorophenyl)cyclopentyl)ethyl)-4,5-dihydronaphtho[1,2-c]isoxazol-7-ol;
(E)-3-(2-(1-(4-chlorophenyl)cyclohexyl)vinyl)-4,5-dihydronaphtho[1,2-c]isoxazol-7-ol;
3-(4-isobutylphenyl)-4,5-dihydronaphtho[1,2-c]isoxazol-7-ol;
1-((2-(2-(1-(4-fluorophenyl)cyclohexyl)ethyl)naphtho[1,2-d]oxazol-7-yl)methyl)azetidine-3-carboxylic acid;
(S)-3-(2-(3-phenyl-4-(trifluoromethyl)isoxazol-5-yl)-4,5-dihydronaphtho[2,1-d]oxazol-7-yloxy) propane-1,2-diol;
1-((3-(3-phenyl-4-(trifluoromethyl)isoxazol-5-yl)-4,5-dihydronaphtho[2,1-d]isoxazol-7-yl)methyl)azetidine-3-carboxylic acid, TFA salt;
1-((3-(2,2-diphenylethylcarbamoyl)-4,5-dihydronaphtho[2,1-d]isoxazol-7-yl)methyl) azetidine-3-carboxylic acid, TFA salt;
1-((3-(2-chlorobenzylcarbamoyl)-4,5-dihydronaphtho[2,1-d]isoxazol-7-yl)methyl)azetidine-3-carboxylic acid;
1-((3-(neopentylcarbamoyl)-4,5-dihydronaphtho[2,1-d]isoxazol-7-yl)methyl)azetidine-3-carboxylic acid;
1-((2-(3-phenyl-4-(trifluoromethyl)isoxazol-5-yl)-4,5-dihydronaphtho[2,1-d]oxazol-7-yl)methyl) azetidine-3-carboxylic acid;
1-((2-(5-phenyl-4-(trifluoromethyl)isoxazol-3-yl)-4,5-dihydronaphtho[2,1-d]oxazol-7-yl)methyl) azetidine-3-carboxylic acid;
2-amino-2-methyl-4-(3-(1-phenyl-5-(trifluoromethyl)-1H-pyrazol-4-yl)-4,5-dihydronaphtho [1,2-c]isoxazol-7-yl)butan-1-ol;
(2S)-2-amino-2-methyl-4-(3-(1-phenyl-5-(trifluoromethyl)-1H-pyrazol-4-yl)-4,5-dihydronaphtho [1,2-c]isoxazol-7-yl)butanoic acid;
2-amino-2-methyl-4-(3-(1-phenyl-5-(trifluoromethyl)-1H-pyrazol-4-yl)-4,5-dihydronaphtho [1,2-c]isoxazol-7-yl)butyl dihydrogen phosphate;
1-((3-(5-phenyl-4-(trifluoromethyl)isoxazol-3-yl)-4H-chromeno[3,4-d]isoxazol-7-yl)methyl) azetidine-3-carboxylic acid;
1-((3-(5-phenyl-4-(trifluoromethyl)isoxazole-3-yl)-2,3-dihydrobenzo[b]oxepino-[4,5-d]isoxazol-8-yl)methyl)-azetidine-3-carboxylic acid;
1-((2-(3-phenyl-4-(trifluoromethyl)isoxazol-5-yl)-4,5-dihydronaphtho[2,1-d]thiazol-7-yl)methyl) azetidine-3-carboxylic acid;
1-((2-(2-(1-(4-fluorophenyl)cyclohexyl)ethyl)-4,5-dihydronaphtho[2,1-d]thiazol-7-yl)methyl) azetidine-3-carboxylic acid, TFA;
1-((2-(4-(4-chlorophenyl)cyclohexyl)-4,5-dihydronaphtho[2,1-d]thiazol-7-yl)methyl) azetidine-3-carboxylic acid, TFA;

1-((2-(5-phenyl-4-(trifluoromethyl)isoxazol-3-yl)-4,5-dihydronaphtho[2,1-d]thiazol-7-yl)methyl) azetidine-3-carboxylic acid;
1-((3-(3-phenyl-4-(trifluoromethyl)isoxazol-5-yl)-4H-chromeno[3,4-d]isoxazol-7-yl)methyl)-azetidine-3-carboxylic acid;
1-((3-(3-phenyl-4-(trifluoromethyl)isoxazol-5-yl)-4H-chromeno[4,3-c]isoxazol-7-yl)methyl)-azetidine-3-carboxylic acid;
1-((3-(5-Phenyl-4-(trifluoromethyl)isoxazol-3-yl)-4H-chromeno[4,3-c]isoxazol-7-yl)methyl)-azetidine-3-carboxylic acid;
1-((3-(3-(Pyridin-2-yl)-4-(trifluoromethyl)isoxazol-5-yl)-4,5-dihydronaphtho[1,2-c]isoxazol-7-yl)methyl)azetidine-3-carboxylic acid;
1-((8-Methyl-3-(5-phenyl-4-(trifluoromethyl)isoxazol-3-yl)-4,5-dihydronaphtho[1,2-c]isoxazol-7-yl)methyl) azetidine-3-carboxylic acid;
(3S)-1-(2-Hydroxy-2-(8-methyl-3-(5-phenyl-4-(trifluoromethyl)isoxazol-3-yl)-4,5-dihydronaphthol[1,2-c]isoxazol-7-yl)ethyl)piperidine-3-carboxylic acid;
1-((5,5-difluoro-3-(5-phenyl-4-(trifluoromethyl)isoxazol-3-yl)-4,5-dihydronaphtho[1,2-c]isoxazol-7-yl)methyl) azetidine-3-carboxylic acid;
1-((8-fluoro-3-(3-phenyl-4-(trifluoromethyl)isoxazol-5-yl)-4,5-dihydronaphtho[1,2-c]isoxazol-7-yl)azetidine-3-carboxylic acid;
3-(methyl((3-(5-phenyl-4-(trifluoromethyl)isoxazol-3-yl)-4,5-dihydronaphtho[1,2-c]isoxazol-7-yl)methyl) amino)propanoic acid;
3-((3-(5-Phenyl-4-(trifluoromethyl)isoxazol-3-yl)-4,5-dihydronaphtho[1,2-c]isoxazol-7-yl)methyl)amino)propanoic acid;
(3S)-1-((3-(5-phenyl-4-(trifluoromethyl)isoxazol-3-yl)-4,5-dihydronaphtho[1,2-c]isoxazol-7-yl)methyl)piperidine-3-carboxylic acid;
2-((3-(5-Phenyl-4-(trifluoromethyl)isoxazol-3-yl)-4,5-dihydronaphtho[1,2-c]isoxazol-7-yl)methylamino)acetic acid;
3-hydroxy-2-((3-(5-phenyl-4-(trifluoromethyl)isoxazol-3-yl)-4,5-dihydronaphtho[1,2-c]isoxazol-7-yl)methylamino)propanoic acid;
3-(methyl((3-(5-phenyl-4-(trifluoromethyl)isoxazol-3-yl)-4,5-dihydronaphtho[1,2-c]isoxazol-7-yl)methyl) amino)propanamide;
4-((3-(5-Phenyl-4-(trifluoromethyl)isoxazol-3-yl)-4,5-dihydronaphtho[1,2-c]isoxazol-7-yl)methyl)morpholino-3-yl)methanol;
1-((3-(5-cyclohexyl-4-(trifluoromethyl)isoxazol-3-yl)-4,5-dihydronaphtho[1,2-c]isoxazol-7-yl)methyl)azetidine-3-carboxylic acid;
3-(5-Cyclohexyl-4-(trifluoromethyl)isoxazol-3-yl)-4,5-dihydronaphtho[1,2-c]isoxazole-7-carboxylic acid;
1-((5-methyl-3-(3-phenyl-4-(trifluoromethyl)isoxazol-5-yl)-4,5-dihydroisoxazolo[4,3-c]quinolin-7-yl)methyl) azetidine-3-carboxylic acid;
1-((1-methyl-3-(5-phenyl-4-(trifluoromethyl)isoxazol-3-yl)-4,5-dihydro-1H-benzo[g]indazol-7-yl)methyl)azetidine-3-carboxylic acid, TFA;
1-((2-methyl-3-(5-phenyl-4-(trifluoromethyl)isoxazol-3-yl)-4,5-dihydro-2H-benzo[g]indazol-7-yl)methyl)azetidine-3-carboxylic acid, TFA;
1-((3-(3,4-diethoxyphenyl)-4,5-dihydronaphtho[1,2-c]isoxazol-7-yl)methyl)azetidine-3-carboxylic acid;
(3S)-1-(2-(3-(3,4-diethoxyphenyl)-4,5-dihydronaphtho[1,2-c]isoxazol-7-yl)-2-hydroxyethyl) piperidine-3-carboxylic acid, HCl;

(3S)-1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylic acid, HCl;

(±)1-(2-(3-phenyl-4-(trifluoromethyl)isoxazol-5-yl)-4,5-dihydronaphtho[2,1-d]thiazol-7-yl) ethane-1,2-diol;

2-hydroxy-N-(2-hydroxyethyl)-2-(2-(3-phenyl-4-(trifluoromethyl)isoxazol-5-yl)-4,5-dihydronaphtho[2,1-d]thiazol-7-yl)acetamide;

N-(1-cyanocyclopropyl)-2-hydroxy-2-(2-(3-phenyl-4-(trifluoromethyl)isoxazol-5-yl)-4,5-dihydronaphtho[2,1-d]thiazol-7-yl)acetamide;

1-((2-pentyl-4,5-dihydronaphtho[2,1-d]thiazol-7-yl)methyl)azetidine-3-carboxylic acid, TFA;

1-((3-(5-phenyl-4-(trifluoromethyl)isoxazol-3-yl)-4H-indeno[1,2-c]isoxazol-6-yl)methyl) azetidine-3-carboxylic acid;

2-(methyl((3-(5-phenyl-4-(trifluoromethyl)isoxazol-3-yl)-4,5-dihydronaphtho[1,2-c]isoxazol-7-yl)methyl)amino)acetic acid;

(±)2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid;

(±)2-(amino(3-(1-phenyl-5-(trifluoromethyl)-1H-pyrazol-4-yl)-4,5-dihydronaphtho[1,2-c]isoxazol-7-yl)methyl)furan-3-carboxylic acid;

(±)2-amino-4-(3-(5-phenyl-4-(trifluoromethyl)isoxazol-3-yl)-4,5-dihydronaphtho[1,2-c]isoxazol-7-yl)butanoic acid;

2-amino-2-(2-(3-(5-phenyl-4-(trifluoromethyl)isoxazol-3-yl)-4,5-dihydronaphtho[1,2-c]isoxazol-7-yl)ethyl)propane-1,3-diol;

2-amino-2-methyl-4-(3-(5-phenyl-4-(trifluoromethyl)isoxazol-3-yl)-4,5-dihydronaphtho[1,2-c]isoxazol-7-yl)butan-1-ol;

2-amino-2-methyl-4-(3-(5-phenyl-4-(trifluoromethyl)isoxazol-3-yl)-4,5-dihydronaphtho[1,2-c]isoxazol-7-yl)butanoic acid;

2-amino-2-methyl-4-(3-(5-phenyl-4-(trifluoromethyl)isoxazol-3-yl)-4,5-dihydronaphtho[1,2-c]isoxazol-7-yl)butyl dihydrogen phosphate;

(±)2-amino-2-methyl-3-(3-(5-phenyl-4-(trifluoromethyl)isoxazol-3-yl)-4,5-dihydronaphtho [1,2-c]isoxazol-7-yl)propyl dihydrogen phosphate;

2-((3-(5-phenyl-4-(trifluoromethyl)isoxazol-3-yl)-4,5-dihydronaphtho[1,2-c]isoxazol-7-yl)methylamino)ethyl dihydrogen phosphate;

2-amino-2-(3-(5-phenyl-4-(trifluoromethyl)isoxazol-3-yl)-4,5-dihydronaphtho[1,2-c]isoxazol-7-yl)propyl dihydrogen phosphate;

(1-amino-3-(3-(5-phenyl-4-(trifluoromethyl)isoxazol-3-yl)-4,5-dihydronaphtho[1,2-c]isoxazol-7-yl)cyclopentyl)methyl dihydrogen phosphate;

(1-amino-3-(2-(3-phenyl-4-(trifluoromethyl)isoxazol-5-yl)-4,5-dihydronaphtho[2,1-d]thiazol-7-yl)cyclopentyl)methyl dihydrogen phosphate;

2-(1-amino-3-(2-(3-phenyl-4-(trifluoromethyl)isoxazol-5-yl)-4,5-dihydronaphtho[2,1-d]thiazol-7-yl)cyclopentyl)ethyl dihydrogen phosphate;

1-(3-(5-phenyl-4-(trifluoromethyl)isoxazol-3-yl)-4,5-dihydronaphtho[1,2-c]isoxazol-7-yl) ethane-1,2-diol;

1-((3-(3-phenyl-4-(trifluoromethyl)isothiazol-5-yl)-4,5-dihydronaphtho[1,2-c]isoxazol-7-yl)methyl)azetidine-3-carboxylic acid;

2-amino-2-methyl-4-(3-(1-phenyl-5-(trifluoromethyl)-1H-pyrazol-4-yl)-4,5-dihydronaphtho [1,2-c]isoxazol-7-yl)butyl dihydrogen phosphate;

1-((3-(5-phenyl-4-(trifluoromethyl)isothiazol-3-yl)-4,5-dihydronaphtho[1,2-c]isoxazol-7-yl)methyl)azetidine-3-carboxylic acid;

1-((3-(4-cyano-3-phenylisothiazol-5-yl)-4,5-dihydronaphtho[1,2-c]isoxazol-7-yl)methyl) azetidine-3-carboxylic acid;

2-amino-2-methyl-3-(3-(5-phenyl-4-(trifluoromethyl)isoxazol-3-yl)-4,5-dihydronaphtho[1,2-c]isoxazol-7-yl)propan-1-ol;

2-((3-(5-phenyl-4-(trifluoromethyl)isoxazol-3-yl)-4,5-dihydronaphtho[1,2-c]isoxazol-7-yl)methylamino)ethanol;

(±)4-hydroxy-4-(3-(5-phenyl-4-(trifluoromethyl)isoxazol-3-yl)-4,5-dihydronaphtho[1,2-c]isoxazol-7-yl)butanoic acid;

2,2'-((3-(5-phenyl-4-(trifluoromethyl)isoxazol-3-yl)-4,5-dihydronaphtho[1,2-c]isoxazol-7-yl)methylazanediyl)diethanol;

(2R)-3-((3-(5-phenyl-4-(trifluoromethyl)isoxazol-3-yl)-4,5-dihydronaphtho[1,2-c]isoxazol-7-yl)methylamino)propane-1,2-diol;

(2S)-3-((3-(5-phenyl-4-(trifluoromethyl)isoxazol-3-yl)-4,5-dihydronaphtho[1,2-c]isoxazol-7-yl)ethylamino)propane-1,2-diol;

2-((3-(5-phenyl-4-(trifluoromethyl)isoxazol-3-yl)-4,5-dihydronaphtho[1,2-c]isoxazol-7-yl)ethylamino)propane-1,3-diol;

(3R)-1-((3-(5-phenyl-4-(trifluoromethyl)isoxazol-3-yl)-4,5-dihydronaphtho[1,2-c]isoxazol-7-yl)methyl)pyrrolidin-3-ol;

(3S)-1-((3-(5-phenyl-4-(trifluoromethyl)isoxazol-3-yl)-4,5-dihydronaphtho[1,2-c]isoxazol-7-yl)methyl)pyrrolidin-3-ol;

((2R)-1-((3-(5-phenyl-4-(trifluoromethyl)isoxazol-3-yl)-4,5-dihydronaphtho[1,2-c]isoxazol-7-yl)methyl)pyrrolidin-2-yl)methanol;

((2S)-1-((3-(5-phenyl-4-(trifluoromethyl)isoxazol-3-yl)-4,5-dihydronaphtho[1,2-c]isoxazol-7-yl)methyl)pyrrolidin-2-yl)methanol;

1-((3-(4-cyclohexyl-3-(trifluoromethyl)phenyl)-4,5-dihydronaphtho[1,2-c]isoxazol-7-yl)methyl)azetidine-3-carboxylic acid;

2-amino-2-methyl-4-(2-(3-phenyl-4-(trifluoromethyl)isoxazol-5-yl)-4,5-dihydronaphtho[2,1-d]thiazol-7-yl)butan-1-ol;

2-amino-2-methyl-4-(2-(3-phenyl-4-(trifluoromethyl)isoxazol-5-yl)-4,5-dihydronaphtho[2,1-d]thiazol-7-yl)butyl dihydrogen phosphate;

(1-amino-3-(3-(5-phenyl-4-(trifluoromethyl)isoxazol-3-yl)-4,5-dihydronaphtho[1,2-c]isoxazol-7-yl)cyclopentyl)methanol;

1-((3-(1-(5-fluoropyridin-2-yl)-5-(trifluoromethyl)-1H-pyrazol-4-yl)-4,5-dihydronaphtho[1,2-c]isoxazol-7-yl)methyl)azetidine-3-carboxylic acid;

(1-amino-3-(2-(3-phenyl-4-(trifluoromethyl)isoxazol-5-yl)-4,5-dihydronaphtho[2,1-d]thiazol-7-yl)cyclopentyl)methanol;

2-(1-amino-3-(2-(3-phenyl-4-(trifluoromethyl)isoxazol-5-yl)-4,5-dihydronaphtho[2,1-d]thiazol-7-yl)cyclopentyl)ethanol;

2-amino-2-(3-(5-phenyl-4-(trifluoromethyl)isoxazol-3-yl)-4,5-dihydronaphtho[1,2-c]isoxazol-7-yl)propan-1-ol;

N-(methylsulfonyl)-1-((3-(3-phenyl-4-(trifluoromethyl)isoxazol-5-yl)-4,5-dihydronaphtho[1,2-c]isoxazol-7-yl)methyl)azetidine-3-carboxamide;

(±)-2-hydroxy-2-(3-(4-propylphenyl)-4,5-dihydronaphtho[1,2-c]isoxazol-7-yl)acetic acid;
(±)-N-(cyanomethyl)-2-hydroxy-2-(3-(4-propylphenyl)-4,5-dihydronaphtho[1,2-c]isoxazol-7-yl) acetamide;
(±)-2-Hydroxy-N-(2-hydroxyethyl)-2-(3-(4-propylphenyl)-4,5-dihydronaphtho[1,2-c]isoxazol-7-yl)acetamide;
(±)-2-hydroxy-N-(2-(methylsulfonyl)ethyl)-2-(3-(4-propylphenyl)-4,5-dihydronaphtho[1,2-c]isoxazol-7-yl) acetamide;
2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)acetamide;
N-(1-cyanocyclopropyl)-2-hydroxy-2-(3-(5-phenyl-4-(trifluoromethyl)isoxazol-3-yl)-4,5-dihydronaphtho[1,2-c]isoxazol-7-yl)acetamide;
2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)acetamide;
2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)propanamide;
2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)propanamide;
1-((3-(4-propylphenyl)-4,5-dihydro-3H-benzo[e]indazol-7-yl)methyl)azetidine-3-carboxylic acid;
(1-amino-3-(2-pentyl-4,5-dihydronaphtho[2,1-d]thiazol-7-yl)cyclopentyl)methanol;
(1-amino-3-(2-pentyl-4,5-dihydronaphtho[2,1-d]thiazol-7-yl)cyclopentyl)methyl dihydrogen phosphate;
N-(7-hydroxy-4,5-dihydronaphtho[1,2-d]thiazol-2-yl) benzamide;
N-(7-hydroxy-4,5-dihydronaphtho[1,2-d]thiazol-2-yl)-2-phenylacetamide;
N-(7-hydroxy-4,5-dihydronaphtho[1,2-d]thiazol-2-yl)-3-phenylpropanamide;
N-(7-hydroxy-4,5-dihydronaphtho[1,2-d]thiazol-2-yl) hexanamide;
1-((3-(2-methoxybenzylcarbamoyl)-4,5-dihydronaphtho[2,1-d]isoxazol-7-yl)methyl) azetidine-3-carboxylic acid;
1-((3-(2-ethoxybenzylcarbamoyl)-4,5-dihydronaphtho[2,1-d]isoxazol-7-yl)methyl)azetidine-3-carboxylic acid;
1-((3-(2-methylbenzylcarbamoyl)-4,5-dihydronaphtho[2,1-d]isoxazol-7-yl)methyl)azetidine-3-carboxylic acid;
1-((3-(4-chlorobenzylcarbamoyl)-4,5-dihydronaphtho[2,1-d]isoxazol-7-yl)methyl)azetidine-3-carboxylic acid;
1-((3-(2,2-diphenylpropylcarbamoyl)-4,5-dihydronaphtho[2,1-d]isoxazol-7-yl)methyl) azetidine-3-carboxylic acid;
1-((3-(2-phenylpropylcarbamoyl)-4,5-dihydronaphtho[2,1-d]isoxazol-7-yl)methyl)azetidine-3-carboxylic acid;
1((3-(phenethylcarbamoyl)-4,5-dihydronaphtho[2,1-d]isoxazol-7-yl)methyl)azetidine-3-carboxylic acid;
1-((3-(2-chlorophenethylcarbamoyl)-4,5-dihydronaphtho[2,1-d]isoxazol-7-yl)methyl) azetidine-3-carboxylic acid;
1-((3-(3-phenylpropylcarbamoyl)-4,5-dihydronaphtho[2,1-d]isoxazol-7-yl)methyl)azetidine-3-carboxylic acid;
1-((3-(benzyl(methyl)carbamoyl)-4,5-dihydronaphtho[2,1-d]isoxazol-7-yl)methyl)azetidine-3-carboxylic acid;
1-((3-(3-chlorobenzylcarbamoyl)-4,5-dihydronaphtho[2,1-d]isoxazol-7-yl)methyl)azetidine-3-carboxylic acid;
1-((3-(3-chlorophenethylcarbamoyl)-4,5-dihydronaphtho[2,1-d]isoxazol-7-yl)methyl) azetidine-3-carboxylic acid;
1-((3-(3-phenylpyrrolidine-1-carbonyl)-4,5-dihydronaphtho[2,1-d]isoxazol-7-yl)methyl) azetidine-3-carboxylic acid;
1-((3-(3-benzylpyrrolidine-1-carbonyl)-4,5-dihydronaphtho[2,1-d]isoxazol-7-yl)methyl) azetidine-3-carboxylic acid;
1-((3-(3-phenethylpyrrolidine-1-carbonyl)-4,5-dihydronaphtho[2,1-d]isoxazol-7-yl)methyl) azetidine-3-carboxylic acid;
1-((3-(2-(4-methoxyphenyl)-2-phenylethylcarbamoyl)-4,5-dihydronaphtho[2,1-d]isoxazol-7-yl)methyl)azetidine-3-carboxylic acid;
1-((3-(3-(naphthalen-1-yl)piperidine-1-carbonyl)-4,5-dihydronaphtho[2,1-d]isoxazol-7-yl)methyl)azetidine-3-carboxylic acid;
1-((3-(3-phenylpiperidine-1-carbonyl)-4,5-dihydronaphtho[2,1-d]isoxazol-7-yl)methyl) azetidine-3-carboxylic acid;
1-((3-((1,2,3,4-tetrahydronaphthalen-1-yl)methylcarbamoyl)-4,5-dihydronaphtho[2,1-d]isoxazol-7-yl)methyl) azetidine-3-carboxylic acid;
1-((3-(3-(4-fluorophenyl)pyrrolidine-1-carbonyl)-4,5-dihydronaphtho[2,1-d]isoxazol-7-yl)methyl)azetidine-3-carboxylic acid;
1-((3-(3-(2-chlorophenyl)pyrrolidine-1-carbonyl)-4,5-dihydronaphtho[2,1-d]isoxazol-7-yl)methyl)azetidine-3-carboxylic acid;
1-((3-(3-(3-methoxyphenyl)pyrrolidine-1-carbonyl)-4,5-dihydronaphtho[2,1-d]isoxazol-7-yl)methyl)azetidine-3-carboxylic acid;
1-((3-(2-isopropoxybenzylcarbamoyl)-4,5-dihydronaphtho[2,1-d]isoxazol-7-yl)methyl) azetidine-3-carboxylic acid;
1-((3-(2-phenoxybenzylcarbamoyl)-4,5-dihydronaphtho[2,1-d]isoxazol-7-yl)methyl) azetidine-3-carboxylic acid;
1-((3-(3-methylbenzylcarbamoyl)-4,5-dihydronaphtho[2,1-d]isoxazol-7-yl)methyl)azetidine-3-carboxylic acid;
1S,3S)-3-((3-(3-phenyl-4-(trifluoromethyl)isoxazol-5-yl)-4,5-dihydronaphtho[1,2-c]isoxazol-7-yl)methylamino)cyclobutanecarboxylic acid;
(1S,3S)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid;
(1R,3R)-3-((3-(3-phenyl-4-(trifluoromethyl)isoxazol-5-yl)-4,5-dihydronaphtho[1,2-c]isoxazol-7-yl)methylamino)cyclobutanecarboxylic acid; and
(1R,3R)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid.

15. A compound of Formula (I):

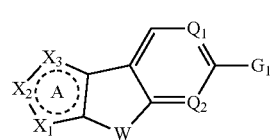

or a stereoisomer or a salt thereof, wherein:
(i) $X_1$ is C-$G_2$, one of $X_2$ and $X_3$ is N, and the other of $X_2$ and $X_3$ is O or S;
(ii) $X_2$ is C-$G_2$, one of $X_1$ and $X_3$ is N, and the other of $X_1$ and $X_3$ is O or S;
(iii) $X_1$ is C-$G_2$, one of $X_2$ and $X_3$ is N, and the other of $X_2$ and $X_3$ is NH or NCH$_3$; or (iv) $X_1$ is $N-G_2$, $X_2$ is N, and $X_3$ is CH;
wherein the broken circle represents two non-adjacent double bonds within Ring A;
$Q_1$ is CH, C(CH$_3$), or CF;
$Q_2$ is CH;
W is —CH$_2$—, —CH$_2$CH$_2$—, —CH$_2$C(CH$_3$)$_2$—, —CH$_2$CF$_2$—, —CH=CH—, —CH$_2$N(CH$_3$)—, —CH$_2$O—, or —CH$_2$CH$_2$O—;
$G_1$ is —CH$_2$OH, —CH(OH)CH$_2$OH, —(CH$_2$)$_{0-2}$COOH, —CH(OH)(CH$_2$)$_{0-2}$COOH, —CH$_2$NH(CH$_2$)$_{1-2}$OH, —CH$_2$NR$_g$(CH$_2$)$_{1-2}$COOH, —CH$_2$NR$_g$(CH$_2$)$_{1-2}$C(O)NH$_2$, —CH$_2$NR$_g$(CH$_2$)$_{1-2}$OP(O)(OH)$_2$, —OCH$_2$CH(OH)CH$_2$OH, —(CH$_2$)$_{0-2}$C(NH$_2$)(CH$_3$)CH$_2$OH, —(CH$_2$)$_{0-2}$CR$_g$(NH$_2$)C(O)OH, —(CH$_2$)$_{0-2}$C(NH$_2$)(CH$_3$)(CH$_2$)$_{1-2}$OP(O)(OH)$_2$, —CH$_2$CH$_2$C(NH$_2$)(CH$_2$OH)$_2$, —CH$_2$NHCH(CH$_2$OH)$_2$, —CH$_2$N(CH$_2$CH$_2$OH)$_2$, —CH$_2$NHCH$_2$CH(OH)CH$_2$OH, —CH(OH)C(O)NHCH$_2$CN, —CH(OH)C(O)NHCH$_2$CH$_2$S(O)$_2$CH$_3$, —CR$_g$(OH)C(O)NHCH$_2$CH$_2$OH, —CH$_2$(hydroxy pyrrolidinyl), —CH$_2$(hydroxymethyl pyrrolidinyl),

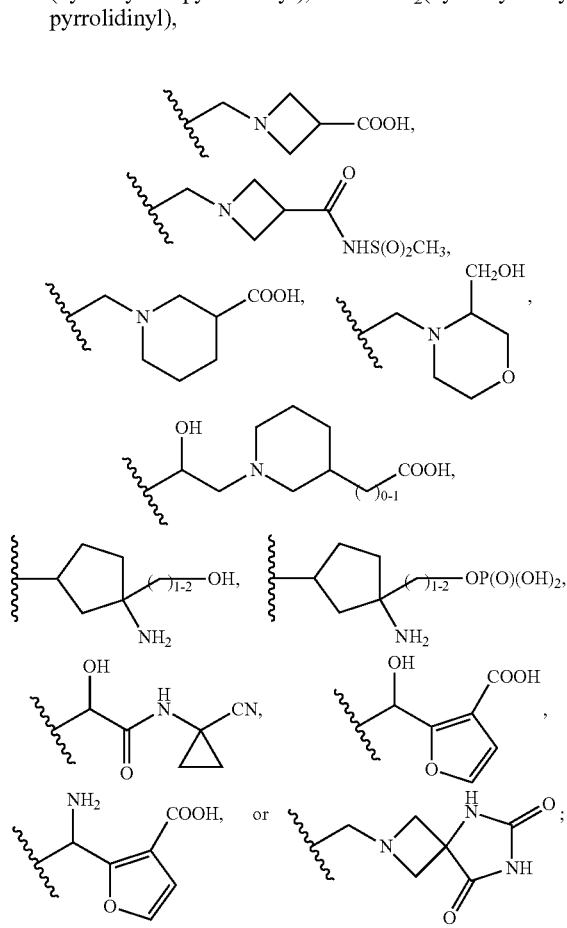

$G_2$ 1 S:
(i) pentyl or —NH$_2$;
(ii) phenyl substituted with one or two substituents independently selected from propyl, butyl, —CN, —CF$_3$, cyclohexyl, —OCH$_2$CH$_3$, and/or —OCH(CH$_3$)$_2$;
(iii) pyrazolyl, isoxazolyl, isothiazolyl, or pyrimidinyl substituted with one or two substituents independently selected from —CF$_3$, —CN, butyl, methyl cyclopropyl, cyclohexyl, phenyl, chlorophenyl, pyridinyl, and/or fluoropyridinyl;
(iv) cyclohexyl substituted with chlorophenyl;
(v) —NHC(O)—(CH$_2$)$_{0-2}$-(phenyl) or —NHC(O)(pentyl);
(vi) —C(O)NHCH$_2$C(CH$_3$)$_3$, —C(O)NR$_g$—(CHR$_g$)$_{0-3}$-A$_1$, —C(O)NR$_g$—CH$_2$C(R$_g$)(A$_1$)(A$_1$), or —C(O)NHCH$_2$(tetrahydronaphthalenyl), wherein A$_1$ is phenyl substituted with zero to 2 substituents independently selected from Cl, —CH$_3$, —OCH$_3$, —OCH$_2$CH$_3$, —OCH(CH$_3$)$_2$, and/or phenoxy;
(vii)

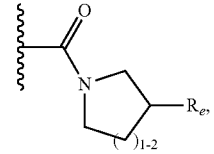

wherein R$_e$ is naphthalenyl or —(CH$_2$)$_{0-2}$(phenyl) and said phenyl is substituted with zero to 1 substituents selected from F, Cl, or OCH$_3$; or
(viii) —(CR$_5$R$_5$)$_a$CR$_e$R$_e$B$_4$, —CH=CH—CR$_e$R$_e$B$_4$, or —(CR$_5$R$_5$)$_a$O (CR$_5$R$_5$)$_a$CR$_e$R$_e$B$_4$, wherein B$_4$ is phenyl substituted with zero to 2 substituents independently selected from F, Cl, —OH, and/or butyl; and each R$_e$ is independently H and/or —CH$_3$, or two geminal R$_e$ along with the carbon atom to which they are attached form a C$_{4-6}$spirocycloalkyl ring;
each a is independently zero, 1, 2, 3, 4, and/or 5;
each R$_5$ is H; and
each R$_g$ is independently H and/or —CH$_3$.
16. The compound according to claim 15 or a stereoisomer or a salt thereof, wherein said compound is selected from:
1-((5,5-dimethyl-3-(3-phenyl-4-(trifluoromethyl)isoxazol-5-yl)-4,5-dihydronaphtho[1,2-c]isoxazol-7-yl)methyl)azetidine-3-carboxylic acid;
1-((3-(4-propylphenyl)-4H-chromeno[4,3-c]isoxazol-7-yl)methyl)azetidine-3-carboxylic acid, trifluoroacetic acid salt;
1-((3-(4-propylphenyl)-4H-chromeno[3,4-d]isoxazol-7-yl)methyl)azetidine-3-carboxylic acid, trifluoroacetic acid salt;
1-((3-(5-(1-methylcyclopropyl)-4-(trifluoromethyl)isoxazol-3-yl)-4,5-dihydronaphtho-[1,2-c]isoxazol-7-yl)methyl)azetidine-3-carboxylic acid;
1-((3-(5-isobutyl-4-(trifluoromethyl)isoxazol-3-yl)-4,5-dihydronaphtho[1,2-c]isoxazol-7-yl)methyl)azetidine-3-carboxylic acid;
1-((3-(5-phenyl-4-(trifluoromethyl)isoxazol-3-yl)-4,5-dihydronaphtho[1,2-c]isoxazol-7-yl) methyl)azetidine-3-carboxylic acid;
1-((3-(3-phenyl-4-(trifluoromethyl)isoxazol-5-yl)-4,5-dihydronaphtho[1,2-c]isoxazol-7-yl)methyl)azetidine-3-carboxylic acid;
1-((3-(4-propylphenyl)-4,5-dihydronaphtho[1,2-c]isoxazol-7-yl)methyl)azetidine-3-carboxylic acid;
(R)-3-(3-(4-propylphenyl)-4,5-dihydronaphtho[1,2-c]isoxazol-7-yloxy)propane-1,2-diol;
(3S)-1-(2-hydroxy-2-(3-(5-phenyl-4-(trifluoromethyl)isoxazol-3-yl)-4,5-dihydronaphtho[1,2-c]isoxazol-7-yl)ethyl)piperidine-3-carboxylic acid;
1-((3-(4-isopropoxy-3-(trifluoromethyl)phenyl)-4,5-dihydronaphtho[1,2-c]isoxazol-7-yl)methyl) azetidine-3-carboxylic acid;

1-((3-(3-cyano-4-isopropoxyphenyl)-4,5-dihydronaphtho[1,2-c]isoxazol-7-yl)methyl)azetidine-3-carboxylic acid;
3-((3-(3-cyano-4-isopropoxyphenyl)-4,5-dihydronaphtho[1,2-c]isoxazol-7-yl)methylamine) propanoic acid;
1-((3-(4-isopropoxy-2-(trifluoromethyl)phenyl)-4,5-dihydronaphtho[1,2-c]isoxazol-7-yl)methyl) azetidine-3-carboxylic acid;
2-((3-(5-phenyl-4-(trifluoromethyl)isoxazol-3-yl)-4,5-dihydronaphtho[1,2-c]isoxazol-7-yl)methyl)-2,5,7-triazaspiro[3.4]octane-6,8-dione;
2-((3R)-1-(2-hydroxy-2-(3-(5-phenyl-4-(trifluoromethyl)isoxazol-3-yl)-4,5-dihydronaphtho [1,2-c]isoxazol-7-yl)ethyl)piperidin-3-yl)acetic acid;
1-((3-(4-propylphenyl)-4,5-dihydronaphtho[2,1-d]isoxazol-7-yl)methyl)azetidine-3-carboxylic acid;
3-(3-(3-cyano-4-isopropoxyphenyl)-4,5-dihydronaphtho[1,2-c]isoxazol-7-yl)propanoic acid;
1-((3-(3-phenyl-4-(trifluoromethyl)isoxazol-5-yl)-4,5-dihydro-2H-benzo[g]indazol-7-yl)methyl) azetidine-3-carboxylic acid;
1-((3-(4-isobutyl-3-(trifluoromethyl)phenyl)-4,5-dihydronaphtho[1,2-c]isoxazol-7-yl)methyl) azetidine-3-carboxylic acid;
(3-(3-(trifluoromethyl)phenyl)-4,5-dihydronaphtho[1,2-c]isoxazol-7-yl)methanol;
1-((3-(3-(trifluoromethyl)phenyl)-4,5-dihydronaphtho[1,2-c]isoxazol-7-yl)methyl)azetidine-3-carboxylic acid;
1-((3-(2-(1-(4-fluorophenyl)cyclohexyl)ethyl)-4,5-dihydronaphtho[1,2-c]isoxazol-7-yl)methyl) azetidine-3-carboxylic acid;
1-((3-(4-(4-chlorophenyl)cyclohexyl)-4,5-dihydronaphtho[1,2-c]isoxazol-7-yl)methyl)azetidine-3-carboxylic acid;
1-((3-(2-(1-(3,5-dichlorophenyl)cyclohexyl)ethyl)-4,5-dihydronaphtho[1,2-c]isoxazol-7-yl)methyl)azetidine-3-carboxylic acid;
1-((3-(3-(4-chlorophenyl)-3-methylbutyl)-4,5-dihydronaphtho[1,2-c]isoxazol-7-yl)methyl) azetidine-3-carboxylic acid;
1-((3-(((1-(4-fluorophenyl)cyclohexyl)methoxy)methyl)-4,5-dihydronaphtho[1,2-c]isoxazol-7-yl)azetidine-3-carboxylic acid;
1-((3-(3-(1-(4-fluorophenyl)cyclohexyl)propyl)-4,5-dihydronaphtho[1,2-c]isoxazol-7-yl)methyl) azetidine-3-carboxylic acid;
1-((2-(2-(1-(4-fluorophenyl)cyclohexyl)ethyl)naphtho[1,2-d]oxazol-7-yl)methyl)azetidine-3-carboxylic acid;
(S)-3-(2-(3-phenyl-4-(trifluoromethyl)isoxazol-5-yl)-4,5-dihydronaphtho[2,1-d]oxazol-7-yloxy) propane-1,2-diol;
1-((3-(3-phenyl-4-(trifluoromethyl)isoxazol-5-yl)-4,5-dihydronaphtho[2,1-d]isoxazol-7-yl)methyl)azetidine-3-carboxylic acid, TFA salt;
1-((3-(2,2-diphenylethylcarbamoyl)-4,5-dihydronaphtho[2,1-d]isoxazol-7-yl)methyl) azetidine-3-carboxylic acid, TFA salt;
1-((3-(2-chlorobenzylcarbamoyl)-4,5-dihydronaphtho[2,1-d]isoxazol-7-yl)methyl)azetidine-3-carboxylic acid;
1-((3-(neopentylcarbamoyl)-4,5-dihydronaphtho[2,1-d]isoxazol-7-yl)methyl)azetidine-3-carboxylic acid;
1-((2-(3-phenyl-4-(trifluoromethyl)isoxazol-5-yl)-4,5-dihydronaphtho[2,1-d]oxazol-7-yl)methyl) azetidine-3-carboxylic acid;
1-((2-(5-phenyl-4-(trifluoromethyl)isoxazol-3-yl)-4,5-dihydronaphtho[2,1-d]oxazol-7-yl)methyl) azetidine-3-carboxylic acid;
2-amino-2-methyl-4-(3-(1-phenyl-5-(trifluoromethyl)-1H-pyrazol-4-yl)-4,5-dihydronaphtho [1,2-c]isoxazol-7-yl)butan-1-ol;
(2S)-2-amino-2-methyl-4-(3-(1-phenyl-5-(trifluoromethyl)-1H-pyrazol-4-yl)-4,5-dihydronaphtho [1,2-c]isoxazol-7-yl)butanoic acid;
2-amino-2-methyl-4-(3-(1-phenyl-5-(trifluoromethyl)-1H-pyrazol-4-yl)-4,5-dihydronaphtho [1,2-c]isoxazol-7-yl)butyl dihydrogen phosphate;
1-((3-(5-phenyl-4-(trifluoromethyl)isoxazol-3-yl)-4H-chromeno[3,4-d]isoxazol-7-yl)methyl) azetidine-3-carboxylic acid;
1-((3-(5-phenyl-4-(trifluoromethyl)isoxazole-3-yl)-2,3-dihydrobenzo[b]oxepino-[4,5-d]isoxazol-8-yl)methyl)-azetidine-3-carboxylic acid;
1-((2-(3-phenyl-4-(trifluoromethyl)isoxazol-5-yl)-4,5-dihydronaphtho[2,1-d]thiazol-7-yl)methyl) azetidine-3-carboxylic acid;
1-((2-(2-(1-(4-fluorophenyl)cyclohexyl)ethyl)-4,5-dihydronaphtho[2,1-d]thiazol-7-yl)methyl) azetidine-3-carboxylic acid, TFA;
1-((2-(4-(4-chlorophenyl)cyclohexyl)-4,5-dihydronaphtho[2,1-d]thiazol-7-yl)methyl) azetidine-3-carboxylic acid, TFA;
1-((2-(5-phenyl-4-(trifluoromethyl)isoxazol-3-yl)-4,5-dihydronaphtho[2,1-d]thiazol-7-yl)methyl) azetidine-3-carboxylic acid;
1-((3-(3-phenyl-4-(trifluoromethyl)isoxazol-5-yl)-4H-chromeno[3,4-d]isoxazol-7-yl)methyl)-azetidine-3-carboxylic acid;
1-((3-(3-phenyl-4-(trifluoromethyl)isoxazol-5-yl)-4H-chromeno[4,3-c]isoxazol-7-yl)methyl)-azetidine-3-carboxylic acid;
1-((3-(5-Phenyl-4-(trifluoromethyl)isoxazol-3-yl)-4H-chromeno[4,3-c]isoxazol-7-yl)methyl)-azetidine-3-carboxylic acid;
1-((3-(3-(Pyridin-2-yl)-4-(trifluoromethyl)isoxazol-5-yl)-4,5-dihydronaphtho[1,2-c]isoxazol-7-yl)methyl)azetidine-3-carboxylic acid;
1-((8-Methyl-3-(5-phenyl-4-(trifluoromethyl)isoxazol-3-yl)-4,5-dihydronaphtho[1,2-c]isoxazol-7-yl)methyl) azetidine-3-carboxylic acid;
(3S)-1-(2-Hydroxy-2-(8-methyl-3-(5-phenyl-4-(trifluoromethyl)isoxazol-3-yl)-4,5-dihydronaphtho[1,2-c]isoxazol-7-yl)ethyl)piperidine-3-carboxylic acid;
1-((5,5-difluoro-3-(5-phenyl-4-(trifluoromethyl)isoxazol-3-yl)-4,5-dihydronaphtho[1,2-c]isoxazol-7-yl)methyl) azetidine-3-carboxylic acid;
1-((8-fluoro-3-(3-phenyl-4-(trifluoromethyl)isoxazol-5-yl)-4,5-dihydronaphtho[1,2-c]isoxazol-7-yl)azetidine-3-carboxylic acid;
3-(methyl((3-(5-phenyl-4-(trifluoromethyl)isoxazol-3-yl)-4,5-dihydronaphtho[1,2-c]isoxazol-7-yl)methyl) amino)propanoic acid;
3-((3-(5-Phenyl-4-(trifluoromethyl)isoxazol-3-yl)-4,5-dihydronaphtho[1,2-c]isoxazol-7-yl)methyl)amino)propanoic acid;
(3S)-1-((3-(5-phenyl-4-(trifluoromethyl)isoxazol-3-yl)-4,5-dihydronaphtho[1,2-c]isoxazol-7-yl)methyl)piperidine-3-carboxylic acid;
2-((3-(5-Phenyl-4-(trifluoromethyl)isoxazol-3-yl)-4,5-dihydronaphtho[1,2-c]isoxazol-7-yl)methylamino)acetic acid;
3-hydroxy-2-((3-(5-phenyl-4-(trifluoromethyl)isoxazol-3-yl)-4,5-dihydronaphtho[1,2-c]isoxazol-7-yl)methylamino)propanoic acid;

3-(methyl((3-(5-phenyl-4-(trifluoromethyl)isoxazol-3-yl)-4,5-dihydronaphtho[1,2-c]isoxazol-7-yl)methyl)amino)propanamide;

4-((3-(5-Phenyl-4-(trifluoromethyl)isoxazol-3-yl)-4,5-dihydronaphtho[1,2-c]isoxazol-7-yl)methyl)morpholino-3-yl)methanol;

1-((3-(5-cyclohexyl-4-(trifluoromethyl)isoxazol-3-yl)-4,5-dihydronaphtho[1,2-c]isoxazol-7-yl)methyl)azetidine-3-carboxylic acid;

3-(5-Cyclohexyl-4-(trifluoromethyl)isoxazol-3-yl)-4,5-dihydronaphtho[1,2-c]isoxazole-7-carboxylic acid;

1-((5-methyl-3-(3-phenyl-4-(trifluoromethyl)isoxazol-5-yl)-4,5-dihydroisoxazolo[4,3-c]quinolin-7-yl)methyl)azetidine-3-carboxylic acid;

1-((l-methyl-3-(5-phenyl-4-(trifluoromethyl)isoxazol-3-yl)-4,5-dihydro-1H-benzo[g]indazol-7-yl)methyl)azetidine-3-carboxylic acid, TFA;

1-((2-methyl-3-(5-phenyl-4-(trifluoromethyl)isoxazol-3-yl)-4,5-dihydro-2H-benzo[g]indazol-7-yl)methyl)azetidine-3-carboxylic acid, TFA;

1-((3-(3,4-diethoxyphenyl)-4,5-dihydronaphtho[1,2-c]isoxazol-7-yl)methyl)azetidine-3-carboxylic acid;

(3S)-1-(2-(3-(3,4-diethoxyphenyl)-4,5-dihydronaphtho[1,2-c]isoxazol-7-yl)-2-hydroxyethyl) piperidine-3-carboxylic acid, HCl;

(3S)-1-(2-hydroxy-2-(2-(3-phenyl-4-(trifluoromethyl)isoxazol-5-yl)-4,5-dihydronaphtho[2,1-d]thiazol-7-yl)ethyl)piperidine-3-carboxylic acid, HCl;

(±)1-(2-(3-phenyl-4-(trifluoromethyl)isoxazol-5-yl)-4,5-dihydronaphtho[2,1-d]thiazol-7-yl) ethane-1,2-diol;

2-hydroxy-N-(2-hydroxyethyl)-2-(2-(3-phenyl-4-(trifluoromethyl)isoxazol-5-yl)-4,5-dihydronaphtho[2,1-d]thiazol-7-yl)acetamide;

N-(1-cyanocyclopropyl)-2-hydroxy-2-(2-(3-phenyl-4-(trifluoromethyl)isoxazol-5-yl)-4,5-dihydronaphtho[2,1-d]thiazol-7-yl)acetamide;

1-((2-pentyl-4,5-dihydronaphtho[2,1-d]thiazol-7-yl)methyl)azetidine-3-carboxylic acid, TFA;

1-((3-(5-phenyl-4-(trifluoromethyl)isoxazol-3-yl)-4H-indeno[1,2-c]isoxazol-6-yl)methyl) azetidine-3-carboxylic acid;

2-(methyl((3-(5-phenyl-4-(trifluoromethyl)isoxazol-3-yl)-4,5-dihydronaphtho[1,2-c]isoxazol-7-yl)methyl)amino)acetic acid;

(±)2-(hydroxy(3-(1-phenyl-5-(trifluoromethyl)-1H-pyrazol-4-yl)-4,5-dihydronaphtho[1,2-c]isoxazol-7-yl)methyl)furan-3-carboxylic acid;

(±)2-(amino(3-(1-phenyl-5-(trifluoromethyl)-1H-pyrazol-4-yl)-4,5-dihydronaphtho[1,2-c]isoxazol-7-yl)methyl)furan-3-carboxylic acid;

(±)2-amino-4-(3-(5-phenyl-4-(trifluoromethyl)isoxazol-3-yl)-4,5-dihydronaphtho[1,2-c]isoxazol-7-yl)butanoic acid;

2-amino-2-(2-(3-(5-phenyl-4-(trifluoromethyl)isoxazol-3-yl)-4,5-dihydronaphtho[1,2-c]isoxazol-7-yl)ethyl)propane-1,3-diol;

2-amino-2-methyl-4-(3-(5-phenyl-4-(trifluoromethyl)isoxazol-3-yl)-4,5-dihydronaphtho[1,2-c]isoxazol-7-yl)butan-1-ol;

2-amino-2-methyl-4-(3-(5-phenyl-4-(trifluoromethyl)isoxazol-3-yl)-4,5-dihydronaphtho[1,2-c]isoxazol-7-yl)butanoic acid;

2-amino-2-methyl-4-(3-(5-phenyl-4-(trifluoromethyl)isoxazol-3-yl)-4,5-dihydronaphtho[1,2-c]isoxazol-7-yl)butyl dihydrogen phosphate;

(±)2-amino-2-methyl-3-(3-(5-phenyl-4-(trifluoromethyl)isoxazol-3-yl)-4,5-dihydronaphtho [1,2-c]isoxazol-7-yl)propyl dihydrogen phosphate;

2-((3-(5-phenyl-4-(trifluoromethyl)isoxazol-3-yl)-4,5-dihydronaphtho[1,2-c]isoxazol-7-yl)methylamino)ethyl dihydrogen phosphate;

2-amino-2-(3-(5-phenyl-4-(trifluoromethyl)isoxazol-3-yl)-4,5-dihydronaphtho[1,2-c]isoxazol-7-yl)propyl dihydrogen phosphate;

(1-amino-3-(3-(5-phenyl-4-(trifluoromethyl)isoxazol-3-yl)-4,5-dihydronaphtho[1,2-c]isoxazol-7-yl)cyclopentyl)methyl dihydrogen phosphate;

(1-amino-3-(2-(3-phenyl-4-(trifluoromethyl)isoxazol-5-yl)-4,5-dihydronaphtho[2,1-d]thiazol-7-yl)cyclopentyl)methyl dihydrogen phosphate;

2-(1-amino-3-(2-(3-phenyl-4-(trifluoromethyl)isoxazol-5-yl)-4,5-dihydronaphtho[2,1-d]thiazol-7-yl)cyclopentyl)ethyl dihydrogen phosphate;

1-(3-(5-phenyl-4-(trifluoromethyl)isoxazol-3-yl)-4,5-dihydronaphtho[1,2-c]isoxazol-7-yl) ethane-1,2-diol;

1-((3-(3-phenyl-4-(trifluoromethyl)isothiazol-5-yl)-4,5-dihydronaphtho[1,2-c]isoxazol-7-yl)methyl)azetidine-3-carboxylic acid;

2-amino-2-methyl-4-(3-(1-phenyl-5-(trifluoromethyl)-1H-pyrazol-4-yl)-4,5-dihydronaphtho [1,2-c]isoxazol-7-yl)butyl dihydrogen phosphate;

1-((3-(5-phenyl-4-(trifluoromethyl)isothiazol-3-yl)-4,5-dihydronaphtho[1,2-c]isoxazol-7-yl)methyl)azetidine-3-carboxylic acid;

1-((3-(4-cyano-3-phenylisothiazol-5-yl)-4,5-dihydronaphtho[1,2-c]isoxazol-7-yl)methyl) azetidine-3-carboxylic acid;

2-amino-2-methyl-3-(3-(5-phenyl-4-(trifluoromethyl)isoxazol-3-yl)-4,5-dihydronaphtho[1,2-c]isoxazol-7-yl)propan-1-ol;

2-((3-(5-phenyl-4-(trifluoromethyl)isoxazol-3-yl)-4,5-dihydronaphtho[1,2-c]isoxazol-7-yl)methylamino)ethanol;

(±)4-hydroxy-4-(3-(5-phenyl-4-(trifluoromethyl)isoxazol-3-yl)-4,5-dihydronaphtho[1,2-c]isoxazol-7-yl)butanoic acid;

2,2'-((3-(5-phenyl-4-(trifluoromethyl)isoxazol-3-yl)-4,5-dihydronaphtho[1,2-c]isoxazol-7-yl)methylazanediyl)diethanol;

(2R)-3-((3-(5-phenyl-4-(trifluoromethyl)isoxazol-3-yl)-4,5-dihydronaphtho[1,2-c]isoxazol-7-yl)methylamino)propane-1,2-diol;

(2S)-3-((3-(5-phenyl-4-(trifluoromethyl)isoxazol-3-yl)-4,5-dihydronaphtho[1,2-c]isoxazol-7-yl)ethylamino)propane-1,2-diol;

2-((3-(5-phenyl-4-(trifluoromethyl)isoxazol-3-yl)-4,5-dihydronaphtho[1,2-c]isoxazol-7-yl)ethylamino)propane-1,3-diol;

(3R)-1-((3-(5-phenyl-4-(trifluoromethyl)isoxazol-3-yl)-4,5-dihydronaphtho[1,2-c]isoxazol-7-yl)methyl)pyrrolidin-3-ol;

(3S)-1-((3-(5-phenyl-4-(trifluoromethyl)isoxazol-3-yl)-4,5-dihydronaphtho[1,2-c]isoxazol-7-yl) methyl)pyrrolidin-3-ol;

((2R)-1-((3-(5-phenyl-4-(trifluoromethyl)isoxazol-3-yl)-4,5-dihydronaphtho[1,2-c]isoxazol-7-yl)methyl)pyrrolidin-2-yl)methanol;

((2S)-1-((3-(5-phenyl-4-(trifluoromethyl)isoxazol-3-yl)-4,5-dihydronaphtho[1,2-c]isoxazol-7-yl)methyl)pyrrolidin-2-yl)methanol;

1-((3-(4-cyclohexyl-3-(trifluoromethyl)phenyl)-4,5-dihydronaphtho[1,2-c]isoxazol-7-yl)methyl)azetidine-3-carboxylic acid;
2-amino-2-methyl-4-(2-(3-phenyl-4-(trifluoromethyl)isoxazol-5-yl)-4,5-dihydronaphtho[2,1-d]thiazol-7-yl) butan-1-ol;
2-amino-2-methyl-4-(2-(3-phenyl-4-(trifluoromethyl)isoxazol-5-yl)-4,5-dihydronaphtho[2,1-d]thiazol-7-yl) butyl dihydrogen phosphate;
(1-amino-3-(3-(5-phenyl-4-(trifluoromethyl)isoxazol-3-yl)-4,5-dihydronaphtho[1,2-c]isoxazol-7-yl)cyclopentyl)methanol;
1-((3-(1-(5-fluoropyridin-2-yl)-5-(trifluoromethyl)-1H-pyrazol-4-yl)-4,5-dihydronaphtho[1,2-c]isoxazol-7-yl)methyl)azetidine-3-carboxylic acid;
(1-amino-3-(2-(3-phenyl-4-(trifluoromethyl)isoxazol-5-yl)-4,5-dihydronaphtho[2,1-d]thiazol-7-yl)cyclopentyl)methanol;
2-(1-amino-3-(2-(3-phenyl-4-(trifluoromethyl)isoxazol-5-yl)-4,5-dihydronaphtho[2,1-d]thiazol-7-yl)cyclopentyl)ethanol;
2-amino-2-(3-(5-phenyl-4-(trifluoromethyl)isoxazol-3-yl)-4,5-dihydronaphtho[1,2-c]isoxazol-7-yl)propan-1-ol;
N-(methylsulfonyl)-1-((3-(3-phenyl-4-(trifluoromethyl)isoxazol-5-yl)-4,5-dihydronaphtho[1,2-c]isoxazol-7-yl)methyl)azetidine-3-carboxamide;
(±)-2-hydroxy-2-(3-(4-propylphenyl)-4,5-dihydronaphtho[1,2-c]isoxazol-7-yl)acetic acid;
(±)-N-(cyanomethyl)-2-hydroxy-2-(3-(4-propylphenyl)-4,5-dihydronaphtho[1,2-c]isoxazol-7-yl) acetamide;
(±)-2-Hydroxy-N-(2-hydroxyethyl)-2-(3-(4-propylphenyl)-4,5-dihydronaphtho[1,2-c]isoxazol-7-yl)acetamide;
(±)-2-hydroxy-N-(2-(methylsulfonyl)ethyl)-2-(3-(4-propylphenyl)-4,5-dihydronaphtho[1,2-c]isoxazol-7-yl) acetamide;
2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)acetamide;
N-(1-cyanocyclopropyl)-2-hydroxy-2-(3-(5-phenyl-4-(trifluoromethyl)isoxazol-3-yl)-4,5-dihydronaphtho[1,2-c]isoxazol-7-yl)acetamide;
2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)acetamide;
2-hydroxy-N-(2-hydroxyethyl)-2-(3-(5-phenyl-4-(trifluoromethyl)isoxazol-3-yl)-4,5-dihydronaphtho[1,2-c]isoxazol-7-yl)propanamide;
2-hydroxy-N-(2-(methylsulfonyl)ethyl)-2-(3-(5-phenyl-4-(trifluoromethyl)isoxazol-3-yl)-4,5-dihydronaphtho[1,2-c]isoxazol-7-yl)propanamide;
1-((3-(4-propylphenyl)-4,5-dihydro-3H-benzo[e]indazol-7-yl)methyl)azetidine-3-carboxylic acid;
(1-amino-3-(2-pentyl-4,5-dihydronaphtho[2,1-d]thiazol-7-yl)cyclopentyl)methanol;
(1-amino-3-(2-pentyl-4,5-dihydronaphtho[2,1-d]thiazol-7-yl)cyclopentyl)methyl dihydrogen phosphate;
(R)-3-(2-amino-4,5-dihydronaphtho[1,2-d]thiazol-7-yloxy)propane-1,2-diol;
1-((3-(2-methoxybenzylcarbamoyl)-4,5-dihydronaphtho[2,1-d]isoxazol-7-yl)methyl) azetidine-3-carboxylic acid;
1-((3-(2-ethoxybenzylcarbamoyl)-4,5-dihydronaphtho[2,1-d]isoxazol-7-yl)methyl)azetidine-3-carboxylic acid;
1-((3-(2-methylbenzylcarbamoyl)-4,5-dihydronaphtho[2,1-d]isoxazol-7-yl)methyl)azetidine-3-carboxylic acid;
1-((3-(4-chlorobenzylcarbamoyl)-4,5-dihydronaphtho[2,1-d]isoxazol-7-yl)methyl)azetidine-3-carboxylic acid;
1-((3-(2,2-diphenylpropylcarbamoyl)-4,5-dihydronaphtho[2,1-d]isoxazol-7-yl)methyl) azetidine-3-carboxylic acid;
1-((3-(2-phenylpropylcarbamoyl)-4,5-dihydronaphtho[2,1-d]isoxazol-7-yl)methyl)azetidine-3-carboxylic acid;
1-((3-(phenethylcarbamoyl)-4,5-dihydronaphtho[2,1-d]isoxazol-7-yl)methyl)azetidine-3-carboxylic acid;
1-((3-(2-chlorophenethylcarbamoyl)-4,5-dihydronaphtho[2,1-d]isoxazol-7-yl)methyl) azetidine-3-carboxylic acid;
1-((3-(3-phenylpropylcarbamoyl)-4,5-dihydronaphtho[2,1-d]isoxazol-7-yl)methyl)azetidine-3-carboxylic acid;
1-((3-(benzyl(methyl)carbamoyl)-4,5-dihydronaphtho[2,1-d]isoxazol-7-yl)methyl)azetidine-3-carboxylic acid;
1-((3-(3-chlorobenzylcarbamoyl)-4,5-dihydronaphtho[2,1-d]isoxazol-7-yl)methyl)azetidine-3-carboxylic acid;
1-((3-(3-chlorophenethylcarbamoyl)-4,5-dihydronaphtho[2,1-d]isoxazol-7-yl)methyl) azetidine-3-carboxylic acid;
1-((3-(3-phenylpyrrolidine-1-carbonyl)-4,5-dihydronaphtho[2,1-d]isoxazol-7-yl)methyl) azetidine-3-carboxylic acid;
1-((3-(3-benzylpyrrolidine-1-carbonyl)-4,5-dihydronaphtho[2,1-d]isoxazol-7-yl)methyl) azetidine-3-carboxylic acid;
1-((3-(3-phenethylpyrrolidine-1-carbonyl)-4,5-dihydronaphtho[2,1-d]isoxazol-7-yl)methyl) azetidine-3-carboxylic acid;
1-((3-(2-(4-methoxyphenyl)-2-phenylethylcarbamoyl)-4,5-dihydronaphtho[2,1-d]isoxazol-7-yl)methyl)azetidine-3-carboxylic acid;
1-((3-(3-(naphthalen-1-yl)piperidine-1-carbonyl)-4,5-dihydronaphtho[2,1-d]isoxazol-7-yl)methyl)azetidine-3-carboxylic acid;
1-((3-(3-phenylpiperidine-1-carbonyl)-4,5-dihydronaphtho[2,1-d]isoxazol-7-yl)methyl) azetidine-3-carboxylic acid;
1-((3-((1,2,3,4-tetrahydronaphthalen-1-yl)methylcarbamoyl)-4,5-dihydronaphtho[2,1-d]isoxazol-7-yl)methyl) azetidine-3-carboxylic acid;
1-((3-(3-(4-fluorophenyl)pyrrolidine-1-carbonyl)-4,5-dihydronaphtho[2,1-d]isoxazol-7-yl)methyl)azetidine-3-carboxylic acid;
1-((3-(3-(2-chlorophenyl)pyrrolidine-1-carbonyl)-4,5-dihydronaphtho[2,1-d]isoxazol-7-yl)methyl)azetidine-3-carboxylic acid;
1-((3-(3-(3-methoxyphenyl)pyrrolidine-1-carbonyl)-4,5-dihydronaphtho[2,1-d]isoxazol-7-yl)methyl)azetidine-3-carboxylic acid;
1-((3-(2-isopropoxybenzylcarbamoyl)-4,5-dihydronaphtho[2,1-d]isoxazol-7-yl)methyl) azetidine-3-carboxylic acid;
1-((3-(2-phenoxybenzylcarbamoyl)-4,5-dihydronaphtho[2,1-d]isoxazol-7-yl)methyl) azetidine-3-carboxylic acid;
1-((3-(3-methylbenzylcarbamoyl)-4,5-dihydronaphtho[2,1-d]isoxazol-7-yl)methyl)azetidine-3-carboxylic acid;
1S,3S)-3-((3-(3-phenyl-4-(trifluoromethyl)isoxazol-5-yl)-4,5-dihydronaphtho[1,2-c]isoxazol-7-yl)methylamino)cyclobutanecarboxylic acid;
(1S,3S)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid;

(1R,3R)-3-((3-(3-phenyl-4-(trifluoromethyl)isoxazol-5-yl)-4,5-dihydronaphtho[1,2-c]isoxazol-7-yl)methylamino)cyclobutanecarboxylic acid; and (1R,3R)-3-(cyano(3-(3-phenyl-4-(trifluoromethyl)isoxazol-5-yl)-4,5-dihydronaphtho[1,2-c]isoxazol-7-yl)methylamino)cyclobutanecarboxylic acid.

\* \* \* \* \*